United States Patent
Dai et al.

(10) Patent No.: US 12,427,146 B2
(45) Date of Patent: Sep. 30, 2025

(54) C-TERMINAL SRC KINASE INHIBITORS

(71) Applicant: INVENTISBIO CO., LTD., Shanghai (CN)

(72) Inventors: Xing Dai, Shanghai (CN); Yaolin Wang, Shanghai (CN); Yueheng Jiang, Shanghai (CN); Yanqin Liu, Shanghai (CN); Zhe Shi, Shanghai (CN); Zhenwu Wang, Shanghai (CN); Zixing Han, Shanghai (CN); Liangshan Tao, Shanghai (CN)

(73) Assignee: INVENTISBIO CO., LTD., Shanghai (CN)

( * ) Notice: Subject to any disclaimer, the term of this patent is extended or adjusted under 35 U.S.C. 154(b) by 983 days.

(21) Appl. No.: 17/416,222

(22) PCT Filed: Dec. 17, 2019

(86) PCT No.: PCT/CN2019/125910
§ 371 (c)(1),
(2) Date: Jun. 18, 2021

(87) PCT Pub. No.: WO2020/125615
PCT Pub. Date: Jun. 25, 2020

(65) Prior Publication Data
US 2022/0040176 A1    Feb. 10, 2022

(30) Foreign Application Priority Data
Dec. 19, 2018    (WO) ................ PCT/CN2018/121877

(51) Int. Cl.
| | | |
|---|---|---|
| *A61K 31/506* | (2006.01) | |
| *A61K 31/5377* | (2006.01) | |
| *A61K 35/17* | (2025.01) | |
| *A61K 39/395* | (2006.01) | |
| *C07D 401/14* | (2006.01) | |
| *C07D 403/04* | (2006.01) | |
| *C07D 417/04* | (2006.01) | |
| *C07D 417/14* | (2006.01) | |
| *C07D 471/04* | (2006.01) | |

(52) U.S. Cl.
CPC ........ *A61K 31/506* (2013.01); *A61K 31/5377* (2013.01); *A61K 35/17* (2013.01); *A61K 39/395* (2013.01); *C07D 401/14* (2013.01); *C07D 403/04* (2013.01); *C07D 417/04* (2013.01); *C07D 417/14* (2013.01); *C07D 471/04* (2013.01)

(58) Field of Classification Search
CPC ............................... A61K 35/17; A61P 35/00
See application file for complete search history.

(56) References Cited

U.S. PATENT DOCUMENTS

| | | |
|---|---|---|
| 5,656,644 A | 8/1997 | Adams et al. |
| 5,686,455 A | 11/1997 | Adams et al. |
| 5,916,891 A | 6/1999 | Adams et al. |
| 6,235,760 B1 | 5/2001 | Feuerstein |
| 6,288,089 B1 | 9/2001 | Zawada et al. |
| 6,514,977 B1 | 2/2003 | Anantanarayan et al. |
| 6,525,059 B1 | 2/2003 | Anantanarayan et al. |
| 6,979,686 B1 | 12/2005 | Naraian et al. |
| 7,153,959 B2 | 12/2006 | Naraian et al. |
| 8,563,549 B2 | 10/2013 | Burger et al. |
| 10,865,384 B2 | 12/2020 | Laco et al. |
| 2012/0022058 A1 | 1/2012 | Arhancet et al. |
| 2013/0040983 A1 | 2/2013 | Vernier et al. |
| 2018/0044316 A1 | 2/2018 | Mobashery et al. |

FOREIGN PATENT DOCUMENTS

| | | |
|---|---|---|
| CN | 103880831 | 6/2014 |
| CN | 103965180 | 8/2014 |
| CN | 104829613 | 8/2015 |

(Continued)

OTHER PUBLICATIONS

Development of potent B-RafV600E inhibitors containing an arylsulfonamide headgroup Stellwagen et al. Bioorg. Med. Chem. Lett. 21 (2011) 4436-4440 (Year: 2011).*

(Continued)

*Primary Examiner* — Jeffrey S Lundgren
*Assistant Examiner* — Eric Tran
(74) *Attorney, Agent, or Firm* — NIXON & VANDERHYE, PC

(57) ABSTRACT

Provided herein are novel C-terminal Srk Kinase (CSK) inhibitors, e.g., having Formula G, I, II, or III. Also provided are methods of preparing the novel CSK inhibitors and method of using the novel CSK inhibitors for treating diseases or disorder such as cancer or for promoting immune response in a subject in need thereof.

Formula G

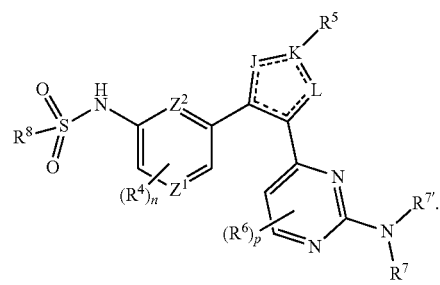

38 Claims, No Drawings

(56) References Cited

FOREIGN PATENT DOCUMENTS

| | | | |
|---|---|---|---|
| CN | 106366080 | | 2/2017 |
| CN | 106366080 A | * | 2/2017 |
| CN | 107987071 | | 5/2018 |
| JP | H0389343 | | 4/1991 |
| WO | 9852940 | | 11/1998 |
| WO | 2009066084 | | 5/2009 |
| WO | 2009137391 | | 11/2009 |
| WO | 2010100127 | | 9/2010 |
| WO | WO-2010104899 A1 | * | 9/2010 ........... C07D 413/04 |
| WO | 2011023773 | | 3/2011 |
| WO | 2011025927 | | 3/2011 |
| WO | 2011038261 | | 3/2011 |
| WO | 2011059610 | | 5/2011 |
| WO | 2011092088 | | 8/2011 |
| WO | 2011161216 | | 12/2011 |
| WO | 2012016993 | | 2/2012 |
| WO | 2012074869 | | 6/2012 |
| WO | 2014182873 | | 11/2014 |
| WO | 2014194127 | | 12/2014 |
| WO | 2015128698 | | 9/2015 |
| WO | 2017146604 | | 8/2017 |
| WO | 2018/055097 | | 3/2018 |

OTHER PUBLICATIONS

International Search Report for PCT/CN2019/125910 dated Mar. 23, 2020, 4 pages.

Written Opinion of the ISA for PCT/CN2019/125910 dated Mar. 23, 2020, 4 pages.

Chakraborty et al., "Insights into the initiation of TCR signaling", Nature Immunology, Sep. 2014, vol. 15, No. 9, pp. 798-807.

Tan et al., "Inhibition of the kinase Csk in thymocytes reveals a requirement for actin remodeling in the initiation of full TCR signaling", Nature Immunology, Dec. 8, 2013, pp. 1-11.

Dustin et al., "TCR signaling: the barrier within", Nature Immunology, Feb. 2014, vol. 15, No. 2, pp. 136-137.

Vang et al., Knockdown of C-terminal Src kinase by siRNAmediated RNA interference augments T cell receptor signaling in mature T cells, European Journal of Immunology, 2004, pp. 2191-2199.

Vikingsson et al. "Simple and cost-effective liquid chromatography-mass spectrometry method to measure dabrafenib quantitatively and six metabolites semi-quantitatively in human plasma", Anal Bioanal Chem, Apr. 20, 2017, 3749-3756, 8 pages.

Rheault et al., "Discovery of Dabrafenib: A Selective Inhibitor of Raf Kinases with Antitumor Activity against B-Raf-Driven Tumors", ACS Medical Chemistry Letters, Mar. 2013, 358-362, 6 pages.

Stellwagen at al., "Development of potent B-RafV600E inhibitors containing an arylsulfonamide headgroup", Bioorganic & Medicinal Chemistry Letters, Aug. 2011, vol. 21, Issue 15, pp. 4436-4440.

Gudmundsson et al., "Synthesis of novel substituted 2-phenylpyrazolopyridines with potent activity against herpesviruses", Bioorganic & Medicinal Chemistry Letters, Jul. 21, 2005, pp. 5346-5361.

* cited by examiner

C-TERMINAL SRC KINASE INHIBITORS

CROSS REFERENCE TO RELATED APPLICATIONS

This application is the U.S. national phase of International Application No. PCT/CN2019/125910 filed Dec. 17, 2019 which designated the U.S. and claims priority to International Patent Application No. PCT/CN2018/121877 filed Dec. 19, 2018, the entire contents of each of which are hereby incorporated by reference.

BACKGROUND OF THE INVENTION

Field of the Invention

In various embodiments, the present invention is generally related to C-terminal Src Kinase (CSK) inhibitors, pharmaceutical compositions comprising the same, synthetic methods therefor, and uses thereof, for example, in immunotherapy.

Background Art

To make an effective immune response, T cells must be able to recognize and respond to their specific antigen. The antigen binding domains in variable chains of T-cell antigen receptor (TCR) allow each lymphocyte to detect the presence of one type of pathogen. However, the information that antigen receptor engagement has occurred also needs to be transduced into the intracellular compartment of the lymphocyte. This function is mediated by invariant accessory proteins that initiate signaling when the receptors bind antigen. Assembly with these accessory proteins is also essential for transport of the receptor to the cell surface. This is especially important for T cells, as an antigen-presenting cell will display on its surface many different peptides from both self and foreign proteins, and the number of peptides: MHC complexes specific for a particular T-cell receptor is likely to be very low.

A key regulator of the TCR signaling cascade is CSK, which is a tyrosine-protein kinase, also known as C-terminal Src kinase. CSK has a related domain architecture to Src, including an SH3 domain, an SH2 domain and a catalytic domain. CSK phosphorylates tyrosine residues located in the C-terminal tails of Src-family kinases (SFKs). CSK is an LCK-inhibitory kinase. In lymphocytes, CSK inhibits T cell activation by phosphorylating LCK at tyrosine 505. To inhibit LCK, CSK is recruited to the plasma membrane via binding to transmembrane proteins or adapter proteins located near the plasma membrane. CSK suppresses signaling by various surface receptors including TCR.

The SRC kinase family member LCK plays an essential role in T-cell receptor signaling during the selection of developing T cells in the thymus and is important for T-cell receptor signaling in naïve T cells and effector T cells. Mice lacking LCK show a complete loss of T-cell development. LCK is constitutively associated with the cytoplasmic domains of CD4 and CD8 and is thought to be the kinase primarily responsible for phosphorylation of the ITAMs (Immunoreceptor tyrosine-based activation motif) of the T-cell receptor. Evidence suggests that binding of the co-receptor to the peptide: MHC complex that binds the T-cell receptor enhances the recruitment of LCK to the engaged T-cell receptor, leading to more efficient phosphorylation of the T-cell receptor ITAMs.

Only active LCK can phosphorylate ITAMs in the signaling chains of the associated T-cell receptor. Full activation of LCK catalytic activity requires autophosphorylation on the activation loop in the kinase domain. Rephosphorylation of the carboxy-terminal tyrosine by the C-terminal Src kinase (CSK) returns LCK to the inactive state.

Taken together, CSK and LCK play important role in the regulation of immune response. Co-clustering TCR and LCK or detaching CSK from the membrane can trigger TCR phosphorylation. Therefore, a selective CSK inhibitor will enhance TCR phosphorylation and improve effectiveness of weak tumor antigens and can overcome the inhibitory activity of checkpoint blockade.

BRIEF SUMMARY OF THE INVENTION

In various embodiments, the present invention provides novel compounds as kinase inhibitors, especially, CSK inhibitors, pharmaceutical compositions comprising the compounds, methods of preparing the compounds, and methods of using the compounds, for example, for the treatment of a disease or disorder, such as cancer, or for promoting immune responses, such as in cancer immunotherapy or a cell therapy.

In some embodiments, the present disclosure provides a compound of Formula G, or a pharmaceutically acceptable salt thereof:

Formula G

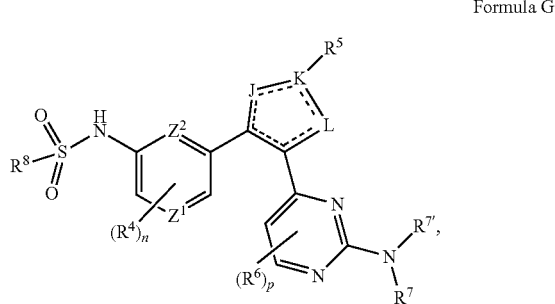

wherein the variables are defined herein.

In more specific embodiments, the present disclosure provides novel compounds having Formula I, II, or III, or pharmaceutically acceptable salts thereof, with the respective variables defined herein.

Formula I

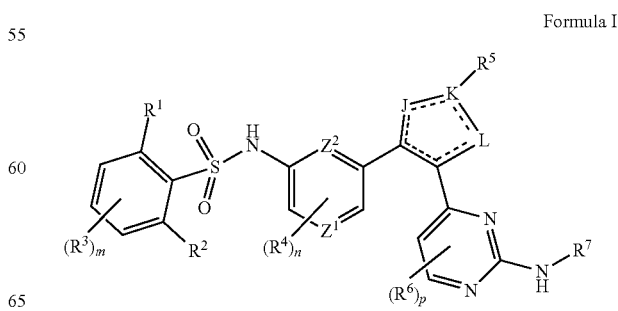

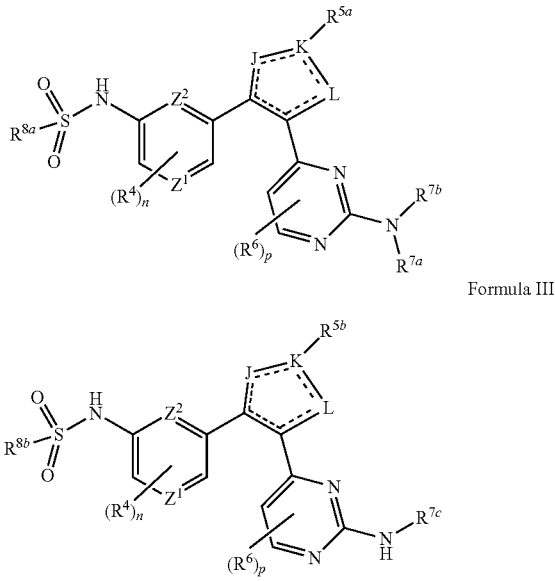

Formula II

Formula III

In some specific embodiments, the compound can have a formula according to Formula IA-IE, IIA-IIE, IIIA-IIIE, or E1-E6. In some embodiments, the compound can also be any one of compounds 1-189.

Certain embodiments of the present disclosure are directed to a pharmaceutical composition comprising one or more of the compounds of the present disclosure, such as a compound of Formula G (e.g., G-1, G-2), a compound of Formula I (e.g., Formula I-A to I-E), a compound of Formula II (e.g., Formula II-A to II-E), a compound of Formula III (e.g., Formula III-A to III-E), a compound of Formula E1 to E6, or any one of compounds 1-189, as defined herein, or a pharmaceutically acceptable salt thereof. The pharmaceutical composition described herein can be formulated for different routes of administration, such as oral administration or parenteral administration.

Certain embodiments of the present disclosure are directed to a method of inhibiting CSK activities in a cell. In some embodiments, the method comprises contacting the cell with an effective amount of a compound of the present disclosure or a pharmaceutical composition described herein. In some embodiments, the present disclosure also provides a method for inhibiting CSK activities in a subject in need thereof. In some embodiments, the method comprises administering to the subject in need thereof a compound of the present disclosure or a pharmaceutical composition described herein. In some embodiments, the subject suffers from cancer or an immune disorder, for example, lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma. In some embodiments, the subject is further administered an immunotherapy (e.g., anti-PD-1 or anti-PD-L1 antibody) or a cell therapy (e.g., CAR-T cell therapy).

Certain embodiments of the present disclosure are directed to a method of promoting immune response (e.g., promoting TCR-mediated signaling) in a subject in need thereof. In some embodiments, the method comprises administering to the subject in need thereof an effective amount of a compound of the present disclosure or a pharmaceutical composition described herein. In some embodiments, the subject suffers from cancer or an immune disorder, for example, lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma. In some embodiments, the subject is further administered an immunotherapy (e.g., anti-PD-1 or anti-PD-L1 antibody) or a cell therapy (e.g., CAR-T cell therapy).

Certain embodiments of the present disclosure are directed to a method of treating a disease or disorder, such as cancer. In some embodiments, the method comprises administering to the subject in need thereof a therapeutically effective amount of a compound of the present disclosure or a pharmaceutical composition described herein. In some embodiments, the cancer is lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma. In some embodiments, the subject is further administered an immunotherapy (e.g., anti-PD-1 or anti-PD-L1 antibody) or a cell therapy (e.g., CAR-T cell therapy).

It is to be understood that both the foregoing summary and the following detailed description are exemplary and explanatory only, and are not restrictive of the invention herein.

DETAILED DESCRIPTION OF THE INVENTION

The present disclosure generally relates to kinase inhibitors, especially novel CSK inhibitors, pharmaceutical compositions comprising the kinase inhibitors, and methods of using the kinase inhibitors, such as for inhibiting CSK or treating cancer. Typically, the kinase inhibitors herein can be characterized as a selective CSK inhibitor, which preferentially inhibits CSK activities over LCK activities. Without wishing to be bound by theories, it is believed that a selective CSK inhibitor can enhance TCR phosphorylation and therefore promote TCR-mediated signaling. In some embodiments, the CSK inhibitors herein can improve the effectiveness of cancer immunotherapy, for example, by enhancing the signals from weak tumor antigens and/or overcoming the inhibitory activity of checkpoint blockade.

Compounds

The kinase inhibitors described herein generally contain a sulfonamide unit. Typically, the sulfonamide compounds are aromatic sulfonic acid derivatives; although in some cases, non-aromatic sulfonic acid derivatives are also useful. The sulfonamide compounds also generally have an aminopyrimidine at the distal end of the molecule. Compounds having similar arrangements of an aminopyrimidine unit and sulfonamide unit were described, for example, in WO2009/137391, WO2014/194127, and WO2011/023773. Dabrafenib, a BRAF inhibitor, also has an aminopyrimidine unit connected to a sulfonamide unit. As detailed herein, the novel kinase inhibitors herein are structurally distinct from existing sulfonamide compounds in various aspects. Further, in various embodiments, this disclosure first shows that the various sulfonamide compounds herein can be potent CSK inhibitors and can inhibit CSK selectively over LCK, in some cases with a selectivity over 2,000-fold.

Formula G

In some embodiments, the kinase inhibitor has a general Formula G, or a pharmaceutically acceptable salt thereof:

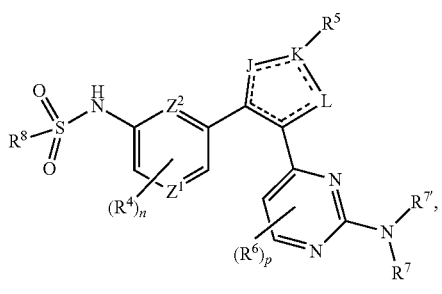

Formula G wherein:
- $R^4$ at each occurrence is independently a halogen, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- n is 0, 1, or 2,
- $Z^1$ and $Z^2$ are independently N or $CR^{100}$;
- wherein $R^{100}$ is hydrogen, halogen, —OH, —CN, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- J and L are each independently O, S, $CR^{101}$, or $NR^{102}$;
- wherein $R^{101}$ is hydrogen, halogen, —OH, —CN, an optionally substituted $C_{1-6}$ alkyl, an optionally substituted $C_{3-6}$ cycloalkyl, an optionally substituted $C_{1-6}$, alkoxy, or an optionally substituted $C_{3-6}$ cycloalkoxy;
- $R^{102}$ is lone pair, hydrogen, —OH, —CN, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- K is C or N;
- provided that at most one of J and L is O or S, and if J or L is O or S, then K is not N;
- $R^5$ is —$NR^{103}R^{103a}$, an optionally substituted $C_{1-6}$ alkyl, an optionally substituted $C_{3-6}$ cycloalkyl, an optionally substituted aryl, an optionally substituted heteroaryl, or an optionally substituted heterocyclyl; wherein $R^{103}$ and $R^{103a}$ are independently hydrogen, a nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl;
- or $R^5$, K, and one of J and L form an optionally substituted heterocyclic or heteroaromatic ring;
- $R^6$ at each occurrence is independently a halogen, cyano, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- p is 0, 1, or 2,
- $R^7$ and $R^{7'}$ are each independently hydrogen, a nitrogen protecting group, an optionally substituted $C_{1-6}$ alkyl, an optionally substituted $C_{3-6}$ cycloalkyl, an optionally substituted aryl, an optionally substituted heteroaryl, or an optionally substituted heterocyclyl; and
- $R^8$ is an optionally substituted $C_{1-6}$ alkyl, —$NR^{200}R^{201}$, an optionally substituted $C_{3-6}$ cycloalkyl, an optionally substituted aryl, an optionally substituted heteroaryl, or an optionally substituted heterocyclyl, wherein $R^{200}$ and $R^{201}$ are independently hydrogen, a nitrogen protecting group, an optionally substituted $C_{1-6}$ alkyl, an optionally substituted $C_{3-6}$ cycloalkyl, an optionally substituted aryl, an optionally substituted heteroaryl, or an optionally substituted heterocyclyl.

The dashed line in

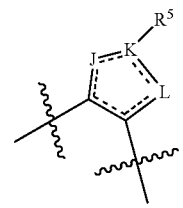

herein should be understood as a single bond (as valence permits) or non-exist according to normal usage in the art. For example, the connection between J and K can be a double bond (as valence permits) or a single bond. As used herein, the

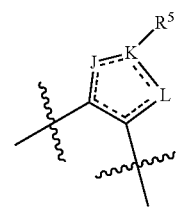

unit should also be understood as containing two double bonds and at least one ring heteroatom (e.g., O, N, S), in other words, at least one of J and L is not $CR^{101}$ or K is not C.

In some embodiments, the compounds of Formula G have either or both of the following features:

1) $R^8$ is not

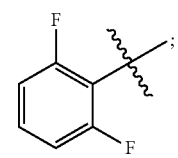 [SMILES: *c1c(F)cccc1F]

2) $R^5$ is an optionally substituted aryl, or an optionally substituted heteroaryl, such as 5-6 membered heteroaryl, or $R^5$, K, and one of J and L form an optionally substituted heterocyclic or heteroaromatic ring.

In some embodiments, the compounds of Formula G have any one of the following features 1), 2) or 3), or the combination of 1) and 2), or 1) and 3):

1) $R^8$ is

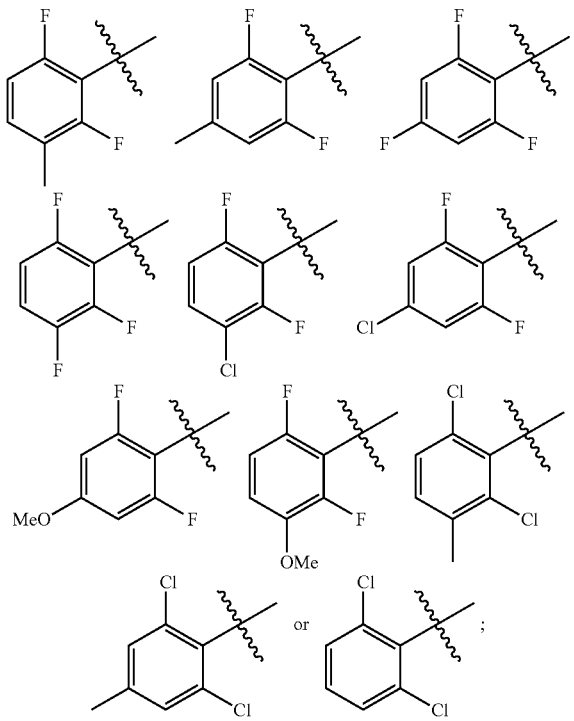

2) $R^5$ is

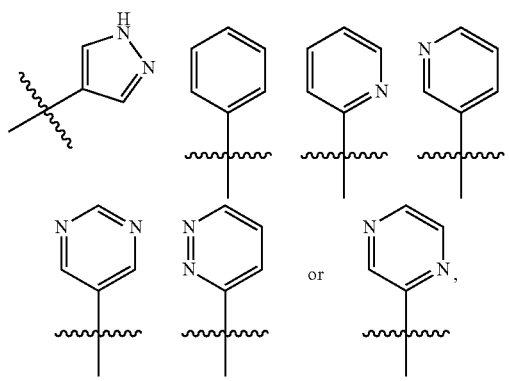

each of which is optionally substituted, e.g., as defined herein;

3)

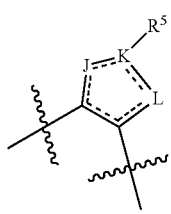

in Formula G is

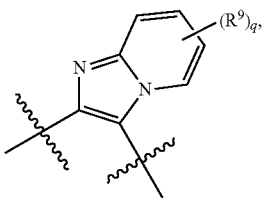

wherein $R^9$ and q are defined herein.

Typically, the compounds of Formula G have the following features: at least one of $R^7$ and $R^{7'}$ is hydrogen; n is 0; p is 0; and $Z^1$ and $Z^2$ are independently $CR^{100}$.

Certain embodiments of the present disclosure are directed to compounds having certain characteristic $R^8$ groups.

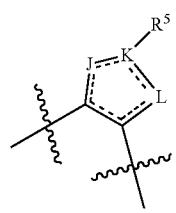

units, or a combination thereof. In more specific embodiments, the present disclosure provides novel compounds having Formula I, II, or III, with the respective variables defined herein. It should be noted that any of the definitions of the variables for Formula I, II, or III, including their respective sub-formulae, are also applicable to the corresponding variables in Formula G and its sub-formulae, unless defined otherwise. It should also be noted that any of the preferred definitions of the variables for Formula I, II, or III, including their respective sub-formulae, can also be the preferred definitions of the corresponding variables in Formula G and its sub-formulae, unless defined otherwise.

Formula I

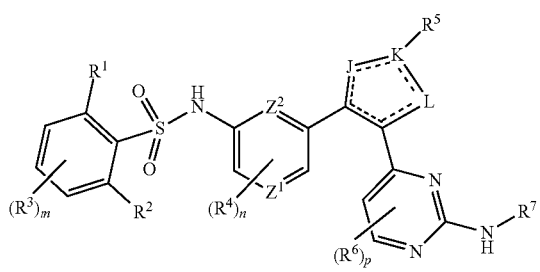

Formula II

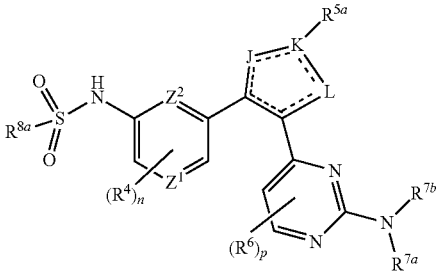

Formula III

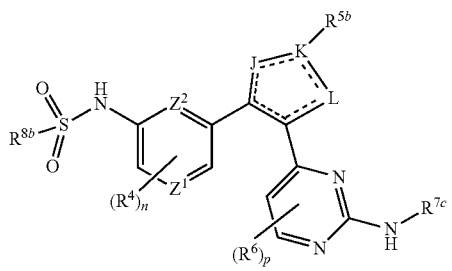

Formula I

In some embodiments, the present disclosure provides a compound of Formula I, or a pharmaceutically acceptable salt thereof:

Formula I

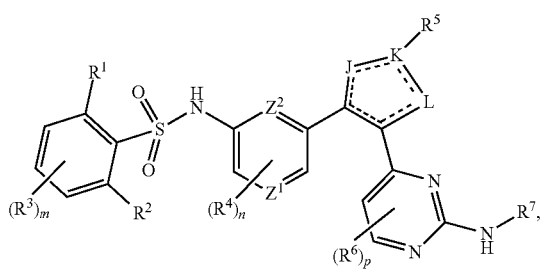

wherein: $R^1$ and $R^2$ are independently a halogen, a $C_{1-4}$ alkyl, or a $C_{1-4}$ alkoxy; $R^3$ at each occurrence is independently a halogen, cyano, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;

m is 0, 1 or 2, provided that when $R^1$ and $R^2$ are both F, then m is not 0;

and $R^4$, n, $Z^1$, $Z^2$, J, K, L, $R^5$, $R^6$, p, and $R^7$ are as defined for Formula G.

In some embodiments, $R^1$ and $R^2$ in Formula I can each independently be F, Cl, methyl, or methoxy. For example, in some embodiments, one or both of $R^1$ and $R^2$ can be Cl. In some embodiments, both $R^1$ and $R^2$ can also be F, with the proviso that m is 1 or 2, preferably m is 1.

The presence of $R^3$ group can sometimes be beneficial in conferring potency and/or selectivity for compounds having Formula I. Accordingly, in some embodiments of Formula I, one $R^3$ group can be present, i.e., m is 1. In such embodiments, the $R^3$ group can be attached to a position, preferably, ortho to $R^1$ or $R^2$; although in some embodiments, the $R^3$ group can also be attached to the meta position to $R^1$ or $R^2$. In some preferred embodiments, m is 1, and $R^3$ can be F, Cl, $C_{1-4}$ alkyl, $C_{3-6}$ cycloalkyl, $C_{1-4}$ alkoxy, or $C_{3-6}$ cycloalkoxy, more preferably, $R^3$ can be F, Cl, methyl or methoxy.

In some specific embodiments, the structural unit

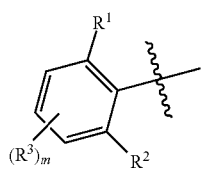

in Formula I can be:

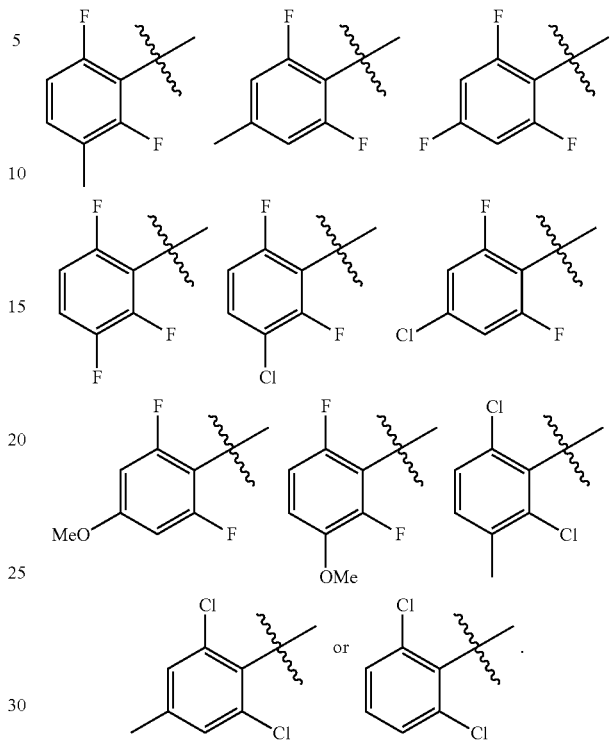

In some preferred embodiments, the structural unit

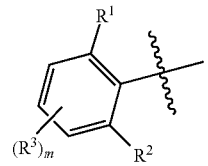

in Formula I can be:

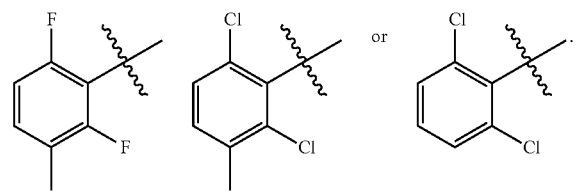

In some preferred embodiments, the structural unit

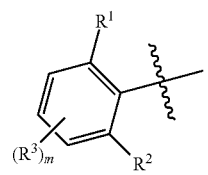

in Formula I can be

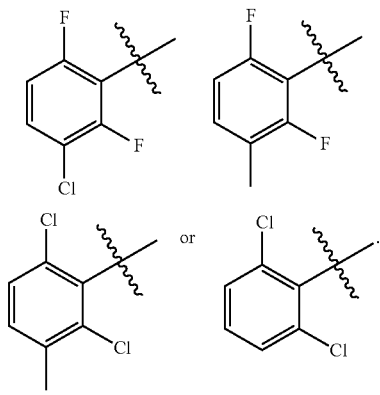

Various groups can be used for the structural unit

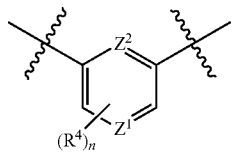

in Formula I. Typically, this structural unit is a phenyl or pyridyl derived radical, preferably, phenyl derived. In some embodiments, both $Z^1$ and $Z^2$ are independently $CR^{100}$, wherein $R^{100}$ at each occurrence is independently hydrogen, F, methyl, or methoxy. In some embodiments, one of $Z^1$ and $Z^2$ is N and the other of $Z^1$ and $Z^2$ is $CR^{100}$, wherein $R^{100}$ is hydrogen, F, methyl, or methoxy. Although not prohibited, $R^4$ is generally not present, i.e., n is 0. In some embodiments, one or two independently selected $R^4$ groups can be attached to the two open positions (positions that are not $Z^1$ or $Z^2$), i.e., n can be 1 or 2 in the structural unit

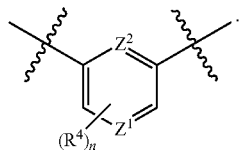

When present, $R^4$ is preferably F, methyl, or methoxy. In some specific embodiments, the structural unit

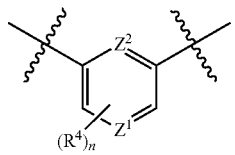

in Formula I can be

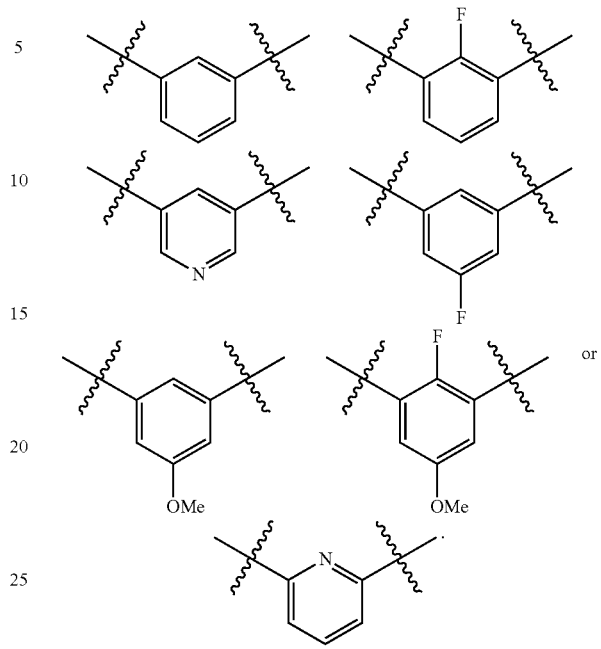

In some preferred embodiments, the structural unit

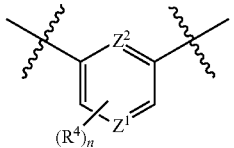

in Formula I can be

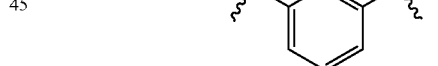

In some embodiments, the

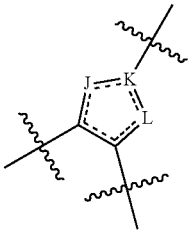

unit in Formula I can be various 5-membered heteroaromatic rings, including for example, thiazole, oxazole, imidazole, pyrazole rings. In some embodiments, $R^5$, K, and one of J and L can form an optionally substituted heterocyclic or heteroaromatic ring, such as an optionally substituted imidazopyridine.

In some embodiments, the

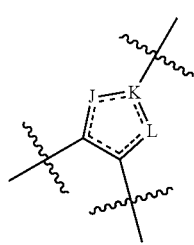

unit in Formula I can be

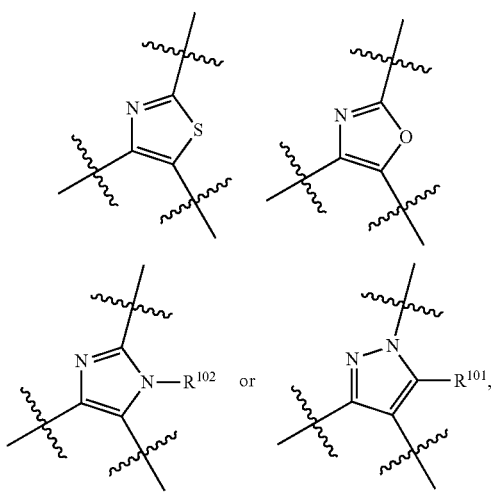

wherein $R^{101}$ and $R^{102}$ can each be hydrogen, —OH, $C_{1-4}$ alkyl, $C_{1-4}$ haloalkyl, cyclopropyl, or $C_{1-4}$ haloalkoxy. For example, in some specific embodiments, the

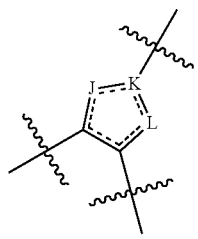

unit in Formula I can be

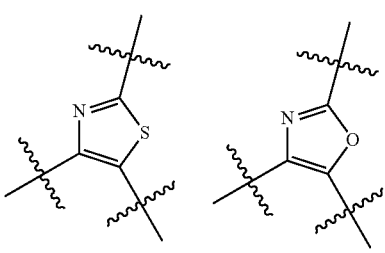

-continued

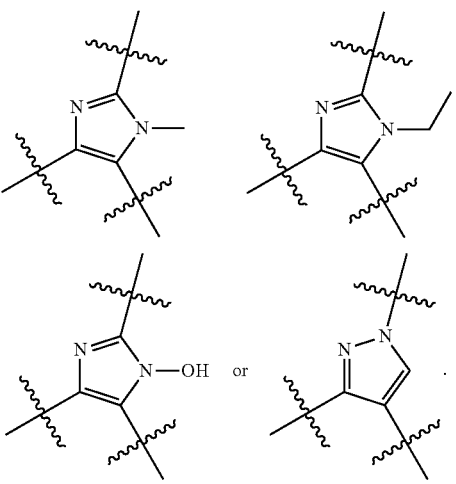

In preferred embodiments, the variable J in any of the

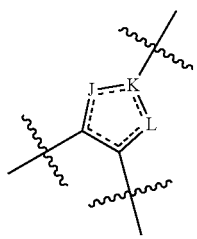

unit described as suitable for Formula I can be $NR^{102}$, and $R^{102}$ is lone pair, typically, the nitrogen lone pair is not explicitly drawn, see, e.g.,

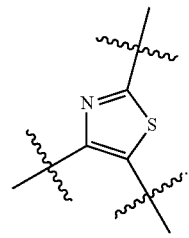 [SMILES: *c1nc(*)c(*)s1]

For example, in some embodiments, the compounds of Formula I can be a compound of Formula I-A to I-E Formula I-A

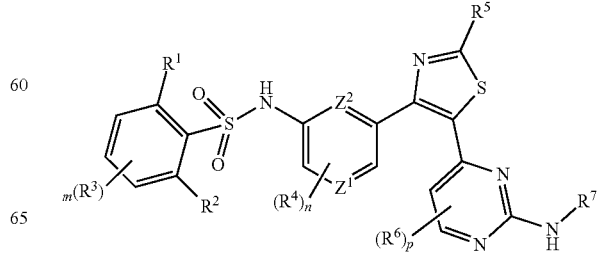

-continued

Formula I-B

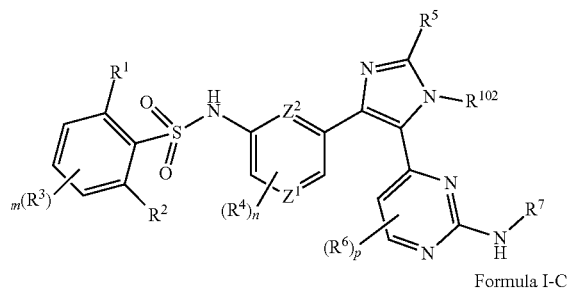

Formula I-C

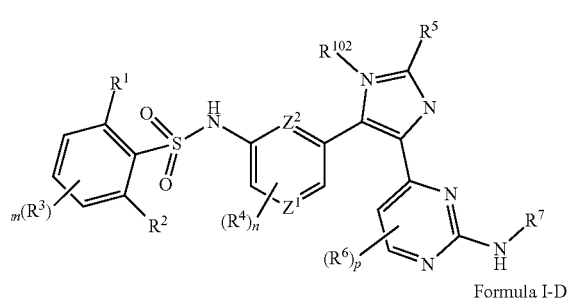

Formula I-D

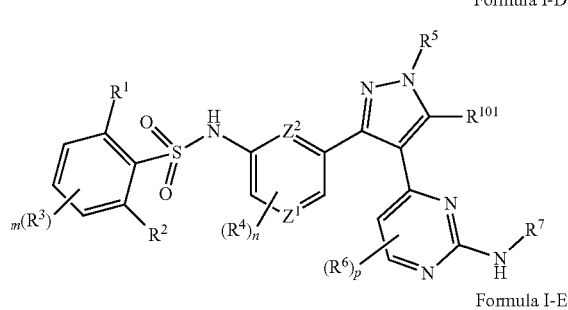

Formula I-E

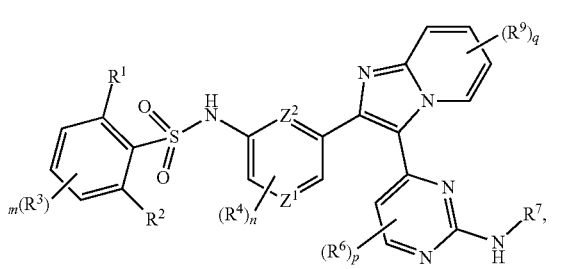

wherein $R^1$, $R^2$, $R^3$, m, $R^4$, n, $Z^1$, $Z^2$, $R^6$, p, $R^5$, $R^7$, $R^9$, q, $R^{101}$, and $R^{102}$ are as defined and preferred herein. It should be clear to those skilled in the art that in cases where the

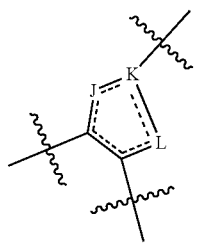

unit is an imidazole ring with no nitrogen substitutions, i.e., both J and L are $NR^{102}$, and one of $R^{102}$ is hydrogen and the other is lone pair, the compounds can exist as a mixture with their tautomers. The present disclosure should not be interpreted as excluding any of such tautomers or mixtures with such tautomers.

Various groups are suited to be $R^5$ for Formula I (e.g., Formula I-A to I-D). In some embodiments, $R^5$ can be —$NR^{103}R^{103a}$, wherein $R^{103}$ and $R^{103a}$ are independently hydrogen, a nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl. In some embodiments, $R^5$ can be —$NR^{103}R^{103a}$, wherein $R^{103}$ and $R^{103a}$ can be independently hydrogen, a nitrogen protecting group, or a $C_{1-4}$ alkyl optionally substituted with 1-3 fluorines. For example, in some preferred embodiments, $R^5$ can be

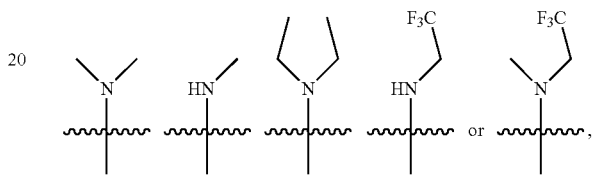

more preferably,

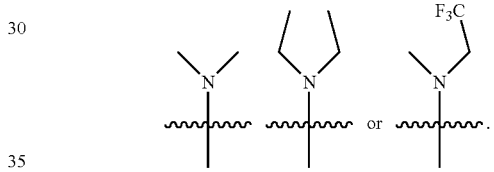

In some embodiments, $R^5$ can be a $C_{1-4}$ alkyl optionally substituted with 1-3 substituents independently selected from F, —OH, $C_{1-4}$alkoxy optionally substituted with 1-3 fluorines, —COOH (or an ester thereof), —$CONH_2$, —CONH($C_{1-4}$ alkyl), and —CON($C_{1-4}$alkyl)($C_{1-4}$ alkyl). For example, in some embodiments, $R^5$ can be isopropyl or tert-butyl. In some embodiments, $R^5$ can be

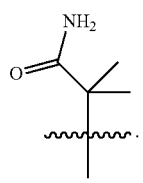 [SMILES: *C(C)(C)C(N)=O]

In some embodiments, $R^5$ can be an optionally substituted $C_{3-6}$ cycloalkyl. For example, in some embodiments, $R^5$ can be cyclohexyl.

In some embodiments, optionally substituted heterocyclyl groups can also be suitable $R^5$. For example, in some embodiments, $R^5$ can be an optionally substituted 4-8 membered heterocylic ring, such as a 4, 5, or 6 membered heterocyclic ring, with 1 or 2 ring heteroatoms independently selected from N and O, which can be optionally substituted with one or more (e.g., 1 or 2) substituents independently selected from F, —OH, $C_{1-4}$ alkyl, and $C_{1-4}$alkoxy. In some embodiments, $R^5$ can be azetidinyl, pyrrolidinyl, piperidinyl, morpholinyl, pyrrolidonyl, each optionally substituted with 1 or 2 substituents independently selected from F and $C_{1-4}$ alkyl. In some specific embodiments, $R^5$ can be

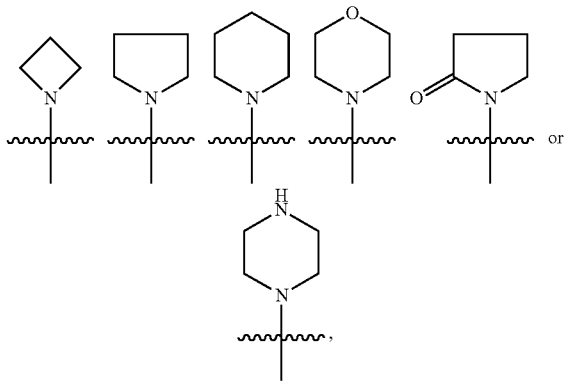

each optionally substituted with 1 or 2 substituents independently selected from F and $C_{1-4}$ alkyl. In some specific embodiments, $R^5$ can be

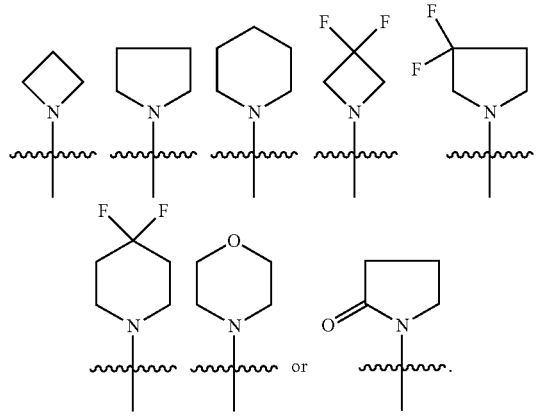

In some preferred embodiments, $R^5$ can be

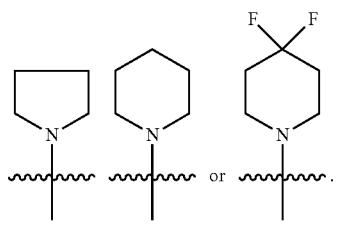

Various optionally substituted aryl and optionally substituted heteroaryl groups are also suitable $R^5$ groups. In some embodiments, $R^5$ can be an optionally substituted phenyl or an optionally substituted 5 or 6 membered heteroaryl. In some embodiments, $R^5$ can be an optionally substituted phenyl, an optionally substituted pyridyl, an optionally substituted pyridazinyl, an optionally substituted pyrimidinyl, an optionally substituted pyrazinyl, or an optionally substituted pyrazolyl. For example, in some embodiments, $R^5$ can be phenyl, pyridyl, pyridazinyl, pyrimidinyl, pyrazinyl, or pyrazolyl, each of which is optionally substituted with one or more (e.g., 1, 2, or 3) substituents independently selected from halogen; —OH; cyano; $C_{1-4}$ alkyl optionally substituted with 1-3 substituents independently selected from $C_{1-4}$ alkyl, $C_{1-4}$ alkoxy, —OH, and fluorine; $C_{1-4}$ alkoxy optionally substituted with 1-3 substituents independently selected from $C_{1-4}$ alkyl, $C_{1-4}$ alkoxy, —OH, and fluorine; $C_{3-6}$ cycloalkyl optionally substituted with 1-3 substituents independently selected from $C_{1-4}$ alkyl and fluorine; $C_{3-6}$ cycloalkoxy optionally substituted with 1-3 substituents independently selected from $C_{1-4}$ alkyl and fluorine; 4-6 membered heterocyclic ring optionally substituted with 1-3 substituents independently selected from $C_{1-4}$ alkyl and fluorine; —COR$^{104}$; —COOR$^{105}$; —OCOR$^{104a}$; —OCOOR$^{105a}$; —CONR$^{106}$R$^{107}$; —OCONR$^{106a}$R$^{107a}$; and —NR$^{108}$R$^{109}$, wherein R$^{104}$, R$^{104a}$, R$^{105}$, and R$^{105a}$ are independently hydrogen, an optionally substituted $C_{1-6}$ alkyl, an optionally substituted $C_{3-6}$ cycloalkyl, an optionally substituted phenyl, an optionally substituted heteroaryl, or an optionally substituted heterocyclyl, provided that R$^{105a}$ is not hydrogen; and R$^{106}$, R$^{107}$, R$^{106a}$, R$^{107a}$, R$^{108}$, and R$^{109}$ are each independently hydrogen, nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl.

In some embodiments, $R^5$ can be phenyl, pyridyl, pyridazinyl, pyrimidinyl, pyrazinyl, or pyrazolyl, each of which is optionally substituted with 1 or 2 substituents independently selected from F, Cl, —OH, cyano, $C_{1-4}$ alkyl, —CF$_3$, $C_{1-4}$alkoxy, —NH$_2$, —NH($C_{1-4}$ alkyl), —N($C_{1-4}$ alkyl)($C_{1-4}$ alkyl), azetidinyl, and cyclopropyl. As used herein, it should be understood that the two alkyl groups in —N($C_{1-4}$ alkyl)($C_{1-4}$ alkyl) (or other analogous expression) are independently selected. When $R^5$ is a heteroaryl derived group, it should be understood that the connecting point is not limited to a particular position relative to the heteroatoms, for example, in the case of pyridyl, the connecting point can be ortho, meta, or para to the ring nitrogen. In some specific embodiments, $R^5$ can be

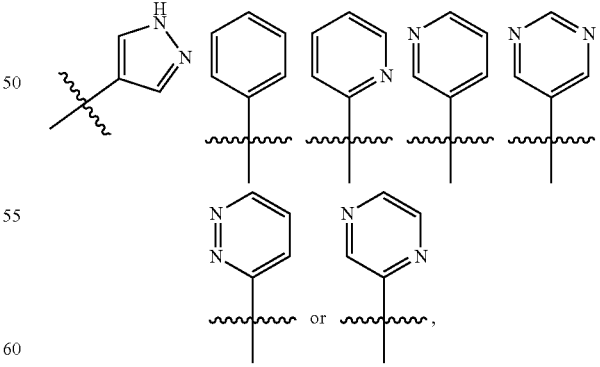

each of which is optionally substituted with 1 or 2 substituents independently selected from F, Cl, —OH, cyano, $C_{1-4}$ alkyl, —CF$_3$, $C_{1-4}$alkoxy, —NH$_2$, —NH($C_{1-4}$ alkyl), —N($C_{1-4}$alkyl)($C_{1-4}$ alkyl), azetidinyl, and cyclopropyl. In some preferred embodiments, $R^5$ can be

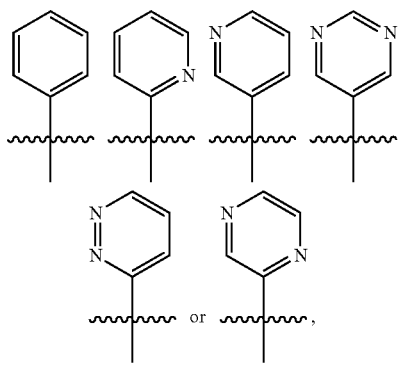

each of which is optionally substituted with 1 or 2 substituents independently selected from F, Cl, —OH, methyl, ethyl, methoxy, ethoxy, —CF$_3$, —NH$_2$, azetidinyl, and cyclopropyl, more preferably, optionally substituted with one substituent selected from F and methyl. Those skilled in the art would understand that when a compound has a hydroxyl group attached to a carbon next to a nitrogen ring atom, the compound may exist predominantly in one or more tautomeric forms. For example, a 2-hydroxyl substituted pyridine may exist predominantly in Form B as shown below

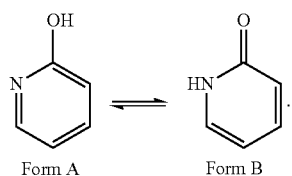 [SMILES: Oc1ccccn1 ; O=c1cccc[nH]1]

Thus, as used herein, a heteroaryl substituted with a hydroxyl group should be understood as encompassing all tautomeric forms and mixtures thereof when possible, e.g., Forms A and B above. When applicable, substitution of a heteroaryl with substituents such as —NH$_2$ or substituted amino group, or thiol etc. should also be understood similarly.

In some specific embodiments, R$^5$ can be

In some embodiments, R$^5$, K, and one of J and L in Formula I can form an optionally substituted heterocyclic or heteroaromatic ring. In some preferred embodiments, R$^5$, K, and one of J and L can form an optionally substituted heteroaromatic ring. For example, in some embodiments,

in Formula I can be an optionally substituted 5,6-bicyclic heteroaryl selected from imidazopyridine, imidazopyrimidine, imidazopyrazine, imidazopyridazine, imidazotriazine, pyrazolopyridine, pyrazolopyrimidine, pyrazolopyridazine, pyrazolopyrazine, pyrazolotriazine, pyrrolopyridine, pyrrolopyrimidine, pyrrolopyridazine, pyrrolopyrazine, and pyrrolotriazine. In some embodiments,

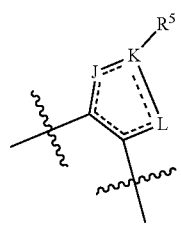

in Formula I can be an optionally substituted imidazopyridine:

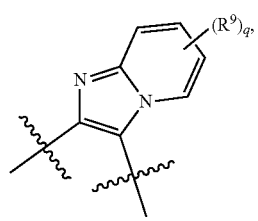

such as shown in Formula I-E, wherein q is 0, 1, or 2, and $R^9$ at each occurrence is independently halogen, an optionally substituted $C_{1-6}$ alkyl, an optionally substituted $C_{3-6}$ cycloalkyl, an optionally substituted $C_{1-6}$ alkoxy, an optionally substituted $C_{3-6}$ cycloalkoxy, an optionally substituted phenyl, an optionally substituted heteroaryl, an optionally substituted heterocyclyl, —OH, cyano, —$COR^{110}$, —$COOR^{111}$, —$CONR^{112}R^{113}$, —$NR^{114}R^{115}$.

wherein $R^{110}$ and $R^{111}$ are independently hydrogen, an optionally substituted $C_{1-6}$ alkyl, an optionally substituted $C_{3-6}$ cycloalkyl, an optionally substituted phenyl, an optionally substituted heteroaryl, or an optionally substituted heterocyclyl; and $R^{112}$, $R^{113}$, $R^{114}$, and $R^{115}$ are each independently hydrogen, nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl.

In some embodiments, q is 0, i.e., the imidazopyridine is not substituted with $R^9$. In some embodiments, q is 1 or 2, preferably 1, and $R^9$ at each occurrence is independently halogen (e.g., F, Cl); —OH; cyano; $C_{1-4}$ alkyl optionally substituted with 1-3 substituents independently selected from $C_{1-4}$ alkyl and fluorine; $C_{1-4}$ alkoxy optionally substituted with 1-3 substituents independently selected from $C_{1-4}$ alkyl and fluorine; $C_{3-6}$ cycloalkyl optionally substituted with 1-3 substituents independently selected from $C_{1-4}$ alkyl and fluorine; $C_{3-6}$ cycloalkoxy optionally substituted with 1-3 substituents independently selected from $C_{1-4}$ alkyl and fluorine; and 4-6 membered heterocyclic ring optionally substituted with 1-3 substituents independently selected from $C_{1-4}$ alkyl and fluorine. In some embodiments, q is 1 or 2, preferably 1, $R^9$ at each occurrence is independently F, Cl, —OH, cyano, $C_{1-4}$ alkyl, $CF_3$, $C_{1-4}$ alkoxy, —$NH_2$, —$NMe_2$, —NHMe, —$NH(C_{2-4}$ alkyl), —$N(C_{1-4}$alkyl)($C_{2-4}$ alkyl), —COOH, —COO($C_{1-4}$ alkyl), —$CONH_2$, —CONH ($C_{1-4}$ alkyl), —CON($C_{1-4}$ alkyl)($C_{1-4}$ alkyl), azetidinyl, or cyclopropyl. In some preferred embodiments, q is 1 or 2, preferably 1, $R^9$ at each occurrence is independently F, Cl, methyl, ethyl, methoxy, ethoxy, isopropoxy, —COOH, —$CONH_2$, or $CF_3$.

In some specific embodiments,

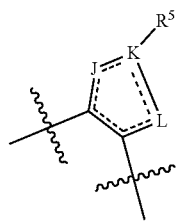

in Formula I (e.g., Formula I-E) can be

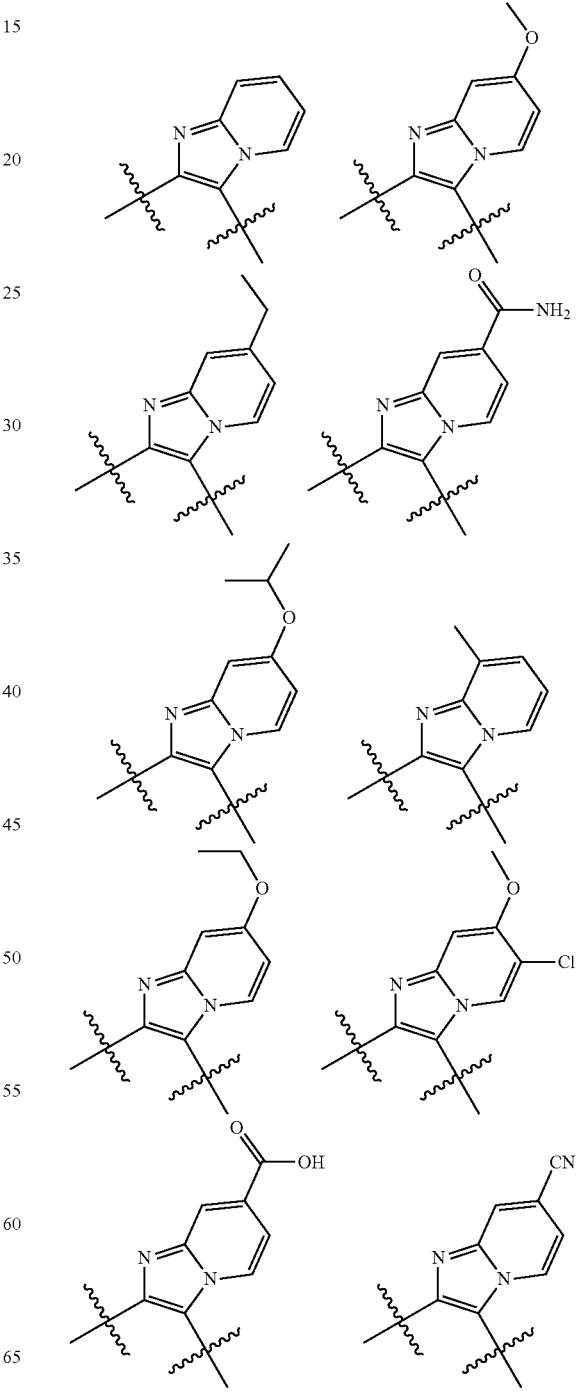

-continued

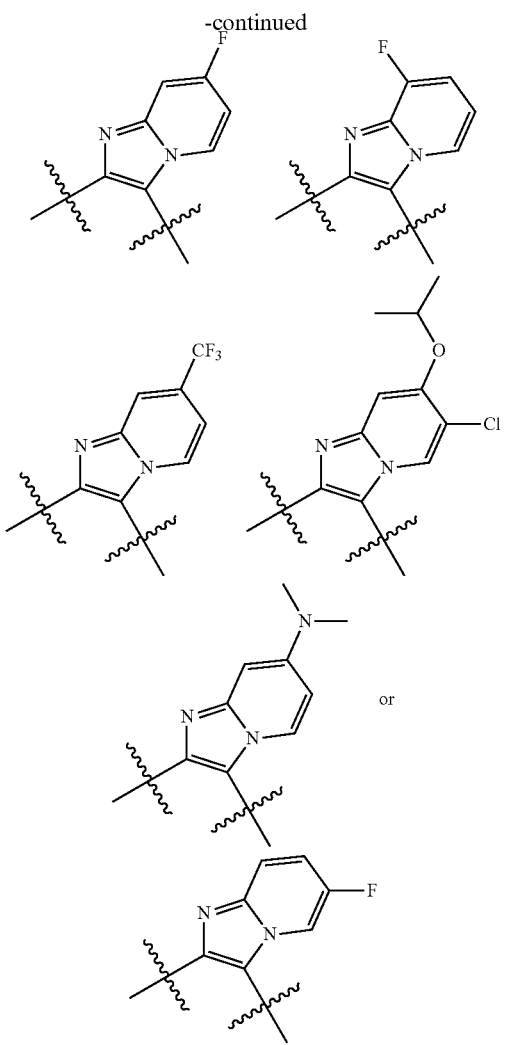

In some preferred embodiments,

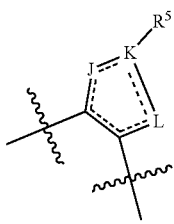

in Formula I (e.g., Formula I-E) can be

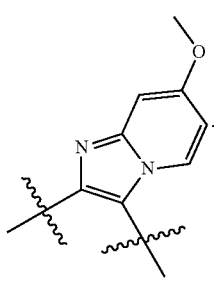 [SMILES: *c1nc2cc(OC)ccn2c1*]

Various groups are suitable for $R^7$ in Formula I (e.g., Formula I-A to I-E). In some embodiments, $R^7$ in Formula I can be hydrogen, nitrogen protecting group, an optionally substituted $C_{1-6}$ alkyl, an optionally substituted $C_{3-6}$ cycloalkyl, an optionally substituted phenyl, an optionally substituted 5 or 6-membered heteroaryl, or an optionally substituted 4-7 membered heterocyclyl.

In some embodiments, $R^7$ can be a $C_{1-6}$ alkyl, preferably a $C_{1-4}$ alkyl, which is optionally substituted with one to three substituents independently selected from —OH; halogen; $C_{1-4}$ alkyl optionally substituted with 1-3 substituents independently selected from $C_{1-4}$ alkyl, $C_{1-4}$alkoxy, —OH, —NH$_2$, and fluorine; $C_{3-6}$ cycloalkyl optionally substituted with 1-3 substituents independently selected from $C_{1-4}$ alkyl and fluorine; $C_{1-4}$alkoxy optionally substituted with 1-3 substituents independently selected from $C_{1-4}$ alkyl, $C_{1-4}$alkoxy, —OH, —NH$_2$, and fluorine; $C_{3-6}$ cycloalkoxy optionally substituted with 1-3 substituents independently selected from $C_{1-4}$ alkyl and fluorine; —NR$^{116}$R$^{117}$; —CONR$^{116a}$R$^{117a}$; —OCONR$^{116b}$R$^{117b}$; —SO$_2$NR$^{116c}$R$^{117c}$; —OSO$_2$NR$^{116d}$R$^{117d}$; —COR$^{118}$; —SO$_2$R$^{119}$; —OCOR$^{118a}$; and —OSO$_2$R$^{119a}$, wherein $R^{116}$ and $R^{117}$ are each independently hydrogen, a nitrogen protecting group, —COR$^{118b}$, —SO$_2$R$^{119b}$, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl, or $R^{116}$ and $R^{117}$ together with the atoms they are bound to form an optionally substituted 4-7 membered heterocyclyl; wherein $R^{118}$, $R^{118a}$, $R^{118b}$, $R^{119}$, $R^{119a}$, and $R^{119b}$ are each independently hydrogen; $C_{1-4}$ alkyl optionally substituted with 1-3 substituents independently selected from $C_{1-4}$ alkyl, $C_{1-4}$ alkoxy, —OH, —NH$_2$, and fluorine; —OH; —NR$^{120}$R$^{121}$; $C_{3-6}$ cycloalkyl optionally substituted with 1-3 substituents independently selected from $C_{1-4}$ alkyl and fluorine; $C_{1-4}$ alkoxy optionally substituted with 1-3 substituents independently selected from $C_{1-4}$ alkyl, $C_{1-4}$ alkoxy, —OH, —NH$_2$, and fluorine; $C_{3-6}$ cycloalkoxy optionally substituted with 1-3 substituents independently selected from $C_{1-4}$ alkyl and fluorine; an optionally substituted phenyl, an optionally substituted 5 or 6 membered heteroaryl; or an optionally substituted 4-7 membered heterocyclyl;

wherein $R^{116a}$, $R^{116b}$, $R^{116c}$, $R^{116d}$, $R^{117a}$, $R^{117b}$, $R^{117c}$, $R^{117d}$, $R^{120}$ and $R^{121}$ are each independently hydrogen; nitrogen protecting group; $C_{1-4}$ alkyl optionally substituted with 1-3 substituents independently selected from $C_{1-4}$ alkyl, $C_{1-4}$ alkoxy, —OH, —NH$_2$, and fluorine; or $C_{3-6}$ cycloalkyl optionally substituted with 1-3 substituents independently selected from $C_{1-4}$ alkyl and fluorine; or $R^{116a}$ and $R^{117a}$, $R^{116b}$ and $R^{117b}$, $R^{116c}$ and $R^{117c}$, $R^{116d}$ and $R^{117d}$, or $R^{120}$ and $R^{121}$, together with the atoms they are bound to form an optionally substituted 4-7 membered heterocyclyl.

In some embodiments, $R^7$ is a $C_{1-6}$, alkyl, preferably a $C_{1-4}$ alkyl, substituted with one substituent —NR$^{116}$R$^{117}$, wherein one of $R^{116}$ and $R^{117}$ is hydrogen, and the other of $R^{116}$ and $R^{117}$ is $C_{1-4}$ alkyl optionally substituted with 1-3 substituents independently selected from $C_{1-4}$ alkyl, $C_{1-4}$alkoxy, —OH, —NH$_2$, and fluorine; $C_{3-6}$ cycloalkyl optionally substituted with 1-3 substituents independently selected from $C_{1-4}$ alkyl and fluorine; or —COR$^{118b}$, wherein $R^{118b}$ is $C_{1-4}$ alkyl optionally substituted with 1-3 substituents independently selected from $C_{1-4}$ alkyl, $C_{1-4}$ alkoxy, —OH, —NH$_2$, and fluorine; —OH;

—NR$^{120}$R$^{121}$; C$_{3-6}$ cycloalkyl optionally substituted with 1-3 substituents independently selected from C$_{1-4}$ alkyl and fluorine; C$_{1-4}$ alkoxy optionally substituted with 1-3 substituents independently selected from C$_{1-4}$ alkyl, C$_{1-4}$ alkoxy, —OH, —NH$_2$, and fluorine; or C$_{3-6}$ cycloalkoxy optionally substituted with 1-3 substituents independently selected from C$_{1-4}$ alkyl and fluorine. In some embodiments, one of R$^{116}$ and R$^{117}$ is hydrogen, and the other of R$^{116}$ and R$^{117}$ is —CO(C$_{1-4}$ alkyl), —COO(C$_{1-4}$ alkyl), —CONH$_2$, —CON(C$_{1-4}$alkyl)(C$_{1-4}$ alkyl) or —CONH(C$_{1-4}$ alkyl).

In some embodiments, R$^7$ is a C$_{3-6}$ cycloalkyl (e.g., cyclopropyl) optionally substituted with 1-3 substituents independently selected from methyl and fluorine. In some embodiments, R$^7$ is cyclopropyl.

In some embodiments, R$^7$ is piperidinyl, phenyl, pyridyl, or pyrimidinyl, each of which is optionally substituted with one or more (e.g., one to three) substituents independently selected from halogen; —OH; C$_{1-4}$ alkyl; 4-6 membered heterocyclyl; C$_{3-6}$ cycloalkyl; C$_{1-4}$ alkanoyl; C$_{3-6}$ cycloalkanoyl; C$_{1-4}$ alkoxy; and C$_{3-6}$ cycloalkoxy; wherein each of the alkyl, heterocyclyl, cycloalkyl, alkanoyl, cycloalkanoyl, alkoxy, and cycloalkoxy, is optionally substituted with 1-3 substituents independently selected from C$_{1-4}$ alkyl and fluorine.

In some specific embodiments, R$^7$ is hydrogen, methyl, ethyl, cyclopropyl, isopropyl,

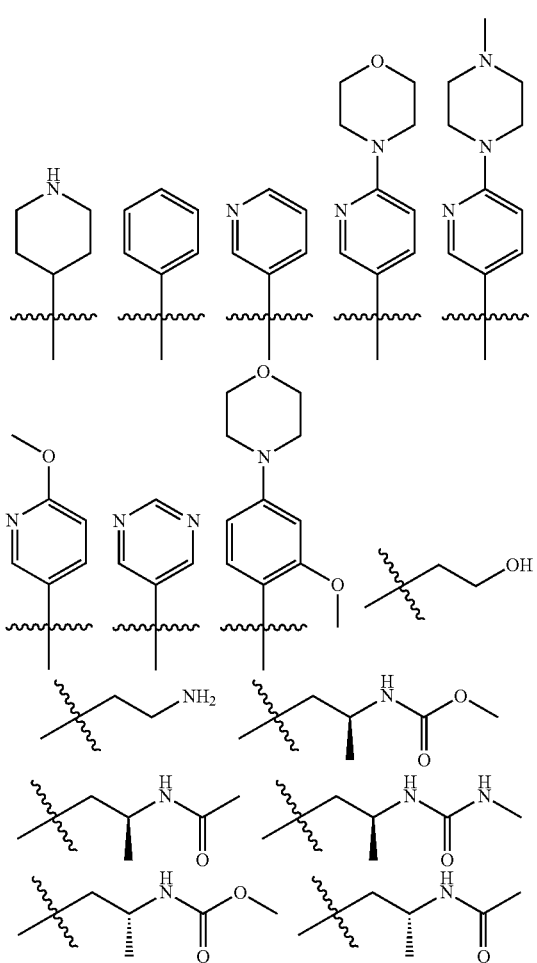

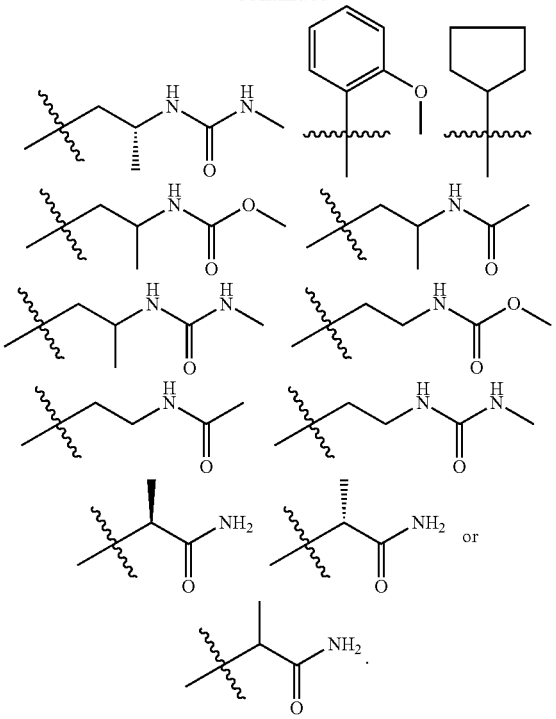

In some preferred embodiments, R$^7$ is hydrogen, methyl, ethyl, cyclopropyl, isopropyl, or

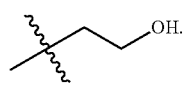 [SMILES: *CCO]

Suitable groups for R$^1$, R$^2$, R$^3$, R$^4$, R$^5$, R$^6$, R$^7$, Z$^1$, Z$^2$, J, K, L, m, n and p in compounds of Formula I (e.g., in I-A to I-E, as applicable) are independently selected. The described embodiments of the present invention can be combined. Such combination is contemplated and within the scope of the present invention. For example, it is contemplated that embodiments for any of R$^1$, R$^2$, R$^3$, R$^4$, R$^5$, R$^6$, R$^7$, Z$^1$, Z$^2$, J, K, L, m, n and p can be combined with embodiments defined for any other of R$^1$, R$^2$, R$^3$, R$^4$, R$^5$, R$^6$, R$^7$, Z$^1$, Z$^2$, J, K, L, m, n and p, as applicable.

Formula II

In some embodiments, the present disclosure provides a compound of Formula II, or a pharmaceutically acceptable salt thereof:

Formula II

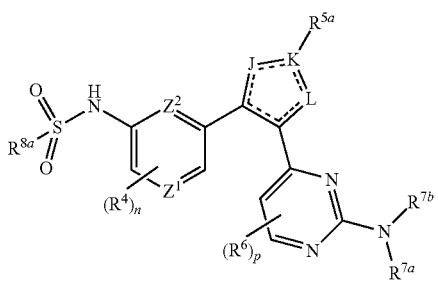

wherein: $R^{5a}$ is an optionally substituted aryl, or an optionally substituted 5-6 membered heteroaryl, or $R^{5a}$, K, and one of J and L form an optionally substituted heterocyclic or heteroaromatic ring;

- $R^{7a}$ and $R^{7b}$ are independently hydrogen, an optionally substituted $C_{1-6}$ alkyl, an optionally substituted $C_{3-6}$ cycloalkyl, an optionally substituted aryl, an optionally substituted heteroaryl, or an optionally substituted heterocyclyl;
- $R^{8a}$ is an optionally substituted aryl or an optionally substituted heteroaryl,
- and $R^4$, n, $Z^1$, $Z^2$, J, K, L, $R^6$, and p are as defined for Formula G.

Typically, compounds of Formula II have aromatic rings as both $R^{5a}$ and $R^{8a}$. $R^{8a}$ in Formula II is preferably an optionally substituted phenyl. In some embodiments, $R^{8a}$ can be phenyl, optionally substituted with 1-3 substituents independently selected from $C_{1-4}$ alkyl, $C_{1-4}$ alkoxy, $C_{3-6}$ cycloalkyl, $C_{3-6}$ cycloalkoxy, and 4-6 membered heterocyclyl, each of which is optionally substituted with 1-3 substituents independently selected from $C_{1-4}$ alkyl and fluorine, halogen, —OH, and cyano. In some embodiments, $R^{8a}$ is phenyl, optionally substituted with 1-3 substituents independently selected from F, Cl, methyl, and methoxy. Preferably, the 2'- and 6'-positions of the phenyl are both substituted. In some embodiments, two adjacent substituents on the phenyl ring can also form an optionally substituted aromatic or non-aromatic ring system, such as a 5 or 6 membered heteroaromatic ring (e.g., oxazole, isoxazole, etc.) or a 5 or 6 membered heterocyclic ring (e.g., pyrrolidine or pyrrolidinone, etc.).

In some specific embodiments, $R^{8a}$ can be

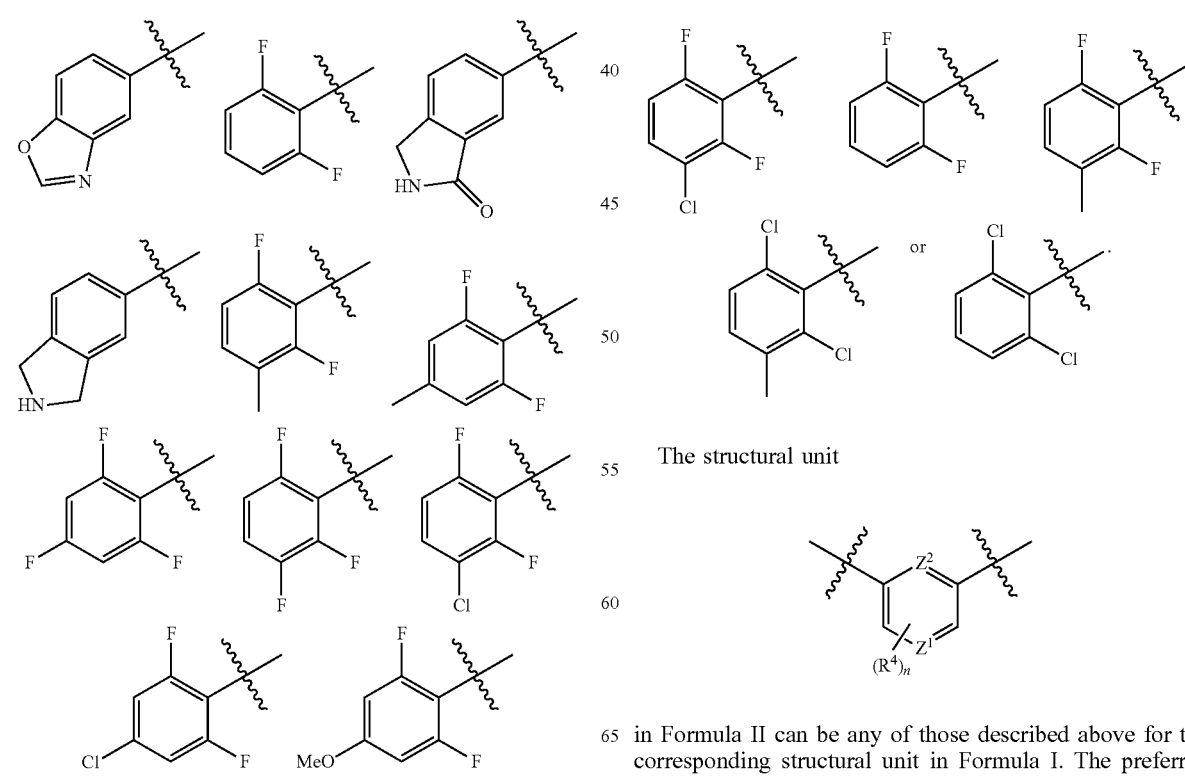

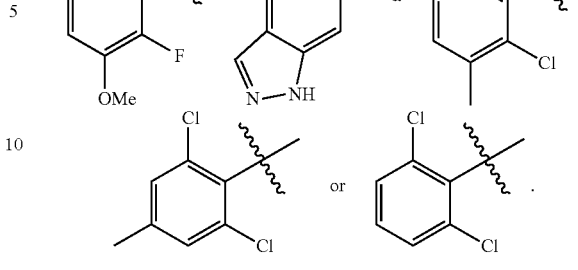

In some preferred embodiments, $R^{8a}$ can be

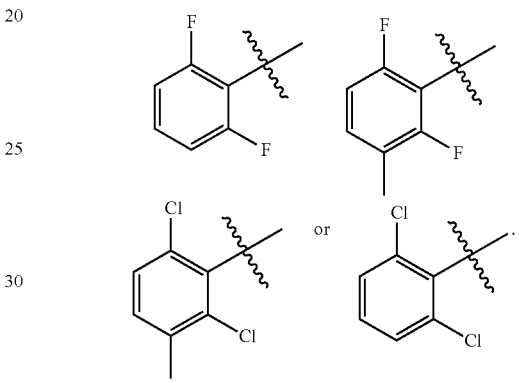

In some preferred embodiments, $R^{8a}$ can be

The structural unit in Formula II can be any of those described above for the corresponding structural unit in Formula I. The preferred structure in Formula II can also be those described as preferred for the corresponding structural unit in Formula I. For example, in some preferred embodiments, the structural unit

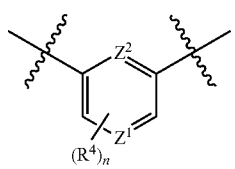

in Formula II can be

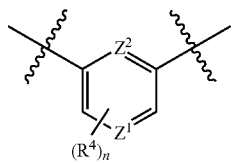

In some embodiments, the

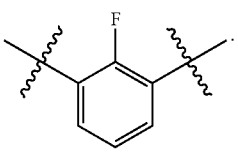

unit in Formula II can be various 5-membered heteroaromatic rings, including for example, thiazole, oxazole, imidazole, pyrazole rings. In some embodiments, $R^{5a}$, K, and one of J and L in Formula II can form an optionally substituted heterocyclic or heteroaromatic ring, such as an optionally substituted imidazopyridine. For example, in some embodiments, the compounds of Formula II can be a compound of Formula II-A to II-E:

Formula II-A

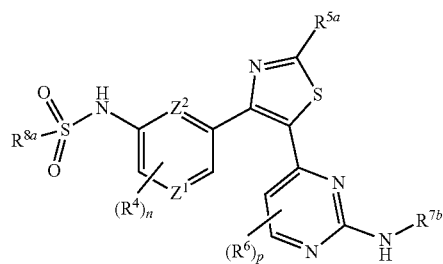

Formula II-B

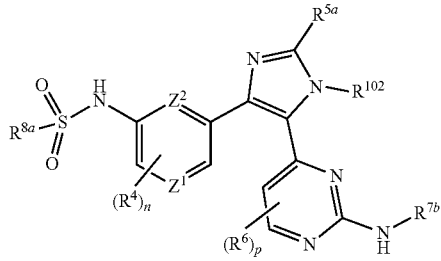

Formula II-C

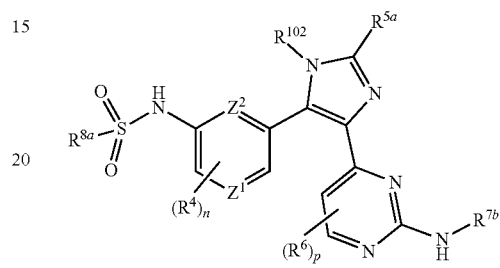

Formula II-D

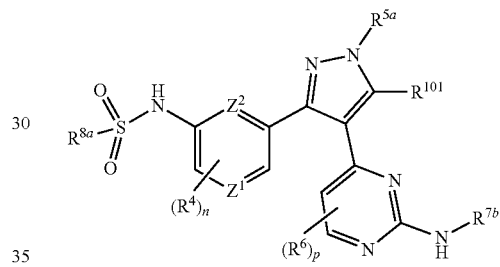

Formula II-E

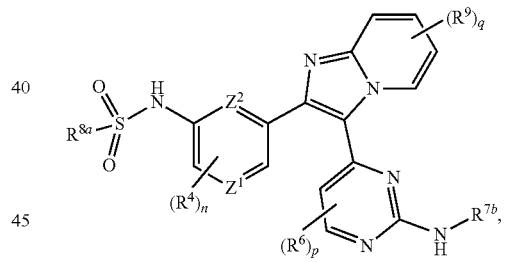

wherein $R^4$, n, $Z^1$, $Z^2$, $R^6$, p, $R^{5a}$, $R^{7b}$, $R^{8a}$, $R^9$, q, $R^{101}$, and $R^{102}$ are as defined and preferred herein. For the avoidance of doubt, $R^{102}$ in Formula II-B or II-C is not lone pair. However, it should be clear to those skilled in the art, when $R^{102}$ in Formula II-B or II-C is hydrogen, the compounds can exist in a mixture with their respective tautomers.

In some embodiments, $R^{5a}$ in Formula II (e.g., II-A to II-D) can be an optionally substituted phenyl or an optionally substituted 5 or 6 membered heteroaryl. In some embodiments, $R^{5a}$ can be an optionally substituted phenyl, an optionally substituted pyridyl, an optionally substituted pyridazinyl, an optionally substituted pyrimidinyl, an optionally substituted pyrazinyl, or an optionally substituted pyrazolyl. For example, in some embodiments, $R^{5a}$ can be phenyl, pyridyl, pyridazinyl, pyrimidinyl, pyrazinyl, or pyrazolyl, each of which is optionally substituted with one or more (e.g., 1, 2, or 3) substituents independently selected from halogen; —OH; cyano; $C_{1-4}$ alkyl optionally substituted with 1-3 substituents independently selected from $C_{1-4}$ alkyl, $C_{1-4}$alkoxy, —OH, and fluorine; $C_{1-4}$alkoxy optionally substituted with 1-3 substituents independently selected from $C_{1-4}$ alkyl, $C_{1-4}$alkoxy, —OH, and fluorine; $C_{3-6}$ cycloalkyl optionally substituted with 1-3 substituents independently selected from $C_{1-4}$ alkyl and fluorine; $C_{3-6}$ cycloalkoxy optionally substituted with 1-3 substituents independently selected from $C_{1-4}$ alkyl and fluorine; 4-6 membered heterocyclic ring optionally substituted with 1-3 substituents independently selected from $C_{1-4}$ alkyl and fluorine; —$COR^{104}$; —$COOR^{105}$; —$OCOR^{104a}$; —$OCOOR^{105a}$; —$CONR^{106}R^{107}$; —$OCONR^{106a}R^{107a}$; and —$NR^{108}R^{109}$, wherein $R^{104}$, $R^{104a}$, $R^{105}$, and $R^{105a}$ are independently hydrogen, an optionally substituted $C_{1-6}$ alkyl, an optionally substituted $C_{3-6}$ cycloalkyl, an optionally substituted phenyl, an optionally substituted heteroaryl, or an optionally substituted heterocyclyl, provided that $R^{105a}$ is not hydrogen; and $R^{106}$, $R^{107}$, $R^{106a}$, $R^{107a}$, $R^{108}$, and $R^{109}$ are each independently hydrogen, nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl.

In some embodiments, $R^{5a}$ in Formula II (e.g., II-A to II-D) can be phenyl, pyridyl, pyridazinyl, pyrimidinyl, pyrazinyl, or pyrazolyl, each of which is optionally substituted with 1 or 2 substituents independently selected from F, Cl, —OH, cyano, $C_{1-4}$ alkyl, —$CF_3$, $C_{1-4}$ alkoxy, —$NH_2$, —NH($C_{1-4}$ alkyl), —N($C_{1-4}$ alkyl)($C_{1-4}$ alkyl), azetidinyl, and cyclopropyl. When $R^{5a}$ is a heteroaryl derived group, it should be understood that the connecting point is not limited to a particular position relative to the heteroatoms, for example, in the case of pyridyl, the connecting point can be ortho, meta, or para to the ring nitrogen. In some specific embodiments, $R^{5a}$ can be

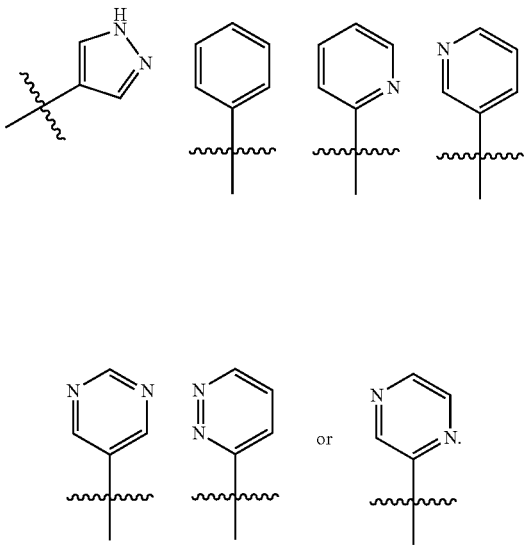

each of which is optionally substituted with 1 or 2 substituents independently selected from F, Cl, —OH, cyano, $C_{1-4}$ alkyl, —$CF_3$, $C_{1-4}$ alkoxy, —$NH_2$, —NH($C_{1-4}$ alkyl), —N($C_{1-4}$alkyl)($C_{1-4}$ alkyl), azetidinyl, and cyclopropyl. In some preferred embodiments, $R^{5a}$ can be

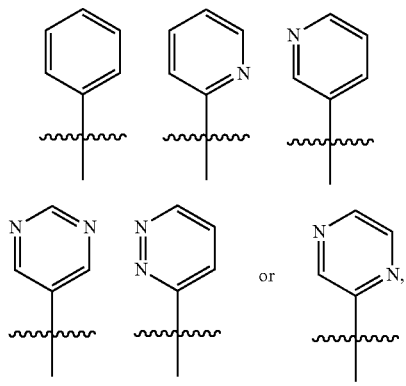

each of which is optionally substituted with 1 or 2 substituents independently selected from F, Cl, —OH, methyl, ethyl, methoxy, —$CF_3$, —$NH_2$, azetidinyl, and cyclopropyl, more preferably, optionally substituted with one substituent selected from F and methyl.

In some specific embodiments, $R^{5a}$ in Formula II (e.g., II-A to II-D) can be

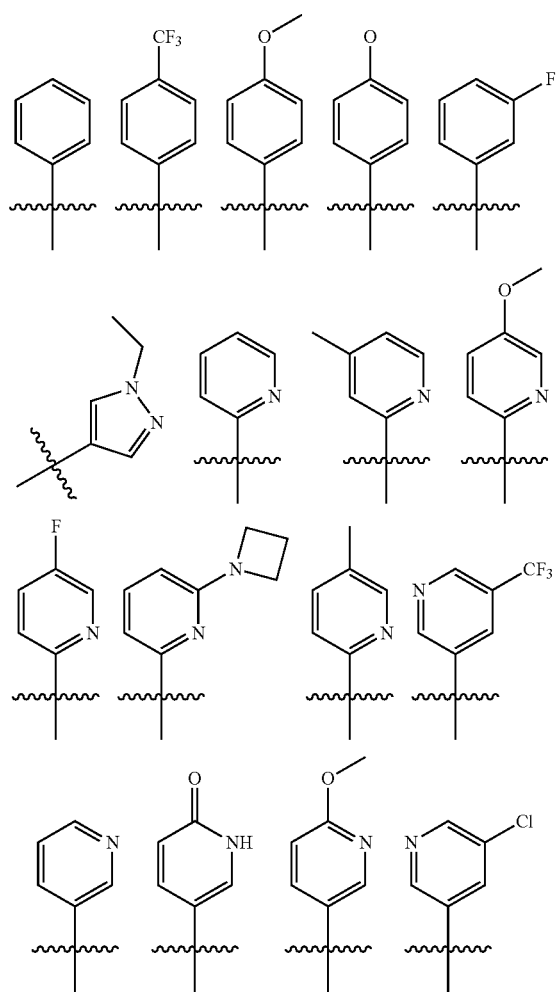

-continued

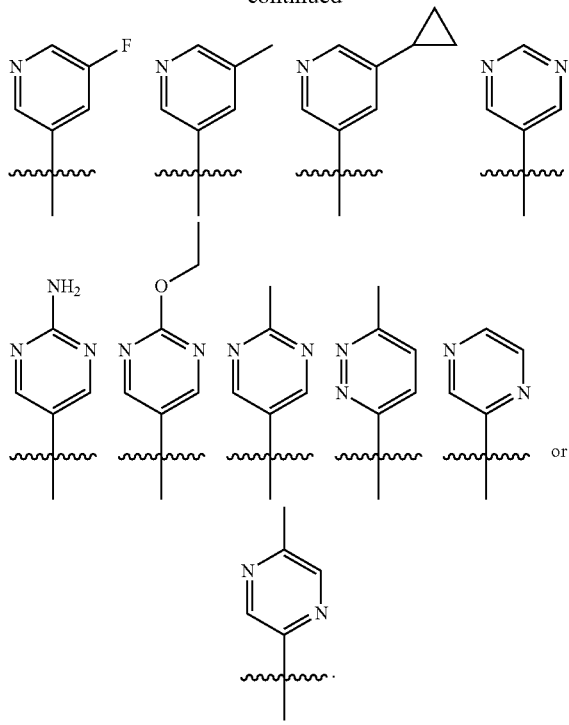

In some embodiments, the compounds of Formula II can have Formula II-E. In some embodiments, the

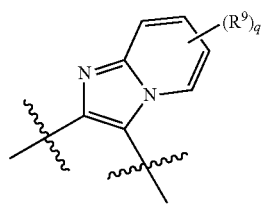

in Formula II-E can be any of those defined for the corresponding structural unit in Formula I. The preferred

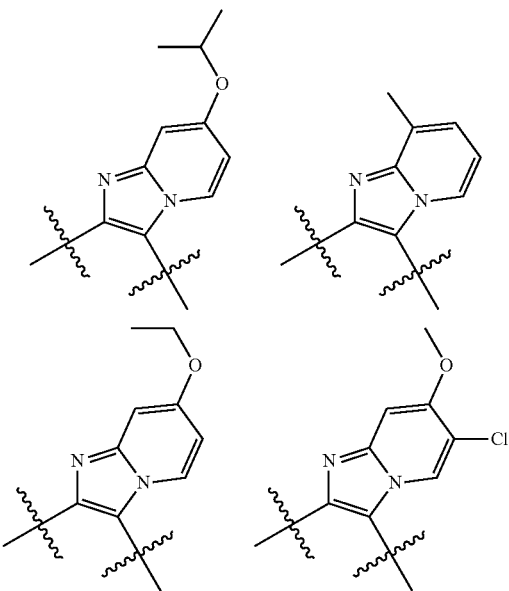

in Formula II-E can also be any of those described as preferred for the corresponding structural unit in Formula I. For example, in some embodiments, q is 0. In some embodiments q is 1 or 2, preferably 1, $R^9$ at each occurrence is independently F, Cl, —OH, cyano, $C_{1-4}$ alkyl, $CF_3$, $C_{1-4}$ alkoxy, —$NH_2$, —$NMe_2$, —NHMe, —NH($C_{2-4}$ alkyl), —N(CH alkyl)($C_{2-4}$ alkyl), —COOH, —COO($C_{1-4}$ alkyl), —$CONH_2$, —CONH($C_{1-4}$ alkyl), —CON($C_{1-4}$ alkyl)($C_{1-4}$ alkyl), azetidinyl, or cyclopropyl. In some preferred embodiments, q is 1 or 2, preferably 1, $R^9$ at each occurrence is independently F, Cl, methyl, ethyl, methoxy, ethoxy, isopropoxy, —COOH, —$CONH_2$, or $CF_3$. In some specific embodiments,

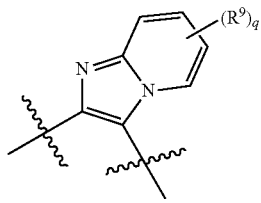

in Formula II (e.g., Formula II-E) can be

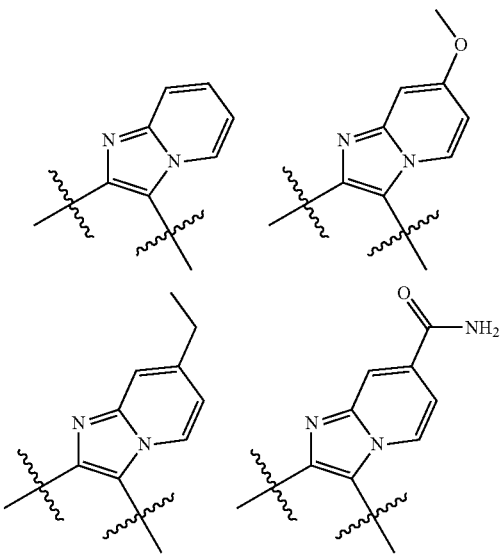

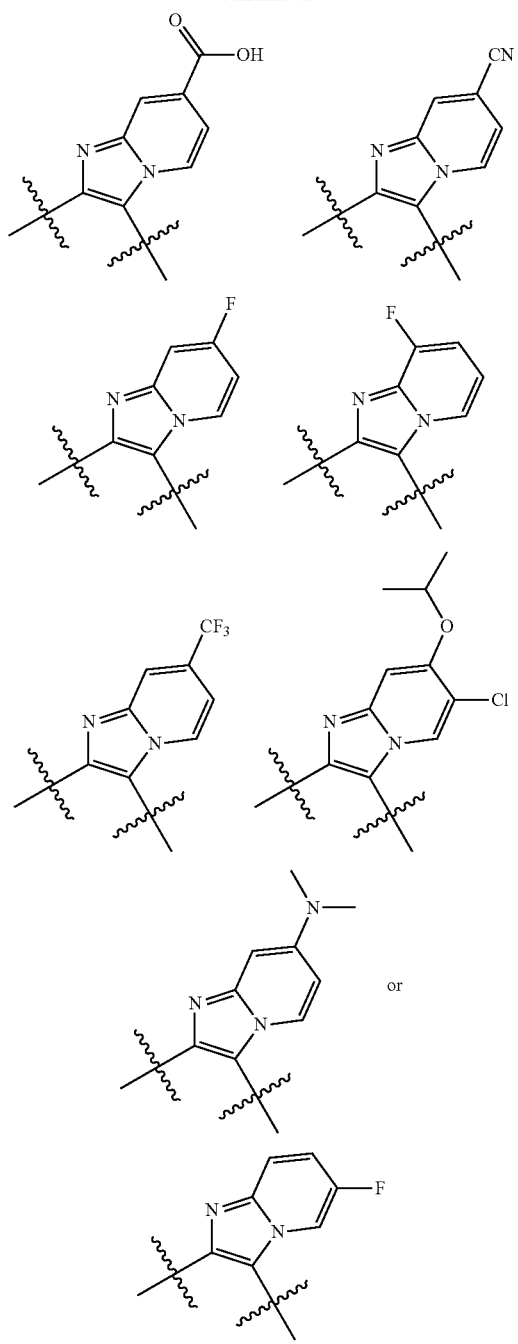

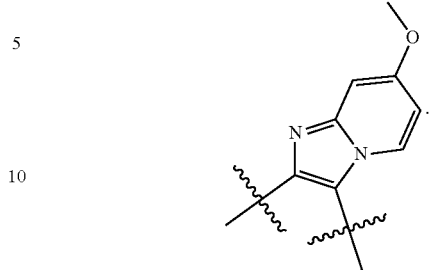

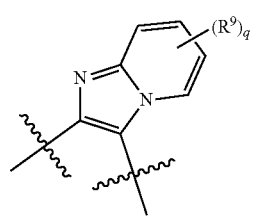

In some preferred embodiments, in Formula II (e.g., Formula II-E) can be

In some embodiments, $R^{7a}$ and $R^{7b}$ in Formula II (e.g., in II-A to II-E as applicable) are independently hydrogen, a nitrogen protecting group, an optionally substituted $C_{1-6}$ alkyl, an optionally substituted $C_{3-6}$ cycloalkyl, an optionally substituted phenyl, an optionally substituted 5 or 6-membered heteroaryl such as pyridyl, or an optionally substituted 5 or 6 membered heterocyclyl group such as piperidinyl. Typically, at least one of $R^{7a}$ and $R^{7b}$ is hydrogen. For example, in some embodiments, $R^{7a}$ is hydrogen, and $R^{7b}$ is hydrogen, an optionally substituted $C_{1-6}$ alkyl, an optionally substituted $C_{3-6}$ cycloalkyl, an optionally substituted phenyl, an optionally substituted 5- or 6-membered heteroaryl, or an optionally substituted 4-7 membered heterocyclyl. In some embodiments, $R^{7a}$ can be a $C_{1-4}$ alkyl such as methyl, and $R^{7b}$ can be hydrogen, an optionally substituted $C_{1-6}$ alkyl, an optionally substituted $C_{3-6}$ cycloalkyl, an optionally substituted phenyl, an optionally substituted 5- or 6-membered heteroaryl, or an optionally substituted 4-7 membered heterocyclyl. In some embodiments, $R^{7a}$ is hydrogen, and $R^{7b}$ can be any of those defined for $R^7$ in Formula I. Preferred $R^{7b}$ can also be those preferred for $R^7$ in Formula I. For example, in some embodiments, $R^{7a}$ is hydrogen, and $R^{7b}$ can be hydrogen, methyl, ethyl, cyclopropyl, isopropyl,

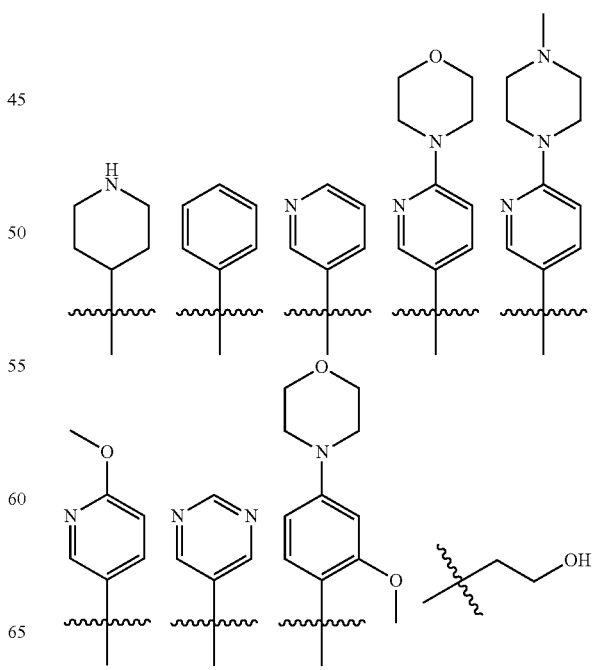

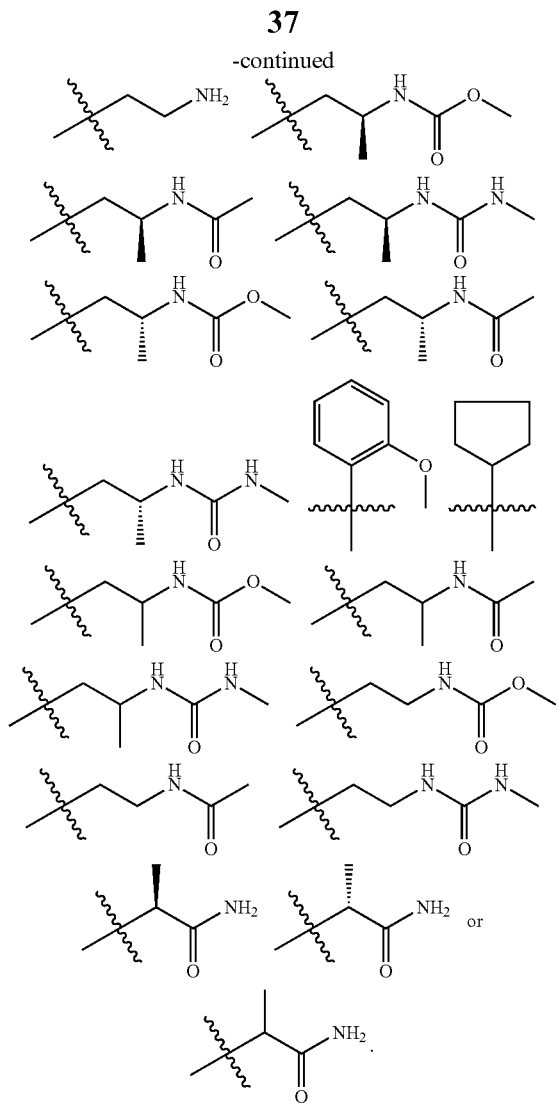

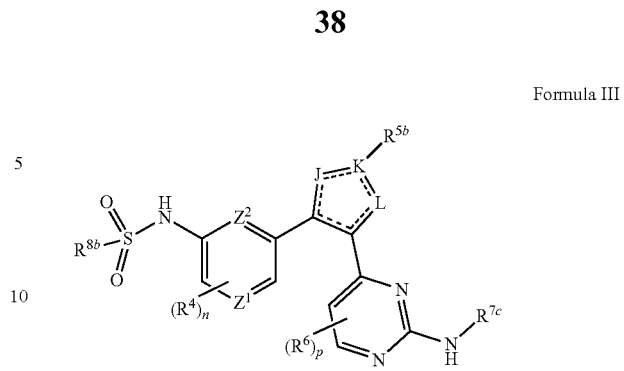

wherein: $R^{5b}$ is an optionally substituted heteroaryl (e.g., 2-pyridyl, 3-pyridyl, pyridazinyl, pyrimidinyl, pyrazinyl, or pyrazolyl), or $R^{5b}$, K, and one of J and L form an optionally substituted heterocyclic or heteroaromatic ring;

$R^{7c}$ is hydrogen, a nitrogen protecting group, an optionally substituted $C_{1-6}$ alkyl, an optionally substituted $C_{3-6}$ cycloalkyl, an optionally substituted aryl, an optionally substituted heteroaryl, or an optionally substituted heterocyclyl;

$R^{8b}$ is an optionally substituted $C_{1-6}$ alkyl, $-NR^{200}R^{201}$, an optionally substituted $C_{3-6}$ cycloalkyl, an optionally substituted aryl, an optionally substituted heteroaryl, or an optionally substituted heterocyclyl, wherein $R^{200}$ and $R^{201}$ are independently hydrogen, a nitrogen protecting group, an optionally substituted $C_{1-6}$ alkyl, an optionally substituted $C_{3-6}$ cycloalkyl, an optionally substituted aryl, an optionally substituted heteroaryl, or an optionally substituted heterocyclyl; and $R^4$, n, $Z^1$, $Z^2$, J, K, L, $R^6$, and p are as defined for Formula G.

In various embodiments, compounds of Formula III are characterized by novel $R^{5b}$ groups. In some embodiments, $R^{5b}$ in Formula III can be 2-pyridyl, 3-pyridyl, pyridazinyl, pyrimidinyl, pyrazinyl, or pyrazolyl, each of which can be optionally substituted. In some specific embodiments, $R^{5b}$ in Formula III can be

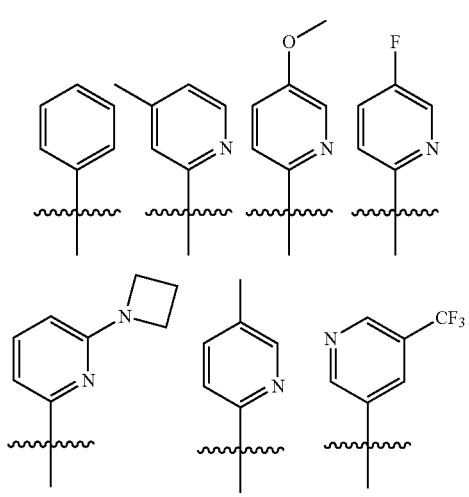

In some preferred embodiments of Formula II (e.g., in II-A to II-E as applicable), $R^{7a}$ is hydrogen, $R^{7b}$ is hydrogen, methyl, ethyl, cyclopropyl, isopropyl, or

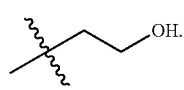 [SMILES: *CCO]

Suitable groups for $R^{8a}$, $R^4$, $R^{5a}$, $R^6$, $R^{7a}$, $R^{7b}$, $Z^1$, $Z^2$, J, K, L, n and p in compounds of Formula II (e.g., Formula IIA-IIE, as applicable) are independently selected. The described embodiments of the present invention can be combined. Such combination is contemplated and within the scope of the present invention. For example, it is contemplated that embodiments for any of $R^{8a}$, $R^4$, $R^{5a}$, $R^6$, $R^{7a}$, $R^{7b}$, $Z^1$, $Z^2$, J, K, L, n and p can be combined with embodiments defined for any other of $R^{8a}$, $R^4$, $R^{5a}$, $R^6$, $R^{7a}$, $R^{7b}$, $Z^1$, $Z^2$, J, K, L, n and p, as applicable.

Formula III

In some embodiments, the present disclosure provides a compound of Formula III, or a pharmaceutically acceptable salt thereof:

-continued

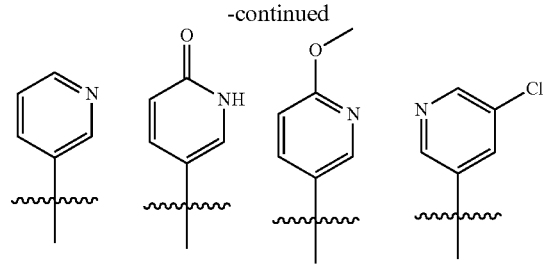

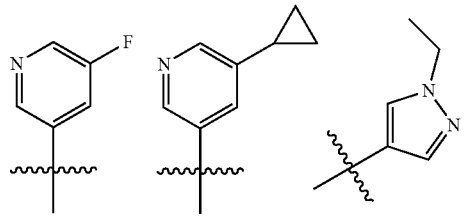

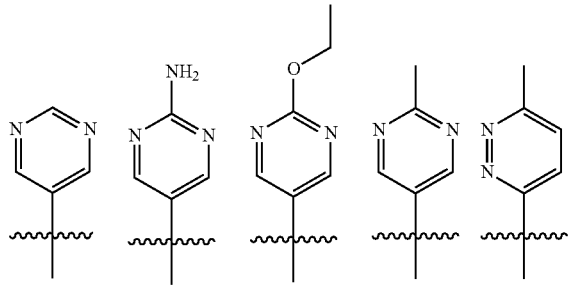

or

The structural unit

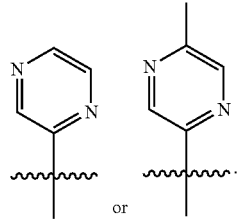

in Formula III (e.g., III-A to III-E) can be any of those described above for the corresponding structural unit in Formula I. Preferred

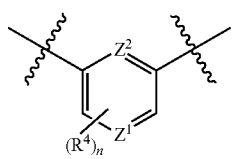

in Formula III can also be those preferred for the corresponding structural unit in Formula I, for example,

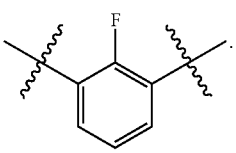

In some embodiments, the

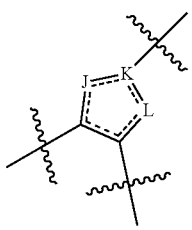

unit in Formula III can be various 5-membered heteroaromatic rings, including for example thiazole, oxazole, imidazole, pyrazole rings. In some embodiments, $R^{5b}$, K, and one of J and L in Formula III can form an optionally substituted heterocyclic or heteroaromatic ring, such as an optionally substituted imidazopyridine. For example, in some embodiments, the compounds of Formula III can be a compound of Formula III-A to III-E:

Formula III-A

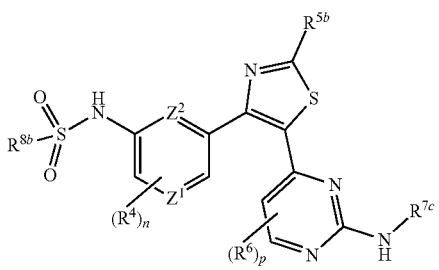

Formula III-B

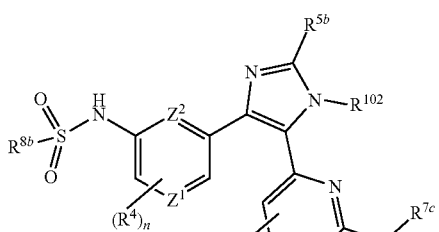

Formula III-C

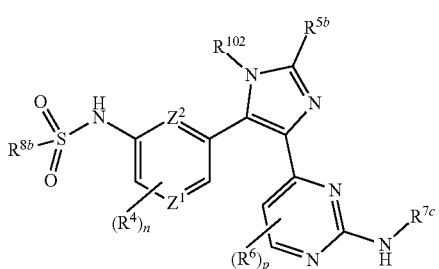

-continued

Formula III-D

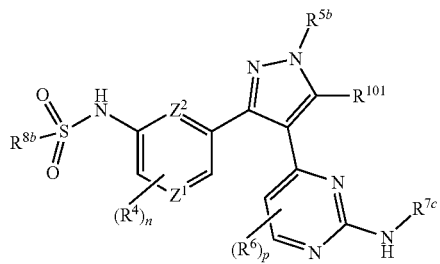

Formula III-E

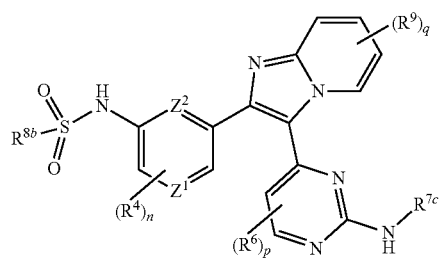

wherein $R^4$, n, $Z^1$, $Z^2$, $R^6$, p, $R^{5b}$, $R^{7c}$, $R^{8b}$, $R^9$, q, $R^{101}$, and $R^{102}$ are as defined and preferred herein. For the avoidance of doubt, $R^{102}$ in Formula III-B or III-C is not lone pair. However, it should be clear to those skilled in the art, when $R^{102}$ in Formula III-B or III-C is hydrogen, the compounds can exist in a mixture with their respective tautomers.

In some embodiments, the

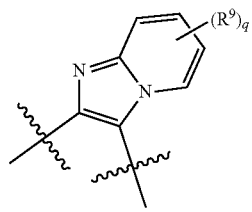

in Formula III-E can be any of those defined for the corresponding structural unit in Formula I. Preferred structures can also be those preferred for the corresponding structural unit in Formula I. For example, in some embodiments, q is 0. In some embodiments q is 1 or 2, preferably 1, $R^9$ at each occurrence is independently F, Cl, —OH, cyano, $C_{1-4}$ alkyl, $CF_3$, $C_{1-4}$ alkoxy, —$NH_2$, —$NMe_2$, —NHMe, —NH($C_{2-4}$ alkyl), —N($C_{1-4}$alkyl)($C_{2-4}$ alkyl), —COOH, —COO($C_{1-4}$ alkyl), —$CONH_2$, —CONH($C_{1-4}$ alkyl), —CON($C_{1-4}$ alkyl)($C_{1-4}$ alkyl), azetidinyl, or cyclopropyl. In some preferred embodiments, q is 1 or 2, preferably 1, $R^9$ at each occurrence is independently F, Cl, methyl, ethyl, methoxy, ethoxy, isopropoxy, —COOH, —$CONH_2$, or $CF_3$. In some specific embodiments,

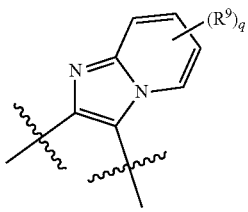

in Formula III-E can be

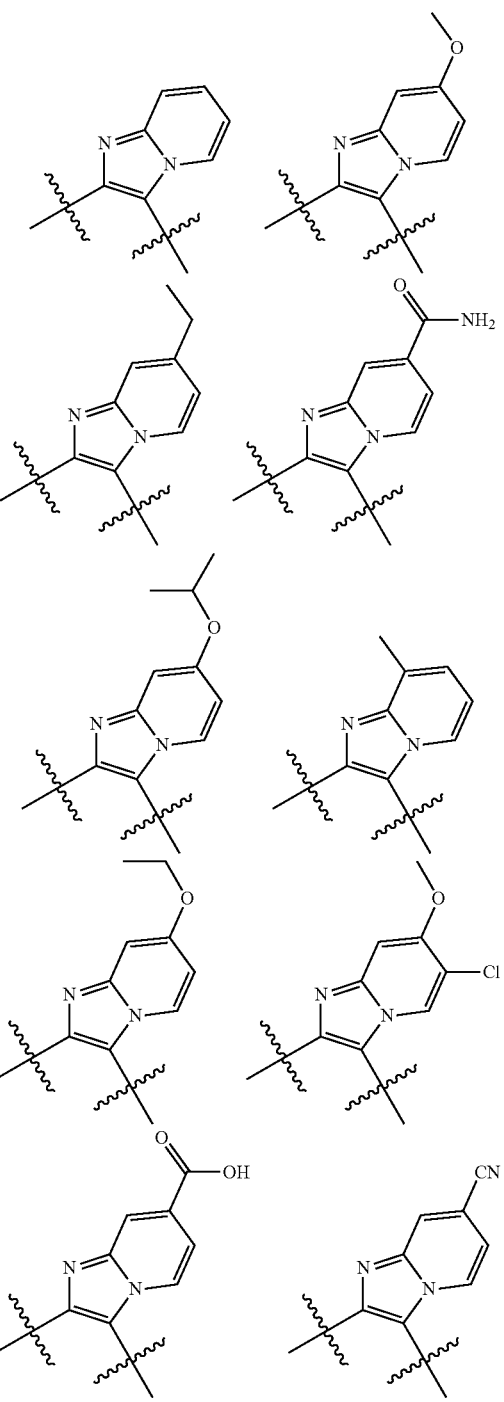

43

-continued

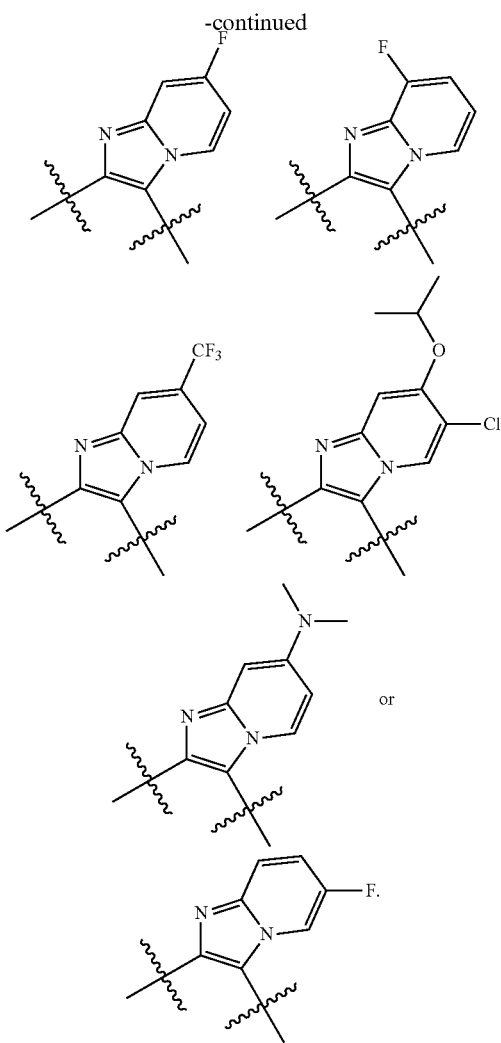

In some preferred embodiments,

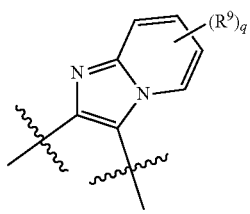

in Formula III-E can be

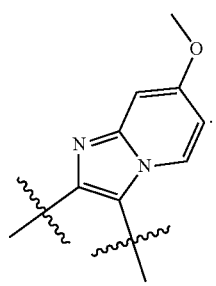 [SMILES: *c1nc2cc(OC)ccn2c1*]

44

$R^{7c}$ in Formula III can be (or be preferred) as any of those defined (or preferred) for $R^7$ in Formula I. For example, in some preferred embodiments of Formula III, $R^{7c}$ is hydrogen, methyl, ethyl, cyclopropyl, isopropyl, or

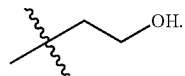 [SMILES: *CCO]

In some embodiments, $R^{8b}$ in Formula III can be (or be preferred) as any of those defined (or preferred) for $R^8$ in Formula I or $R^{8a}$ in Formula II. In some embodiments, $R^{8b}$ in Formula III can be an optionally substituted $C_{1-6}$ alkyl, —$NR^{200}R^{201}$, an optionally substituted $C_{3-6}$ cycloalkyl, or an optionally substituted 4-7 membered heterocyclyl. In some preferred embodiments, $R^{8b}$ can be

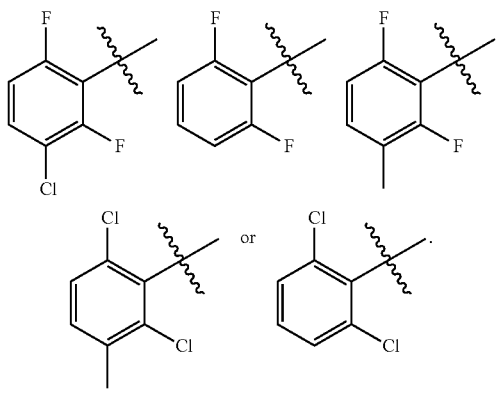

Suitable groups for $R^{8b}$, $R^4$, $R^{5b}$, $R^6$, $R^{7c}$, $Z^1$, $Z^2$, J, K, L, n and p in compounds of Formula III (e.g., Formula III-A-III-E, as applicable) are independently selected. The described embodiments of the present invention can be combined. Such combination is contemplated and within the scope of the present invention. For example, it is contemplated that embodiments for any of $R^{8b}$, $R^4$, $R^{5b}$, $R^6$, $R^{7c}$, $Z^1$, $Z^2$, J, K, L, n and p can be combined with embodiments defined for any other of $R^{8b}$, $R^4$, $R^{5b}$, $R^6$, $R^{7c}$, $Z^1$, $Z^2$, J, K, L, n and p, as applicable.

Exemplary Compounds

In some embodiments, the present disclosure also provides certain exemplary compounds having Formula E1 or E2, or a pharmaceutically acceptable salt thereof:

Formula E1

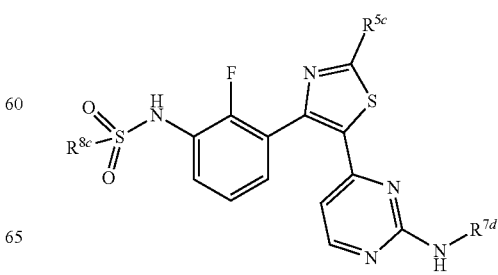

Formula E2

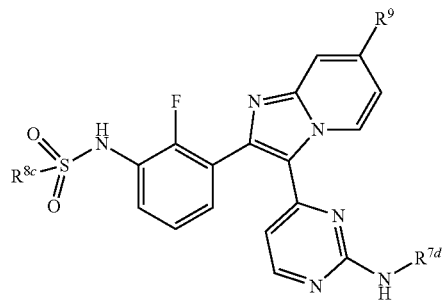

wherein:

R⁵ᶜ is

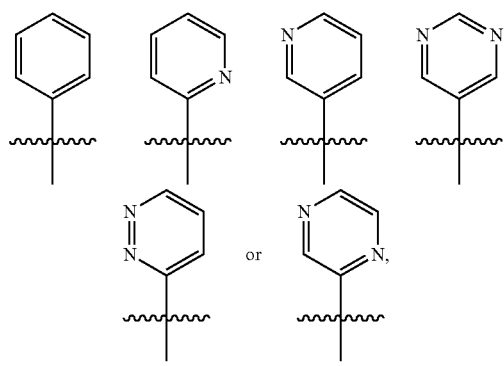

each of which is optionally substituted, preferably unsubstituted or substituted with one substituent, which is F or methyl;

R⁸ᶜ is phenyl, optionally substituted with 1-3 substituents independently selected from F, Cl, methyl, and methoxy;

R⁷ᵈ is any of those defined (or preferred) for R⁷ in Formula I, R⁷ᵇ in Formula II, or R⁷ᶜ in Formula III, for example, R⁷ᵈ can preferably be hydrogen, methyl, ethyl, cyclopropyl, isopropyl, or

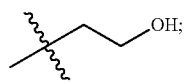 [SMILES: *CCO]

and

R⁹ is hydrogen, F, or methoxy.

In some preferred embodiments, R⁸ᶜ can be

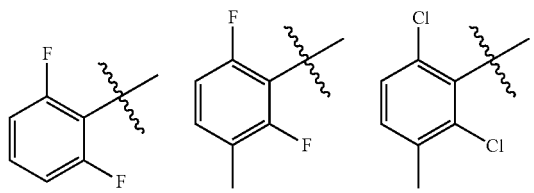

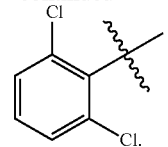

In some preferred embodiments, R⁸ᶜ can be

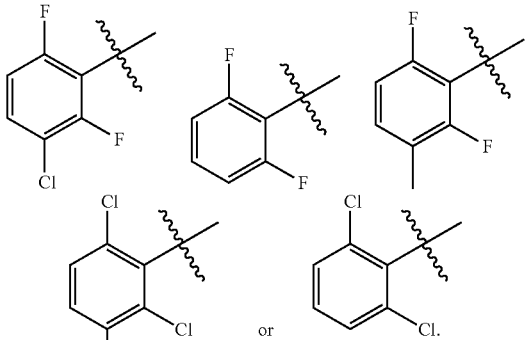

In some embodiments, the present disclosure also provides certain exemplary compounds having Formula E3, E4, E5 or E6, or a pharmaceutically acceptable salt thereof:

Formula E3

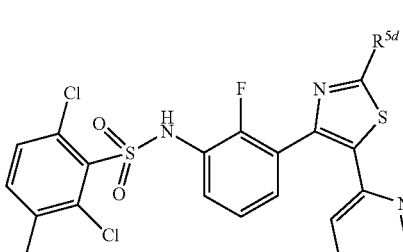

Formula E4

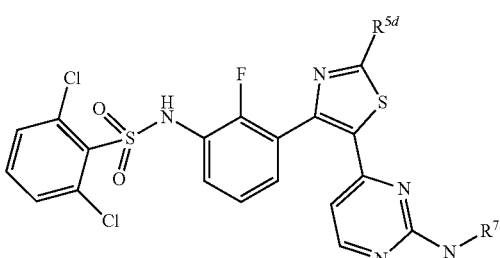

Formula E5

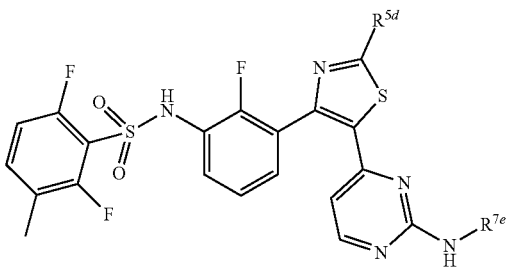

-continued

Formula E6

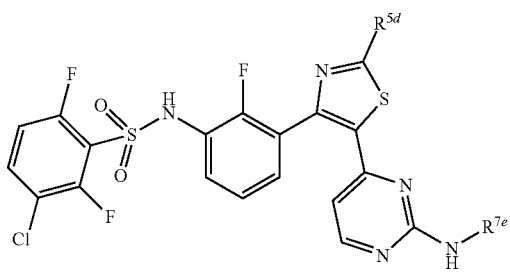

wherein:

R^{5d} is (1) $C_{1-4}$ alkyl (e.g., isopropyl or tert-butyl); (2) —NR$^{103}$R$^{103a}$ (e.g., 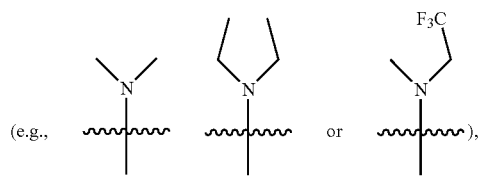), wherein R$^{103}$ and R$^{103a}$ are defined herein; (3) azetidinyl, pyrrolidinyl, piperidinyl, morpholinyl, or pyrrolidonyl, each optionally substituted with 1 or 2 substituents independently selected from F and $C_{1-4}$ alkyl, e.g.,

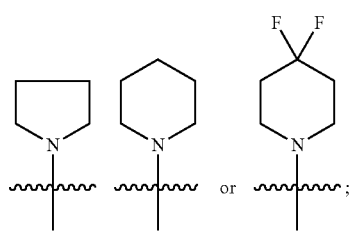

or (4) phenyl, pyridyl, pyridazinyl, pyrimidinyl, pyrazinyl, or pyrazolyl, each of which is optionally substituted with one or more (e.g., 1, 2, or 3, preferably 1) substituents independently selected from F, Cl, —OH, cyano, $C_{1-4}$ alkyl, —CF$_3$, $C_{1-4}$alkoxy, —NH$_2$, —NH($C_{1-4}$ alkyl), —N($C_{1-4}$alkyl)($C_{1-4}$ alkyl), azetidinyl, and cyclopropyl; and R$^{7e}$ is any of those defined (or preferred) for R$^7$ in Formula I, R$^{7b}$ in Formula II, or R$^{7c}$ in Formula III, for example, R$^{7e}$ can preferably be hydrogen, methyl, ethyl, cyclopropyl, isopropyl, or

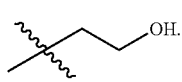 [SMILES: *CCO]

In some embodiments, the present disclosure also provides specific compound, compound No. 1-189, or a pharmaceutically acceptable salt thereof.

1

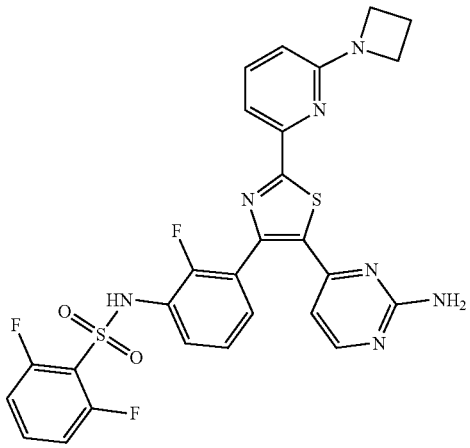

2

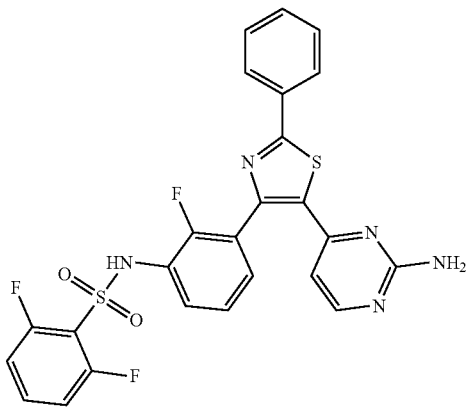

3

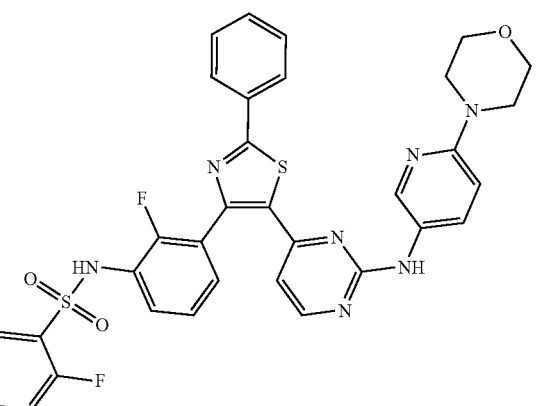

4
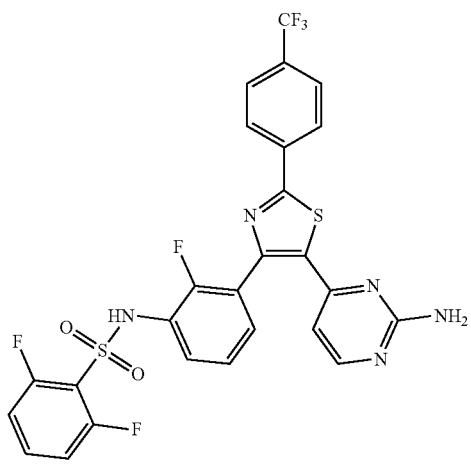
5
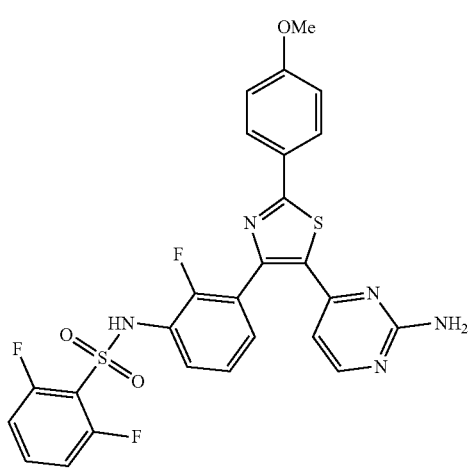
6
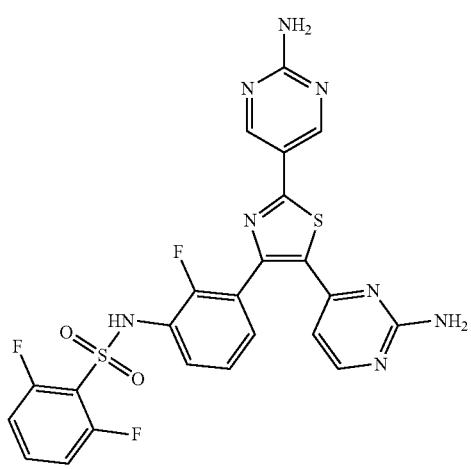
7
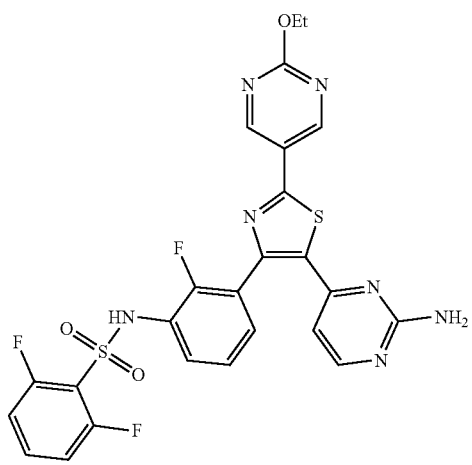
8
9
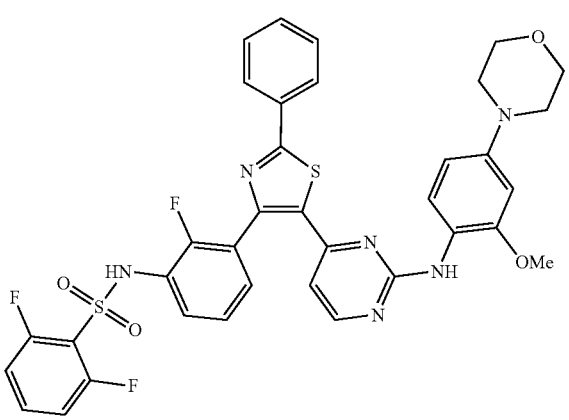

51
-continued
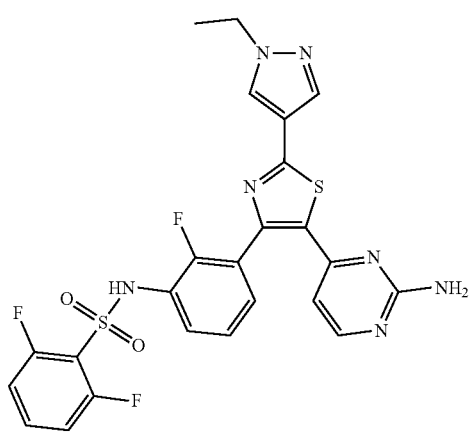
10
11
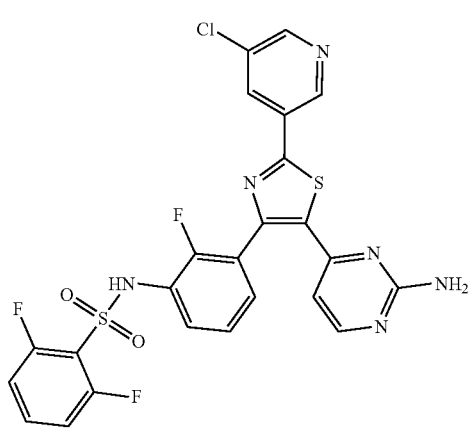
12
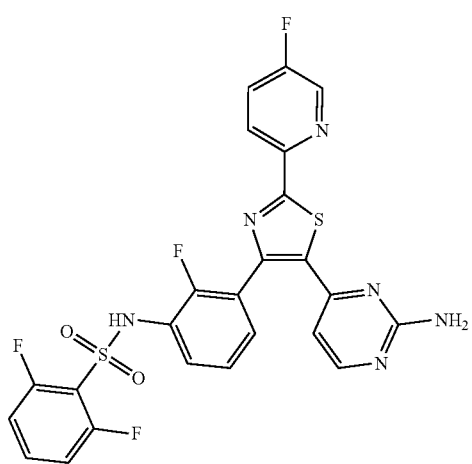
52
-continued
13
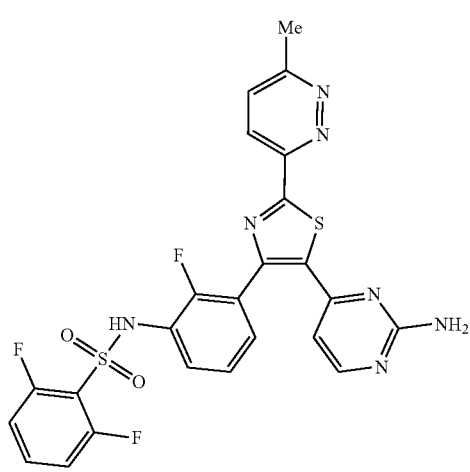
14
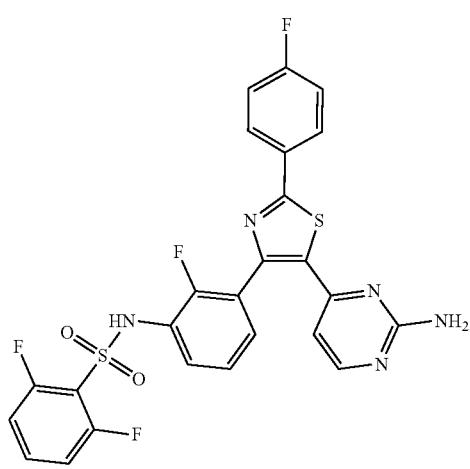
15
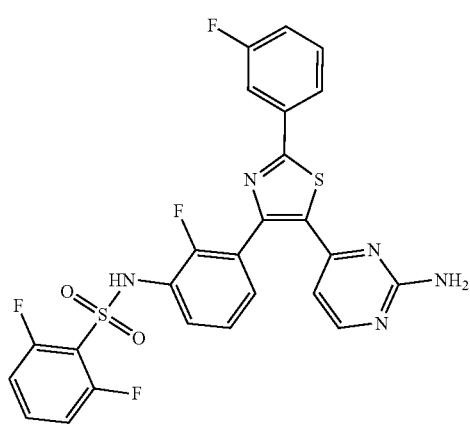

16
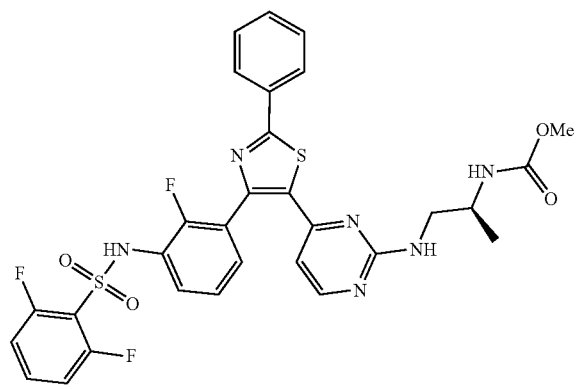
17
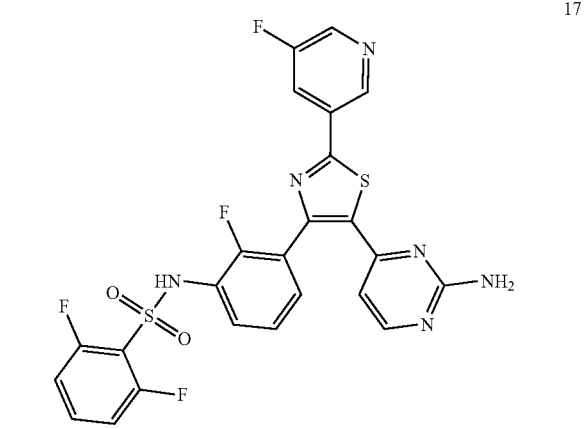
18
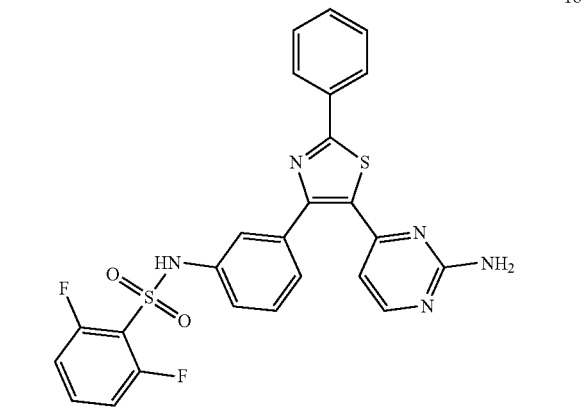
19
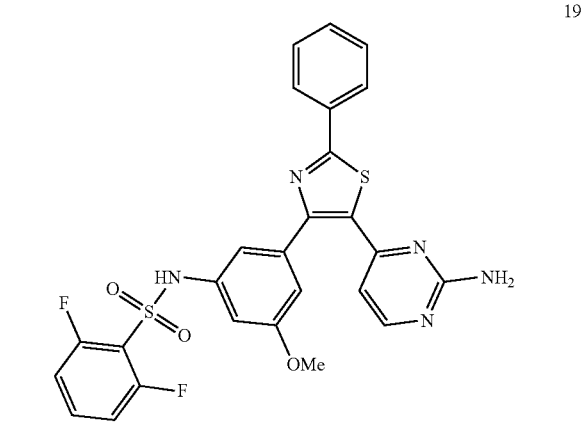
20
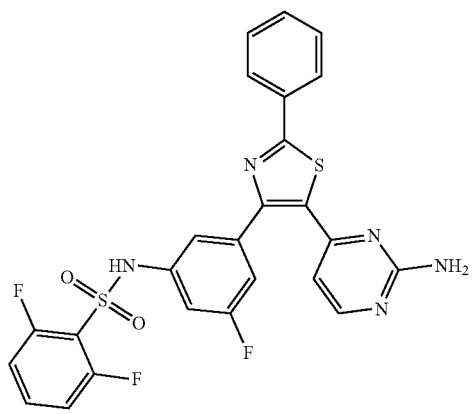
21
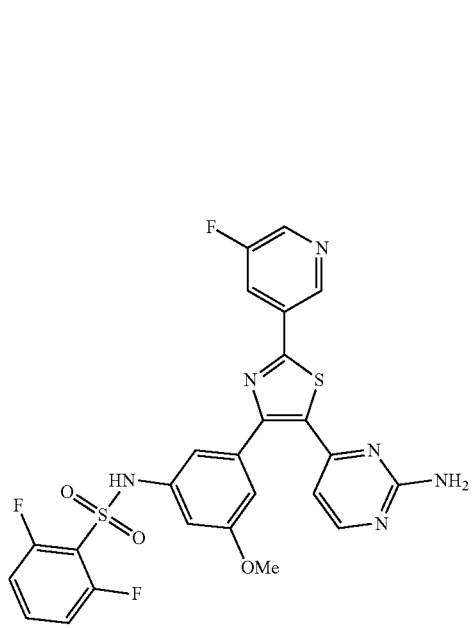
22
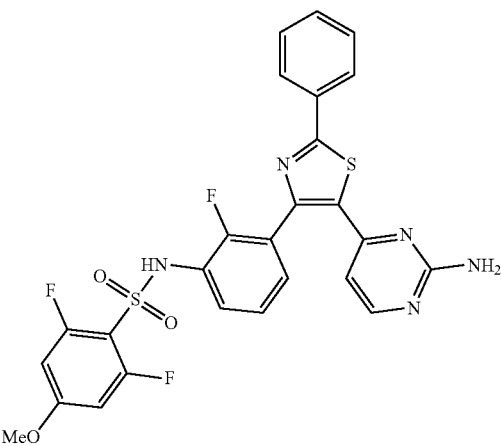

23
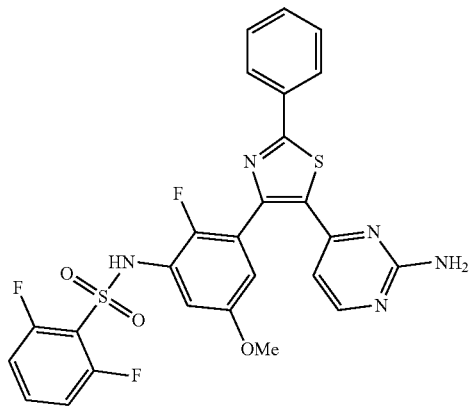
24
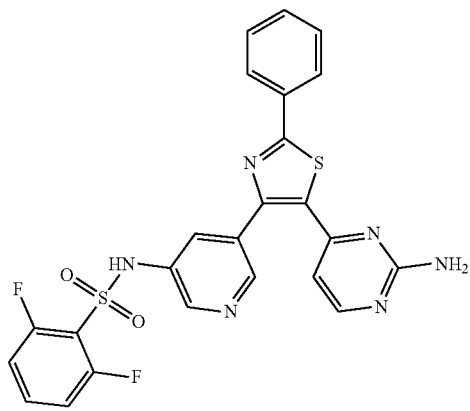
25
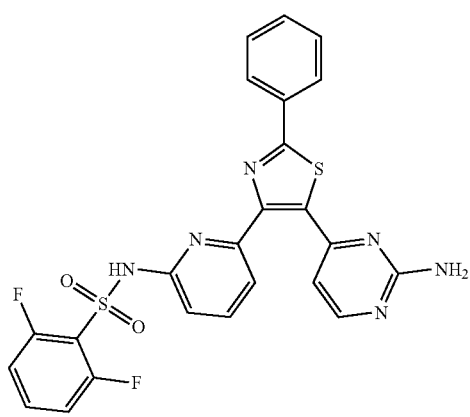
26
27
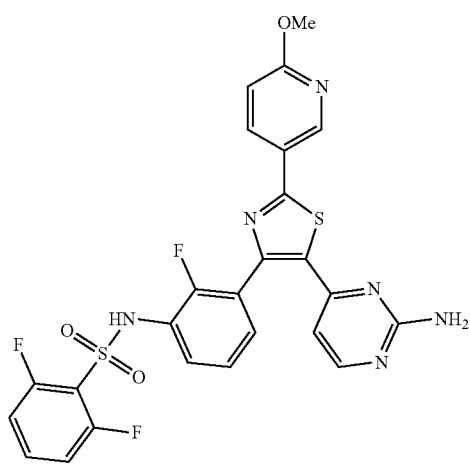
28
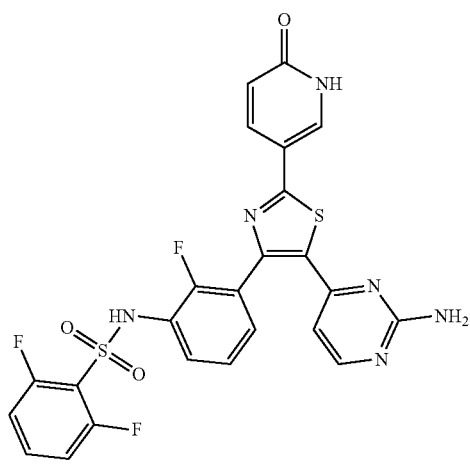
29
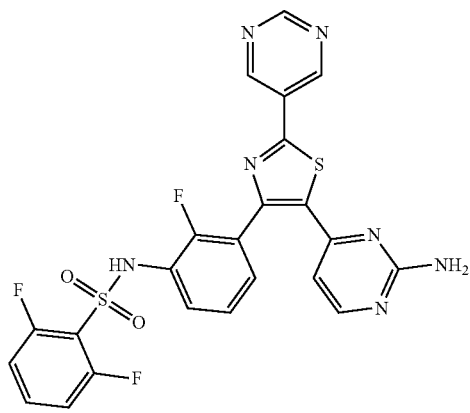

30
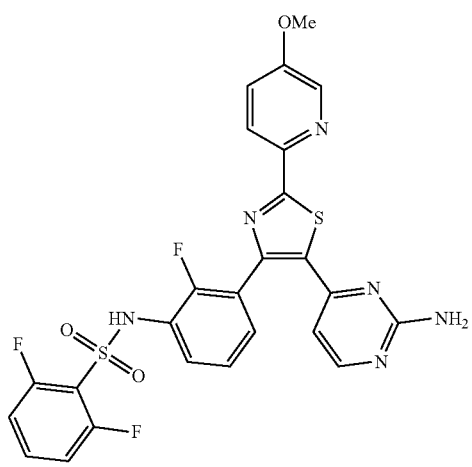
31
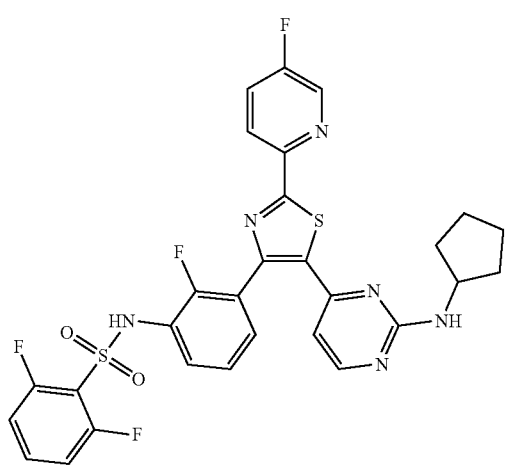
32
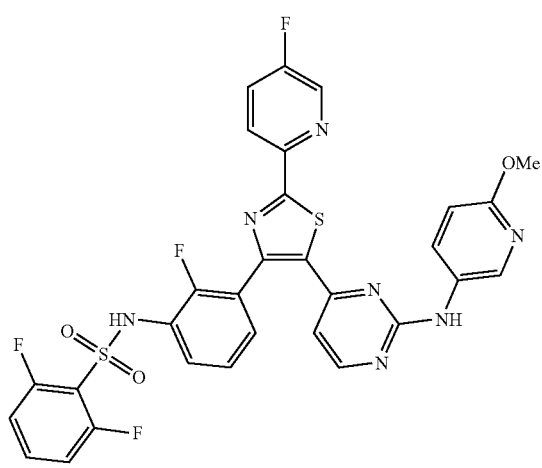
33
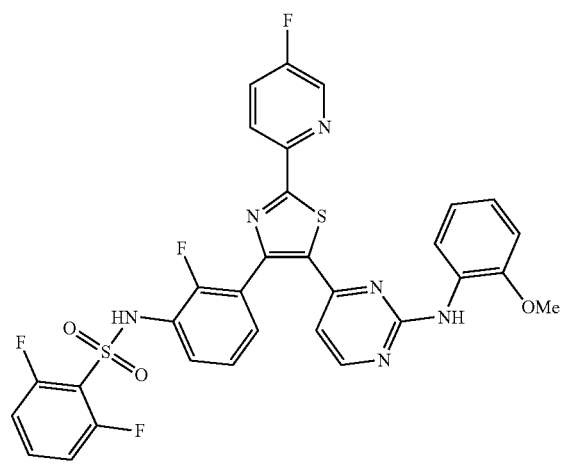
34
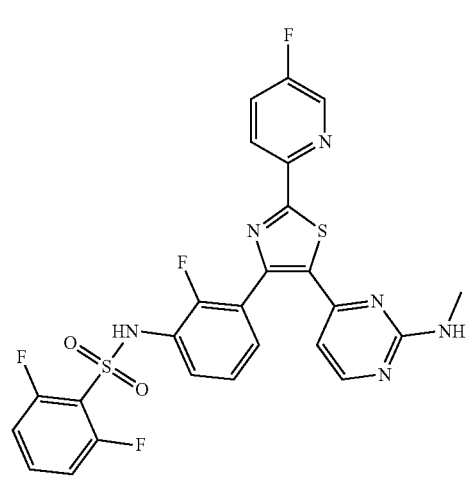
35
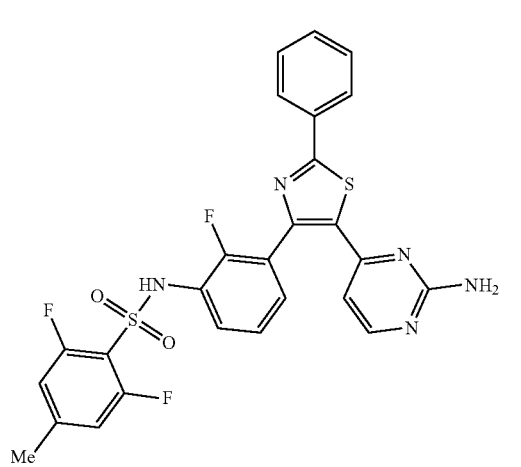

36
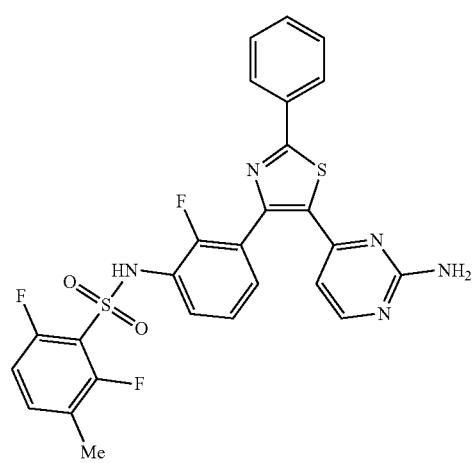
37
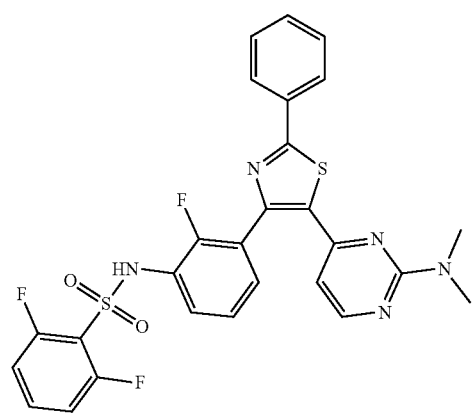
38
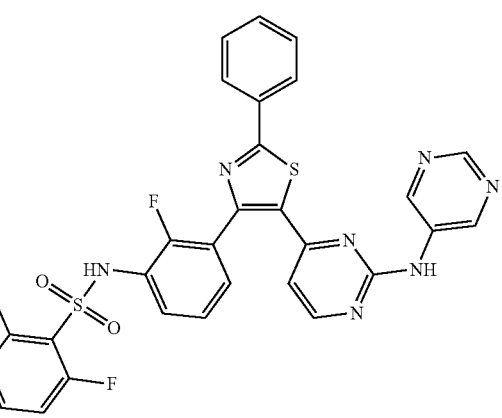
39
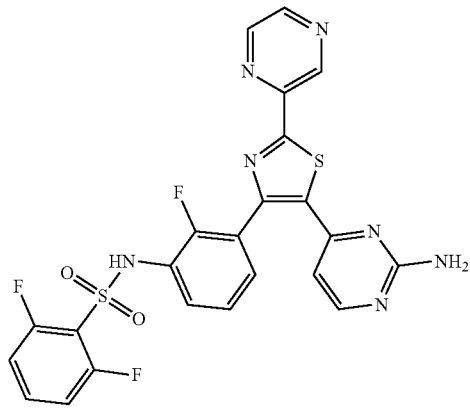
40
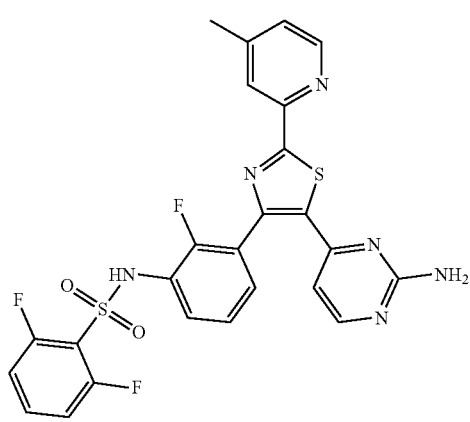
41
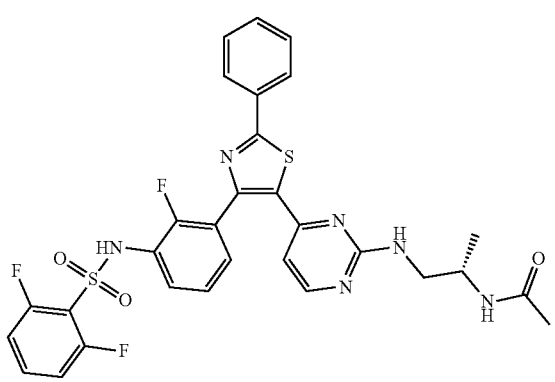
42
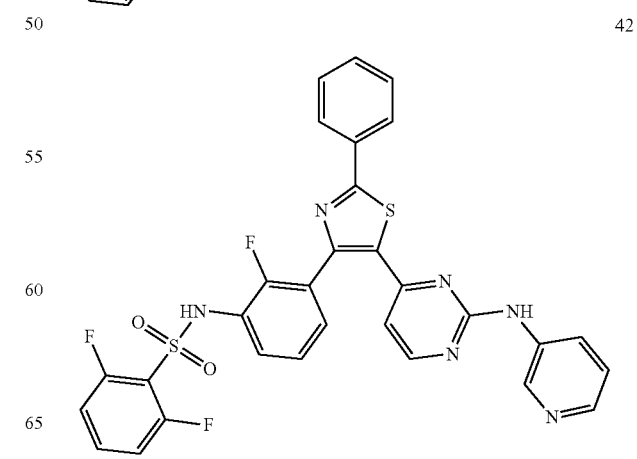

43
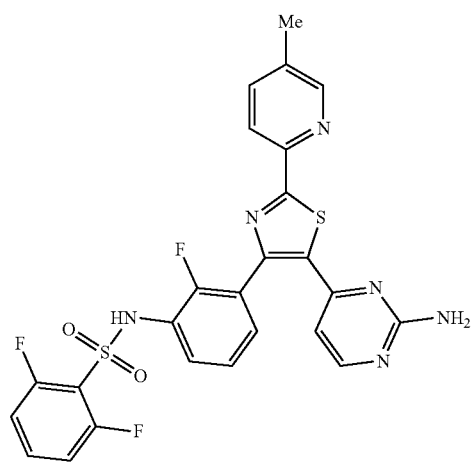
44
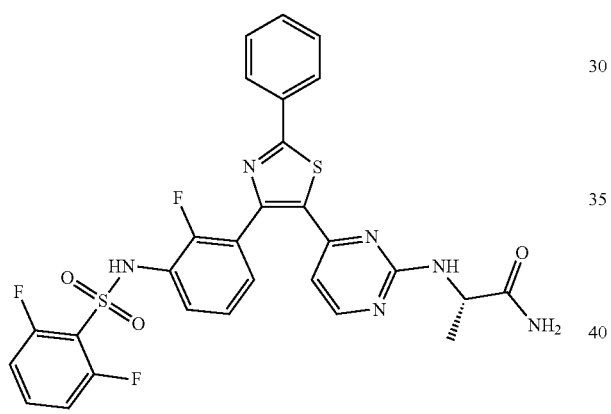
46
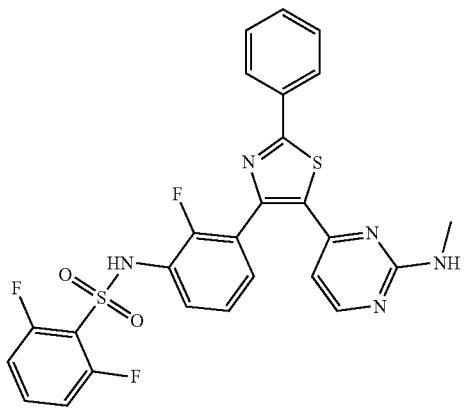
47
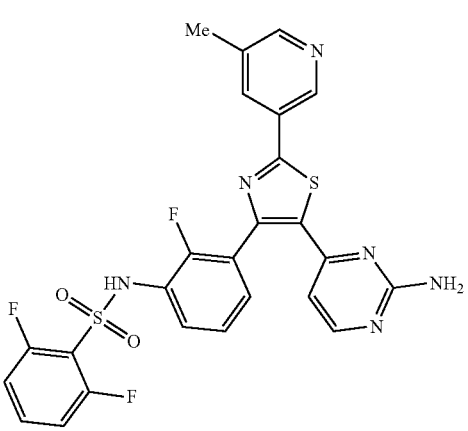
48
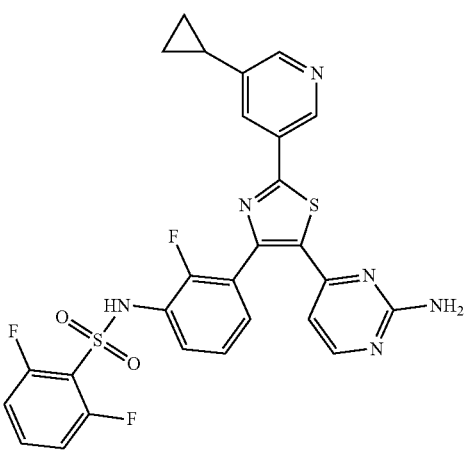

49
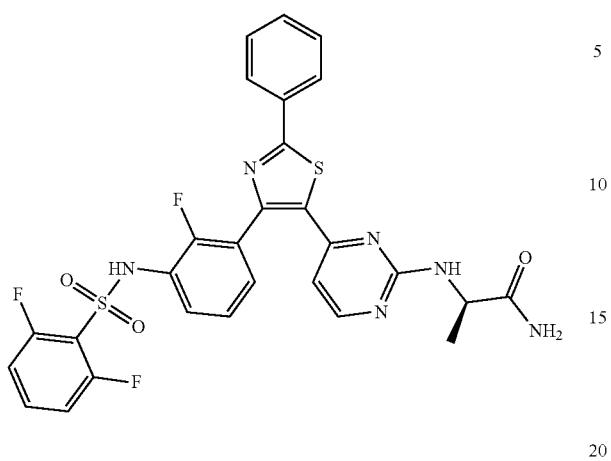
50
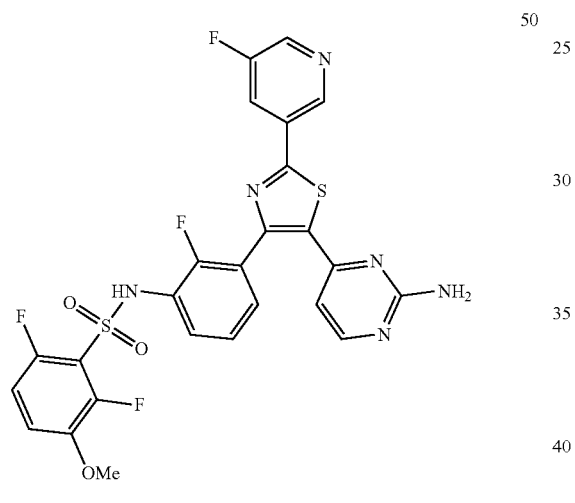
51
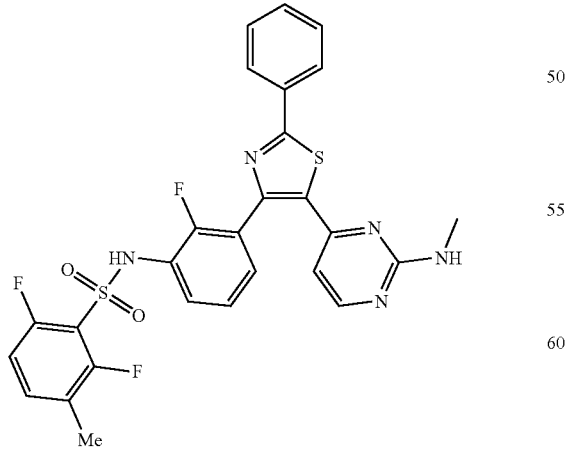
52
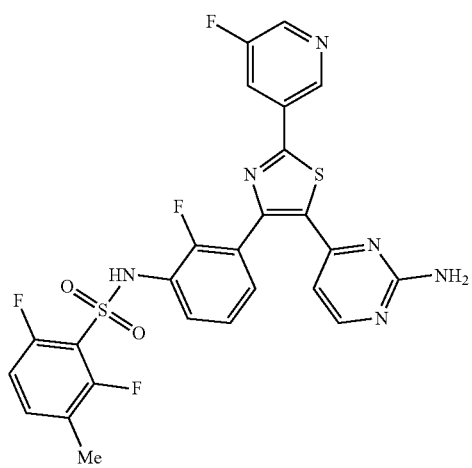
53
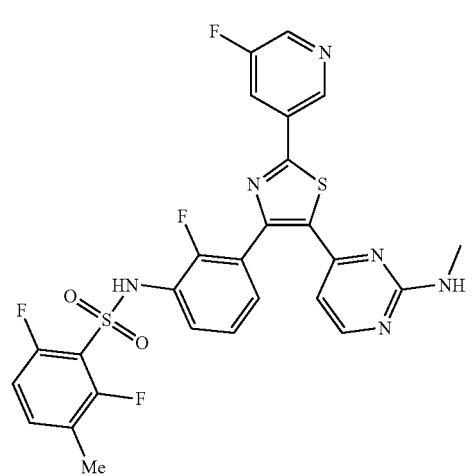
54
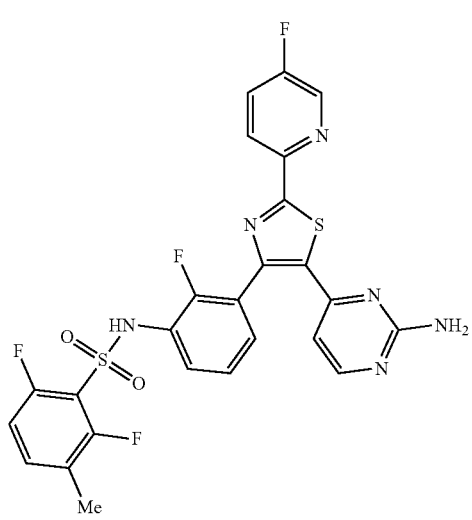

-continued
55
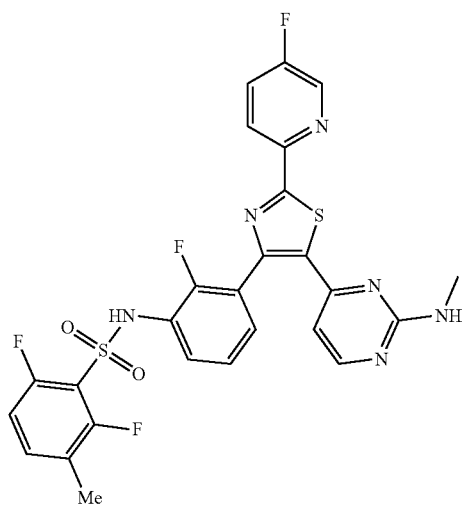
56
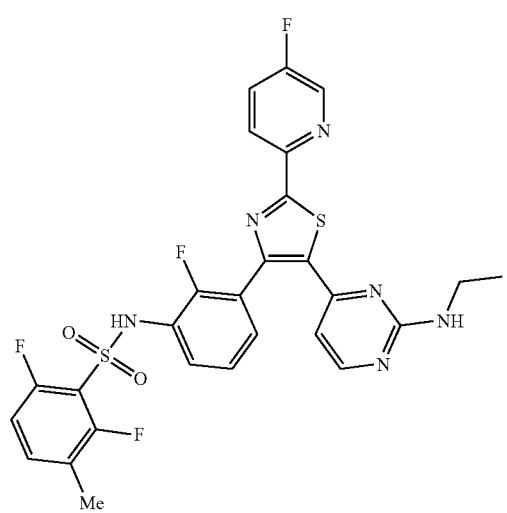
57
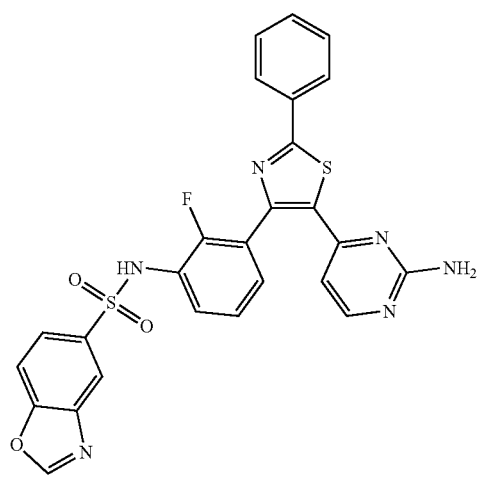
-continued
58
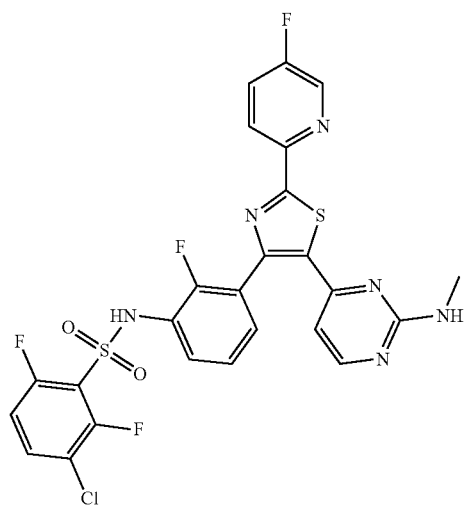
59
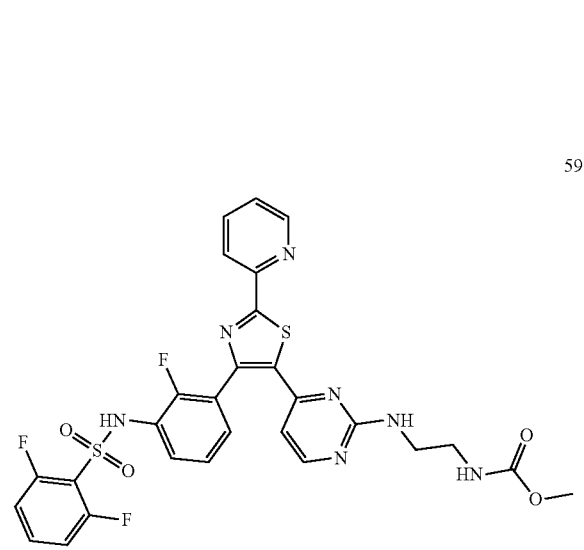
60
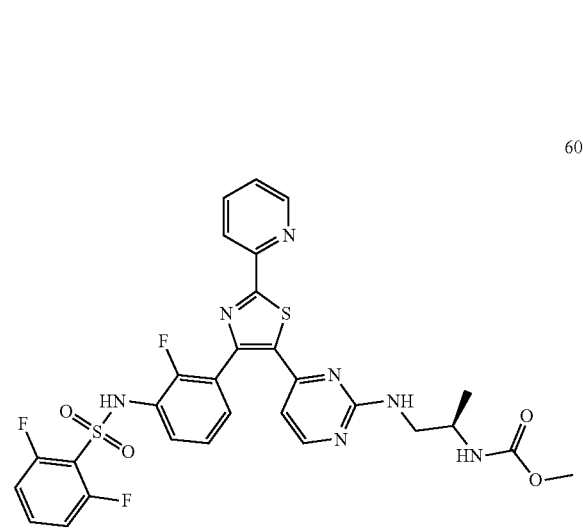

61
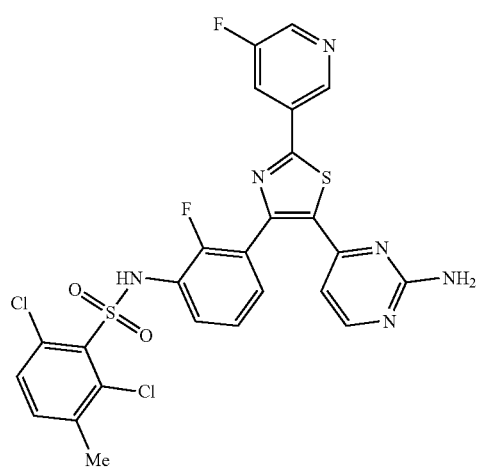
62
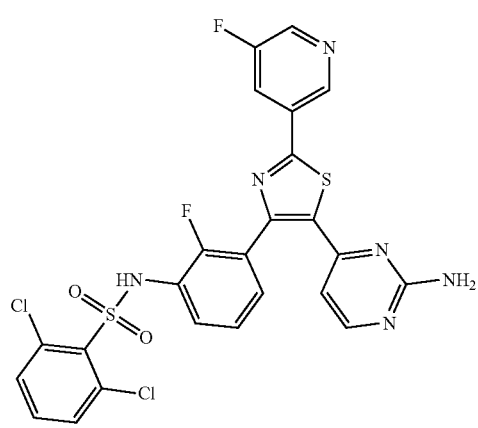
63
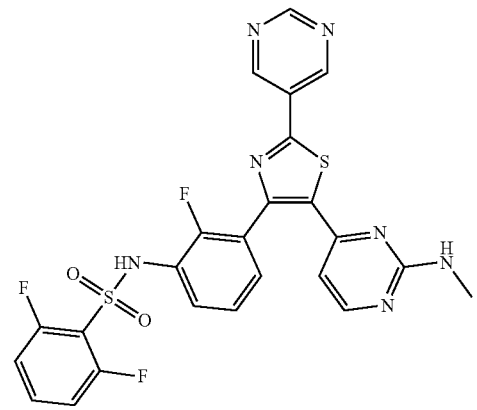
64
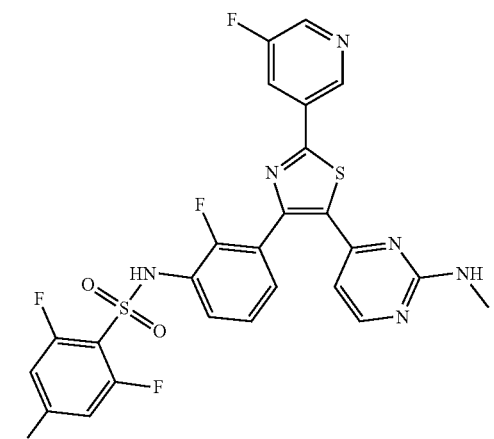
65
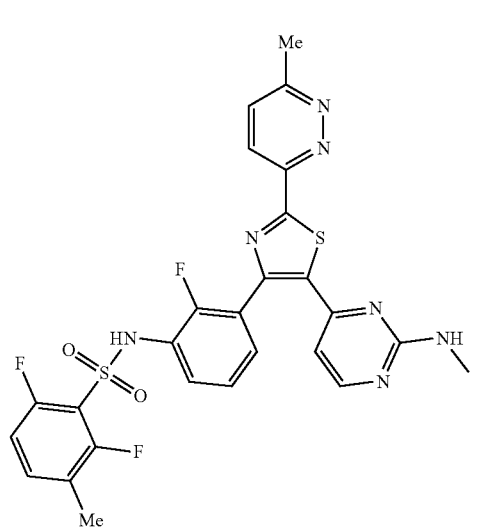
66
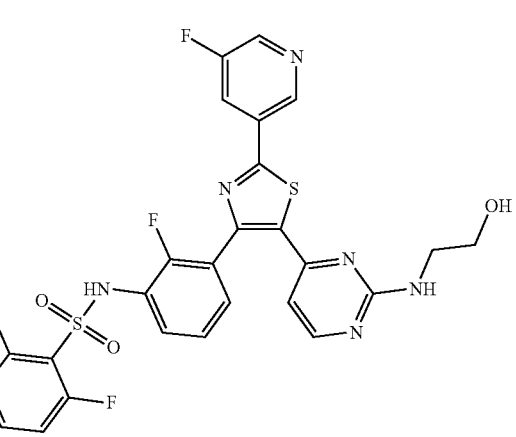

69
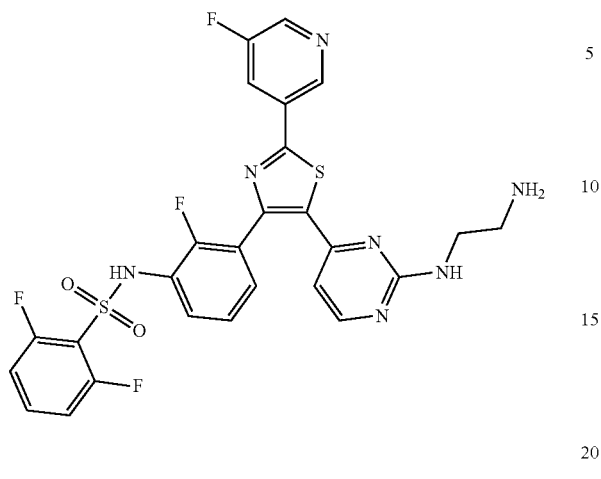
67
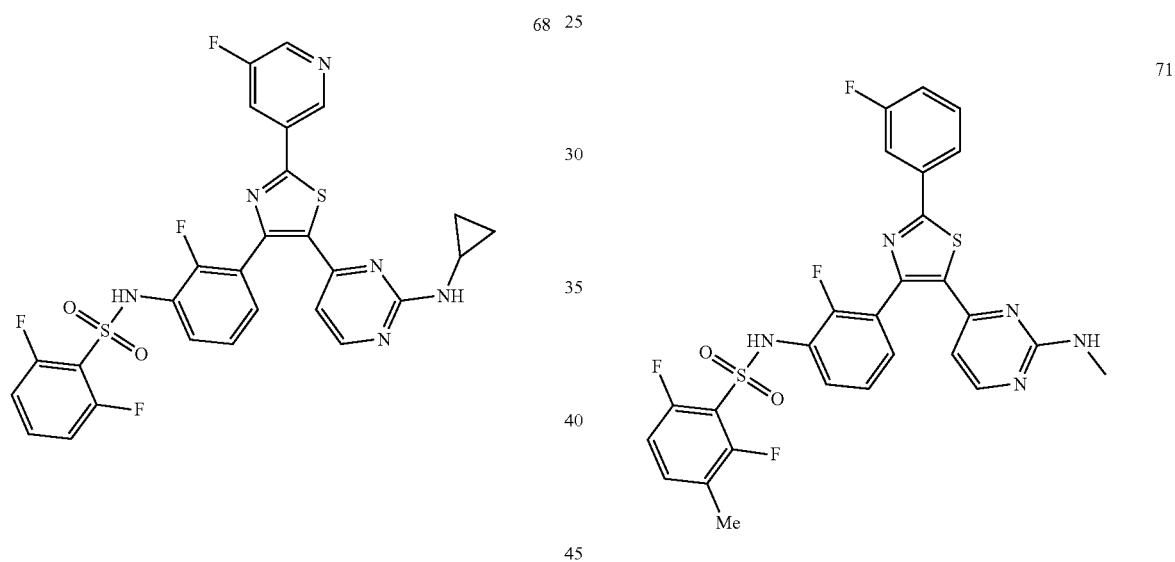
68
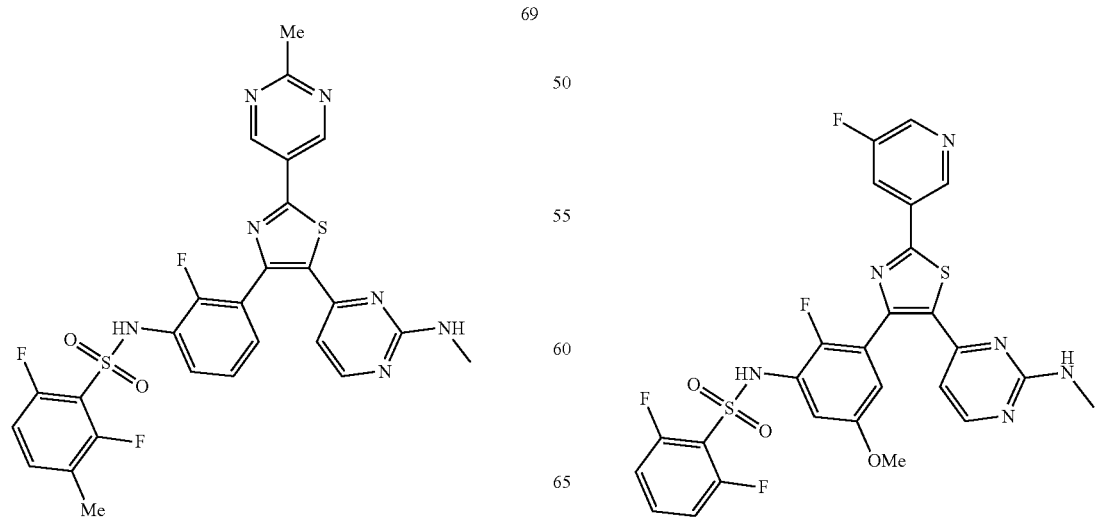
69
70
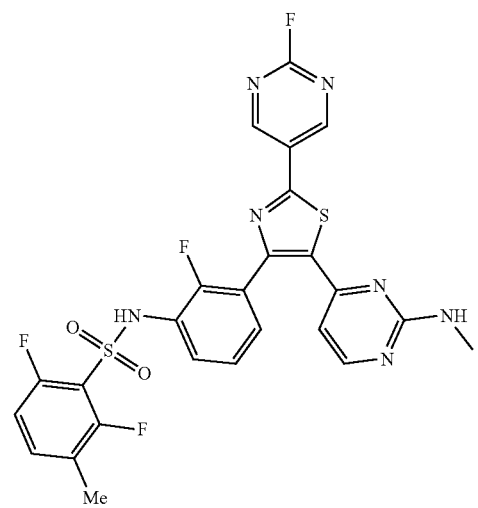
70
71
72

| 71 | 72 |
|---|---|
| -continued | -continued |
73
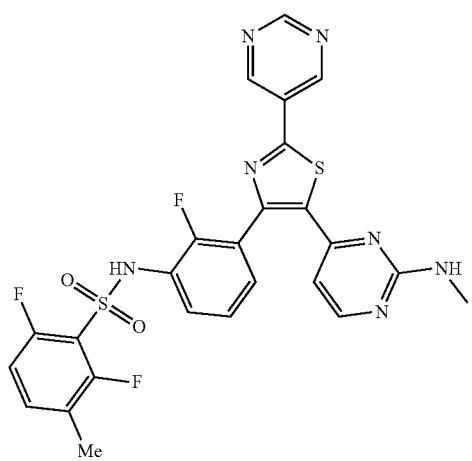
76
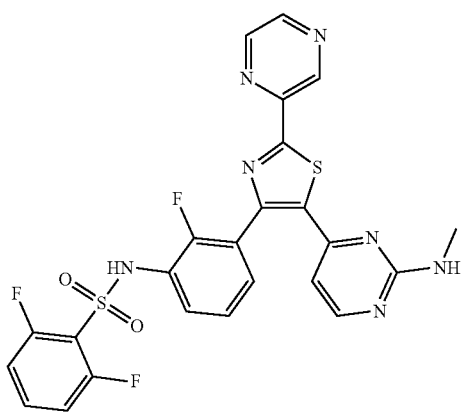
74
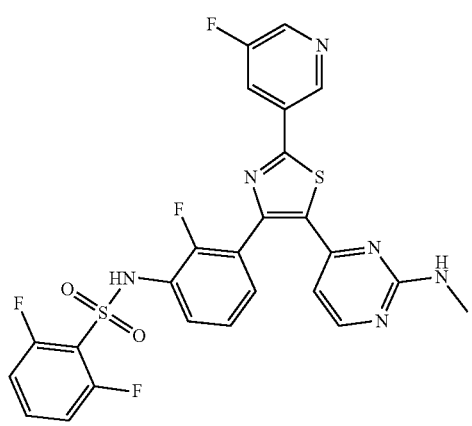
77
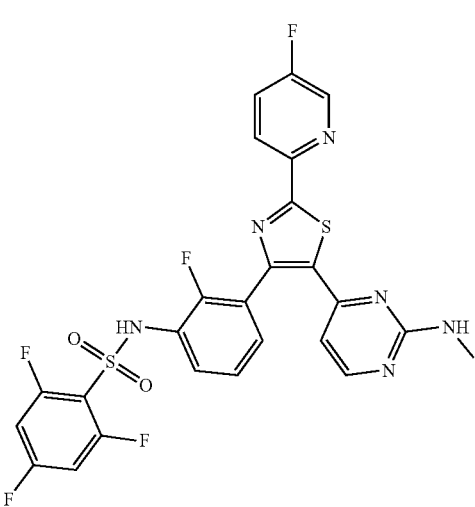
75
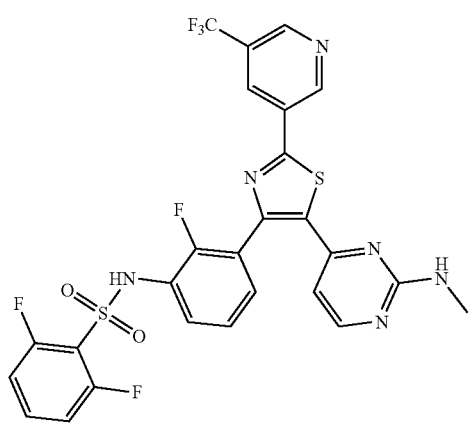
78
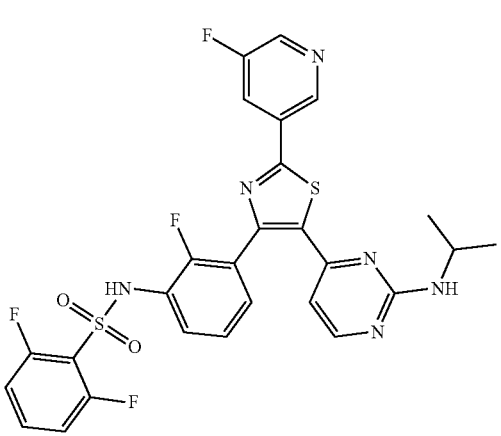

79
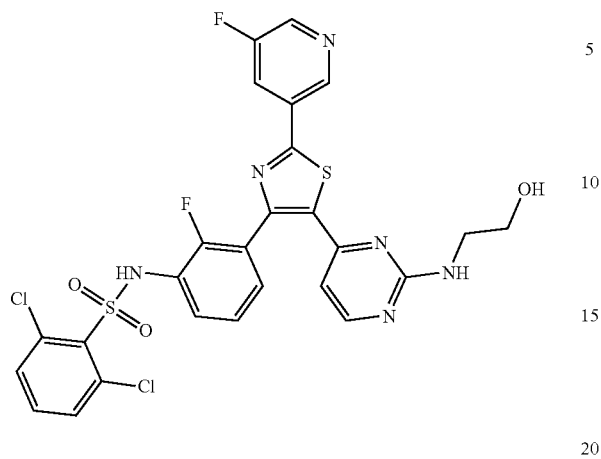
80
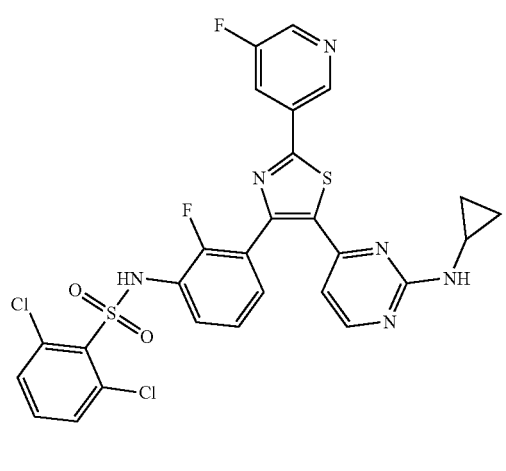
81
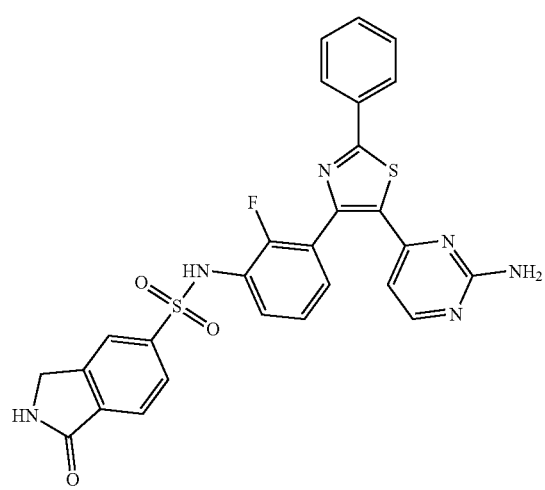
82
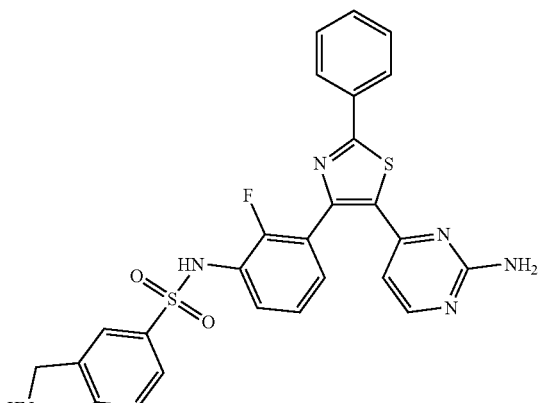
83
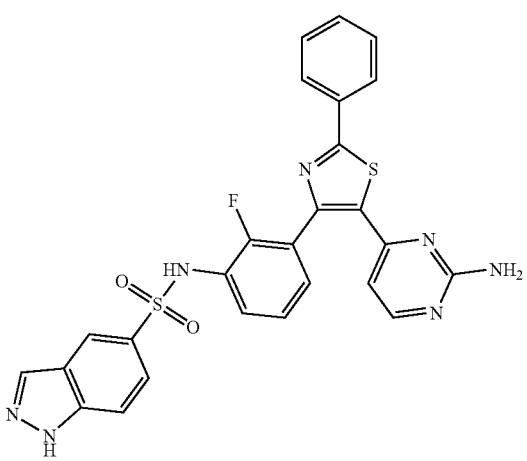
84
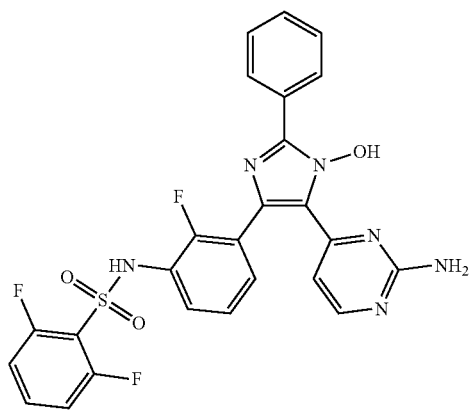

85
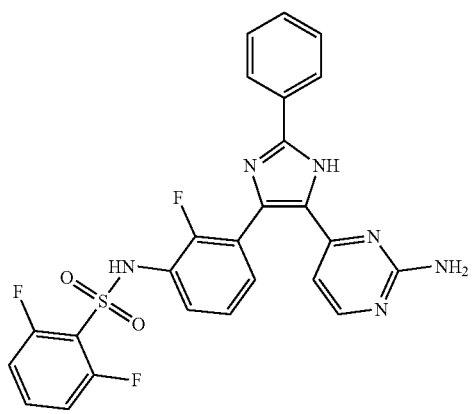
86
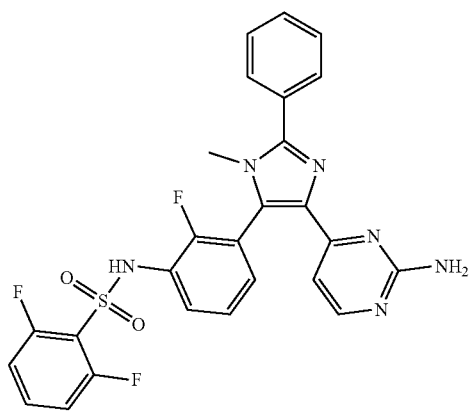
87
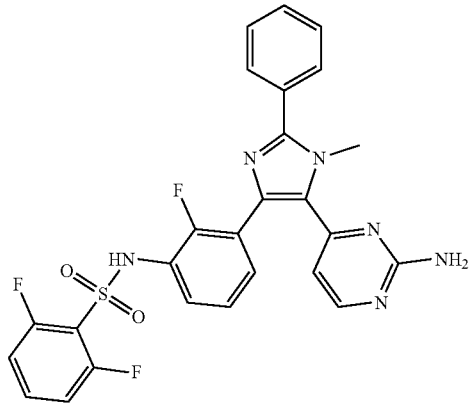
88
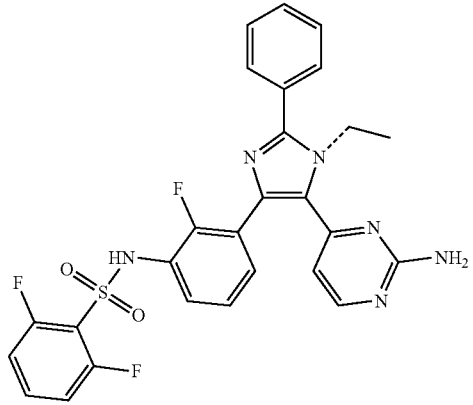
89
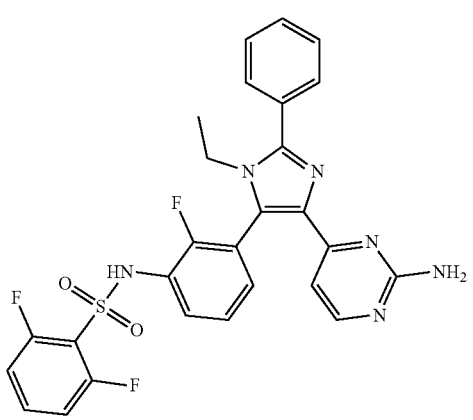
90
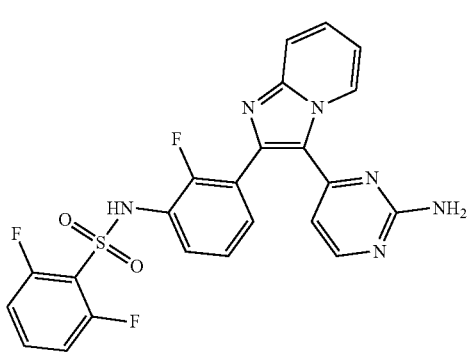
91
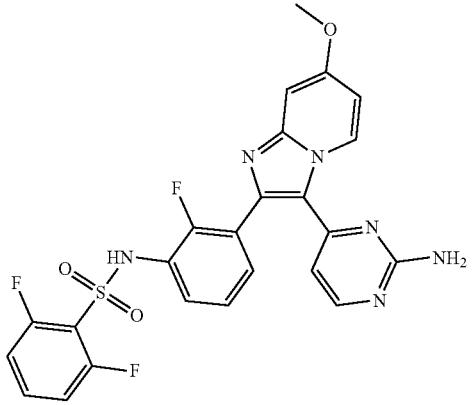
92
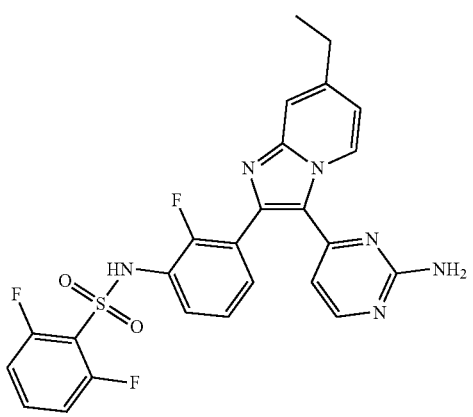

93
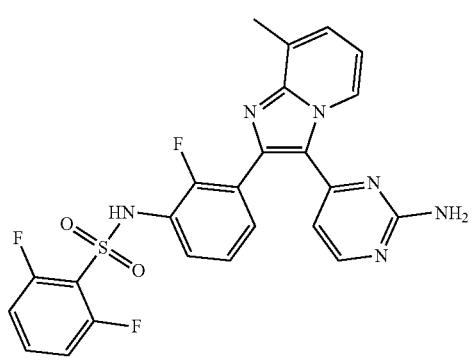
94
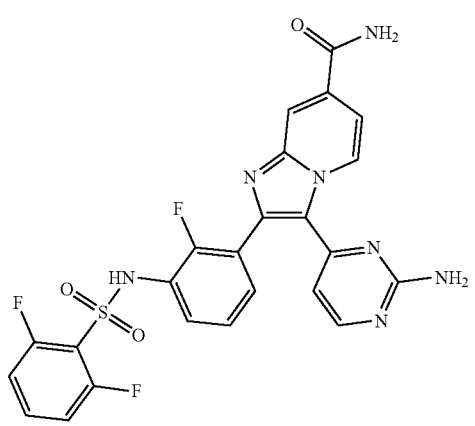
95
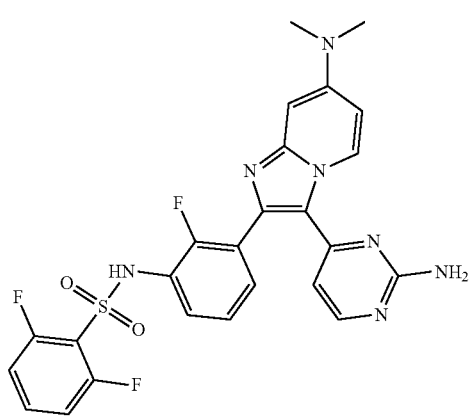
96
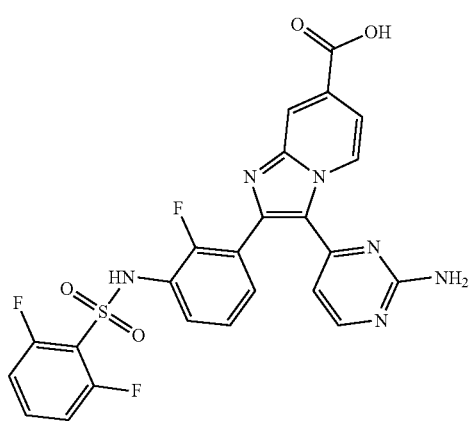
97
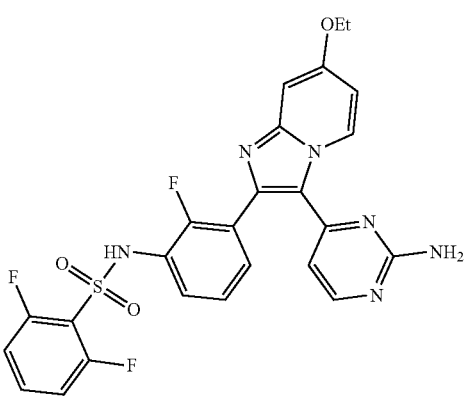
98
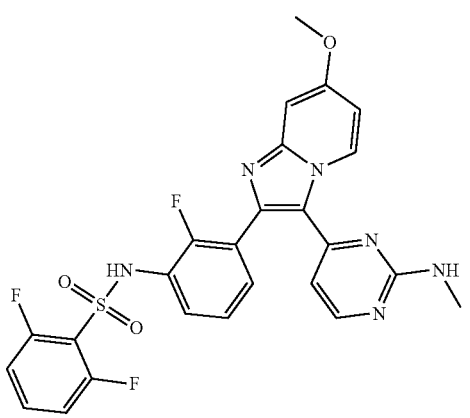
99
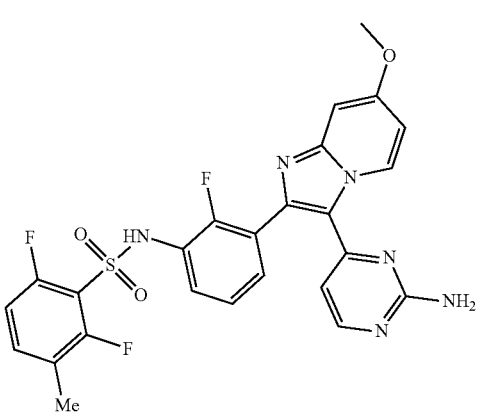
100
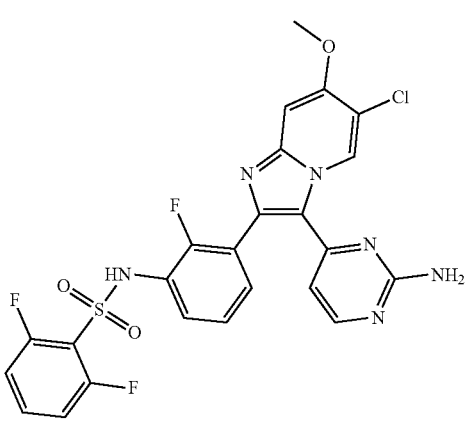

-continued
101
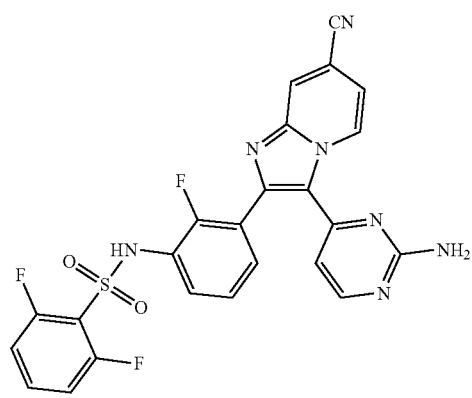
102
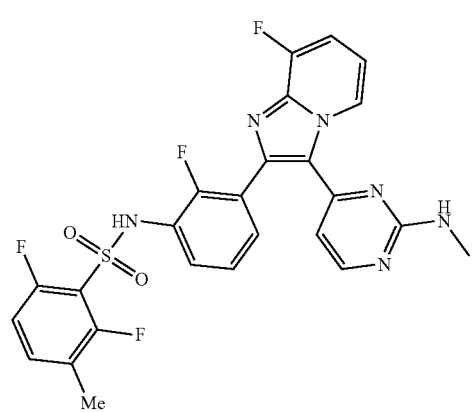
103
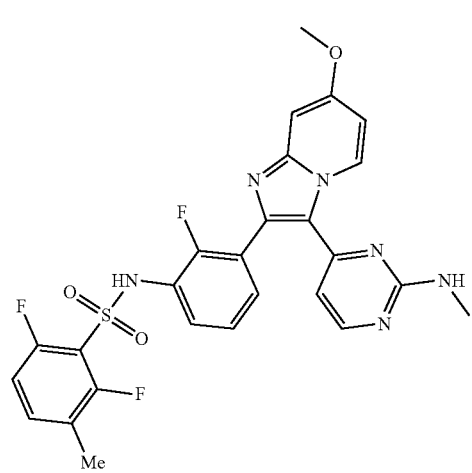
-continued
104
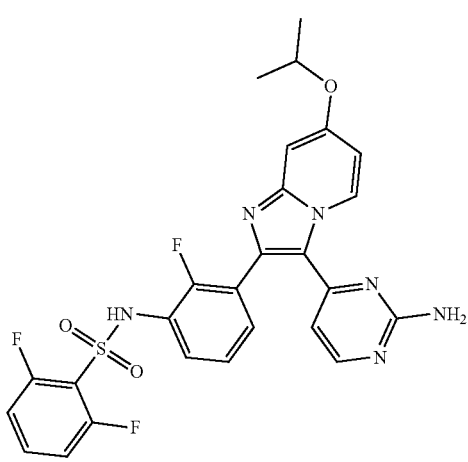
105
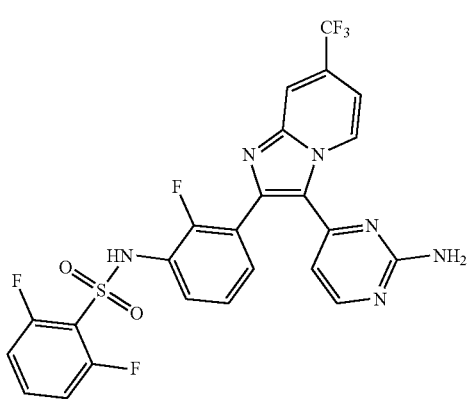
106
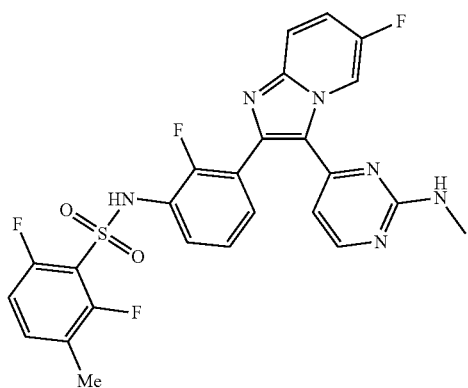

107 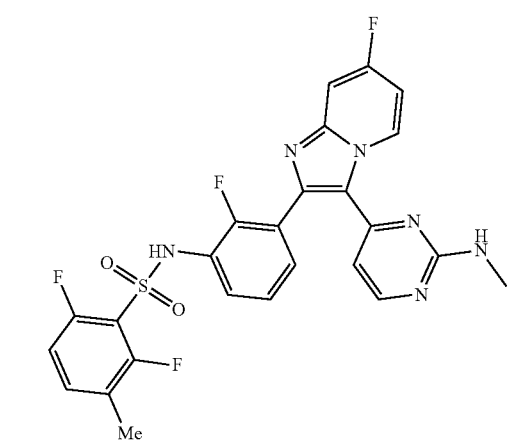
108 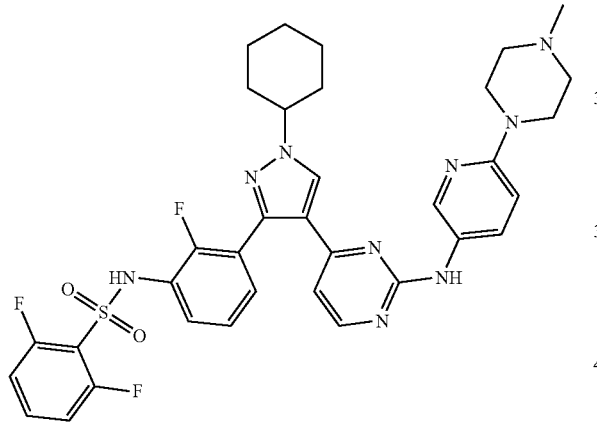
109 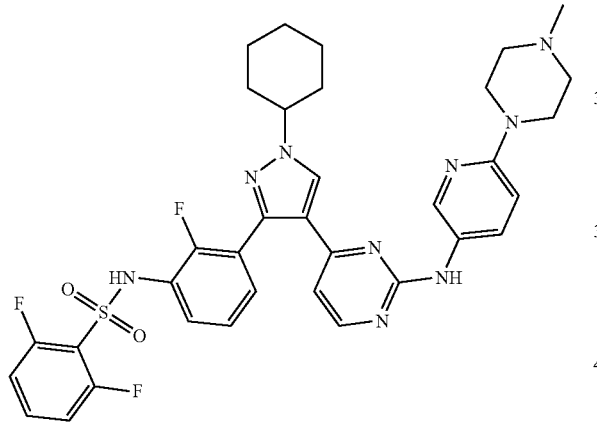
110 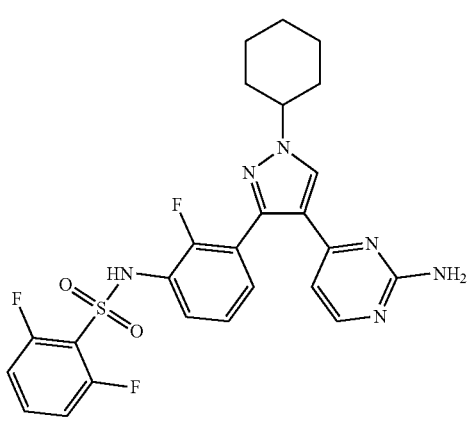
111 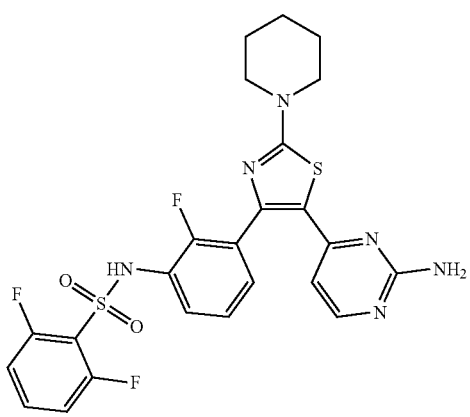
112 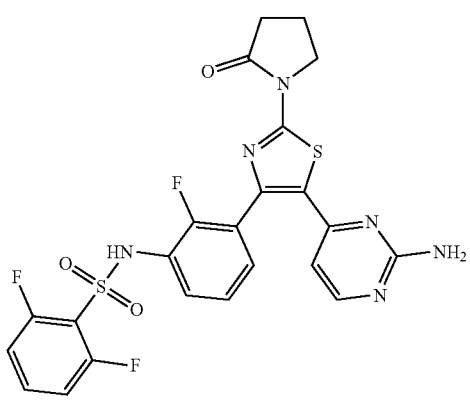
113 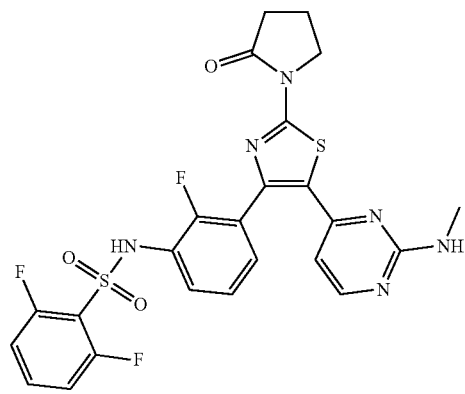

114 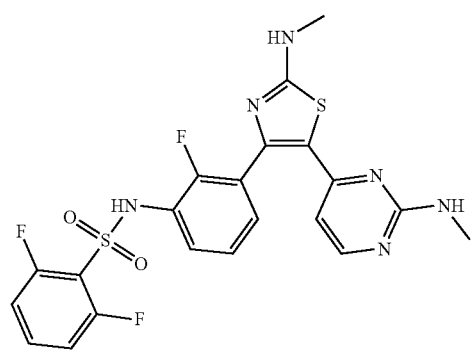
115 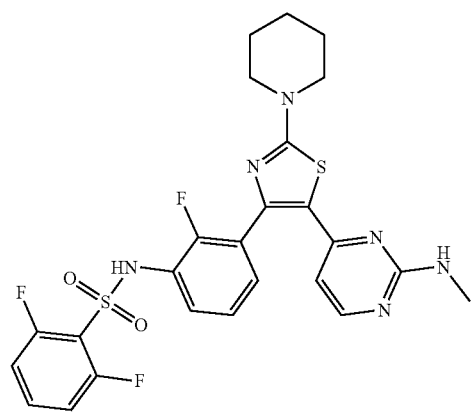
116 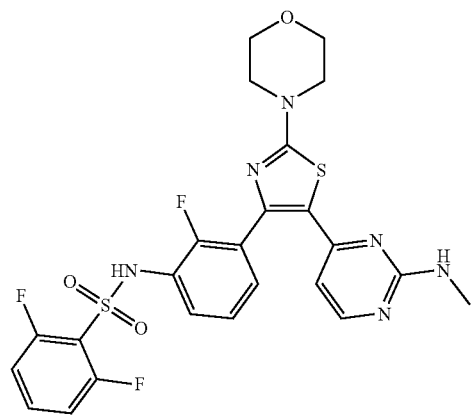
117 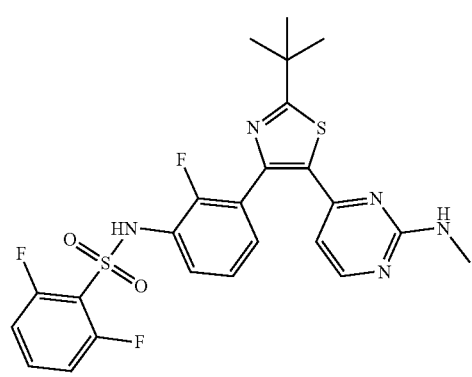
118 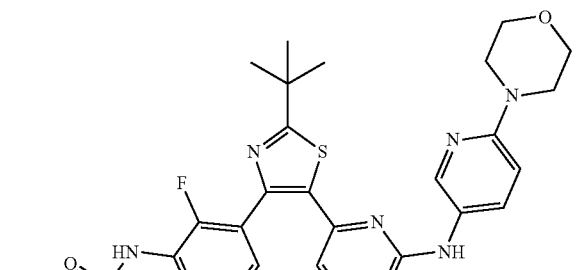
119 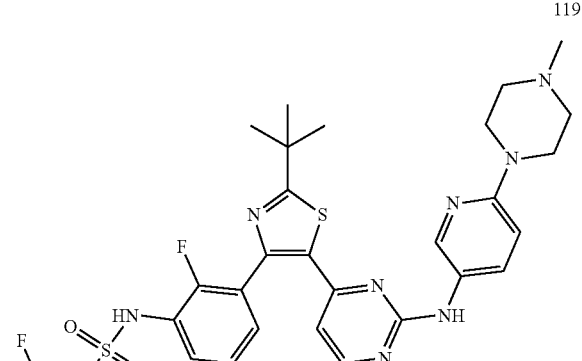
120 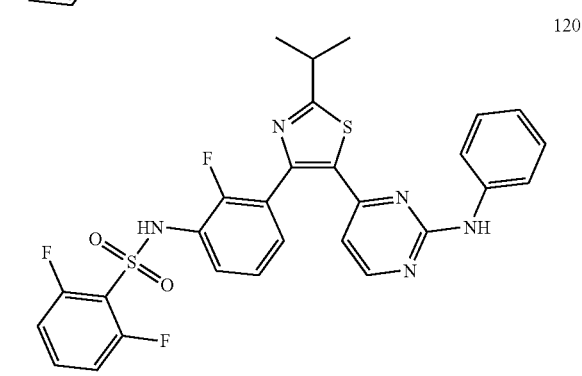
121 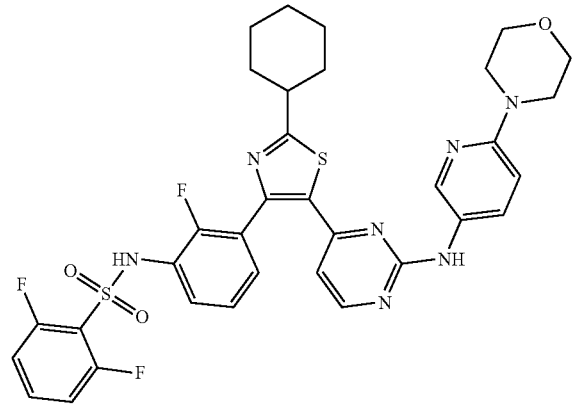

122 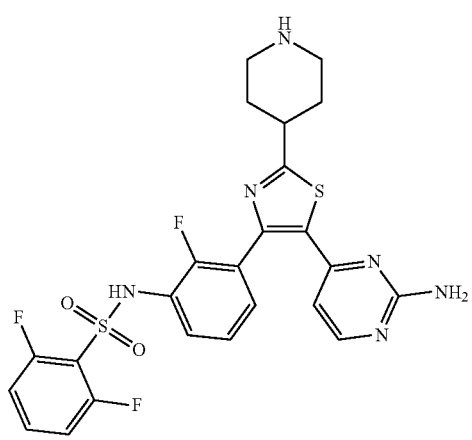
123 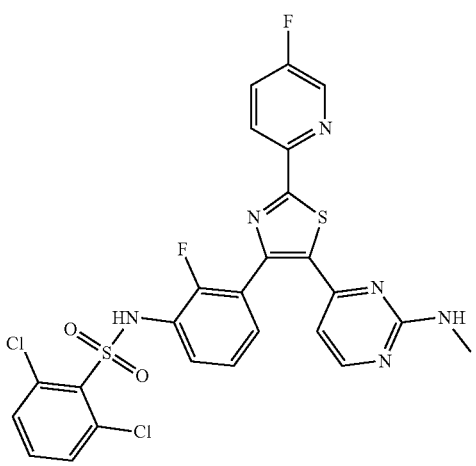
124 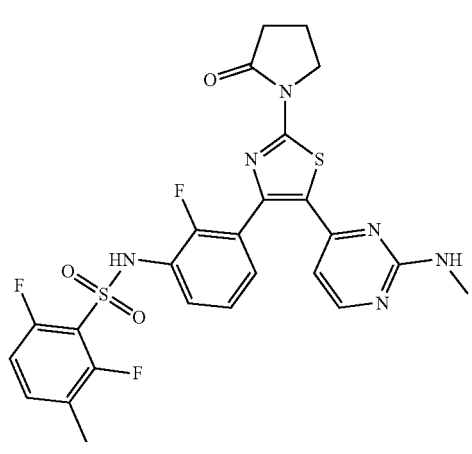
125 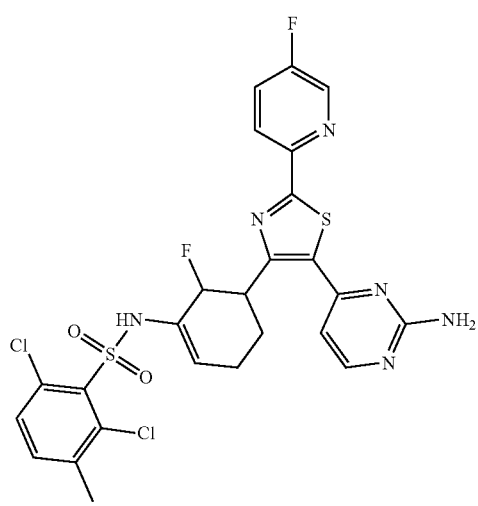
126 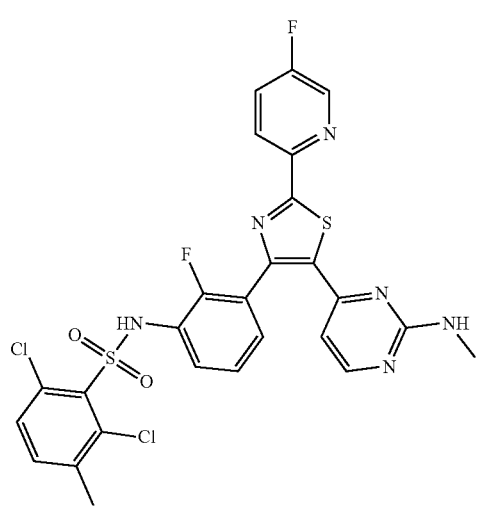
127 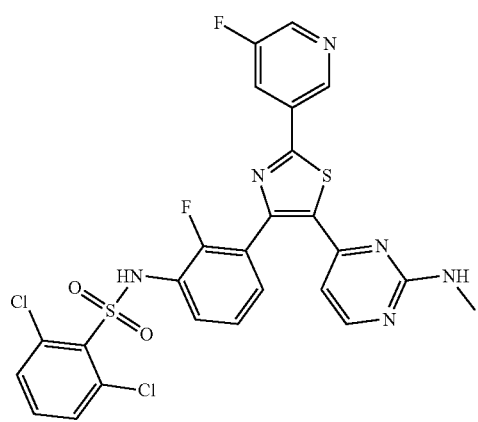

87
-continued
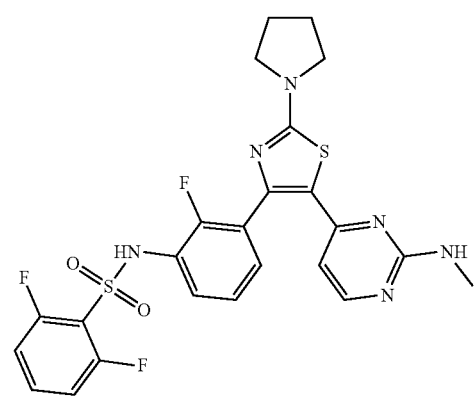
128
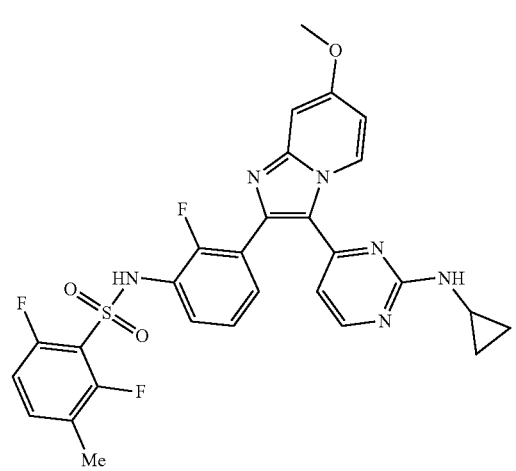
129
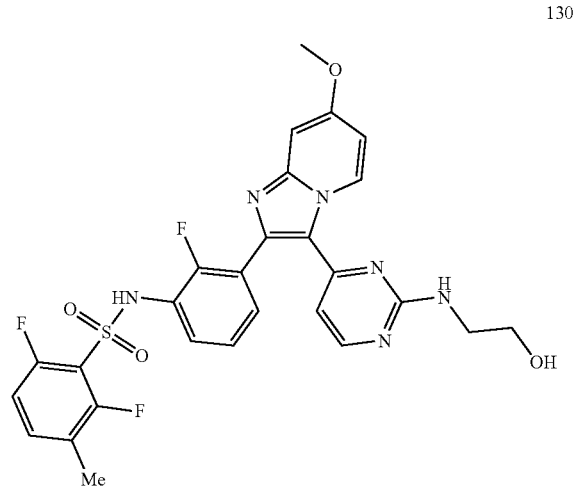
130
88
-continued
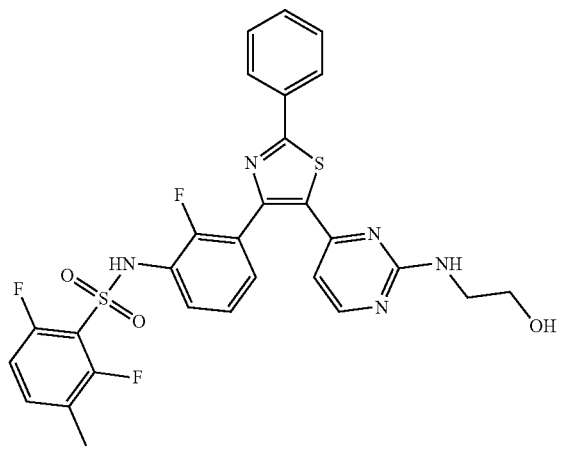
131
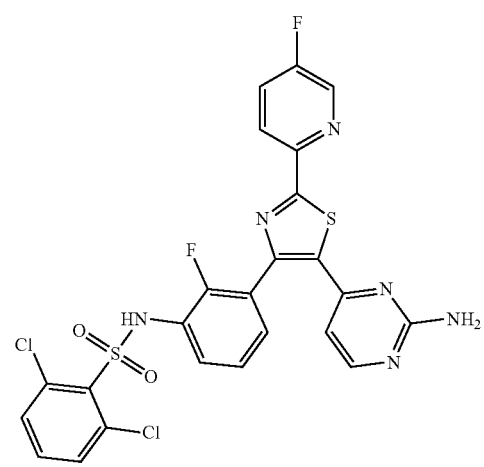
132
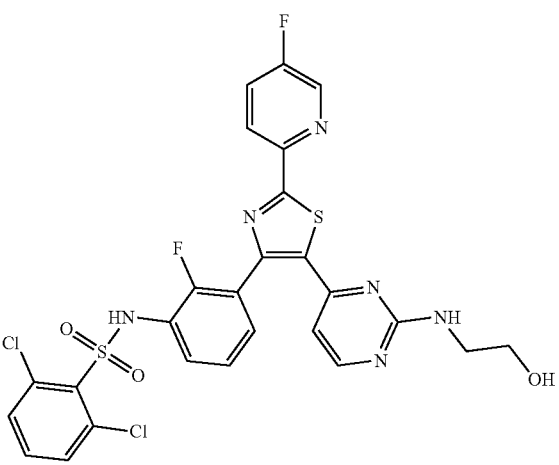
133

| | |
|---|---|
| 134 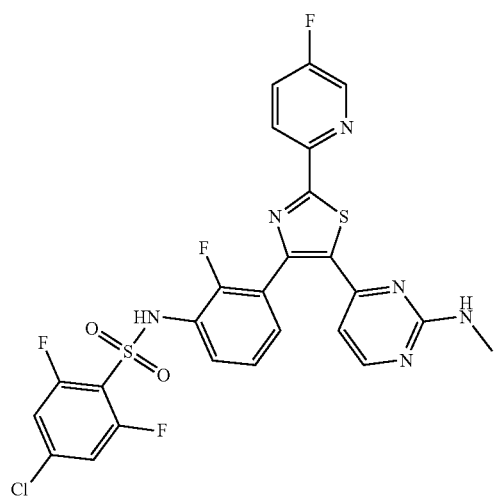 | 137 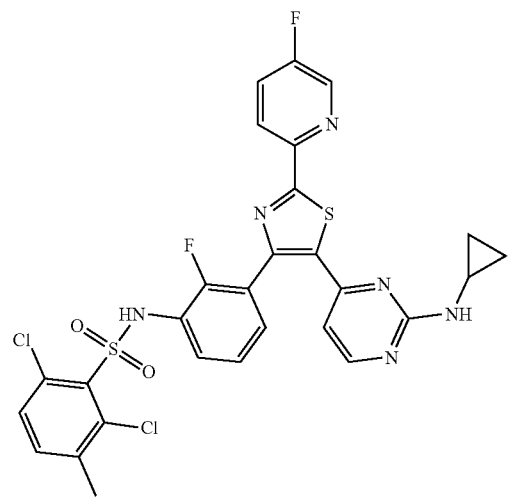 |
| 135 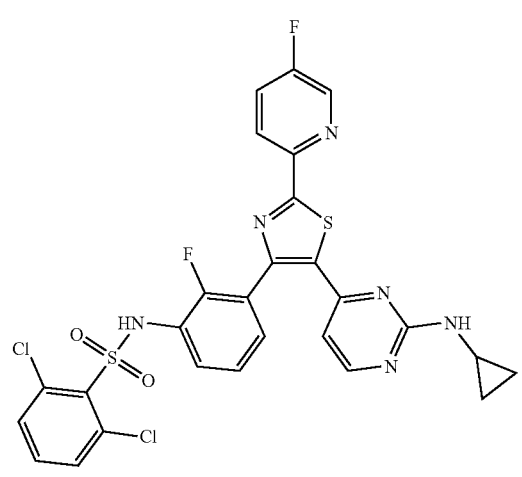 | |
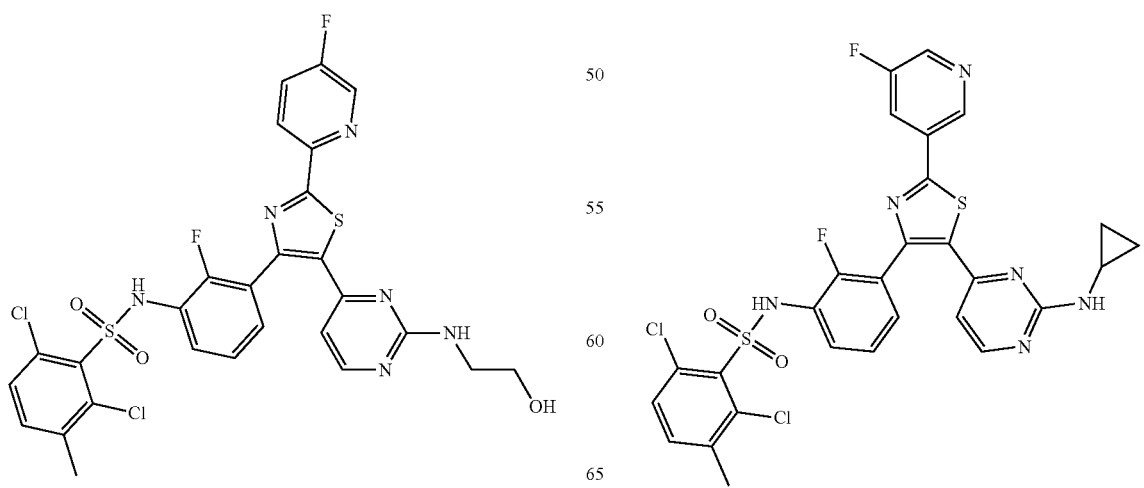

140
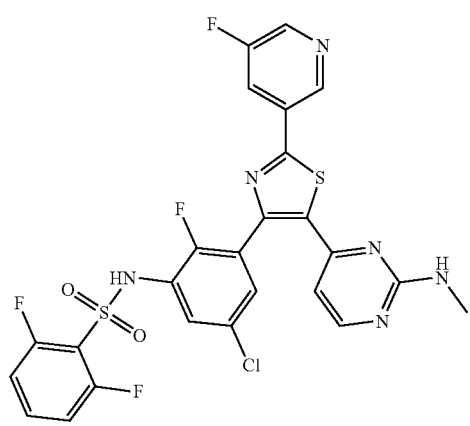
141
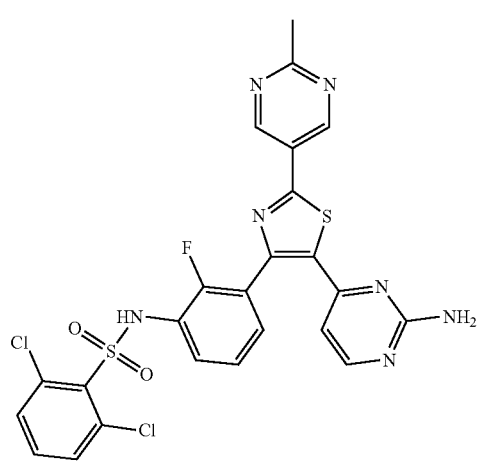
142
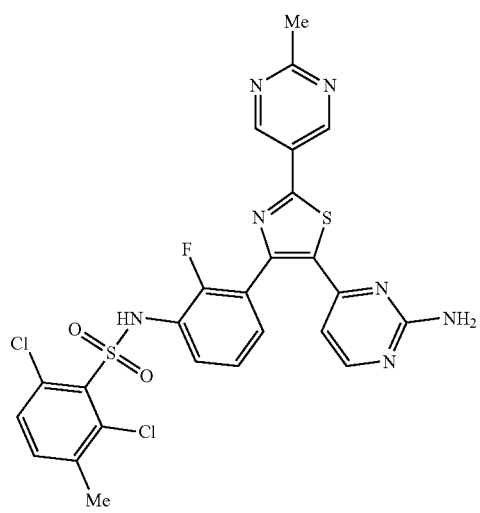
143
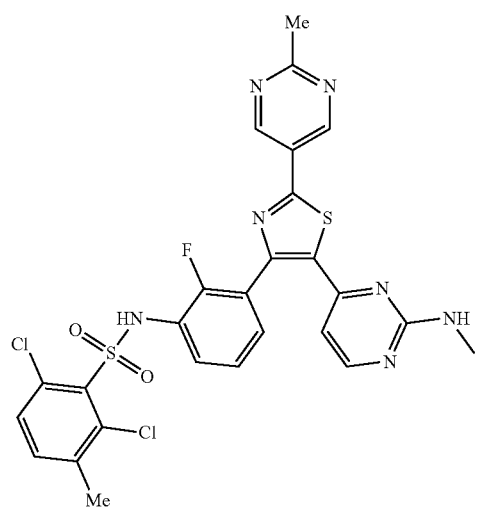
144
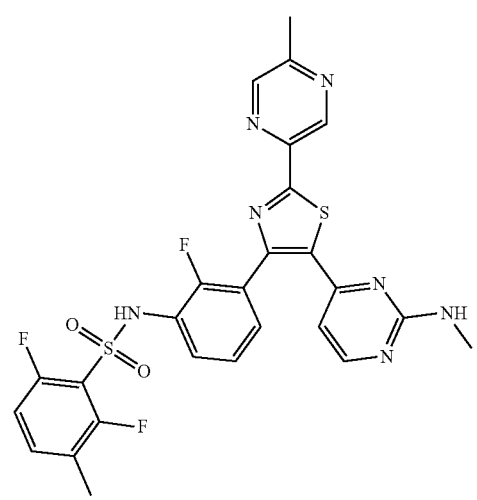
145
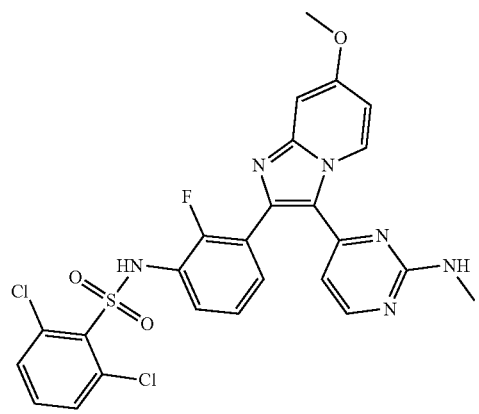

93
-continued
146
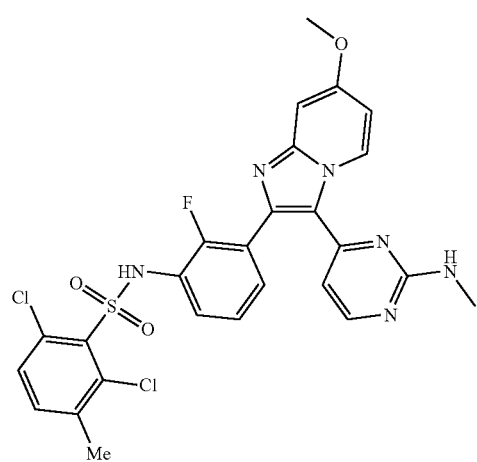
147
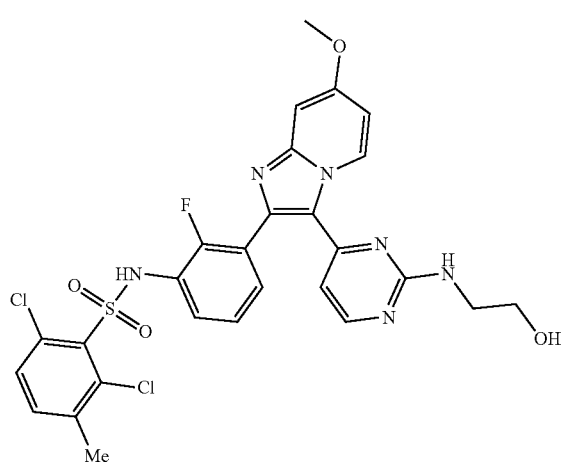
148
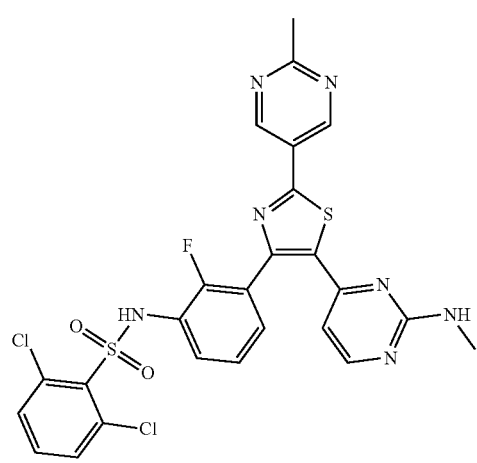
94
-continued
149
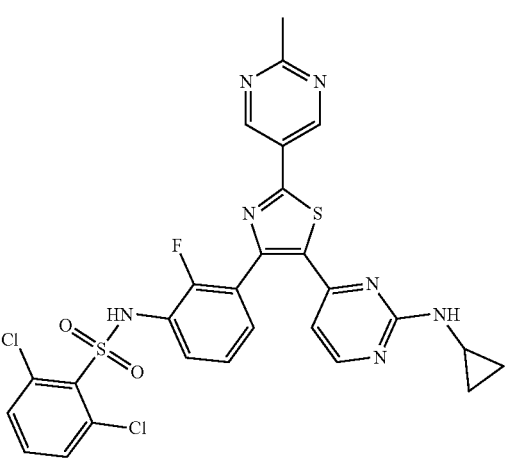
150
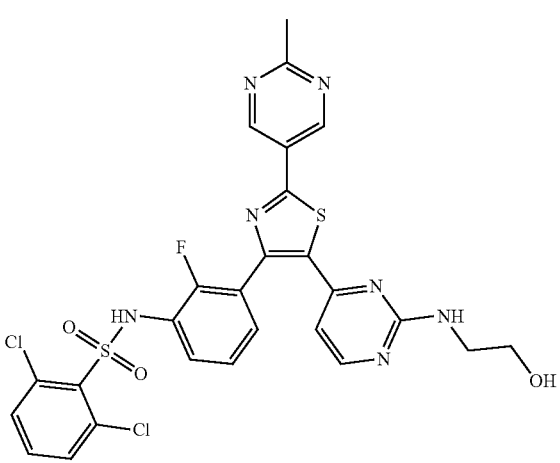
151
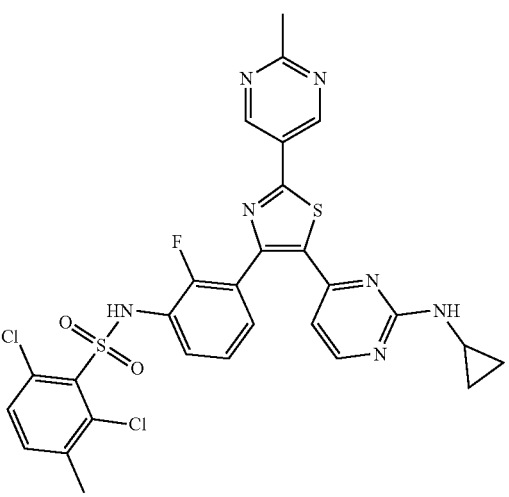

-continued
152
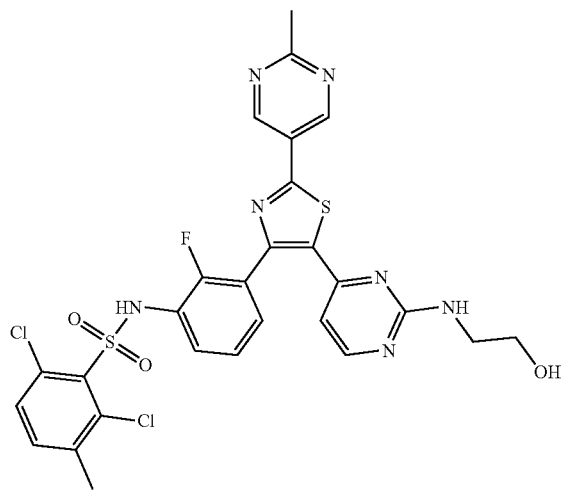
153
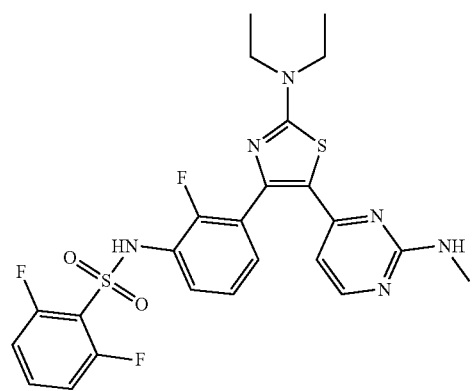
154
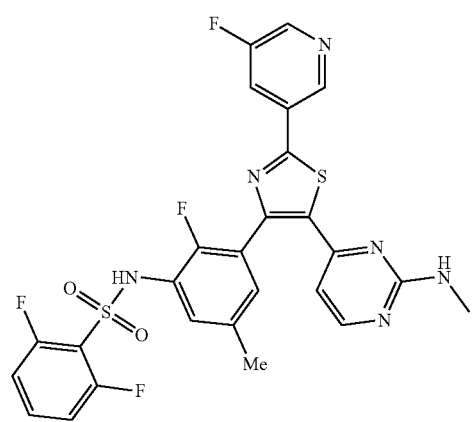
-continued
155
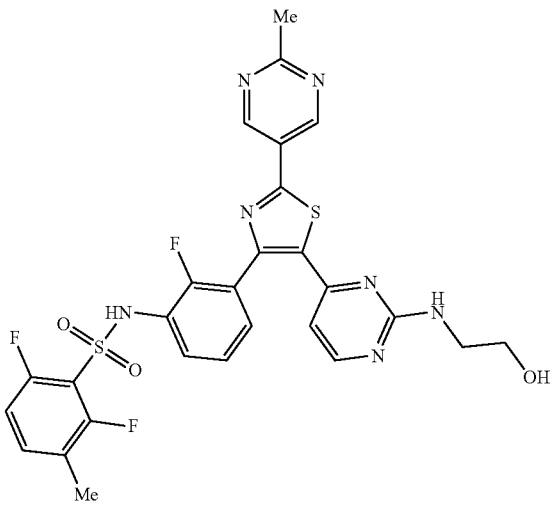
156
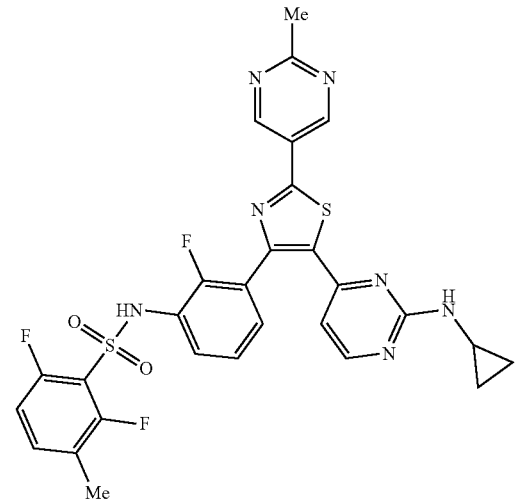
157
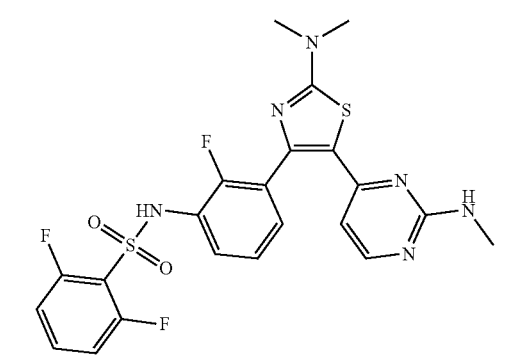

158
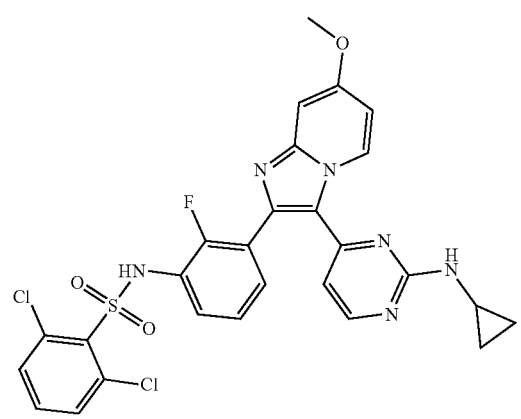
159
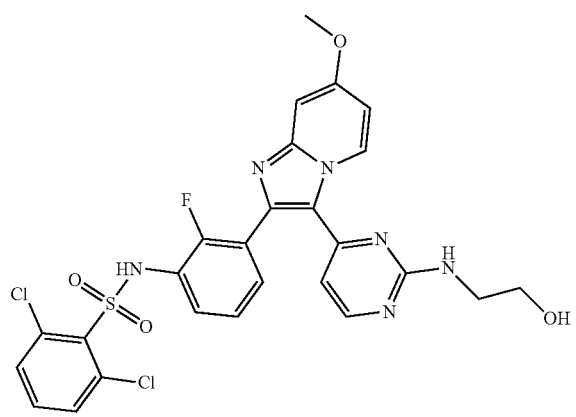
160
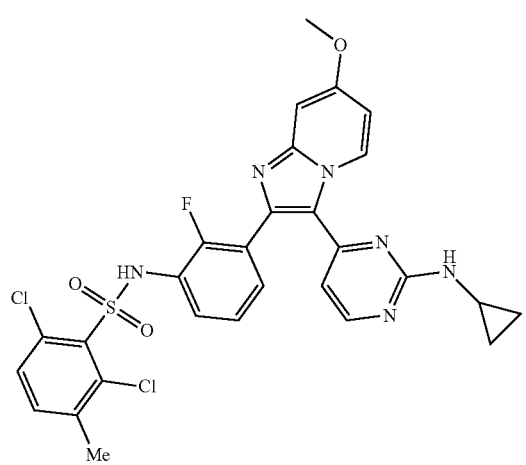
161
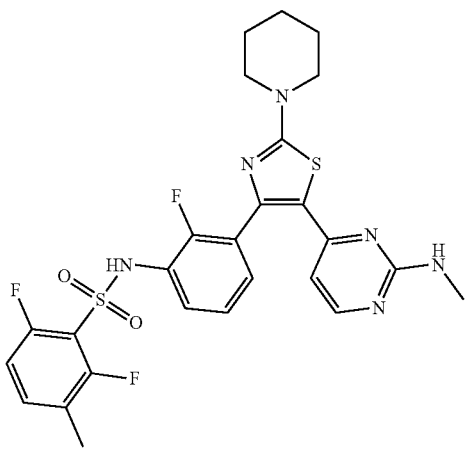
162
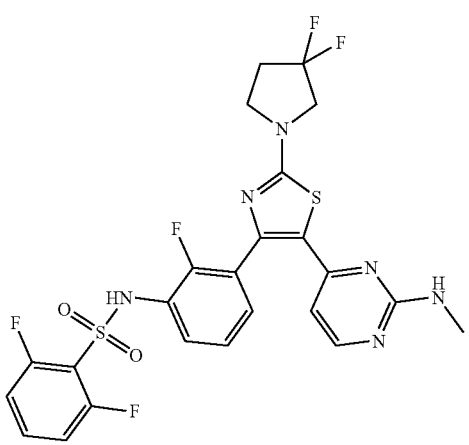
163
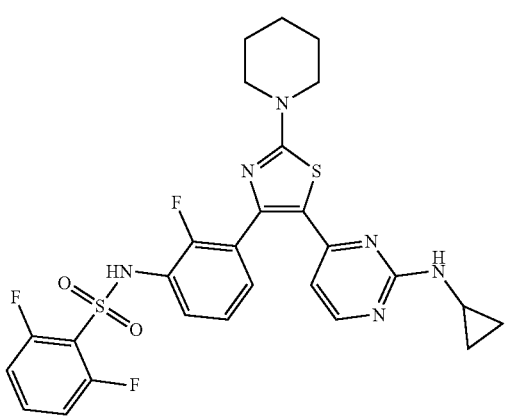

| 164 | 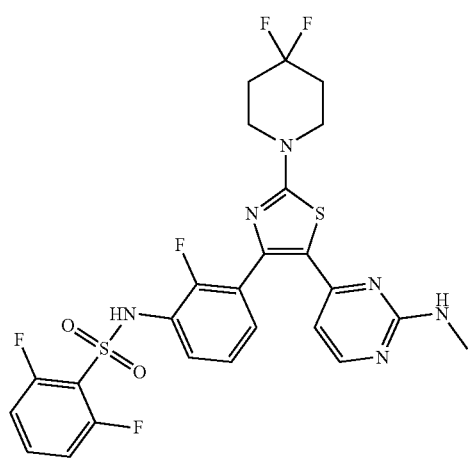 | 167 | 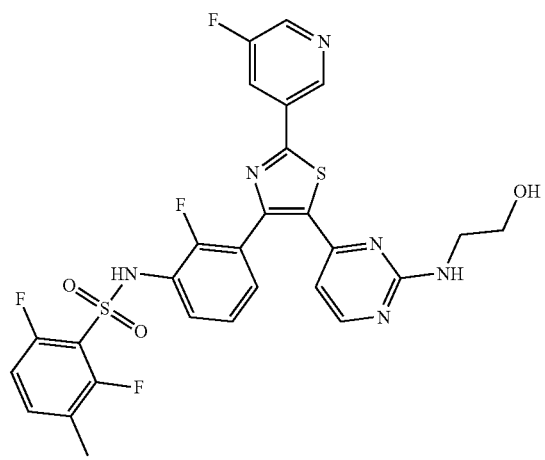 |
| 165 | 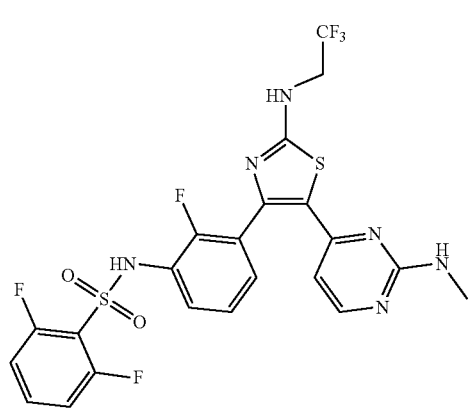 | 168 | 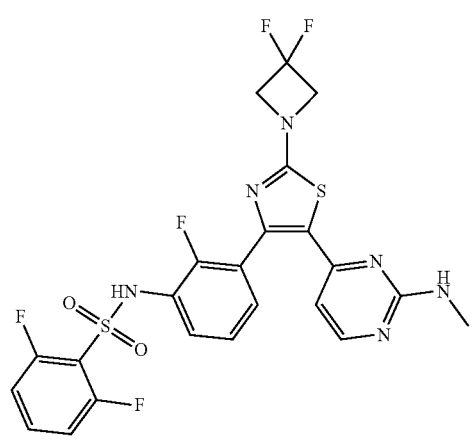 |
| 166 | 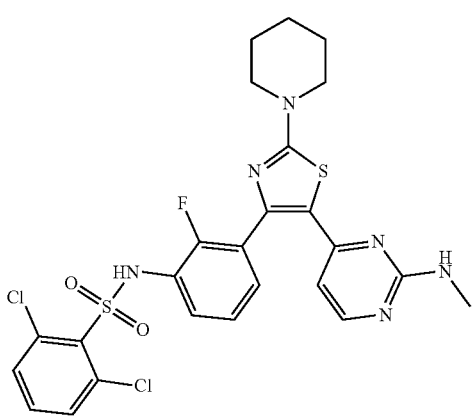 | 169 | 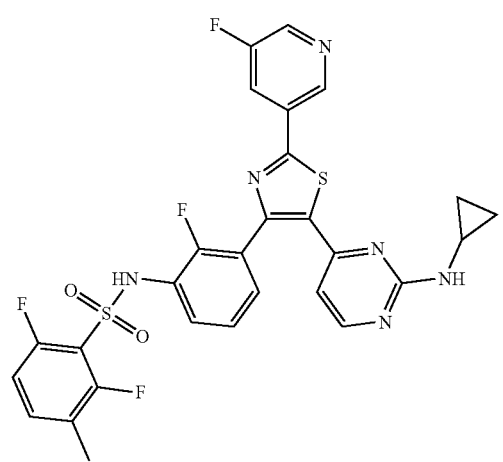 |

-continued
170
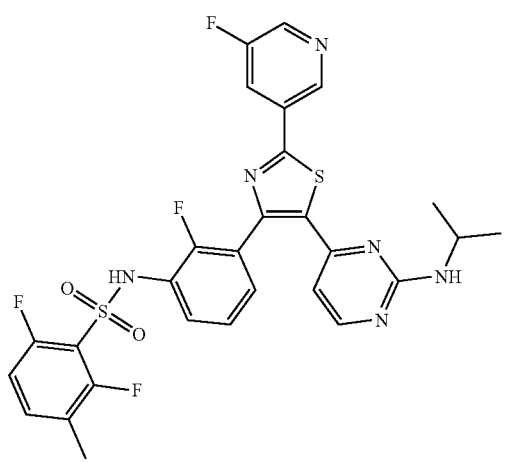
171
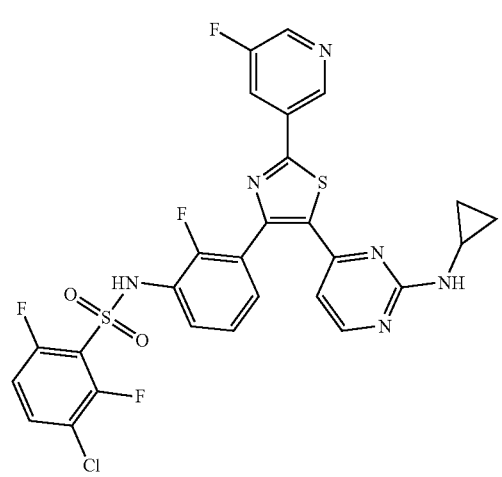
172
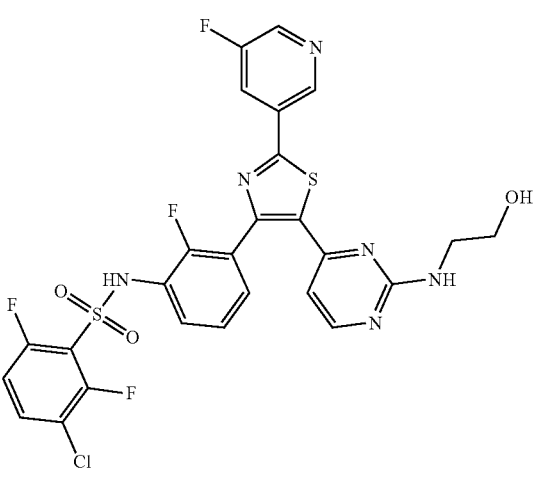
-continued
173
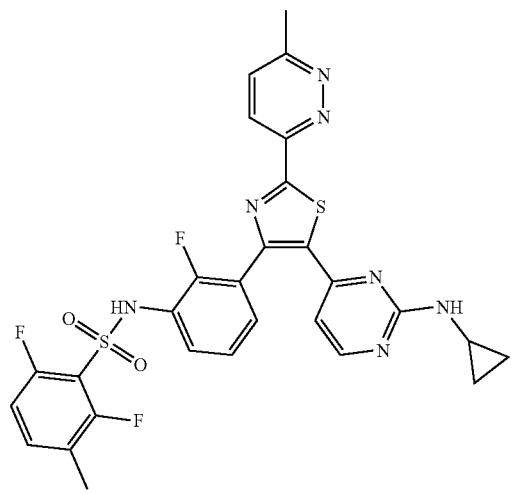
174
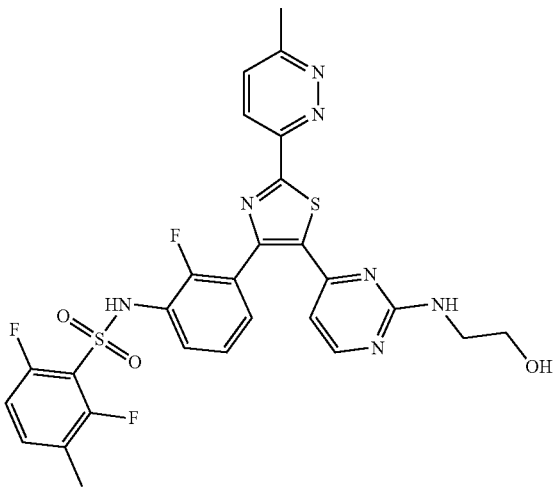
175
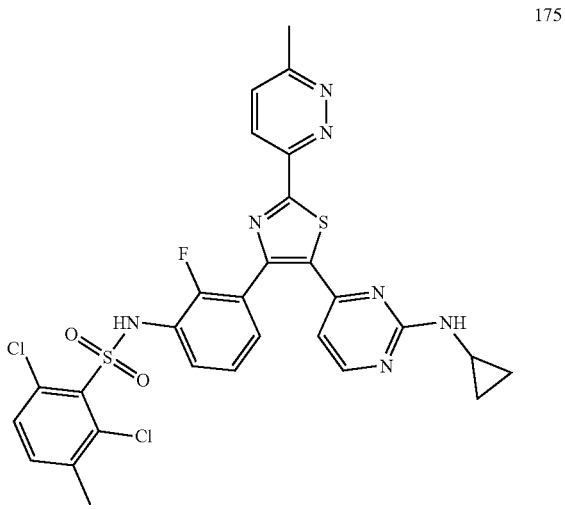

| 176 | 179 |
|---|---|
| 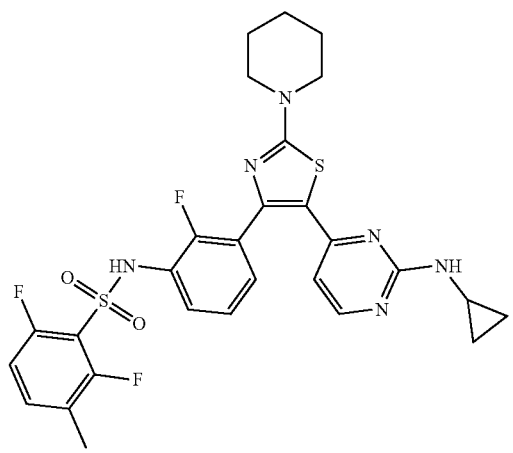 | 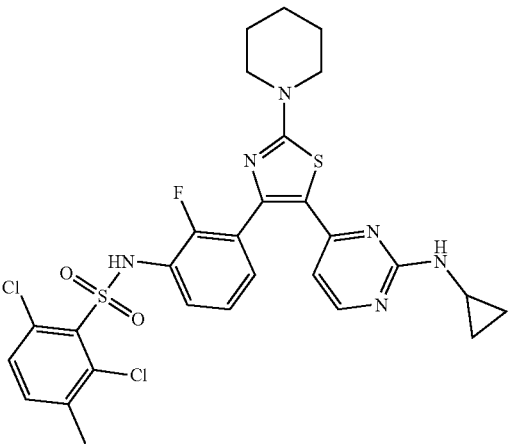 |
| 177 | 180 |
| 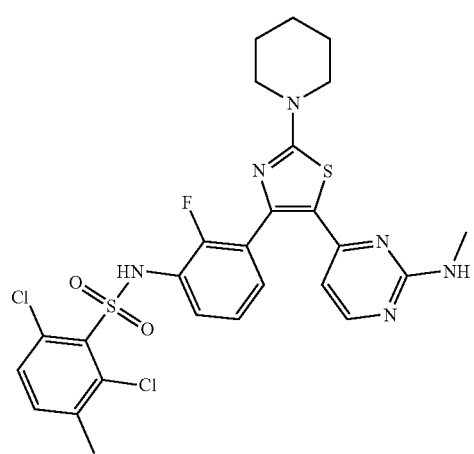 | 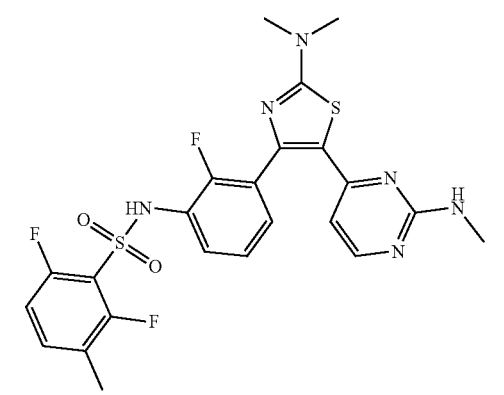 |
|  | 181 |
|  | 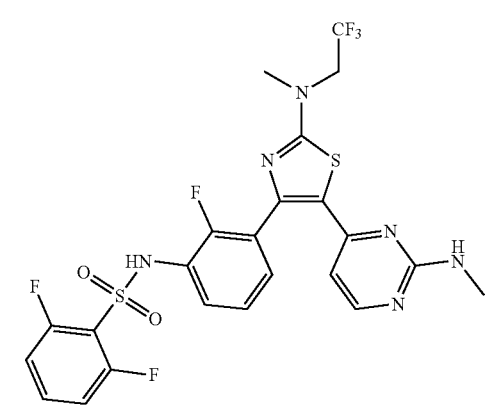 |
| 178 | 182 |
| 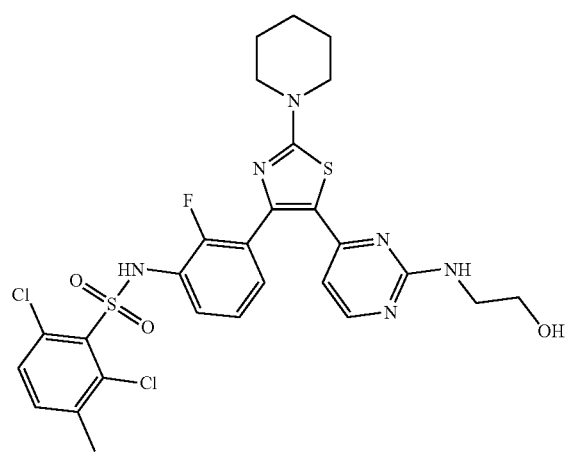 | 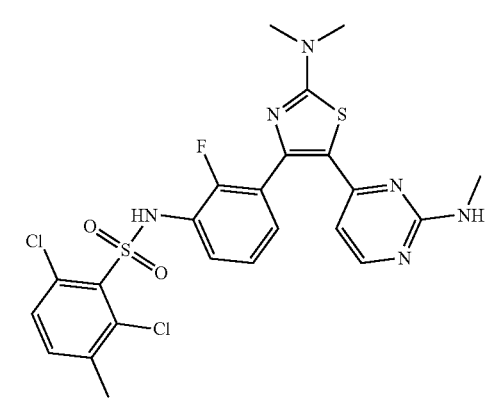 |

-continued
183
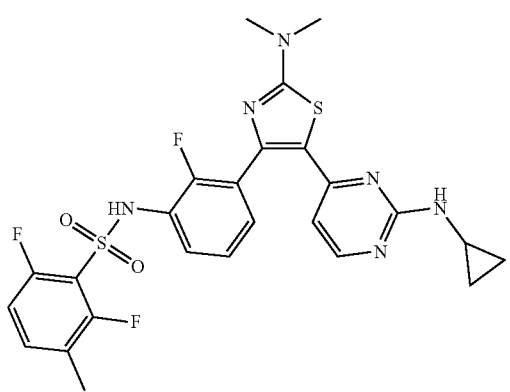
184
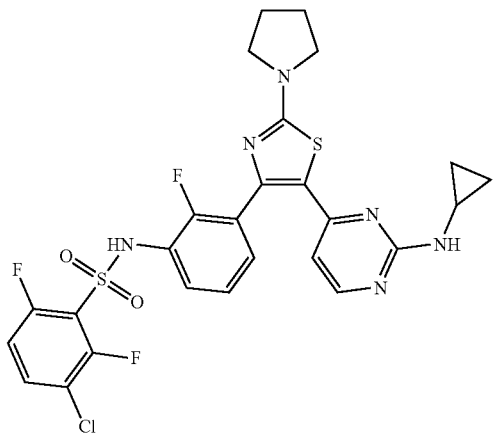
185
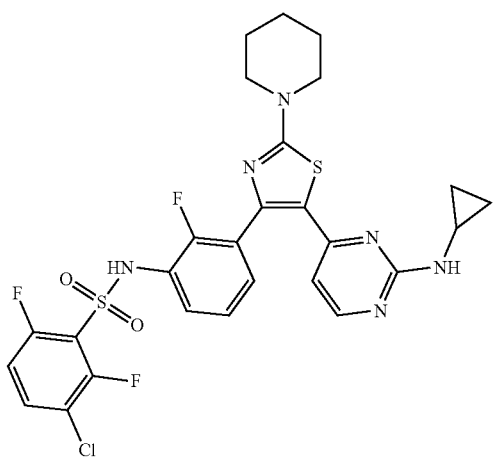
-continued
186
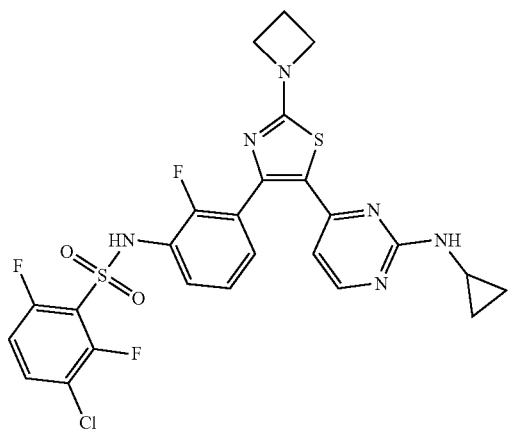
187
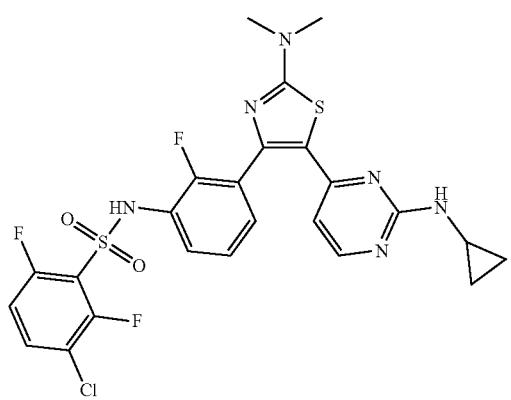
188
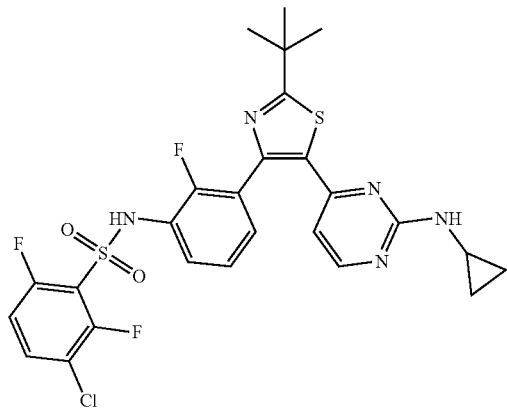

-continued

189

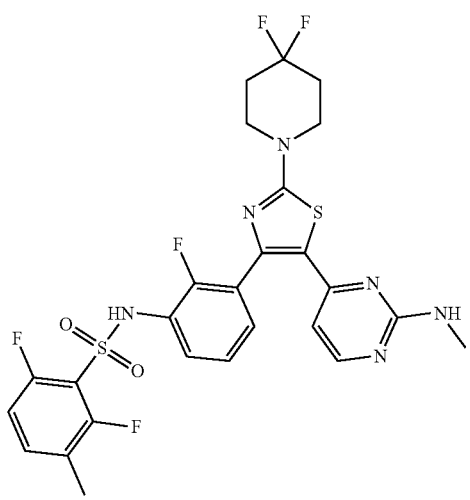

Method of Synthesis

Certain embodiments of the present disclosure are also directed to methods of synthesizing the compounds herein.

The compounds described herein can be prepared from readily available starting materials using methods described herein (see e.g., the Examples section) and those known in the art. For example, Scheme 1 shows one method of preparing a compound of Formula G-1, wherein $R^8$, $R^5$, $R^7$, and $R^7$ are defined as in Formula G. Scheme 1 employs a thiazole synthesis as one key step. Thus, a pyrimidine starting material S-1, wherein $G^1$ is a leaving group, preferably Cl, can be deprotonated with a suitable base and then react with an acyl compound S-2, wherein $G^2$ is a leaving group, preferably $C_{1-4}$ alkoxy such as methoxy, to form a ketone S-3. This ketone S-3 can then be converted into a thioketone S-5, typically through a two-step sequence: introducing a leaving group at the alpha-position of the ketone, and substituting the leaving group with thioamide S-4 under suitable conditions. The thioketone S-5 can then be cyclized to form thiazole S-6. After which, the $G^1$ group in S-6 can be replaced with a suitable amine to form a compound of Formula G-1. Example 1 shows an exemplary synthesis according to Scheme 1. Those skilled in the art can readily adapt the methods described in Scheme 1 for the synthesis of other thiazole compounds herein, such as those of Formula I, II, III, E1, E3-E6, etc.

Scheme 1

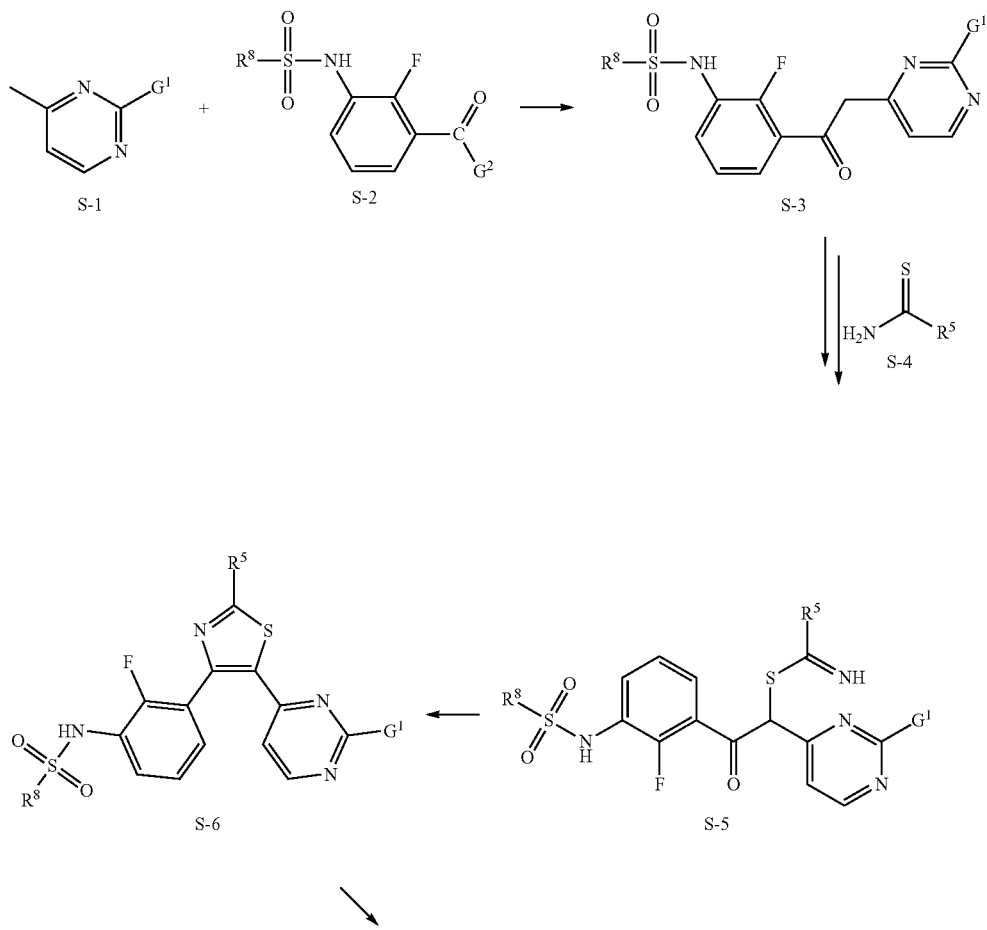

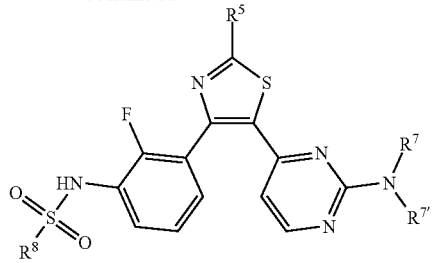

Formula G-1

Scheme 2 shows an alternative method for preparing compounds of Formula G-1. In Scheme 2, a protected aniline compound S-7 is used as a starting material, which allows introduction of various $R^8SO_2$— through the same intermediate S-9. Pg in Scheme 2 refers to a nitrogen protecting group, e.g., as described herein. $G^1$ and $G^2$ in Scheme 2 are leaving groups as defined herein, e.g., for Scheme 1. $G^3$ in Scheme 2 is also a leaving group, such as Cl. $R^8$ and $R^5$ are defined as in Formula G.

Compounds herein with

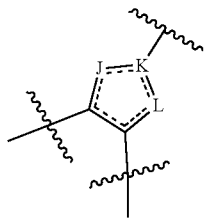

being an imidazole unit can also be prepared from a ketone intermediate S-3, similar to the preparation of thiazole compounds, except that an imidazole synthesis is employed. Exemplary methods are shown in the Examples section, e.g., Example 18.

Compounds herein with

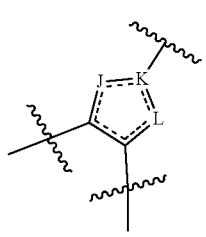

being an imidazopyridine unit can also be prepared from a ketone intermediate S-3. As shown in Scheme 3, ketone S-3 can be converted into imidazopyridine S-11, typically through a multiple step sequence involving introducing a leaving group at the alpha-position of the ketone, and substituting the leaving group with aminopyridine S-10, which is then followed by cyclization. After replacing $G^1$ (typically Cl, other leaving groups such as $SO_2Me$ can also be used) in S-11 with an appropriate amino group, compound of Formula G-2 can then be obtained. As would be obvious to those skilled in the art, similar strategies shown in Scheme 2 can also be used to allow easier introduction of various $R^8SO_2$— through the same intermediate when synthesizing the imidazopyridine compounds herein. The variables in Scheme 3, $R^8$, $R^5$, $R^9$, q, $R^7$, and $R^{7'}$ are defined herein. $G^1$ in Scheme 3 is a leaving group as defined herein, e.g., for Scheme 1.

Scheme 2

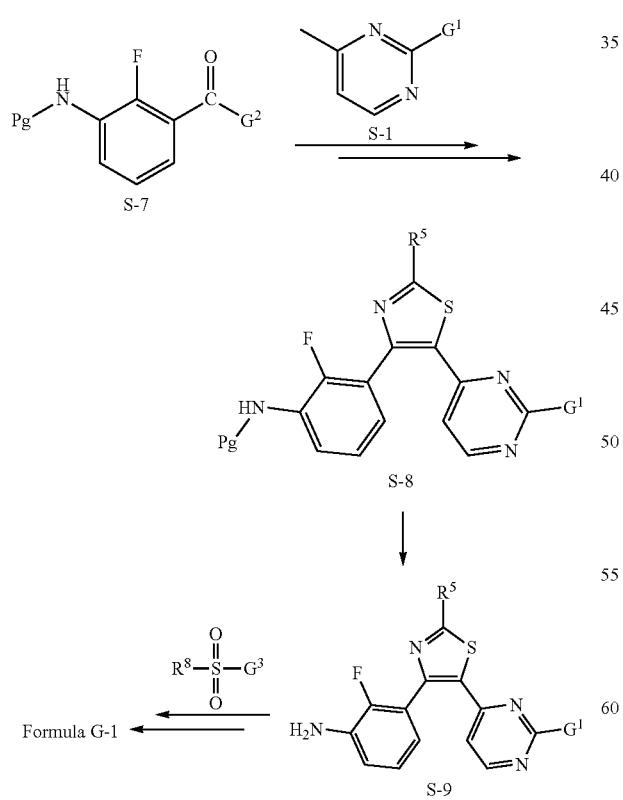

Scheme 3

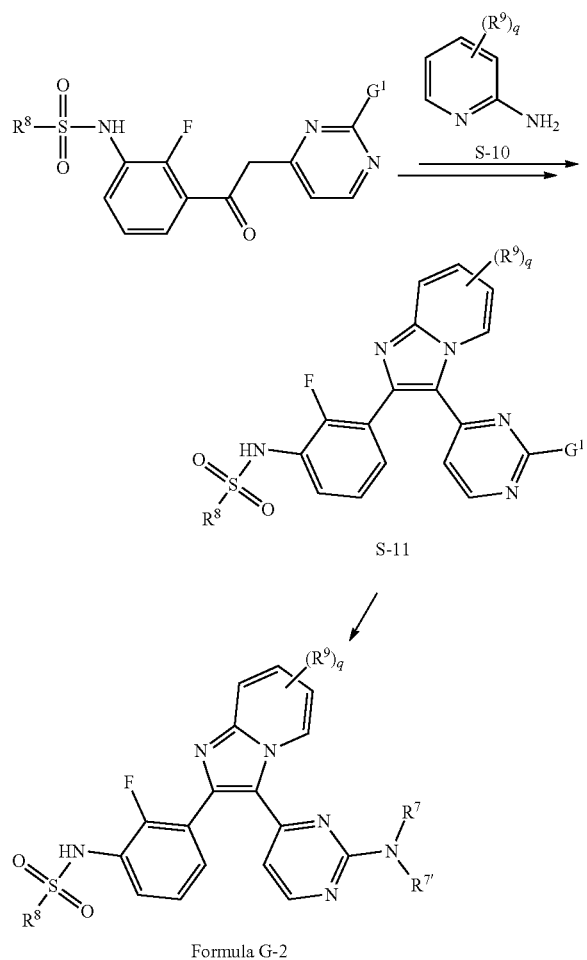

Formula G-2

Other compounds described herein can also be readily synthesized by those skilled in the art in view of the present disclosure and literature procedures, such as those described in WO 2009/137391, WO2014/194127, and WO2011/023773.

It will be appreciated that the methods described above can additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and F. Paquette, ed., *Encyclopedia of Reagents for Organic Synthesis*, John Wiley and Sons (1995) and subsequent editions thereof.

Pharmaceutical Compositions

Certain embodiments are directed to a pharmaceutical composition comprising one or more of the compounds of the present disclosure, and optionally contain a pharmaceutically acceptable excipient. In some embodiments, the pharmaceutical composition comprises a compound of the present disclosure and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Fippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises a compound of Formula G (e.g., G-1, G-2), a compound of Formula I (e.g., Formula I-A to I-E), a compound of Formula II (e.g., Formula II-A to II-E), a compound of Formula III (e.g., Formula III-A to III-E), a compound of Formula E1 to E6, or any one of compounds 1-189, or a pharmaceutically acceptable salt thereof. In any of the embodiments described herein, the pharmaceutical composition can comprise a compound selected from compounds 1-189, or a pharmaceutically acceptable salt thereof.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure and a pharmaceutically acceptable excipient. As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

In various embodiments, the pharmaceutical compositions described herein are useful in immunotherapy, for example, to promote immune response in cancer immunotherapy or cell therapy. In some embodiments, the pharmaceutical compositions described herein are useful for treating or preventing a disease or disorder mediated with aberrant CSK activities or where inhibition of CSK is beneficial, such as cancer. Accordingly, in some embodiments, a therapeutically effective amount of a compound of the present disclosure can be an amount effective to promote immune response, such as TCR-mediated signaling, or an amount effective to enhance an immunotherapy or cell therapy as described herein. For example, in some embodiments, the compound of the present disclosure can be provided in an amount effective to produce an observable enhancement of a given immunotherapy or cell therapy compared to a control without the compound of the present disclosure. In some embodiments, the compound of the present disclosure can also be provided in a therapeutically effective amount for treating cancer, either alone or in combination with another anticancer therapy, wherein the cancer can include for example, lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered.

The pharmaceutical composition described herein can be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

Compounds of the present disclosure can be used as a monotherapy or in a combination treatment. For example, in certain embodiments, the pharmaceutical composition described herein can further include an immunotherapeutic medicine, for example, a PD-1 or PDL-1 antibody, or a cell, such as a T-cell, e.g., CAR-T cell. In some embodiments, such immunotherapeutic medicine can be included in a separate dosage form.

Methods of Treatment

Compounds of the present disclosure are useful as therapeutic active substances for the treatment and/or prophylaxis of diseases or disorders that are mediated by aberrant CSK activities or where inhibition of CSK is beneficial. In various embodiments, compounds of the present disclosure can be used for inhibiting CSK activities. In some embodiments, compounds of the present disclosure can be used for promoting immune response, for example, in cancer immunotherapy or cell therapy. In some embodiments, compounds of the present disclosure can also be used for treating cancer, either alone or in combination with another anticancer agent/therapy.

In some embodiments, the present disclosure provides a method of inhibiting CSK activities in a cell. In some embodiments, the method comprises contacting the cell with an effective amount of a compound of the present disclosure or a pharmaceutical composition described herein. In some embodiments, the contacting can be in vitro, ex vivo, or in vivo.

In some embodiments, the present disclosure also provides a method for inhibiting CSK activities in a subject in need thereof. In some embodiments, the method comprises administering to the subject a compound of the present disclosure (e.g., a compound of Formula G (e.g., G-1, G-2), a compound of Formula I (e.g., Formula I-A to I-E), a compound of Formula II (e.g., Formula II-A to II-E), a compound of Formula III (e.g., Formula III-A to III-E), a compound of Formula E1 to E6, or any one of compounds 1-189, or a pharmaceutically acceptable salt thereof), or a pharmaceutical composition described herein. Dabrafenib also inhibits CSK, with an $IC_{50}$ of about 50 nM and a selectivity over LCK of about 10 fold. In some embodiments, the method can comprise administering to the subject a therapeutically effective amount of dabrafenib, or a pharmaceutically acceptable salt thereof, or a therapeutically effective amount of a pharmaceutical composition comprising dabrafenib or pharmaceutically acceptable salt thereof. In some embodiments, the compound or pharmaceutical composition is administered in an amount effective for inhibiting CSK activity or promoting immune response in the subject. In some embodiments, the subject suffers from cancer or an immune disorder for example, lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma. In some embodiments, the subject is further administered an immunotherapy (e.g., anti-PD-1 or anti-PD-L1 antibody) or a cell therapy (e.g., CAR-T cell therapy). In such embodiments, the immunotherapy or cell therapy can be administered to the subject either concurrently or sequentially in any order with the compounds of the present disclosure or pharmaceutical compositions herein.

As shown in the Examples below, exemplary compounds described herein showed potent CSK inhibition with a selectivity over LCK, which is in some cases over 2,000 fold. Without wishing to be bound by theories, it is believed that CSK inhibition, such as selective CSK inhibition over LCK, can promote immune responses toward antigen challenges, such as cancer antigen challenges, thereby can effectively enhance the subject's own immune response to cancer cells or enhance the efficacy of an immunotherapy, such as cancer immunotherapy or a cell therapy (e.g., CAR-T cell therapy).

In some embodiments, the present disclosure provides a method of promoting immune response (e.g., promoting TCR-mediated signaling) in a subject in need thereof. In some embodiments, the method comprises administering to the subject a compound of the present disclosure (e.g., a compound of Formula G (e.g., G-1, G-2), a compound of Formula I (e.g., Formula I-A to I-E), a compound of Formula II (e.g., Formula II-A to II-E), a compound of Formula III (e.g., Formula III-A to III-E), a compound of Formula E1 to E6, or any one of compounds 1-189, or a pharmaceutically acceptable salt thereof), or a pharmaceutical composition described herein. In some embodiments, the method can comprise administering to the subject a therapeutically effective amount of dabrafenib, or a pharmaceutically acceptable salt thereof, or a therapeutically effective amount of a pharmaceutical composition comprising dabrafenib or pharmaceutically acceptable salt thereof. In some embodiments, the compound or pharmaceutical composition is administered in an amount effective for inhibiting CSK activity or promoting immune response in the subject. In some embodiments, the subject suffers from cancer or an immune disorder, for example, lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma. In some embodiments, the subject is further administered an immunotherapy (e.g., anti-PD-1 or anti-PD-L1 antibody) or a cell therapy (e.g., CAR-T cell therapy). In such embodiments, the immunotherapy or cell therapy can be administered to the subject either concurrently or sequentially in any order with the compounds of the present disclosure or pharmaceutical compositions herein.

In some embodiments, the present disclosure provides a method of treating cancer in a subject in need thereof. In some embodiments, the method comprises administering to the subject a therapeutically effective amount of a compound of the present disclosure (e.g., a compound of Formula G (e.g., G-1, G-2), a compound of Formula I (e.g., Formula I-A to I-E), a compound of Formula II (e.g., Formula II-A to II-E), a compound of Formula III (e.g., Formula III-A to III-E), a compound of Formula E1 to E6, or any one of compounds 1-189, or a pharmaceutically acceptable salt thereof), or a therapeutically effective amount of a pharmaceutical composition described herein. In some embodiments, the method can comprise administering to the subject a therapeutically effective amount of dabrafenib, or a pharmaceutically acceptable salt thereof, or a therapeutically effective amount of a pharmaceutical composition comprising dabrafenib or pharmaceutically acceptable salt thereof. In some embodiments, the method further comprises administering to the subject an immunotherapy (e.g., anti-PD-1 or anti-PD-F1 antibody) or a cell therapy (e.g., CAR-T cell therapy). In some embodiments, the cancer can be lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma.

The administering herein is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the administering is orally.

The dosing regimen such as amounts and frequencies will vary depending on various factors such as the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable groups for the variables in compounds of Formula G, I, II, or III, as applicable, are independently selected. The described embodiments of the present invention can be combined. Such combination is contemplated and within the scope of the present invention. For example, definitions of one of the variables can be combined with any of the definitions of any other of the variables in Formula G, I, II, or III.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers including racemic mixtures.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, the term "compound(s) of the present disclosure" or "compound(s) of the present invention" refers to any of the compounds described herein according to a Formula G (e.g., G-1, G-2), Formula I (e.g., Formula I-A to I-E), Formula II (e.g., Formula II-A to II-E), Formula III (e.g., Formula III-A to III-E), Formula E1 to E6, or any one of compounds 1-189, isotopically labeled compound(s) thereof (such as a deuterated analog wherein one or more of the hydrogen atoms is/are substituted with a deuterium atom with an abundance above its natural abundance), possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt or base addition salt such as Na salt). Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

As used herein, the phrase "administration" of a compound, "administering" a compound, or other variants thereof means providing the compound or a prodrug of the compound to the individual in need of treatment.

As used herein, the term "alkyl" as used by itself or as part of another group refers to a straight- or branched-chain aliphatic hydrocarbon, typically has 1-12 carbons. In one embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group, i.e., methyl, ethyl, propyl(n-propyl), or butyl(n-butyl). Non-limiting exemplary $C_{1-4}$ alkyl groups include methyl, ethyl, propyl(n-propyl), isopropyl, butyl(n-butyl), sec-butyl, tert-butyl, and isobutyl.

As used herein, the term "alkenyl" as used by itself or as part of another group refers to an alkyl group as defined above containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to an alkyl group as defined above containing one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "alkoxy" as used by itself or as part of another group refers to a radical of the formula $OR^{a1}$, wherein $R^{a1}$ is an alkyl.

As used herein, the term "cycloalkoxy" as used by itself or as part of another group refers to a radical of the formula $OR^{a1}$, wherein $R^{a1}$ is a cycloalkyl.

As used herein, the term "alkanoyl" as used by itself or as part of another group refers to —C(O)$R^{a1}$, wherein $R^{a1}$ is hydrogen or an alkyl. For example, $C_1$ alkanoyl refers to —C(O)H, $C_2$ alkanoyl refers to —C(O)CH$_3$.

As used herein, the term "cycloalkanoyl" as used by itself or as part of another group refers to —C(O)$R^{a1}$, wherein $R^{a1}$ is a cycloalkyl.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms.

"Cycloalkyl" as used by itself or as part of another group refers to a radical of a non-aromatic cyclic hydrocarbon group, for example, having from 3 to 10 ring carbon atoms ("$C_{3-10}$ cycloalkyl") and zero heteroatoms in the non-aromatic ring system. The cycloalkyl group can be either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the carbocyclic ring, as defined above, is fused with one or more aryl or heteroaryl groups wherein the point of attachment is on the cycloalkyl ring, and in such instances, the number of carbons continue to designate the number of carbons in the cycloalkyl ring system. Non-limiting exemplary cycloalkyl groups include cyclopropyl, cyclobutyl, cyclopentyl, cyclohexyl, cycloheptyl, cyclooctyl, norbornyl, decalin, adamantyl, cyclopentenyl, and cyclohexenyl. In preferred embodiments, the term "cycloalkyl" refers to monocyclic, saturated group having from 3 to 8, more preferably, 3 to 6 ring carbon atoms.

"Heterocyclyl" or "heterocyclic" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more cycloalkyl groups wherein the point of attachment is either on the cycloalkyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidone, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfirranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" as used by itself or as part of another group refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group is a phenyl. "Aryl" also includes ring systems wherein the aryl ring, as defined above, is fused with one or more cycloalkyl or heterocyclyl groups wherein the radical or point of attachment is on the aryl ring, and in such instances, the number of carbon atoms continue to designate the number of carbon atoms in the aryl ring system.

"Aralkyl" as used by itself or as part of another group refers to an alkyl substituted with one or more aryl groups, preferably, substituted with one aryl group. When an aralkyl is said to be optionally substituted, either the alkyl portion or the aryl portion of the aralkyl can be optionally substituted.

"Heteroaryl" as used by itself or as part of another group refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more cycloalkyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, imidazopyridine, imidazopyrimidine, imidazopyrazine, imidazopyridazine, imidazotriazine, pyrazolopyridine, pyrazolopyrimidine, pyrazolopyridazine, pyrazolopyrazine, pyrazolotriazine, pyrrolopyridine, pyrrolopyrimidine, pyrrolopyridazine, pyrrolopyrazine, and pyrrolotriazine. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

An "optionally substituted" group, such as an optionally substituted alkyl, an optionally substituted alkenyl, an optionally substituted alkynyl, an optionally substituted cycloalkyl, an optionally substituted heterocyclyl, an optionally substituted aryl, and an optionally substituted heteroaryl groups, refers to the respective group that is unsubstituted or substituted. In general, the term "substituted", means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Typically, a "stable" compound is a compound that can be prepared and isolated and whose structure and properties remain or can be caused to remain essentially unchanged for a period of time sufficient to allow use of the compound for the purposes described herein (e.g., therapeutic administration to a subject). Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable. Substitution can occur on any available carbon, oxygen, or nitrogen atom, and in some cases can form a spirocycle, as applicable. In some cases, two of the optional substituents can join to form an optionally substituted cycloalkyl, heterocylyl, aryl, or heteroaryl ring.

In any of the embodiments described herein, unless otherwise indicated, the "optionally substituted" non-aromatic group can be unsubstituted or substituted with 1, 2, or 3 substituents independently selected from F, Cl, —OH, oxo (as applicable), $C_{1-4}$ alkyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl and $C_{1-4}$ alkoxy. In any of the embodiments described herein, unless otherwise indicated, the "optionally substituted" aromatic group (including aryl and heteroaryl groups) can be unsubstituted or substituted with 1, 2, or 3 substituents independently selected from F, Cl, —OH, —CN, $C_{1-4}$ alkyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl and $C_{1-4}$ alkoxy.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3{}^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3{}^+$X$^-$, —P(OR$^{cc}$)$_3{}^+$X$^-$, —P(R$^{cc}$)$_4$, —P(OR$^{cc}$)$_4$, —OP(R$^{cc}$)$_2$, —OP(R$^{cc}$)$_3{}^+$X$^-$, —OP(OR$^{cc}$)$_2$, —OP(OR$^{cc}$)$_3{}^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-4}$ aryl, and 5-14 membered heteroaryl, wherein each alkyl, alkenyl, alkynyl, cycloalkyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, G, u aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, G, u aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3{}^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ haloalkyl, $C_{2-6}$ alkenyl, $C_{2-6}$ alkynyl, $C_{3-10}$ cycloalkyl, 3-10 membered heterocyclyl, G, 10 aryl, 5-10 membered heteroaryl, wherein each alkyl, alkenyl, alkynyl, cycloalkyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 3-10 membered heterocyclyl, and 3-10 membered heteroaryl, wherein each alkyl, alkenyl, alkynyl, cycloalkyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ cycloalkyl, 3-10 membered heterocyclyl, $C_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$X$^-$, —NH$_3{}^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ ($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=NR$^{bb}$)$R^{aa}$, —C(=NR$^{bb}$)O$R^{aa}$, —C(=NR$^{bb}$)N($R^{bb}$)$_2$, —C(=O)NR$^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, G, u aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group. Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl, ar-$C_{1-10}$ alkyl, heteroar-$C_{1-10}$ alkyl, $C_{2-10}$ alkenyl, $C_{2-10}$ alkynyl, $C_{3-10}$ cycloalkyl, 3-14 membered heterocyclyl, G, u aryl, and 5-14 membered heteroaryl groups, wherein each alkyl, alkenyl, alkynyl, cycloalkyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protective Groups in Organic Synthesis*, T. W. Greene and P. G. M. Wuts, 3$^{rd}$ edition, John Wiley & Sons, 1999, incorporated by reference herein. Nonlimiting useful nitrogen protecting groups include, for example, acetyl, Carbobenzyloxy (Cbz), p-Methoxybenzyl carbonyl, Fmoc, Boc (tert-Butyloxycarbonyl), benzoyl(Bz), benzyl, carbamates, tosyl(Ts) and other sulfonamides such as Nosyl or Nps, p-methoxybenzyl, 3,4-dimethoxybenzyl, and trichloroethyl chloroformate. Where "nitrogen protecting group" is recited, followed by recitations of specific nitrogen substituents such as optionally substituted $C_{1-6}$ alkyl etc., it will be understood that the terms "nitrogen protecting group" and nitrogen substituents are not redundant or mutually exclusive. Rather, the specific nitrogen substituents are recited to add clarity. Thus, the term "nitrogen protecting group" should not be interpreted herein as excluding any specific nitrogen substituents and vice versa.

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group. Oxygen protecting groups are well known in the art and include those described in detail in *Protective Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Examples of pharmaceutically acceptable, nontoxic acid addition salts include those formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa).

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990.

EXAMPLES

The synthetic and biological examples described in this application are offered to illustrate the compounds, pharmaceutical compositions, and methods provided herein and are not to be construed in any way as limiting their scope.

Example 1

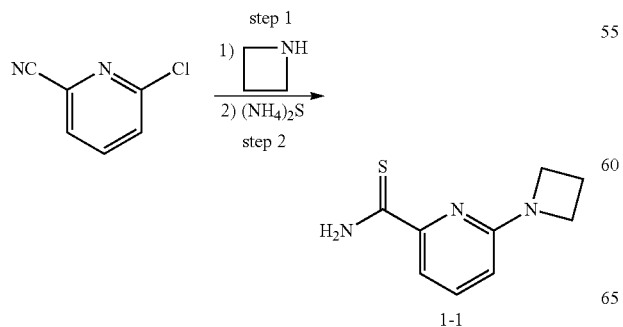

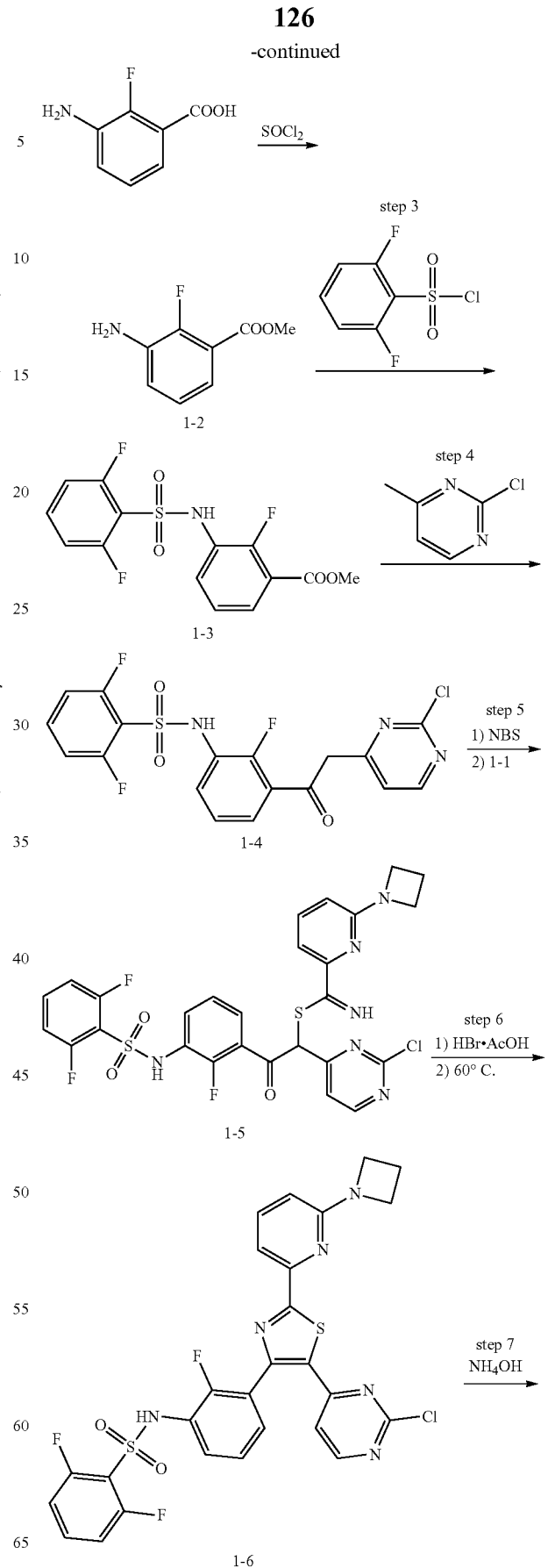

-continued

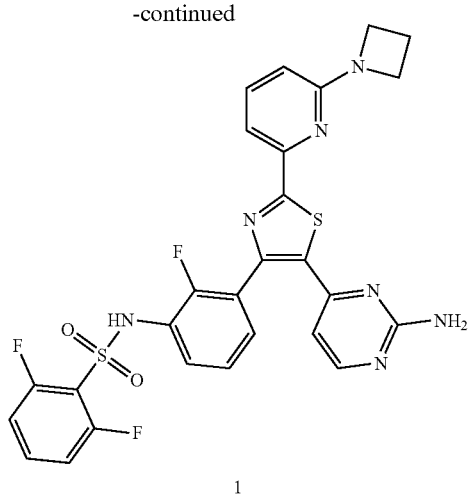

1

Step 1. Synthesis of 1-1

To a mixture of azetidine hydrochloride (1.67 g, 18 mmol) and triethylamine (4.5 g, 45 mmol) in dimethyl sulfoxide (8 mL) was added 2-chloro-6-cyanopyridine (2.07 g, 15 mmol), and then stirred at 80° C. for 16 h. Ethyl acetate (50 mL) was added and washed with water (50 mL) and brine (50 mL). The organic layer was dried over sodium sulfate, filtered, and concentrated. To the crude product in pyridine (5 mL) was added a solution of ammonium sulfide (2.8 g, 16.5 mmol, 40% aq) and triethylamine (2 mL). Then the reaction mixture was stirred at 60° C. for 3 h. Ethyl acetate (50 mL) was added and washed with water (50 mL) and brine (50 mL). The organic layer was dried over sodium sulfate, filtered, and concentrated. The residue was crystallized with ethanol/water to give 1-1 (750 mg, 26% yield for two steps).

Step 2. Synthesis of 1-2

To a stirred solution of 3-amino-2-fluorobenzoic acid (3.1 g, 20 mmol) in methanol (60 mL) was added thionyl chloride (3.57 g, 30 mmol) dropwise at 0° C. Then the mixture was refluxed for 16 h before cooling to room temperature. The reaction mixture was concentrated and the residue was dissolved in ethyl acetate (50 mL), washed with saturated aqueous sodium bicarbonate solution, dried over sodium sulfate and concentrated to afford 1-2 (3.4 g).

Step 3. Synthesis of 1-3

To a solution of 1-2 (3.4 g, 20 mmol) and pyridine (2.05 g, 26 mmol) in dichloromethane (60 mL) was added 2,6-difluorobenzenesulfonyl chloride (4.7 g, 22 mmol) dropwise at 0° C. The resulting mixture was stirred at room temperature for 16 h. The reaction was diluted with dichloromethane (40 mL), and washed with water (100 mL) and brine (100 mL). The organic layer was dried over sodium sulfate, filtered and concentrated. The residue was crystallized with ethanol/ethyl acetate/petroleum ether to give 1-3 (6.15 g, 89% yield).

Step 4. Synthesis of 1-4

To a solution of 1-3 (3.45 g, 10 mmol) in tetrahydrofuran (20 mL) was added lithium bis(trimethylsilyl)amide (30 mL, 30 mmol) at 0° C. Another solution of 2-chloro-4-methylpyrimidine (1.4 g, 11 mmol) in tetrahydrofuran (40 mL) was added dropwise. Then the reaction mixture was allowed to warm to room temperature over 1 h before treated with 6 N of hydrochloric acid. Ethyl acetate (50 mL) was added and the aqueous layer was extracted with ethyl acetate (2×50 mL). The combined organic layer was washed with brine, dried over sodium sulfate, and concentrated. The residue was crystallized with ethanol/dichloromethane/petroleum ether to give 1-4 (3.0 g, 68% yield).

Step 5. Synthesis of 1-5

To a solution of 1-4 (441 mg, 1 mmol) in dimethylformamide (20 mL) was added N-bromosuccinimide (178 mg, 1 mmol) at room temperature. The reaction was stirred for 1 h before addition of pyridine (95 mg, 1.2 mmol) and 1-1 (193 mg, 1 mmol). After stirring for another 2 h, the reaction mixture was purified by a prep-HPLC (acetonitrile with 0.05% of TFA: 10% to 95%) to give 1-6 (375 mg, 59% yield for two steps).

Step 6. Synthesis of 1-6

To a solution of 1-5 (375 mg, 0.6 mmol) in dimethylformamide (3 mL) was added hydrobromic acid in acetic acid (0.8 mL, 33% w/w) at room temperature. The resulting mixture was stirred for 16 h, and then heated at 60° C. for another 24 h. The reaction mixture was purified directly by a prep-HPLC (acetonitrile with 0.05% of TFA: 10% to 95%) to give 1-6 (242 mg, 66% yield for two steps).

Step 7. Synthesis of 1

To a solution of 1-6 (90 mg, 0.15 mmol) in dimethyl sulfoxide (2 mL) was added ammonium hydroxide (0.5 mL, 28% aq. w/w) at room temperature. The mixture was then stirred at 90° C. for 1.5 h under microwave condition. The reaction mixture was purified by a prep-HPLC (acetonitrile with 0.05% of TFA: 10% to 95%) to afford 1 (29 mg, 32% yield).

Example 2

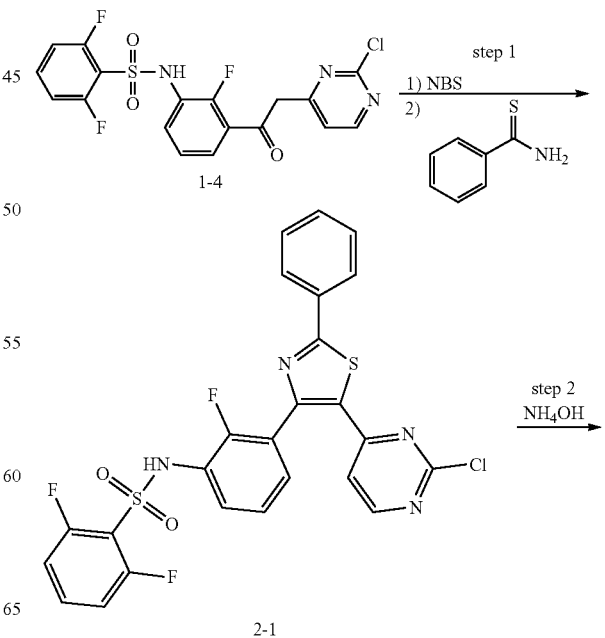

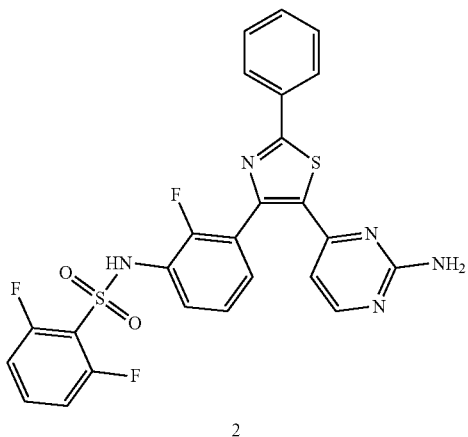

2

Step 1. Synthesis of 2-1

To a solution of 1-4 (220 mg, 0.5 mmol) in dimethylacetamide (10 mL) was added N-bromosuccinimide (88 mg, 0.5 mmol) at room temperature, and stirred for 1 h. Then benzothioamide (69 mg, 0.5 mmol) was added, and the reaction was heated at 80° C. for 1 h. Ethyl acetate (30 mL) was added. The organic layer was washed with water (30 mL) and brine (50 mL), dried over sodium sulfate, filtered, and concentrated. The crude residue was purified by a prep-TLC plate (petroleum ether/ethyl acetate=2:1) to give 2-1 (160 mg, 57% yield for two steps).

Step 2. Synthesis of 2

A mixture of 2-1 (160 mg, 0.28 mmol) in 1,4-dioxane (2 mL) was added ammonium hydroxide. The resulted solution was stirred at 100° C. for overnight. After regular work up, the crude residue was purified by a prep-TLC plate (petroleum ether/ethyl acetate=2:1) to afford 2 (50 mg, 33% yield).

Example 3

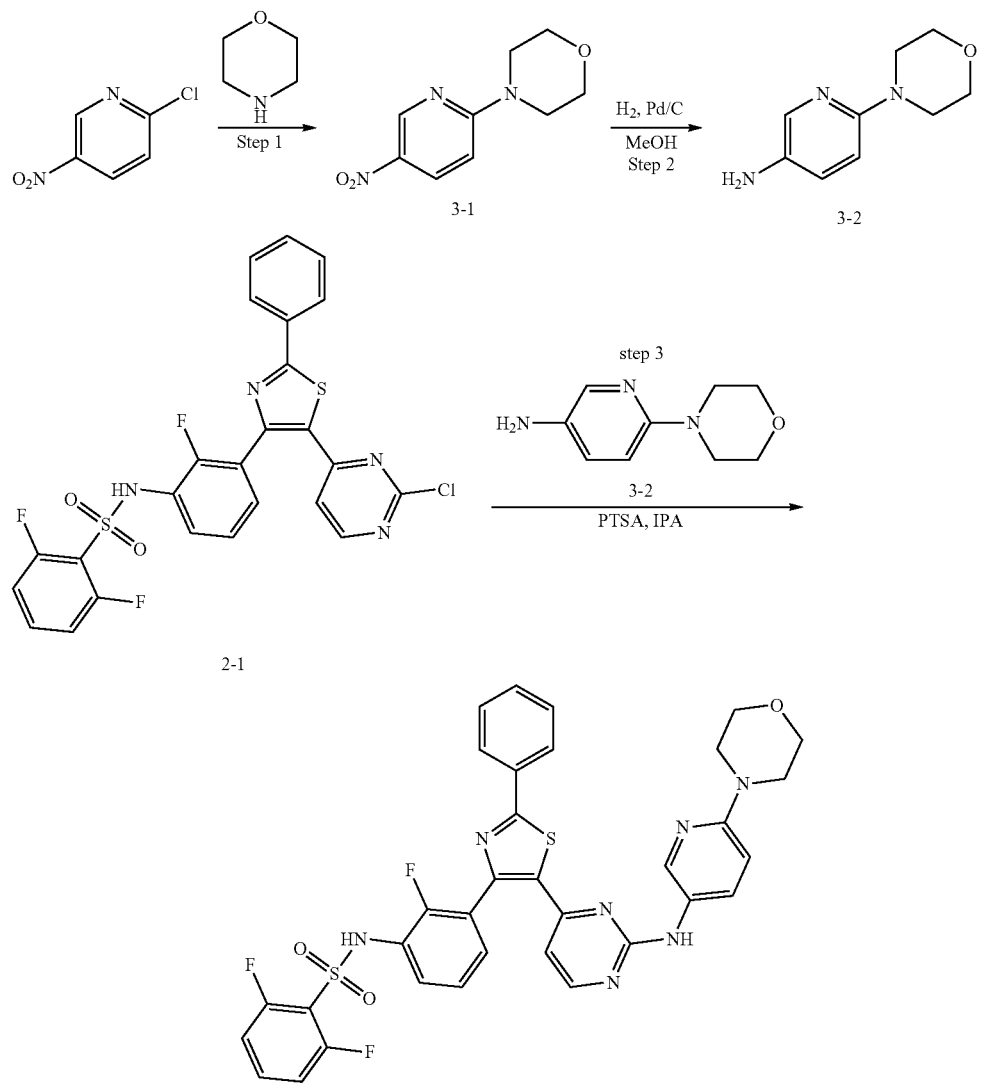

Step 1. Synthesis of 3-1

A mixture of 2-chloro-5-nitropyridine (1 g, 6.3 mmol) and morpholine (2.75 g, 31.5 mmol) was stirred at room temperature for 1 h. The mixture was poured into water (10 mL), filtered, and the filter cake was dried to give 3-1 (1.2 g, 91% yield) as a yellow solid.

Step 2. Synthesis of 3-2

To a solution of 3-1 (1 g, 4.8 mmol) in methanol (20 mL) was added 5% Pd/C (wet, 200 mg). The reaction was stirred at room temperature under hydrogen for 16 h. The mixture was filtered and concentrated. The residue was purified by chromatography on a silica gel column (petroleum ether/ethyl acetate=2:1) to give 3-2 (380 mg, 44% yield) as a red solid.

Step 3. Synthesis of 3

To a solution of 2-1 (80 mg, 0.14 mmol) in isopropanol (20 mL) was added 3-1 (26 mg, 0.14 mmol) and p-toluenesulfonic acid (25 mg, 0.14 mmol) at room temperature. The resulting mixture was heated at 105° C. for 16 h. The reaction was concentrated and purified by a prep-HPLC (acetonitrile with 0.05% of trifluoroacetic acid: 10% to 95%) to give 3 (70 mg, 71% yield).

Example 4

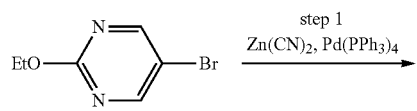

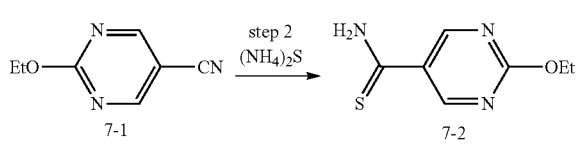

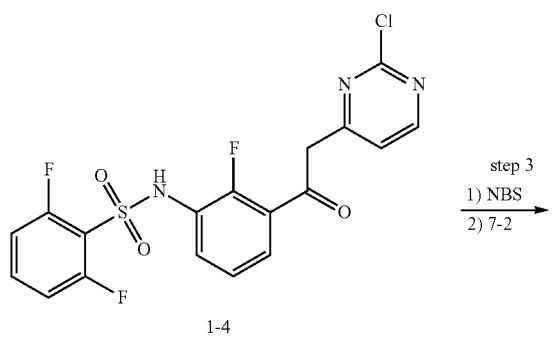

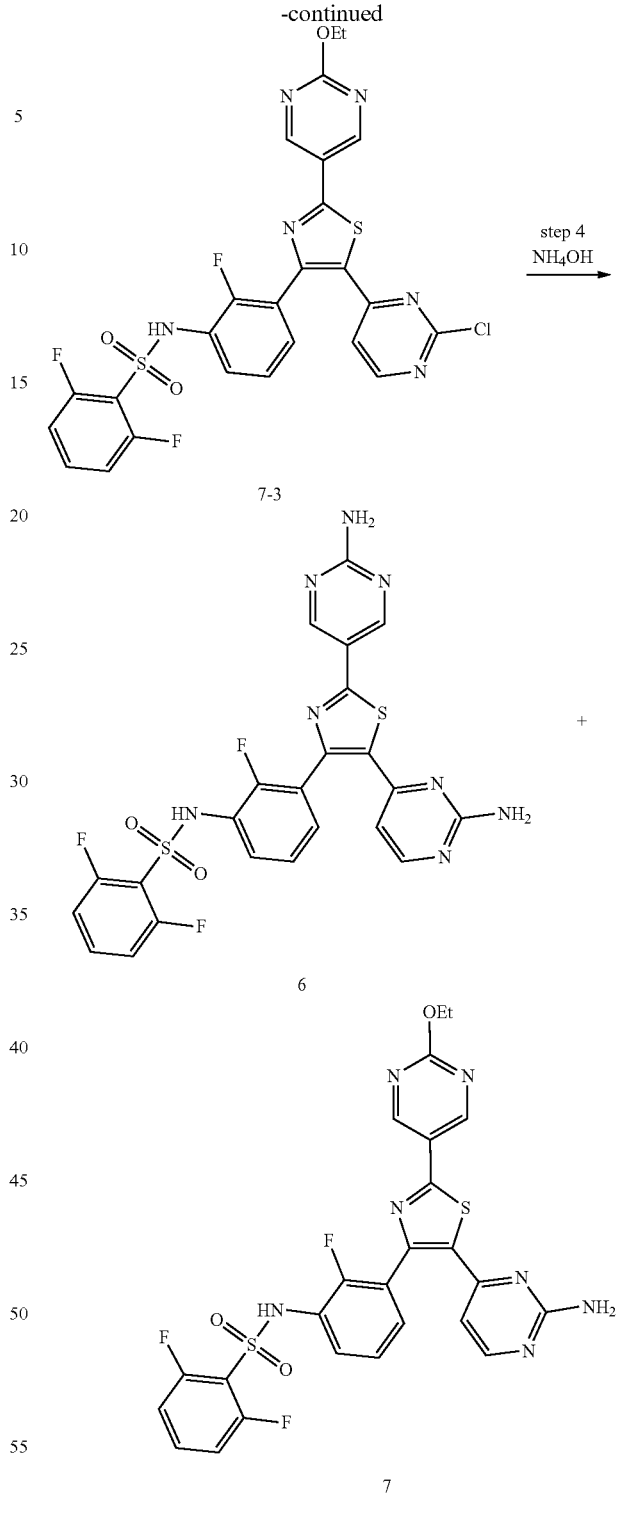

Step 1. Synthesis of 7-1

To a solution of 5-bromo-2-ethoxy-pyrimidine (500 mg, 2.5 mmol) in dimethylformamide (5 mL) at room temperature was added zinc cyanide (590 mg, 5 mmol) and tetrakis (triphenylphosphine)palladium (289 mg, 0.25 mmol). After purging with $N_2$, the reaction was sealed and heated at 100° C. for 2 h under microwave condition. After work up, the

133 crude residue was purified by silica column (petroleum ether to petroleum ether/ethyl acetate=4:1) to give 7-1 (350 mg, 94% yield).

Step 2. Synthesis of 7-2

To a solution of 7-1 (350 mg, 2.35 mmol) in pyridine (3 mL) was added ammonium sulfide (438 mg, 2.58 mmol, 40% aq) and triethylamine (1 mL). The mixture was stirred at 60° C. for 3 h. Water (50 mL) was added and extracted with ethyl acetate (3×50 mL). The organic layer was dried over sodium sulfate, filtered, and concentrated. The crude residue was purified by silica column (petroleum ether to petroleum ether/ethyl acetate=1:1) to give 7-2 (350 mg, 81% yield).

Step 3. Synthesis of 7-3

To a solution of 1-4 (180 mg, 0.41 mmol) in dimethylacetamide (20 mL) at room temperature was added N-bromosuccinimide (73 mg, 0.41 mmol). The mixture was stirred for 1 h. After addition of 7-2 (75 mg, 0.41 mmol), the reaction was heated to 80° C. for 5 h. Ethyl acetate (50 mL) was added, and then washed with water (50 mL) and brine (50 mL). The organic layer was dried over sodium sulfate, filtered, and concentrated. The crude residue was purified by a prep-HPLC (acetonitrile with 0.05% of trifluoroacetic acid: 10% to 95%) to give 7-3 (60 mg, 24% yield for two steps).

Step 4. Synthesis of 6 and 7

A solution of 7-3 (60 mg, 0.1 mmol) in dioxane (1 mL) and aqueous ammonia (0.5 mL) in a sealed tube was heated at 95° C. under microwave condition for 1 h. The reaction mixture was purified by a prep-HPLC (acetonitrile with 0.05% of trifluoroacetic acid: 10% to 95%) to afford 6 and 7.

Example 5

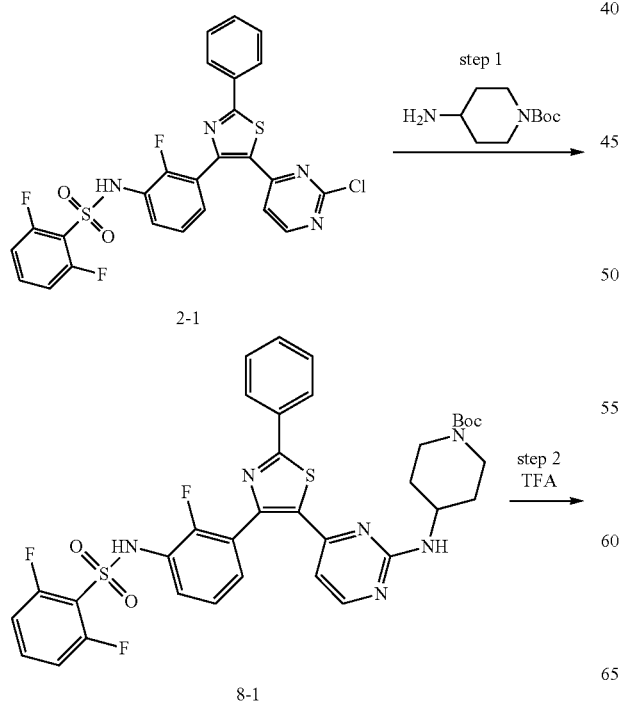

134

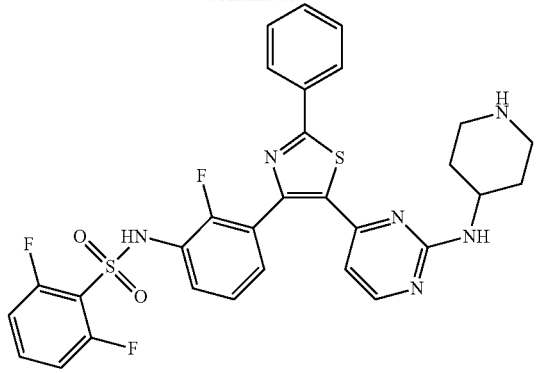

8

Step 1. Synthesis of 8-1

To a solution of 4-amino-1-boc-piperidine (56 mg, 0.28 mmol) in tetrahydrofuran (10 mL) at room temperature was added LiHMDS (0.56 mL, 0.56 mmol) and 2-1 (80 mg, 0.14 mmol). The mixture was stirred at 30° C. for 16 h. The reaction was quenched with a saturated aqueous NH₄Cl solution. Ethyl acetate (50 mL) was added, and the organic layer was washed with water (50 mL) and brine (50 mL). The separated organic layer was dried over sodium sulfate, filtered, and concentrated. The crude residue was purified by silica column (dichloromethane to dichloromethane/methanol=10:1) to give 8-1 (80 mg).

Step 2. Synthesis of 8

To a solution of 8-1 (80 mg, 0.11 mmol) in dichloromethane (4 mL) was added trifluoroacetic acid (1 mL) at room temperature, and then stirred for 2 h. After work up, the residue was purified by a prep-HPLC (acetonitrile with 0.05% of trifluoroacetic acid: 10% to 95%) to give 8 (17 mg, 21% yield for two steps).

Example 6

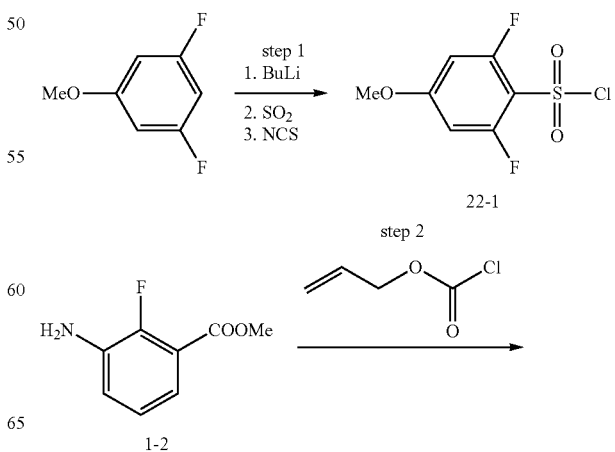

135
-continued

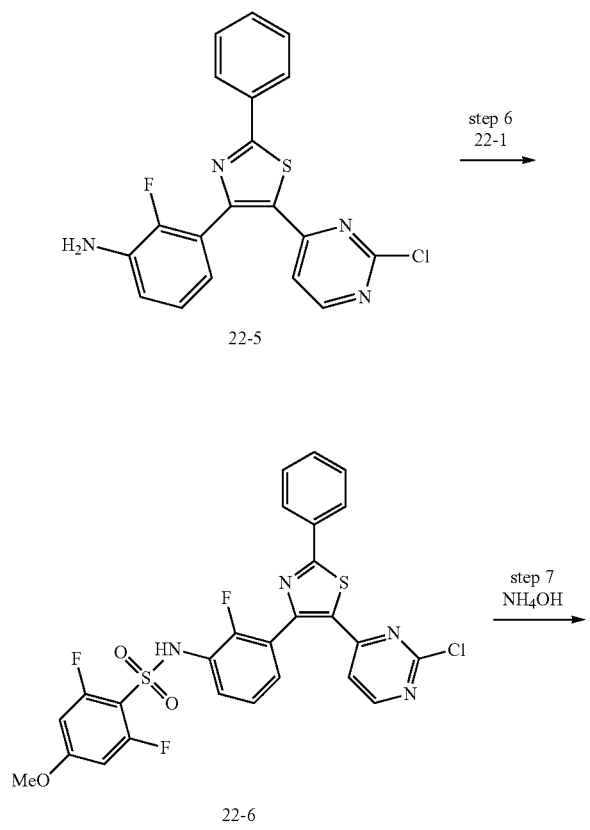

136
-continued

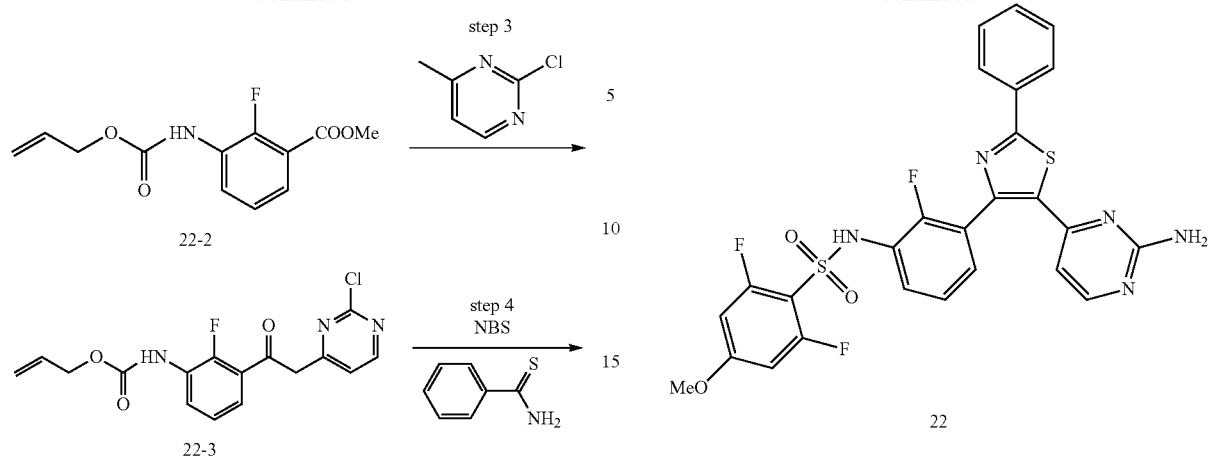

Step 1. Synthesis of 22-1

To a stirred solution of 1,3-difluoro-5-methoxybenzene (1.0 g, 7 mmol) in tetrahydrofuran (20 mL) was added a n-butyllithium solution (3.1 mL, 7.7 mmol, 2.5 M in hexane) at −78° C. under nitrogen. The mixture was stirred at −78° C. for 1 h and then degassed with a $SO_2$ balloon. After 1 h, N-chlorosuccinimide (938 mg, 7 mmol) was added, and the reaction was warmed to room temperature for 1 h. The mixture was filtered and the filtrate was concentrated to give 22-1 (1.0 g, 59% yield).

Step 2. Synthesis of 22-2

To a stirred solution of 1-2 (4.5 g, 26.6 mmol) in tetrahydrofuran (40 mL) was added a solution of sodium bicarbonate (3.4 g, 40 mmol) in water (40 mL). Allyl chloroformate (3.8 g, 32 mmol) was added dropwise at 0° C. The reaction was then stirred at room temperature for 2 h. The mixture was extracted with ethyl acetate (200 mL). The organic phase was washed with brine (50 mL), dried over sodium sulfate, and concentrated. The crude residue was purified by a prep-TLC plate (petroleum ether/ethyl acetate=3:1) to give 22-2 (6.7 g, 99% yield).

Step 3. Synthesis of 22-3

To a solution of 22-2 (4.3 g, 17.1 mmol) in tetrahydrofuran (100 mL) at −10° C. was added lithium bis(trimethylsilyl)amide (60 mL, 60 mmol, 1 M in tetrahydrofuran). The mixture was stirred at 0° C. for 1 h, and then a solution of 2-chloro-4-methylpyrimidine (2.6 g, 20.5 mmol) in tetrahydrofuran (20 mL) was added dropwise. The reaction was warmed up to room temperature in 1 h. The mixture was quenched by an ammonium chloride solution (50 mL) at 0° C. and extracted with ethyl acetate (200 mL). The organic phase was concentrated and the residue was slurried with petroleum ether/ethyl acetate (45 mL: 15 mL) to give 22-3 (3.9 g, 65% yield).

Step 4. Synthesis of 22-4

To a stirred solution of 22-3 (1.0 g, 2.9 mmol) in dimethylacetamide (10 mL) was added N-bromosuccinimide (510 mg, 2.9 mmol). The mixture was stirred at room temperature for 1 h and then benzothioamide (397 mg, 2.9 mmol) was added. The reaction was heated at 80° C. for 3 h. The mixture was cooled, extracted with ethyl acetate (100 mL) and washed with water (50 mL). The organic phase was concentrated and the resulting residue was purified by chromatography on a silica gel column (petroleum ether/ethyl acetate=2:1) to give 22-4 (640 mg, 47% yield).

Step 5. Synthesis of 22-5

To a solution of 22-4 (640 mg, 1.37 mmol) in dichloromethane (30 mL) was added acetic acid (200 mg, 3.3 mmol), bis(triphylphosphine)palladium(II) chloride (21 mg, 0.3 mmol) and tri-n-butyltin hydride (580 mg, 2 mmol) at 0° C. under nitrogen stream. The reaction mixture was warmed to room temperature, extracted with dichloromethane (50 mL) and washed with brine (50 mL). The organic phase was concentrated and treated with petroleum ether (20 mL). The mixture was filtered to give 22-5 (520 mg, 99% yield).

Step 6. Synthesis of 22-6

To a solution of 22-5 (100 mg, 0.26 mmol) in dichloromethane (5 mL) was added pyridine (42 mg, 0.52 mmol) and 22-1 (126 mg, 0.52 mmol). The reaction mixture was stirred at room temperature for 16 h. The mixture was concentrated and purified by a prep-TLC (petroleum ether/ethyl acetate=2:1) to give 22-6 (100 mg, 65% yield).

Step 7. Synthesis of 22

To a stirred solution of 22-6 (100 mg, 0.17 mmol) in 1,4-dioxane (4 mL) was added ammonium hydroxide (2 mL). The reaction was stirred at 80° C. in a sealed tube for 16 h. The mixture was concentrated and purified by a prep-HPLC (acetonitrile with 0.05% of TFA: 5% to 95%) to give 22 (41 mg, 42% yield).

Example 7

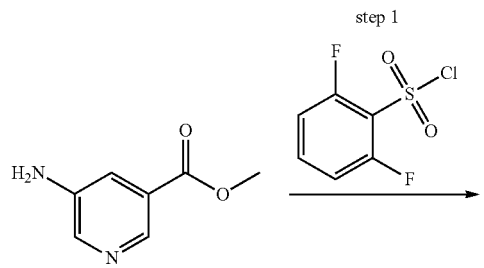

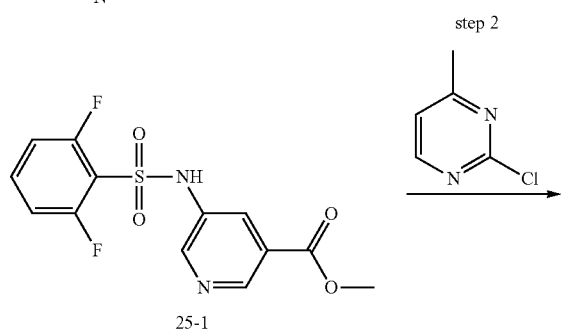

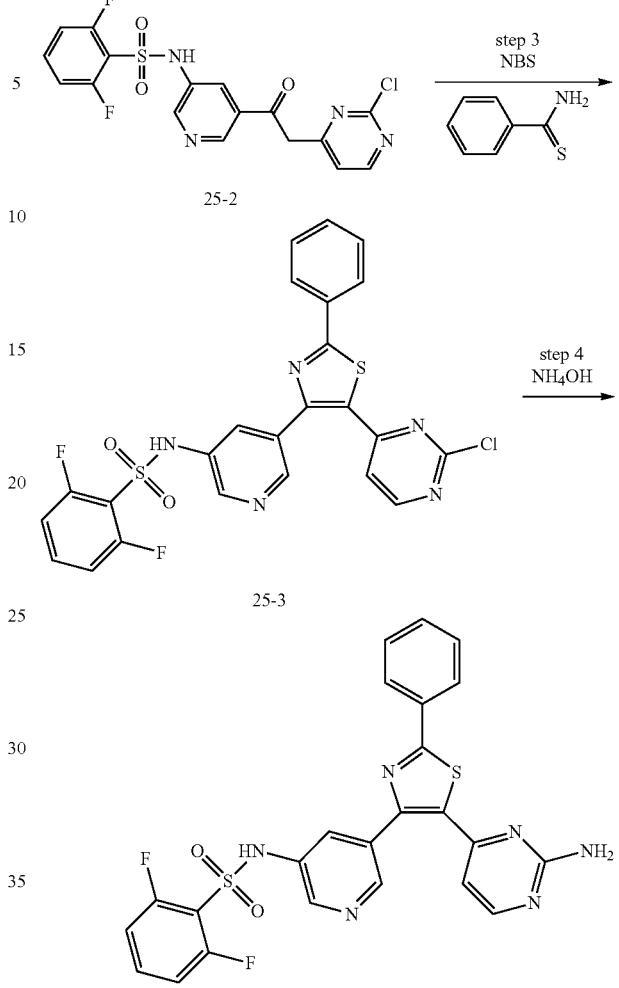

Step 1. Synthesis of 25-1

To a solution of methyl 5-aminonicotinate (960 mg, 6.24 mmol) in pyridine (3 mL) was added 2,6-difluorobenzenesulfonyl chloride (1.46 g, 6.87 mmol) at 0° C. The mixture was heated at 80° C. for 16 h. The reaction was cooled, diluted with water (10 mL) and filtered to give a crude product which was slurried with petroleum ether/ethyl acetate (9:1) to give 25-1 (1.7 g, 82% yield).

Step 2. Synthesis of 25-2

To a solution of 25-1 (700 mg, 2.13 mmol) in tetrahydrofuran (10 mL) was added lithium bis(trimethylsilyl)amide (8.5 mL, 8.52 mmol, 1.0 M in tetrahydrofuran) at 0° C. After stirring at 0° C. for 0.5 h, a solution of 2-chloro-4-methylpyrimidine (330 mg, 2.56 mmol) in tetrahydrofuran (20 mL) was added dropwise. The reaction was then warmed to room temperature and stirred for another 2 h. The mixture was acidified with 1 N of hydrochloric acid and extracted with ethyl acetate. The combined organic layer was washed with water (10 mL) and brine (10 mL), dried over sodium sulfate, and concentrated. The residue was purified by column chromatography on silica gel (petroleum ether to petroleum ether/ethyl acetate=1:1) to give 25-2 (350 mg, 39% yield).

Step 3. Synthesis of 25-3

To a solution of 25-2 (350 mg, 0.82 mmol) in dimethylacetamide (3 mL) at room temperature was added N-bromosuccinimide (147 mg, 0.82 mmol), and then stirred for 0.5 h. After addition of benzothioamide (135 mg, 0.98 mmol), the reaction was heated to 80° C. for 3 h. The mixture was diluted with water (10 mL) and extracted with ethyl acetate. The combined organic layer was washed with brine (10 mL), dried over sodium sulfate, and concentrated. The residue was purified by column chromatography on silica gel (petroleum ether to petroleum ether/ethyl acetate=1:1) to give 25-3 (125 mg, 28% yield).

Step 4. Synthesis of 25

A solution of 25-3 (125 mg, 0.23 mmol) in 1,4-dioxane (1 mL) and aqueous ammonia (1 mL) in a sealed tube was heated at 80° C. for 16 h. The reaction mixture was concentrated and the residue was purified by a prep-HPLC (methanol with 0.05% of TFA in water: 5% to 95%) to give 25 (20.3 mg, 17% yield).

Example 8

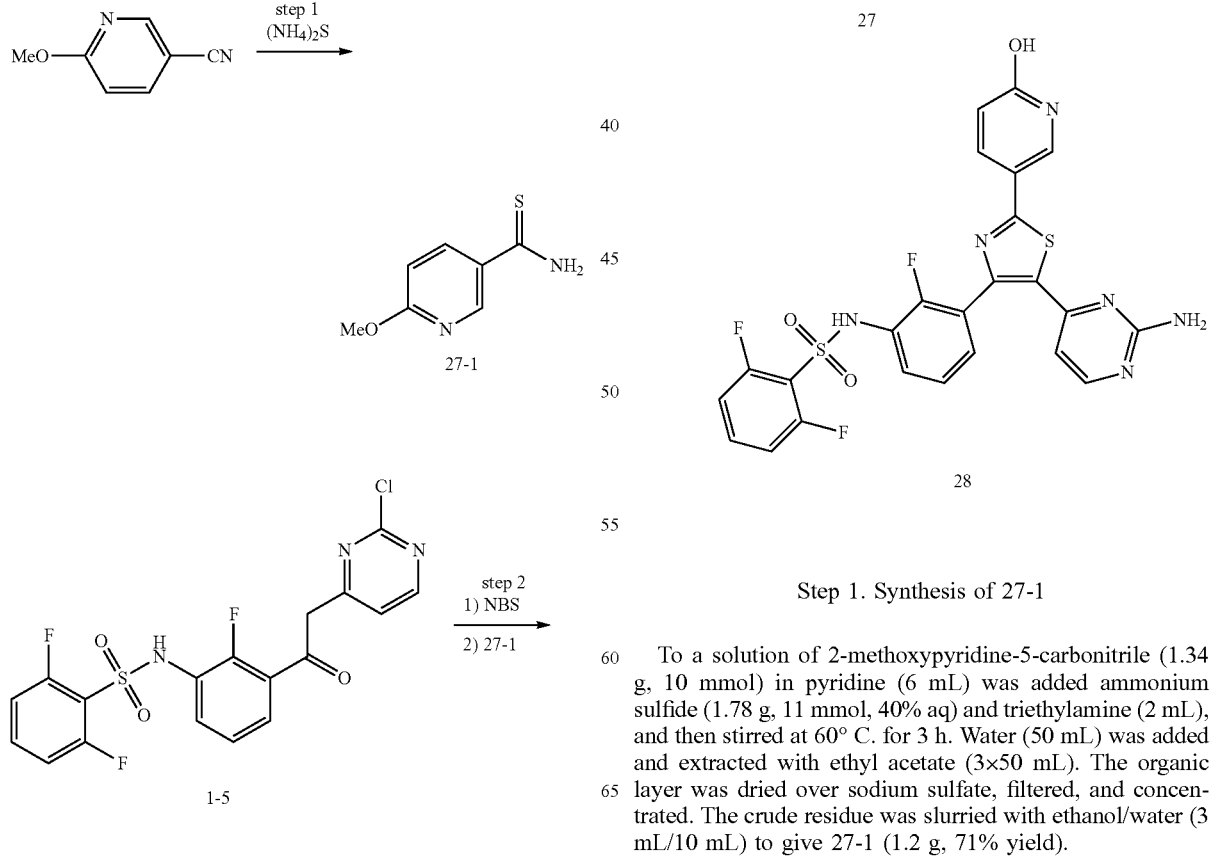

Step 1. Synthesis of 27-1

To a solution of 2-methoxypyridine-5-carbonitrile (1.34 g, 10 mmol) in pyridine (6 mL) was added ammonium sulfide (1.78 g, 11 mmol, 40% aq) and triethylamine (2 mL), and then stirred at 60° C. for 3 h. Water (50 mL) was added and extracted with ethyl acetate (3×50 mL). The organic layer was dried over sodium sulfate, filtered, and concentrated. The crude residue was slurried with ethanol/water (3 mL/10 mL) to give 27-1 (1.2 g, 71% yield).

Step 2. Synthesis of 27-2

To a solution of 1-4 (441 mg, 1 mmol) in dimethylacetamide (10 mL) was added N-bromosuccinimide (178 mg, 1 mmol) at room temperature. The resulted mixture was stirred for 0.5 h, and then sodium bicarbonate (168 mg, 2 mmol) was added followed by 27-1 (168 g, 1 mmol). The mixture was stirred for another 2 h. Ethyl acetate (100 mL) was added and washed with a saturated aqueous ammonium chloride solution (100 mL), water (100 mL) and brine (100 mL). The organic layer was dried over sodium sulfate, filtered, and concentrated. The residue was purified by silica column (petroleum ether to petroleum ether/ethyl acetate=1/1) to give 27-2 (270 mg, 45% yield).

Step 3. Synthesis of 27

A solution of 27-2 (270 mg, 0.45 mmol) in 1,4-dioxane (3 mL) and aqueous ammonia (3 mL) in a sealed tube was heated at 80° C. for 16 h. The mixture was poured into water (50 mL), and the pH of the solution was adjusted to ~7 with 1 M of hydrochloric acid. The precipitated solid was collected by filtration, and slurried with methanol (8 mL) to give 27 (180 mg, 70% yield).

Step 4. Synthesis of 28

A solution of 27 (112 mg, 0.21 mmol) in 1,4-dioxane (4 mL) and concentrated hydrochloric acid (2 mL) in a sealed tube was heated at 60° C. for 4 h. After work up, the residue was purified by a prep-HPLC (acetonitrile with 0.05% TFA in water=10% to 95%) to give 28 (45 mg, 39% yield).

Example 9

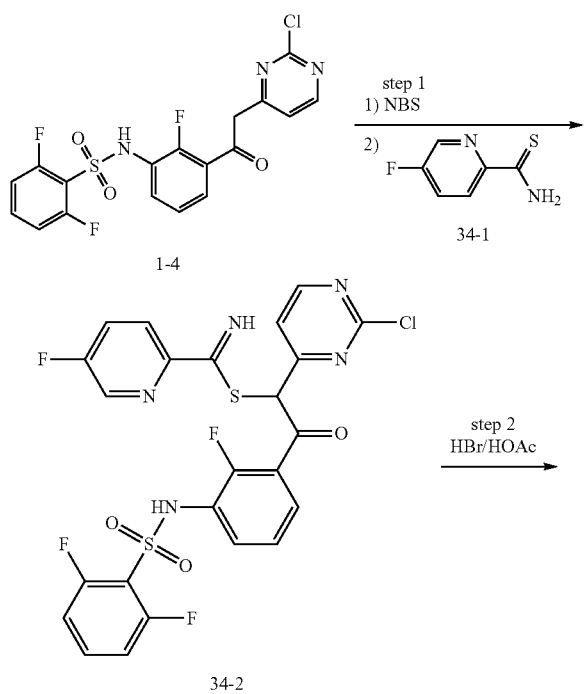

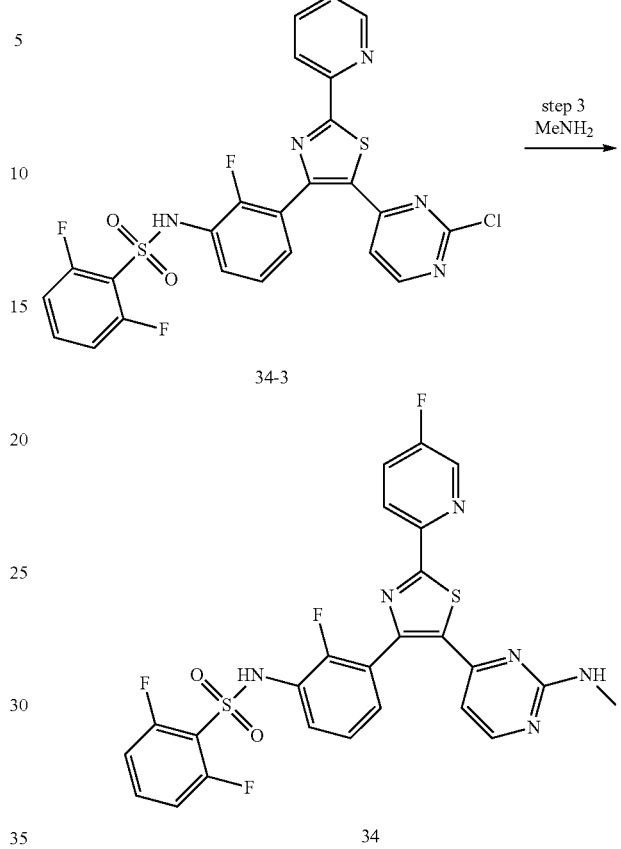

Step 1. Synthesis of 34-2

To a solution of 1-4 (3.74 g, 8.5 mmol) in dimethylacetamide (35 mL) was added N-bromosuccinimide (1.52 g, 8.5 mmol) at room temperature, and then stirred for 0.5 h. To the reaction mixture was added sodium bicarbonate (1.43 g, 17 mmol) and 34-1 (1.33 g, 7.5 mmol) at room temperature, and then stirred for another 2 h. Ethyl acetate (100 mL) was added and washed with a saturated aqueous ammonium chloride solution (100 mL), water (100 mL) and brine (100 mL). The organic layer was dried over sodium sulfate, filtered, concentrated. The residue was purified by silica column (petroleum ether to petroleum ether/ethyl acetate=1:1) to give 34-2 (2.75 g, 54% yield).

Step 2. Synthesis of 34-3

To a solution of 34-2 (700 mg, 1.18 mmol) in dimethylformamide (6 mL) was added hydrobromic acid in acetic acid (2 mL, 33% w/w) at room temperature, and then stirred for 16 h. The reaction mixture was poured into water (50 mL), and solid was collected by filtration and slurried with methanol (10 mL) to give 34-3 (600 mg, 88% yield) as an orange solid.

Step 3. Synthesis of 34

To a solution of 34-3 (60 mg, 0.1 mmol) in 1,4-dioxane (1 mL) was added a methanamine solution (0.5 mL, 40% in Example 10

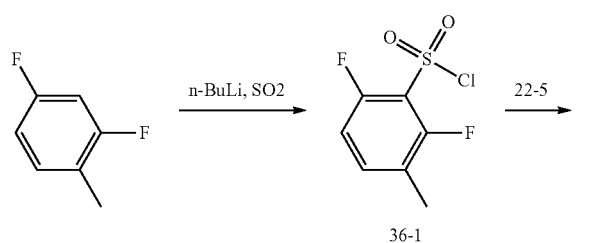

36-1

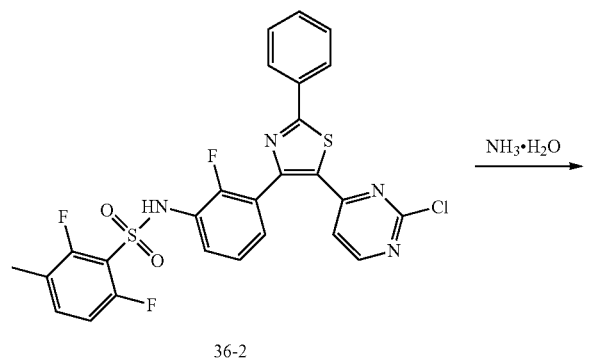

36-2

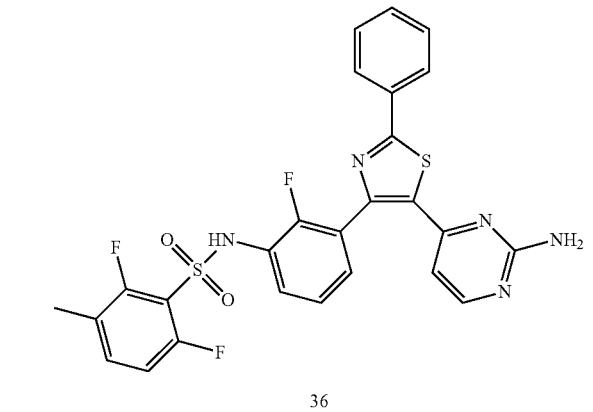

36

Step 1. Synthesis of 36-1

To a stirred solution of 2,4-difluoro-5-methylbenzene (1.0 g, 7.2 mmol) in tetrahydrofuran (20 mL) was added a N-butyllithium solution (3.4 mL, 8.6 mmol, 2.5 M in hexane) at −78° C. under nitrogen. The reaction mixture was stirred at −78° C. for 1 h, degassed with a SO₂ balloon, and N-chlorosuccinimide (1.0 g, 7.8 mmol) was added. The mixture was warmed to room temperature, filtered and the filtrate was concentrated to give 36-1 (700 mg, Yield: 39.5%) as a light yellow solid.

Step 2. Synthesis of 36-2

To a stirred solution of 22-5 (100 mg, 0.26 mmol) in dichloromethane (5 mL) was added pyridine (42 mg, 0.52 mmol) and 36-1 (118 mg, 0.52 mmol). The mixture was stirred at room temperature for 16 h, and then concentrated. The residue was purified by a prep-TLC plate (petroleum ether/ethyl acetate=3:1) to give 36-2 (30 mg, 20.2% yield) as a light yellow solid.

Step 3. Synthesis of 36

To a stirred solution of 36-2 (30 mg, 0.05 mmol) in 1,4-dioxane (1.0 mL) was added ammonium hydroxide (1.0 mL). The reaction was heated at 80° C. in a sealed tube for 16 h. The mixture was concentrated and the resulting residue was slurried with 2 mL of water to give 36 (25 mg, 92.5% yield) as a light yellow solid.

Example 11

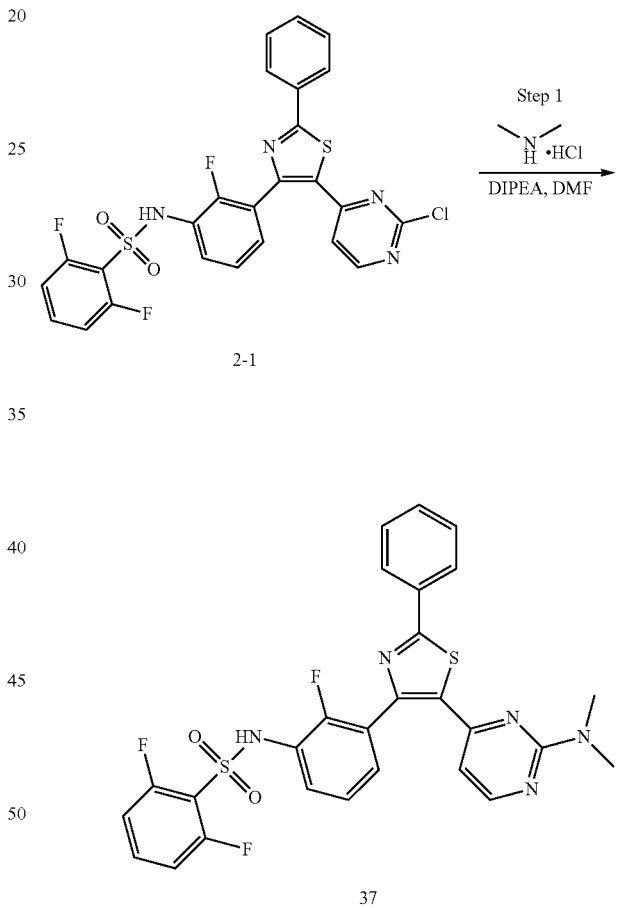

Step 1. Synthesis of 37

To a stirred solution of 2-1 (56 mg, 0.1 mmol) in dimethylformamide (2 mL) was added NN-diisopropylethylamine (65 mg, 0.5 mmol) and dimethylamine hydrochloride (41 mg, 0.5 mmol). The mixture was stirred at room temperature for 2 h, and then extracted with ethyl acetate (50 mL) and washed with water (50 mL). The organic phase was concentrated and the residue was purified by a prep-HPLC (acetonitrile with 0.05% of TFA: 5% to 80%) to give 37 (36 mg, 63% yield) as a pale yellow solid.

Example 12

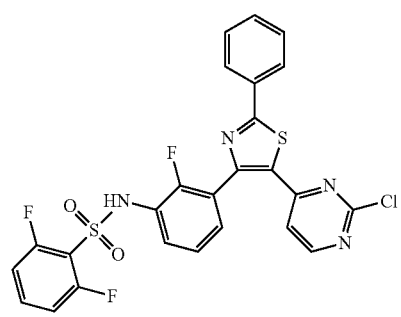

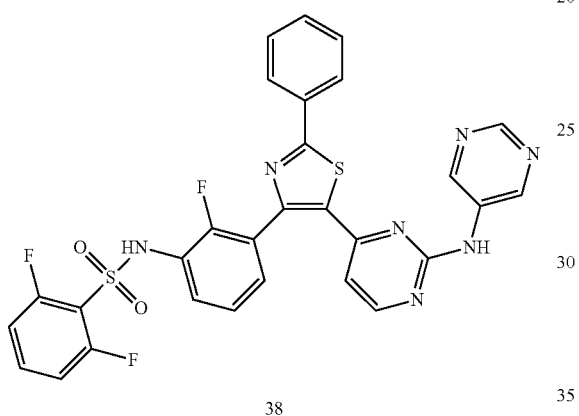

Step 1. Synthesis of 38

To a solution of pyrimidin-5-amine (34 mg, 0.36 mmol) and 2-1 (100 mg, 0.18 mmol) in tetrahydrofuran (6 mL) was added lithium bis(trimethylsilyl)amide (1 M in tetrahydrofuran, 0.9 mL, 0.9 mmol) at 0° C. under nitrogen stream, and then stirred at 0° C. for 2 hours. The reaction mixture was quenched with saturated ammonium chloride (10 mL), and diluted with ethyl acetate (50 mL). The organic layer was washed with brine (10 mL), dried over sodium sulfate, filtered, and concentrated. The residue was purified by a prep-HPLC (acetonitrile with 0.05% of TFA in water: 5% to 95%) to give 38 (36 mg, 32% yield) as a yellow solid.

Example 13

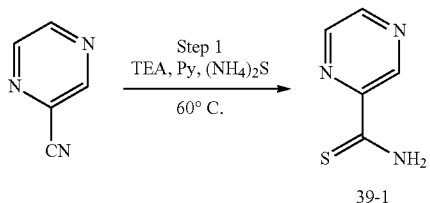

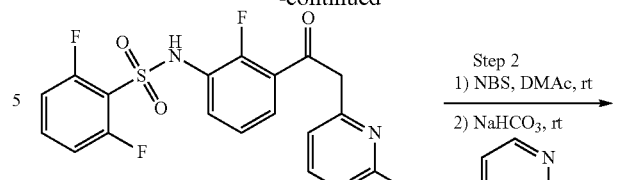

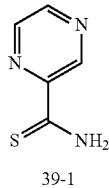

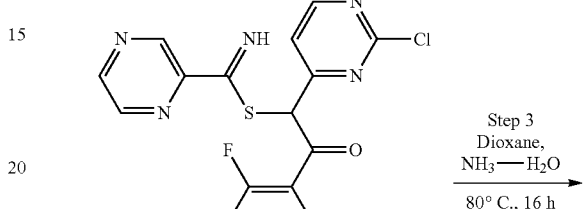

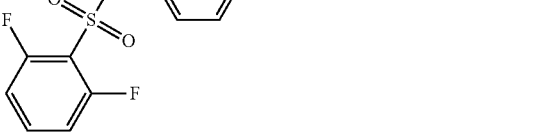

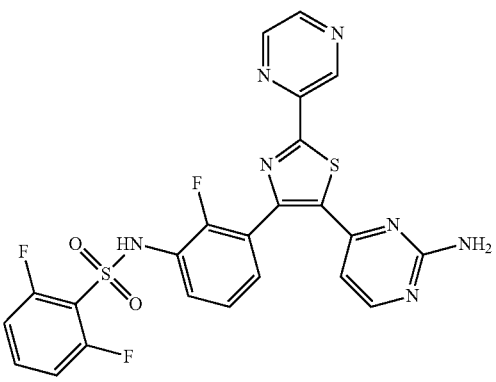

Step 1. Synthesis of 39-1

To a solution of pyrazine-2-carbonitrile (1 g, 9.51 mmol) in pyridine (6 mL) was added ammonium sulfide (1.78 g, 10.47 mmol, 40% in water) and triethylamine (2 mL), and then heated at 60° C. for 3 h. The mixture was diluted with water (15 mL) and extracted with ethyl acetate. The organic layer was washed with a saturated aqueous ammonium chloride solution (10 mL) and brine (10 mL), dried over sodium sulfate, and concentrated. The crude residue was slurried with ethanol/water (3 mL/10 mL) to give 39-1 (1.18 g, 89% yield) as a yellow solid.

Step 2. Synthesis of 39-2

To a solution of 1-4 (200 mg, 0.45 mmol) in dimethylacetamide (3 mL) was added N-bromosuccinimide (81 mg, 0.45 mmol) at room temperature, and then stirred for 0.5 hour. To the reaction mixture was added sodium bicarbonate (76 mg, 0.90 mmol) and 39-1 (75 mg, 0.54 mmol) at room temperature, and then stirred for 2 h. The mixture was diluted with water (15 mL) and extracted with ethyl acetate (3×15 mL). The combined organic layer was washed with brine (10 mL), dried over sodium sulfate, and concentrated. The crude residue was purified by column chromatography on silica gel (petroleum ether to petroleum ether/ethyl acetate=1:1) to give 39-2 (70 mg, 27% yield) as a brown oil.

Step 3. Synthesis of 39

A solution of 39-2 (70 mg, 0.12 mmol) in 1,4-dioxane (1 mL) and aqueous ammonia (1 mL) in a sealed tube was heated at 80° C. for 16 h. The reaction mixture was concentrated to give a crude residue which was purified by a prep-HPLC (acetonitrile with 0.05% of TFA in water: 5% to 95%) to give 39 (4 mg, 6% yield) as a pale yellow solid.

Example 14

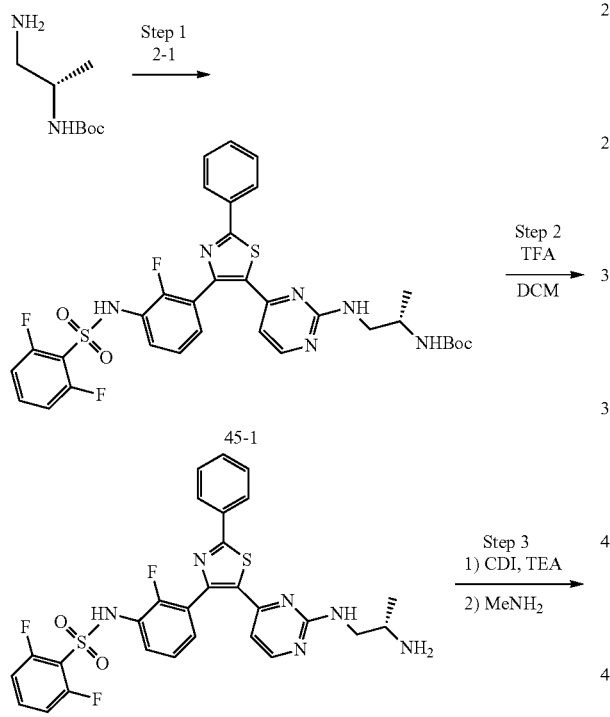

Step 1. Synthesis of 45-1

To a solution of 2-1 (200 mg, 0.36 mmol) and tert-butyl (S)-(1-aminopropan-2-yl)carbamate (187 mg, 1.08 mmol) in dimethyl sulfoxide (6 mL) was added ethyldiisopropylamine (138 mg, 1.08 mmol). The solution was heated at 80° C. for 24 h. The reaction was poured into water, and the mixture was filtered. The collected solid was dried to give 45-1 (200 mg, 81% yield) as a light yellow solid.

Step 2. Synthesis of 45-2

To a solution of 45-1 (200 mg, 0.29 mmol) in dichloromethane (4 mL) was added trifluoroacetic acid (4 mL). The reaction was stirred at room temperature for 2 h. Then the mixture was concentrated and the residue was purified by column chromatography on gel silica (dichloromethane to dichloromethane/methanol=10:1) to give 45-2 (150 mg, 96% yield) as a light yellow solid.

Step 3. Synthesis of 45

To a solution of 45-2 (30 mg, 0.05 mmol) and triethylamine (15 mg, 0.15 mmol) in tetrahydrofuran (10 mL) was added 1,1'-carbonyldiimidazole (12 mg, 0.075 mmol) at room temperature. After stirred for 30 min, methylamine (40% in water, 0.5 mL) was added and the reaction mixture was stirred for another 30 min. Then the reaction mixture was concentrated and the residue was purified by a prep-HPLC (acetonitrile with 0.05% of TFA: 5% to 75%) to give 45 (16 mg, 52% yield) as a light yellow solid.

Example 15

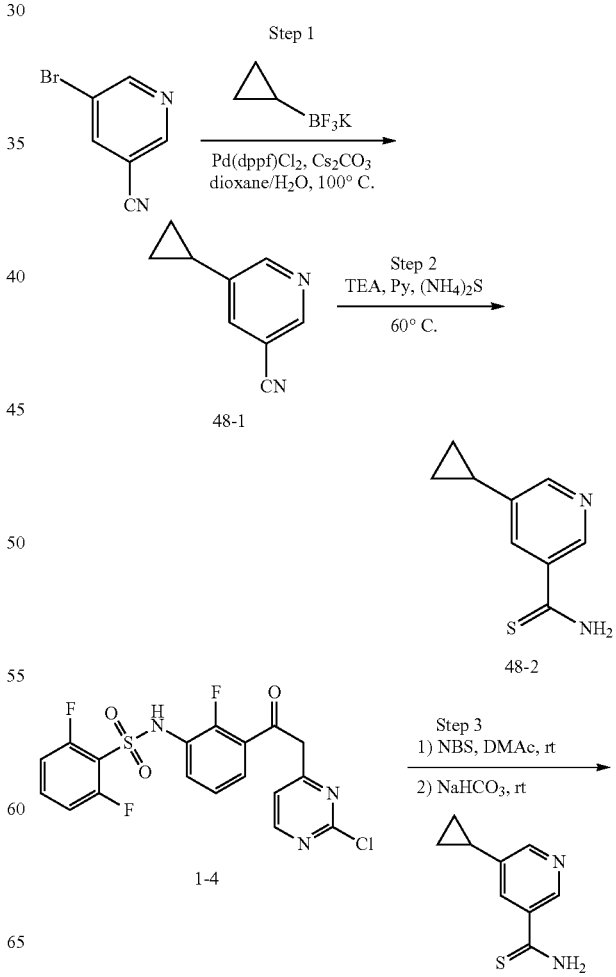

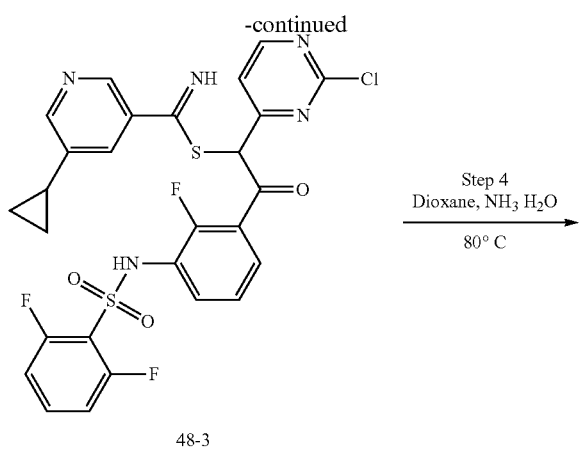

48-3

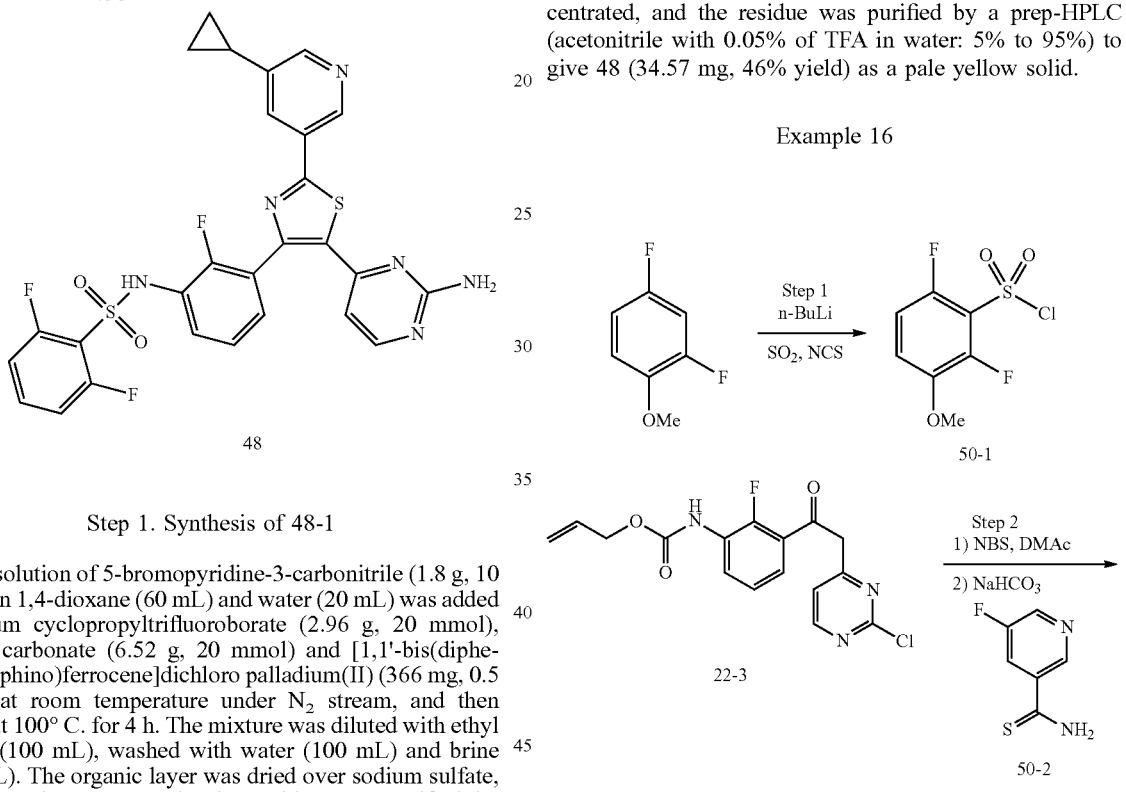

48

Step 1. Synthesis of 48-1

To a solution of 5-bromopyridine-3-carbonitrile (1.8 g, 10 mmol) in 1,4-dioxane (60 mL) and water (20 mL) was added potassium cyclopropyltrifluoroborate (2.96 g, 20 mmol), cesium carbonate (6.52 g, 20 mmol) and [1,1'-bis(diphenylphosphino)ferrocene]dichloro palladium(II) (366 mg, 0.5 mmol) at room temperature under $N_2$ stream, and then stirred at 100° C. for 4 h. The mixture was diluted with ethyl acetate (100 mL), washed with water (100 mL) and brine (100 mL). The organic layer was dried over sodium sulfate, filtrated and concentrated. The residue was purified by column chromatography on silica gel (petroleum ether to petroleum ether/ethyl acetate=4:1) to give 48-1 (350 mg, 23% yield) as a white solid.

Step 2. Synthesis of 48-2

To a solution of 48-1 (350 mg, 2.4 mmol) in pyridine (3 mL) was added ammonium sulfide (448 mg, 2.6 mmol, 40% in water) and triethylamine (1 mL), and then heated at 60° C. for 3 h. The mixture was diluted with ethyl acetate (50 mL), and washed with water (50 mL) and brine (50 mL). The organic layer was dried over sodium sulfate, filtrated and concentrated. The residue was purified by column chromatography on silica gel (petroleum ether to petroleum ether/ethyl acetate=1:3) to give 48-2 (300 mg, 70% yield) as a yellow solid.

Step 3. Synthesis of 48-3

To a solution of 1-4 (154 mg, 0.35 mmol) in dimethylacetamide (5 mL) was added N-bromosuccinimide (62 mg, 0.35 mmol) at room temperature, and then stirred for 1 h. To the mixture was then added sodium bicarbonate (59 mg, 0.7 mmol) and 48-2 (62 mg, 0.35 mmol) at room temperature, and then stirred for 3 h. The mixture was diluted with ethyl acetate (50 mL), washed with water (50 mL) and brine (50 mL). The organic layer was dried over sodium sulfate, filtrated and concentrated. The residue was slurried with ethyl acetate (5 mL), filtrated and dried to give 48-3 (80 mg, 37% yield) as a brown solid.

Step 4. Synthesis of 48

A solution of 48-3 (80 mg, 0.13 mmol) in 1,4-dioxane (1 mL) and aqueous ammonia (1 mL) in a sealed tube was heated at 80° C. for 16 h. The reaction mixture was concentrated, and the residue was purified by a prep-HPLC (acetonitrile with 0.05% of TFA in water: 5% to 95%) to give 48 (34.57 mg, 46% yield) as a pale yellow solid.

Example 16

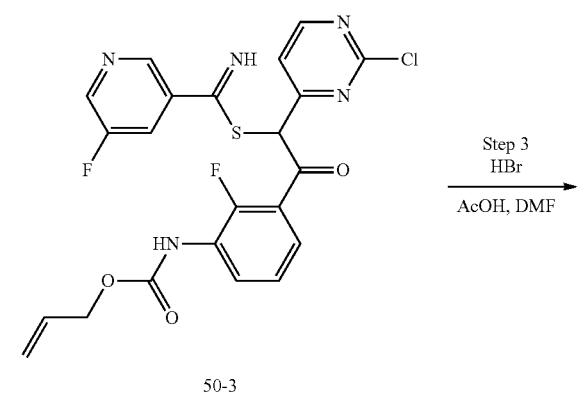

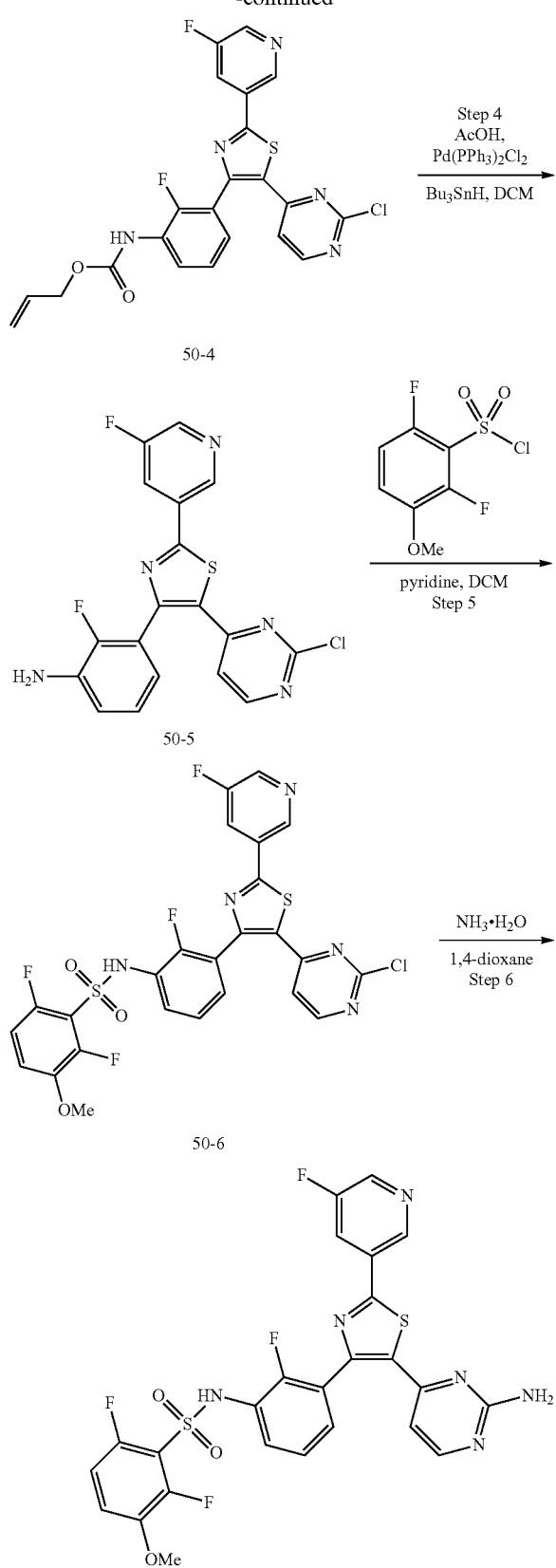

Step 1. Synthesis of 50-1

To a stirred solution of 2,4-difluoro-1-methoxybenzene (1.0 g, 6.9 mmol) in tetrahydrofuran (20 mL) was added n-butyllithium solution (2.5 M in tetrahydrofuran, 2.8 mL, 6.9 mmol) at −78° C. The reaction mixture was stirred at −78° C. for 1 h, and then degassed with a $SO_2$ balloon. After stirring for 1 h, N-chlorosuccinimide (0.8 g, 6.9 mmol) was added, and the reaction mixture was warmed to room temperature and stirred for another 1 h. The mixture was filtered and the filtrate was concentrated to give 50-1 (600 mg, 33.7% yield) as a light yellow solid.

Step 2. Synthesis of 50-3

To a solution of 22-3 (2.15 g, 6.15 mmol) in dimethylacetamide (10 mL) was added N-bromosuccinimide (1.1 g, 6.15 mmol) at room temperature, and then stirred for 0.5 h. To the mixture was added sodium bicarbonate (1.03 g, 12.30 mmol) and 50-2 (960 mg, 6.15 mmol) at room temperature, then stirred for 2 h. The mixture was diluted with water (30 mL) and extracted with ethyl acetate (3×40 mL). The combined organic layer was washed with brine (10 mL), dried over sodium sulfate, and concentrated. The residue was purified by column chromatography on silica gel (petroleum ether to petroleum ether/ethyl acetate=1:1) to give 50-3 (1.57 g, 51% yield) as a yellow solid.

Step 3. Synthesis of 50-4

To a solution of 50-3 (1.54 g, 3.06 mmol, 1.0 eq) in dimethylformamide (6 mL) was added hydrobromic acid in acetic acid (2 mL, 33%) at 0° C., and then stirred at room temperature for 2 h. The mixture was poured into water (50 mL) and stirred for 10 minutes. The resulting mixture was filtered and the solid was dried to give 50-4 (1.29 g, 87% yield) as a yellow solid.

Step 4. Synthesis of 50-5

To a solution of 50-4 (1.29 g, 2.65 mmol) in dichloromethane (20 mL) was added acetic acid (383 mg, 6.37 mmol), bis(triphenylphosphine)palladium(II) chloride (37 mg, 0.053 mmol) and tributylstannane (1.16 g, 3.98 mmol) under nitrogen stream. The mixture was stirred at room temperature for 1 h. Then the mixture was diluted with dichloromethane (50 mL), washed with saturated sodium bicarbonate solution (10 mL) and brine (10 mL), dried over sodium sulfate, and concentrated. The residue was slurried with petroleum ether to give 50-5 (988 mg, 93% yield) as a yellow solid.

Step 5. Synthesis of 50-6

To a stirred solution of 50-5 (30 mg, 0.075 mmol) in dichloromethane (5 mL) were added pyridine (10 mg, 0.15 mmol) and 50-1 (36 mg, 0.15 mmol). The reaction mixture was stirred at room temperature for 16 h. Then the solution was concentrated and the residue was slurried with methanol (4 mL) to give 50-6 (30 mg, 81.1% yield) as a light yellow solid.

Step 6. Synthesis of 50

To a stirred solution of 50-6 (30 mg, 0.05 mmol) in 1,4-dioxane (1.0 mL) was added ammonium hydroxide (28% solution, 1.0 mL). Then the reaction solution was heated in a sealed tube at 80° C. for 16 h. The reaction solution was concentrated and the residue was purified a prep-HPLC (acetonitrile with 0.05% of TFA in water: 5% to 75%) to give 50 (20 mg, 67% yield) as an off white solid.

Example 17

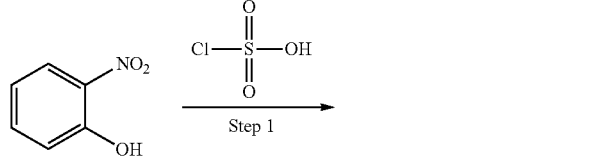

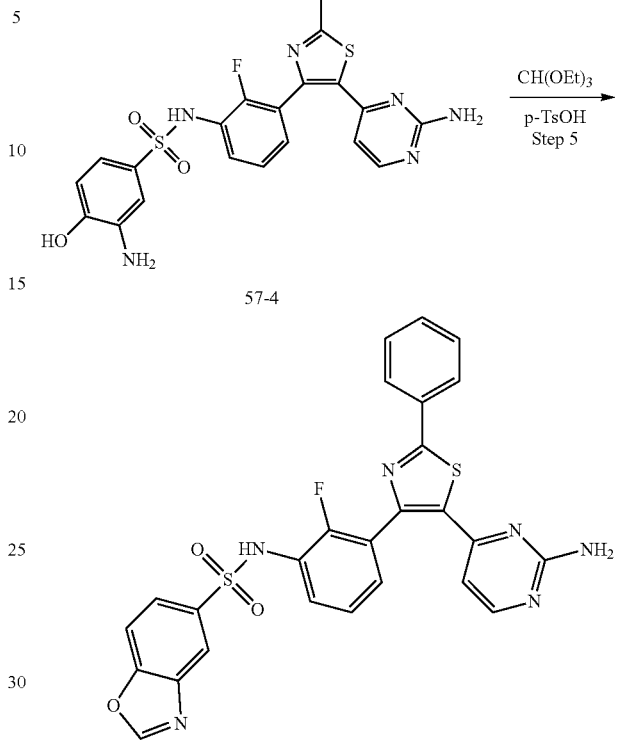

Step 1. Synthesis of 57-1

To a stirred chlorosulfonic acid (1.5 mL) cooled in an ice-water bath was added 2-nitrophenol (1.1 g, 7.91 mmol) at a rate to keep the temperature below 10° C. Then the reaction mixture was heated to 100° C. and stirred for 20 min. Ice water was added and extracted with ethyl acetate (2×100 mL). The combined organic layers were washed with brine, dried over sodium sulfate, filtered and concentrated. The residue was purified by column chromatography on gel silica (petroleum ether to petroleum ether/ethyl acetate=5:1) to give 57-1 (900 mg, 48% yield) as a brown oil.

Step 2. Synthesis of 57-2

To a stirred solution of 22-5 (150 mg, 0.39 mmol) in dimethylacetamide (8 mL) was added 57-1 (112 mg, 0.47 mmol) at room temperature. The reaction mixture was stirred at room temperature for 4 h. Water was added and extracted with methyl tert-butyl ether (3×50 mL). The combined organic layer was washed with brine, dried over sodium sulfate, filtered and concentrated. The residue was purified by column chromatography on gel silica (petroleum ether to petroleum ether/ethyl acetate=1:1) to give 57-2 (120 mg, 53% yield) as a brown solid.

Step 3. Synthesis of 57-3

A mixture of 57-2 (120 mg, 0.21 mmol) and Rh/C (10% on carbon, 10 mg) in tetrahydrofuran (10 mL) was stirred under a hydrogen balloon at room temperature for overnight. The reaction mixture was filtered and the filtrate was concentrated. The residue was purified by column chromatography on gel silica (petroleum ether to petroleum ether/ethyl acetate=1:1) to give 57-3 (80 mg, 69% yield) as a yellow solid.

Step 4. Synthesis of 57-4

To a stirred solution of 57-3 (70 mg, 0.13 mmol) in 1,4-dioxane (4 mL) was added ammonium hydroxide (28% solution, 1 mL). The reaction mixture was stirred at 80° C. for overnight. The reaction mixture was concentrated and the crude residue was purified by a prep-HPLC (acetonitrile with 0.05% of TFA in water: 5% to 75%) to give 57-4 (40 mg, 58% yield) as a yellow solid.

Step 5. Synthesis of 57

To a stirred solution of 57-4 (20 mg, 0.037 mmol) and triethoxymethane (0.5 mL) in dimethylformamide (2 mL) was added p-toluenesulfonic acid (3 mg). The reaction mixture was stirred at room temperature for 2 h. The reaction was quenched by aqueous sodium bicarbonate (5 mL), and extracted with ethyl acetate (3×40 mL). The combined organic layer was washed with brine, dried over sodium sulfate, filtered and concentrated. The residue was purified by a prep-HPLC (acetonitrile with 0.05% of TFA in water: 5% to 75%) to give 57 (9.2 mg, 46% yield) as a pale yellow solid.

Example 18

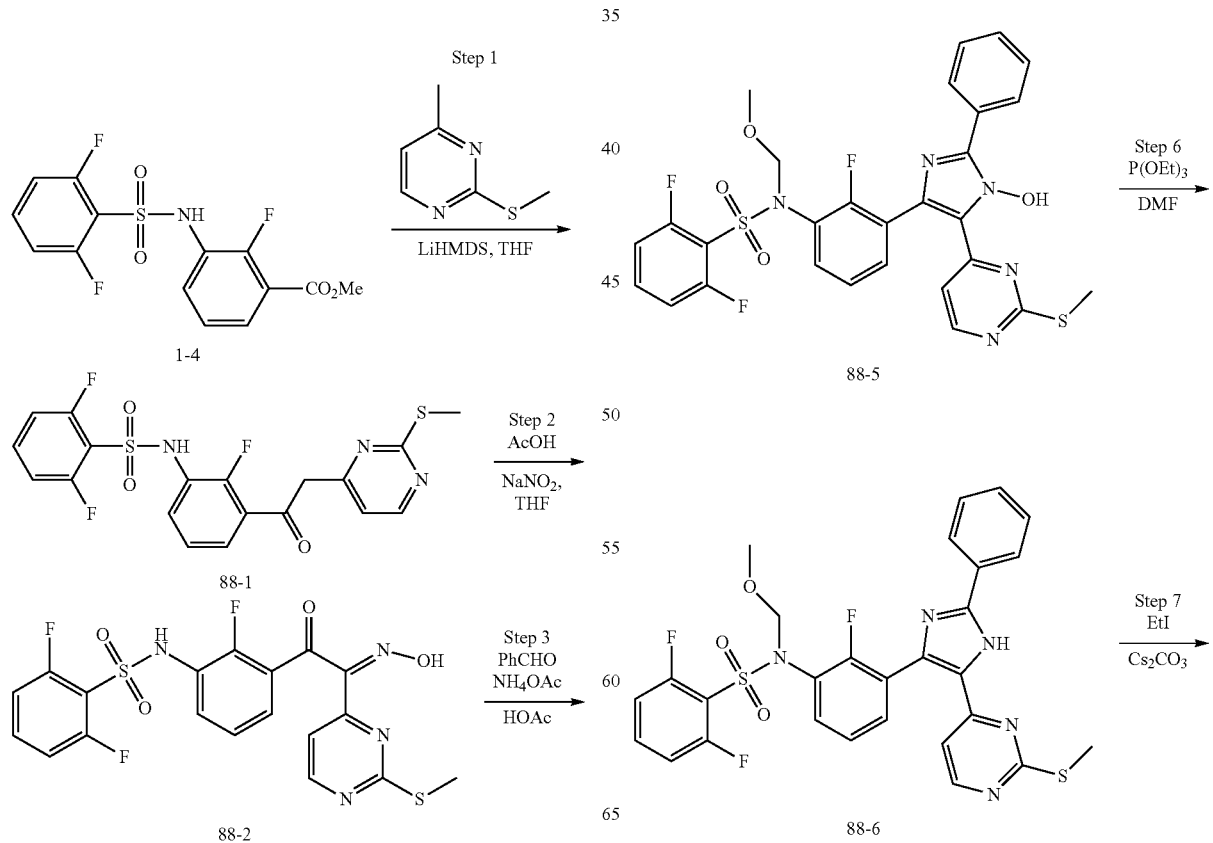

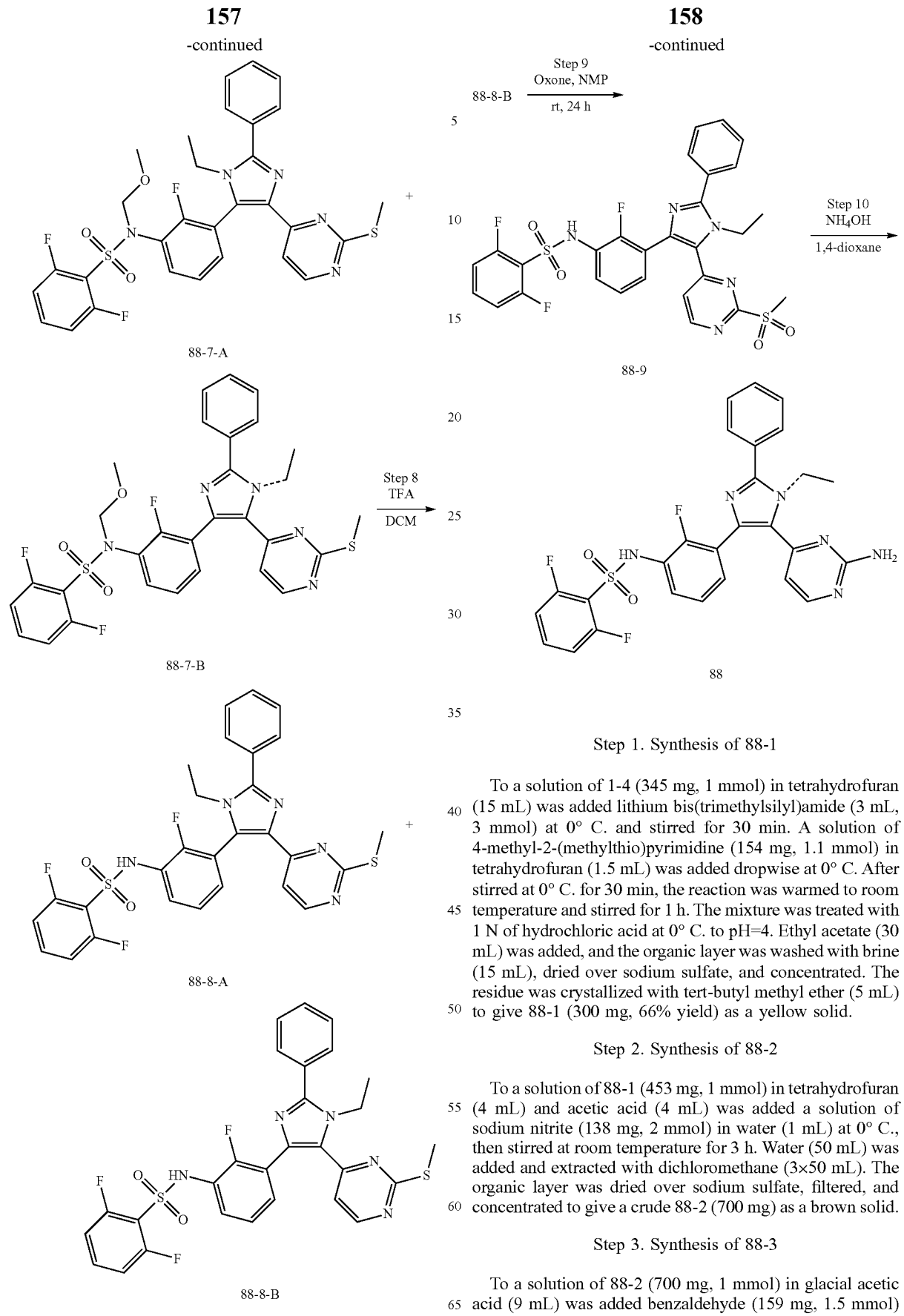

Step 1. Synthesis of 88-1

To a solution of 1-4 (345 mg, 1 mmol) in tetrahydrofuran (15 mL) was added lithium bis(trimethylsilyl)amide (3 mL, 3 mmol) at 0° C. and stirred for 30 min. A solution of 4-methyl-2-(methylthio)pyrimidine (154 mg, 1.1 mmol) in tetrahydrofuran (1.5 mL) was added dropwise at 0° C. After stirred at 0° C. for 30 min, the reaction was warmed to room temperature and stirred for 1 h. The mixture was treated with 1 N of hydrochloric acid at 0° C. to pH=4. Ethyl acetate (30 mL) was added, and the organic layer was washed with brine (15 mL), dried over sodium sulfate, and concentrated. The residue was crystallized with tert-butyl methyl ether (5 mL) to give 88-1 (300 mg, 66% yield) as a yellow solid.

Step 2. Synthesis of 88-2

To a solution of 88-1 (453 mg, 1 mmol) in tetrahydrofuran (4 mL) and acetic acid (4 mL) was added a solution of sodium nitrite (138 mg, 2 mmol) in water (1 mL) at 0° C., then stirred at room temperature for 3 h. Water (50 mL) was added and extracted with dichloromethane (3×50 mL). The organic layer was dried over sodium sulfate, filtered, and concentrated to give a crude 88-2 (700 mg) as a brown solid.

Step 3. Synthesis of 88-3

To a solution of 88-2 (700 mg, 1 mmol) in glacial acetic acid (9 mL) was added benzaldehyde (159 mg, 1.5 mmol) and ammonium acetate (770 mg, 10 mmol), and then stirred at 60° C. for 24 h. The reaction mixture was poured into water (60 mL), and the solid was collected by filtration and dried to give 88-3 (550 mg, 97% yield for two steps) as a pale yellow solid.

Step 4. Synthesis of 88-4

To a solution of 88-3 (400 mg, 0.7 mmol) in dichloromethane (20 mL) was added chloro(methoxy)methane (168 mg, 2.1 mmol) and N/N-diisopropylethylamine (102 mg, 3.5 mmol) at 0° C., and then stirred at room temperature for 2 h. Dichloromethane (30 mL) was added and the organic phase was washed with water (50 mL) and brine (50 mL), dried over sodium sulfate, filtered, and concentrated. The residue was purified by silica column (petroleum ether to petroleum ether/ethyl acetate=1:2) to give 88-4 (450 mg, 98% yield) as a pale yellow solid.

Step 5. Synthesis of 88-5

To a solution of 88-4 (450 mg, 0.68 mmol) in methanol (60 mL) was added triethylamine (692 mg, 6.8 mmol), and then stirred at 70° C. for 11 days. The reaction mixture was concentrated and dissolved in ethyl acetate (50 mL). The organic phase was washed with aqueous ammonium chloride (50 mL), water (50 mL) and brine (50 mL), dried over sodium sulfate, filtered, and concentrated to give a crude 88-5 (430 mg) as a pale yellow solid.

Step 6. Synthesis of 88-6

To a solution of 88-5 (430 mg) in dimethylformamide (5 mL) was added triethyl phosphite (1 mL) at room temperature, and then stirred at 75° C. for 2 h. Ethyl acetate (50 mL) was added and washed with water (50 mL) and brine (50 mL). The organic layer was dried over sodium sulfate, filtered, and concentrated. The residue was purified by a prep-HPLC (acetonitrile with 0.05% of TFA in water: 5% to 95%) to give 88-6 (300 mg, 73% yield for two steps) as a pale yellow solid.

Step 7. Synthesis of 88-7-A and 88-7-B

To a solution of 88-6 (150 mg, 0.25 mmol) in dimethylformamide (5 mL) was added cesium carbonate (163 mg, 0.5 mmol) and iodoethane (78 mg, 0.5 mmol) at 0° C., and then stirred at room temperature for 2 h. Ethyl acetate (50 mL) was added and washed with water (50 mL) and brine (50 mL). The organic layer was dried over sodium sulfate, filtered, and concentrated to give a crude mixture of 88-7-A/B (140 mg) as a light yellow oil.

Step 8. Synthesis of 57-1

To a solution of 88-7-A/B (140 mg) in dichloromethane (1 mL) was added trifluoroacetic acid (2 mL) at room temperature, and then stirred for 24 h. The reaction mixture was concentrated and purified by a prep-HPLC (acetonitrile with 0.05% of TFA in water: 5% to 95%) to give 88-8-A (20 mg, 15.6% yield) as a light yellow solid and 88-8-B (60 mg, 46.8% yield) as a light yellow solid, respectively.

Step 9. Synthesis of 88-9

To a solution of 88-B (60 mg, 0.1 mmol) in A-methyl pyrrolidone (3 mL) was added Oxone (615 mg, 1.0 mmol) at room temperature, and then stirred for 24 h. The reaction mixture was poured into water (50 mL), and solid was collected by filtration and dried to give 88-9 (50 mg, 81% yield) as a white solid.

Step 10. Synthesis of 88

To a solution of 88-8-B (50 mg, 0.08 mmol) in 1,4-dioxane (1 mL) was added aqueous ammonia (1 mL) in a sealed tube, and then heated at 80° C. for 16 h. The reaction mixture was concentrated and purified by a prep-HPLC (acetonitrile with 0.05% of TFA in water: 5% to 95%) to give 88 (12 mg, 27% yield) as a white solid.

Example 19

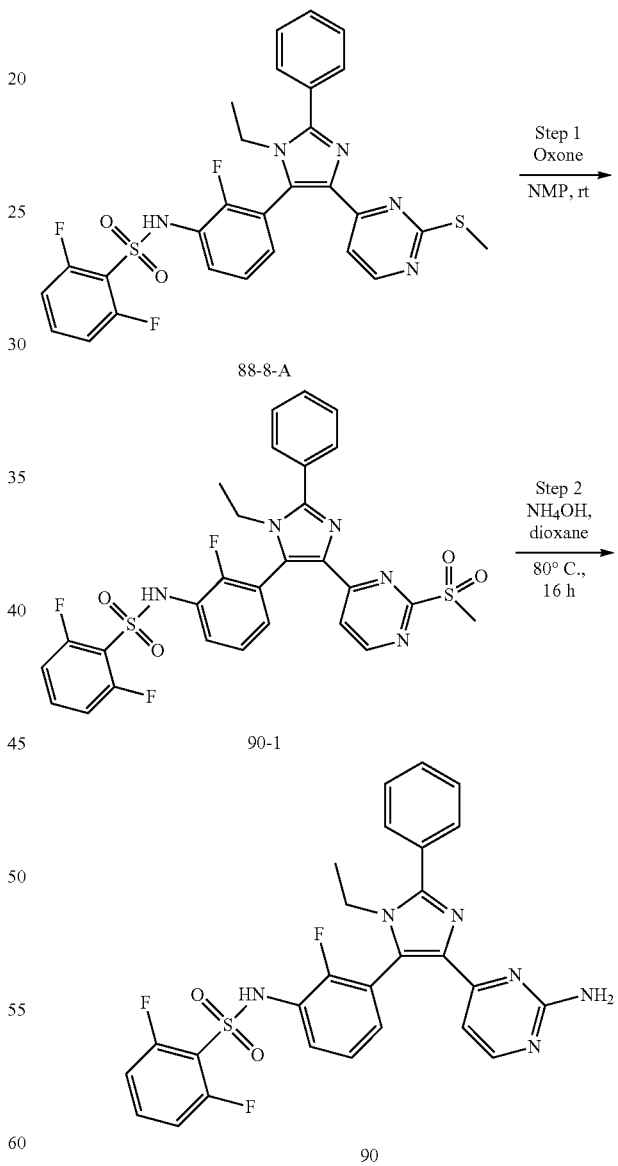

Step 1. Synthesis of 90-1

To a solution of 88-8-A (20 mg, 0.03 mmol) in/V-methyl pyrrolidone (3 mL) was added Oxone (184 mg, 0.3 mmol)

at room temperature, and then stirred for 48 h. Dichloromethane (50 mL) was added and washed with water (50 mL) and brine (50 mL). The organic layer was dried over sodium sulfate, filtered, and concentrate to give a crude 90-1 (70 mg) as a light yellow oil.

Step 2. Synthesis of 90

To a solution of 90-1 (70 mg) in 1,4-dioxane (1 mL) was added aqueous ammonia (1 mL) in a sealed tube at room temperature, and then heated at 80° C. for 16 h. The reaction mixture was concentrated and purified by a prep-HPLC (acetonitrile with 0.05% of TFA in water: 5% to 95%) to give 90 (3 mg, 18% yield) as a light yellow solid.

Example 20

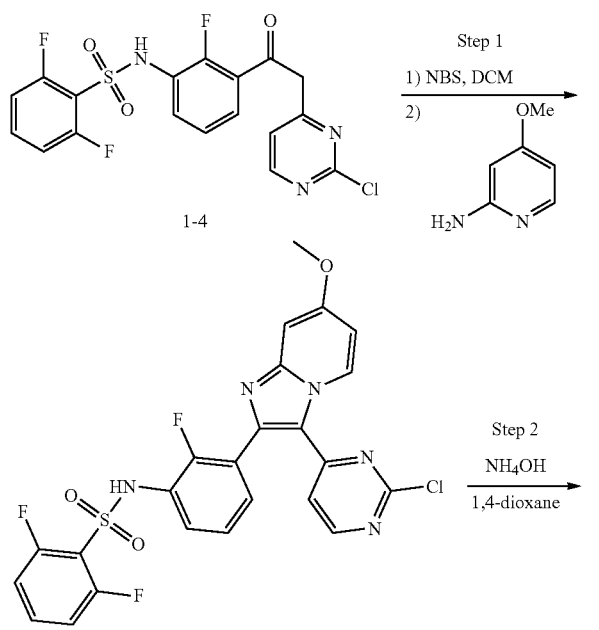

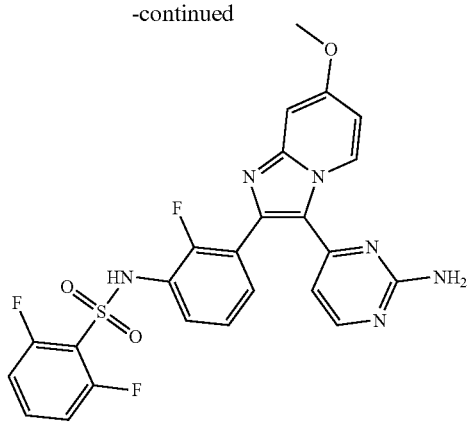

Step 1. Synthesis of 91-1

To a solution of 1-4 (100 mg, 0.22 mmol) in dichloromethane (5 mL) was added N-bromosuccinimide (40 mg, 0.22 mmol) at room temperature, and then stirred for 0.5 h. The mixture was concentrated and the residue was dissolved in 1,4-dioxane (5 mL). To the mixture was added 4-methoxypyridin-2-amine (80 mg, 0.66 mmol) and stirred at 60° C. for 16 h. The mixture was cooled to room temperature, filtered and the solid was dried to give 91-1 (45 mg, 36% yield) as a yellow solid.

Step 2. Synthesis of 91

A solution of 91-1 (45 mg, 0.08 mmol) in 1,4-dioxane (3 mL) and aqueous ammonia (1.5 mL, 28%) in a sealed tube was heated at 80° C. for 2 days. The reaction mixture was concentrated, and the residue was purified by a prep-HPLC (methanol with 0.05% TFA in water: 5% to 50%) to give 91 (14.5 mg, 32% yield) as a yellow solid.

Example 21

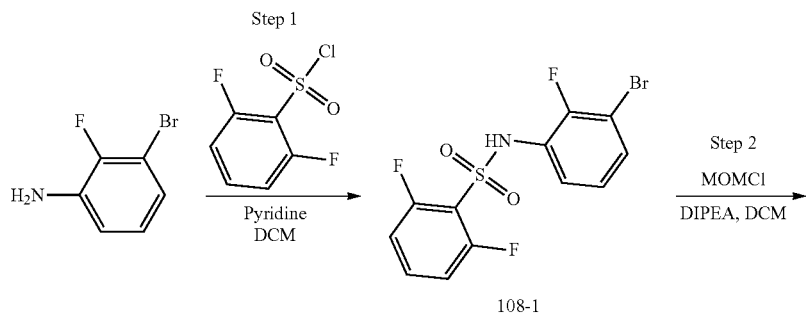

-continued
Step 3
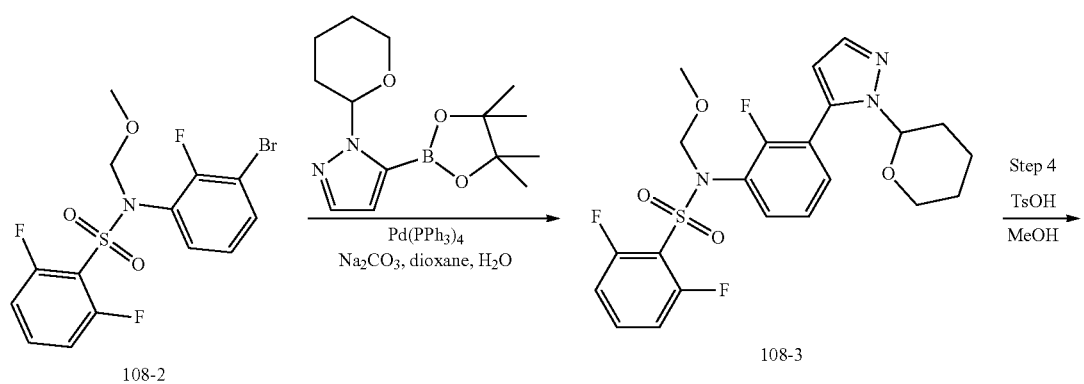
Step 4
TsOH
MeOH
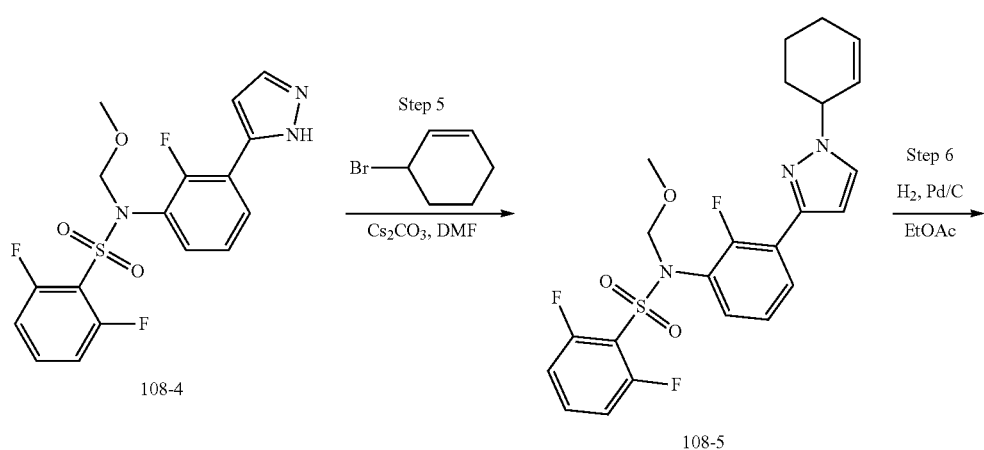
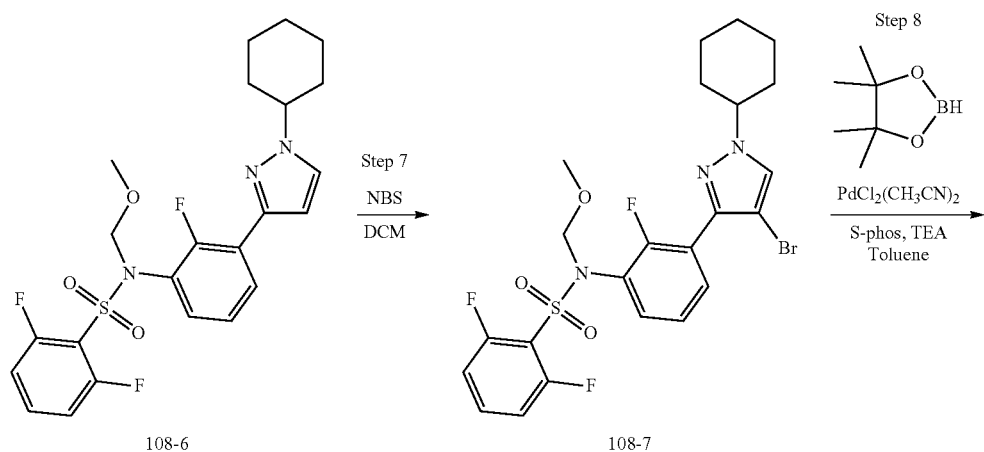

-continued
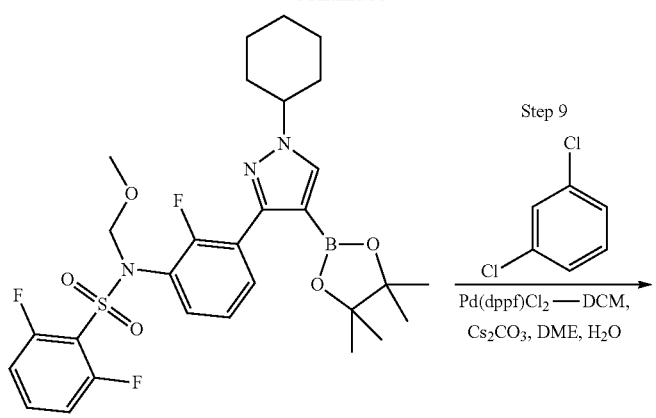
108-8
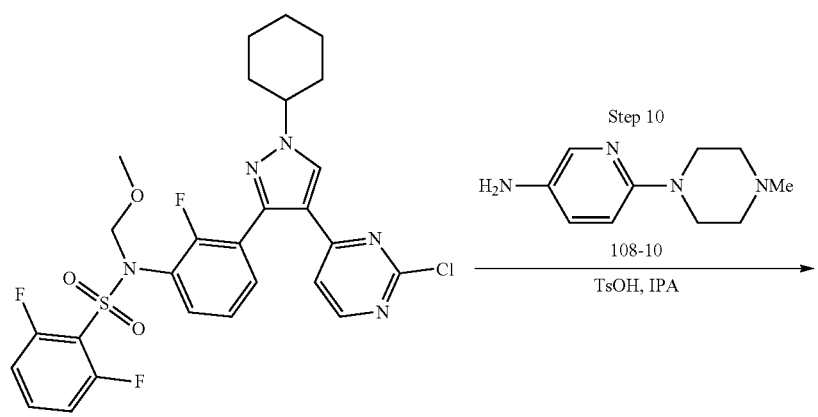
108-9
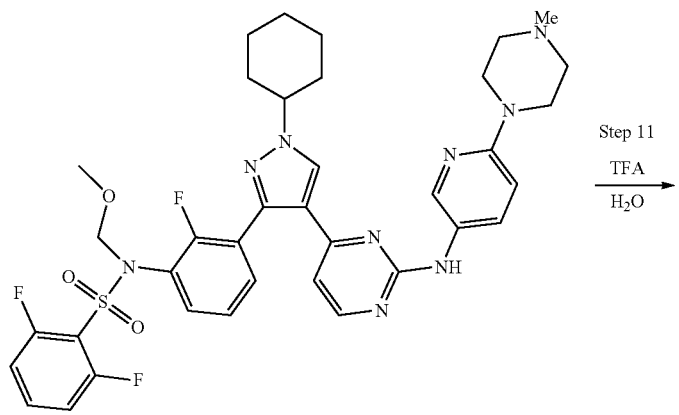
108-11

-continued

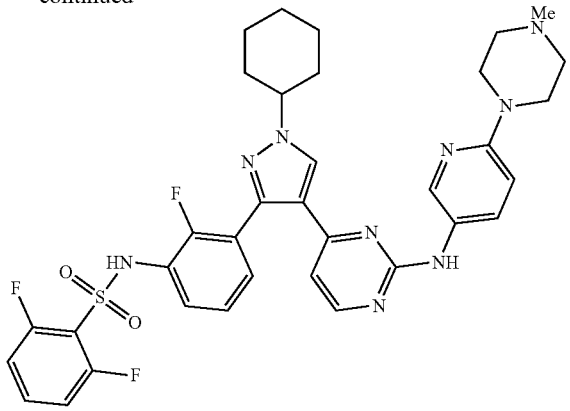

108

Step 1. Synthesis of 108-1

To a solution of 3-bromo-2-fluoroaniline (570 mg, 3 mmol) and pyridine (474 mg, 6 mmol) in dichloromethane (15 mL) was added 2,6-difluorobenzenesulfonyl chloride (667 mg, 3.2 mmol) dropwise at 0° C., and then stirred at room temperature for 2 h. Dichloromethane (30 mL) was added, and washed with 1 N of hydrochloric acid (20 mL) and brine (20 mL). The organic layer was dried over sodium sulfate, filtered and concentrated to give 108-1 (700 mg, 63% yield).

Step 2. Synthesis of 108-2

To a solution of 108-1 (6.8 g, 18.5 mmol) and N,N-diisopropylethylamine (3.6 g, 27.8 mmol) in dichloromethane (100 mL) was added chloro(methoxy)methane (2.2 g, 27.8 mmol) at 0° C. The mixture was warmed to room temperature and stirred for 2 h, and then was quenched with saturated ammonium chloride solution (20 mL). The organic phase was washed with brine (30 mL), dried over sodium sulfate, filtered, and concentrated. The residue was crystallized with heptane (50 mL) to give 108-2 (7 g, 95% yield) as a white solid.

Step 3. Synthesis of 108-3

To a mixture of 108-2 (2.5 g, 6 mmol) and 1-(tetrahydro-2H-pyran-2-yl)-5-(4,4,5,5-tetramethyl-1,3,2-dioxaborolan-2-yl)-1H-pyrazole (2.5 g, 9 mmol) in 1,4-dioxane (50 mL) was added a solution of sodium carbonate (1.2 g, 11 mmol) in water (5 mL) and tetrakis(triphenylphosphine) palladium (600 mg, 0.52 mmol). After degassed with $N_2$, the mixture was stirred at 95° C. for 16 h. The reaction mixture was cooled to room temperature, and filtered through Celite. The filtrate was washed with brine (100 mL), dried over sodium sulfate, filtered, and concentrated. The residue was purified by chromatography on a silica gel column (petroleum ether to petroleum ether/ethyl acetate=2:1) to give 108-3 (1.8 g, 60% yield).

Step 4. Synthesis of 108-4

A mixture of 108-3 (1.2 g, 2.5 mmol) and p-toluenesulfonic acid (86 mg, 0.5 mmol) in methanol (20 mL) was stirred at room temperature for 2 h. The mixture was extracted with ethyl acetate (100 mL). The organic phase was washed with saturated sodium bicarbonate (10 mL), dried over sodium sulfate, filtered, and concentrated. The residue was purified by chromatography on a silica gel column (petroleum ether to petroleum ether/ethyl acetate=1:1) to give 108-4 (1 g, 100% yield).

Step 5. Synthesis of 108-5

To a stirred solution of 108-4 (1 g, 2.5 mmol) and 3-bromocyclohex-1-ene (480 mg, 3 mmol) in dimethylformamide (20 mL) was added cesium carbonate (1.6 g, 5 mmol). The reaction was stirred at 10° C. for 16 h. The mixture was extracted with ethyl acetate (100 mL). The organic phase was washed with water (100 mL) and brine (15 mL), dried over sodium sulfate and concentrated. The residue was purified by chromatography on a silica gel column (petroleum ether to petroleum ether/ethyl acetate=1:1) to give 108-5 (900 mg, 75% yield) as a white solid.

Step 6. Synthesis of 108-6

A mixture of 108-5 (850 mg, 1.8 mmol) and Pd/C (5%, 230 mg) in ethyl acetate (30 mL) was stirred under hydrogen atmosphere at room temperature for 1 h. The reaction mixture was filtered through Celite, and the filtrate was concentrated to give 108-6 (820 mg, 96% yield) as a white solid.

Step 7. Synthesis of 108-7

To a stirred solution of 108-6 (800 mg, 1.7 mmol) in dichloromethane (20 mL) was added N-bromosuccinimide (363 mg, 2 mmol). The mixture was stirred at room temperature for 16 h, and then was extracted with dichloromethane (20 mL). The organic phase was washed with a 10% aqueous sodium bisulfite solution (10 mL) and brine (15 mL), dried over sodium sulfate, and concentrated. The residue was purified by chromatography on a silica gel column (petroleum ether/ethyl acetate=4:1) to give 108-7 (800 mg, 84% yield) as a white solid.

Step 8. Synthesis of 108-8

To a mixture of 108-7 (800 mg, 1.43 mmol), 4,4,5,5-tetramethyl-1,3,2-dioxaborolane (1.2 g, 9.36 mmol) and triethylamine (360 mg, 3.57 mmol) in toluene (17 mL) was added bis(acetonitrile)dichloropalladium(II) (32 mg, 0.12 mmol) and 2-dicyclohexylphosphino-2',6'-dimethoxybiphenyl (100 mg, 0.24 mmol). The mixture was stirred under microwave at 90° C. for 1.5 h. After cooled to room temperature, the mixture was filtered through Celite, and the filtrate was concentrated. The residue was purified by column chromatography on silica gel (petroleum ether/ethyl acetate=2:1) to give 108-8 (900 mg, 100% yield) as a white solid.

Step 9. Synthesis of 108-9

To a mixture of 108-8 (550 mg, 0.9 mmol), 2,4-dichloropyrimidine (175 mg, 1.18 mmol) and cesium carbonate (591 mg, 1.8 mmol) in 1,2-dimethoxyethane (12 mL) and water (1.2 mL) was added 1,1'-bis(diphenylphosphino)ferrocenepalladium(II)dichloride dichloromethane complex (106 mg, 0.13 mmol). The reaction mixture was stirred under microwave at 100° C. for 3 h. The reaction mixture was filtered through Celite, and the filtrate was concentrated. The residue was purified by column chromatography on silica gel (petroleum ether/ethyl acetate=1:1) to give 108-9 (380 mg, 71% yield).

Step 10. Synthesis of 108-11

To a mixture of 108-9 (90 mg, 0.15 mmol) in isopropanol (3 mL) was added p-toluenesulfonic acid (26 mg, 0.15 mmol) and 108-10 (29 mg, 0.15 mmol), and the mixture was heated at 105° C. for overnight. The mixture was cooled and then extracted with ethyl acetate (50 mL). The organic phase was washed with saturated sodium bicarbonate (10 mL), dried over sodium sulfate, filtered, and concentrated. The residue was purified by a prep-HPLC (dichloromethane/methanol=20:1) to give 108-11 (56 mg, 50% yield).

Step 11. Synthesis of 108

A mixture of 108-11 (56 mg, 0.07 mmol) in trifluoroacetic acid (1 mL) and water (0.1 mL) was stirred at 55° C. for 2 h. Water (30 mL) was added, and the mixture was dried via lyophilization to give 108 (56 mg, 90% yield) as a yellow solid.

Example 22

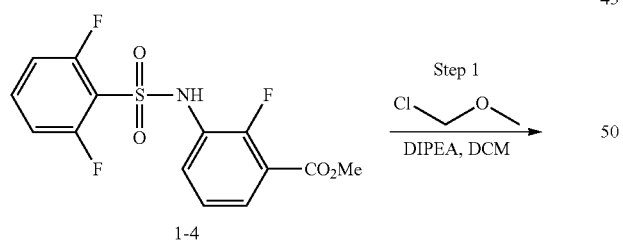

1-4

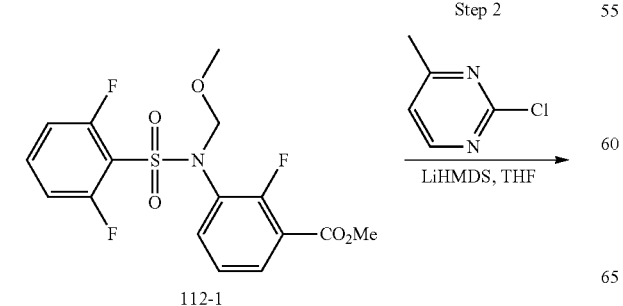

112-1

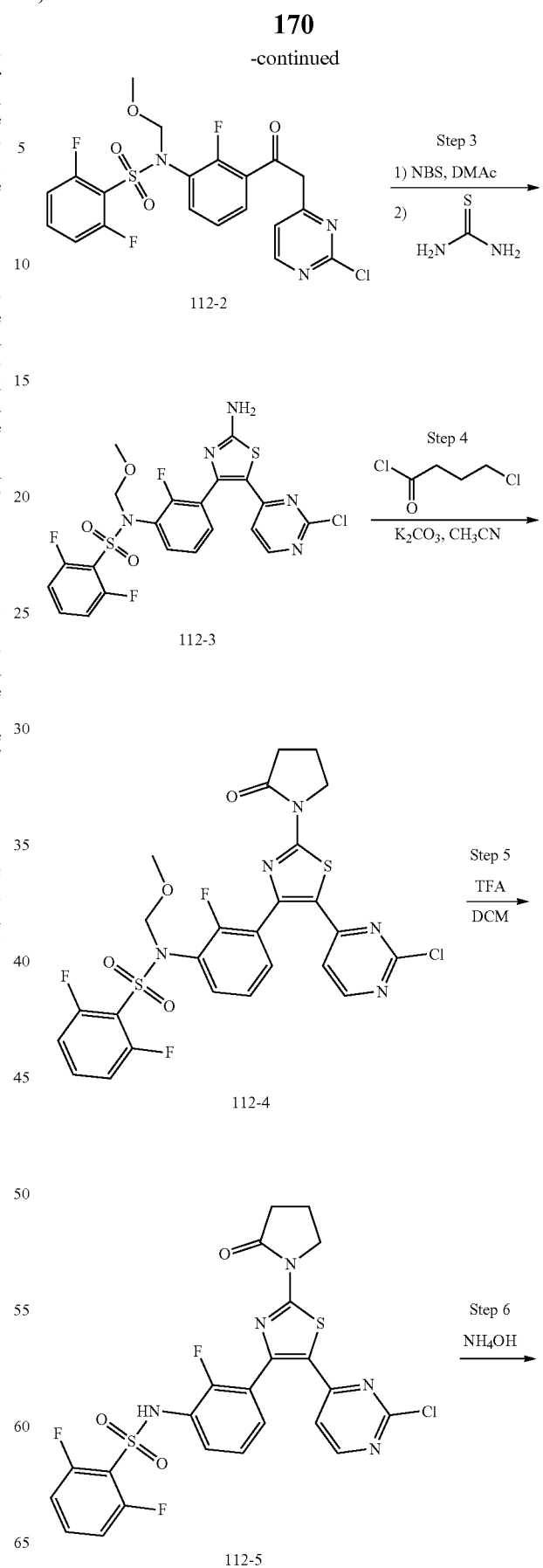

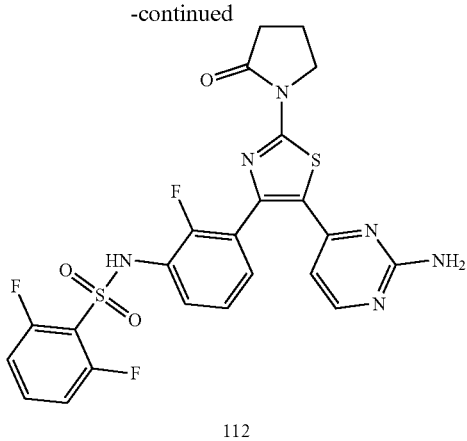

112

Step 1. Synthesis of 112-1

To a solution of 1-4 (5 g, 14.48 mmol) and AX-diisopropylethylamine (2.8 g, 21.72 mmol) in dichloromethane (50 mL) was added chloro(methoxy)methane (1.75 g, 21.72 mmol) at 0° C. After stirring for 10 minutes at 0° C., the mixture was warmed to room temperature and stirred for 2 h. The mixture was diluted with dichloromethane (100 mL) and washed with water (10 mL), brine (10 mL), dried over sodium sulfate, and concentrated. The residue was purified by column chromatography on silica gel (petroleum ether to petroleum ether/ethyl acetate=3:1) to give 112-1 (5 g, 89% yield) as a yellow solid.

Step 2. Synthesis of 112-2

To a solution of 112-1 (4 g, 10.28 mmol) in tetrahydrofuran (40 mL) was added lithium bis(trimethylsilyl)amide (41 mL, 41.12 mmol) at 0° C. After stirring at 0° C. for 0.5 h, a solution of 2-chloro-4-methylpyrimidine (1.59 g, 12.34 mmol) in tetrahydrofuran (20 mL) was added dropwise. After the addition, the reaction was allowed to warm to room temperature and stirred for 2 h. The mixture was acidified with 1 N of hydrochloric acid and extracted with ethyl acetate (3×50 mL). The combined organic layer was washed with water (10 mL) and brine (10 mL), dried over sodium sulfate, and concentrated. The residue was purified by column chromatography on silica gel (petroleum ether to petroleum ether/ethyl acetate=2:1) to give 112-2 (3.4 g, 68% yield) as a yellow solid.

Step 3. Synthesis of 112-3

To a solution of 112-2 (1.78 g, 3.67 mmol) in dimethylacetamide (8 mL) was added N-bromosuccinimide (654 mg, 3.67 mmol) at room temperature, and then stirred for 0.5 h. Then thiourea (559 mg, 7.34 mmol) was added, and the reaction mixture was stirred for 2 h. The mixture was diluted with water (10 mL) and extracted with ethyl acetate (3×50 mL). The combined organic layer was washed with brine (10 mL), dried over sodium sulfate, and concentrated. The residue was purified by column chromatography on silica gel (petroleum ether to petroleum ether/ethyl acetate=2:3) to give 112-3 (1.06 g, 53% yield) as a yellow solid.

Step 4. Synthesis of 112-4

To a solution of 112-3 (220 mg, 0.41 mmol) and potassium carbonate (340 mg, 2.46 mmol) in acetonitrile (5 mL) was added 4-chlorobutanoyl chloride (145 mg, 1.03 mmol). The mixture was stirred at room temperature for 6 h, and then diluted with water (10 mL) and extracted with ethyl acetate (3×20 mL). The combined organic layer was washed with brine (10 mL), dried over sodium sulfate, and concentrated. The residue was slurried with a mixed solvents of petroleum ether and ethyl acetate (9:1) to give 112-4 (223 mg, 90% yield) as a white solid.

Step 5. Synthesis of 112-5

To a solution of 112-4 (144 mg, 0.24 mmol) in dichloromethane (5 mL) was added trifluoroacetic acid (2 mL). The mixture was stirred at room temperature for 24 h and concentrated to give a crude 112-5 (114 mg, 85% yield) as a white solid.

Step 6. Synthesis of 112

A solution of 112-5 (70 mg, 0.12 mmol) in 1,4-dioxane (1 mL) and aqueous ammonia (1 mL) in a sealed tube was heated at 80° C. for 16 h. The reaction mixture was concentrated. The residue was purified by a prep-HPLC (acetonitrile with 0.05% of TFA in water: 5% to 95%) to give 112 (3.8 mg, 6% yield) as a pale yellow solid.

Example 23

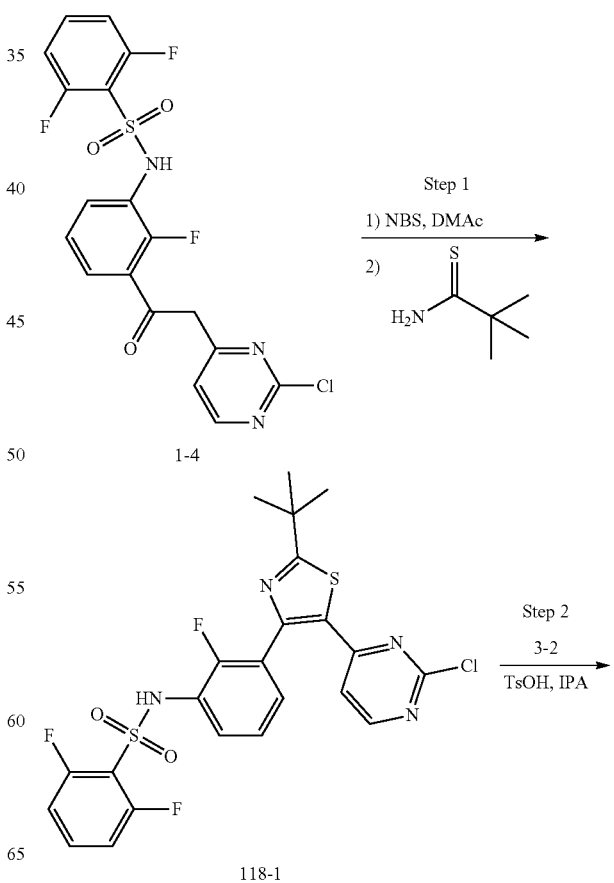

173

-continued

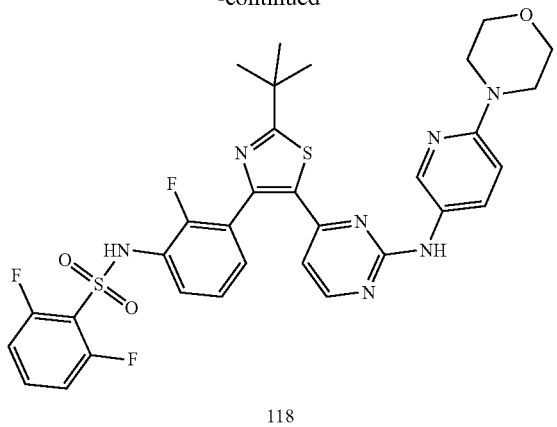

118

Step 1. Synthesis of 118-1

To a solution of 1-4 (200 mg, 0.45 mmol) in dimethyl-acetamide (15 mL) was added N-bromosuccinimide (81 mg, 0.45 mmol) at room temperature, and then stirred for 1 h. 2,2-dimethylthiopropionamide (53 mg, 0.45 mmol) was added at room temperature, and then heated at 80° C. for 3 h. Ethyl acetate (50 mL) was added and the organic phase was washed with water (50 mL) and brine (50 mL), dried over sodium sulfate, filtered, and concentrated. The crude residue was purified by silica column (petroleum ether to petroleum ether/ethyl acetate=1:1) to give 118-1 (190 mg, 84% for two steps) as a white solid.

Step 2. Synthesis of 118

To a stirred solution of 118-1 (54 mg, 0.1 mmol) in isopropanol (10 mL) was added 3-2 (18 mg, 0.1 mmol) and p-toluenesulfonic acid (18 mg, 0.1 mmol). The reaction was stirred at 110° C. for 48 h. The mixture was concentrated and purified by a prep-HPLC (acetonitrile with 0.05% of TFA: 5% to 80%) to give 118 (37 mg, 54% yield) as a pale yellow solid.

Example 24

174

-continued

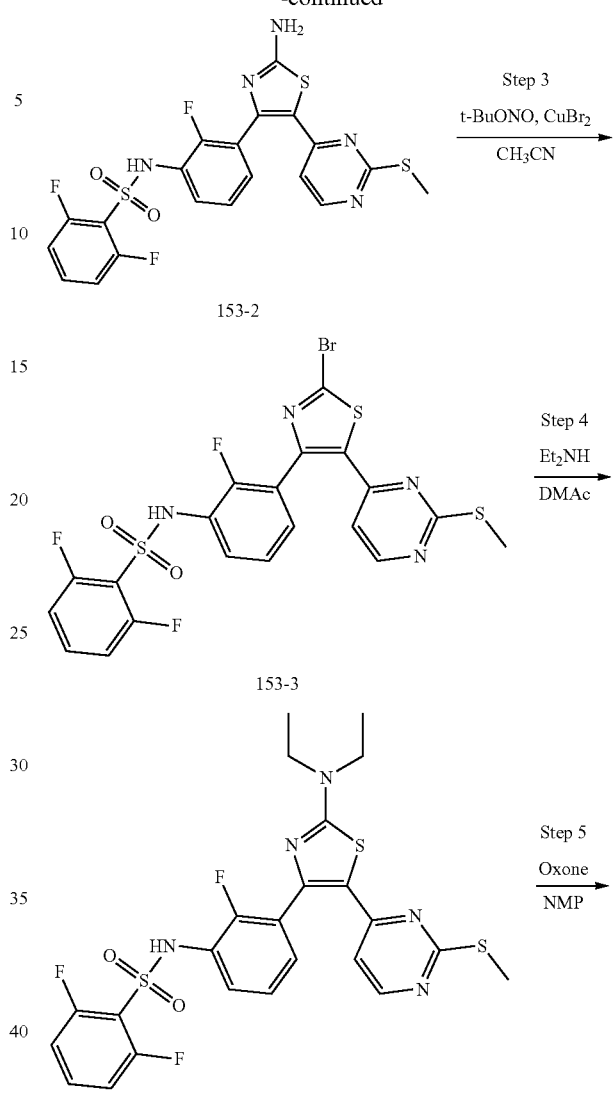

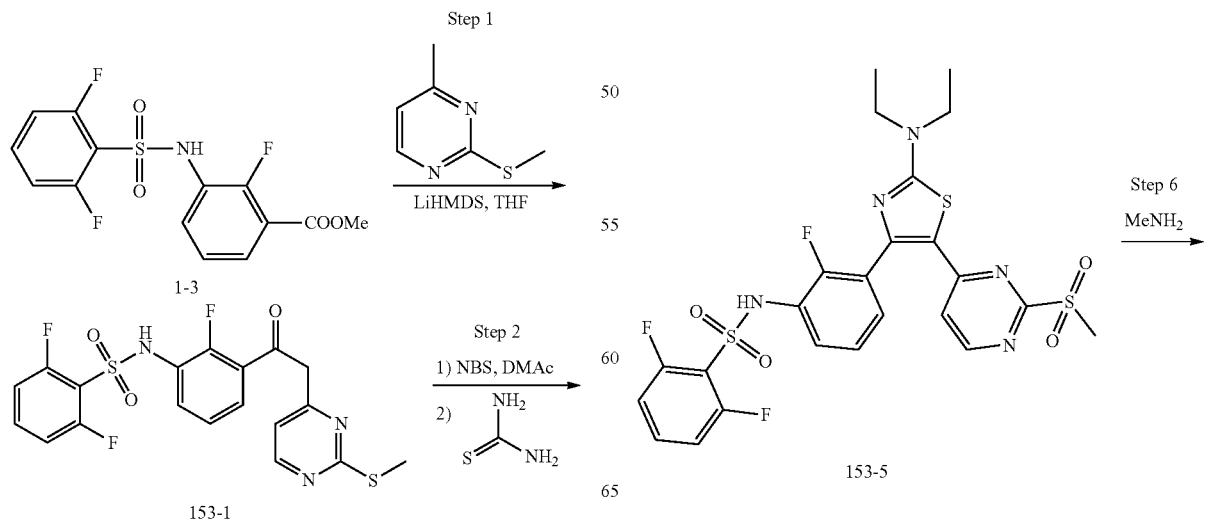

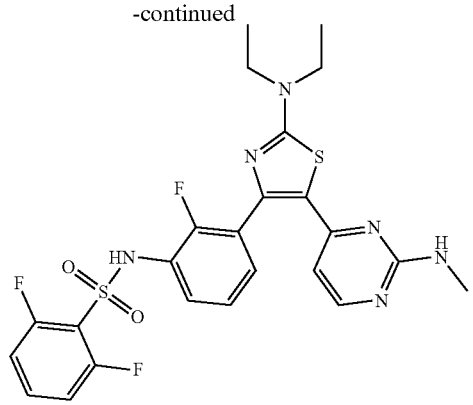

153

Step 1. Synthesis of 153-1

To a solution of 1-3 (345 mg, 1 mmol) in tetrahydrofuran (15 mL) was added lithium bis(trimethylsilyl)amide (3 mL, 3 mmol, 1 M in tetrahydrofuran) at 0° C. Another solution of 4-methyl-2-(methylthio)pyrimidine (154 mg, 1.1 mmol) in tetrahydrofuran (1.5 mL) was added dropwise. Then the mixture was warmed to room temperature over 1 h before treated with 1N hydrochloric acid. Ethyl acetate (30 mL) was added and the organic layer was washed with brine (15 mL), dried over sodium sulfate, and concentrated. The residue was recrystallized with tert-butyl methyl ether to give 153-1 (300 mg, 66% yield).

Step 2. Synthesis of 153-2

To a solution of 153-1 (3.5 g, 7.7 mmol) in dimethylacetamide (40 mL) was added N-bromosuccinimide (1.38 g, 7.7 mmol). The mixture was stirred at room temperature for 0.5 h and then thiourea (1.17 g, 15.4 mmol) was added. The reaction was stirred at room temperature for 3 h. The mixture was diluted with ethyl acetate (100 mL) and washed with water (100 mL). The organic phase was dried over sodium sulfate, filtered, and concentrated. The crude residue was purified by flash chromatography (petroleum ether/ethyl acetate=2:3) to give 153-2 (2.0 g, 51% yield).

Step 3. Synthesis of 153-3

To a solution of cupric bromide (1.1 g, 5 mmol) in acetonitrile (30 mL) was added tert-butyl nitrite (6.8 g, 66 mmol) at 0° C. under nitrogen. 153-2 (1.7 g, 3.3 mmol) was added and the reaction was stirred at 0° C. for 30 min. The mixture was diluted with dichloromethane (100 mL) and washed with water (100 mL). The organic phase was dried over sodium sulfate, filtered, and concentrated. The residue was slurried with petroleum ether/dichloromethane (20 mL/5 mL) and filtered. The filtered cake was dried to give 153-3 (1.3 g, 69% yield).

Step 4. Synthesis of 153-4

To a solution of 153-3 (120 mg, 0.21 mmol) in dimethylacetamide (2 mL) was added diethylamine (77 mg, 1.05 mmol). The reaction was heated at 80° C. for 6 h in a sealed tube. The mixture was diluted with ethyl acetate (50 mL) and washed with water (50 mL). The organic phase was dried over sodium sulfate, filtered, and concentrated to give 153-4 (100 mg, 84% yield).

Step 5. Synthesis of 153-5

To a solution of 153-4 (100 mg, 0.18 mmol) in N-methyl pyrrolidone (5 mL) was added potassium peroxomonosulfate (543 mg, 0.9 mmol), and the mixture was stirred at room temperature for 48 h. The mixture was diluted with ethyl acetate (50 mL) and washed with water (50 mL). The organic phase was dried over sodium sulfate, filtered, and concentrated to give 153-5 (100 mg, 93% yield).

Step 6. Synthesis of 153

To a solution of 153-5 (100 mg, 0.17 mmol) in 1,4-dioxane (3 mL) was added aqueous methylamine (1 mL, 40%), and the reaction was stirred at room temperature for 2 h. The mixture was diluted with ethyl acetate (50 mL) and washed with water (50 mL). The organic phase was dried over sodium sulfate, filtered, and concentrated. The residue was purified by a pre-HPLC (acetonitrile with 0.05% of TFA: 5% to 60%) to give 153 (47 mg, 50% yield).

Example 25

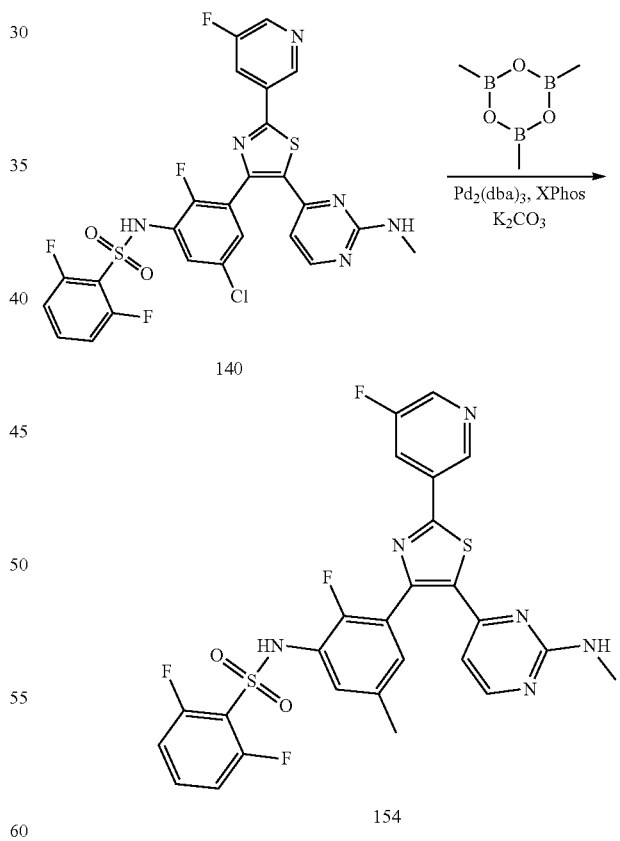

Synthesis of 154

To a mixture of 140 (40 mg, 0.066 mmol), tris(dibenzylideneacetone)dipalladium (6.0 mg, 0.007 mmol), 2-dicyclohexylphosphino-2',4',6'-triisopropylbiphenyl (6.0 mg, 0.013 mmol) and potassium carbonate (32 mg, 0.23 mmol) in 1,4-dioxane/H$_2$O (5 mL/1 mL) was added trimethylboroxine (0.05 mL, 0.18 mmol, 3.5 M in THF) under N$_2$ atmosphere, and the reaction mixture was heated at 130° C. in a microwave reactor for 3 hr. The mixture was then cooled, diluted with water (20 mL) and extracted with ethyl acetate (3×30 mL). The combined organic layer was washed with brine, dried over sodium sulfate, and concentrated to give a crude product which was purified by column chromatography on gel silica (petroleum ether to petroleum ether/ethyl acetate=1:2) to give 154 (15 mg, 39% yield).

Exemplary CSK inhibitory compounds as described herein and their characterization are provided in Table 1 below:

TABLE 1

Characterization of the compounds

| Compound No. | Structure | [M + H]$^+$ | NMR |
|---|---|---|---|
| 1 | 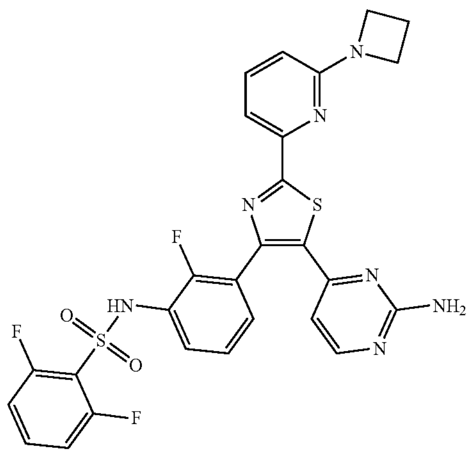 [SMILES: Nc1nccc(-c2sc(-c3cccc(N4CCC4)n3)nc2-c2cccc(NS(=O)(=O)c3c(F)cccc3F)c2F)n1] | 596.1 | HNMR (400 MHz, DMSO-d$_6$, ppm): δ 10.94 (s, 1H), 9.70 (s, 1H), 8.07 (d, J = 4.2 Hz, 1H), 7.81-7.77 (m, 1H), 7.69-7.64 (m, 1H), 7.50-7.41 (m, 2H), 7.31 (t, J = 8.0 Hz, 1H), 7.23-7.20 (m, 3H), 7.11-7.08 (m, 1H), 6.95-6.91 (m, 2H), 5.96 (d, J = 4.2 Hz, 1H), 4.30-4.27 (m, 2H), 3.41-3.39 (m, 2H), 2.01-1.92 (m, 2H). FNMR (376 MHz, DMSO-d$_6$, ppm): δ –107.49 (2 F), –124.16 (1 F). |
| 2 | 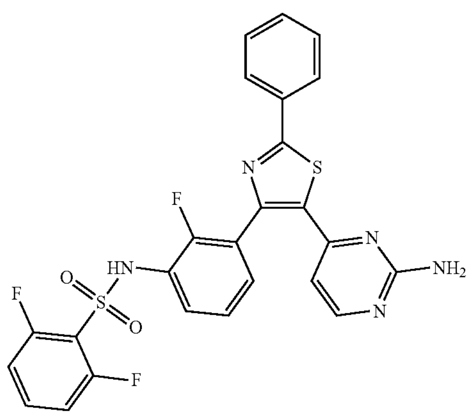 [SMILES: Nc1nccc(-c2sc(-c3ccccc3)nc2-c2cccc(NS(=O)(=O)c3c(F)cccc3F)c2F)n1] | 540.0 | HNMR (400 MHz, DMSO-d$_6$, ppm): δ 10.89 (s, 1H), 8.00 (d, J = 2.4 Hz, 1H), 7.99-7.93 (m, 2H), 7.67-7.63 (m, 1H), 7.51-7.49 (m, 3H), 7.47-7.32 (m, 2H), 7.27-7.21 (m, 1H), 7.21 (t, J = 9.2 Hz, 2H), 6.79 (s, 2H), 5.87 (d, J = 5.2 Hz, 1H). |
| 3 | 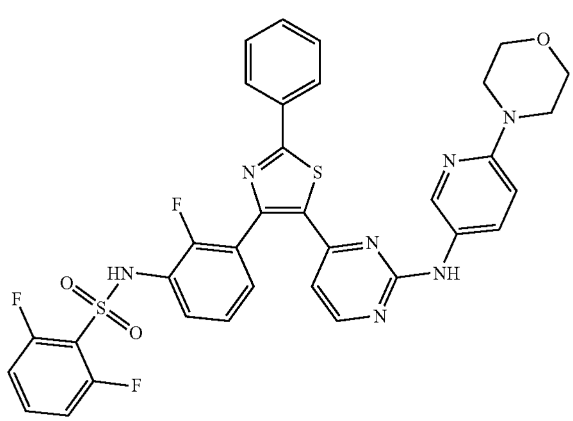 [SMILES: O=S(=O)(Nc1cccc(-c2nc(-c3ccccc3)sc2-c2ccnc(Nc3ccc(N4CCOCC4)nc3)n2)c1F)c1c(F)cccc1F] | 702.1 | HNMR (400 MHz, DMSO-d$_6$, ppm): δ 10.91 (s, 1H), 9.68 (s, 1H), 8.44-8.40 (m, 1H), 8.22 (d, J = 5.2 Hz, 1H), 7.98-7.92 (m, 3H), 7.68-7.60 (m, 1H), 7.52-7.42 (m, 5H), 7.31 (t, J = 8.0 Hz, 1H), 7.20 (t, J = 9.2 Hz, 2H), 7.02-6.95 (m, 1H), 6.14-6.13 (m, 1H), 3.71-3.68 (m, 4H), 3.42-3.38 (m, 4H). FNMR (376 MHz, DMSO-d$_6$, ppm): δ –107.25 (2 F), –124.30 (1 F). |

TABLE 1-continued

Characterization of the compounds

| Compound No. | Structure | [M + H]+ | NMR |
|---|---|---|---|
| 4 | 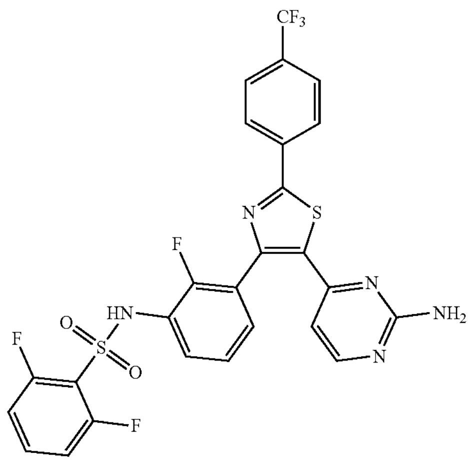 | 608.0 | HNMR (400 MHz, DMSO-d$_6$, ppm): δ 10.91 (s, 1H), 8.16 (d, J = 8.0 Hz, 2H), 8.03 (d, J = 5.2 Hz, 1H), 7.86 (t, J = 8.4 Hz, 2H), 7.69-7.64 (m, 1H), 7.46 (t, J = 7.2 Hz, 2H), 7.31 (t, J = 8.0 Hz, 1H), 7.22 (t, J = 8.8 Hz, 2H), 6.85 (s, 2H), 5.89 (d, J = 5.2 Hz, 1H). FNMR (376 MHz, DMSO-d$_6$, ppm): δ −61.41 (3 F), −107.39 (2 F), −124.42 (1 F). |
| 5 | 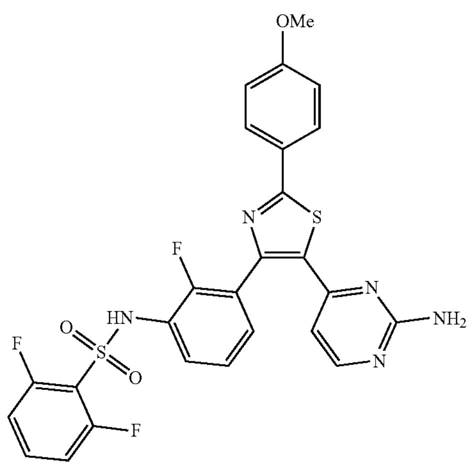 [SMILES: COc1ccc(-c2nc(-c3cccc(NS(=O)(=O)c4c(F)cccc4F)c3F)c(-c3ccnc(N)n3)s2)cc1] | 570.0 | HNMR (400 MHz, DMSO-d$_6$, ppm): δ 10.90 (s, 1H), 7.98 (d, J = 5.2 Hz, 1H), 7.88 (d, J = 9.2 Hz, 2H), 7.68-7.64 (m, 1H), 7.46-7.40 (m, 2H), 7.30 (t, J = 8.0 Hz, 1H), 7.22 (t, J = 8.8 Hz, 2H), 7.05 (d, J = 8.8 Hz, 2H), 6.88 (br s, 2H), 5.86 (d, J = 5.2 Hz, 1H), 3.81 (s, 3H). FNMR (376 MHz, DMSO-d$_6$, ppm): δ −107.39 (2 F), −124.49 (1 F). |
| 6 | 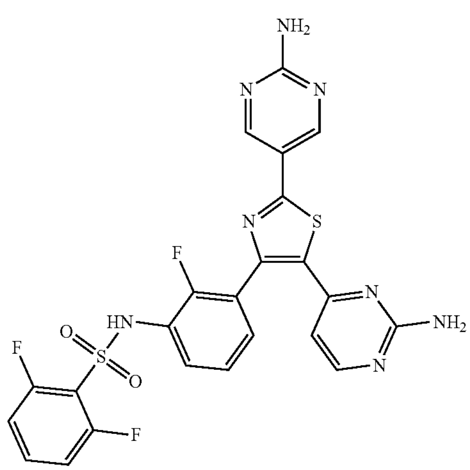 | 557.0 | HNMR (400 MHz, DMSO-d$_6$, ppm): δ 10.89 (s, 1H), 8.73 (s, 2H), 7.96 (d, J = 5.2 Hz, 1H), 7.66-7.62 (m, 1H), 7.45-7.18 (m, 7H), 6.76 (s, 2H), 5.82 (d, J = 5.2 Hz, 1H). FNMR (376 MHz, DMSO-d$_6$, ppm): δ −107.37 (2 F), −124.48 (1 F). |

TABLE 1-continued

Characterization of the compounds

| Compound No. | Structure | [M + H]⁺ | NMR |
|---|---|---|---|
| 7 | 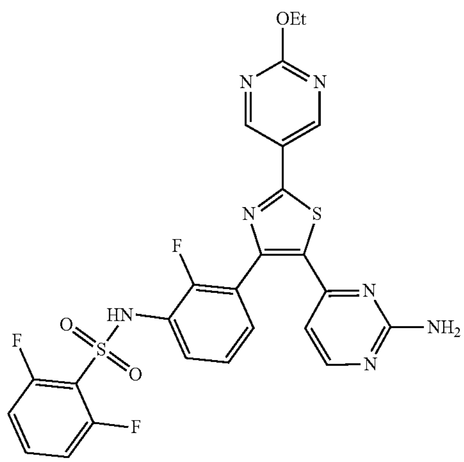 [SMILES: CCOc1ncc(-c2nc(-c3cccc(NS(=O)(=O)c4c(F)cccc4F)c3F)c(-c3ccnc(N)n3)s2)cn1] | 586.0 | HNMR (400 MHz, DMSO-d₆, ppm): δ 9.10 (s, 2H), 7.98 (d, J = 6.0 Hz, 1H), 7.61-7.55 (m, 2H), 7.45-7.41 (m, 1H), 7.29 (t, J = 8.0 Hz, 1H), 7.07 (t, J = 8.8 Hz, 2H), 6.19 (d, J = 5.2 Hz, 1H), 4.51 (q, J = 7.2 Hz, 2H), 1.42 (t, J = 7.2 Hz, 3H). FNMR (376 MHz, DMSO-d₆, ppm): δ −108.72 (2 F), −126.87 (1 F). |
| 8 | 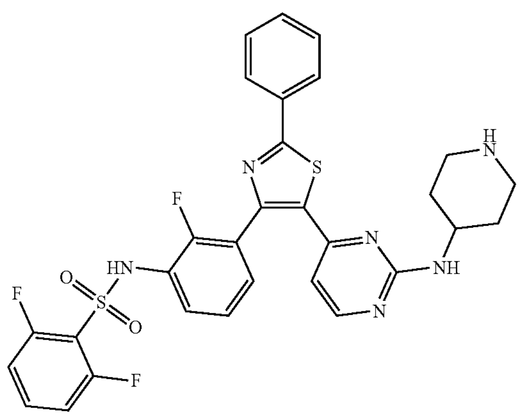 [SMILES: O=S(=O)(Nc1cccc(-c2nc(-c3ccccc3)sc2-c2ccnc(NC3CCNCC3)n2)c1F)c1c(F)cccc1F] | 623.0 | HNMR (400 MHz, CD₃OD, ppm): δ 8.18 (d, J = 7.2 Hz, 1H), 8.05-8.03 (m, 2H), 7.63-7.50 (m, 5H), 7.41-7.31 (m, 2H), 7.13 (t, J = 8.8 Hz, 2H), 6.67 (d, J = 7.2 Hz, 1H), 4.59-4.56 (m, 1H), 3.67-3.64 (m, 2H), 3.24-3.17 (m, 2H), 2.97 (s, 0.5H), 2.84 (s, 0.5H), 2.39-2.36 (m, 2H), 2.23-2.13 (m, 2H). FNMR (376 MHz, CD₃OD, ppm): δ −107.63 (2 F), −124.86 (1 F). |
| 9 | 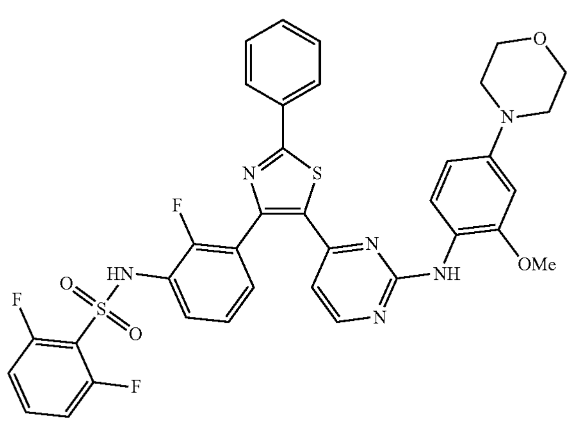 [SMILES: COc1cc(N2CCOCC2)ccc1Nc1nccc(-c2sc(-c3ccccc3)nc2-c2cccc(NS(=O)(=O)c3c(F)cccc3F)c2F)n1] | 731.0 | HNMR (400 MHz, DMSO-d₆, ppm): δ 10.95 (s, 1H), 8.16 (d, J = 5.2 Hz, 1H), 8.10 (s, 1H), 7.99-7.97 (m, 2H), 7.69-7.67 (m, 1H), 7.57-7.52 (m, 4H), 7.43-7.41 (m, 1H), 7.22-7.11 (m, 3H), 6.65 (d, J = 2.0 Hz, 1H), 6.53 (dd, J = 8.8, 2.0 Hz, 1H), 6.14 (s, 1H), 3.81 (s, 3H), 3.74 (t, J = 4.4 Hz, 4H), 3.10 (t, J = 4.4 Hz, 4H). FNMR (376 MHz, DMSO-d₆, ppm): δ −107.38 (2 F), −124.63 (1 F). |

TABLE 1-continued

Characterization of the compounds

| Compound No. | Structure | [M + H]+ | NMR |
|---|---|---|---|
| 10 | 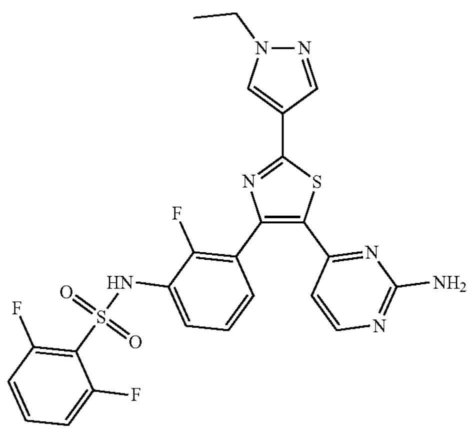 [SMILES: CCn1cc(-c2nc(-c3cccc(NS(=O)(=O)c4c(F)cccc4F)c3F)c(-c3ccnc(N)n3)s2)cn1] | 558.0 | HNMR (400 MHz, DMSO-d$_6$, ppm): δ 10.90 (s, 1H), 8.42 (s, 1H), 7.95 (d, J = 3.6 Hz, 2H), 7.67-7.63 (m, 1H), 7.45-7.35 (m, 2H), 7.30-7.19 (m, 3H), 6.74 (s, 2H), 5.79 (d, J = 5.2 Hz, 1H), 4.18-4.13 (m, 2H), 1.39-1.36 (m, 3H).<br>FNMR (376 MHz, DMSO-d$_6$, ppm): δ −107.39 (2 F), −124.68 (1 F). |
| 11 | 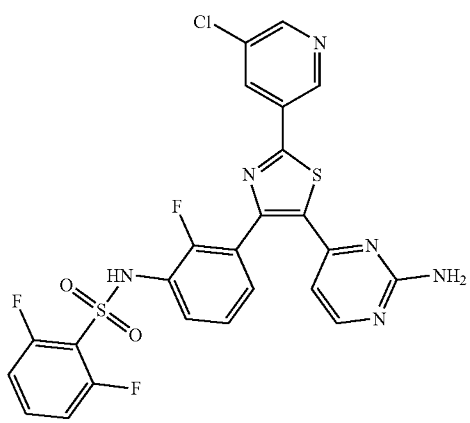 | 574.9 | HNMR (400 MHz, DMSO-d$_6$, ppm): δ 10.93 (s, 1H), 9.07-9.05 (m, 1H), 8.74-8.50 (m, 1H), 8.40-8.19 (m, 1H), 8.03-8.01 (m, 1H), 7.65-7.62 (m, 1H), 7.53-7.41 (m, 2H), 7.31-7.19 (m, 3H), 6.85-6.82 (m, 2H), 5.91-5.73 (m, 1H).<br>FNMR (376 MHz, DMSO-d$_6$, ppm): δ −107.41 (2 F), −126.36 (1 F). |
| 12 | 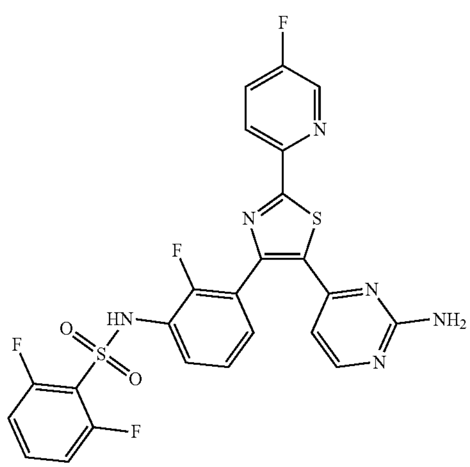 [SMILES: Nc1nccc(-c2sc(-c3ccc(F)cn3)nc2-c2cccc(NS(=O)(=O)c3c(F)cccc3F)c2F)n1] | 558.9 | HNMR (400 MHz, DMSO-d$_6$, ppm): δ 10.90 (s, 1H), 8.68 (d, J = 2.8 Hz, 1H), 8.16-8.14 (m, 1H), 8.01 (d, J = 5.2 Hz, 1H), 7.92-7.86 (m, 1H), 7.68-7.64 (m, 1H), 7.47-7.42 (m, 2H), 7.32-7.28 (m, 1H), 7.24-7.19 (m, 2H), 6.82 (s, 2H), 5.88 (d, J = 5.2 Hz, 1H).<br>FNMR (376 MHz, DMSO-d$_6$, ppm): δ −106.60 (2 F), −122.68 (1 F), −123.73 (1 F). |

TABLE 1-continued

Characterization of the compounds

| Compound No. | Structure | [M + H]+ | NMR |
|---|---|---|---|
| 13 | 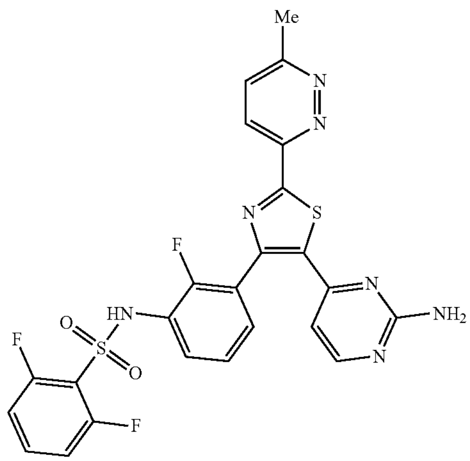 [SMILES: Cc1ccc(-c2nc(-c3cccc(NS(=O)(=O)c4c(F)cccc4F)c3F)c(-c3ccnc(N)n3)s2)nn1] | 556.0 | HNMR (400 MHz, CD₃OD-d₄, ppm): δ 8.32 (d, J = 8.8 Hz, 1H), 8.01 (d, J = 5.6 Hz, 1H), 7.74 (d, J = 8.8 Hz, 1H), 7.62-7.56 (m, 2H), 7.54-7.47 (m, 1H), 7.34-7.30 (m, 1H), 7.11-7.06 (m, 2H), 6.33 (d, J = 5.6 Hz, 1H), 2.75 (s, 3H). |
| 14 | 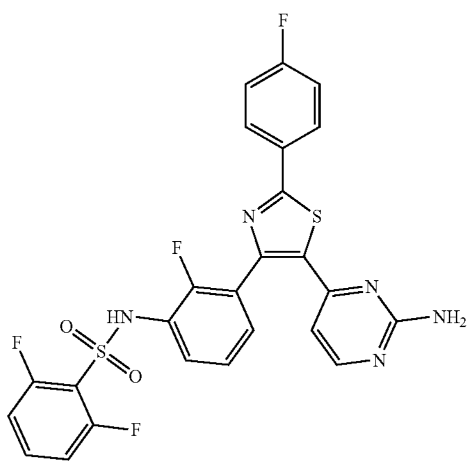 | 557.9 | HNMR (400 MHz, DMSO-d₆, ppm): δ 8.01-7.97 (m, 3H), 7.68-7.60 (m, 1H), 7.45-7.42 (m, 2H), 7.35-7.28 (m, 3H), 7.20 (t, J = 9.2 Hz, 2H), 6.80 (s, 2H), 5.85 (d, J = 5.2 Hz, 1H). |
| 15 | 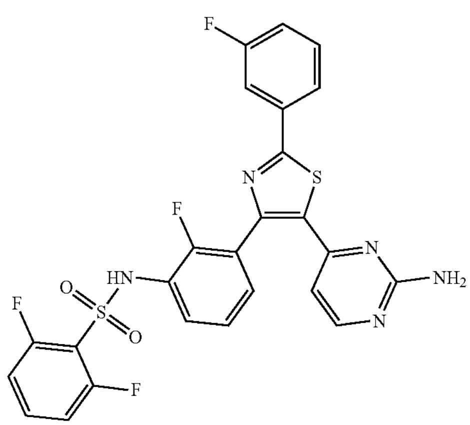 | 557.9 | HNMR (400 MHz, DMSO-d₆, ppm): δ 10.93 (s, 1H), 8.01 (d, J = 8.0 Hz, 1H), 7.80-7.75 (m, 2H), 7.73-7.68 (m, 1H), 7.66-7.59 (m, 1H), 7.57-7.47 (m, 2H), 7.45-7.35 (m, 2H), 7.33-7.20 (m, 2H), 6.83 (s, 2H), 5.88 (d, J = 4.0 Hz, 1H). |

TABLE 1-continued

Characterization of the compounds

| Compound No. | Structure | [M + H]+ | NMR |
|---|---|---|---|
| 16 | 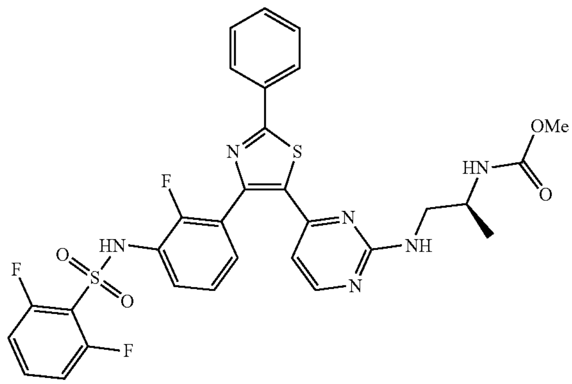 [SMILES: COC(=O)N[C@@H](C)CNc1nccc(-c2sc(-c3ccccc3)nc2-c2cccc(NS(=O)(=O)c3c(F)cccc3F)c2F)n1] | 655.0 | HNMR (400 MHz, DMSO-d$_6$, ppm): δ 10.91 (s, 1H), 8.05 (d, J = 5.2 Hz, 1H), 7.95-7.93 (m, 2H), 7.68-7.61 (m, 1H), 7.51-7.42 (m, 5H), 7.30 (t, J = 8.0 Hz, 2H), 7.21 (t, J = 8.8 Hz, 2H), 7.02 (d, J = 8.0 Hz, 1H), 5.93-5.87 (m, 1H), 3.74-3.72 (m, 2H), 3.33-3.21 (m, 3H), 1.03 (d, J = 6.8 Hz, 3H). FNMR (376 MHz, DMSO-d$_6$, ppm): δ −107.40 (2 F), −124.59 (1 F). |
| 17 | 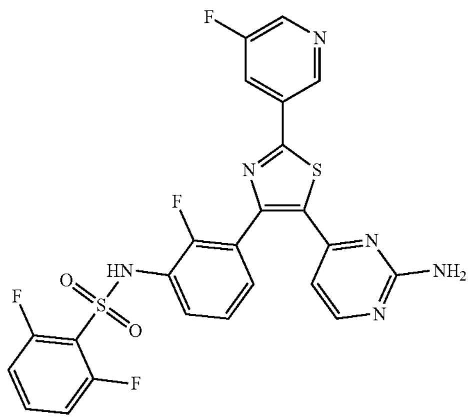 [SMILES: Nc1nccc(-c2sc(-c3cncc(F)c3)nc2-c2cccc(NS(=O)(=O)c3c(F)cccc3F)c2F)n1] | 559.1 | HNMR (400 MHz, DMSO-d$_6$, ppm): δ 10.93 (s, 1H), 9.00 (s, 1H), 8.71 (d, J = 2.4 Hz, 1H), 8.25-8.22 (m, 1H), 8.02 (d, J = 5.2 Hz, 1H), 7.65-7.62 (m, 1H), 7.46-7.40 (m, 2H), 7.31-7.18 (m, 3H), 6.84 (s, 2H), 5.91 (d, J = 4.8 Hz, 1H). FNMR (376 MHz, DMSO-d$_6$, ppm): δ −107.41 (2 F), −126.00 (1 F). |
| 18 | 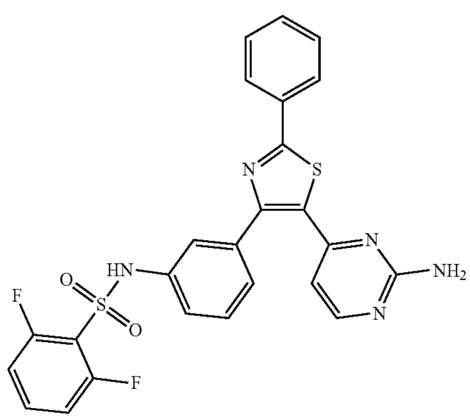 [SMILES: Nc1nccc(-c2sc(-c3ccccc3)nc2-c2cccc(NS(=O)(=O)c3c(F)cccc3F)c2)n1] | 522.0 | HNMR (400 MHz, DMSO-d$_6$, ppm): δ 11.07 (s, 1H), 7.99-7.94 (m, 3H), 7.71-7.67 (m, 1H), 7.54-7.52 (m, 3H), 7.40-7.34 (m, 2H), 7.28-7.23 (m, 4H), 7.03 (br s, 1H), 6.06 (d, J = 5.6 Hz, 1H). FNMR (376 MHz, DMSO-d$_6$, ppm): δ −107.77 (2 F). |

TABLE 1-continued

Characterization of the compounds

| Compound No. | Structure | [M + H]+ | NMR |
|---|---|---|---|
| 19 | 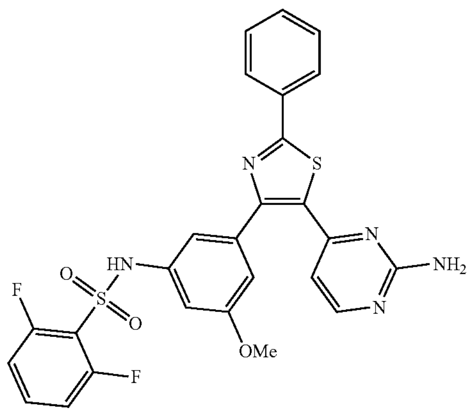 [SMILES: COc1cc(NS(=O)(=O)c2c(F)cccc2F)cc(-c2nc(-c3ccccc3)sc2-c2ccnc(N)n2)c1] | 551.9 | HNMR (400 MHz, DMSO-d6, ppm): δ 11.09 (s, 1H), 8.00 (d, J = 5.6 Hz, 1H), 7.97-7.94 (m, 2H), 7.75-7.65 (m, 1H), 7.54-7.52 (m, 3H), 7.26 (t, J = 8.8 Hz, 2H), 7.05 (br s, 1H), 6.90 (s, 1H), 6.85-6.81 (m, 2H), 6.11 (d, J = 5.2 Hz, 1H), 3.67 (s, 3H).<br>FNMR (376 MHz, DMSO-d6, ppm): δ–107.87 (2 F). |
| 20 | 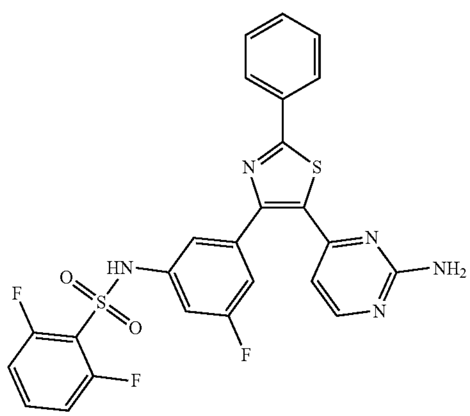 [SMILES: Nc1nccc(-c2sc(-c3ccccc3)nc2-c2cc(F)cc(NS(=O)(=O)c3c(F)cccc3F)c2)n1] | 539.5 | HNMR (400 MHz, DMSO-d6, ppm): δ11.37 (s, 1H), 8.01 (d, J = 5.2 Hz, 1H), 7.97-7.94 (m, 2H), 7.64 (s, 1H), 7.53-7.51 (m, 3H), 7.23-7.18 (m, 2H), 7.10 (s, 1H), 6.99-6.96 (m, 2H), 6.80 (s, 2H), 6.13 (d, J = 5.2 Hz, 1H). |
| 21 | 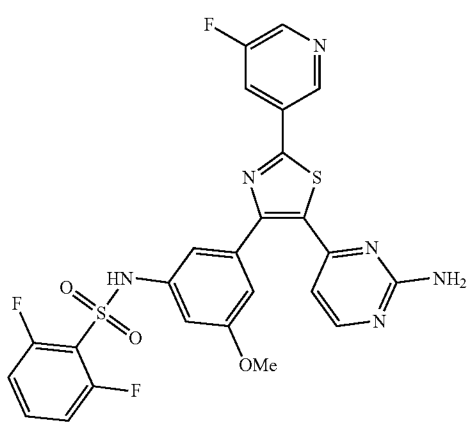 [SMILES: COc1cc(NS(=O)(=O)c2c(F)cccc2F)cc(-c2nc(-c3cncc(F)c3)sc2-c2ccnc(N)n2)c1] | 570.5 | HNMR (400 MHz, DMSO-d6, ppm): δ 11.08 (s, 1H), 9.02 (s, 1H), 8.72 (d, J = 2.8 Hz, 1H), 8.25-8.22 (m, 1H), 8.02 (d, J = 5.2 Hz, 1H), 7.71-7.67 (m, 1H), 7.28-7.22 (m, 2H), 6.90-6.81 (m, 5H), 6.10 (d, J = 5.2 Hz, 1H), 3.67(s, 3H).<br>FNMR (376 MHz, DMSO-d6, ppm): δ –107.86 (2 F), –126.09 (1 F). |

TABLE 1-continued

Characterization of the compounds

| Compound No. | Structure | [M + H]⁺ | NMR |
|---|---|---|---|
| 22 | 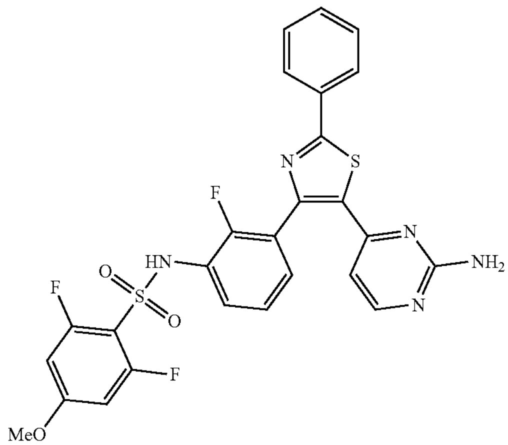 [SMILES: COc1cc(F)c(S(=O)(=O)Nc2cccc(-c3nc(-c4ccccc4)sc3-c3ccnc(N)n3)c2F)c(F)c1] | 569.5 | HNMR (400 MHz, DMSO-d₆, ppm): δ 10.69 (s, 1H), 7.98-7.93 (m, 3H), 7.51-7.40 (m, 5H), 7.32-7.28 (m, 1H), 6.85-6.81 (m, 4H), 5.85 (d, J = 5.2 Hz, 1H), 3.77 (s, 3H).<br>FNMR (376 MHz, DMSO-d₆, ppm): δ −106.12 (2 F), −124.75 (1 F). |
| 23 | 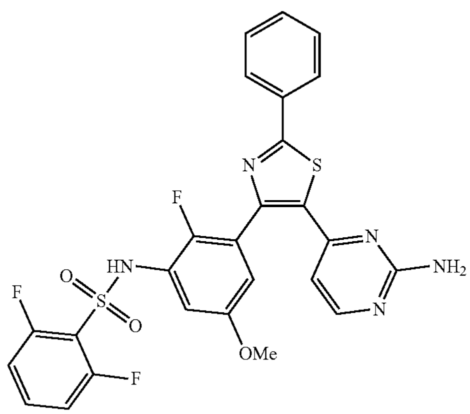 [SMILES: COc1cc(NS(=O)(=O)c2c(F)cccc2F)c(F)c(-c2nc(-c3ccccc3)sc2-c2ccnc(N)n2)c1] | 569.5 | HNMR (400 MHz, DMSO-d₆, ppm): δ 10.95 (s, 1H), 8.01 (d, J = 5.2 Hz, 1H), 7.96-7.93 (m, 2H), 7.70-7.63 (m, 1H), 7.51-7.48 (m, 3H), 7.23 (t, J = 9.2 Hz, 2H), 6.97 (d, J = 5.2 Hz, 2H), 6.80 (s, 2H), 5.93 (d, J = 5.2 Hz, 1H), 3.70 (s, 3H).<br>FNMR (376 MHz, DMSO-d₆, ppm): δ −107.41 (2 F), −135.11 (1 F). |
| 24 | 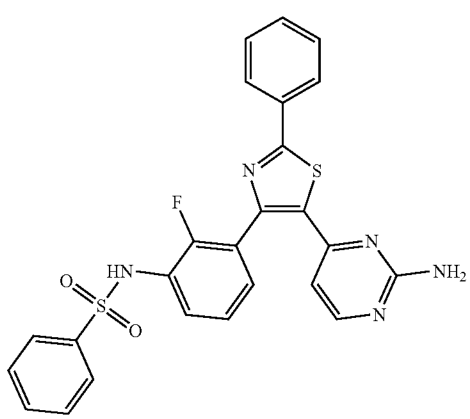 [SMILES: Nc1nccc(-c2sc(-c3ccccc3)nc2-c2cccc(NS(=O)(=O)c3ccccc3)c2F)n1] | 504.1 | HNMR (376 MHz, CD₃OD-d₄, ppm): δ 7.94-7.91 (m, 2H), 7.90 (d, J = 5.2 Hz, 1H), 7.80-7.78 (m, 2H), 7.65 (t, J = 5.6 Hz, 1H), 7.58-7.54 (m, 1H), 7.50-7.45 (m, 5H), 7.34-7.24 (m, 2H), 5.98 (d, J = 5.2 Hz, 1H). |

TABLE 1-continued

Characterization of the compounds

| Compound No. | Structure | [M + H]⁺ | NMR |
|---|---|---|---|
| 25 | 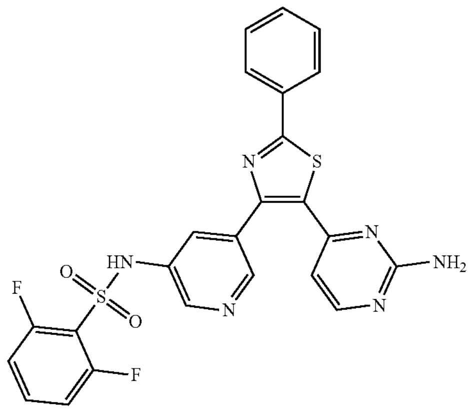 | 523.1 | HNMR (400 MHz, DMSO-d$_6$, ppm): δ 11.40 (s, 1H), 8.50 (d, J = 1.6 Hz, 1H), 8.42 (d, J = 2.4 Hz, 1H), 8.04 (d, J = 5.2 Hz, 1H), 7.98-7.95 (m, 2H), 7.75-7.70 (m, 2H), 7.54-7.52(m, 3H), 7.28 (t, J = 8.8 Hz, 2H), 6.87 (s, 2H), 6.13 (d, J = 4.8 Hz, 1H).<br>FNMR (376 MHz, DMSO-d$_6$, ppm): δ −107.71 (2 F). |
| 26 | 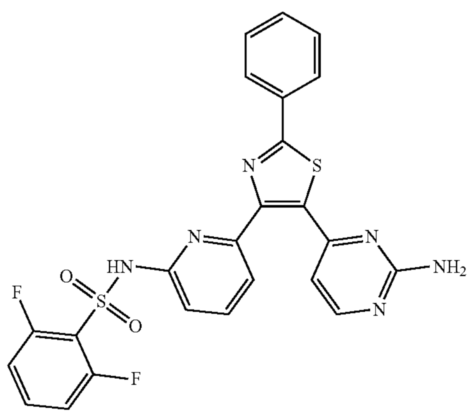 [SMILES: Nc1nccc(-c2sc(-c3ccccc3)nc2-c2cccc(NS(=O)(=O)c3c(F)cccc3F)n2)n1] | 523.0 | HNMR (400 MHz, DMSO-d$_6$, ppm): δ 8.09 (d, J = 6.4 Hz, 1H), 7.99-7.97(m, 2H), 7.91 (t, J = 8.0 Hz, 1H), 7.60 (d, J = 7.6 Hz, 1H), 7.46-7.52 (m, 4H), 7.10 (d, J = 8.0 Hz, 1H), 7.01 (t, J = 8.8 Hz, 2H), 6.49 (d, J = 6.4 Hz, 1H).<br>FNMR (376 MHz, DMSO-d$_6$, ppm): δ −108.20(2 F). |
| 27 | 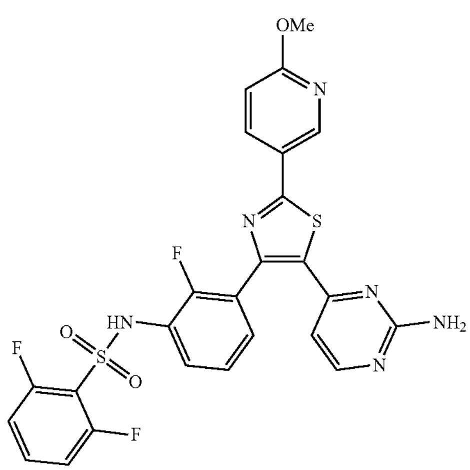 [SMILES: COc1ccc(-c2nc(-c3cccc(NS(=O)(=O)c4c(F)cccc4F)c3F)c(-c3ccnc(N)n3)s2)cn1] | 571.0 | HNMR (400 MHz, DMSO-d$_6$, ppm): δ 10.91 (s, 1H), 8.75 (d, J = 2.4 Hz, 1H), 8.20 (dd, J = 8.8, 2.4 Hz, 1H), 7.98 (d, J = 5.2 Hz, 1H), 7.68-7.61 (m, 1H), 7.46-7.40 (m, 2H), 7.29 (t, J = 8.0 Hz, 1H), 7.21 (t, J = 8.8 Hz, 2H), 6.94 (d, J = 8.8 Hz, 1H), 6.80 (s, 2H), 5.84 (d, J = 5.2 Hz, 1H), 3.90 (s, 3H).<br>FNMR (376 MHz, DMSO-d$_6$, ppm): δ −107.39 (2 F), −124.46 (1 F). |

TABLE 1-continued

Characterization of the compounds

| Compound No. | Structure | [M + H]+ | NMR |
|---|---|---|---|
| 28 | 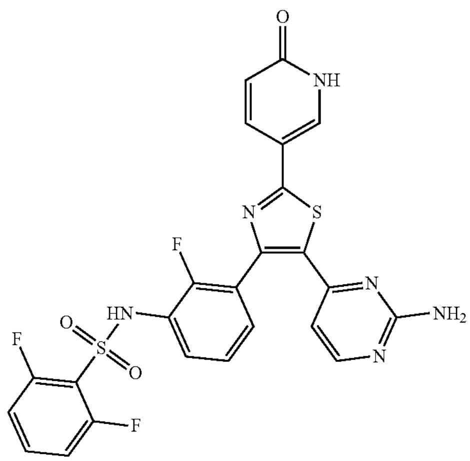 [SMILES: Nc1nccc(-c2sc(-c3ccc(=O)[nH]c3)nc2-c2cccc(NS(=O)(=O)c3c(F)cccc3F)c2F)n1] | 557.0 | HNMR (400 MHz, DMSO-d$_6$, ppm): δ 12.13 (s, 1H), 10.88 (s, 1H), 8.05 (d, J = 2.4 Hz, 1H), 7.95 (d, J = 5.2 Hz, 1H), 7.90 (dd, J = 8.8, 2.4 Hz, 1H), 7.69-7.61 (m, 1H), 7.44-7.36 (m, 2H), 7.27 (t, J = 8.0 Hz, 1H), 7.21 (t, J = 8.8 Hz, 2H), 6.74(s, 2H), 6.43 (d, J = 9.6 Hz, 1H), 5.82 (d, J = 5.2 Hz, 1H).<br>FNMR (376 MHz, DMSO-d$_6$, ppm): δ −107.37 (2 F), −124.47 (1 F). |
| 29 | 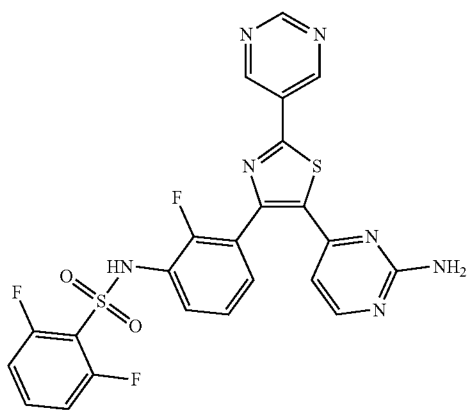 [SMILES: Nc1nccc(-c2sc(-c3cncnc3)nc2-c2cccc(NS(=O)(=O)c3c(F)cccc3F)c2F)n1] | 542.0 | HNMR (400 MHz, DMSO-d$_6$, ppm): δ 10.93 (s, 1H), 9.31 (s, 2H), 9.29 (s, 1H), 8.03 (d, J = 5.2 Hz, 1H), 7.69-7.62 (m, 1H), 7.46 (t, J = 7.2 Hz, 2H), 7.32 (t, J = 8.0 Hz, 1H), 7.22 (t, J = 8.8 Hz, 2H), 6.88 (s, 2H), 5.89 (d, J = 5.2 Hz, 1H).<br>FNMR (376 MHz, DMSO-d$_6$, ppm): δ −107.40 (2 F), −124.35 (1 F). |
| 30 | 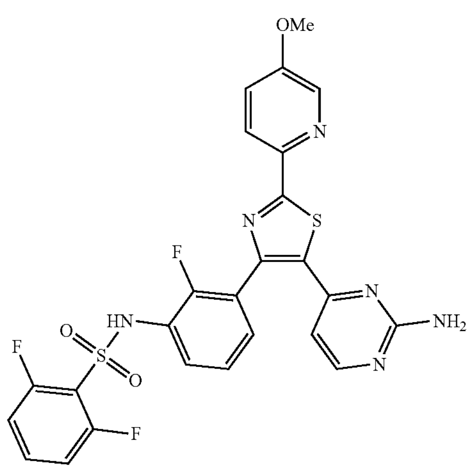 | 571.0 | HNMR (400 MHz, DMSO-d$_6$, ppm): δ 10.90 (s, 1H), 8.35 (d, J = 2.8 Hz, 1H), 8.03 (d, J = 8.8 Hz, 1H), 7.98 (d, J = 5.2 Hz, 1H), 7.69-7.62 (m, 1H), 7.52 (dd, J = 8.8, 2.8 Hz, 1H), 7.46-7.41 (m, 2H), 7.29 (t, J = 8.0 Hz, 1H), 7.21 (t, J = 9.2 Hz, 2H), 6.78 (s, 2H), 5.85 (d, J = 5.2 Hz, 1H), 3.88 (s, 3H).<br>FNMR (376 MHz, DMSO-d$_6$, ppm): δ −107.38 (2 F), −124.55 (1 F). |

TABLE 1-continued

Characterization of the compounds

| Compound No. | Structure | [M + H]+ | NMR |
|---|---|---|---|
| 31 | 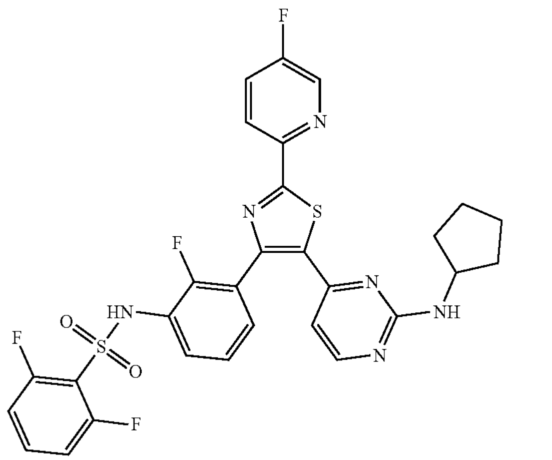 [SMILES: O=S(=O)(Nc1cccc(-c2nc(-c3ccc(F)cn3)sc2-c2ccnc(NC3CCCC3)n2)c1F)c1c(F)cccc1F] | 627.1 | HNMR (400 MHz, DMSO-d$_6$, ppm): δ 10.91 (s, 1H), 8.67 (d, J = 2.4 Hz, 1H), 8.16-8.13 (m, 1H), 8.03 (d, J = 5.2 Hz, 1H), 7.90-7.85 (m, 1H), 7.66-7.62 (m, 1H), 7.45-7.40 (m, 2H), 7.31-7.27 (m, 2H), 7.20 (t, J = 8.8 Hz, 2H), 5.94-5.91 (m, 1H), 4.01-3.94 (m, 1H), 1.88-1.82 (m, 2H), 1.64-1.47 (m, 6H). FNMR (376 MHz, DMSO-d$_6$, ppm): δ −107.39 (2 F), −123.46 (1 F), −124.65 (1 F). |
| 32 | 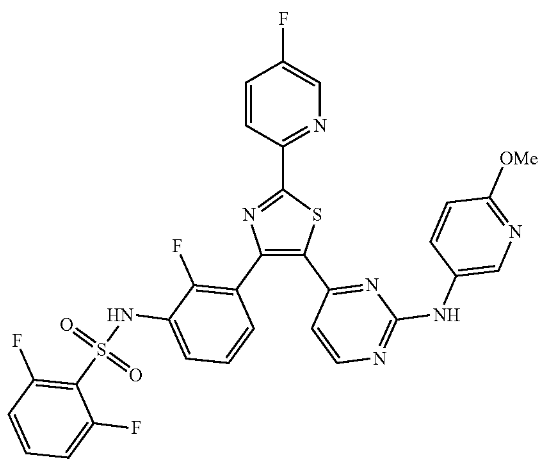 [SMILES: COc1ccc(Nc2nccc(-c3sc(-c4ccc(F)cn4)nc3-c3cccc(NS(=O)(=O)c4c(F)cccc4F)c3F)n2)cn1] | 666.0 | HNMR (400 MHz, DMSO-d$_6$, ppm): δ 10.91 (s, 1H), 9.66 (s, 1H), 8.70 (d, J = 2.8 Hz, 1H), 8.47 (d, J = 2.4 Hz, 1H), 8.24 (d, J = 5.2 Hz, 1H), 8.21-8.16 (m, 1H), 7.92-7.83 (m, 2H), 7.67-7.59 (m, 1H), 7.49-7.43 (m, 2H), 7.32 (t, J = 8.0 Hz, 1H), 7.19 (t, J = 9.2 Hz, 2H), 6.74 (d, J = 9.2 Hz, 1H), 6.17 (d, J = 5.2 Hz, 1H), 3.80 (s, 3H). FNMR (376 MHz, DMSO-d$_6$, ppm): δ −107.44 (2 F), −123.18 (1 F), −124.59 (1 F). |
| 33 | 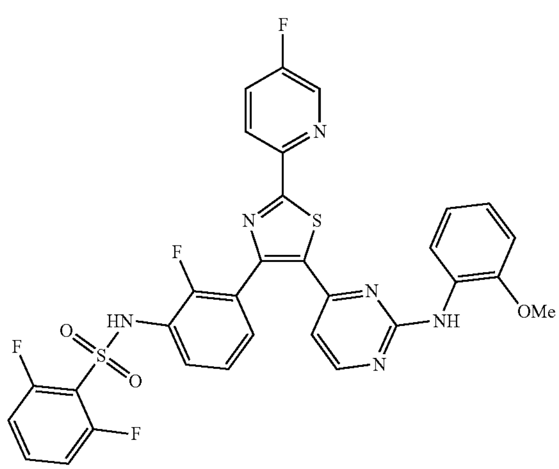 [SMILES: COc1ccccc1Nc1nccc(-c2sc(-c3ccc(F)cn3)nc2-c2cccc(NS(=O)(=O)c3c(F)cccc3F)c2F)n1] | 665.0 | HNMR (400 MHz, DMSO-d$_6$, ppm): δ 10.92 (s, 1H), 8.70 (d, J = 2.4 Hz, 1H), 8.25-8.23 (m, 2H), 8.19-8.16 (m, 1H), 7.92-7.87 (m, 2H), 7.67-7.60 (m, 1H), 7.50-7.45 (m, 2H), 7.33 (t, J = 8.0 Hz, 1H), 7.19 (t, J = 8.8 Hz, 2H), 7.04-7.00 (m, 2H), 6.92-6.88 (m, 1H), 6.20 (d, J = 5.2 Hz, 1H), 3.83 (s, 3H). FNMR (376 MHz, DMSO-d$_6$, ppm): δ −107.42 (2 F), −123.23 (1 F), −124.59 (1 F). |

TABLE 1-continued

Characterization of the compounds

| Compound No. | Structure | [M + H]⁺ | NMR |
|---|---|---|---|
| 34 | 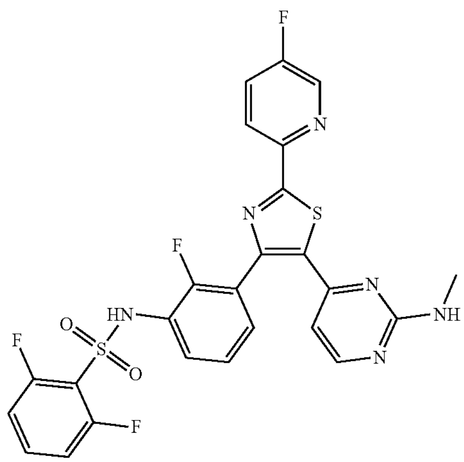 [SMILES: CNc1nccc(-c2sc(-c3ccc(F)cn3)nc2-c2cccc(NS(=O)(=O)c3c(F)cccc3F)c2F)n1] | 573.0 | HNMR (400 MHz, DMSO-d₆, ppm): δ 10.90 (s, 1H), 8.68 (d, J = 2.4 Hz, 1H), 8.16 (dd, J = 8.8, 4.4 Hz, 1H), 8.06 (d, J = 4.8 Hz, 1H), 7.91-7.86 (m, 1H), 7.69-7.62 (m, 1H), 7.46-7.41 (m, 2H), 7.29 (t, J = 8.0 Hz, 1H), 7.24-7.19 (m, 3H), 5.99 (s, 1H), 2.68 (s, 3H). FNMR (376 MHz, DMSO-d₆, ppm): δ −107.40 (2 F), −123.50 (1 F), −124.57 (1 F). |
| 35 | 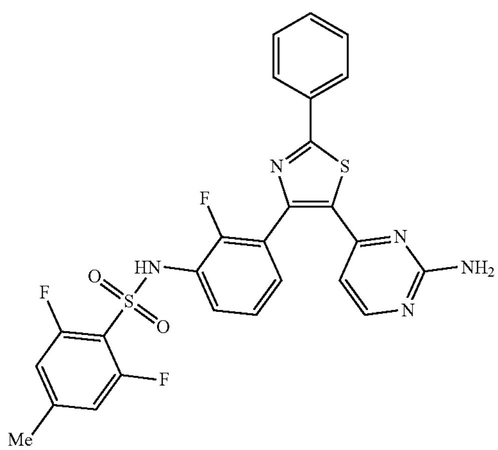 [SMILES: Cc1cc(F)c(S(=O)(=O)Nc2cccc(-c3nc(-c4ccccc4)sc3-c3ccnc(N)n3)c2F)c(F)c1] | 554.0 | HNMR (400 MHz, DMSO-d₆, ppm): δ 10.81 (s, 1H), 8.00-7.85 (m, 3H), 7.54-7.05 (m, 6H), 7.07 (d, J = 10.8 Hz, 2H), 6.80 (s, 2H), 5.89 (d, J = 5.2 Hz, 1H), 2.30 (s, 3H). |
| 36 | 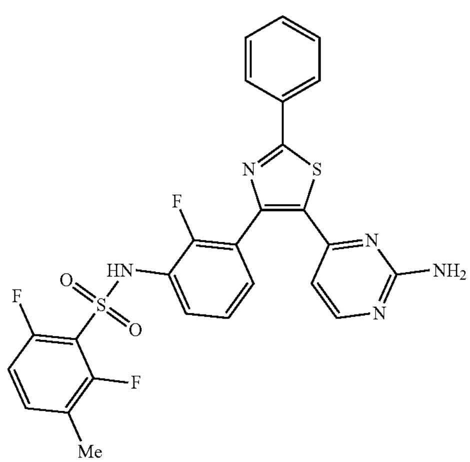 [SMILES: Cc1ccc(F)c(S(=O)(=O)Nc2cccc(-c3nc(-c4ccccc4)sc3-c3ccnc(N)n3)c2F)c1F] | 554.0 | HNMR (400 MHz, DMSO-d₆, ppm): δ 10.86 (s, 1H), 7.96-7.54 (m, 3H), 7.51-7.41 (m, 6H), 7.30-7.26 (m, 1H), 7.12-7.07 (m, 1H), 6.79 (s, 2H), 5.90 (d, J = 5.2 Hz, 1H), 2.13 (d, J = 9.2 Hz, 3H). |

TABLE 1-continued

Characterization of the compounds

| Compound No. | Structure | [M + H]⁺ | NMR |
|---|---|---|---|
| 37 | 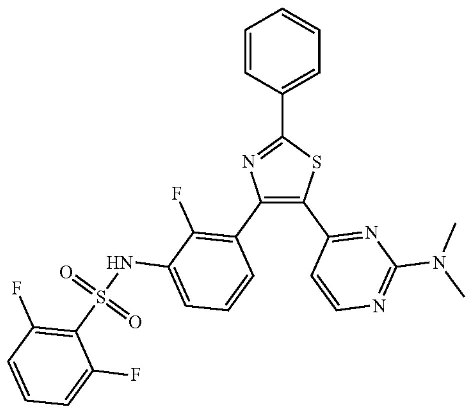 [SMILES: CN(C)c1nccc(-c2sc(-c3ccccc3)nc2-c2cccc(NS(=O)(=O)c3c(F)cccc3F)c2F)n1] | 568.0 | HNMR (400 MHz, DMSO-d₆, ppm): δ 10.87 (s, 1H), 8.14 (d, J = 5.2 Hz, 1H), 7.98-7.95 (m, 2H), 7.69-7.62 (m, 1H), 7.51-7.40 (m, 5H), 7.31-7.19 (m, 3H), 6.02 (d, J = 5.2 Hz, 1H), 3.02 (s, 6H). |
| 38 | 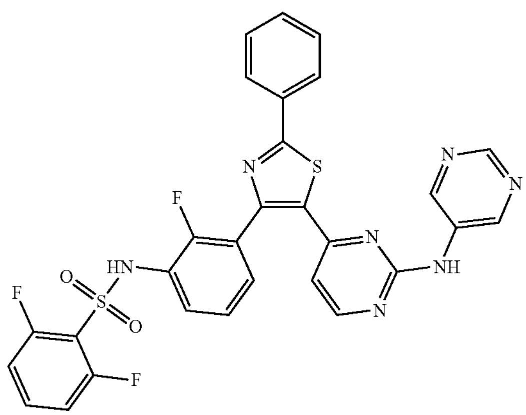 [SMILES: O=S(=O)(Nc1cccc(-c2nc(-c3ccccc3)sc2-c2ccnc(Nc3cncnc3)n2)c1F)c1c(F)cccc1F] | 618.0 | HNMR (400 MHz, CD₃OD-d₄, ppm): δ 9.44 (s, 1H), 9.11 (s, 2H), 8.13 (d, J = 7.2 Hz, 1H), 8.07 (dd, J = 8.0, 1.2 Hz, 2H), 7.62-7.48 (m, 6H), 7.34 (t, J = 8.0 Hz, 1H), 7.11 (t, J = 8.8 Hz, 2H), 6.71 (dd, J = 7.2, 0.8 Hz, 1H). |
| 39 | 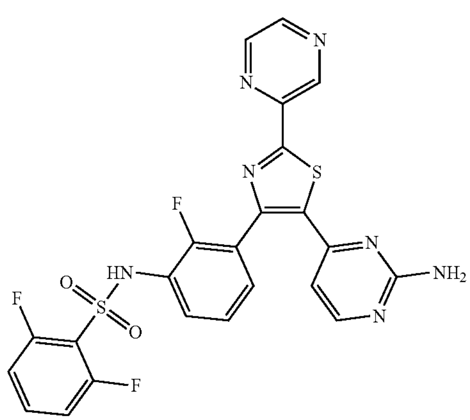 [SMILES: Nc1nccc(-c2sc(-c3cnccn3)nc2-c2cccc(NS(=O)(=O)c3c(F)cccc3F)c2F)n1] | 542.0 | HNMR (400 MHz, DMSO-d₆, ppm): δ 10.90 (s, 1H), 9.26 (d, J = 1.2 Hz, 1H), 8.77 (d, J = 2.4 Hz, 1H), 8.74-8.73 (m, 1H), 8.03 (d, J = 5.2 Hz, 1H), 7.68-7.63 (m, 1H), 7.46 (t, J = 7.6 Hz, 2H), 7.32 (t, J = 8.0 Hz, 1H), 7.21 (t, J = 8.8 Hz, 2H), 6.84 (s, 2H), 5.91 (d, J = 5.2 Hz, 1H). FNMR (376 MHz, DMSO-d₆, ppm): δ -107.38 (2 F), -124.40 (1 F). |

TABLE 1-continued

Characterization of the compounds

| Compound No. | Structure | [M + H]+ | NMR |
|---|---|---|---|
| 40 | 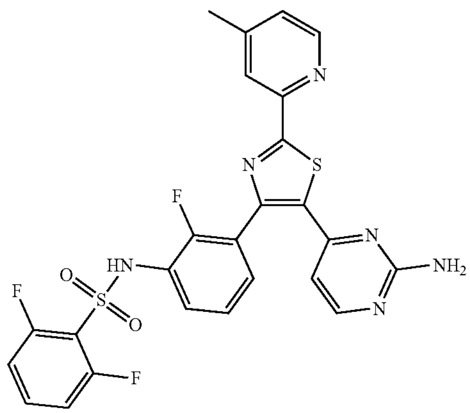 [SMILES: Cc1ccnc(-c2nc(-c3cccc(NS(=O)(=O)c4c(F)cccc4F)c3F)c(-c3ccnc(N)n3)s2)c1] | 555.0 | HNMR (400 MHz, DMSO-d$_6$, ppm): δ 10.89 (s, 1H), 8.49 (d, J = 5.2 Hz, 1H), 8.01 (d, J = 5.2 Hz, 1H), 7.94 (s, 1H), 7.69-7.62 (m, 1H), 7.46-7.42 (m, 2H), 7.35 (d, J = 4.8 Hz, 1H), 7.30 (t, J = 8.0 Hz, 1H), 7.21 (t, J = 9.2 Hz, 2H), 6.87 (s, 2H), 5.92-5.90 (m, 1H), 2.38 (s, 3H).<br>FNMR (376 MHz, DMSO-d$_6$, ppm): δ −107.39 (2 F), −124.55 (1 F). |
| 41 | 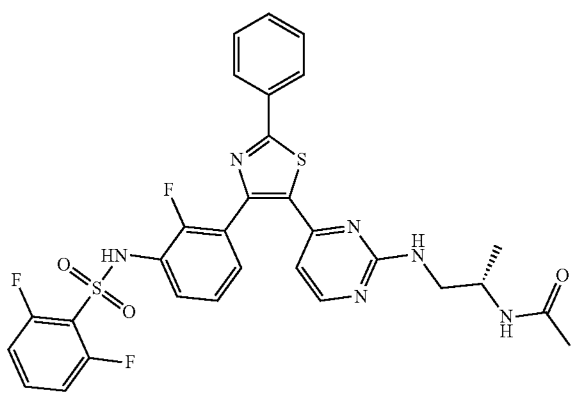 [SMILES: CC(=O)N[C@@H](C)CNc1nccc(-c2sc(-c3ccccc3)nc2-c2cccc(NS(=O)(=O)c3c(F)cccc3F)c2F)n1] | 639.1 | HNMR (400 MHz, DMSO-d$_6$, ppm): δ 10.88 (s, 1H), 8.05 (d, J = 5.2 Hz, 1H), 7.96-7.94 (m, 2H), 7.69-7.63 (m, 2H), 7.52-7.42 (m, 5H), 7.32-7.19 (m, 4H), 5.94 (br s, 1H), 3.98-3.94 (m, 1H), 3.26 (s, 2H), 1.77 (s, 3H), 1.02 (d, J = 6.8 Hz, 3H). |
| 42 | 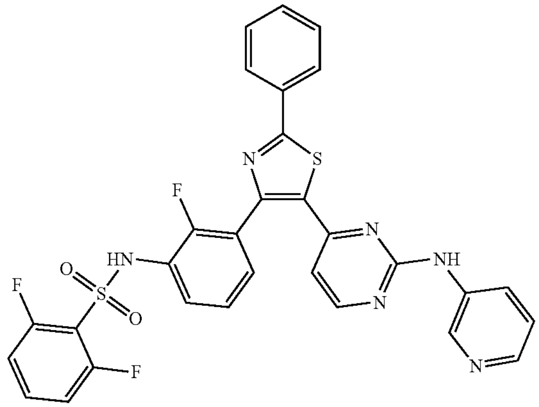 [SMILES: O=S(=O)(Nc1cccc(-c2nc(-c3ccccc3)sc2-c2ccnc(Nc3cccnc3)n2)c1F)c1c(F)cccc1F] | 617.0 | HNMR (400 MHz, DMSO-d$_6$, ppm): δ 10.88 (s, 1H), 9.17 (br s, 1H), 8.98 (d, J = 5.6 Hz, 1H), 8.75-8.67 (m, 1H), 8.08-8.00 (m, 2H), 7.91-7.85 (m, 2H), 7.70-7.52 (m, 5H), 7.51-7.34 (m, 3H), 7.20 (t, J = 9.2 Hz, 2H), 6.93 (s, 2H). |

TABLE 1-continued

Characterization of the compounds

| Compound No. | Structure | [M + H]⁺ | NMR |
|---|---|---|---|
| 43 | 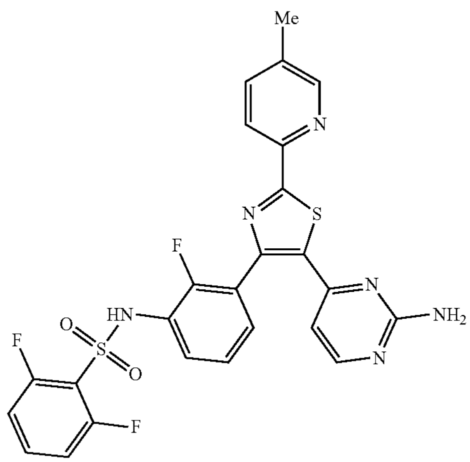 [SMILES: Cc1ccc(-c2nc(-c3cccc(NS(=O)(=O)c4c(F)cccc4F)c3F)c(-c3ccnc(N)n3)s2)nc1] | 555.0 | HNMR (400 MHz, DMSO-d₆, ppm): δ 10.87 (s, 1H), 8.49 (br s, 1H), 8.03-7.95 (m, 2H), 7.80-7.72 (m, 1H), 7.71-7.59 (m, 1H), 7.49-7.35 (m, 2H), 7.49-7.34 (m, 3H), 6.76 (s, 2H), 5.88 (d, J = 4.8 Hz, 1H), 2.34 (s, 3H). |
| 44 | 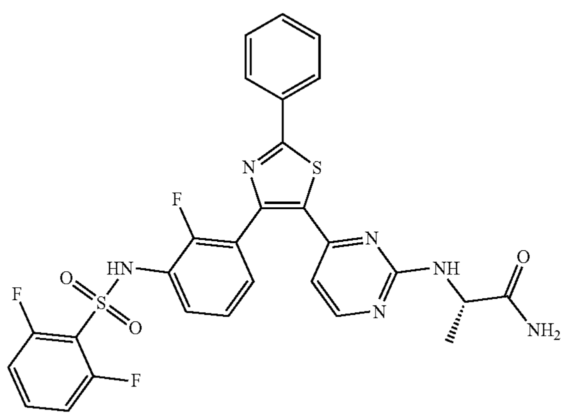 [SMILES: C[C@H](Nc1nccc(-c2sc(-c3ccccc3)nc2-c2cccc(NS(=O)(=O)c3c(F)cccc3F)c2F)n1)C(N)=O] | 611.1 | HNMR (400 MHz, DMSO-d₆, ppm): δ 10.90 (s, 1H), 8.09 (d, J = 5.2 Hz, 1H), 8.02-7.93 (m, 2H), 7.74-7.62 (m, 1H), 7.60-7.52 (m, 3H), 7.52-7.43 (m, 2H), 7.42-7.31 (m, 2 H), 7.30-7.18 (m, 3 H), 7.05-6.91 (m, 1H), 5.95 (d, J = 5.2 Hz, 1H), 4.30 (br s, 1 H), 1.35 (d, J = 7.2 Hz, 3H). |
| 45 | 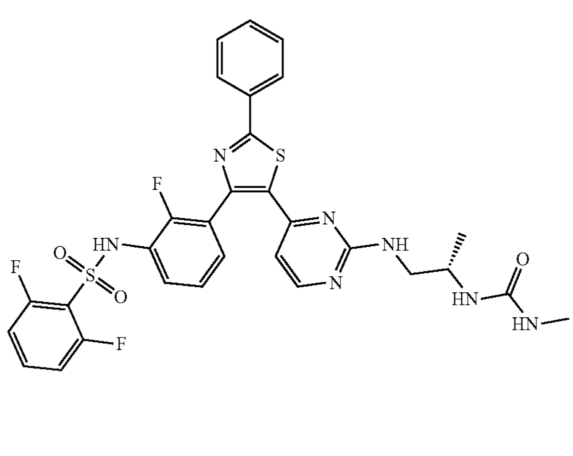 [SMILES: CNC(=O)N[C@@H](C)CNc1nccc(-c2sc(-c3ccccc3)nc2-c2cccc(NS(=O)(=O)c3c(F)cccc3F)c2F)n1] | 654.1 | HNMR (400 MHz, DMSO-d₆, ppm): δ 10.88 (s, 1H), 8.04 (d, J = 5.2 Hz, 1H), 7.96-7.94 (m, 2H), 7.67-7.63 (m, 1H), 7.52-7.42 (m, 5H), 7.32-7.18 (m, 4H), 5.95-5.69 (m, 3H), 3.80 (br s, 1H), 3.22-3.20 (m, 2H), 2.47 (s, 3H), 1.01 (d, J = 6.4 Hz, 3H). |

TABLE 1-continued

Characterization of the compounds

| Compound No. | Structure | [M + H]+ | NMR |
|---|---|---|---|
| 46 | 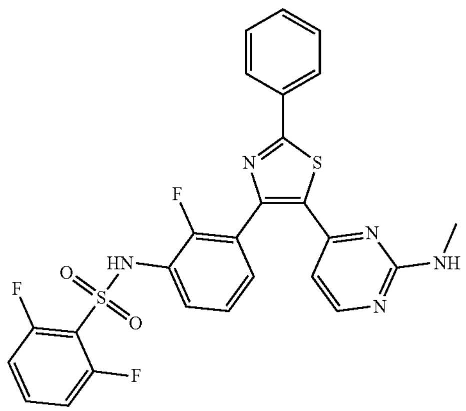 | 554.0 | HNMR (400 MHz, DMSO-d$_6$, ppm): δ 10.89 (s, 1H), 8.05 (d, J = 5.2 Hz, 1H), 7.96-7.94 (m, 2H), 7.69-7.61 (m, 1H), 7.51-7.41 (m, 5H), 7.31-7.19 (m, 4H), 5.95 (br s, 1H), 2.72 (br s, 3H). |
| 47 | 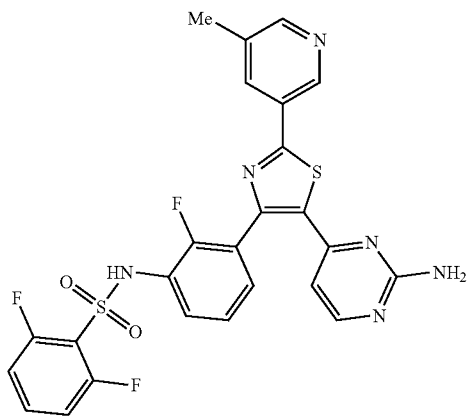 [SMILES: Cc1cncc(-c2nc(-c3cccc(NS(=O)(=O)c4c(F)cccc4F)c3F)c(-c3ccnc(N)n3)s2)c1] | 555.0 | HNMR (400 MHz, DMSO-d$_6$, ppm): δ 10.91 (s, 1H), 8.93 (s, 1H), 8.54 (s, 1H), 8.17 (s, 1H), 8.01 (d, J = 5.2 Hz, 1H), 7.67-7.63 (m, 1H), 7.47-7.43 (m, 2H), 7.31 (t, J = 8.0 Hz, 1H), 7.21 (t, J = 9.2 Hz, 2H), 6.87 (br s, 2H), 5.90 (d, J = 5.6 Hz, 1H), 2.37 (s, 3 H). |
| 48 | 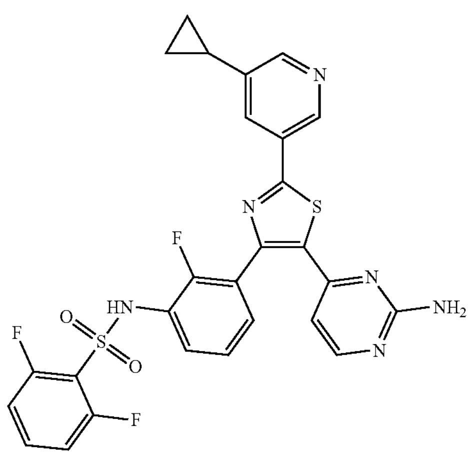 [SMILES: Nc1nccc(-c2sc(-c3cncc(C4CC4)c3)nc2-c2cccc(NS(=O)(=O)c3c(F)cccc3F)c2F)n1] | 581.0 | HNMR (400 MHz, DMSO-d$_6$, ppm): δ 10.90 (s, 1H), 8.88 (s, 1H), 8.50 (s, 1H), 8.02 (d, J = 5.2 Hz, 1H), 7.90-7.85 (m, 1H), 7.69-7.61 (m, 1H), 7.45 (t, J = 7.2 Hz, 2H), 7.31 (t, J = 8.0 Hz, 1H), 7.21 (t, J = 9.2 Hz, 2H), 6.83 (s, 2H), 5.88 (d, J = 4.8 Hz, 1H), 2.09-2.02 (m, 1H), 1.05-1.00 (m, 2H), 0.85-0.81 (m, 2H). FNMR (376 MHz, DMSO-d$_6$, ppm): δ −107.39 (2 F), −124.42 (1 F). |

TABLE 1-continued

Characterization of the compounds

| Compound No. | Structure | [M + H]⁺ | NMR |
|---|---|---|---|
| 49 | 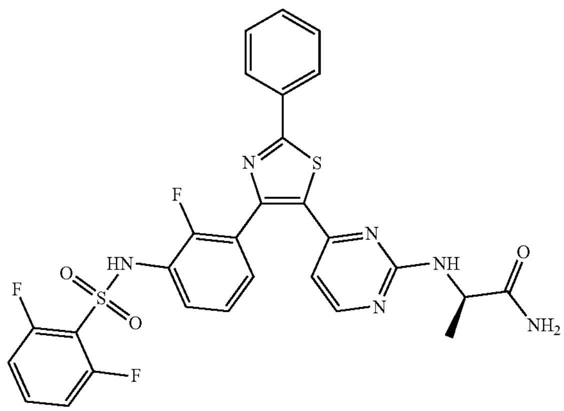 [SMILES: C[C@@H](Nc1nccc(-c2sc(-c3ccccc3)nc2-c2cccc(NS(=O)(=O)c3c(F)cccc3F)c2F)n1)C(N)=O] | 611.0 | HNMR (400 MHz, DMSO-d₆, ppm): δ 10.89 (s, 1H), 8.07-8.05 (m, 1H), 7.96-7.94 (m, 2H), 7.63-7.18 (m, 10H), 6.95 (s, 1H), 5.93-5.90 (m, 1H), 4.26-4.24 (m, 1H), 1.31 (d, J = 7.2 Hz, 3H). |
| 50 | 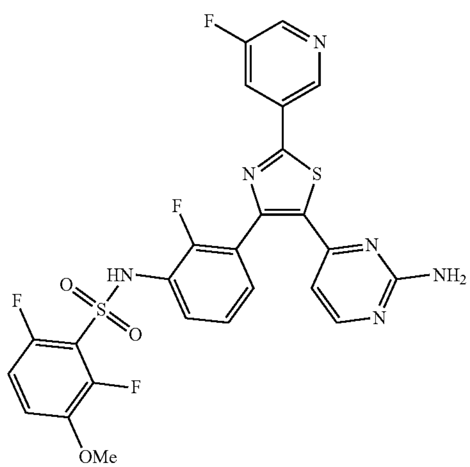 [SMILES: COc1ccc(F)c(S(=O)(=O)Nc2cccc(-c3nc(-c4cncc(F)c4)sc3-c3ccnc(N)n3)c2F)c1F] | 589.0 | HNMR (400 MHz, DMSO-d₆, ppm): δ 10.92 (s, 1H), 9.02 (s, 1H), 8.72 (d, J = 2.8 Hz, 1H), 8.27-8.17 (m, 1H), 7.99 (d, J = 5.2 Hz, 1H), 7.48-7.30 (m, 4H), 7.19-7.14 (m, 1H), 6.85 (br s, 2H), 5.90 (d, J = 5.2 Hz, 1H), 3.79 (s, 3H). |
| 51 | 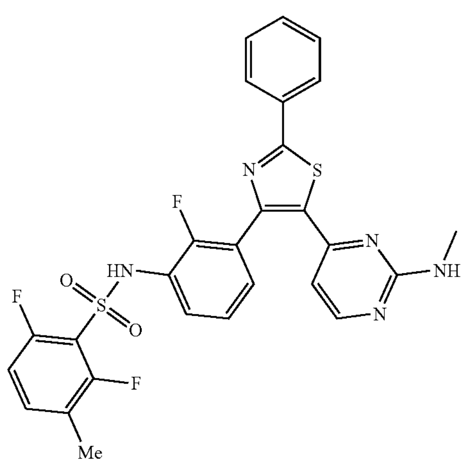 [SMILES: CNc1nccc(-c2sc(-c3ccccc3)nc2-c2cccc(NS(=O)(=O)c3c(F)ccc(C)c3F)c2F)n1] | 568.1 | HNMR (400 MHz, DMSO-d₆, ppm): δ 10.83 (s, 1H), 8.03 (d, J = 5.2 Hz, 1H), 7.96-7.95 (m, 2H), 7.55-7.49 (m, 4H), 7.43 (t, J = 7.2 Hz, 2H), 7.29 (t, J = 8.0 Hz, 1H), 7.23 (br s, 1H), 7.11 (t, J = 9.2 Hz, 1H), 5.98 (br s, 1H), 2.72 (br s, 3H), 2.14 (s, 3H). |

TABLE 1-continued

Characterization of the compounds

| Compound No. | Structure | [M + H]+ | NMR |
|---|---|---|---|
| 52 | 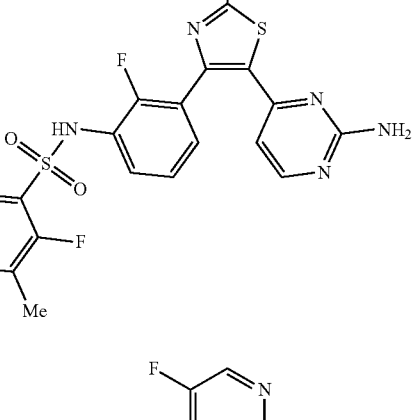 | 573.0 | HNMR (400 MHz, DMSO-d$_6$, ppm): δ 10.85 (s, 1H), 9.01 (s, 1H), 8.72 (d, J = 2.4 Hz, 1H), 8.26-8.22 (m, 1H), 8.00 (d, J = 5.2 Hz, 1H), 7.57-7.51(m, 1H), 7.48-7.43 (m, 2H), 7.31 (t, J = 8.0 Hz, 1H), 7.11 (t, J = 8.8 Hz, 1H), 6.87(s, 2H), 5.93 (d, J = 5.2 Hz, 1H), 2.14 (s, 3H).<br>FNMR (376 MHz, DMSO-d$_6$, ppm): δ −109.90 (1 F), −111.35 (1 F), −124.29 (1 F), −126.02 (1 F). |
| 53 | 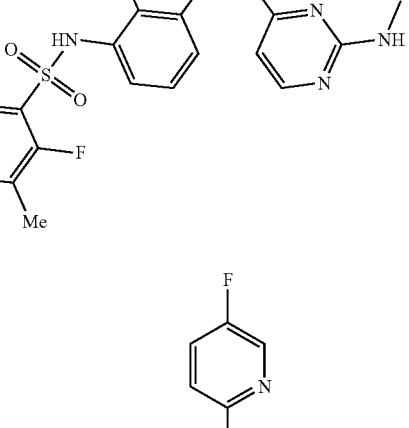 | 587.0 | HNMR (400 MHz, DMSO-d$_6$, ppm): δ 10.85 (s, 1H), 9.02 (s, 1H), 8.71 (d, J = 2.4 Hz, 1H), 8.25 (d, J = 9.2 Hz, 1H), 8.05 (d, J = 5.2 Hz, 1H), 7.56-7.51 (m, 1H), 7.46-7.42 (m, 2H), 7.32-7.28 (m, 2H), 7.11 (t, J = 9.2 Hz, 1H), 5.99 (s, 1H), 2.73 (s, 3H), 2.14 (s, 3H).<br>FNMR (376 MHz, DMSO-d$_6$, ppm): δ −109.91 (1 F), −111.35 (1 F), −124.36 (1 F), −126.09 (1 F). |
| 54 | 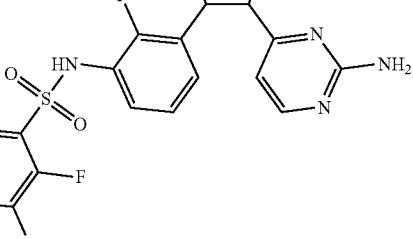 | 573.0 | HNMR (400 MHz, DMSO-d$_6$, ppm): δ 10.84 (s, 1H), 8.68 (d, J = 2.8 Hz, 1H), 8.16-8.13 (m, 1H), 7.98 (d, J = 5.2 Hz, 1H), 7.91-7.86 (m, 1H), 7.57-7.51 (m, 1H), 7.43 (t, J = 7.2 Hz, 2H), 7.29 (t, J = 8.0 Hz, 1H), 7.11 (t, J = 9.2 Hz, 1H), 6.81 (s, 2H), 5.91 (d, J = 5.2 Hz, 1H), 2.14 (s, 3H).<br>FNMR (376 MHz, DMSO-d$_6$, ppm): δ −109.90 (1 F), −111.36 (1 F), −123.48 (1 F), −124.43 (1 F). |

TABLE 1-continued

Characterization of the compounds

| Compound No. | Structure | [M + H]⁺ | NMR |
|---|---|---|---|
| 55 | 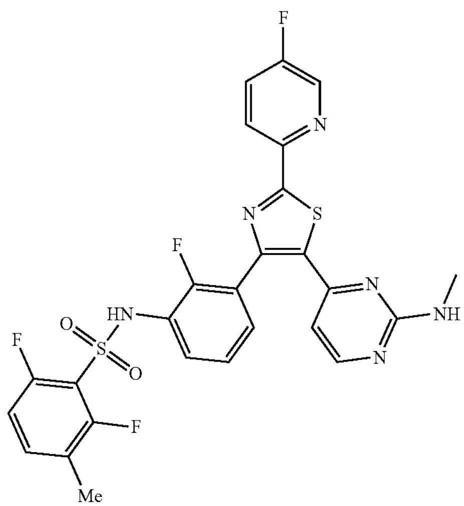 [SMILES: CNc1nccc(-c2sc(-c3ccc(F)cn3)nc2-c2cccc(NS(=O)(=O)c3c(F)ccc(C)c3F)c2F)n1] | 587.0 | HNMR (400 MHz, DMSO-d₆, ppm): δ 10.82 (s, 1H), 8.68 (d, J = 2.8 Hz, 1H), 8.17-8.14 (m, 1H), 8.04 (d, J = 4.8 Hz, 1H), 7.91-7.86 (m, 1H), 7.57-7.51 (m, 1H), 7.43 (t, J = 7.2 Hz, 2H), 7.29 (t, J = 8.0 Hz, 1H), 7.21-7.20 (m, 1 H), 7.11 (t, J = 9.2 Hz, 1H), 6.02-5.93 (m, 1H), 2.69 (s, 3H), 2.14 (s, 3H).<br>FNMR (376 MHz, DMSO-d₆, ppm): δ −109.89 (1 F), −111.36 (1 F), −123.47 (1 F), −124.53 (1 F). |
| 56 | 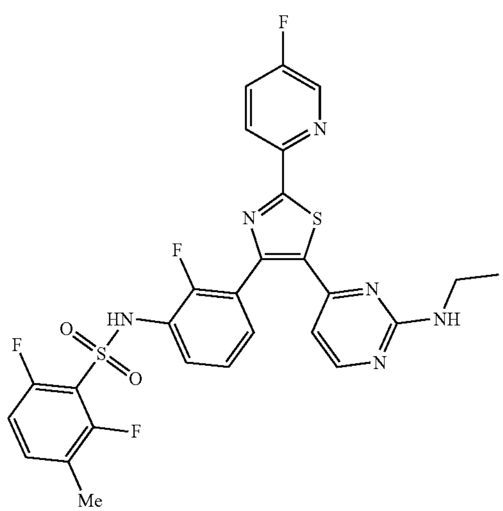 [SMILES: CCNc1nccc(-c2sc(-c3ccc(F)cn3)nc2-c2cccc(NS(=O)(=O)c3c(F)ccc(C)c3F)c2F)n1] | 601.1 | HNMR (400 MHz, DMSO-d₆, ppm): δ 10.84 (s, 1H), 8.68 (d, J = 2.8 Hz, 1H), 8.17-8.13 (m, 1H), 8.02 (d, J = 5.2 Hz, 1H), 7.91-7.86 (m, 1H), 7.57-7.51 (m, 1H), 7.44-7.41 (m, 2H), 7.31-7.27 (m, 2H), 7.11 (t, J = 9.2 Hz, 1H), 6.01-5.91 (m, 1H), 2.82-2.75 (m, 2H), 2.14 (s, 3H), 1.10 (t, J = 7.2 Hz, 3H).<br>FNMR (376 MHz, DMSO-d₆, ppm): δ −109.87 (1 F), −111.35 (1 F), −123.49 (1 F), −124.55 (1 F). |
| 57 | 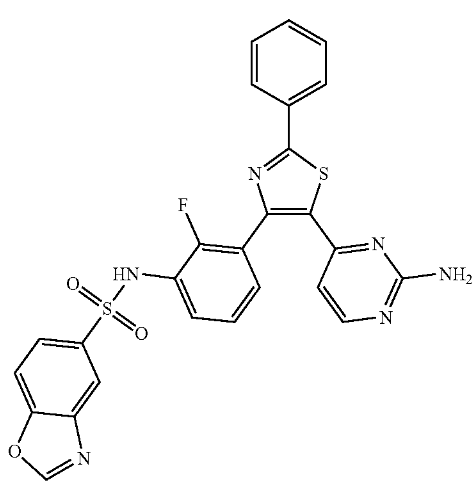 [SMILES: Nc1nccc(-c2sc(-c3ccccc3)nc2-c2cccc(NS(=O)(=O)c3ccc4ocnc4c3)c2F)n1] | 545.0 | HNMR (400 MHz, DMSO-d₆, ppm): δ 10.45 (s, 1H), 8.89 (s, 1H), 8.13 (s, 1H), 7.94-7.89 (m, 3H), 7.85-7.80 (m, 2H), 7.50-7.49 (m, 3H), 7.46-7.43 (m, 1H), 7.34-7.33 (m, 1H), 7.27-7.23 (m, 1H), 6.75 (s, 2H), 5.77 (d, J = 5.2 Hz, 1H). |

TABLE 1-continued

Characterization of the compounds

| Compound No. | Structure | [M + H]⁺ | NMR |
|---|---|---|---|
| 58 | 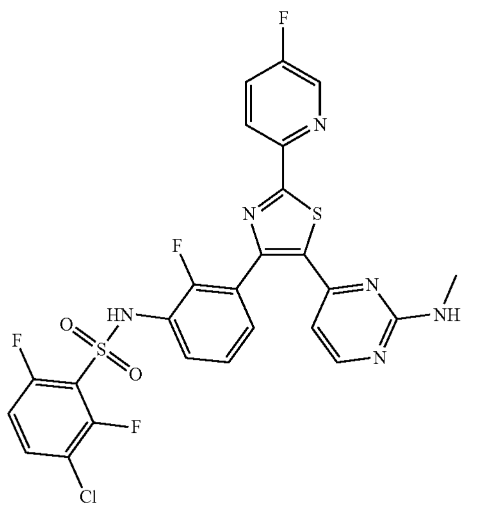 | 607.0 | HNMR (400 MHz, DMSO-d₆, ppm): δ 11.09 (s, 1H), 8.68 (d, J = 2.8 Hz, 1H), 8.16 (dd, J = 8.8, 4.4 Hz, 1H), 8.06 (d, J = 5.2 Hz, 1H), 7.93-7.87 (m, 2H), 7.49-7.42 (m, 2H), 7.33-7.29 (m, 2H), 7.22 (d, J = 4.4 Hz, 1H), 6.03 (s, 1H), 2.67-2.63 (m, 3H). FNMR (376 MHz, DMSO-d₆, ppm): δ −107.64 (1 F), −107.76 (1 F), −123.47 (1 F), −124.46 (1 F). |
| 59 | 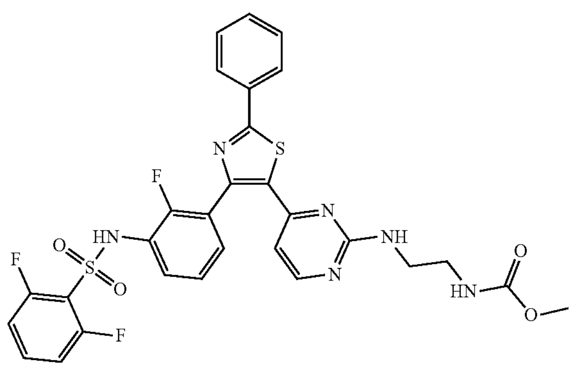 [SMILES: COC(=O)NCCNc1nccc(-c2sc(-c3ccccc3)nc2-c2cccc(NS(=O)(=O)c3c(F)cccc3F)c2F)n1] | 641.0 | HNMR (400 MHz, DMSO-d₆, ppm): δ 10.89 (s, 1H), 8.05 (d, J = 5.2 Hz, 1H), 7.96 (d, J = 3.6 Hz, 2H), 7.69-7.62 (m, 1H), 7.52-7.49 (m, 3H), 7.48-7.42 (m, 2H), 7.32-7.28 (m, 2H), 7.23-7.15 (m, 3H), 5.92 (s, 1H), 3.50 (s, 3H), 3.28-3.26 (m, 2H), 3.16-3.13 (m, 2H). FNMR (376 MHz, DMSO-d₆, ppm): δ −107.38 (2 F), −124.54 (1 F). |
| 60 | 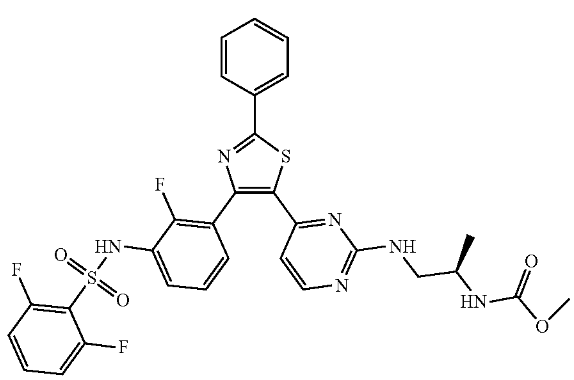 [SMILES: COC(=O)N[C@H](C)CNc1nccc(-c2sc(-c3ccccc3)nc2-c2cccc(NS(=O)(=O)c3c(F)cccc3F)c2F)n1] | 655.0 | HNMR (400 MHz, DMSO-d₆, ppm): δ 10.88 (s, 1H), 8.04 (d, J = 5.2 Hz, 1H), 7.96-7.94 (m, 2H), 7.67-7.63 (m, 1H), 7.52-7.42 (m, 5H), 7.32-7.19 (m, 4H), 6.99 (d, J = 8.4 Hz, 1H), 5.91 (br s, 1H), 3.75 (br s, 1H), 3.49 (s, 3H), 3.27-3.25 (m, 2H), 1.03 (d, J = 6.4 Hz, 3H). |

TABLE 1-continued

Characterization of the compounds

| Compound No. | Structure | [M + H]⁺ | NMR |
|---|---|---|---|
| 61 | 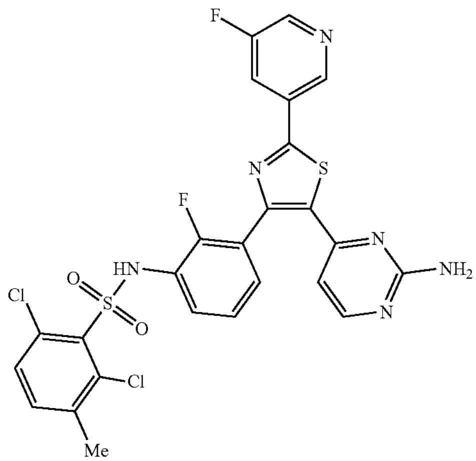 [SMILES: Cc1ccc(Cl)c(S(=O)(=O)Nc2cccc(-c3nc(-c4cncc(F)c4)sc3-c3ccnc(N)n3)c2F)c1Cl] | 605.0 | HNMR (400 MHz, DMSO-d₆, ppm): δ 10.73 (s, 1H), 9.01 (d, J = 1.6 Hz, 1H), 8.72 (d, J = 2.8 Hz, 1H), 8.25-8.22 (m, 1H), 8.00 (d, J = 5.2 Hz, 1H), 7.55-7.39 (m, 4H), 7.29 (t, J = 8.0 Hz, 1H), 6.88 (br s, 2H), 5.93 (d, J = 5.2 Hz, 1H), 2.31 (s, 3H). |
| 62 | 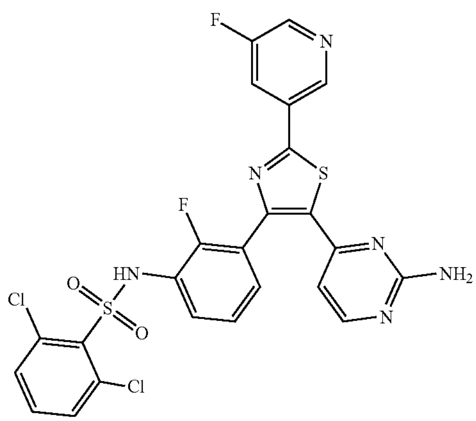 [SMILES: Nc1nccc(-c2sc(-c3cncc(F)c3)nc2-c2cccc(NS(=O)(=O)c3c(Cl)cccc3Cl)c2F)n1] | 590.9 | HNMR (400 MHz, DMSO-d₆, ppm): δ 10.77 (s, 1H), 9.01 (d, J = 1.2 Hz, 1H), 8.71 (d, J = 2.4 Hz, 1H), 8.25-8.21 (m, 1H), 8.03 (d, J = 5.2 Hz, 1H), 7.59-7.57 (m, 2H), 7.51-7.41 (m, 3H), 7.29 (t, J = 8.0 Hz, 1H), 6.83 (br s, 2H), 5.89 (d, J = 5.2 Hz, 1H). |
| 63 | 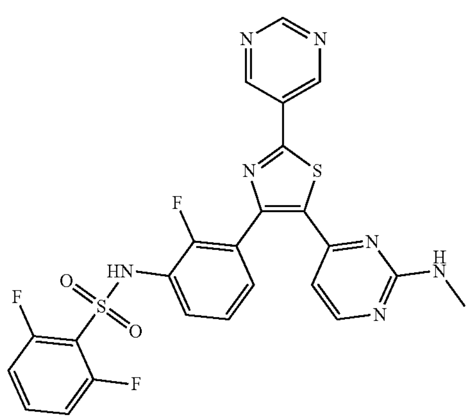 [SMILES: CNc1nccc(-c2sc(-c3cncnc3)nc2-c2cccc(NS(=O)(=O)c3c(F)cccc3F)c2F)n1] | 556.0 | HNMR (400 MHz, DMSO-d₆, ppm): δ 10.90 (s, 1H), 9.32 (s, 1H), 9.28 (s, 1H), 8.08 (d, J = 5.2 Hz, 1H), 7.69-7.61 (m, 1H), 7.47-7.43 (m, 2H), 7.33-7.19 (m, 4H), 7.06-6.93 (m, 1H), 5.96 (s, 1H), 2.74 (s, 3H). FNMR (376 MHz, DMSO-d₆, ppm): δ −107.41 (2 F), −124.37 (1 F). |

TABLE 1-continued

Characterization of the compounds

| Compound No. | Structure | [M + H]⁺ | NMR |
|---|---|---|---|
| 64 | 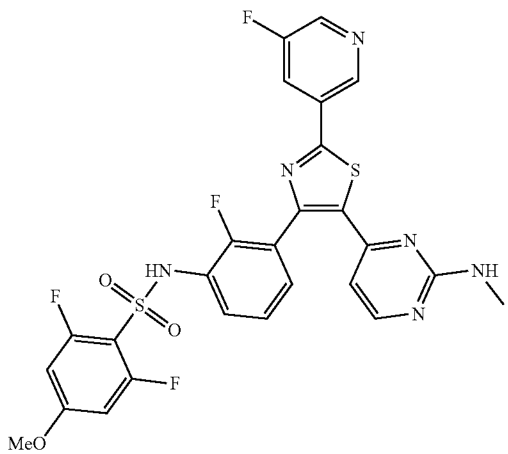 [SMILES: CNc1nccc(-c2sc(-c3cncc(F)c3)nc2-c2cccc(NS(=O)(=O)c3c(F)cc(OC)cc3F)c2F)n1] | 603.0 | HNMR (400 MHz, DMSO-d$_6$, ppm): δ 10.68 (s, 1H), 9.02 (s, 1H), 8.72 (d, J = 2.4 Hz, 1H), 8.26 (d, J = 9.2 Hz, 1H), 8.06 (d, J = 5.2 Hz, 1H), 7.48-7.42 (m, 2H), 7.33-7.26 (m, 2H), 6.86-6.81 (m, 2H), 5.95 (s, 1H), 3.77 (s, 3H), 2.74 (s, 3H). FNMR (376 MHz, DMSO-d$_6$, ppm): δ −106.13(2 F), −124.64 (1 F), −126.09 (1 F). |
| 65 | 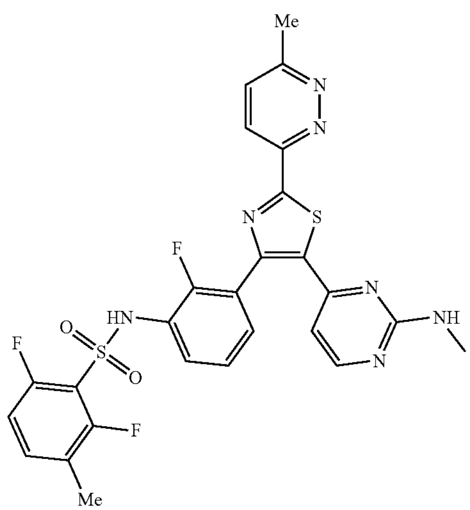 [SMILES: CNc1nccc(-c2sc(-c3ccc(C)nn3)nc2-c2cccc(NS(=O)(=O)c3c(F)ccc(C)c3F)c2F)n1] | 584.0 | HNMR (400 MHz, DMSO-d$_6$, ppm): δ 8.14 (d, J = 8.8 Hz, 1H), 7.97 (d, J = 5.2 Hz, 1H), 7.68 (d, J = 8.8 Hz, 1H), 7.54-7.34 (m, 3H), 7.28 (t, J = 8.0 Hz, 1H), 7.02 (t, J = 9.2 Hz, 1H), 6.06 (br s, 1H), 2.63 (br s, 6H), 2.08 (s, 3H). |
| 66 | 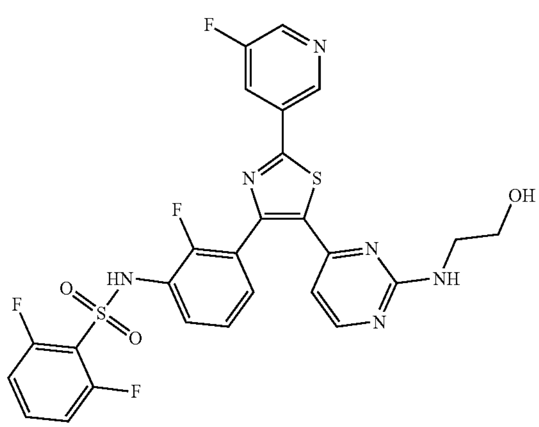 [SMILES: O=S(=O)(Nc1cccc(-c2nc(-c3cncc(F)c3)sc2-c2ccnc(NCCO)n2)c1F)c1c(F)cccc1F] | 603.0 | HNMR (400 MHz, DMSO-d$_6$, ppm): δ 10.90 (s, 1H), 9.01 (s, 1H), 8.71 (d, J = 2.4 Hz, 1H), 8.25 (d, J = 9.6 Hz, 1H), 8.07 (d, J = 5.2 Hz, 1H), 7.69-7.61 (m, 1H), 7.45 (t, J = 7.6 Hz, 2H), 7.31 (t, J = 8.0 Hz, 1H), 7.21 (t, J = 9.2 Hz, 3H), 5.92 (s, 1H), 3.52-3.47 (m, 4H). FNMR (376 MHz, DMSO-d$_6$, ppm): δ −107.40 (2 F), −124.43 (1 F), −126.07 (1 F). |

TABLE 1-continued

Characterization of the compounds

| Compound No. | Structure | [M + H]⁺ | NMR |
|---|---|---|---|
| 67 | 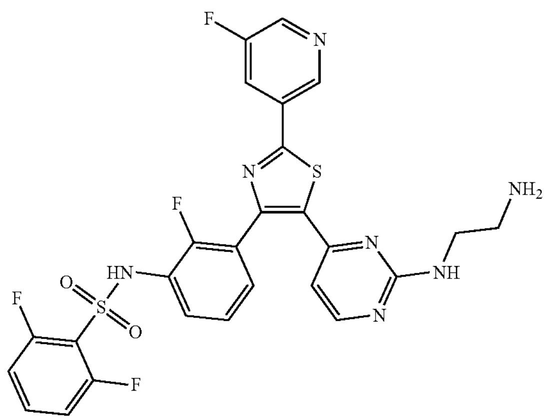 [SMILES: NCCNc1nccc(-c2sc(-c3cncc(F)c3)nc2-c2cccc(NS(=O)(=O)c3c(F)cccc3F)c2F)n1] | 602.0 | HNMR (400 MHz, DMSO-d₆, ppm): δ 10.90 (s, 1H), 9.02 (s, 1H), 8.73 (s, 1H), 8.25-8.22 (m, 1H), 8.14 (d, J = 5.2 Hz, 1H), 7.80 (s, 3H), 7.70-7.64 (m, 1H), 7.48-7.42 (m, 3H), 7.32 (t, J = 8.0 Hz, 1H), 7.23 (t, J = 9.2 Hz, 2H), 6.04 (s, 1H), 3.48-3.44 (m, 2H), 3.01-2.96 (m, 2H).<br>FNMR (376 MHz, DMSO-d₆, ppm): δ −107.41 (2 F), −124.16 (1 F), −125.96 (1 F). |
| 68 | 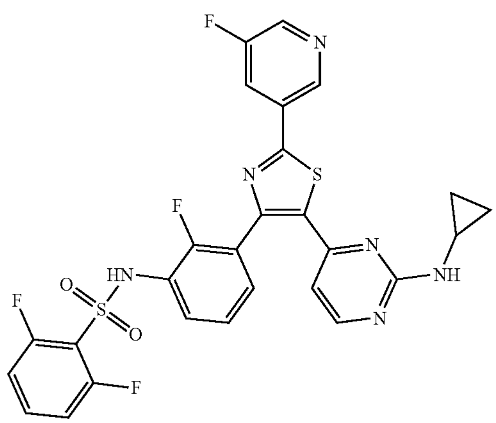 [SMILES: O=S(=O)(Nc1cccc(-c2nc(-c3cncc(F)c3)sc2-c2ccnc(NC3CC3)n2)c1F)c1c(F)cccc1F] | 599.0 | HNMR (400 MHz, DMSO-d₆, ppm): δ 10.91 (s, 1H), 9.01 (s, 1H), 8.71 (d, J = 2.8 Hz, 1H), 8.24 (d, J = 9.2 Hz, 1H), 8.10 (d, J = 5.2 Hz, 1H), 7.67-7.63 (m, 1H), 7.56 (d, J = 3.6 Hz, 1H), 7.47-7.43 (m, 2H), 7.31 (t, J = 8.0 Hz, 1H), 7.21 (t, J = 9.2 Hz, 2H), 5.98 (d, J = 4.0 Hz, 1H), 2.66-2.64 (m, 1H), 0.66-0.62 (m, 2H), 0.46-0.41 (m, 2H).<br>FNMR (376 MHz, DMSO-d₆, ppm): δ −107.40 (2 F), −124.42 (1 F), −126.06 (1 F). |
| 69 | 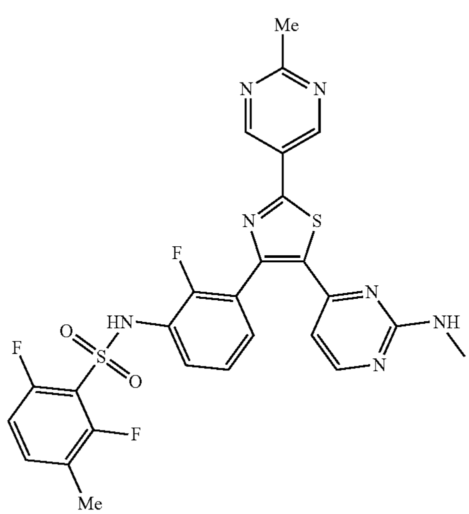 [SMILES: CNc1nccc(-c2sc(-c3cnc(C)nc3)nc2-c2cccc(NS(=O)(=O)c3c(F)ccc(C)c3F)c2F)n1] | 584.0 | HNMR (400 MHz, DMSO-d₆, ppm): δ 10.84 (s, 1H), 9.20 (s, 2H), 8.05 (d, J = 5.2 Hz, 1H), 7.57-7.51 (m, 1H), 7.46-7.42 (m, 2H), 7.30 (t, J = 8.0 Hz, 2H), 7.11 (t, J = 9.2 Hz, 1H), 5.98 (br s, 1H), 2.73-2.68 (m, 6H), 2.14 (s, 3H). |

TABLE 1-continued

Characterization of the compounds

| Compound No. | Structure | [M + H]+ | NMR |
|---|---|---|---|
| 70 | 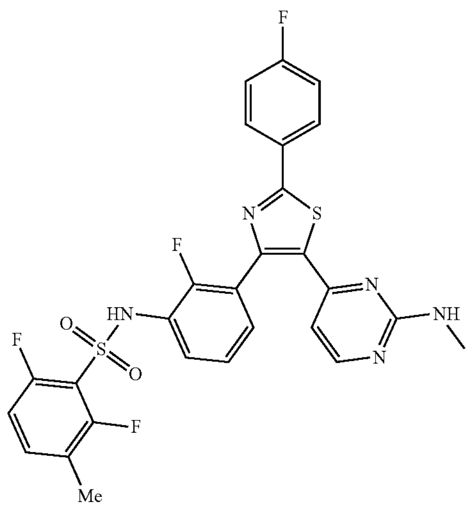 [SMILES: CNc1nccc(-c2sc(-c3ccc(F)cc3)nc2-c2cccc(NS(=O)(=O)c3c(F)ccc(C)c3F)c2F)n1] | 586.0 | HNMR (400 MHz, DMSO-d$_6$, ppm): δ 10.83 (s, 1H), 8.03-8.00 (m, 3H), 7.56-7.53 (m, 1H), 7.44-7.22 (m, 6H), 7.13-7.09 (m, 1H), 5.98 (br s, 1H), 2.72 (br s, 3H), 2.14 (s, 3H). |
| 71 | 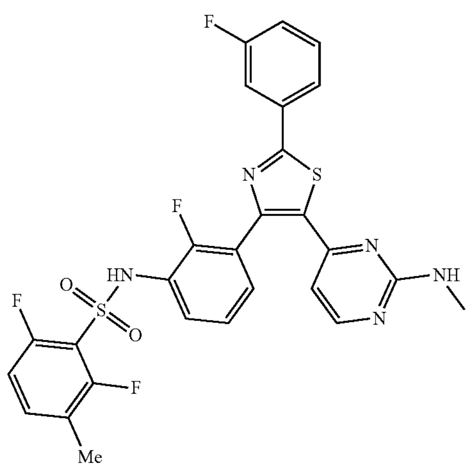 [SMILES: CNc1nccc(-c2sc(-c3cccc(F)c3)nc2-c2cccc(NS(=O)(=O)c3c(F)ccc(C)c3F)c2F)n1] | 586.0 | HNMR (400 MHz, DMSO-d$_6$, ppm): δ 10.84 (s, 1H), 8.02 (d, J = 5.2 Hz, 1H), 7.80 (d, J = 8.0 Hz, 1H), 7.74 (d, J = 9.6 Hz, 1H), 7.58-7.53 (m, 2H), 7.45-7.41 (m, 2H), 7.39-7.27 (m, 2H), 7.22 (br s, 1H), 7.10 (t, J = 5.2 Hz, 1H), 6.00 (br s, 1H), 2.71 (br s, 3H), 2.13 (s, 3H). |
| 72 | 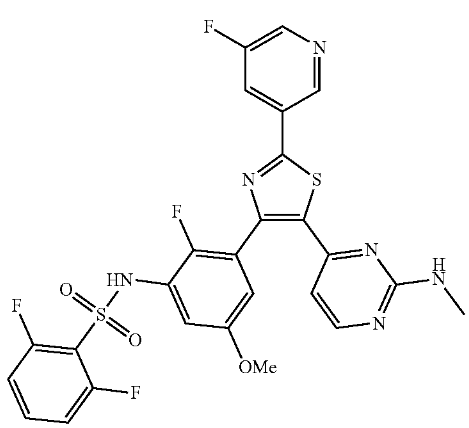 [SMILES: CNc1nccc(-c2sc(-c3cncc(F)c3)nc2-c2cc(OC)cc(NS(=O)(=O)c3c(F)cccc3F)c2F)n1] | 603.0 | HNMR (400 MHz, DMSO-d$_6$, ppm): δ 10.94 (s, 1H), 9.02 (s, 1H), 8.71 (d, J = 2.4 Hz, 1H), 8.26 (d, J = 9.6 Hz, 1H), 8.09 (d, J = 4.8 Hz, 1H), 7.68-7.64 (m, 1H), 7.25-7.20 (m, 3H), 6.99-6.96 (m, 2H), 6.01 (s, 1H), 3.70 (s, 3H), 2.75 (s, 3H).<br>FNMR (376 MHz, DMSO-d$_6$, ppm): δ −107.42 (2 F), −126.09 (1 F), −134.97 (1 F). |

TABLE 1-continued

Characterization of the compounds

| Compound No. | Structure | [M + H]+ | NMR |
|---|---|---|---|
| 73 | 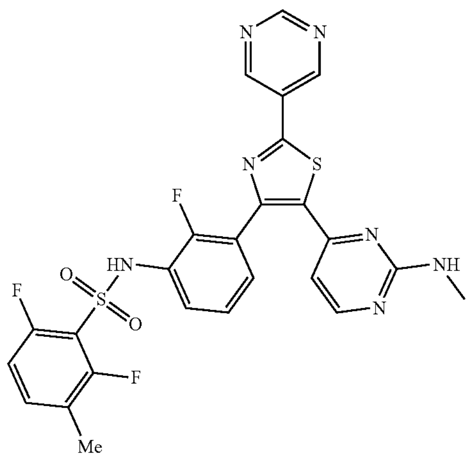 [SMILES: CNc1nccc(-c2sc(-c3cncnc3)nc2-c2cccc(NS(=O)(=O)c3c(F)ccc(C)c3F)c2F)n1] | 570.0 | HNMR (400 MHz, DMSO-d$_6$, ppm): δ 10.85 (s, 1H), 9.32-9.28 (m, 3H), 8.05 (d, J = 5.2 Hz, 1H), 7.56-7.51 (m, 1H), 7.47-7.42(m, 2H), 7.31 (t, J = 7.6 Hz, 2H), 7.10 (t, J = 9.2 Hz, 1H), 6.02-6.00 (m, 1H), 2.73 (br s, 3H), 2.13 (s, 3H). |
| 74 | 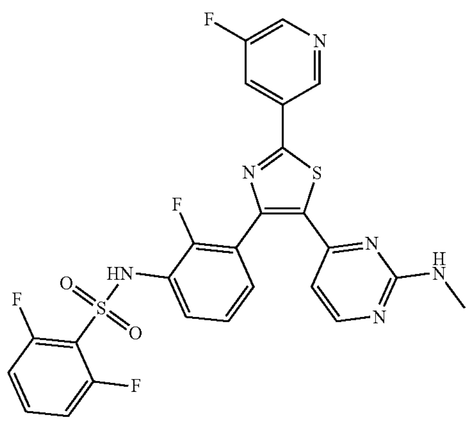 [SMILES: CNc1nccc(-c2sc(-c3cncc(F)c3)nc2-c2cccc(NS(=O)(=O)c3c(F)cccc3F)c2F)n1] | 573.0 | HNMR (400 MHz, DMSO-d$_6$, ppm): δ 10.94 (s, 1H), 9.06 (s, 1H), 8.76 (d, J = 2.4 Hz, 1H), 8.30 (d, J = 9.6 Hz, 1H), 8.13 (d, J = 5.2 Hz, 1H), 7.73-7.66 (m, 1H), 7.51-7.48 (m, 2H), 7.37-7.24 (m, 4H), 6.01 (s, 1H), 2.78 (s, 3H).<br>FNMR (376 MHz, DMSO-d$_6$, ppm): δ -107.41(2 F), -124.42 (1 F), -126.10 (1 F). |
| 75 | 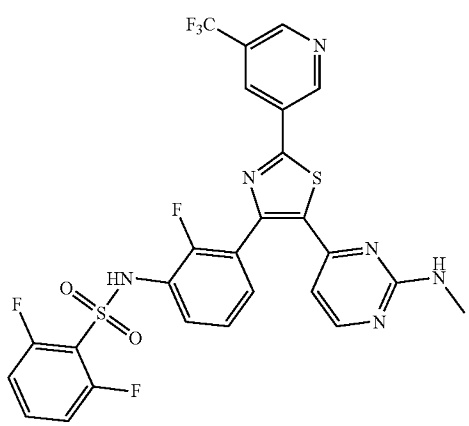 [SMILES: CNc1nccc(-c2sc(-c3cncc(C(F)(F)F)c3)nc2-c2cccc(NS(=O)(=O)c3c(F)cccc3F)c2F)n1] | 623.0 | HNMR (400 MHz, DMSO-d$_6$, ppm): δ 10.90 (s, 1H), 9.42 (s, 1H), 9.10 (s, 1H), 8.62 (s, 1H), 8.10 (d, J = 5.2 Hz, 1H), 7.69-7.61 (m, 1H), 7.49-7.44 (m, 2H), 7.33-7.19 (m, 4H), 5.99 (s, 1H), 2.74 (s, 3H).<br>FNMR (376 MHz, DMSO-d$_6$, ppm): δ -61.02(3 F), -107.41(2 F), -124.38 (1 F). |

TABLE 1-continued

Characterization of the compounds

| Compound No. | Structure | [M + H]+ | NMR |
|---|---|---|---|
| 76 | 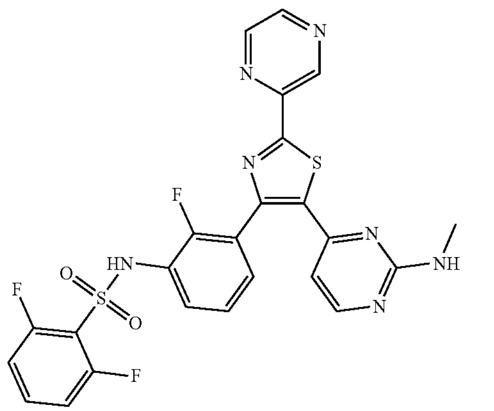 [SMILES: CNc1nccc(-c2sc(-c3cnccn3)nc2-c2cccc(NS(=O)(=O)c3c(F)cccc3F)c2F)n1] | 556.0 | HNMR (400 MHz, DMSO-d$_6$, ppm): δ 10.94 (s, 1H), 9.30 (d, J = 1.6 Hz, 1H), 8.81 (d, J = 2.4 Hz, 1H), 8.79-8.75 (m, 1H), 8.12 (d, J = 4.8 Hz, 1H), 7.74-7.63 (m, 1H) 7.49 (t, J = 7.6 Hz, 2H), 7.34 (t, J = 8.0 Hz, 1H), 7.31-7.20 (m, 3H), 6.04 (br s, 1H), 2.74 (br s, 3H). |
| 77 | 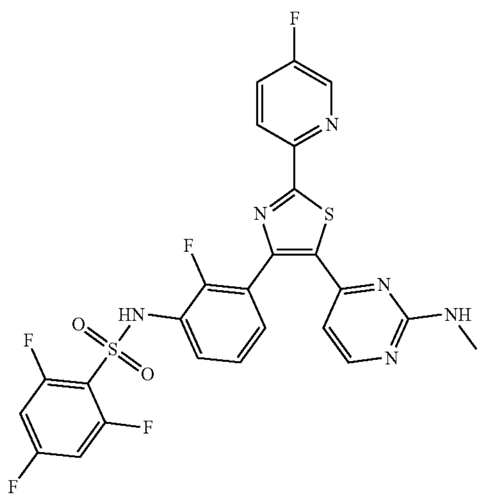 [SMILES: CNc1nccc(-c2sc(-c3ccc(F)cn3)nc2-c2cccc(NS(=O)(=O)c3c(F)cc(F)cc3F)c2F)n1] | 591.0 | HNMR (400 MHz, DMSO-d$_6$, ppm): δ 10.96 (s, 1H), 8.72 (d, J = 2.8 Hz, 1H), 8.20 (dd, J = 8.8, 4.4 Hz, 1H), 8.10 (d, J = 4.8 Hz, 1H), 7.92 (dt, J = 8.8, 2.8 Hz, 1H), 7.55-7.20 (m, 6H), 6.04 (br s, 1H), 2.73 (br s, 3H).<br>FNMR (376 MHz, DMSO-d$_6$, ppm): δ −98.97 (1 F), −103.56 (3 F), −123.47 (1 F). |
| 78 | 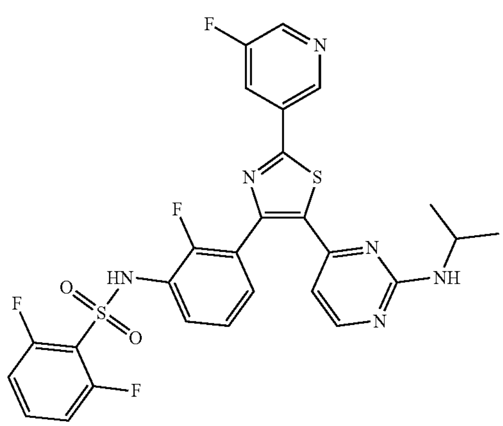 [SMILES: CC(C)Nc1nccc(-c2sc(-c3cncc(F)c3)nc2-c2cccc(NS(=O)(=O)c3c(F)cccc3F)c2F)n1] | 601.0 | HNMR (400 MHz, DMSO-d$_6$, ppm): δ 10.91 (s, 1H), 9.01 (s, 1H), 8.72 (d, J = 2.8 Hz, 1H), 8.25 (d, J = 8.0 Hz, 1H), 8.07 (d, J = 5.2 Hz, 1H), 7.69-7.62 (m, 1H), 7.47-7.43 (m, 2H), 7.33-7.29 (m, 1H), 7.24-7.20 (m, 3H), 5.92 (d, J = 3.2 Hz, 1H), 3.65-3.62 (m, 1H), 1.12 (d, J = 6.4 Hz, 6H).<br>FNMR (376 MHz, DMSO-d$_6$, ppm): δ −107.38(2 F), −124.46 (1 F), −126.13 (1 F). |

TABLE 1-continued

Characterization of the compounds

| Compound No. | Structure | [M + H]+ | NMR |
|---|---|---|---|
| 79 | 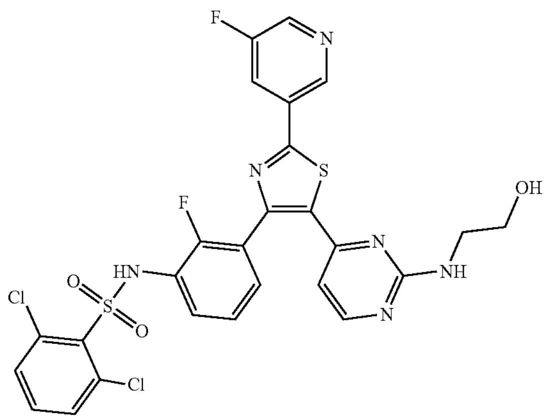 [SMILES: O=S(=O)(Nc1cccc(-c2nc(-c3cncc(F)c3)sc2-c2ccnc(NCCO)n2)c1F)c1c(Cl)cccc1Cl] | 634.9 | HNMR (400 MHz, DMSO-d6, ppm): δ 10.77 (s, 1H), 9.01 (s, 1H), 8.71 (d, J = 2.4 Hz, 1H), 8.24 (d, J = 9.6 Hz, 1H), 8.07 (d, J = 4.8 Hz, 1H), 7.59-7.56 (m, 2H), 7.51-7.40 (m, 3H), 7.31-7.22 (m, 2H), 5.91 (s, 1H), 3.52-3.49 (m, 4H).<br>FNMR (376 MHz, DMSO-d6, ppm): δ −123.88(1 F), −126.02 (1 F). |
| 80 | 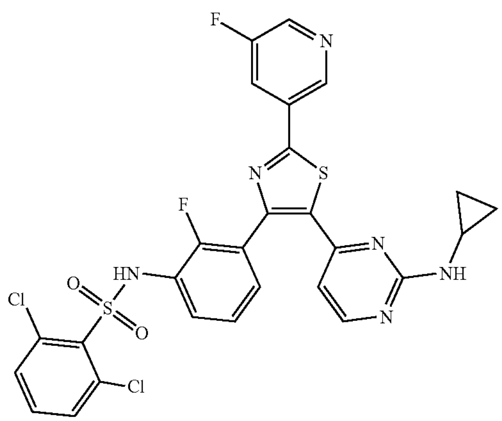 [SMILES: O=S(=O)(Nc1cccc(-c2nc(-c3cncc(F)c3)sc2-c2ccnc(NC3CC3)n2)c1F)c1c(Cl)cccc1Cl] | 630.9 | HNMR (400 MHz, DMSO-d6, ppm): δ 10.78 (s, 1H), 9.01 (s, 1H), 8.71 (d, J = 2.4 Hz, 1H), 8.24 (d, J = 9.6 Hz, 1H), 8.10 (d, J = 4.8 Hz, 1H), 7.59-7.57 (m, 3H), 7.51-7.40 (m, 3H), 7.31-7.27 (m, 1H), 5.97 (d, J = 4.0 Hz, 1H), 2.66-2.63 (m, 1H), 0.67-0.62 (m, 2H), 0.46 (s, 2H).<br>FNMR (376 MHz, DMSO-d6, ppm): δ −123.88(1 F), −126.07 (1 F). |
| 81 | 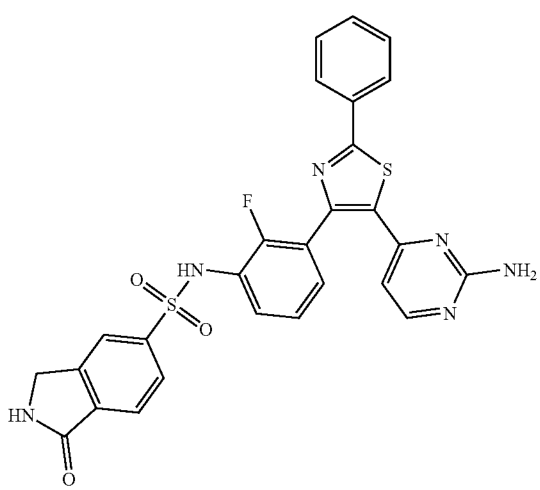 [SMILES: Nc1nccc(-c2sc(-c3ccccc3)nc2-c2cccc(NS(=O)(=O)c3ccc4c(c3)CNC4=O)c2F)n1] | 558.5 | HNMR (400 MHz, DMSO-d6, ppm): δ 10.50 (s, 1H), 8.83 (s, 1H), 7.99-7.94 (m, 2H), 7.94-7.86 (m, 2H), 7.84-7.77 (m, 2H), 7.53-7.47 (m, 3H), 5.45-7.36 (m, 2H), 7.27 (t, J = 8.0 Hz, 1H), 6.79 (s, 2H), 5.88 (d, J = 5.2 Hz, 1H), 4.38 (s, 2H). |

TABLE 1-continued

Characterization of the compounds

| Compound No. | Structure | [M + H]+ | NMR |
|---|---|---|---|
| 82 | 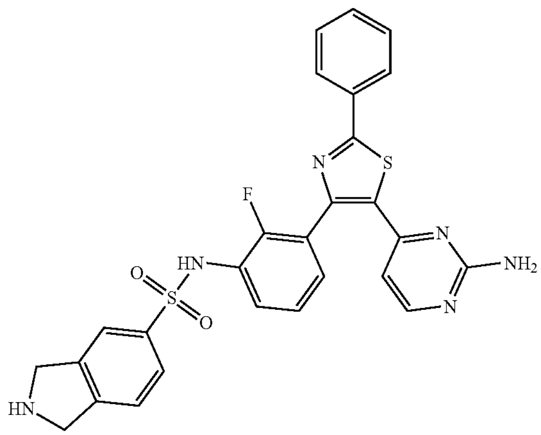 [SMILES: Nc1nccc(-c2sc(-c3ccccc3)nc2-c2cccc(NS(=O)(=O)c3ccc4c(c3)CNC4)c2F)n1] | 544.5 | HNMR (400 MHz, DMSO-d$_6$, ppm): δ7.98-7.96 (m, 2H), 7.93 (d, J = 6.0 Hz, 1H), 7.88 (s, 1H), 7.81 (d, J = 8.4 Hz, 1H), 7.68-7.64 (m, 1H), 7.52-7.41 (m, 5H), 7.34-7.31 (m, 1H), 6.17 (d, J = 5.6 Hz, 1H), 4.63 (d, J = 9.2 Hz, 4H). |
| 83 | 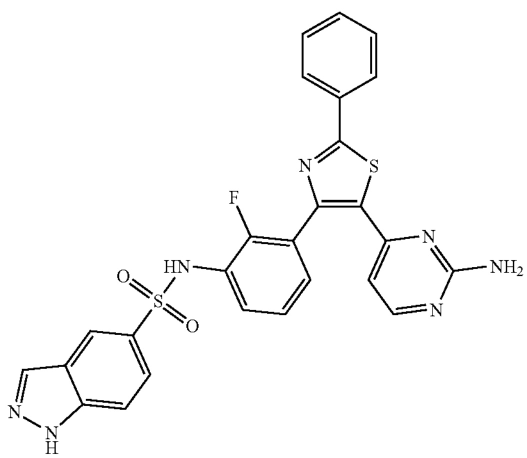 [SMILES: Nc1nccc(-c2sc(-c3ccccc3)nc2-c2cccc(NS(=O)(=O)c3ccc4[nH]ncc4c3)c2F)n1] | 544.0 | HNMR (400 MHz, DMSO-d$_6$, ppm): δ 13.49 (s, 1H), 10.26 (s, 1H), 8.22 (d, J = 8.0 Hz, 2H), 7.90-7.88 (m, 2H), 7.75 (d, J = 5.2 Hz, 1H), 7.70-7.64 (m, 2H), 7.50-7.44 (m, 4H), 7.32-7.21 (m, 2H), 6.79 (br s, 2H), 5.72 (d, J = 5.2 Hz, 1H). |
| 84 | 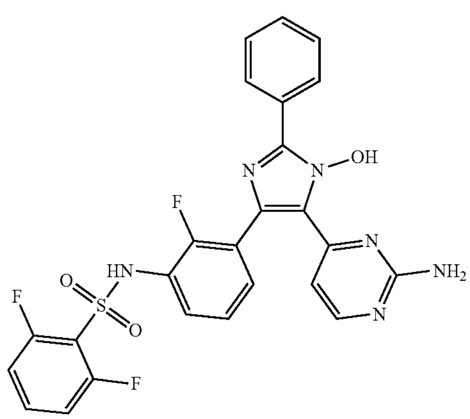 [SMILES: Nc1nccc(-c2c(-c3cccc(NS(=O)(=O)c4c(F)cccc4F)c3F)nc(-c3ccccc3)n2O)n1] | 539.1 | HNMR (400 MHz, DMSO-d$_6$, ppm): δ 10.80 (s, 1H), 8.13 (d, J = 5.2 Hz, 1H), 8.11-8.09 (m, 2H), 7.69-7.62 (m, 1H), 7.50-7.47 (m, 2H), 7.44-7.38 (m, 2H), 7.33-7.29 (m, 1H), 7.26-7.19 (m, 3H), 7.04 (s, 2H), 6.15 (d, J = 5.6 Hz, 1H)). <br> FNMR (376 MHz, DMSO-d$_6$, ppm): δ -107.47 (2 F), -123.96 (1 F). |

TABLE 1-continued

Characterization of the compounds

| Compound No. | Structure | [M + H]+ | NMR |
|---|---|---|---|
| 85 | 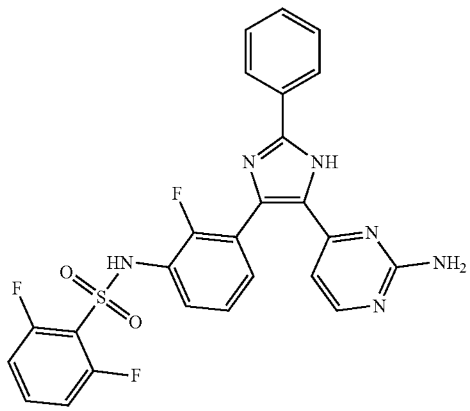 [SMILES: Nc1nccc(-c2[nH]c(-c3ccccc3)nc2-c2cccc(NS(=O)(=O)c3c(F)cccc3F)c2F)n1] | 523.1 | HNMR (400 MHz, DMSO-d6, ppm): δ 10.85 (s, 1H), 8.19 (d, J = 5.6 Hz, 1H), 8.08 (d, J = 7.2 Hz, 2H), 7.70-7.63 (m, 1H), 7.49-7.39 (m, 4H), 7.35-7.31 (m, 1H), 7.27-6.95 (m, 6H).<br>FNMR (376 MHz, DMSO-d6, ppm): δ −107.48 (2 F), −121.24 (1 F). |
| 86 | 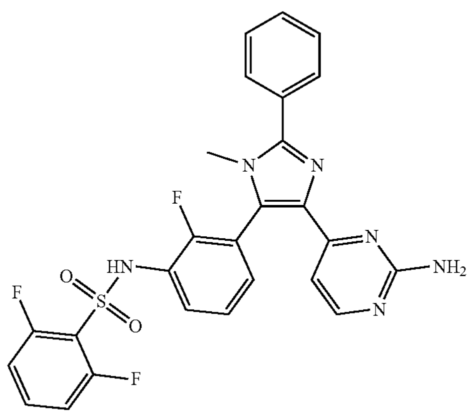 [SMILES: Cn1c(-c2ccccc2)nc(-c2ccnc(N)n2)c1-c1cccc(NS(=O)(=O)c2c(F)cccc2F)c1F] | 537.1 | HNMR (400 MHz, DMSO-d6, ppm): δ 10.74 (s, 1H), 8.04 (d, J = 5.2 Hz, 1H), 7.71-7.62 (m, 3H), 7.54-7.47 (m, 3H), 7.40-7.36 (m, 1H), 7.29-7.25 (m, 1H), 7.21-7.17 (m, 3H), 7.02 (br s, 2H), 6.12 (d, J = 5.6 Hz, 1H), 3.81 (s, 3H).<br>FNMR (376 MHz, DMSO-d6, ppm): δ −107.51 (2 F), −124.10 (1 F). |
| 87 | 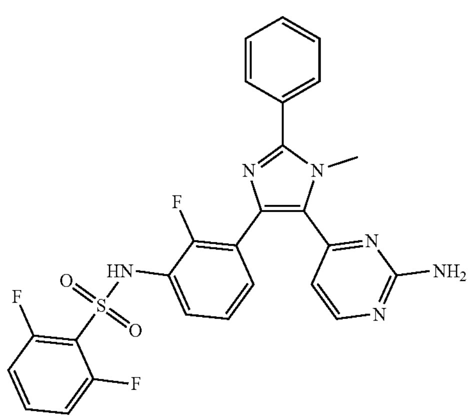 [SMILES: Cn1c(-c2ccccc2)nc(-c2cccc(NS(=O)(=O)c3c(F)cccc3F)c2F)c1-c1ccnc(N)n1] | 537.1 | HNMR (400 MHz, DMSO-d6, ppm): δ 10.87 (s, 1H), 8.20 (d, J = 5.6 Hz, 1H), 7.75-7.73 (m, 2H), 7.69-7.65 (m, 1H), 7.56-7.51 (m, 3H), 7.44-7.38 (m, 2H), 7.30 (t, J = 8.0 Hz, 1H), 7.23 (t, J = 9.2 Hz, 2H), 6.96 (br s, 2H), 3.29 (s, 3H).<br>FNMR (376 MHz, DMSO-d6, ppm): δ −107.31 (2 F), −121.36 (1 F). |

TABLE 1-continued

Characterization of the compounds

| Compound No. | Structure | [M + H]+ | NMR |
|---|---|---|---|
| 88 | 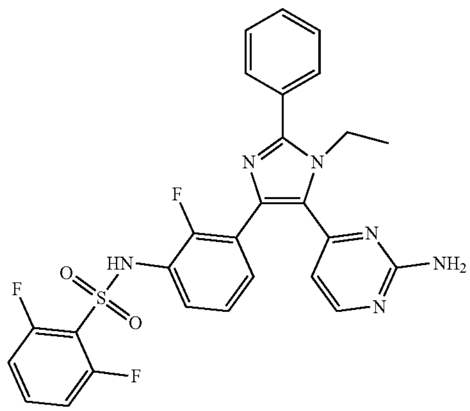 [SMILES: CCn1c(-c2ccccc2)nc(-c2cccc(NS(=O)(=O)c3c(F)cccc3F)c2F)c1-c1ccnc(N)n1] | 551.1 | HNMR (400 MHz, DMSO-d$_6$, ppm): δ 10.86 (s, 1H), 8.18 (d, J = 5.6 Hz, 1H), 7.68-7.61 (m, 3H), 7.56-7.52 (m, 3H), 7.47 (t, J = 7.6 Hz, 1H), 7.39 (t, J = 6.4 Hz, 1H), 7.31 (t, J = 7.6 Hz, 1H), 7.20 (t, J = 9.2 Hz, 2H), 7.09-6.81 (m, 3H), 3.78-3.63 (m, 2H), 0.71 (t, J = 7.2 Hz, 3H).<br>FNMR (376 MHz, DMSO-d$_6$, ppm): δ −107.26 (2 F), −121.44 (1 F). |
| 89 | 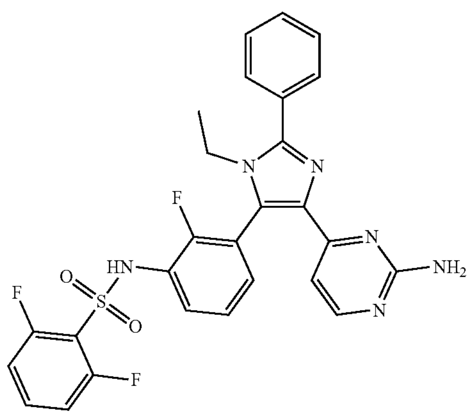 [SMILES: CCn1c(-c2ccccc2)nc(-c2ccnc(N)n2)c1-c1cccc(NS(=O)(=O)c2c(F)cccc2F)c1F] | 551.1 | HNMR (400 MHz, DMSO-d$_6$, ppm): δ 10.75 (s, 1H), 8.04 (d, J = 5.2 Hz, 1H), 7.68-7.63 (m, 3H), 7.53-7.51 (m, 3H), 7.38 (t, J = 6.4 Hz, 1H), 7.28-6.73 (m, 6H), 6.10 (d, J = 5.2 Hz, 1H), 4.37 (q, J = 6.8 Hz, 2H), 1.06 (t, J = 6.8 Hz, 3H). |
| 90 | 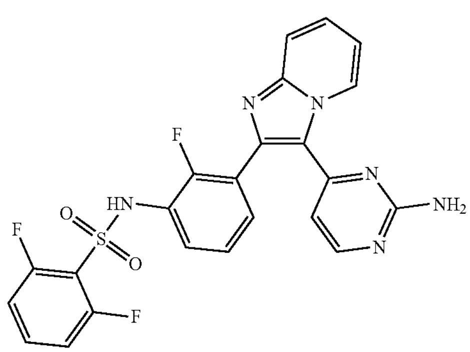 [SMILES: Nc1nccc(-c2c(-c3cccc(NS(=O)(=O)c4c(F)cccc4F)c3F)nc3ccccn23)n1] | 497.0 | HNMR (400 MHz, DMSO-d$_6$, ppm): δ 10.86 (br s, 1H), 9.77 (d, J = 6.8 Hz, 1H), 7.94 (d, J = 5.2 Hz, 1H), 7.69-7.62 (m, 2H), 7.48-7.37 (m, 3H), 7.28-7.24 (m, 1H), 7.19 (t, J = 8.8 Hz, 2H), 7.09-7.05 (m, 1H), 6.81(s, 2H), 5.91 (d, J = 5.2 Hz, 1H). |

TABLE 1-continued

Characterization of the compounds

| Compound No. | Structure | [M + H]⁺ | NMR |
|---|---|---|---|
| 91 | 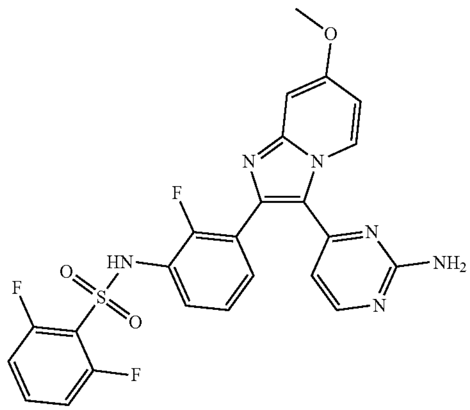 | 527.1 | HNMR (400 MHz, DMSO-d₆, ppm): δ 10.90 (s, 1H), 9.77 (d, J = 7.6 Hz, 1H), 7.90 (d, J = 6.0 Hz, 1H), 7.69-7.39 (m, 5H), 7.30 (t, J = 8.0 Hz, 1H), 7.24-7.16 (m, 3H), 6.86 (dd, J = 8.0, 2.8 Hz, 1H), 5.95 (d, J = 6.0 Hz, 1H), 3.71 (s, 3H). FNMR (376 MHz, DMSO-d₆, ppm): δ −107.47 (2 F), −124.21 (1 F). |
| 92 | 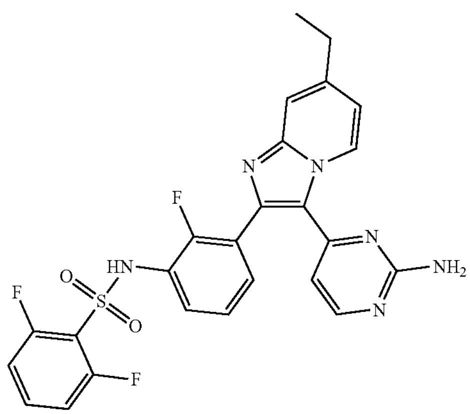 [SMILES: CCc1ccn2c(-c3ccnc(N)n3)c(-c3cccc(NS(=O)(=O)c4c(F)cccc4F)c3F)nc2c1] | 525.1 | HNMR (400 MHz, DMSO-d₆, ppm): δ 10.84 (br s, 1H), 9.70 (d, J = 7.2 Hz, 1H), 7.91 (d, J = 5.2 Hz, 1H), 7.64-7.61 (m, 1H), 7.46 (s, 1H), 7.39-7.33 (m, 2H), 7.26-7.16 (m, 3H), 6.96 (dd, J = 7.2, 1.6 Hz, 1H), 6.77 (s, 2H), 5.89 (d, J = 5.6 Hz, 1H), 2.70 (q, J = 7.6 Hz, 2H), 1.22 (t, J = 7.6 Hz, 3H). |
| 93 | 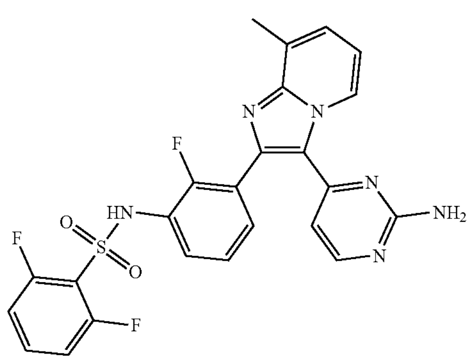 [SMILES: Cc1cccn2c(-c3ccnc(N)n3)c(-c3cccc(NS(=O)(=O)c4c(F)cccc4F)c3F)nc12] | 511.1 | HNMR (400 MHz, DMSO-d₆, ppm): δ 10.86 (s, 1H), 9.67 (d, J = 7.6 Hz, 1H), 7.96 (d, J = 5.2 Hz, 1H), 7.73-7.60 (m, 1H), 7.50-7.37 (m, 2H), 7.36-7.26 (m, 2H), 7.22 (t, J = 8.8 Hz, 2H), 7.01 (t, J = 5.1 Hz, 1H), 6.83 (s, 2H), 5.92 (d, J = 5.2 Hz, 1H), 2.53 (s, 3H). |

TABLE 1-continued

Characterization of the compounds

| Compound No. | Structure | [M + H]⁺ | NMR |
|---|---|---|---|
| 94 | 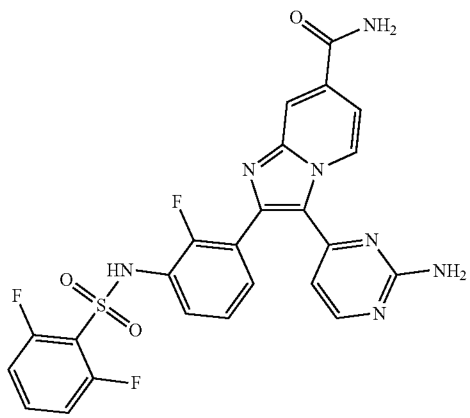 | 540.1 | HNMR (400 MHz, DMSO-d₆, ppm): δ 10.86 (s, 1H), 9.79 (d, J = 7.2 Hz, 1H), 8.28-8.25 (m, 2H), 8.00 (s, 1H), 7.69-7.61 (m, 2H), 7.50-7.40 (m, 3H), 7.32-7.18 (m, 5H), 5.99 (d, J = 5.2 Hz, 1H).<br>FNMR (376 MHz, DMSO-d₆, ppm): δ −107.44 (2 F), −124.37 (1 F). |
| 95 | 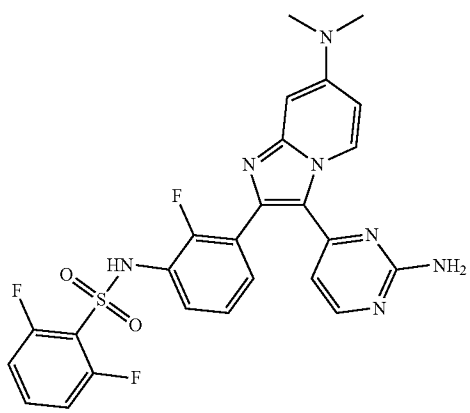 [SMILES: CN(C)c1ccn2c(-c3ccnc(N)n3)c(-c3cccc(NS(=O)(=O)c4c(F)cccc4F)c3F)nc2c1] | 540.0 | HNMR (400 MHz, DMSO-d₆, ppm): δ 11.00 (br s, 1H), 9.60 (d, J = 2.4 Hz, 1H), 7.94 (s, 1H), 7.71-7.63 (m, 1H), 7.49-7.43 (m, 2H), 7.36-7.29 (m, 1H), 7.25-7.20 (m, 2H), 6.95 (d, J = 8.0 Hz, 1H), 6.55 (d, J = 0.8 Hz, 1H), 5.91 (d, J = 6.0 Hz, 1H), 3.17 (s, 6H). |
| 96 | 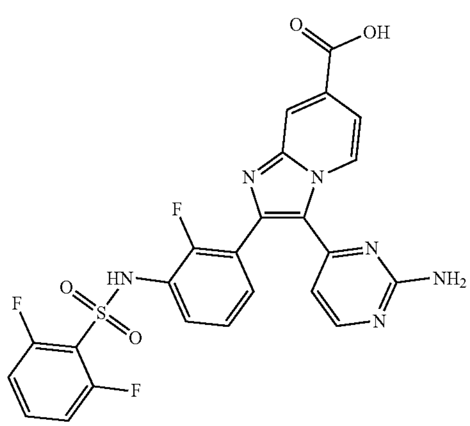 [SMILES: Nc1nccc(-c2c(-c3cccc(NS(=O)(=O)c4c(F)cccc4F)c3F)nc3cc(C(=O)O)ccn23)n1] | 541.0 | HNMR (400 MHz, DMSO-d₆, ppm): δ 13.57 (s, 1H), 10.86 (s, 1H), 9.78 (d, J = 5.6 Hz, 1H), 8.20 (s, 1H), 8.01 (d, J = 5.2 Hz, 1H), 7.68-7.63 (m, 1H), 7.46-7.40 (m, 3H), 7.31-7.27 (m, 1H), 7.22-7.18 (m, 2H), 7.05-7.03 (m, 2H), 5.99 (d, J = 5.2 Hz, 1H).<br>FNMR (376 MHz, DMSO-d₆, ppm): δ −107.44 (2 F), −124.36 (1 F). |

TABLE 1-continued

Characterization of the compounds

| Compound No. | Structure | [M + H]+ | NMR |
|---|---|---|---|
| 97 | 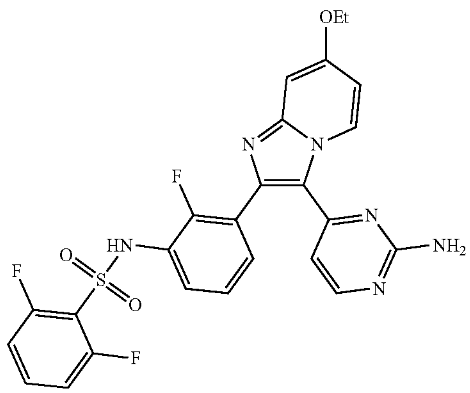 | 541.1 | HNMR (400 MHz, DMSO-d$_6$, ppm): δ 10.88 (s, 1H), 9.76 (d, J = 7.6 Hz, 1H), 7.90 (d, J = 5.6 Hz, 1H), 7.67-7.62 (m, 1H), 7.43-7.27 (m, 5H), 7.21 (t, J = 9.2 Hz, 2H), 7.13 (d, J = 2.8 Hz, 1H), 6.83 (dd, J = 8.0, 2.4 Hz, 1H), 5.94 (d, J = 5.6 Hz, 1H), 4.17 (q, J = 6.8 Hz, 2H), 1.37 (t, J = 6.8 Hz, 3H).<br>FNMR (376 MHz, DMSO-d$_6$, ppm): δ −107.45 (2 F), −124.19 (1 F). |
| 98 | 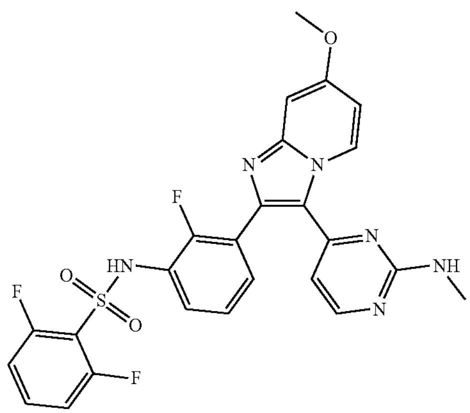 [SMILES: CNc1nccc(-c2c(-c3cccc(NS(=O)(=O)c4c(F)cccc4F)c3F)nc3cc(OC)ccn23)n1] | 541.1 | HNMR (400 MHz, DMSO-d$_6$, ppm): δ 10.87 (s, 1H), 9.66 (s, 1H), 7.98 (d, J = 5.6 Hz, 1H), 7.76-7.62 (m, 1H), 7.57-7.35 (m, 3H), 7.30 (t, J = 8.0 Hz, 1H), 7.23 (t, J = 9.2 Hz, 2H), 7.12 (d, J = 2.8 Hz, 1H), 6.86 (br s, 1H), 5.92 (d, J = 5.2 Hz, 1H), 3.90 (s, 3H), 2.88 (s, 3H).<br>FNMR (376 MHz, DMSO-d$_6$, ppm): δ −107.41 (2 F), −124.24 (1 F). |
| 99 | 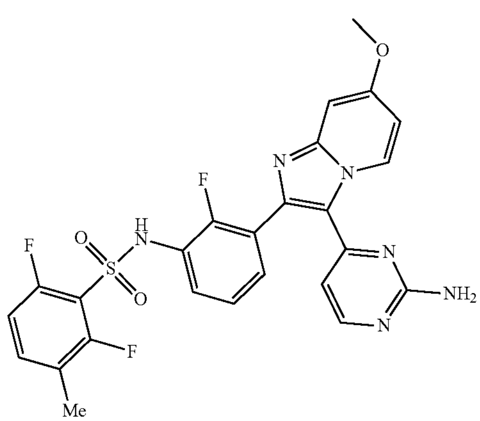 [SMILES: COc1ccn2c(-c3ccnc(N)n3)c(-c3cccc(NS(=O)(=O)c4c(F)ccc(C)c4F)c3F)nc2c1] | 541.0 | HNMR (400 MHz, DMSO-d$_6$, ppm): δ 10.83 (s, 1H), 9.77 (d, J = 8.0 Hz, 1H), 7.88 (d, J = 6.0 Hz, 1H), 7.57-7.38 (m, 5H), 7.30 (t, J = 7.6 Hz, 1H), 7.18 (s, 1H), 7.11 (t, J = 9.2 Hz, 1H), 6.88-6.86 (m, 1H), 5.99-5.98 (m, 1H), 3.90 (s, 3H), 2.15 (s, 3H).<br>FNMR (376 MHz, DMSO-d$_6$, ppm): δ −110.00 (1 F), −111.41 (1 F), −124.07 (1 F). |

TABLE 1-continued

Characterization of the compounds

| Compound No. | Structure | [M + H]⁺ | NMR |
|---|---|---|---|
| 100 | 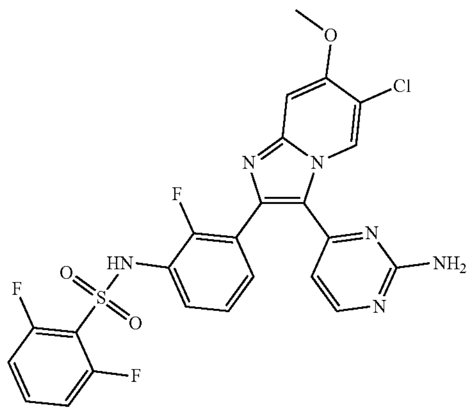 [SMILES: COc1cc2nc(-c3cccc(NS(=O)(=O)c4c(F)cccc4F)c3F)c(-c3ccnc(N)n3)n2cc1Cl] | 561.0 | HNMR (400 MHz, CD$_3$OD-d$_4$, ppm): δ 10.04 (s, 1H), 7.85 (d, J = 6.4 Hz, 1H), 7.63-7.54 (m, 2H), 7.46-7.42 (m, 1H), 7.34-7.30 (m, 1H), 7.20 (s, 1H), 7.10-7.05 (m, 2H), 6.27 (d, J = 6.4 Hz, 1H), 4.06 (s, 3H). |
| 101 | 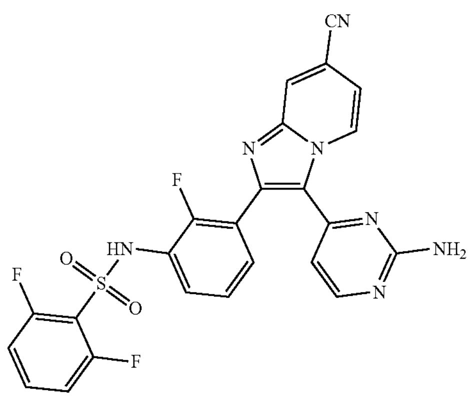 [SMILES: N#Cc1ccn2c(-c3ccnc(N)n3)c(-c3cccc(NS(=O)(=O)c4c(F)cccc4F)c3F)nc2c1] | 522.0 | HNMR (400 MHz, DMSO-d$_6$, ppm): δ 10.85 (s, 1H), 9.82 (d, J = 4.4 Hz, 1H), 8.46 (s, 1H), 8.02 (d, J = 5.2 Hz, 1H), 7.65-7.59 (m, 1H), 7.38-7.33 (m, 3H), 7.23-7.14 (m, 3H), 6.89 (s, 2H), 6.01 (s, 1H). |
| 102 | 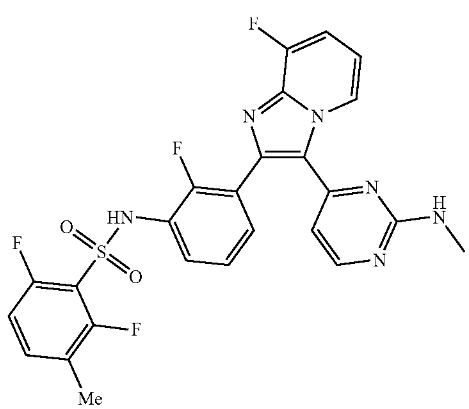 [SMILES: CNc1nccc(-c2c(-c3cccc(NS(=O)(=O)c4c(F)ccc(C)c4F)c3F)nc3c(F)cccn23)n1] | 543.1 | HNMR (400 MHz, DMSO-d$_6$, ppm): δ 10.80 (s, 1H), 9.50 (s, 1H), 8.01 (d, J = 5.2 Hz, 1H), 7.56-7.38 (m, 5H), 7.30-7.27 (m, 1H), 7.12-7.08 (m, 2H), 6.01 (s, 1H), 2.86 (s, 3H), 2.14 (s, 3H). FNMR (376 MHz, DMSO-d$_6$, ppm): δ −109.97 (1 F), −111.38 (1 F), −124.32 (1 F), −131.09 (1 F). |

TABLE 1-continued

Characterization of the compounds

| Compound No. | Structure | [M + H]⁺ | NMR |
|---|---|---|---|
| 103 | 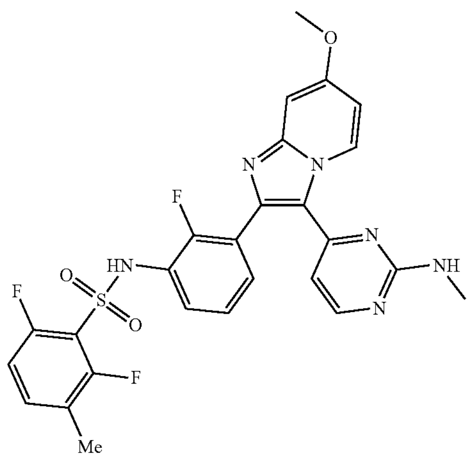 [SMILES: CNc1nccc(-c2c(-c3cccc(NS(=O)(=O)c4c(F)ccc(C)c4F)c3F)nc3cc(OC)ccn23)n1] | 555.1 | HNMR (400 MHz, DMSO-d₆, ppm): δ 10.84 (s, 1H), 9.68 (br s, 1H), 7.96 (d, J = 5.6 Hz, 1H), 7.63-7.52 (m, 1H), 7.43 (t, J = 7.2 Hz, 2H), 7.31 (t, J = 7.6 Hz, 1H), 7.20-7.07 (m, 2H), 6.91 (br s, 1H), 5.98 (br s, 1H), 3.92 (s, 3H), 2.89 (s, 3H), 2.18 (s, 3H). |
| 104 | 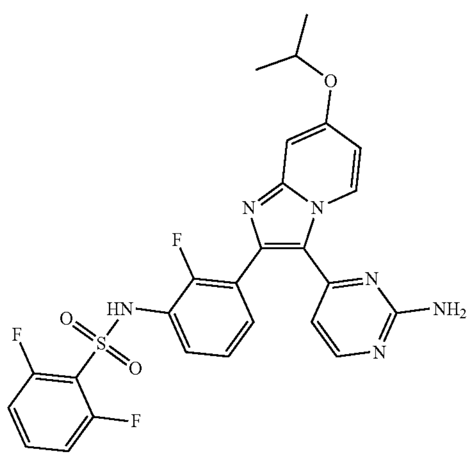 [SMILES: CC(C)Oc1ccn2c(-c3ccnc(N)n3)c(-c3cccc(NS(=O)(=O)c4c(F)cccc4F)c3F)nc2c1] | 555.1 | HNMR (400 MHz, DMSO-d₆, ppm): δ 10.89 (s, 1H), 9.77 (d, J = 7.6 Hz, 1H), 7.90 (d, J = 6.0 Hz, 1H), 7.66-7.64 (m, 1H), 7.41 (t, J = 8.0 Hz, 2H), 7.32-7.28 (m, 1H), 7.24-7.18 (m, 3H), 6.81 (d, J = 7.6 Hz, 1H), 5.96-5.95 (m, 1H), 4.85-4.83 (m, 1H), 1.32 (t, J = 6.4 Hz, 6H).<br>FNMR (376 MHz, DMSO-d₆, ppm): δ -107.45 (2 F), -124.13 (1 F). |
| 105 | 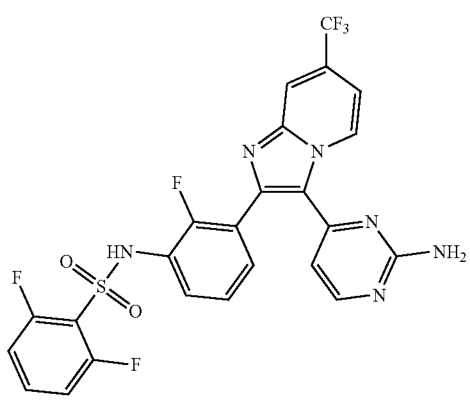 | 565.0 | HNMR (400 MHz, CD₃OD, ppm): δ 9.96 (d, J = 7.2 Hz, 1H), 8.00-7.98 (m, 2H), 7.63-7.56 (m, 2H), 7.45 (t, J = 6.4 Hz, 1H), 7.32-7.28 (m, 2H), 7.05 (t, J = 8.8 Hz, 2H), 6.17(d, J = 5.2 Hz, 1H).<br>FNMR (376 MHz, CD₃OD, ppm): δ -65.50 (3 F), -108.82 (2 F), -126.42 (1 F). |

TABLE 1-continued

Characterization of the compounds

| Compound No. | Structure | [M + H]⁺ | NMR |
|---|---|---|---|
| 106 | 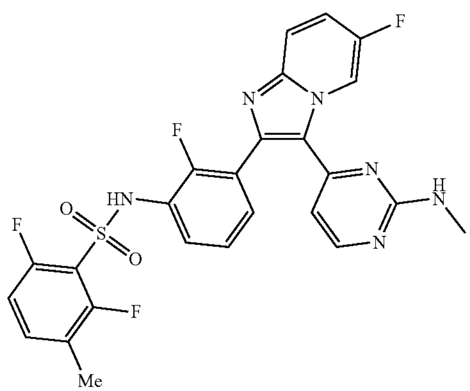 [SMILES: CNc1nccc(-c2c(-c3cccc(NS(=O)(=O)c4c(F)ccc(C)c4F)c3F)nc3ccc(F)cn23)n1] | 543.0 | HNMR (400 MHz, DMSO-d$_6$): δ 10.82 (s, 1H), 9.92 (s, 1H), 8.01 (d, J = 5.2 Hz, 1H), 7.83 (dd, J = 10.0, 5.2 Hz, 1H), 7.67-7.52 (m, 2H), 7.47-7.38 (m, 2H), 7.31 (t, J = 8.0 Hz, 1H), 7.13 (t, J = 9.6 Hz, 1H), 5.98 (br s, 1H), 2.90 (s, 3H), 2.17 (s, 3H). |
| 107 | 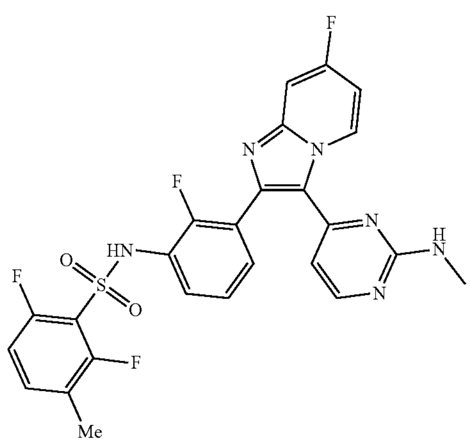 [SMILES: CNc1nccc(-c2c(-c3cccc(NS(=O)(=O)c4c(F)ccc(C)c4F)c3F)nc3cc(F)ccn23)n1] | 543.1 | HNMR (400 MHz, DMSO-d$_6$, ppm): δ 10.80 (s, 1H), 9.79 (br s, 1H), 7.97 (d, J = 5.2 Hz, 1H), 7.63 (d, J = 9.2 Hz, 1H), 7.57-7.51 (m, 1H), 7.43-7.37 (m, 2H), 7.28 (t, J = 8.0 Hz, 1H), 7.20 (s, 1H), 7.13-7.08 (m, 1H), 5.98(s, 1H), 2.87 (s, 3H), 2.14 (s, 3H). |
| 108 | 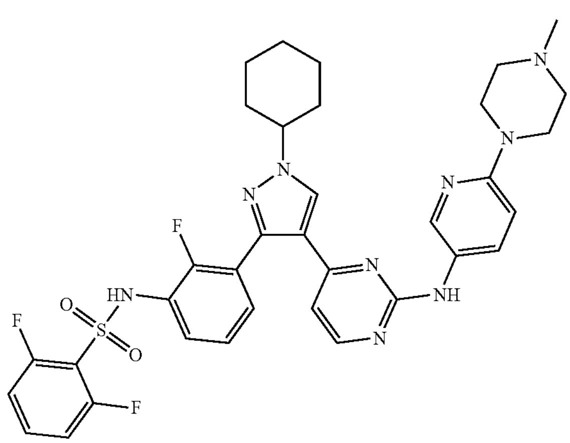 [SMILES: CN1CCN(c2ccc(Nc3nccc(-c4cn(C5CCCCC5)nc4-c4cccc(NS(=O)(=O)c5c(F)cccc5F)c4F)n3)cn2)CC1] | 704.2 | HNMR (400 MHz, CD$_3$OD-d$_4$, ppm): δ 8.41(s, 1H), 8.22 (d, J = 5.6 Hz, 1H), 8.14 (s, 1H), 7.63 (dd, J = 9.2, 2.8 Hz, 1H), 7.57-7.53 (m, 1H), 7.44-7.39 (m, 1H), 7.30-7.26 (m, 1H), 7.16 (t, J = 8.0 Hz, 1H), 7.02 (t, J = 8.8 Hz, 2H), 6.88 (d, J = 6.0 Hz, 1H), 6.81 (d, J = 9.6 Hz, 1H), 4.25-4.19 (m, 1H), 3.55-3.35 (m, 8H), 2.99 (s, 3H), 2.17-2.15 (m, 2H), 1.94-1.90 (m, 2H), 1.88-1.73 (m, 3H), 1.50-1.44(m, 2H), 1.33-1.28 (m, 1H). |

TABLE 1-continued

Characterization of the compounds

| Compound No. | Structure | [M + H]⁺ | NMR |
|---|---|---|---|
| 109 | 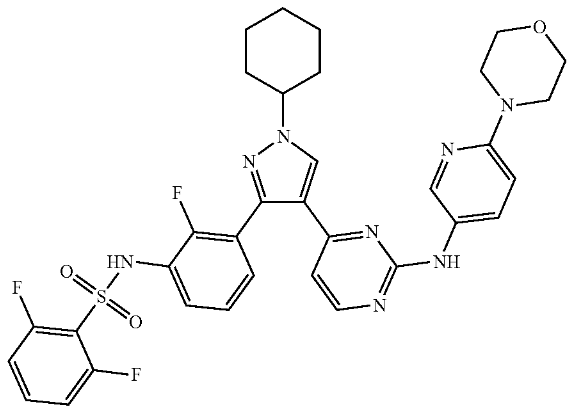 [SMILES: O=S(=O)(Nc1cccc(-c2nn(C3CCCCC3)cc2-c2ccnc(Nc3ccc(N4CCOCC4)nc3)n2)c1F)c1c(F)cccc1F] | 691.1 | HNMR (400 MHz, DMSO-d₆, ppm): δ 7.55(s, 1H), 7.47 (d, J = 5.6 Hz, 1H), 7.32 (s, 1H), 7.12 (dd, J_ 9.6, 2.4 Hz, 1H), 6.78-6.73 (m, 1H), 6.54-6.49 (m, 2H), 6.34 (t, J = 8.0 Hz, 1H), 6.28-6.21 (m, 3H), 6.05 (d, J = 5.6 Hz, 1H), 3.43-3.37 (m, 1H), 3.09 (t, J = 4.8 Hz, 4H), 2.79 (t, J = 4.8 Hz, 4H), 1, 36-1.33 (m, 2H), 1.13-0.92 (m, 5H), 0.70-0.65 (m, 2H), 0.51-0.46 (m, 1H). |
| 110 | 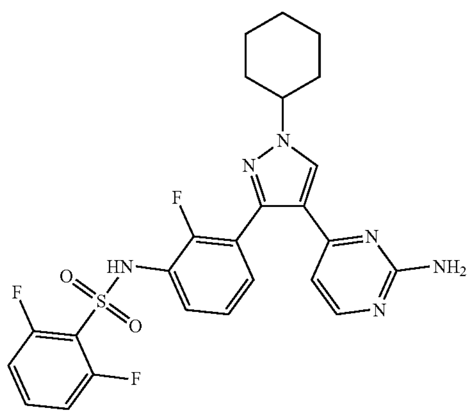 [SMILES: Nc1nccc(-c2cn(C3CCCCC3)nc2-c2cccc(NS(=O)(=O)c3c(F)cccc3F)c2F)n1] | 529.0 | HNMR (400 MHz, CD₃OD-d₄, ppm): δ 8.25 (s, 1H), 7.90 (d, J = 5.6 Hz, 1H), 7.56-7.49 (m, 2H), 7.20-7.18 (m, 2H), 7.04 (t, J = 8.8 Hz, 2H), 6.17 (d, J = 5.2 Hz, 1H), 4.18-4.12 (m, 1H), 2.16-2.13 (m, 2H), 1.93-1.89 (m, 2H), 1.81-1.74 (m, 3H), 1.49-1.46 (m, 2H), 1.32-1.26 (m, 1H). |
| 111 | 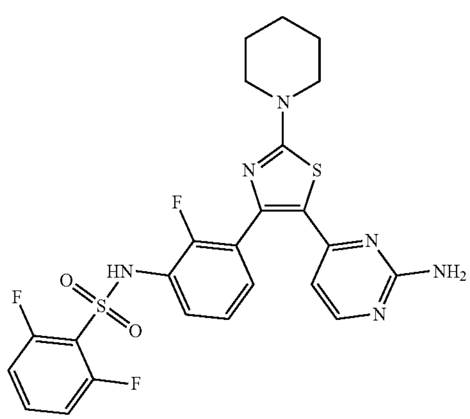 [SMILES: Nc1nccc(-c2sc(N3CCCCC3)nc2-c2cccc(NS(=O)(=O)c3c(F)cccc3F)c2F)n1] | 547.1 | HNMR (400 MHz, DMSO-d₆, ppm): δ 10.84 (s, 1H), 7.80-7.77 (m, 1H), 7.69-7.62 (m, 1H), 7.41-7.19 (m, 7H), 5.71-5.68 (m, 1H), 3.47 (s, 4H), 1.58 (s, 6H). FNMR (376 MHz, DMSO-d₆, ppm): δ −107.37 (2 F), −124.61 (1 F). |

TABLE 1-continued

Characterization of the compounds

| Compound No. | Structure | [M + H]+ | NMR |
|---|---|---|---|
| 112 | 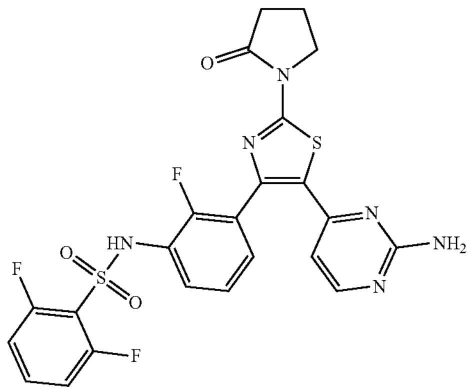 [SMILES: Nc1nccc(-c2sc(N3CCCC3=O)nc2-c2cccc(NS(=O)(=O)c3c(F)cccc3F)c2F)n1] | 547.0 | HNMR (400 MHz, DMSO-d$_6$, ppm): δ 10.85 (s, 1H), 7.90 (d, J = 5.2 Hz, 1H), 7.69-7.61 (m, 1H), 7.44-7.39 (m, 1H), 7.32-7.18 (m, 4H), 6.77 (s, 2H), 5.76 (d, J = 5.2 Hz, 1H), 3.96 (t, J = 7.2 Hz, 2H), 2.61 (t, J = 8.0 Hz, 2H), 2.15-2.07 (m, 2H).<br>FNMR (376 MHz, DMSO-d$_6$, ppm): δ -102.60 (2 F), -119.77 (1 F). |
| 113 | 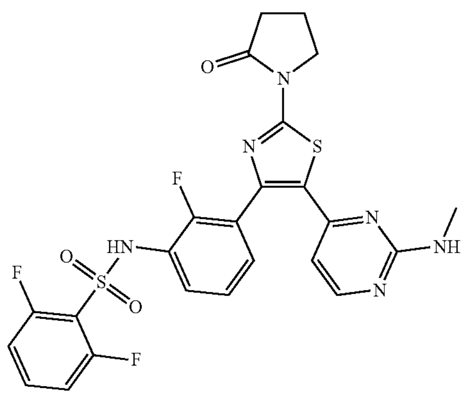 [SMILES: CNc1nccc(-c2sc(N3CCCC3=O)nc2-c2cccc(NS(=O)(=O)c3c(F)cccc3F)c2F)n1] | 561.0 | HNMR (400 MHz, DMSO-d$_6$, ppm): δ 10.89 (s, 1H), 7.98 (d, J = 5.2 Hz, 1H), 7.70-7.66 (m, 1H), 7.45-7.42 (m, 1H), 7.35-7.31 (m, 2H), 7.29-7.21 (m, 3H), 5.88-5.85 (m, 1H), 3.99 (t, J = 7.2 Hz, 2H), 2.74 (br s, 3H), 2.65 (s, t, J = 7.2 Hz, 2H), 2.18-2.11 (m, 2H). |
| 114 | 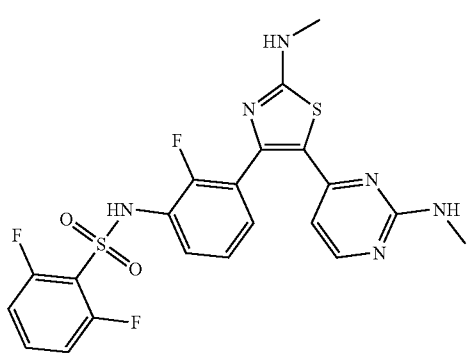 [SMILES: CNc1nccc(-c2sc(NC)nc2-c2cccc(NS(=O)(=O)c3c(F)cccc3F)c2F)n1] | 507.0 | HNMR (400 MHz, DMSO-d$_6$, ppm): δ 10.87 (s, 1H), 8.54 (s, 1H), 7.83-7.62 (m, 3H), 7.38 (t, J = 7.6 Hz, 1H), 7.31-7.19 (m, 4H), 5.77(s, 1H), 2.85 (d, J = 2.4 Hz, 3H), 2.73 (s, 3H).<br>FNMR (376 MHz, DMSO-d$_6$, ppm): δ -107.42 (2 F), -124.75 (1 F). |

TABLE 1-continued
Characterization of the compounds
| Compound No. | Structure | [M + H]+ | NMR |
|---|---|---|---|
| 115 | 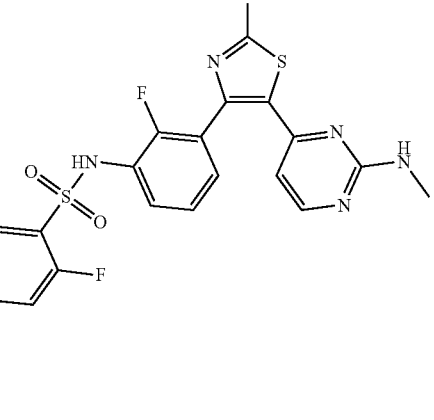 | 561.0 | HNMR (400 MHz, DMSO-d$_6$, ppm): δ 10.86 (s, 1H), 7.83 (d, J = 6.0 Hz, 1H), 7.69-7.62 (m, 2H), 7.40-7.37 (m, 1H), 7.30-7.19 (m, 4H), 5.75 (s, 1H), 3.48 (s, 4H), 2.73 (s, 3H), 1.58 (s, 6H).<br>FNMR (376 MHz, DMSO-d$_6$, ppm): δ −107.40 (2 F), −124.71 (1 F). |
| 116 | 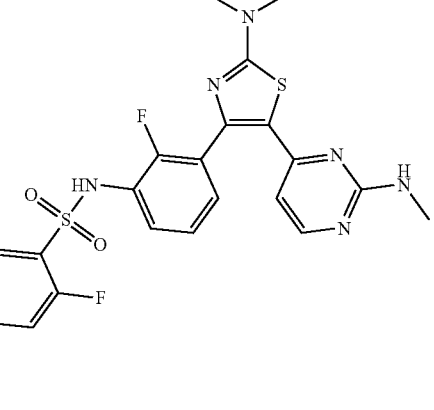 | 563.0 | HNMR (400 MHz, DMSO-d$_6$, ppm): δ 10.85 (s, 1H), 7.85 (d, J = 6.0 Hz, 1H), 7.69-7.61 (m, 1H), 7.47-7.19 (m, 6H), 5.73 (s, 1H), 3.68-3.66 (m, 4H), 3.50-3.40 (m, 4H), 2.72 (s, 3H).<br>FNMR (376 MHz, DMSO-d$_6$, ppm): δ −107.40 (2 F), −124.66 (1 F). |
| 117 | 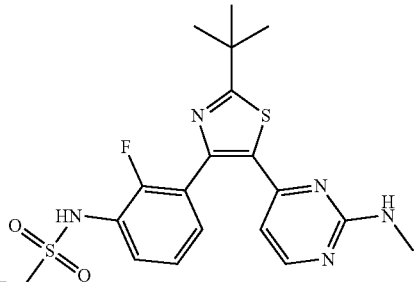 | 534.0 | HNMR (400 MHz, DMSO-d$_6$, ppm): δ 10.82 (s, 1H), 8.01 (d, J = 5.2 Hz, 1H), 7.67-7.60 (m, 1H), 7.38 (t, J = 7.2 Hz, 1H), 7.34-7.30 (m, 1 H), 7.26-7.17 (m, 4H), 5.92 (br s, 1H), 2.66 (s, 3H), 1.37 (s, 9H).<br>FNMR (376 MHz, DMSO-d$_6$, ppm): δ −107.42 (1 F), −124.50 (2 F). |

TABLE 1-continued

Characterization of the compounds

| Compound No. | Structure | [M + H]⁺ | NMR |
|---|---|---|---|
| 118 | 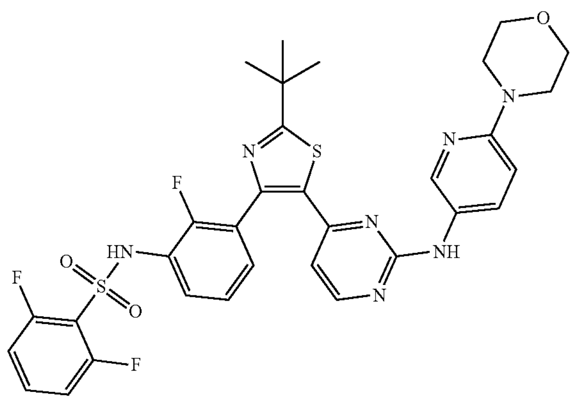 [SMILES: CC(C)(C)c1nc(-c2cccc(NS(=O)(=O)c3c(F)cccc3F)c2F)c(-c2ccnc(Nc3ccc(N4CCOCC4)nc3)n2)s1] | 682.0 | HNMR (400 MHz, CD₃OD-d₄, ppm): δ 8.40 (d, J = 2.8 Hz, 1H), 8.06 (d, J = 5.2 Hz, 1H), 7.87-7.84 (m, 1H), 7.44-7.33 (m, 2H), 7.02-6.98 (m, 1H), 6.93-6.88 (m, 2H), 6.85-6.80 (m, 2H), 6.31 (d, J = 5.2 Hz, 1H), 3.82-3.79 (m, 4H), 3.41-3.38 (m, 4H), 1.46 (s, 9H). |
| 119 | 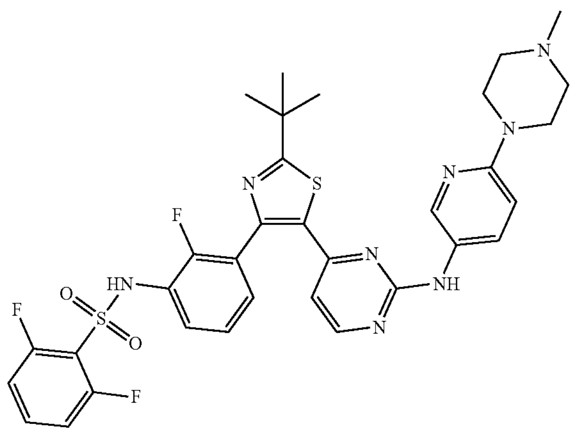 [SMILES: CN1CCN(c2ccc(Nc3nccc(-c4sc(C(C)(C)C)nc4-c4cccc(NS(=O)(=O)c5c(F)cccc5F)c4F)n3)cn2)CC1] | 695.1 | HNMR (400 MHz, DMSO-d₆, ppm): δ 10.75 (s, 1H), 9.44 (s, 1H), 8.35 (d, J = 2.8 Hz, 1H), 8.15 (d, J = 5.2 Hz, 1H), 7.81 (dd, J = 9.2, 2.8 Hz, 1H), 7.57-7.49 (m, 1H), 7.37-7.33 (m, 1H), 7.15-7.09 (m, 4H), 6.82 (d, J = 8.8 Hz, 1H), 6.13 (d, J = 5.2 Hz, 1H), 3.52-3.44 (m, 4H), 2.73-2.65 (m, 4H), 2.39 (s, 3H), 1.38 (s, 9H). FNMR (376 MHz, DMSO-d₆, ppm): δ −107.42 (2 F), −125.87 (1 F). |
| 120 | 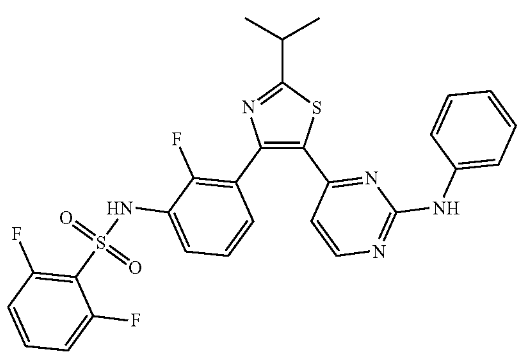 [SMILES: CC(C)c1nc(-c2cccc(NS(=O)(=O)c3c(F)cccc3F)c2F)c(-c2ccnc(Nc3ccccc3)n2)s1] | 582.0 | HNMR (400 MHz, DMSO-d₆, ppm): δ 10.86 (s, 1H), 9.67 (s, 1H), 8.21 (d, J = 5.2 Hz, 1H), 7.66-7.61 (m, 3H), 7.42-7.38 (m, 2H), 7.28-7.15 (m, 5H), 6.92 (t, J = 7.6 Hz, 1H), 6.12 (d, J = 4.8 Hz, 1H), 3.33-3.26 (m, 1H), 1.33 (d, J = 6.8 Hz, 6H). FNMR (376 MHz, DMSO-d₆, ppm): δ −107.46 (2 F), −124.66 (1 F). |

TABLE 1-continued

Characterization of the compounds

| Compound No. | Structure | [M + H]+ | NMR |
|---|---|---|---|
| 121 | 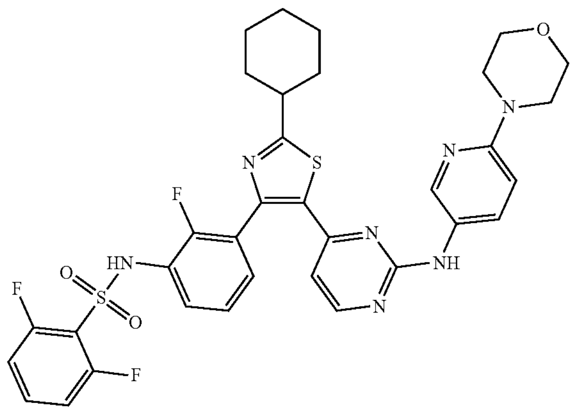 [SMILES: O=S(=O)(Nc1cccc(-c2nc(C3CCCCC3)sc2-c2ccnc(Nc3ccc(N4CCOCC4)nc3)n2)c1F)c1c(F)cccc1F] | 708.0 | HNMR (400 MHz, CD$_3$OD-d$_4$, ppm): δ 8.38-8.37 (m, 1H), 8.08 (d, J = 5.2 Hz, 1H), 7.80-7.77 (m, 1H), 7.59-7.51 (m, 2H), 7.32-7.23 (m, 2H), 7.05-7.01 (m, 2H), 6.78 (d, J = 9.2 Hz, 1H), 6.19 (d, J = 5.2 Hz, 1H), 3.82-3.79 (m, 4H), 3.41-3.39 (m, 4H), 3.03-2.97 (m, 1H), 2.15-2.11 (m, 2H), 1.89-1.85 (m, 2H), 1.77-1.74 (m, 1H), 1.62-1.40 (m, 5H). |
| 122 | 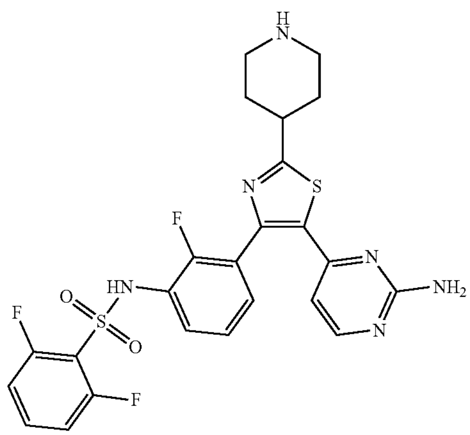 [SMILES: Nc1nccc(-c2sc(C3CCNCC3)nc2-c2cccc(NS(=O)(=O)c3c(F)cccc3F)c2F)n1] | 547.0 | HNMR (400 MHz, CD$_3$OD, ppm): δ 7.97 (d, J = 6.0 Hz, 1H), 7.62-7.50 (m, 2H), 7.37-7.33 (m, 1H), 7.28-7.24 (m, 1H), 7.07 (t, J = 8.4 Hz, 2H), 6.21 (dd, J = 6.0, 0.8 Hz, 1H), 3.52-3.42 (m, 3H), 3.19-3.13 (m, 2H), 2.37-2.32 (m, 2H), 2.09-2.00 (m, 2H). <br> FNMR (376 MHz, CD$_3$OD, ppm): δ −109.58 (2 F), −127.80 (1 F). |
| 123 | 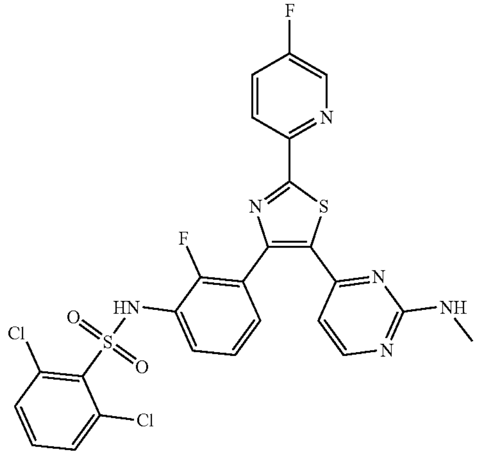 [SMILES: CNc1nccc(-c2sc(-c3ccc(F)cn3)nc2-c2cccc(NS(=O)(=O)c3c(Cl)cccc3Cl)c2F)n1] | 604.9 | HNMR (400 MHz, DMSO-d$_6$, ppm): δ 10.80 (s, 1H), 8.72 (d, J = 2.8 Hz, 1H), 8.19 (dd, J = 8.8, 4.4 Hz, 1H), 8.10 (d, J = 5.2 Hz, 1H), 7.92 (dt, J = 8.8, 2.8 Hz, 1H), 7.64-7.59 (m, 2H), 7.56-7.49 (m, 1 H), 7.48-7.40 (m, 2H), 7.38-7.24 (m, 2H), 6.03 (br s, 1H), 2.73 (br s, 3H). <br> FNMR (376 MHz, DMSO-d$_6$, ppm): δ −123.44 (1 F), −124.05 (1 F). |

TABLE 1-continued

Characterization of the compounds

| Compound No. | Structure | [M + H]+ | NMR |
|---|---|---|---|
| 124 | 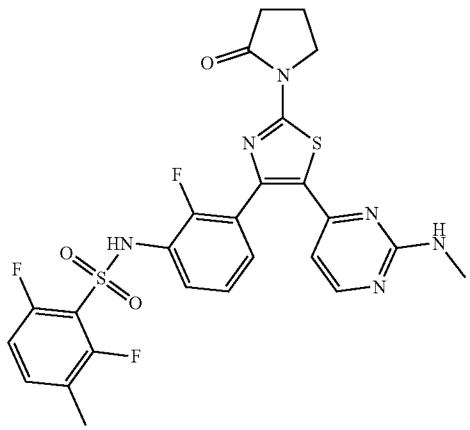 [SMILES: CNc1nccc(-c2sc(N3CCCC3=O)nc2-c2cccc(NS(=O)(=O)c3c(F)ccc(C)c3F)c2F)n1] | 575.0 | HNMR (400 MHz, DMSO-d₆, ppm) δ 10.80 (s, 1H), 7.93 (d, J = 5.2 Hz, 1H), 7.55-7.53 (m, 1H), 7.41-7.39 (m, 1H), 7.29-7.24 (m, 2H), 7.17-7.08 (m, 2H), 5.84 (br s, 1H), 3.96 (t, J = 7.2 Hz, 2H), 2.70 (br s, 3H), 2.63-2.60 (m, 2H), 2.13-2.09 (m, 5H). |
| 125 | 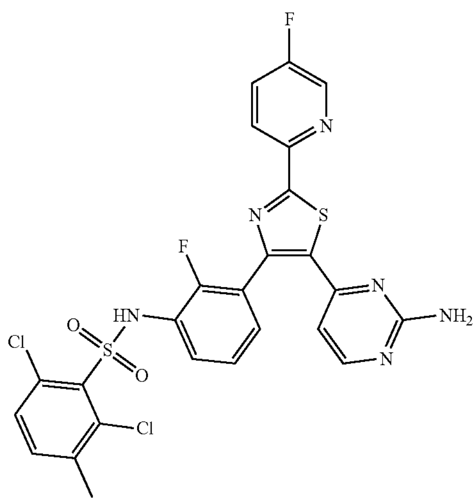 [SMILES: Cc1ccc(Cl)c(S(=O)(=O)Nc2cccc(-c3nc(-c4ccc(F)cn4)sc3-c3ccnc(N)n3)c2F)c1Cl] | 604.9 | HNMR (400 MHz, DMSO-d₆, ppm): δ 10.72 (s, 1H), 8.68 (d, J = 2.8 Hz, 1H), 8.15 (dd, J = 8.8, 4.4 Hz, 1H), 7.99-7.86 (m, 2H), 7.55-7.38 (m, 4H), 7.29-7.25 (m, 1H), 6.89 (s, 2H), 5.92 (d, J = 5.2 Hz, 1H), 2.30 (s, 3H).<br>FNMR (376 MHz, DMSO-d₆, ppm): δ −123.43 (1 F), −123.89 (1 F). |
| 126 | 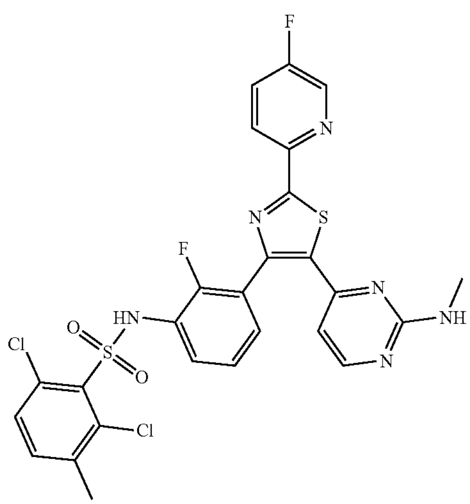 [SMILES: CNc1nccc(-c2sc(-c3ccc(F)cn3)nc2-c2cccc(NS(=O)(=O)c3c(Cl)ccc(C)c3Cl)c2F)n1] | 618.9 | HNMR (400 MHz, DMSO-d₆, ppm): δ 10.72 (s, 1H), 8.68 (d, J = 2.8 Hz, 1H), 8.15 (dd, J = 8.8, 4.8 Hz, 1H), 8.03 (d, J = 5.2 Hz, 1H), 7.91-7.86 (m, 1H), 7.54 (d, J = 8.4 Hz, 1H), 7.47 (d, J = 8.4 Hz, 1H), 7.41-7.37 (m, 2H), 7.28-7.24 (m, 2H), 6.01 (br s, 1H), 2.68 (s, 3H), 2.30 (s, 3H).<br>FNMR (376 MHz, DMSO-d₆, ppm): δ −123.46 (1 F), −124.03 (1 F). |

TABLE 1-continued

Characterization of the compounds

| Compound No. | Structure | [M + H]⁺ | NMR |
|---|---|---|---|
| 127 | 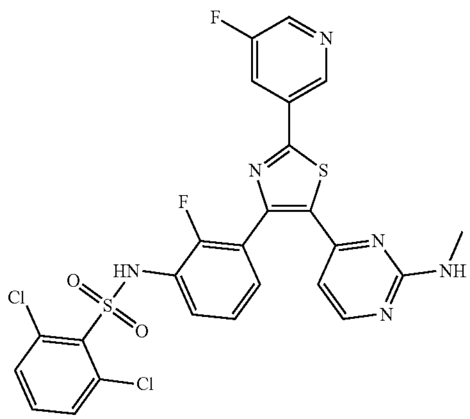 [SMILES: CNc1nccc(-c2sc(-c3cncc(F)c3)nc2-c2cccc(NS(=O)(=O)c3c(Cl)cccc3Cl)c2F)n1] | 604.9 | HNMR (400 MHz, DMSO-d$_6$, ppm): δ 10.77 (s, 1H), 9.01 (s, 1H), 8.71 (d, J = 2.8 Hz, 1H), 8.25 (d, J = 9.2 Hz, 1H), 8.08 (d, J = 5.2 Hz, 1H), 7.59-7.57 (m, 2H), 7.51-7.47 (m, 1H), 7.44-7.40 (m, 2H), 7.30-7.26 (m, 2H), 5.95 (br s, 1H), 2.74 (s, 3H). FNMR (376 MHz, DMSO-d$_6$, ppm): δ −123.89 (1 F), −126.09 (1 F). |
| 128 | 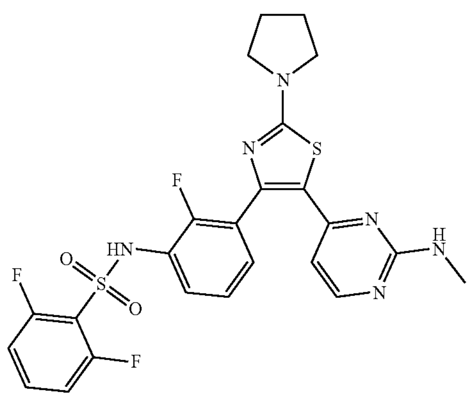 [SMILES: CNc1nccc(-c2sc(N3CCCC3)nc2-c2cccc(NS(=O)(=O)c3c(F)cccc3F)c2F)n1] | 547.0 | HNMR (400 MHz, DMSO-d$_6$, ppm): δ 10.87 (s, 1H), 7.81 (dd, J = 6.0, 2.4 Hz, 1H), 7.69-7.62 (m, 2H), 7.41-7.37 (m, 1H), 7.29-7.19 (m, 4H), 5.69 (br s, 1H), 3.49-3.41 (m, 4H), 2.73 (s, 3H), 1.98-1.95 (m, 4H). FNMR (376 MHz, DMSO-d$_6$, ppm): δ −107.41 (2 F), −124.88 (1 F). |
| 129 | 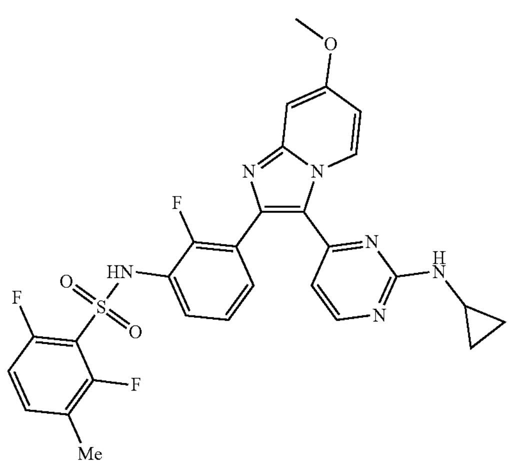 [SMILES: COc1ccn2c(-c3ccnc(NC4CC4)n3)c(-c3cccc(NS(=O)(=O)c4c(F)ccc(C)c4F)c3F)nc2c1] | 581.0 | HNMR (400 MHz, DMSO-d$_6$, ppm): δ 10.81 (s, 1H), 9.89 (s, 1H), 7.92 (d, J = 4.8 Hz, 1H), 7.55-7.53 (m, 1H), 7.41-7.38 (m, 2H), 7.30-7.26 (m, 1H), 7.13-7.08 (m, 2H), 6.89 (s, 1H), 5.96 (d, J = 5.2 Hz, 1H), 3.88 (s, 3H), 2.71-2.69 (m, 1H), 2.14 (s, 3H), 0.75-0.74 (m, 2H), 0.55-0.52 (m, 2H). FNMR (376 MHz, DMSO-d$_6$, ppm): δ −109.97 (1 F), −111.38 (1 F), −124.15 (1 F). |

TABLE 1-continued

Characterization of the compounds

| Compound No. | Structure | [M + H]+ | NMR |
|---|---|---|---|
| 130 | 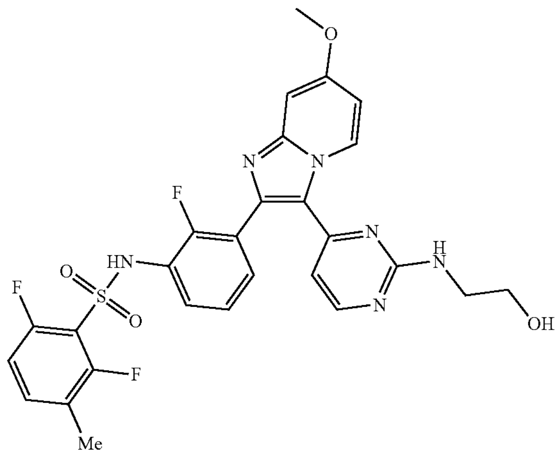 [SMILES: COc1ccn2c(-c3ccnc(NCCO)n3)c(-c3cccc(NS(=O)(=O)c4c(F)ccc(C)c4F)c3F)nc2c1] | 585.0 | HNMR (400 MHz, DMSO-d$_6$, ppm): δ 10.84 (s, 1H), 9.70 (br s, 1H), 7.93 (d, J = 5.6 Hz, 1H), 7.57-7.51 (m, 1H), 7.43-7.39 (m, 2H), 7.31-7.27 (m, 1H), 7.15-7.08 (m, 2H), 6.89 (d, J = 4.4 Hz, 1H), 5.94 (s, 1H), 3.90 (s, 3H), 3.58-3.55 (m, 2H), 3.53-3.40 (m, 2H), 2.14 (s, 3H). FNMR (376 MHz, DMSO-d$_6$, ppm): δ −109.99 (1 F), −111.42 (1 F), −124.02 (1 F). |
| 131 | 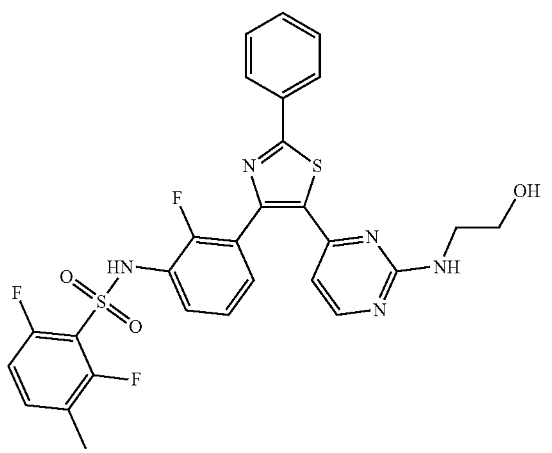 [SMILES: Cc1ccc(F)c(S(=O)(=O)Nc2cccc(-c3nc(-c4ccccc4)sc3-c3ccnc(NCCO)n3)c2F)c1F] | 598.0 | HNMR (400 MHz, DMSO-d$_6$, ppm): δ 10.88 (s, 1H), 8.05 (d, J = 5.2 Hz, 1H), 8.03-7.92 (m, 2H), 7.63-7.51 (m, 4H), 7.51-7.42 (m, 2H) 7.33 (t, J = 8.0 Hz, 1H), 7.27 (s, 1H), 7.14 (t, J = 9.2 Hz, 1H), 5.98 (br s, 1H), 3.53 (t, J = 6.4 Hz, 2H), 3.33 (br s, 2H), 2.17 (s, 3H). FNMR (376 MHz, DMSO-d$_6$, ppm): δ −109.87 (1 F), −111.34 (1 F), −124.51 (1 F). |
| 132 | 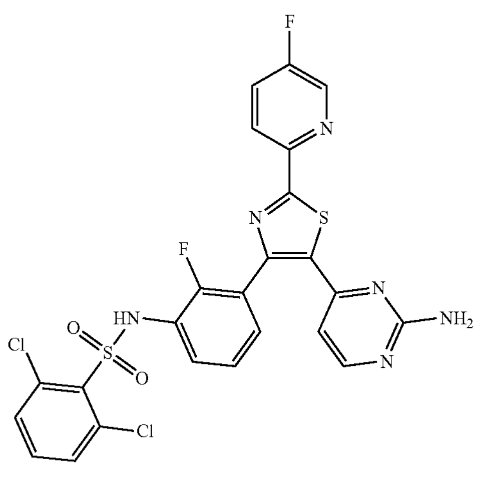 [SMILES: Nc1nccc(-c2sc(-c3ccc(F)cn3)nc2-c2cccc(NS(=O)(=O)c3c(Cl)cccc3Cl)c2F)n1] | 590.9 | HNMR (400 MHz, DMSO-d$_6$, ppm): δ 10.79 (s, 1H), 8.71 (d, J = 2.8 Hz, 1H), 8.18 (dd, J = 8.8, 4.4 Hz, 1H), 8.04 (d, J = 5.2 Hz, 1H), 7.92 (dt, J = 8.8, 2.8 Hz, 1H), 7.65-7.58 (m, 2H), 7.57-7.50 (m, 1 H), 7.49-7.39 (m, 2H), 7.36-7.28 (m, 1H), 6.86 (br s, 2H), 5.92 (d, J = 5.2 Hz, 1H). FNMR (376 MHz, DMSO-d$_6$, ppm): δ −123.49 (1 F), −123.94 (1 F). |

TABLE 1-continued

Characterization of the compounds

| Compound No. | Structure | [M + H]⁺ | NMR |
|---|---|---|---|
| 133 | 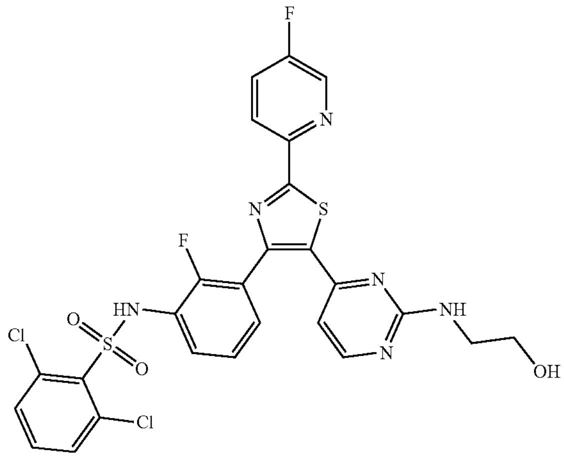 [SMILES: O=S(=O)(Nc1cccc(-c2nc(-c3ccc(F)cn3)sc2-c2ccnc(NCCO)n2)c1F)c1c(Cl)cccc1Cl] | 634.9 | HNMR (400 MHz, DMSO-d₆, ppm): δ 8.66 (d, J = 2.8 Hz, 1H), 8.16 (dd, J = 8.8, 4.4 Hz, 1H), 8.04 (d, J = 5.2 Hz, 1H), 7.86 (dt, J = 8.8, 2.8 Hz, 1H), 7.60-7.55 (m, 2H), 7.53-7.46 (m, 1H), 7.46-7.38 (m, 2H), 7.30 (t, J = 8.0 Hz, 1H), 5.97 (br s, 1H), 3.51 (t, J = 6.0 Hz, 2H), 3.30 (br s, 2H).<br>FNMR (376 MHz, DMSO-d₆, ppm): δ −123.47 (1 F), −124.06 (1 F). |
| 134 | 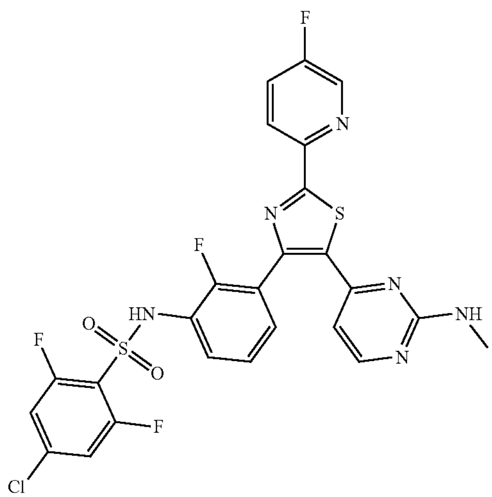 [SMILES: CNc1nccc(-c2sc(-c3ccc(F)cn3)nc2-c2cccc(NS(=O)(=O)c3c(F)cc(Cl)cc3F)c2F)n1] | 606.9 | HNMR (400 MHz, DMSO-d₆, ppm): δ 10.98 (s, 1H), 8.68 (d, J = 2.8 Hz, 1H), 8.16 (dd, J = 8.4, 4.4 Hz, 1H), 8.07 (d, J = 5.2 Hz, 1H), 7.91-7.86 (m, 1H), 7.54 (s, 1H), 7.52 (s, 1H), 7.47-7.42 (m, 2H), 7.31 (t, J = 7.6 Hz, 1H), 7.24 (s, 1H), 6.00 (s, 1H), 2.68 (br s, 3H).<br>FNMR (376 MHz, DMSO-d₆, ppm): δ −105.39 (2 F), −123.46 (1 F), −124.50 (1 F). |
| 135 | 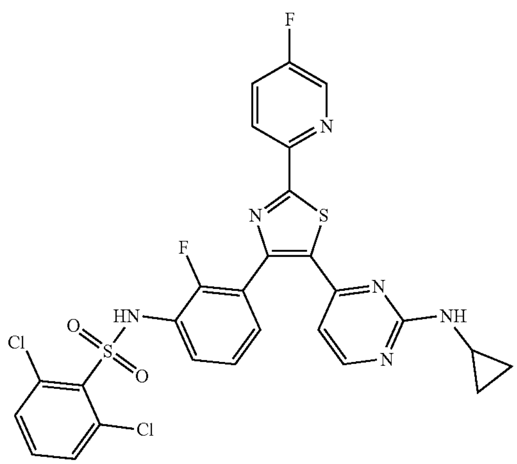 [SMILES: O=S(=O)(Nc1cccc(-c2nc(-c3ccc(F)cn3)sc2-c2ccnc(NC3CC3)n2)c1F)c1c(Cl)cccc1Cl] | 630.9 | HNMR (400 MHz, DMSO-d₆, ppm): δ 10.76 (s, 1H), 8.67 (d, J = 2.4 Hz, 1H), 8.14 (dd, J = 8.8 Hz, 4.4 Hz, 1H), 8.07 (d, J = 4.8 Hz, 1H), 7.90-7.85 (m, 1H), 7.58-7.47 (m, 4H), 7.42-7.39 (m, 2H), 7.27 (t, J = 8.0 Hz, 1H), 5.97 (s, 1H), 2.64-2.62 (m, 1H), 0.65-0.60 (m, 2H), 0.45-0.43 (m, 2H).<br>FNMR (376 MHz, DMSO-d₆, ppm): δ −123.52 (1 F), −124.01 (1 F). |

TABLE 1-continued

Characterization of the compounds

| Compound No. | Structure | [M + H]+ | NMR |
|---|---|---|---|
| 136 | 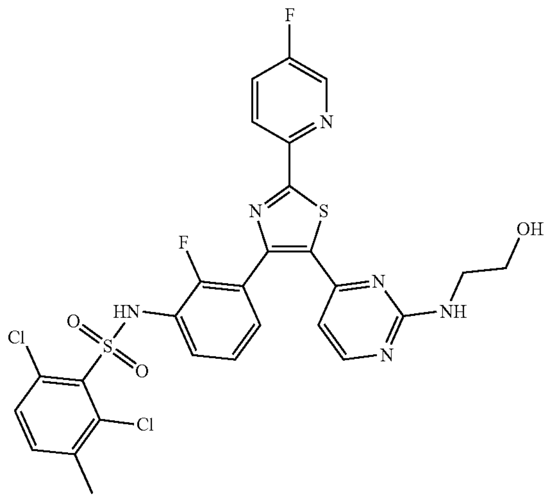 [SMILES: Cc1ccc(Cl)c(S(=O)(=O)Nc2cccc(-c3nc(-c4ccc(F)cn4)sc3-c3ccnc(NCCO)n3)c2F)c1Cl] | 648.9 | HNMR (400 MHz, DMSO-d$_6$, ppm): δ 10.72 (s, 1H), 8.68 (d, J = 2.8 Hz, 1H), 8.15 (dd, J = 8.8, 4.8 Hz, 1H), 8.02 (d, J = 5.2 Hz, 1H), 7.91-7.86 (m, 1H), 7.54-7.37 (m, 4H), 7.28-7.19 (m, 2H), 5.93 (s, 1H), 4.67-4.64 (m, 1H), 3.52-3.47 (m, 2H), 3.29-2.28 (m, 2H), 2.30 (s, 3H). FNMR (376 MHz, DMSO-d$_6$, ppm): δ −123.51 (1 F), −123.98 (1 F). |
| 137 | 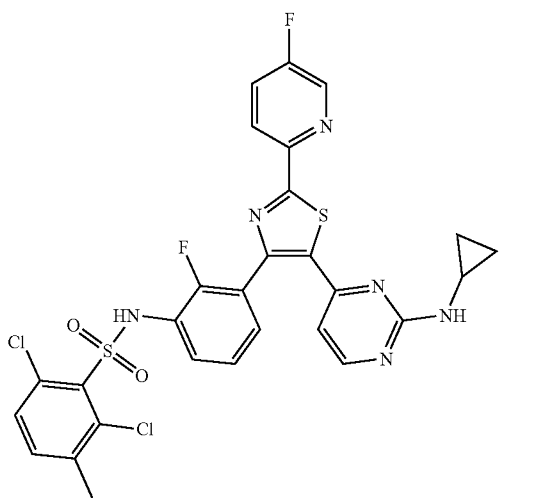 [SMILES: Cc1ccc(Cl)c(S(=O)(=O)Nc2cccc(-c3nc(-c4ccc(F)cn4)sc3-c3ccnc(NC4CC4)n3)c2F)c1Cl] | 644.9 | HNMR (400 MHz, DMSO-d$_6$, ppm): δ 10.72 (s, 1H), 8.68 (d, J = 2.8 Hz, 1H), 8.16-8.13 (m, 1H), 8.05 (d, J = 5.2 Hz, 1H), 7.91-7.86 (m, 1H), 7.55-7.46 (m, 3H), 7.41-7.37 (m, 2H), 7.28-7.24 (m, 1H), 6.00 (s, 1H), 2.69-2.59 (m, 1H), 2.30 (s, 3H), 0.63-0.62 (m, 2H), 0.44-0.43 (m, 2H). FNMR (376 MHz, DMSO-d$_6$, ppm): δ −123.50 (1 F), −123.96 (1 F). |
| 138 | 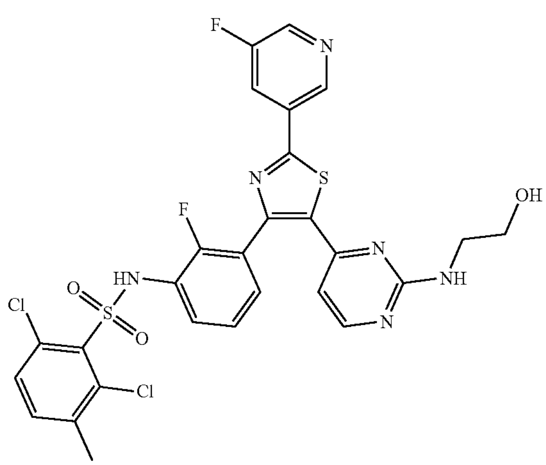 [SMILES: Cc1ccc(Cl)c(S(=O)(=O)Nc2cccc(-c3nc(-c4cncc(F)c4)sc3-c3ccnc(NCCO)n3)c2F)c1Cl] | 648.9 | HNMR (400 MHz, DMSO-d$_6$, ppm): δ 10.73 (s, 1H), 9.01 (s, 1H), 8.71 (d, J = 2.8 Hz, 1H), 8.25 (d, J = 9.2 Hz, 1H), 8.04 (d, J = 4.8 Hz, 1H), 7.53 (d, J = 8.4 Hz, 1H), 7.46 (d, J = 8.4 Hz, 1H), 7.41-7.38 (m, 2H), 7.29-7.21 (m, 2H), 5.94 (s, 1H), 4.66 (t, J = 5.6 Hz, 1H), 3.52-3.47 (m, 2H), 3.40-3.36 (m, 2H), 2.30 (s, 3H). FNMR (376 MHz, DMSO-d$_6$, ppm): δ −123.81 (1 F), −126.11 (1 F). |

| Compound No. | Structure | [M + H]⁺ | NMR |
|---|---|---|---|
| 139 | 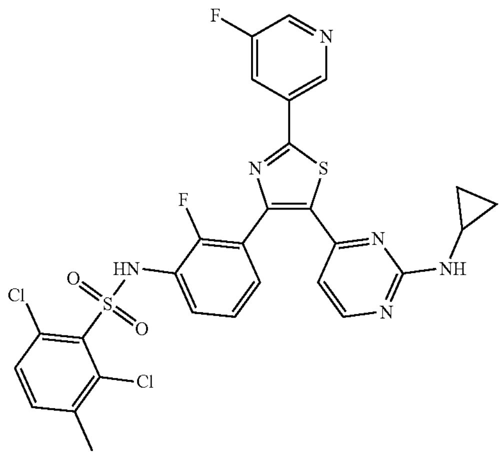 [SMILES: Cc1ccc(Cl)c(S(=O)(=O)Nc2cccc(-c3nc(-c4cncc(F)c4)sc3-c3ccnc(NC4CC4)n3)c2F)c1Cl] | 644.9 | HNMR (400 MHz, DMSO-d$_6$, ppm): δ 10.74 (s, 1H), 9.00 (s, 1H), 8.71 (d, J = 2.8 Hz, 1H), 8.24 (d, J = 9.2 Hz, 1H), 8.07 (d, J = 5.2 Hz, 1H), 7.58 (br s, 1H), 7.53 (d, J = 8.4 Hz, 1H), 7.47 (d, J = 8.4 Hz, 1H), 7.44-7.38 (m, 2H), 7.29-7.25 (m, 1H), 6.00 (d, J = 4.0 Hz, 1H), 2.65-2.63 (m, 1H), 2.30 (s, 3H), 0.65-0.62 (m, 2H), 0.45-0.44 (m, 2H).<br>FNMR (376 MHz, DMSO-d$_6$, ppm): δ −123.80 (1 F), −126.07 (1 F). |
| 140 | 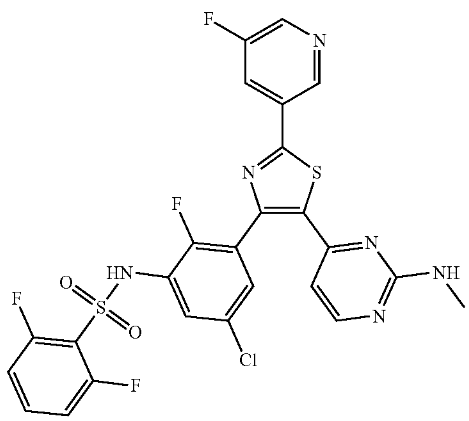 [SMILES: CNc1nccc(-c2sc(-c3cncc(F)c3)nc2-c2cc(Cl)cc(NS(=O)(=O)c3c(F)cccc3F)c2F)n1] | 606.9 | HNMR (400 MHz, DMSO-d$_6$, ppm): δ 10.23 (s, 1H), 9.03 (s, 1H), 8.71 (d, J = 2.4 Hz, 1H), 8.28 (d, J = 9.6 Hz, 1H), 8.15 (d, J = 4.8 Hz, 1H), 7.56-7.52 (m, 1H), 7.44 (s, 1H), 7.25 (d, J = 4.8 Hz, 1H), 7.15 (br s, 3H), 6.15 (br s, 1H), 2.72 (s, 3H). |
| 141 | 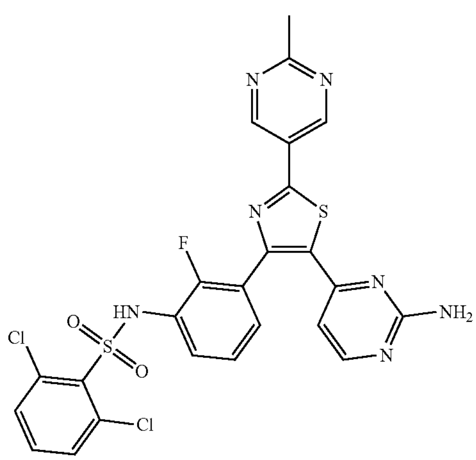 [SMILES: Cc1ncc(-c2nc(-c3cccc(NS(=O)(=O)c4c(Cl)cccc4Cl)c3F)c(-c3ccnc(N)n3)s2)cn1] | 587.9 | HNMR (400 MHz, DMSO-d$_6$, ppm): δ 10.76 (s, 1H), 9.18 (s, 2H), 8.02 (d, J = 5.2 Hz, 1H), 7.59-7.56 (m, 2H), 7.50-7.46 (m, 1H), 7.44-7.40 (m, 2H), 7.29 (t, J = 8.0 Hz, 1H), 6.86 (s, 2H), 5.88 (d, J = 5.2 Hz, 1H), 2.67 (s, 3H).<br>F-NMR (376 MHz, DMSO-d$_6$, ppm): δ −123.80 (1 F). |

TABLE 1-continued

Characterization of the compounds

| Compound No. | Structure | [M + H]⁺ | NMR |
|---|---|---|---|
| 142 | 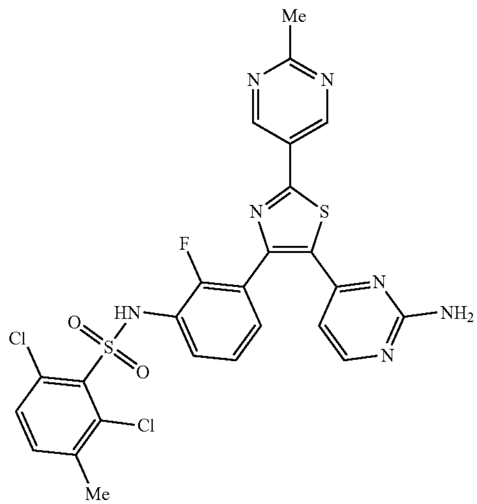 [SMILES: Cc1ncc(-c2nc(-c3cccc(NS(=O)(=O)c4c(Cl)ccc(C)c4Cl)c3F)c(-c3ccnc(N)n3)s2)cn1] | 601.9 | HNMR (400 MHz, DMSO-d₆, ppm): δ 10.72 (s, 1H), 9.18 (s, 2H), 8.00 (d, J = 5.2 Hz, 1H), 7.43-7.18 (m, 5H), 6.81 (s, 2H), 5.96 (s, 1H), 2.67 (s, 3H), 2.29 (s, 3H). |
| 143 | 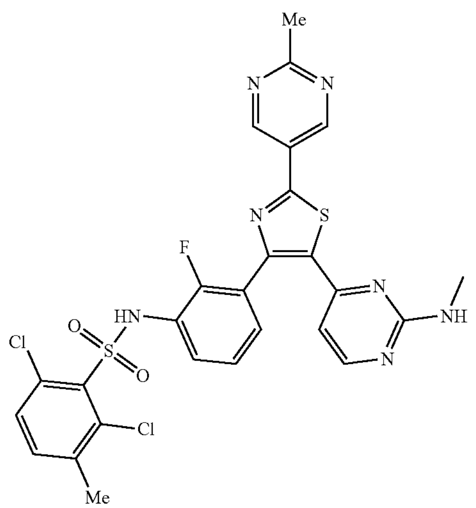 [SMILES: CNc1nccc(-c2sc(-c3cnc(C)nc3)nc2-c2cccc(NS(=O)(=O)c3c(Cl)ccc(C)c3Cl)c2F)n1] | 615.9 | HNMR (400 MHz, DMSO-d₆, ppm): δ 10.71 (s, 1H), 9.19 (s, 2H), 8.04 (d, J = 5.2 Hz, 1H), 7.54-7.38 (m, 4H), 7.29-7.25 (m, 2H), 5.96 (s, 1H), 2.73 (s, 3H), 2.67 (s, 3H), 2.30 (s, 3H).<br>FNMR (376 MHz, DMSO-d₆, ppm): δ −123.83 (1 F). |
| 144 | 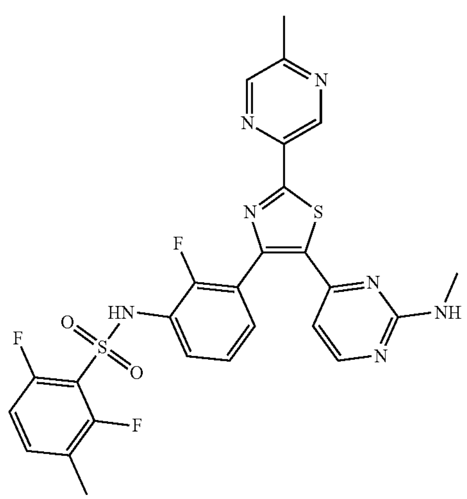 [SMILES: CNc1nccc(-c2sc(-c3cnc(C)cn3)nc2-c2cccc(NS(=O)(=O)c3c(F)ccc(C)c3F)c2F)n1] | 584.0 | HNMR (400 MHz, DMSO-d₆, ppm): δ 10.87 (s, 1H), 9.16 (d, J = 1.2 Hz, 1H), 8.66 (s, 1H), 8.09 (d, J = 4.8 Hz, 1H), 7.57 (dd, J = 14.4, 8.4 Hz, 1H), 7.52-7.42 (m, 2H), 7.49-7.23 (m, 2H), 7.14 (t, J = 9.2 Hz, 1H), 6.06 (br s, 1H), 2.73 (br s, 3H), 2.59 (s, 3H), 2.17 (s, 3H).<br>FNMR (376 MHz, DMSO-d₆, ppm): δ −109.91 (1 F), −111.35 (1 F), −124.49 (1 F). |

TABLE 1-continued

Characterization of the compounds

| Compound No. | Structure | [M + H]⁺ | NMR |
|---|---|---|---|
| 145 | 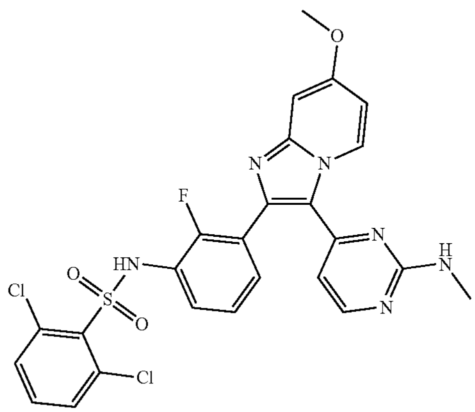 [SMILES: CNc1nccc(-c2c(-c3cccc(NS(=O)(=O)c4c(Cl)cccc4Cl)c3F)nc3cc(OC)ccn23)n1] | 573.0 | HNMR (400 MHz, DMSO-d₆, ppm): δ 10.69 (s, 1H), 9.63 (br s, 1H), 7.94 (d, J = 5.2 Hz, 1H), 7.58-7.56 (m, 2H), 7.50-7.46 (m, 1H), 7.36-7.32 (m, 2H), 7.25-7.21 (m, 2H), 7.07 (d, J = 2.4 Hz, 1H), 6.81-6.78 (m, 1H), 5.87 (d, J = 5.6 Hz, 1H), 3.86 (s, 3H), 2.83 (d, J = 4.4 Hz, 3H).<br>FNMR (376 MHz, DMSO-d₆, ppm): δ −123.80 (1 F). |
| 146 | 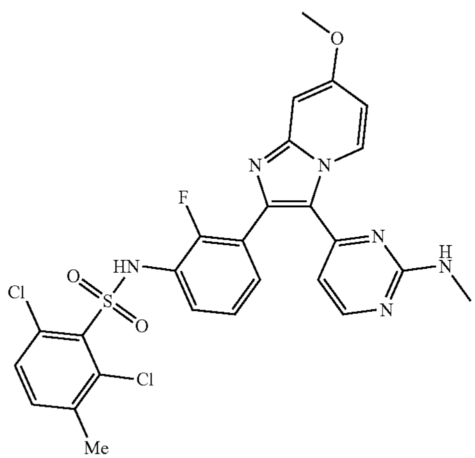 [SMILES: CNc1nccc(-c2c(-c3cccc(NS(=O)(=O)c4c(Cl)ccc(C)c4Cl)c3F)nc3cc(OC)ccn23)n1] | 587.0 | HNMR (400 MHz, DMSO-d₆, ppm): δ 10.68 (s, 1H), 9.62 (s, 1H), 7.93 (d, J = 5.2 Hz, 1H), 7.53 (d, J = 8.4 Hz, 1H), 7.46 (d, J = 8.4 Hz, 1H), 7.35 (t, J = 8.0 Hz, 2H), 7.25 (t, J = 8.0 Hz, 1H), 7.11 (d, J = 2.4 Hz, 1H), 6.87 (s, 1H), 5.93 (d, J = 3.2 Hz, 1H), 3.88 (s, 3H), 2.85 (s, 3H), 2.30 (s, 3H).<br>FNMR (376 MHz, DMSO-d₆, ppm): δ−123.55 (1 F). |
| 147 | 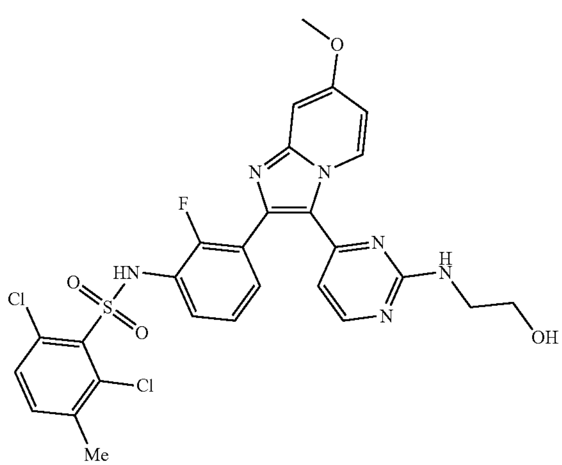 [SMILES: COc1ccn2c(-c3ccnc(NCCO)n3)c(-c3cccc(NS(=O)(=O)c4c(Cl)ccc(C)c4Cl)c3F)nc2c1] | 617.0 | HNMR (400 MHz, DMSO-d₆, ppm): δ 10.63 (s, 1H), 9.70 (br s, 1H), 7.89 (d, J = 5.2 Hz, 1H), 7.52 (d, J = 8.4 Hz, 1H), 7.45 (d, J = 8.0 Hz, 1H), 7.34-7.21 (m, 4H), 7.06 (d, J = 2.4 Hz, 1H), 6.76-6.75 (m, 1H), 5.87 (d, J = 4.4 Hz, 1H), 4.70 (t, J = 5.2 Hz, 1H), 3.85 (s, 3H), 3.55-3.51 (m, 2H), 3.39-3.34 (m, 2H), 2.30 (s, 3H).<br>FNMR (376 MHz, DMSO-d₆, ppm): δ −123.78 (1 F). |

TABLE 1-continued

Characterization of the compounds

| Compound No. | Structure | [M + H]+ | NMR |
|---|---|---|---|
| 148 | 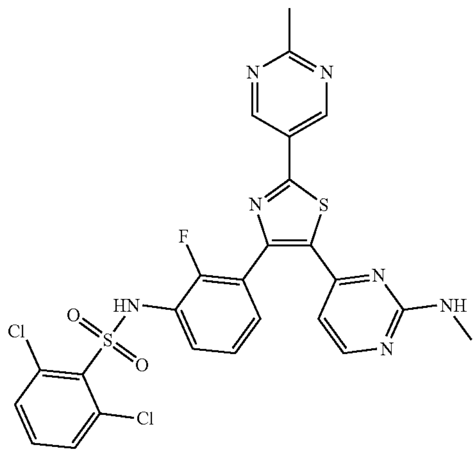 [SMILES: CNc1nccc(-c2sc(-c3cnc(C)nc3)nc2-c2cccc(NS(=O)(=O)c3c(Cl)cccc3Cl)c2F)n1] | 601.9 | HNMR (400 MHz, DMSO-d$_6$, ppm): δ 10.77 (s, 1H), 9.19 (s, 2H), 8.07 (d, J = 5.2 Hz, 1H), 7.58-7.56 (m, 2H), 7.50-7.46 (m, 1H), 7.43-7.39 (m, 2H), 7.32-7.26 (m, 2H), 5.94 (s, 1H), 2.73 (s, 3H), 2.66 (s, 3H). |
| 149 | 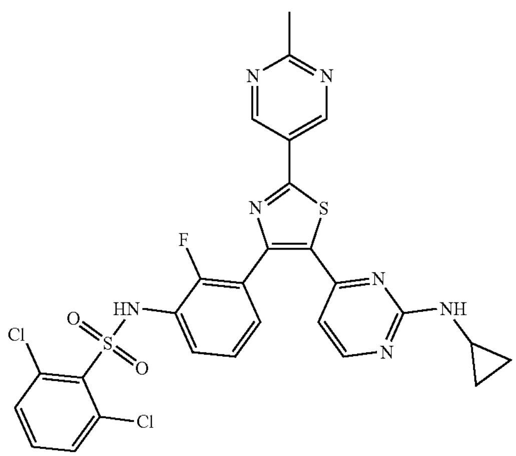 [SMILES: Cc1ncc(-c2nc(-c3cccc(NS(=O)(=O)c4c(Cl)cccc4Cl)c3F)c(-c3ccnc(NC4CC4)n3)s2)cn1] | 627.9 | HNMR (400 MHz, DMSO-d$_6$, ppm): δ 10.77 (s, 1H), 9.18 (s, 2H), 8.09 (d, J = 5.2 Hz, 1H), 7.59-7.54 (m, 3H), 7.50-7.46 (m, 1H), 7.44-7.39 (m, 2H), 7.28 (t, J = 8.0 Hz, 1H), 5.95 (d, J = 3.6 Hz, 1H), 2.66 (s, 3H), 2.65-2.63 (m, 1H), 0.66-0.61 (m, 2H), 0.47-0.43 (m, 2H). FNMR (376 MHz, DMSO-d$_6$, ppm): δ −123.85 (1 F). |
| 150 | 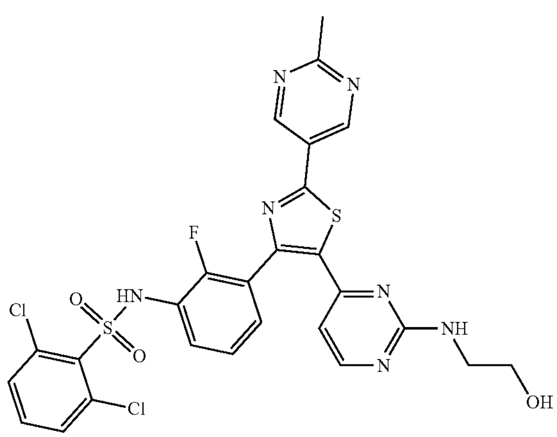 [SMILES: Cc1ncc(-c2nc(-c3cccc(NS(=O)(=O)c4c(Cl)cccc4Cl)c3F)c(-c3ccnc(NCCO)n3)s2)cn1] | 631.9 | HNMR (400 MHz, DMSO-d$_6$, ppm): δ 10.76 (s, 1H), 9.19 (s, 2H), 8.06 (d, J = 5.2 Hz, 1H), 7.58-7.56 (m, 2H), 7.50-7.46 (m, 1H), 7.44-7.39 (m, 2H), 7.28 (t, J = 8.0 Hz, 1H), 7.21 (t, J = 5.6 Hz, 1H), 5.90 (s, 1H), 4.65 (t, J = 5.2 Hz, 1H), 3.52-3.47 (m, 2H), 3.33-3.29 (m, 2H), 2.67 (s, 3H). FNMR (376 MHz, DMSO-d$_6$, ppm): δ −123.86 (1 F). |

TABLE 1-continued

Characterization of the compounds

| Compound No. | Structure | [M + H]+ | NMR |
|---|---|---|---|
| 151 | 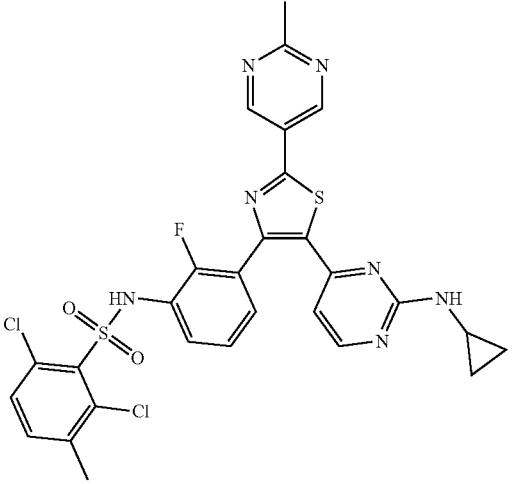 [SMILES: Cc1ncc(-c2nc(-c3cccc(NS(=O)(=O)c4c(Cl)ccc(C)c4Cl)c3F)c(-c3ccnc(NC4CC4)n3)s2)cn1] | 642.0 | HNMR (400 MHz, DMSO-d$_6$, ppm): δ 10.73 (s, 1H), 9.18 (s, 2H), 8.07 (d, J = 4.8 Hz, 1H), 7.60 (s, 1H), 7.53 (d, J = 8.4 Hz, 1H), 7.47 (d, J = 8.4 Hz, 1H), 7.42-7.37 (m, 2H), 7.27 (t, J = 8.0 Hz, 1H), 5.99 (d, J = 4.4 Hz, 1H), 2.67 (s, 3H), 2.65-2.63 (m, 1H), 2.30 (s, 3H), 0.66-0.61 (m, 2H), 0.46-0.44 (m, 2H). FNMR (376 MHz, DMSO-d$_6$, ppm): δ −123.78 (1 F). |
| 152 | 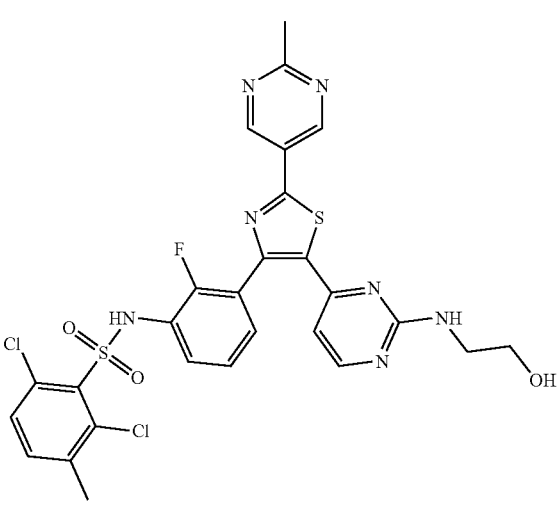 [SMILES: Cc1ncc(-c2nc(-c3cccc(NS(=O)(=O)c4c(Cl)ccc(C)c4Cl)c3F)c(-c3ccnc(NCCO)n3)s2)cn1] | 646.0 | HNMR (400 MHz, DMSO-d$_6$, ppm): δ 10.72 (s, 1H), 9.19 (s, 2H), 8.03 (d, J = 5.2 Hz, 1H), 7.53 (d, J = 8.4 Hz, 1H), 7.47 (d, J = 8.4 Hz, 1H), 7.40 (t, J = 7.6 Hz, 2H), 7.27 (t, J = 8.0 Hz, 1H), 7.24-7.22 (m, 1H), 5.93 (s, 1H), 3.48-3.46 (m, 2H), 3.33-3.30 (m, 2H), 2.67 (s, 3H) 2.30 (s, 3H). FNMR (376 MHz, DMSO-d$_6$, ppm): δ −123.79 (1 F). |
| 153 | 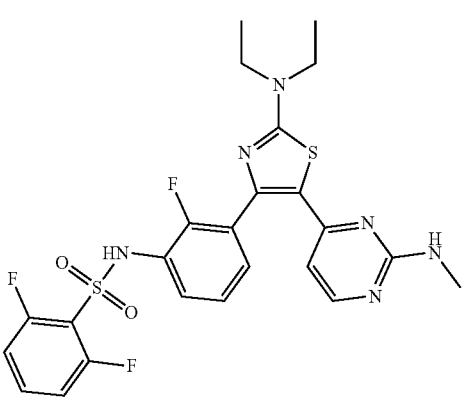 [SMILES: CCN(CC)c1nc(-c2cccc(NS(=O)(=O)c3c(F)cccc3F)c2F)c(-c2ccnc(NC)n2)s1] | 549.0 | HNMR (400 MHz, DMSO-d$_6$, ppm): δ 10.86 (s, 1H), 7.82 (d, J = 6.0 Hz, 1H), 7.69-7.62 (m, 2H), 7.41-7.37 (m, 1H), 7.32-7.19 (m, 4H), 5.75 (s, 1H), 3.48 (q, J = 7.2 Hz, 4H), 2.73 (s, 3H), 1.15 (t, J = 7.2 Hz, 6H). FNMR (376 MHz, DMSO-d$_6$, ppm): δ −107.40 (2 F), −124.80 (1 F). |

TABLE 1-continued

Characterization of the compounds

| Compound No. | Structure | [M + H]⁺ | NMR |
|---|---|---|---|
| 154 | 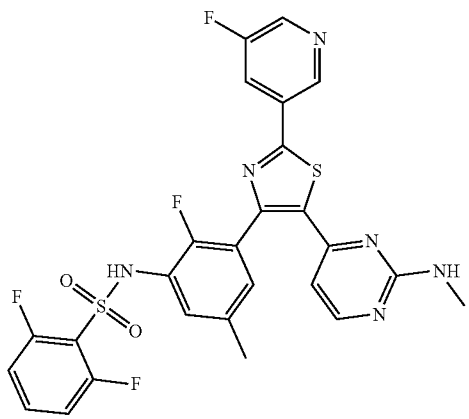 [SMILES: CNc1nccc(-c2sc(-c3cncc(F)c3)nc2-c2cc(C)cc(NS(=O)(=O)c3c(F)cccc3F)c2F)n1] | 587.0 | HNMR (400 MHz, DMSO-d$_6$, ppm): δ 10.81 (s, 1H), 9.01 (s, 1H), 8.71 (d, J = 2.4 Hz, 1H), 8.25 (d, J = 9.2 Hz, 1H), 8.07 (d, J = 5.2 Hz, 1H), 7.67-7.60 (m, 1H), 7.26-7.18 (m, 5H), 5.98 (br s, 1H), 2.75 (s, 3H), 2.27 (s, 3H). |
| 155 | 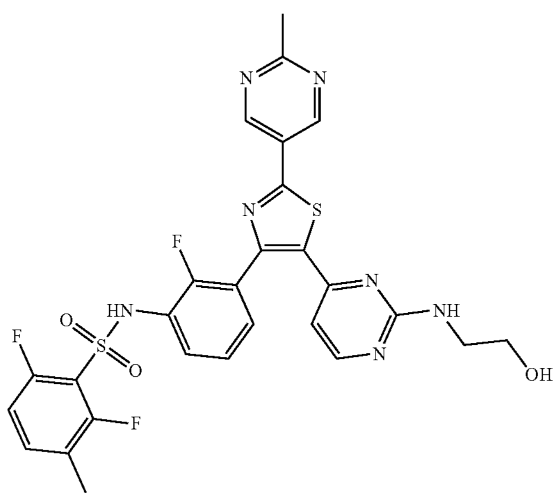 [SMILES: Cc1ncc(-c2nc(-c3cccc(NS(=O)(=O)c4c(F)ccc(C)c4F)c3F)c(-c3ccnc(NCCO)n3)s2)cn1] | 614.0 | HNMR (400 MHz, DMSO-d$_6$, ppm): δ 10.84 (s, 1H), 9.19 (s, 2H), 8.03 (d, J = 5.2 Hz, 1H), 7.57-7.51 (m, 1H), 7.44 (t, J = 7.2 Hz, 2H), 7.30 (t, J = 8.0 Hz, 1H), 7.20 (t, J = 5.2 Hz, 1H), 7.11 (t, J = 9.2 Hz, 1H), 5.93 (br s, 1H), 4.64 (br s, 1H), 3.49 (t, J = 6.4 Hz, 2H), 3.29-3.32 (m, 2H), 2.67 (s, 3H), 2.13 (s, 3H). FNMR (376 MHz, DMSO-d$_6$, ppm): δ −109.90 (1 F), −111.35 (1 F), −124.39 (1 F). |
| 156 | 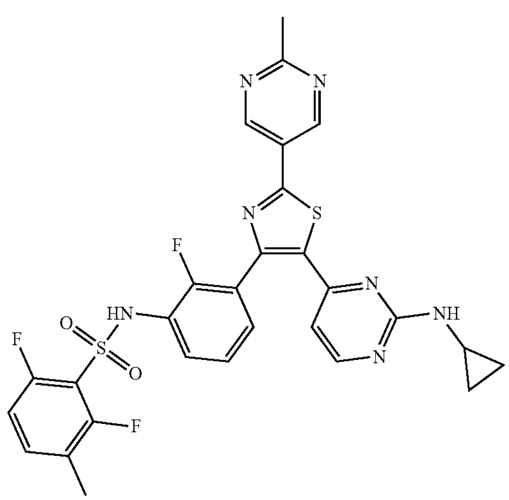 [SMILES: Cc1ncc(-c2nc(-c3cccc(NS(=O)(=O)c4c(F)ccc(C)c4F)c3F)c(-c3ccnc(NC4CC4)n3)s2)cn1] | 610.0 | HNMR (400 MHz, DMSO-d$_6$, ppm): δ 10.85 (s, 1H), 9.19 (s, 2H), 8.07 (d, J = 5.2 Hz, 1H), 7.57-7.53 (m, 2H), 7.46-7.42 (m, 2H), 7.30 (t, J = 8.0 Hz, 1H), 7.11 (t, J = 8.8 Hz, 1H), 6.00 (br s, 1H), 2.67 (s, 3H), 2.64-2.63 (m, 1H), 2.14 (s, 3H), 0.66-0.61 (m, 2H), 0.49-0.45 (m, 2H). FNMR (376 MHz, DMSO-d$_6$, ppm): δ −109.90 (1 F), −111.34 (1 F), −124.36 (1 F). |

TABLE 1-continued
Characterization of the compounds
| Compound No. | Structure | [M + H]+ | NMR |
|---|---|---|---|
| 157 | 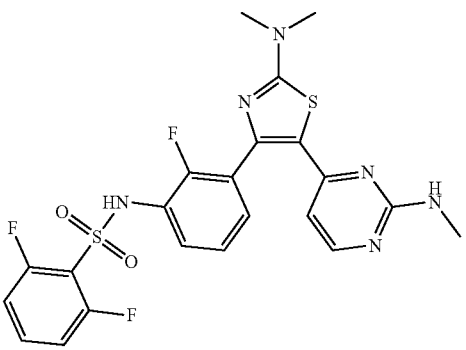 [SMILES: CNc1nccc(-c2sc(N(C)C)nc2-c2cccc(NS(=O)(=O)c3c(F)cccc3F)c2F)n1] | 521.0 | HNMR (400 MHz, DMSO-d$_6$, ppm): δ 10.86 (s, 1H), 7.82 (d, J = 6.0 Hz, 1H), 7.69-7.53 (m, 2H), 7.41-7.35 (m, 1H), 7.30-7.19 (m, 4H), 5.71 (s, 1H), 3.08 (s, 6H), 2.73 (s, 3H). FNMR (376 MHz, DMSO-d$_6$, ppm): δ -107.40 (2 F), -124.83 (1 F). |
| 158 | 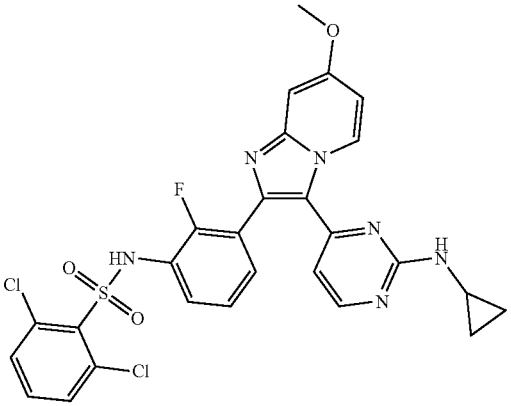 [SMILES: COc1ccn2c(-c3ccnc(NC4CC4)n3)c(-c3cccc(NS(=O)(=O)c4c(Cl)cccc4Cl)c3F)nc2c1] | 599.0 | HNMR (400 MHz, DMSO-d$_6$, ppm): δ 10.81 (s, 1H), 9.89 (s, 1H), 7.98 (d, J = 6.4 Hz, 1H), 7.61-7.57 (m, 2H), 7.52-7.48 (m, 1H), 7.43-7.39 (m, 2H), 7.33-7.29 (m, 1H), 7.20 (d, J = 2.0 Hz, 1H), 7.03 (d, J = 1.2 Hz, 1H), 6.05-6.03 (m, 1H), 3.92 (s, 3H), 2.75-2.73 (m, 1H), 0.82-0.78 (m, 2H), 0.60-0.59 (m, 2H). |
| 159 | 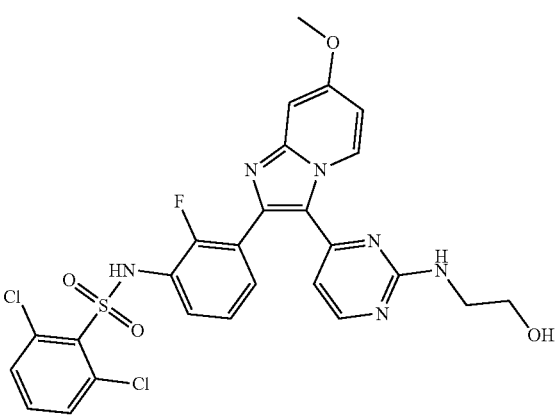 [SMILES: COc1ccn2c(-c3ccnc(NCCO)n3)c(-c3cccc(NS(=O)(=O)c4c(Cl)cccc4Cl)c3F)nc2c1] | 603.0 | HNMR (400 MHz, DMSO-d$_6$, ppm): δ 10.72 (s, 1H), 9.60 (br s, 1H), 7.95 (d, J = 5.2 Hz, 1H), 7.58-7.56 (m, 2H), 7.51-7.47 (m, 1H), 7.38-7.34 (m, 2H), 7.25 (t, J = 8.0 Hz, 1H), 7.10 (d, J = 2.4 Hz, 1H), 6.83 (s, 1H), 5.89 (d, J = 1.2 Hz, 1H), 3.88 (s, 3H), 3.55 (t, J = 6.0 Hz, 2H), 3.39 (t, J = 6.0 Hz, 2H). |

TABLE 1-continued
Characterization of the compounds
| Compound No. | Structure | [M + H]+ | NMR |
|---|---|---|---|
| 160 | 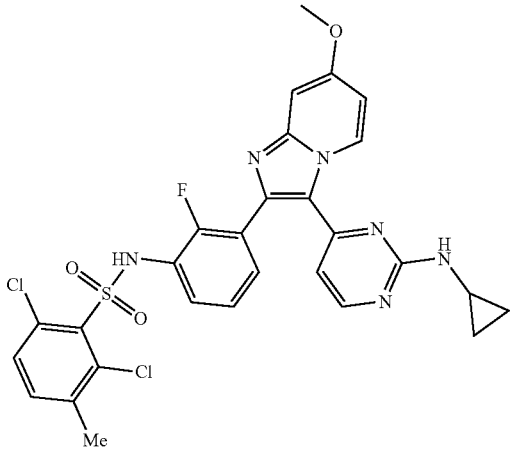 [SMILES: COc1ccn2c(-c3ccnc(NC4CC4)n3)c(-c3cccc(NS(=O)(=O)c4c(Cl)ccc(C)c4Cl)c3F)nc2c1] | 613.0 | HNMR (400 MHz, DMSO-d$_6$, ppm): δ 10.71 (s, 1H), 9.88 (s, 1H), 7.94 (d, J = 5.6 Hz, 1H), 7.53 (d, J = 8.4 Hz, 1H), 7.47 (d, J = 8.4 Hz, 1H), 7.37 (t, J = 7.6 Hz, 2H), 7.26 (t, J = 8.0 Hz, 1H), 7.13 (s, 1H), 6.92 (s, 1H), 5.98 (d, J = 5.6 Hz, 1H), 3.88 (s, 3H), 2.72-2.70 (m, 1H), 2.31 (s, 3H), 0.77-0.75 (m, 2H), 0.54-0.52 (m, 2H). |
| 161 | 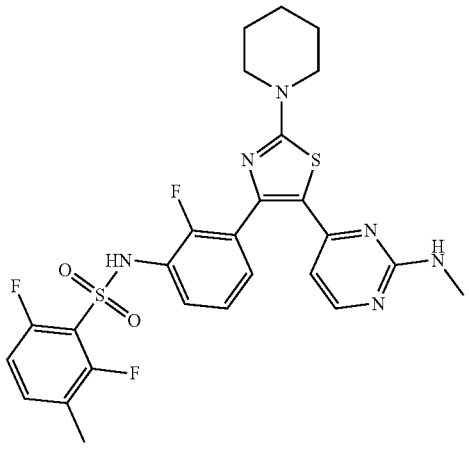 [SMILES: CNc1nccc(-c2sc(N3CCCCC3)nc2-c2cccc(NS(=O)(=O)c3c(F)ccc(C)c3F)c2F)n1] | 575.0 | HNMR (400 MHz, DMSO-d$_6$, ppm): δ 10.76 (s, 1H), 7.79 (d, J = 5.2 Hz, 1H), 7.54-7.52 (m, 1H), 7.38-7.34 (m, 1H), 7.24-7.18 (m, 2H), 7.10 (t, J = 8.8 Hz, 1H), 6.90 (d, J = 4.4 Hz, 1H), 5.64 (d, J = 4.4 Hz, 1H), 3.40-3.50 (m, 4H), 2.68 (s, 3H), 2.13 (s, 3H), 1.50-1.60 (m, 6H). |
| 162 | 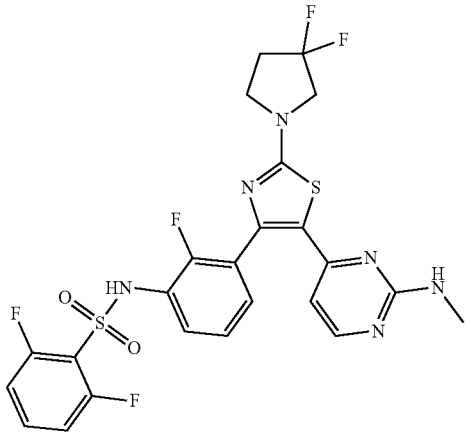 [SMILES: CNc1nccc(-c2sc(N3CCC(F)(F)C3)nc2-c2cccc(NS(=O)(=O)c3c(F)cccc3F)c2F)n1] | 583.0 | HNMR (400 MHz, DMSO-d$_6$, ppm): δ 10.86 (s, 1H), 7.86 (d, J = 6.0 Hz, 1H), 7.69-7.62 (m, 1H), 7.50-7.38 (m, 2H), 7.30-7.19 (m, 4H), 5.71 (s, 1H), 3.90 (t, J = 12.4 Hz, 2H), 3.65 (t, J = 7.2 Hz, 2H), 2.73 (s, 3H), 2.63-2.54 (m, 2H).<br>FNMR (376 MHz, DMSO-d$_6$, ppm): δ −99.86 (2 F), −107.41 (2 F), −124.73 (1 F). |

TABLE 1-continued
Characterization of the compounds
| Compound No. | Structure | [M + H]+ | NMR |
|---|---|---|---|
| 163 | 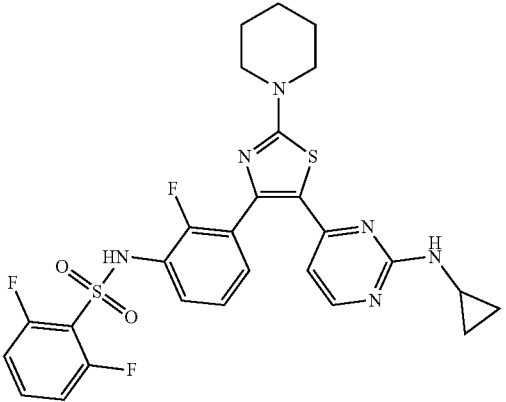 [SMILES: O=S(=O)(Nc1cccc(-c2nc(N3CCCCC3)sc2-c2ccnc(NC3CC3)n2)c1F)c1c(F)cccc1F] | 587.0 | HNMR (400 MHz, DMSO-d$_6$, ppm): δ 10.88 (s, 1H), 7.84 (d, J = 6.0 Hz, 1H), 7.68-7.64 (m, 1H), 7.41-7.38 (m, 1H), 7.31-7.20 (m, 4H), 5.76 (d, J = 5.2 Hz, 1H), 3.44-3.55 (m, 4H), 2.63-2.61 (m, 1H), 1.52-1.62 (s, 6H), 0.63-0.73 (s, 2H), 0.45-0.55 (s, 2H).<br>FNMR (376 MHz, DMSO-d$_6$, ppm): δ −107.40 (2 F), −124.70 (1 F). |
| 164 | 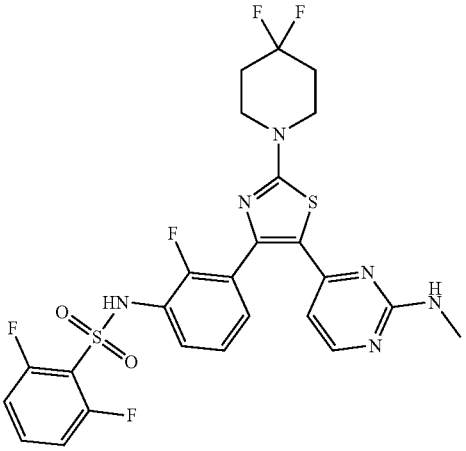 [SMILES: CNc1nccc(-c2sc(N3CCC(F)(F)CC3)nc2-c2cccc(NS(=O)(=O)c3c(F)cccc3F)c2F)n1] | 597.0 | HNMR (400 MHz, DMSO-d$_6$, ppm): δ 10.85 (s, 1H), 7.87 (d, J = 5.6 Hz, 1H), 7.69-7.63 (m, 1H), 7.62-7.37 (m, 2H), 7.31-7.19 (m, 4H), 5.74 (s, 1H), 3.58-3.68 (s, 4H), 2.72 (s, 3H), 2.12-2.05 (m, 4H).<br>FNMR (376 MHz, DMSO-d$_6$, ppm): δ −96.11 (2 F), −107.41 (2 F), −124.56 (1 F). |
| 165 | 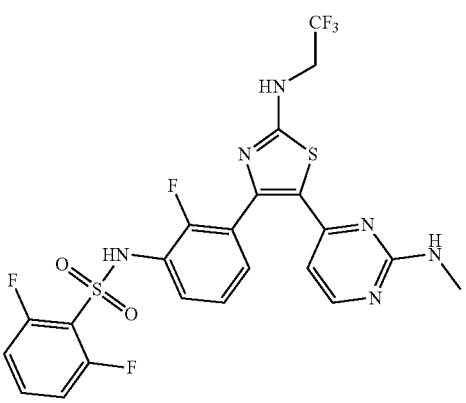 [SMILES: CNc1nccc(-c2sc(NCC(F)(F)F)nc2-c2cccc(NS(=O)(=O)c3c(F)cccc3F)c2F)n1] | 575.0 | HNMR (400 MHz, DMSO-d$_6$, ppm): δ 10.85 (s, 1H), 8.76-8.74 (m, 1H), 7.86 (d, J = 5.6 Hz, 1H), 7.68-7.61 (m, 1H), 7.40-7.35 (m, 1H), 7.29-7.18 (m, 5H), 5.71 (s, 1H), 4.18-4.12 (m, 2H), 2.69 (s, 3H).<br>FNMR (376 MHz, DMSO-d$_6$, ppm): δ −70.71 (3 F), −107.39 (2 F), −124.62 (1 F). |

TABLE 1-continued

Characterization of the compounds

| Compound No. | Structure | [M + H]⁺ | NMR |
|---|---|---|---|
| 166 | 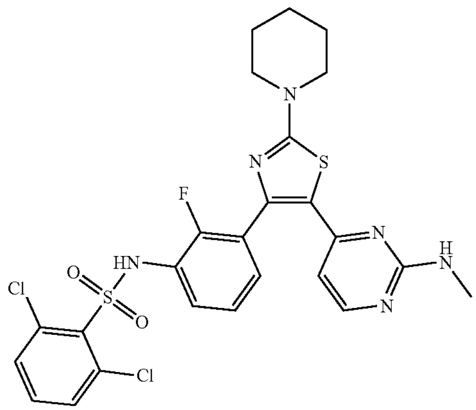 [SMILES: CNc1nccc(-c2sc(N3CCCCC3)nc2-c2cccc(NS(=O)(=O)c3c(Cl)cccc3Cl)c2F)n1] | 593.0 | HNMR (400 MHz, DMSO-d$_6$, ppm): δ 10.67 (s, 1H), 7.81 (d, J = 5.2 Hz, 1H), 7.55-7.57 (m, 2H), 7.49-7.45 (m, 1H), 7.36-7.32 (m, 1H), 7.20-7.18 (m, 2H), 6.88-6.91 (m, 1H), 5.60 (d, J = 4.8 Hz, 1H), 3.38-3.48 (m, 4H), 2.69 (d, J = 3.6 Hz, 3H), 1.51-1.61 (m, 6H). |
| 167 | 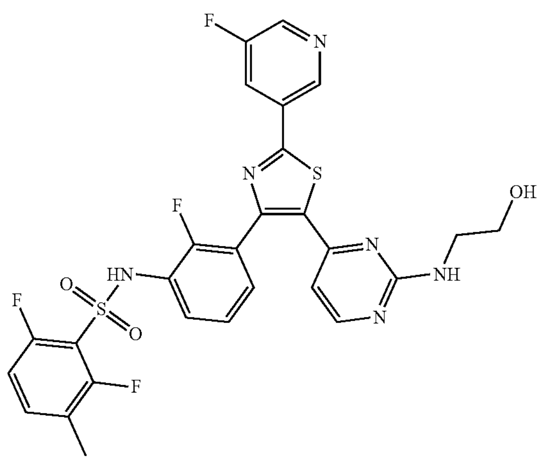 [SMILES: Cc1ccc(F)c(S(=O)(=O)Nc2cccc(-c3nc(-c4cncc(F)c4)sc3-c3ccnc(NCCO)n3)c2F)c1F] | 617.0 | HNMR (400 MHz, DMSO-d$_6$, ppm): δ 10.86 (s, 1H), 9.02 (s, 1H), 8.72 (d, J = 2.8 Hz, 1H), 8.25 (d, J = 8.8 Hz, 1H), 8.04 (d, J = 5.2 Hz, 1H), 7.54 (dd, J = 8.0, 14.4 Hz, 1H), 7.47-7.42 (m, 2H), 7.31 (t, J = 8.0 Hz, 1H), 7.23 (s, 1H), 7.13-7.09 (m, 1H), 5.94 (br s, 1H), 3.49 (t, J = 6.4 Hz, 2H), 3.35-3.45 (m, 2H), 2.13 (s, 3H). |
| 168 | 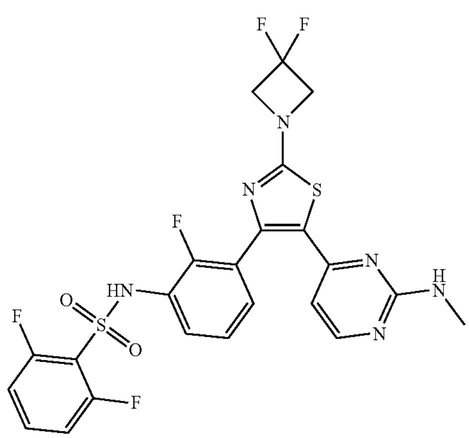 [SMILES: CNc1nccc(-c2sc(N3CC(F)(F)C3)nc2-c2cccc(NS(=O)(=O)c3c(F)cccc3F)c2F)n1] | 569.0 | HNMR (400 MHz, DMSO-d$_6$, ppm): δ 10.87 (s, 1H), 7.90 (d, J = 5.6 Hz, 1H), 7.68-7.64 (m, 1H), 7.42-7.30 (m, 2H), 7.29-7.19 (m, 4H), 5.75 (s, 1H), 4.57 (t, J = 12.0 Hz, 4H), 2.72 (s, 3H).<br>FNMR (376 MHz, DMSO-d$_6$, ppm): δ −98.43 (2 F), −107.43 (2 F), −124.49 (1 F). |

TABLE 1-continued

Characterization of the compounds

| Compound No. | Structure | [M + H]⁺ | NMR |
|---|---|---|---|
| 169 | 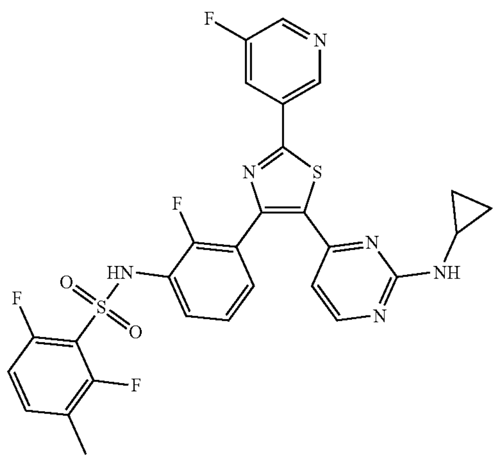 [SMILES: Cc1ccc(F)c(S(=O)(=O)Nc2cccc(-c3nc(-c4cncc(F)c4)sc3-c3ccnc(NC4CC4)n3)c2F)c1F] | 613.0 | HNMR (400 MHz, DMSO-d₆, ppm): δ 10.86 (s, 1H), 9.01 (s, 1H), 8.71 (d, J = 2.8 Hz, 1H), 8.24 (d, J = 9.2 Hz, 1H), 8.07 (d, J = 5.2 Hz, 1H), 7.58-7.51(m, 2H), 7.47-7.42 (m, 2H), 7.30 (t, J = 8.0 Hz, 1H), 7.11 (t, J = 9.2 Hz, 1H), 6.00 (s, 1H), 2.64-2.62 (m, 1H), 2.14 (s, 3H), 0.66-0.61 (m, 2H), 0.46-0.43 (m, 2H). FNMR (376 MHz, DMSO-d₆, ppm): δ −109.90 (1 F), −111.34 (1 F), −124.34 (1 F), −126.09 (1 F). |
| 170 | 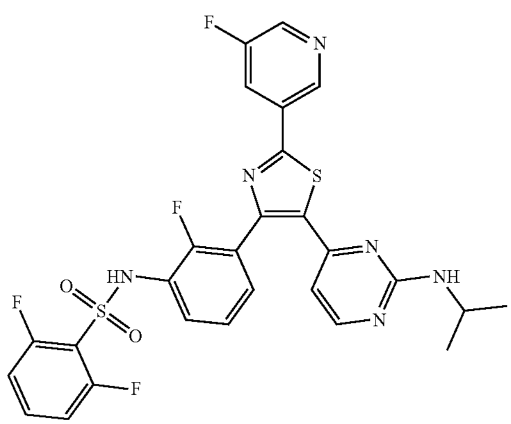 [SMILES: CC(C)Nc1nccc(-c2sc(-c3cncc(F)c3)nc2-c2cccc(NS(=O)(=O)c3c(F)cccc3F)c2F)n1] | 615.0 | HNMR (400 MHz, DMSO-d₆, ppm): δ 10.89 (s, 1H), 9.04 (s, 1H), 8.75 (d, J = 2.8 Hz, 1H), 8.28 (d, J = 8.4 Hz, 1H), 8.07 (d, J = 5.2 Hz, 1H), 7.57 (dd, J = 8.4, 14.4 Hz, 1H), 7.47-7.43 (m, 2H), 7.34 (t, J = 8.0 Hz, 1H), 7.31-7.22 (m, 1 H) 7.15 (t, J = 9.2 Hz, 1H), 5.98 (br s, 1H), 3.95-4.05 (m, 1H), 2.17 (s, 3H), 1.15 (d, J = 6.4 Hz, 6H). FNMR (376 MHz, DMSO-d₆, ppm): δ−109.88 (1 F), −111.34 (1 F), −124.40 (1 F), −126.12 (1 F). |
| 171 | 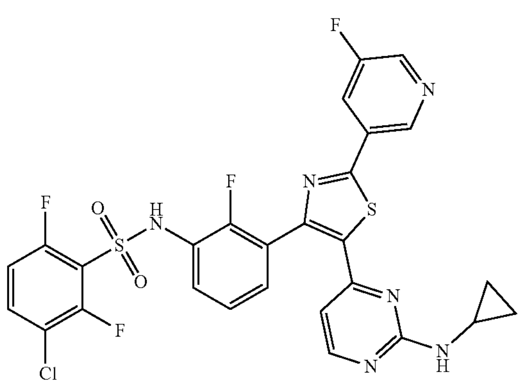 [SMILES: O=S(=O)(Nc1cccc(-c2nc(-c3cncc(F)c3)sc2-c2ccnc(NC3CC3)n2)c1F)c1c(F)ccc(Cl)c1F] | 633.0 | HNMR (400 MHz, DMSO-d₆, ppm): δ 11.12 (s, 1H), 9.01 (s, 1H), 8.72 (d, J = 2.8 Hz, 1H), 8.24 (d, J = 9.2 Hz, 1H), 8.08 (d, J = 5.2 Hz, 1H), 7.92-7.86 (m, 1H), 7.58 (d, J = 3.2 Hz, 1H), 7.52-7.43 (m, 2H), 7.35-7.29 (m, 2H), 6.00 (s, 1H), 2.66-2.61 (m, 1H), 0.66-0.61 (m, 2H), 0.47-0.41 (m, 2H). FNMR (376 MHz, DMSO-d₆, ppm): δ −107.64 (1 F), −107.76 (1 F), −124.30 (1 F), −126.09 (1 F). |

TABLE 1-continued

Characterization of the compounds

| Compound No. | Structure | [M + H]⁺ | NMR |
|---|---|---|---|
| 172 | 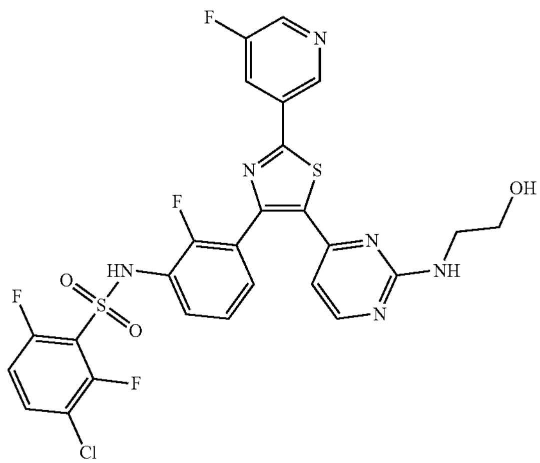 [SMILES: O=S(=O)(Nc1cccc(-c2nc(-c3cncc(F)c3)sc2-c2ccnc(NCCO)n2)c1F)c1c(F)ccc(Cl)c1F] | 637.0 | HNMR (400 MHz, DMSO-d$_6$, ppm): δ 11.11 (s, 1H), 9.02 (s, 1H), 8.71 (d, J = 2.4 Hz, 1H), 8.25 (d, J = 8.8 Hz, 1H), 8.06 (d, J = 5.2 Hz, 1H), 7.92-7.86 (m, 1H), 7.51-7.44 (m, 2H), 7.35-7.22 (m, 3H), 5.96 (s, 1H), 3.51-3.48 (m, 2H), 3.33-3.27 (m, 2H). FNMR (376 MHz, DMSO-d$_6$, ppm): δ −107.63 (1 F), −107.77 (1 F), −124.32 (1 F), −126.09 (1 F). |
| 173 | 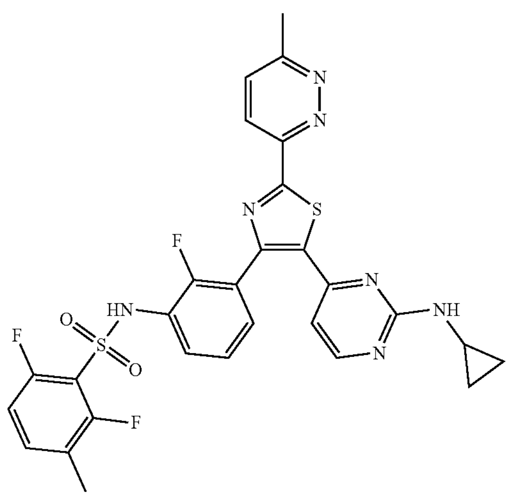 [SMILES: Cc1ccc(-c2nc(-c3cccc(NS(=O)(=O)c4c(F)ccc(C)c4F)c3F)c(-c3ccnc(NC4CC4)n3)s2)nn1] | 610.0 | HNMR (400 MHz, DMSO-d$_6$, ppm): δ 10.87 (s, 1H), 8.19 (d, J = 8.4 Hz, 1H), 8.08 (d, J = 5.2 Hz, 1H), 7.73 (d, J = 8.8 Hz, 1H), 7.59-7.52 (m, 2H), 7.47-7.42 (m, 2H), 7.30 (t, J = 8.0 Hz, 1H), 7.12 (t, J = 9.2 Hz, 1H), 6.03 (s, 1H), 2.67-2.63 (m, 4H), 2.14 (s, 3H), 0.65-0.61 (m, 2H), 0.47-0.45 (m, 2H). FNMR (376 MHz, DMSO-d$_6$, ppm): δ −109.92 (1 F), −111.37 (1 F), −124.46 (1 F). |
| 174 | 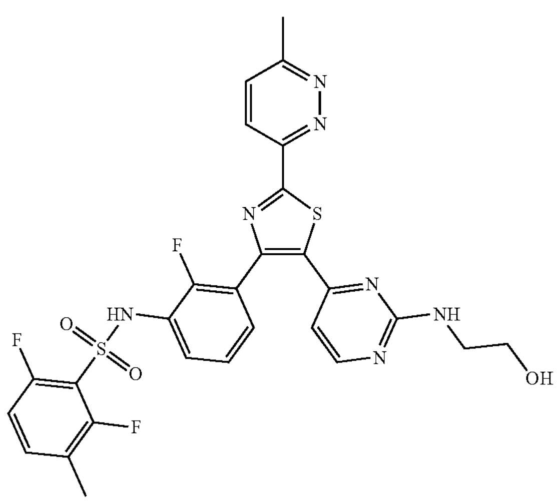 [SMILES: Cc1ccc(-c2nc(-c3cccc(NS(=O)(=O)c4c(F)ccc(C)c4F)c3F)c(-c3ccnc(NCCO)n3)s2)nn1] | 614.0 | HNMR (400 MHz, DMSO-d$_6$, ppm): δ 10.86 (s, 1H), 8.19 (d, J = 8.4 Hz, 1H), 8.05 (d, J = 5.2 Hz, 1H), 7.73 (d, J = 8.8 Hz, 1H), 7.54 (dd, J = 8.0, 14.4 Hz, 1H), 7.42-7.45 (m, 2H), 7.32-7.28 (m, 2H), 7.13-7.09 (m, 1H), 6.00 (s, 1H), 3.52-3.48 (m, 2H), 3.32-3.28 (m, 2H), 2.68 (s, 3H), 2.13 (s, 3H). FNMR (376 MHz, DMSO-d$_6$, ppm): δ −109.92 (1 F), −111.37 (1 F), −124.49 (1 F). |

TABLE 1-continued
Characterization of the compounds
| Compound No. | Structure | [M + H]⁺ | NMR |
|---|---|---|---|
| 175 | 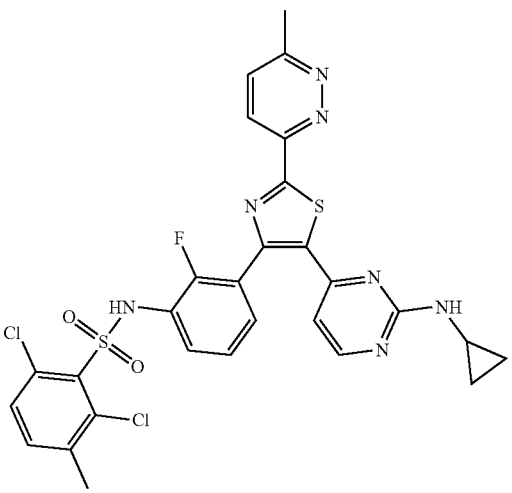 [SMILES: Cc1ccc(-c2nc(-c3cccc(NS(=O)(=O)c4c(Cl)ccc(C)c4Cl)c3F)c(-c3ccnc(NC4CC4)n3)s2)nn1] | 641.9 | HNMR (400 MHz, DMSO-d$_6$, ppm): δ 10.75 (s, 1H), 8.18 (d, J = 8.8 Hz, 1H), 8.08 (d, J = 5.2 Hz, 1H), 7.73 (d, J = 8.4 Hz, 1H), 7.61 (s, 1H), 7.54 (d, J = 8.4 Hz, 1H), 7.48 (d, J = 8.4 Hz, 1H), 7.43-7.38 (m, 2H), 7.29-7.25 (m, 1H), 6.03 (s, 1H), 2.67-2.63 (m, 4H), 2.30 (s, 3H), 0.63-0.64 (m, 2H), 0.47-0.46 (m, 2H). FNMR (376 MHz, DMSO-d$_6$, ppm): δ −123.92 (1 F). |
| 176 | 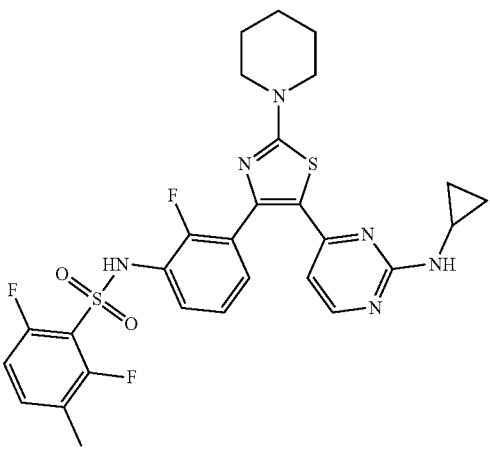 [SMILES: Cc1ccc(F)c(S(=O)(=O)Nc2cccc(-c3nc(N4CCCCC4)sc3-c3ccnc(NC4CC4)n3)c2F)c1F] | 601.1 | HNMR (400 MHz, DMSO-d$_6$, ppm): δ 10.85 (s, 1H), 7.85 (d, J = 5.6 Hz, 1H), 7.58 (dd, J = 8.4, 14.4 Hz, 1H), 7.43-7.39 (m, 1H), 7.33-7.25 (m, 2H), 7.15 (t, J = 9.6 Hz, 1H), 5.78 (d, J = 5.6 Hz, 1H), 3.44-3.54 (m, 4H), 2.65-2.62 (m, 1H), 2.17 (s, 3H), 1.56-1.66 (s, 6H), 0.69-0.67 (m, 2H), 0.45-0.55 (m, 2H). FNMR (376 MHz, DMSO-d$_6$, ppm): δ −109.89 (1 F), −111.31 (1 F), −124.70 (1 F). |
| 177 | 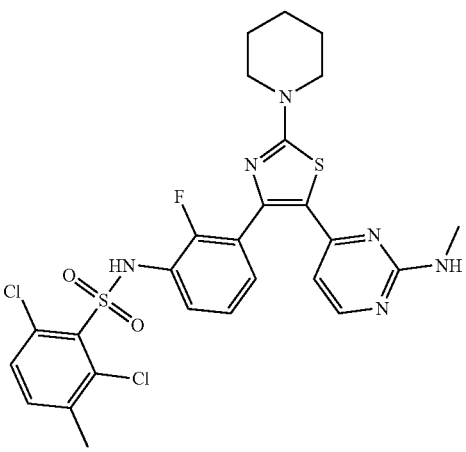 [SMILES: CNc1nccc(-c2sc(N3CCCCC3)nc2-c2cccc(NS(=O)(=O)c3c(Cl)ccc(C)c3Cl)c2F)n1] | 607.0 | HNMR (400 MHz, DMSO-d$_6$, ppm): 10.71 (s, 1H), 7.81 (d, J = 6.0 Hz, 1H), 7.67-7.63 (m, 1H), 7.54 (d, J = 8.4 Hz, 1H), 7.47 (d, J = 8.4 Hz, 1H), 7.35-7.32 (m, 1H), 7.26-7.19 (m, 2H), 5.79 (br s, 1H), 3.44-3.54 (m, 4H), 2.73 (s, 3H), 2.30 (s, 3H), 1.52-1.62 (m, 6H). |

TABLE 1-continued

Characterization of the compounds

| Compound No. | Structure | [M + H]+ | NMR |
|---|---|---|---|
| 178 | 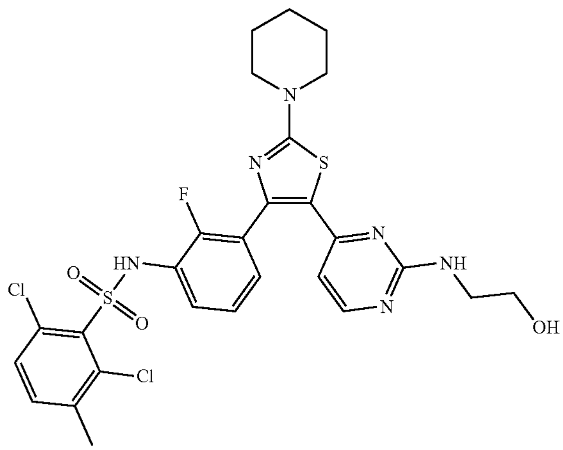 [SMILES: Cc1ccc(Cl)c(S(=O)(=O)Nc2cccc(-c3nc(N4CCCCC4)sc3-c3ccnc(NCCO)n3)c2F)c1Cl] | 637.0 | HNMR (400 MHz, DMSO-d$_6$, ppm): δ 10.69 (s, 1H), 7.80 (d, J = 6.0 Hz, 1H), 7.54 (d, J = 8.4 Hz, 1H), 7.52-7.55 (m, 1H), 7.47 (d, J = 8.4 Hz, 1H), 7.32-7.35 (m, 1H), 7.26-7.19 (m, 2H), 5.75 (br s, 1H), 3.49-3.46 (m, 6H), 3.22-3.30 (m, 2H), 2.30 (s, 3H), 1.52-1.62 (m, 6H). |
| 179 | 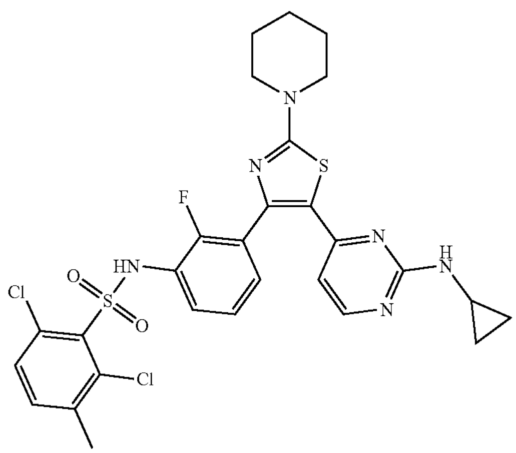 [SMILES: Cc1ccc(Cl)c(S(=O)(=O)Nc2cccc(-c3nc(N4CCCCC4)sc3-c3ccnc(NC4CC4)n3)c2F)c1Cl] | 633.0 | HNMR (400 MHz, DMSO-d$_6$, ppm): δ 10.72 (s, 1H), 7.82 (d, J = 6.0 Hz, 1H), 7.54 (d, J = 8.4 Hz, 1H), 7.48 (d, J = 8.4 Hz, 1H), 7.36-7, 32 (m, 1H), 7.26-7.22 (m, 2H), 5.81 (d, J = 6.0 Hz, 1H), 3.43-3.53 (s, 4H), 2.55-2.65 (m, 1H), 2.31 (s, 3H), 1.52-1.62 (m, 6H), 0.64-0.74 (s, 2H), 0.47-0.57 (s, 2H). |
| 180 | 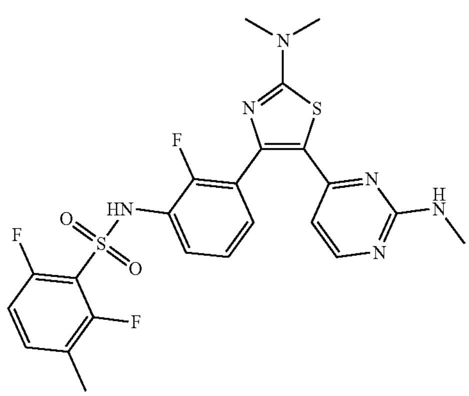 [SMILES: CNc1nccc(-c2sc(N(C)C)nc2-c2cccc(NS(=O)(=O)c3c(F)ccc(C)c3F)c2F)n1] | 535.0 | HNMR (400 MHz, DMSO-d$_6$, ppm): δ 10.84 (s, 1H), 7.95-7.66 (m, 1H), 7.82 (d, J = 6.4 Hz, 1H), 7.56 (dd, J = 8.4, 14.4 Hz, 1H), 7.40-7.36 (m, 1H), 7.30-7.23 (m, 2H), 7.12 (t, J = 9.2 Hz, 1H), 5.78 (s, 1H), 3.10 (s, 6H), 2.74 (s, 3H), 2.14 (s, 3H).<br>FNMR (376 MHz, DMSO-d$_6$, ppm): δ -109.94 (1 F), -111.37 (1 F), -124.82 (1 F). |

TABLE 1-continued

Characterization of the compounds

| Compound No. | Structure | [M + H]⁺ | NMR |
|---|---|---|---|
| 181 | 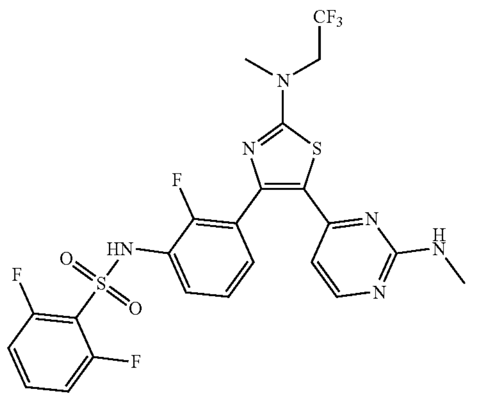 [SMILES: CNc1nccc(-c2sc(N(C)CC(F)(F)F)nc2-c2cccc(NS(=O)(=O)c3c(F)cccc3F)c2F)n1] | 589.0 | HNMR (400 MHz, DMSO-d$_6$, ppm): δ 10.88 (s, 1H), 7.90-7.88 (m, 1H), 7.69-7.38 (m, 3H), 7.31-7.18 (m, 4H), 5.76 (s, 1H), 4.45-4.39 (m, 2H), 3.17 (s, 3H), 2.73 (s, 3H).<br>FNMR (376 MHz, DMSO-d$_6$, ppm): δ −68.75 (3 F), −107.41 (2 F), −124.66 (1 F). |
| 182 | 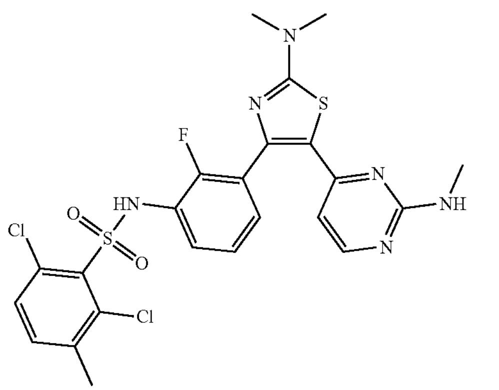 [SMILES: CNc1nccc(-c2sc(N(C)C)nc2-c2cccc(NS(=O)(=O)c3c(Cl)ccc(C)c3Cl)c2F)n1] | 567.0 | HNMR (400 MHz, DMSO-d$_6$, ppm): δ 10.72 (s, 1H), 7.81 (d, J = 6.0 Hz, 1H), 7.73-7.61 (m, 1H), 7.54 (d, J = 8.4 Hz, 1H), 7.48 (d, J = 8.4 Hz, 1H), 7.37-7.32 (m, 1H), 7.27-7.20 (m, 2H), 5.76 (br s, 1H), 3.09 (s, 6H), 2.74 (s, 3H), 2.31 (s, 3H). |
| 183 | 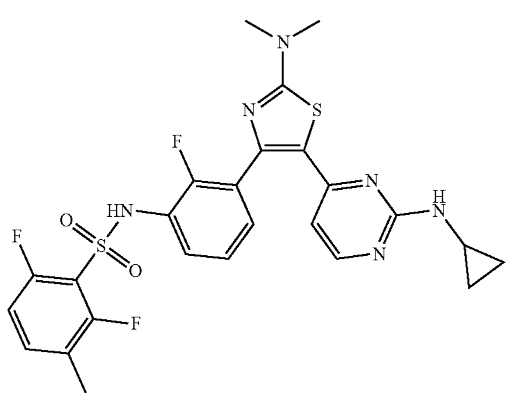 [SMILES: Cc1ccc(F)c(S(=O)(=O)Nc2cccc(-c3nc(N(C)C)sc3-c3ccnc(NC4CC4)n3)c2F)c1F] | 561.1 | HNMR (400 MHz, DMSO-d$_6$, ppm): δ 10.86 (s, 1H), 8.75-8.49 (br s, 1H), 7.83 (d, J = 6.4 Hz, 1H), 7.55 (dd, J = 8.4, 14.4 Hz, 1H), 7.41-7.37 (m, 1H), 7.32-7.24 (m, 2H), 7.12 (t, J = 9.2 Hz, 1H), 5.80 (d, J = 6.0 Hz, 1H), 3.09 (s, 6H), 2.64-2.56 (m, 1H), 2.15 (s, 3H), 0.78-0.65 (m, 2H), 0.61-0.45 (m, 2H).<br>FNMR (376 MHz, DMSO-d$_6$, ppm): δ −109.94 (1 F), −111.37 (1 F), −124.79 (1 F). |

TABLE 1-continued

Characterization of the compounds

| Compound No. | Structure | [M + H]⁺ | NMR |
|---|---|---|---|
| 184 | 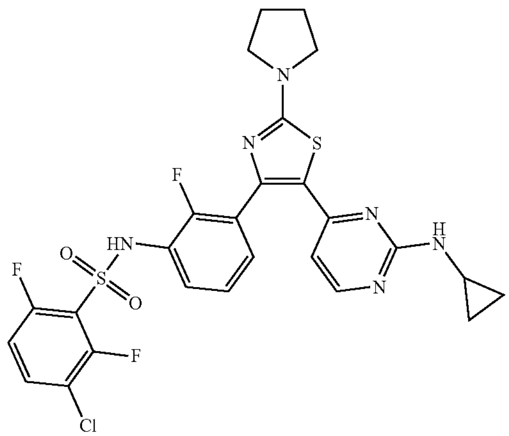 [SMILES: O=S(=O)(Nc1cccc(-c2nc(N3CCCC3)sc2-c2ccnc(NC3CC3)n2)c1F)c1c(F)ccc(Cl)c1F] | 607.5 | HNMR (400 MHz, CD$_3$OD, ppm): δ 7.76-7.69 (m, 2H), 7.55-7.52 (m, 1H), 7.38-7.29 (m, 2H), 7.15 (t, J = 9.2 Hz, 1H), 6.11 (d, J = 6.8 Hz, 1H), 364-3.39 (m, 4H), 2.76-2.58 (m, 1H), 2.14-2.05 (m, 4H), 0.94-0.92 (m, 2H), 0.75-0.65 (m, 2H).<br>FNMR (376 MHz, CD$_3$OD, ppm): δ −107.62 (1 F), −107.85 (1 F), −124.58 (1 F). |
| 185 | 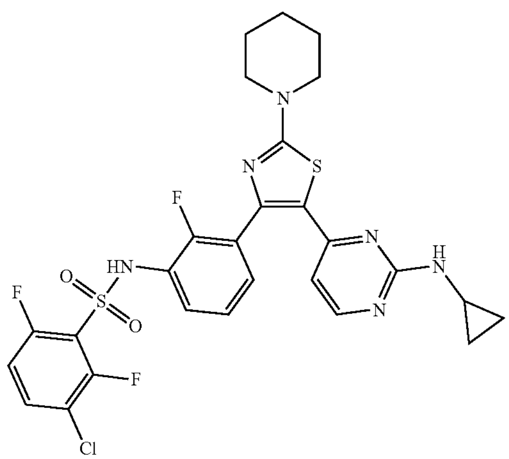 [SMILES: O=S(=O)(Nc1cccc(-c2nc(N3CCCCC3)sc2-c2ccnc(NC3CC3)n2)c1F)c1c(F)ccc(Cl)c1F] | 621.5 | HNMR (400 MHz, DMSO-d$_6$, ppm): δ 11.08 (s, 1H), 7.92-7.88 (m, 1H), 7.83 (d, J = 6.0 Hz, 1H), 7.42-7.39 (m, 1H), 7.35-7.25 (m, 3H), 5.77 (d, J = 5.6 Hz, 1H), 3.47-3.39 (m, 4H), 2.65-2.54 (m, 1H), 1.60-1.52 (m, 6H), 0.72-0.59 (m, 2H), 0.58-0.39 (m, 2H). |
| 186 | 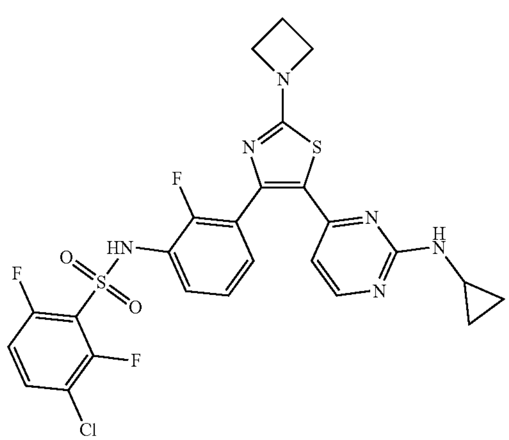 [SMILES: O=S(=O)(Nc1cccc(-c2nc(N3CCC3)sc2-c2ccnc(NC3CC3)n2)c1F)c1c(F)ccc(Cl)c1F] | 593.5 | HNMR (400 MHz, DMSO-d$_6$, ppm): δ 11.10 (s, 1H), 8.02-7.98 (m, 1H), 7.94-7.88 (m, 1H), 7.84 (d, J = 6.0 Hz, 1H), 7.42-7.38 (m, 1H), 7.34-7.25 (m, 3H), 5.79 (d, J = 6.0 Hz, 1H), 4.08 (t, J = 7.6 Hz, 4H), 2.66-2.55 (m, 1H), 2.45-2.38 (m, 2H), 0.75-0.64 (m, 2H), 0.58-0.43 (m, 2H).<br>FNMR (376 MHz, DMSO-d$_6$, ppm): δ −107.62 (1 F), −107.84 (1 F), −124.58 (1 F). |

TABLE 1-continued

Characterization of the compounds

| Compound No. | Structure | [M + H]⁺ | NMR |
|---|---|---|---|
| 187 | 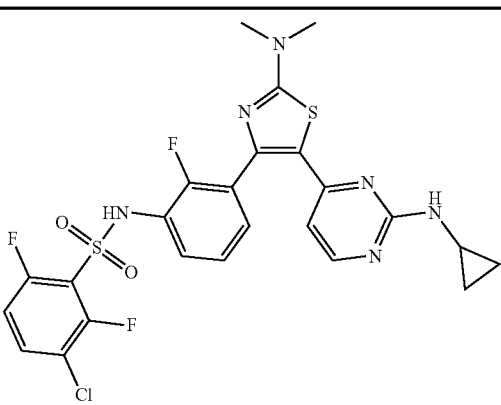 | 581.4 | HNMR (400 MHz, DMSO-d$_6$, ppm): δ 11.08 (s, 1H), 7.93-7.88 (m, 1H), 7.83 (d, J = 6.0 Hz, 1H), 7.42-7.38 (m, 1H), 7.34-7.25 (m, 3H), 5.73 (d, J = 5.6 Hz, 1H), 3.07 (s, 6H), 2.63-2.60 (m, 1H), 0.72-0.60 (m, 2H), 0.49 (s, 2H).<br>FNMR (376 MHz, DMSO-d$_6$, ppm): δ −107.59 (1 F), −107.80 (1 F), −124.76 (1 F). |
| 188 | 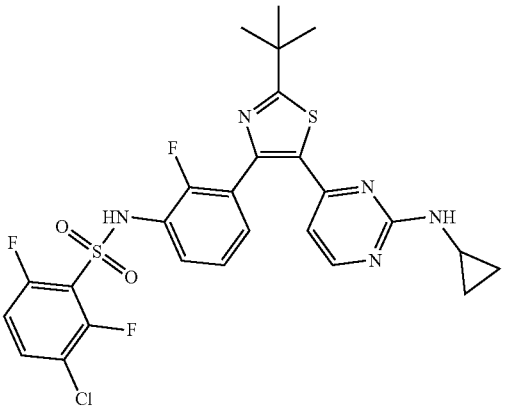 [SMILES: CC(C)(C)c1nc(-c2cccc(NS(=O)(=O)c3c(F)ccc(Cl)c3F)c2F)c(-c2ccnc(NC3CC3)n2)s1] | 594.5 | HNMR (400 MHz, DMSO-d$_6$, ppm): δ 11.05 (s, 1H), 8.02 (d, J = 4.8 Hz, 1H), 7.89 (dd, J = 14.0, 8.0 Hz, 1H), 7.54-7.50 (m, 1H), 7.41-7.36 (m, 2H), 7.31-7.25 (m, 2H), 5.96 (s, 1H), 2.60-2.57 (m, 1H), 1.37 (s, 9H), 0.60-0.57 (m, 2H), 0.42-0.40 (m, 2H).<br>FNMR (376 MHz, DMSO-d$_6$, ppm): δ −107.67 (1 F), −107.78 (1 F), −124.36 (1 F). |
| 189 | 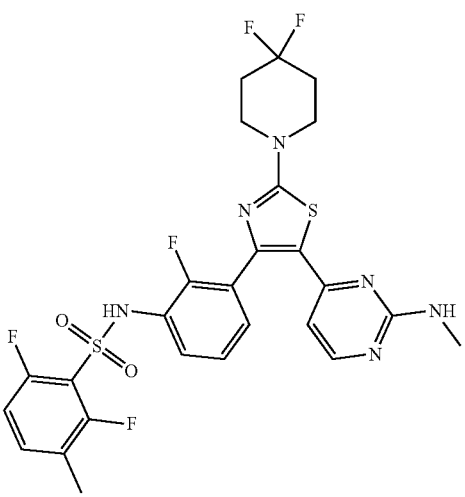 [SMILES: CNc1nccc(-c2sc(N3CCC(F)(F)CC3)nc2-c2cccc(NS(=O)(=O)c3c(F)ccc(C)c3F)c2F)n1] | 611.1 | HNMR (400 MHz, DMSO-d$_6$, ppm): δ 7.78 (d, J = 5.6 Hz, 1H), 7.60-7.49 (m, 1H), 7.42-7.34 (m, 1H), 7.34-7.23 (m, 2H), 7.08 (t, J = 9.6 Hz, 1H), 5.84 (s, 1H), 3.70-3.60 (m, 4H), 2.80-2.60 (m, 3H), 2.17-2.02 (m, 7H).<br>FNMR (376 MHz, DMSO-d$_6$, ppm): δ −96.13 (2 F), −110.04 (1 F), −111.55 (1 F), −124.76 (1 F). |

Biological Example 1. CSK Inhibition Assay

Test compound was dissolved in DMSO at 10 mM. 45 uL of compound was transferred into a 384-well compound source plate (LABCYTE cat #P-05525) and serially diluted at 1:3 ratio to create a 11-point dilutions. The same volume of DMSO was adopted as high control. 20 nL of these compounds DMSO dilutes were dispensed into a new 384-well assay plate by Echo 550. CSK protein (2.15 nM, SignalChem, cat #C63-10G), florescent labeled substrate FLPeptide22 (2 μM, PerkinElmer, cat #760366) was prepared in kinase assay buffer (50 mM HEPES (pH 7.5), 10 mM MgCl$_2$, 10 mM MnCl$_2$, 0.01% Brij-35, 2 mM DTT and 0.005 mg/mL BSA). 15 uL of kinase assay buffer containing CSK protein and substrate was transferred to assay plate and incubated at RT for 30 minutes. Kinase assay buffer supplemented with substrate peptides was employed as low control to monitor the background. 4 μM of ATP was prepared in kinase assay buffer and 5 μL of ATP solution was added to each well to start the reaction. The assay plate was incubated at 25° C. for 90 minutes and the reaction was stopped by adding 40 μL of 0.5 M EDTA.

Phosphorylated fluorescent-tagged peptides were differentiated from non-phosphorylated peptides by separating using Caliper EZ Reader II and the detection was directly converted to conversion ratio.

For estimation of $IC_{50}$, the % substrate conversion values are transformed to % Inhibition Ratio by applying the following equation:

$$\% \text{ Inhibition Ratio} = \frac{Ratio_{HC} - Ratio_{cpd}}{Ratio_{HC} - Ratio_{LC}}.$$

TABLE 2

CSK Inhibition Activity of Representative Compounds

| Compound | CSK $IC_{50}$ (nM) |
|---|---|
| 1 | 1057.1 |
| 2 | 43.3 |
| 3 | 13.4 |
| 4 | 327.9 |
| 5 | 62.7 |
| 6 | 19.8 |
| 7 | 305.5 |
| 8 | >10000.0 |
| 9 | 50.3 |
| 10 | 30.1 |
| 11 | 103.4 |
| 12 | 61.6 |
| 13 | 51.0 |
| 14 | 55.3 |
| 15 | 51.4 |
| 16 | 63.6 |
| 17 | 25.0 |
| 18 | 144.3 |
| 19 | 28.2 |
| 20 | 132.1 |
| 21 | 25.2 |
| 22 | 44.8 |
| 23 | 4.1 |
| 24 | 500.8 |
| 25 | 236.7 |
| 26 | >10000.0 |
| 27 | 26.9 |
| 28 | 63.3 |
| 29 | 20.5 |
| 30 | 41.0 |
| 31 | >10000.0 |
| 32 | 2.9 |
| 33 | 595.3 |
| 34 | 42.9 |
| 35 | 81.2 |
| 36 | 22.3 |
| 37 | >10000.0 |
| 38 | 14.9 |
| 39 | 33.9 |
| 40 | 48.0 |
| 41 | 87.3 |
| 42 | 37.7 |
| 43 | 37.6 |
| 44 | 43.9 |
| 45 | 41.3 |
| 46 | 27.3 |
| 47 | 29.4 |
| 48 | 75.8 |
| 49 | 345.1 |
| 50 | 76.3 |
| 51 | 33.1 |
| 52 | 19.5 |
| 53 | 15.6 |
| 54 | 92.8 |
| 55 | 30.3 |
| 56 | 47.0 |
| 57 | 251.1 |
| 58 | 31.5 |
| 59 | 68.4 |
| 60 | 119.9 |
| 61 | 12.6 |
| 62 | 9.4 |
| 63 | 20.6 |
| 64 | 18.3 |
| 65 | 14.9 |
| 66 | 19.6 |
| 67 | 616.8 |
| 68 | 16.2 |
| 69 | 13.4 |
| 70 | 92.3 |
| 71 | 41.8 |
| 72 | 26.1 |
| 73 | 14.8 |
| 74 | 8.8 |
| 75 | 73.9 |
| 76 | 19.1 |
| 77 | 85.5 |
| 78 | 11.8 |
| 79 | 7.6 |
| 80 | 6.0 |
| 81 | 4508.0 |
| 82 | >10000.0 |
| 83 | 841.5 |
| 84 | 133.3 |
| 85 | 33.2 |
| 86 | 1221.5 |
| 87 | 947.4 |
| 88 | >10000.0 |
| 89 | 321.1 |
| 90 | 77.0 |
| 91 | 52.7 |
| 92 | 89.2 |
| 93 | 41.8 |
| 94 | 98.6 |
| 95 | 71.6 |
| 96 | 127.3 |
| 97 | 98.2 |
| 98 | 78.3 |
| 99 | 104.6 |
| 100 | 136.6 |
| 101 | 436.2 |
| 102 | 96.5 |
| 103 | 51.8 |
| 104 | 134.0 |
| 105 | 400.1 |
| 106 | 91.7 |
| 107 | 112.6 |
| 108 | 2.5 |
| 109 | 4.6 |
| 110 | 220.7 |
| 111 | 16.4 |
| 112 | 30.3 |
| 113 | 23.8 |
| 114 | 18.5 |
| 115 | 7.1 |
| 116 | 13.5 |
| 117 | 81.5 |
| 118 | 2.8 |
| 119 | 3.7 |
| 120 | 20.6 |
| 121 | 15.5 |
| 122 | 633.9 |
| 123 | 23.2 |
| 124 | 14.9 |
| 125 | 15.3 |
| 126 | 30.2 |
| 127 | 5.8 |
| 128 | 12.0 |

TABLE 2-continued

CSK Inhibition Activity of Representative Compounds

| Compound | CSK IC$_{50}$ (nM) |
|---|---|
| 129 | 7.4 |
| 130 | 214.8 |
| 131 | 13.1 |
| 132 | 62.0 |
| 133 | 17.8 |
| 134 | 184.3 |
| 135 | 15.7 |
| 136 | 108.1 |
| 137 | 21.3 |
| 138 | 8.5 |
| 139 | 2.7 |
| 140 | 16.5 |
| 141 | 6.8 |
| 142 | 10.5 |
| 143 | 3.6 |
| 144 | 23.9 |
| 145 | 112.7 |
| 146 | 41.3 |
| 147 | 30.3 |
| 148 | 6.9 |
| 149 | 4.5 |
| 150 | 8.1 |
| 151 | 4.8 |
| 152 | 6.0 |
| 153 | 7.4 |
| 154 | 12.5 |
| 155 | 16.6 |
| 156 | 9.3 |
| 157 | 25.8 |
| 158 | 170.5 |
| 159 | 28.4 |
| 160 | 111.9 |
| 161 | 10.1 |
| 162 | 6.4 |
| 163 | 7.4 |
| 164 | 25.4 |
| 165 | 9.9 |
| 166 | 13.5 |
| 167 | 15.9 |
| 168 | 12.7 |
| 169 | 9.1 |
| 170 | 15.0 |
| 171 | 5.6 |
| 172 | 5.4 |
| 173 | 10.3 |
| 174 | 17.5 |
| 175 | 6.5 |
| 176 | 10.2 |
| 177 | 14.1 |
| 178 | 7.5 |
| 179 | 6.2 |
| 180 | 13.0 |
| 181 | 7.8 |
| 182 | 8.3 |
| 183 | 11.2 |
| 184 | 5.2 |
| 185 | 4.9 |
| 186 | 4.1 |
| 187 | 7.3 |
| 188 | 11.4 |
| 189 | 18.5 |

Biological Example 2. LCK Inhibition Assay

Test compound was dissolved in DMSO at 10 mM. 45 uL of compound was transfer into a 384-well compound source plate (LABCYTE cat #P-05525) and serially diluted at 1:3 ratio to create a 11-point dilutions. The same volume of DMSO was adopted as high control. 20 nL of these compounds DMSO dilutes were dispensed into a new 384-well assay plate by Echo 550. LCK protein (0.50 nM, Cama Biosciences, cat #08-170), florescent labeled substrate FLPeptide4 (2 μM, PerkinElmer, cat #760348) was prepared in kinase assay buffer (50 mM HEPES (pH 7.5), 10 mM MgCl$_2$, 0.01% Brij-35, 2 mM DTT and 0.005 mg/ml BSA). 15 uL of kinase assay buffer containing LCK protein and substrate was transferred to assay plate and incubate at RT for 30 minutes. Kinase assay buffer supplemented with substrate peptides was employed as low control to monitor the background. 400 μM ATP was prepared in kinase assay buffer and 5 μL of ATP solution was added to each well to start the reaction. The assay plate was incubated at 25° C. for 90 minutes and the reaction was stopped by adding 40 μL of 0.5 M EDTA.

Phosphorylated fluorescent-tagged peptides were differentiated from non-phosphorylated peptides by separating using Caliper EZ Reader II and the detection was directly converted to conversion ratio.

For estimation of IC$_{50}$, the % substrate conversion values are transformed to % Inhibition Ratio by applying the following equation:

$$\% \text{ Inhibition Ratio} = \frac{Ratio_{HC} - Ratio_{cpd}}{Ratio_{HC} - Ratio_{LC}}.$$

TABLE 3

LCK inhibition Activity of Representative Compounds

| Compound | LCK IC$_{50}$ (nM) |
|---|---|
| 2 | + |
| 3 | +++ |
| 4 | + |
| 5 | + |
| 6 | ++ |
| 7 | + |
| 9 | + |
| 10 | ++ |
| 11 | + |
| 12 | + |
| 13 | + |
| 14 | + |
| 15 | + |
| 16 | + |
| 17 | + |
| 18 | + |
| 19 | ++ |
| 20 | + |
| 21 | ++ |
| 22 | + |
| 23 | +++ |
| 24 | + |
| 25 | + |
| 27 | ++ |
| 28 | + |
| 29 | + |
| 30 | ++ |
| 32 | ++ |
| 33 | + |
| 34 | + |
| 35 | + |
| 36 | + |
| 38 | ++ |
| 39 | + |
| 40 | + |
| 41 | + |
| 42 | ++ |
| 43 | ++ |
| 44 | + |
| 45 | + |
| 46 | + |
| 47 | ++ |
| 48 | + |
| 50 | + |
| 51 | + |

TABLE 3-continued

LCK inhibition Activity of Representative Compounds

| Compound | LCK IC$_{50}$ (nM) |
|---|---|
| 52 | + |
| 53 | + |
| 54 | + |
| 55 | + |
| 56 | + |
| 58 | + |
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 83 | + |
| 84 | + |
| 85 | ++ |
| 90 | + |
| 91 | + |
| 92 | + |
| 93 | + |
| 94 | + |
| 95 | + |
| 96 | + |
| 97 | + |
| 98 | + |
| 100 | + |
| 101 | + |
| 102 | + |
| 103 | + |
| 104 | + |
| 105 | + |
| 106 | + |
| 107 | + |
| 108 | +++ |
| 109 | +++ |
| 110 | + |
| 111 | ++ |
| 112 | + |
| 113 | + |
| 114 | ++ |
| 115 | + |
| 116 | ++ |
| 117 | + |
| 118 | +++ |
| 119 | +++ |
| 120 | +++ |
| 121 | +++ |
| 122 | ++ |
| 123 | + |
| 124 | + |
| 125 | + |
| 126 | + |
| 127 | + |
| 128 | + |
| 129 | + |
| 130 | + |
| 131 | + |
| 132 | ++ |
| 133 | + |
| 134 | + |
| 135 | + |
| 136 | + |
| 137 | + |
| 138 | + |
| 139 | + |
| 140 | + |
| 141 | ++ |
| 142 | + |
| 143 | + |
| 144 | + |
| 145 | + |
| 146 | + |
| 147 | + |
| 148 | ++ |
| 149 | + |
| 150 | + |
| 151 | + |
| 152 | + |
| 153 | ++ |
| 154 | ++ |
| 155 | + |
| 156 | + |
| 157 | + |
| 158 | + |
| 159 | + |
| 160 | + |
| 161 | + |
| 162 | ++ |
| 163 | ++ |
| 164 | ++ |
| 165 | ++ |
| 166 | ++ |
| 167 | + |
| 168 | ++ |
| 169 | + |
| 170 | + |
| 171 | + |
| 172 | + |
| 173 | + |
| 174 | + |
| 175 | + |
| 176 | + |
| 177 | + |
| 178 | + |
| 179 | + |
| 180 | + |
| 181 | ++ |
| 182 | + |
| 183 | + |
| 184 | + |
| 185 | + |
| 186 | + |
| 187 | + |
| 188 | + |
| 189 | + |

+ indicates IC$_{50}$ greater than 1000 nM
++ indicates IC$_{50}$ between 100 nM and 1000 nM
+++ indicates IC$_{50}$ less than 100 nM The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound of Formula I, or a pharmaceutically acceptable salt thereof,

Formula I wherein:
- $R^1$ and $R^2$ are independently a halogen, a $C_{1-4}$ alkyl, or a $C_{1-4}$ alkoxy;
- $R^3$ at each occurrence is independently a halogen, cyano, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- m is 0, 1 or 2, provided that when $R^1$ and $R^2$ are both F, then m is not 0;
- $R^4$ at each occurrence is independently a halogen, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- n is 0, 1, or 2,
- $Z^1$ and $Z^2$ are independently N or $CR^{100}$;
- wherein $R^{100}$ is hydrogen, halogen, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- J and L are each independently O, S, $CR^{101}$, or $NR^{102}$;
- wherein $R^{101}$ is hydrogen, halogen, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- $R^{102}$ is lone pair, hydrogen, nitrogen protecting group, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- K is C or N;
- provided that at most one of J and L is O or S, and if J or L is O or S, then K is not N; and at least one of J and L is not $CR^{101}$ or K is not C;
- $R^5$ is —$NR^{103}R^{103a}$, an optionally substituted $C_{3-6}$ cycloalkyl, an optionally substituted aryl, an optionally substituted heteroaryl, or an optionally substituted heterocyclyl; wherein $R^{103}$ and $R^{103a}$ are independently hydrogen, nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl;
- or $R^5$, K, and one of J and L form an optionally substituted heterocyclic or heteroaromatic ring;
- $R^6$ at each occurrence is independently a halogen, cyano, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- p is 0, 1, or 2, and
- $R^7$ is hydrogen, nitrogen protecting group, an optionally substituted $C_{1-6}$ alkyl, an optionally substituted $C_{3-6}$ cycloalkyl, an optionally substituted aryl, an optionally substituted heteroaryl, or an optionally substituted heterocyclyl.

2. The compound of claim 1, or a pharmaceutically acceptable salt thereof, wherein $R^1$ and $R^2$ are independently F, Cl, methyl, or methoxy.

3. The compound of claim 1, or a pharmaceutically acceptable salt thereof, wherein m is 1, and $R^3$ is F, Cl, $C_{1-4}$ alkyl, $C_{3-6}$ cycloalkyl, $C_{1-4}$ alkoxy, or $C_{3-6}$ cycloalkoxy.

4. The compound of claim 1, or a pharmaceutically acceptable salt thereof,
wherein the structural unit in Formula I is

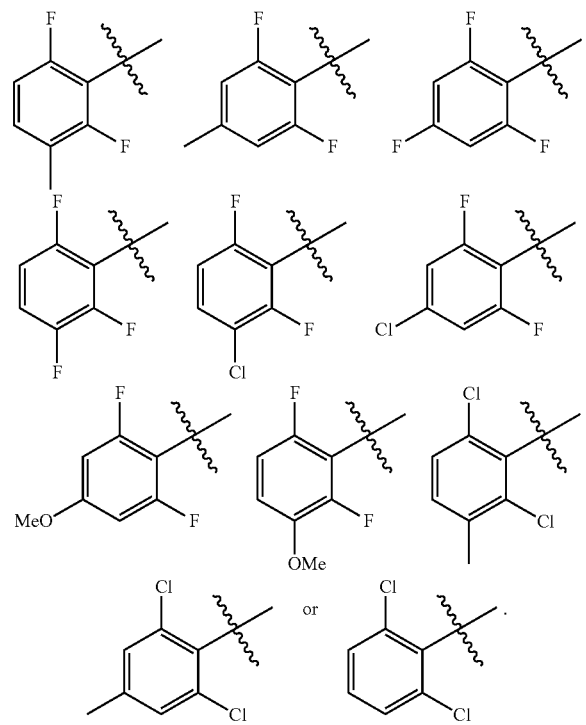

5. The compound of claim 1, or a pharmaceutically acceptable salt thereof, wherein the structural unit

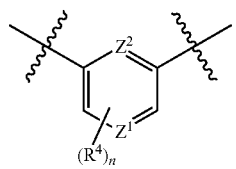

in Formula I is

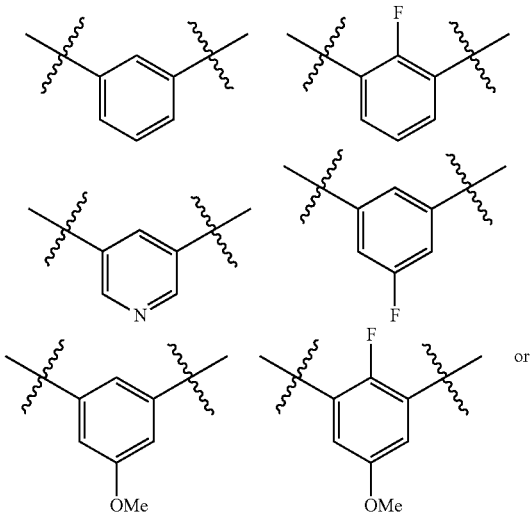

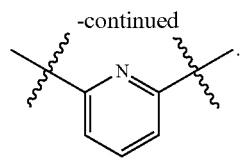

6. The compound of claim 1, or a pharmaceutically acceptable salt thereof, wherein

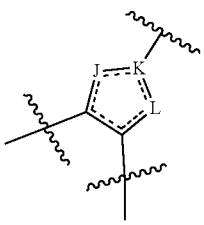

in Formula I is

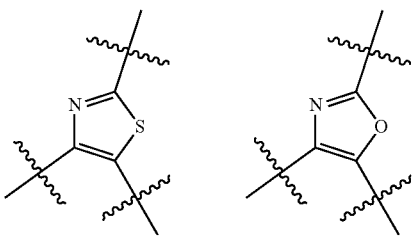

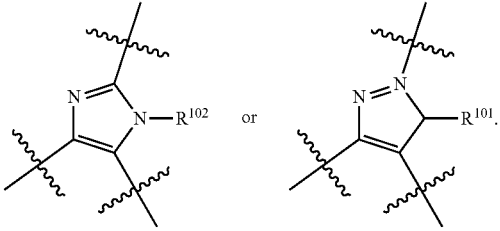

7. The compound of claim 1, or a pharmaceutically acceptable salt thereof, wherein $R^5$ is an optionally substituted phenyl or an optionally substituted 5 or 6 membered heteroaryl.

8. The compound of claim 1, or a pharmaceutically acceptable salt thereof, wherein $R^5$ is phenyl, pyridyl, pyridazinyl, pyrimidinyl, pyrazinyl, or pyrazolyl, each of which is optionally substituted with 1 or 2 substituents independently selected from F, Cl, —OH, cyano, $C_{1-4}$ alkyl, —$CF_3$, $C_{1-4}$ alkoxy, —$NH_2$, —NH($C_{1-4}$ alkyl), —N($C_{1-4}$ alkyl)($C_{1-4}$ alkyl), azetidinyl, and cyclopropyl.

9. The compound of claim 1, or a pharmaceutically acceptable salt thereof, wherein $R^5$ is

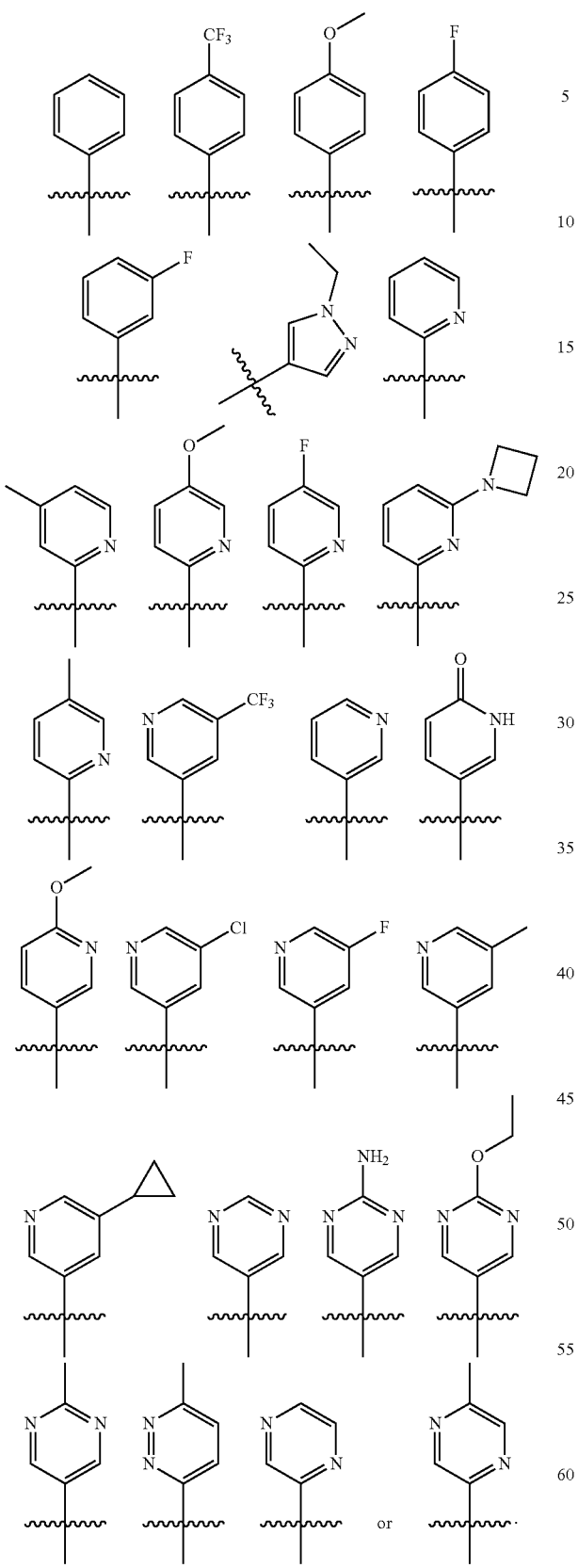

10. The compound of claim 1, or a pharmaceutically acceptable salt thereof, wherein $R^5$ is —NR$^{103}$R$^{103a}$, an optionally substituted $C_{3-6}$ cycloalkyl, or an optionally substituted 4-6 membered heterocyclyl.

11. The compound of claim 1, or a pharmaceutically acceptable salt thereof, wherein

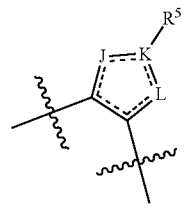

in Formula I is

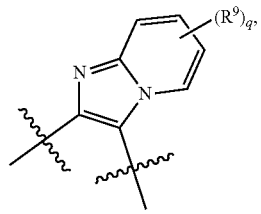

wherein q is 0, 1, or 2,
R$^9$ at each occurrence is independently halogen, an optionally substituted $C_{1-6}$ alkyl, an optionally substituted $C_{3-6}$ cycloalkyl, an optionally substituted $C_{1-6}$ alkoxy, an optionally substituted $C_{3-6}$ cycloalkoxy, an optionally substituted phenyl, an optionally substituted heteroaryl, an optionally substituted heterocyclyl, —OH, cyano, —COR$^{110}$, —COOR$^{111}$, —CONR$^{112}$R$^{113}$, —NR$^{114}$R$^{115}$,
wherein R$^{110}$ and R$^{111}$ are independently hydrogen, an optionally substituted $C_{1-6}$ alkyl, an optionally substituted $C_{3-6}$ cycloalkyl, an optionally substituted phenyl, an optionally substituted heteroaryl, or an optionally substituted heterocyclyl; and
R$^{112}$, R$^{113}$, R$^{114}$, and R$^{115}$ are each independently hydrogen, nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl.

12. The compound of claim 11, or a pharmaceutically acceptable salt thereof, wherein R$^9$ at each occurrence is independently F, Cl, —OH, cyano, $C_{1-4}$ alkyl, CF$_3$, $C_{1-4}$ alkoxy, —NH$_2$, —NMe$_2$, —NHMe, —NH(C$_{2-4}$ alkyl), —N(C$_{1-4}$ alkyl) (C$_{2-4}$ alkyl), —COOH, —COO(C$_{1-4}$ alkyl), —CONH$_2$, —CONH(C$_{1-4}$ alkyl), —CON(C$_{1-4}$ alkyl) (C$_{1-4}$ alkyl), azetidinyl, or cyclopropyl.

13. The compound of claim 11, or a pharmaceutically acceptable salt thereof, wherein

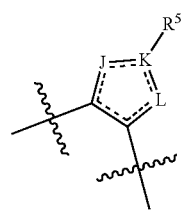

in Formula I is

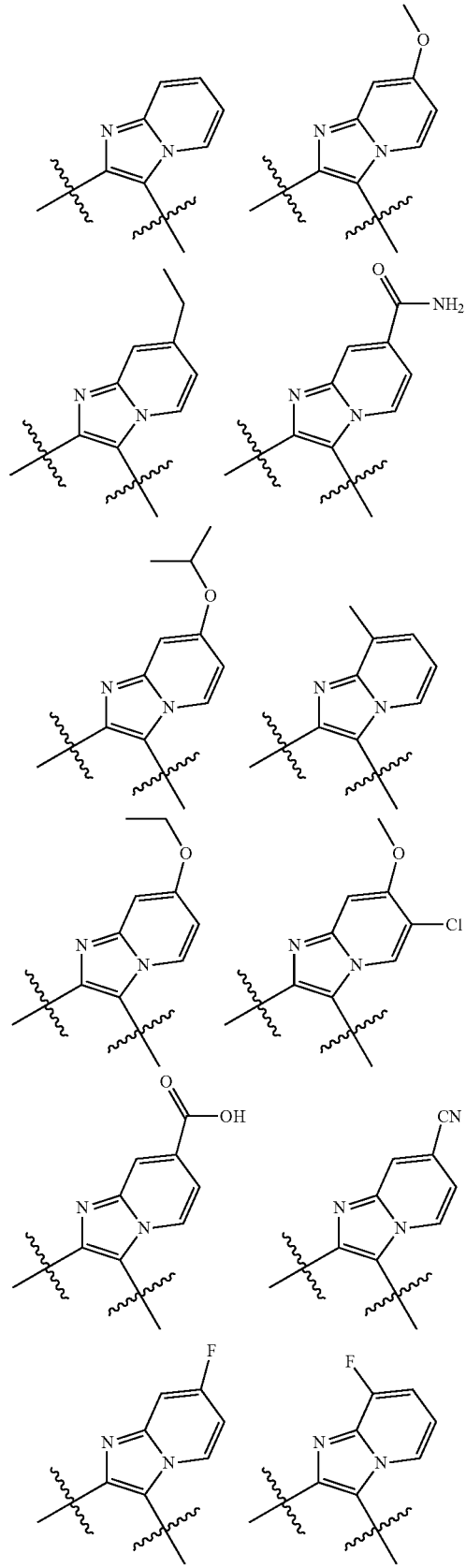

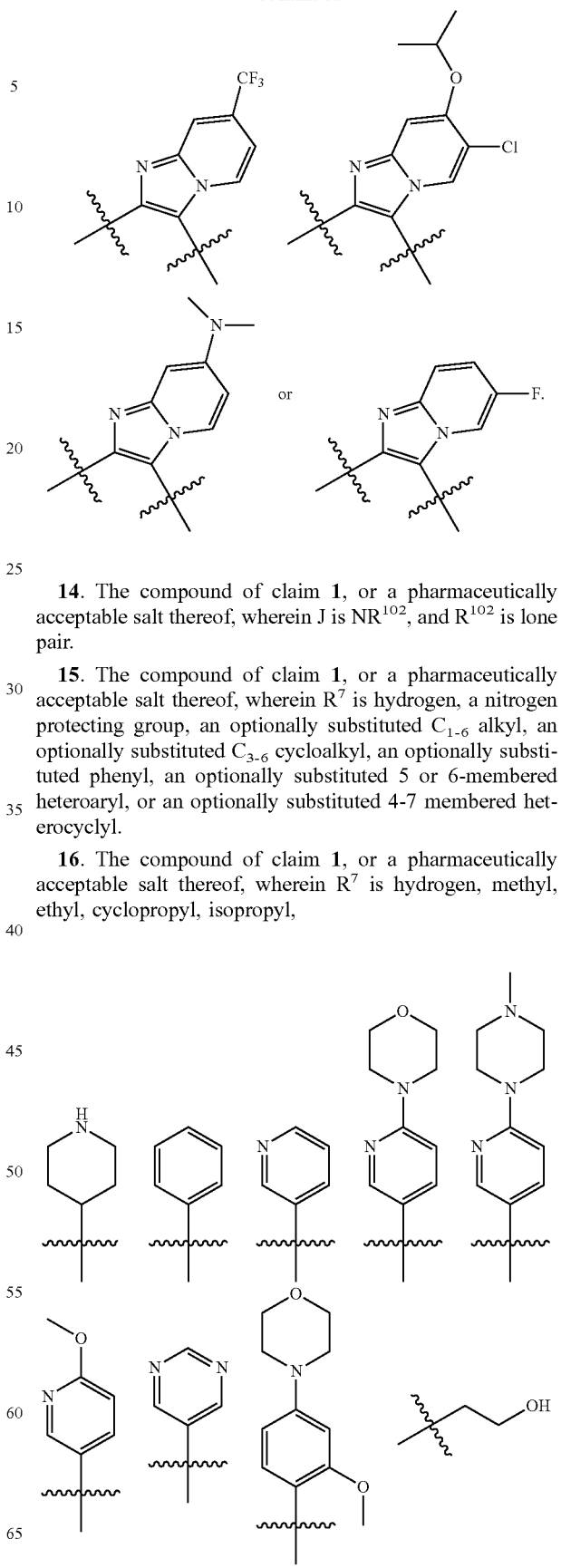

14. The compound of claim 1, or a pharmaceutically acceptable salt thereof, wherein J is $NR^{102}$, and $R^{102}$ is lone pair.

15. The compound of claim 1, or a pharmaceutically acceptable salt thereof, wherein $R^7$ is hydrogen, a nitrogen protecting group, an optionally substituted $C_{1-6}$ alkyl, an optionally substituted $C_{3-6}$ cycloalkyl, an optionally substituted phenyl, an optionally substituted 5 or 6-membered heteroaryl, or an optionally substituted 4-7 membered heterocyclyl.

16. The compound of claim 1, or a pharmaceutically acceptable salt thereof, wherein $R^7$ is hydrogen, methyl, ethyl, cyclopropyl, isopropyl, -continued

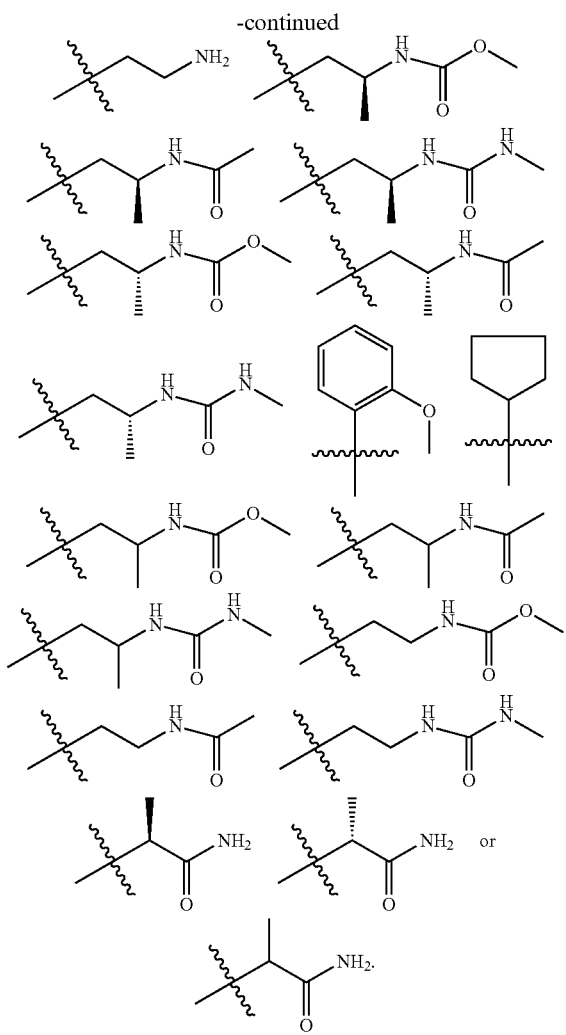

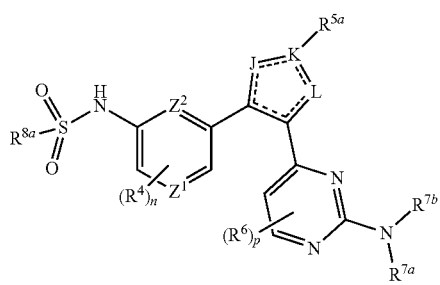

17. A compound of Formula II, or a pharmaceutically acceptable salt thereof, Formula II

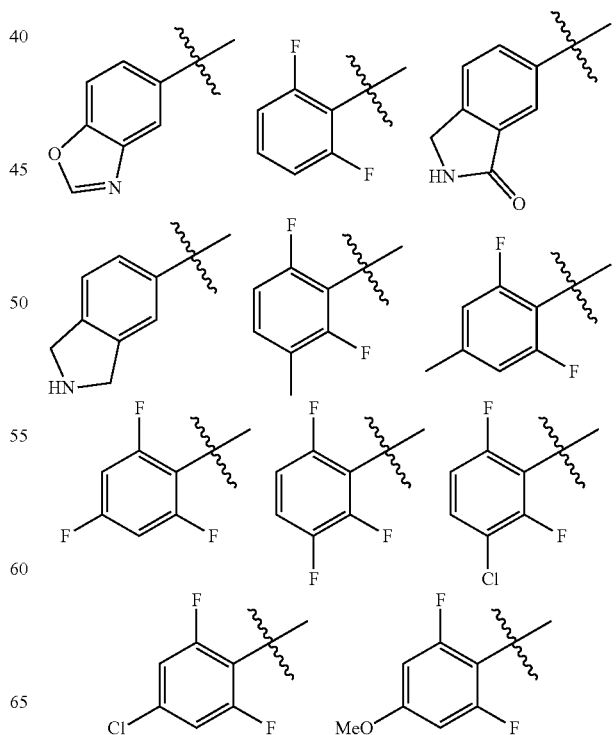

wherein:
R$^4$ at each occurrence is independently a halogen, an optionally substituted C$_{1-6}$ alkyl, an optionally substituted C$_{3-6}$ cycloalkyl, an optionally substituted C$_{1-6}$ alkoxy, or an optionally substituted C$_{3-6}$ cycloalkoxy;
n is 0, 1, or 2,
Z$^1$ and Z$^2$ are independently N or CR$^{100}$;
wherein R$^{100}$ is hydrogen, halogen, an optionally substituted C$_{1-6}$ alkyl, an optionally substituted C$_{3-6}$ cycloalkyl, an optionally substituted C$_{1-6}$ alkoxy, or an optionally substituted C$_{3-6}$ cycloalkoxy;
J and L are each independently O, S, CR$^{101}$, or NR$^{102}$;
wherein R$^{101}$ is hydrogen, —OH, an optionally substituted C$_{1-6}$ alkyl, an optionally substituted C$_{3-6}$ cycloalkyl, an optionally substituted C$_{1-6}$ alkoxy, or an optionally substituted C$_{3-6}$ cycloalkoxy;
R$^{102}$ is lone pair, hydrogen, nitrogen protecting group, —OH, an optionally substituted C$_{1-6}$ alkyl, an optionally substituted C$_{3-6}$ cycloalkyl, an optionally substituted C$_{1-6}$ alkoxy, or an optionally substituted C$_{3-6}$ cycloalkoxy;
K is C or N;
provided that at most one of J and L is O or S, and if J or L is O or S, then K is C; and at least one of J and L is not CR$^{101}$ or K is not C;
R$^{5a}$ is an optionally substituted 5-6 membered heteroaryl;
R$^6$ at each occurrence is independently a halogen, cyano, —OH, an optionally substituted C$_{1-6}$ alkyl, an optionally substituted C$_{3-6}$ cycloalkyl, an optionally substituted C$_{1-6}$ alkoxy, or an optionally substituted C$_{3-6}$ cycloalkoxy;
p is 0, 1, or 2;
R$^{7a}$ and R$^{7b}$ are independently hydrogen, an optionally substituted C$_{1-6}$ alkyl, an optionally substituted C$_{3-6}$ cycloalkyl, an optionally substituted aryl, an optionally substituted heteroaryl, or an optionally substituted heterocyclyl; and
R$^{8a}$ is an optionally substituted aryl or an optionally substituted heteroaryl.

18. The compound of claim 17, or a pharmaceutically acceptable salt thereof, wherein R$^{8a}$ is

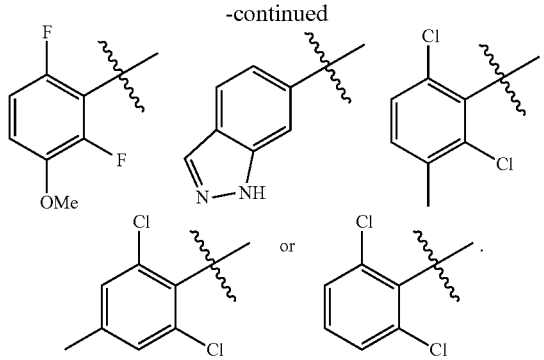

19. The compound of claim 17, or a pharmaceutically acceptable salt thereof, having a formula according to any one of Formula II-A to Formula II-D:

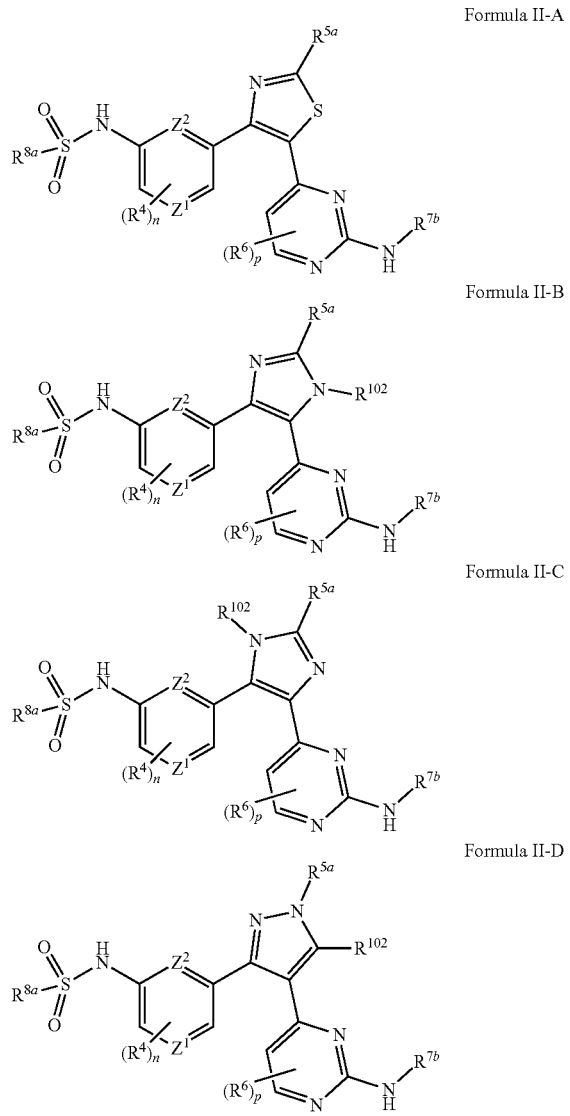

Formula II-A

Formula II-B

Formula II-C

Formula II-D wherein R¹⁰² in Formula II-B or II-C is not lone pair.

20. The compound of claim 18, or a pharmaceutically acceptable salt thereof, wherein $R^{5a}$ is

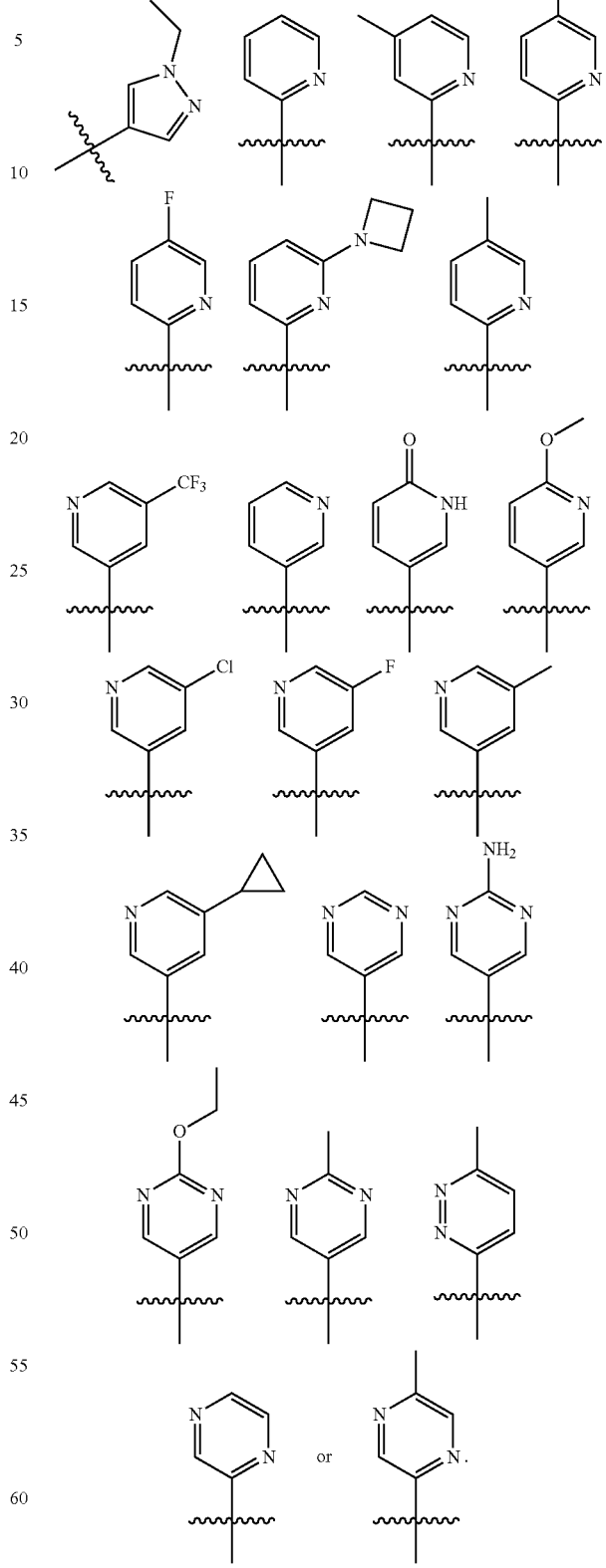

21. The compound of claim 17, or a pharmaceutically acceptable salt thereof, wherein $R^{7a}$ is hydrogen, and $R^{7b}$ is hydrogen, an optionally substituted $C_{1-6}$ alkyl, an optionally substituted $C_{3-6}$ cycloalkyl, an optionally substituted phenyl, an optionally substituted 5- or 6-membered heteroaryl, or an optionally substituted 4-7 membered heterocyclyl.

22. The compound of claim 21, or a pharmaceutically acceptable salt thereof, wherein $R^{7b}$ is hydrogen, methyl, ethyl, cyclopropyl, isopropyl,

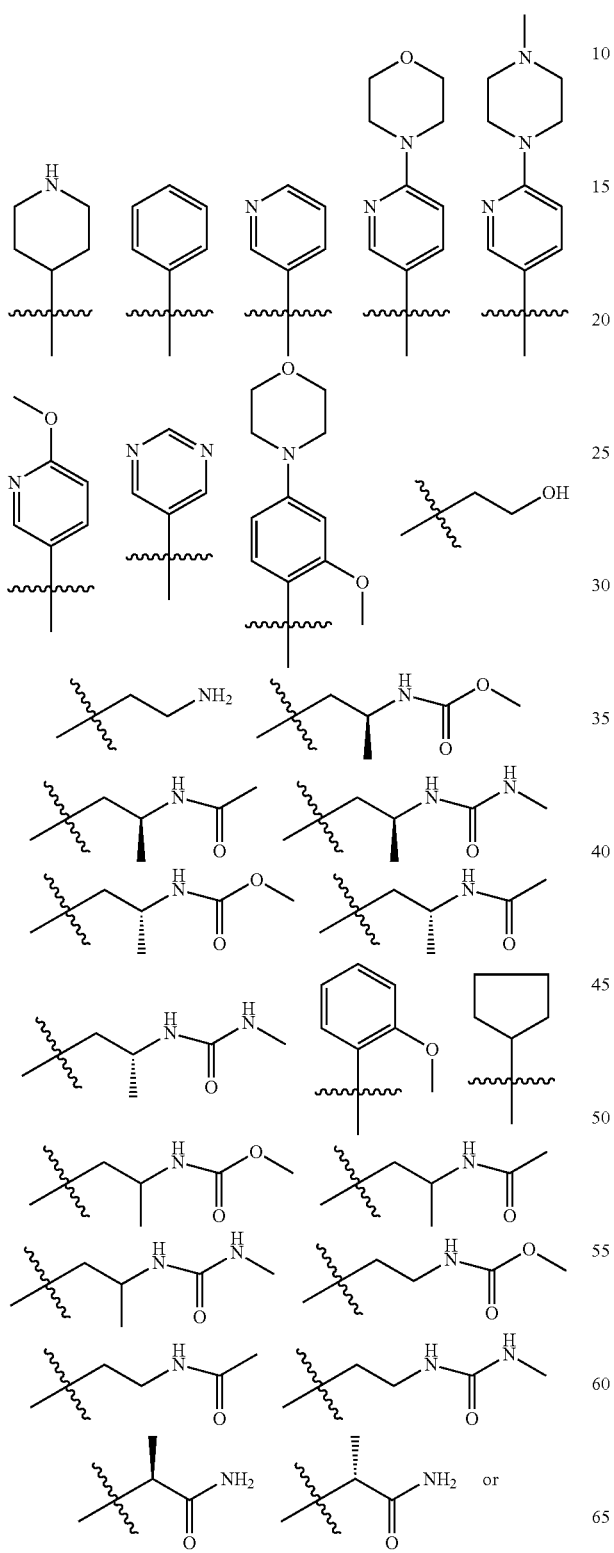

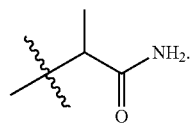

23. The compound of claim 17, or a pharmaceutically acceptable salt thereof, wherein the moiety

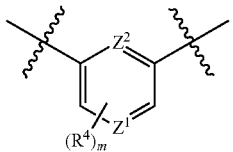

in Formula II is

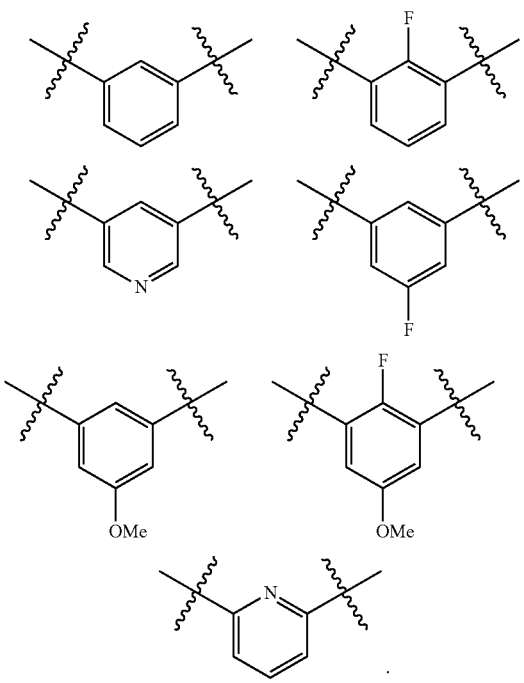

or

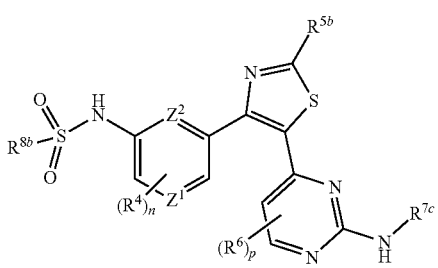

24. A compound according to one of Formula III-A to Formula III-D, or a pharmaceutically acceptable salt thereof, Formula III-A 323
-continued

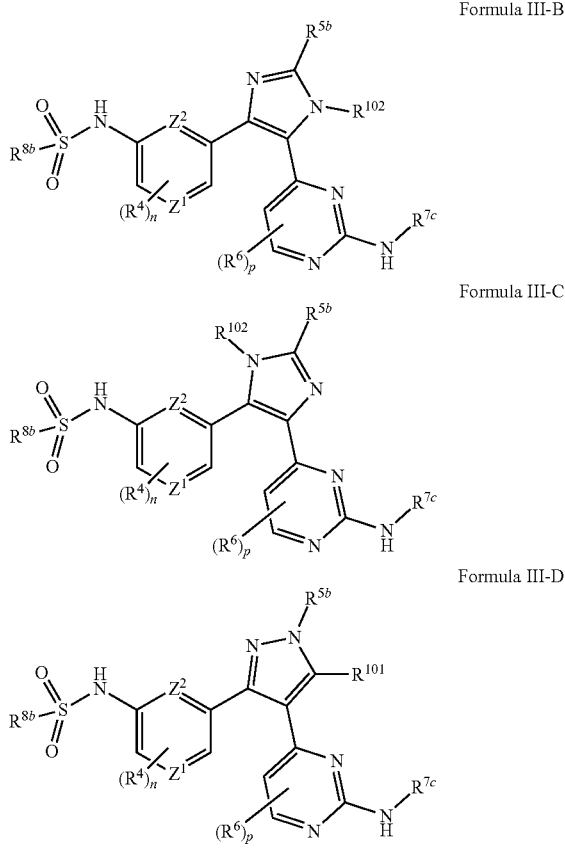

Formula III-B

Formula III-C

Formula III-D wherein:
R⁴ at each occurrence is independently a halogen, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
n is 0, 1, or 2,
$Z^1$ and $Z^2$ are independently N or $CR^{100}$;
wherein $R^{100}$ is hydrogen, halogen, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
$R^{102}$ is hydrogen, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
$R^{5b}$ is 2-pyridyl, 3-pyridyl, pyridazinyl, pyrimidinyl, pyrazinyl, or pyrazolyl, each of which is optionally substituted with 1 or 2 substituents independently selected from F, Cl, —OH, cyano, $C_{1-4}$ alkyl, —CF₃, $C_{1-4}$ alkoxy, —NH₂, —NH($C_{1-4}$ alkyl), —N($C_{1-4}$ alkyl)($C_{1-4}$ alkyl), azetidinyl, and cyclopropyl;
R⁶ at each occurrence is independently a halogen, cyano, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
p is 0, 1, or 2;
$R^{7c}$ is hydrogen, an optionally substituted $C_{1-6}$ alkyl, an optionally substituted $C_{3-6}$ cycloalkyl, an optionally substituted aryl, an optionally substituted heteroaryl, or an optionally substituted heterocyclyl;

324

$R^{8b}$ is an optionally substituted aryl or an optionally substituted heteroaryl.

25. The compound of claim 24, or a pharmaceutically acceptable salt thereof, wherein $R^{5b}$ is

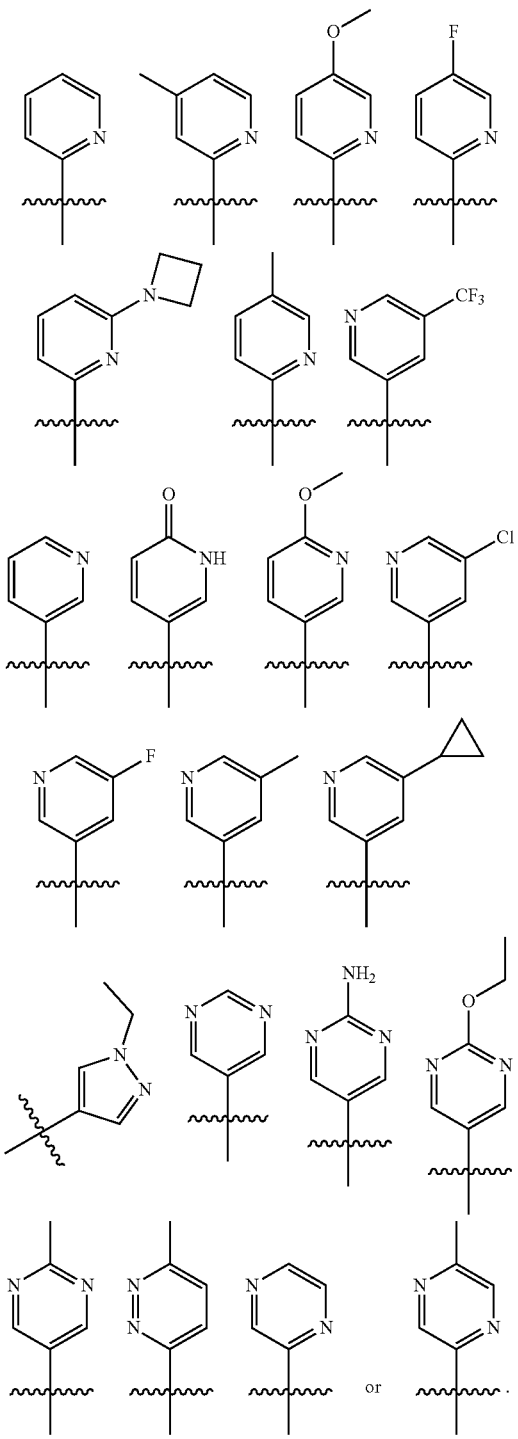

26. A compound selected from compound No. 1-121 and 123-189, or a pharmaceutically acceptable salt thereof:

1
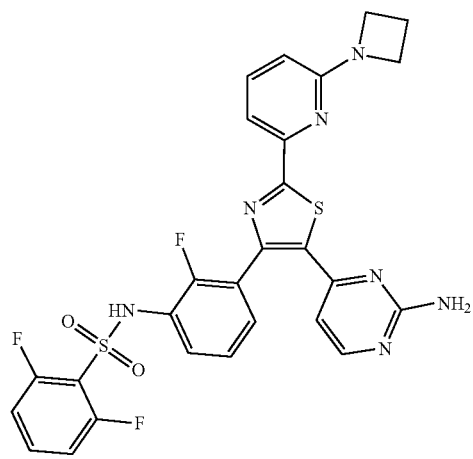
2
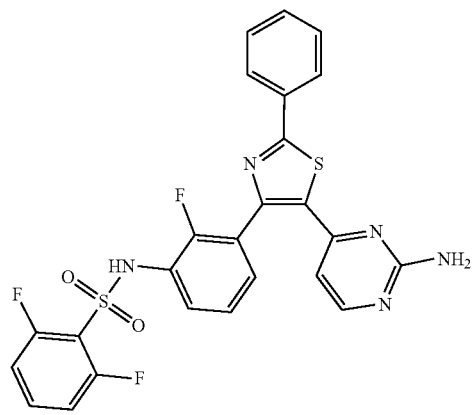
3
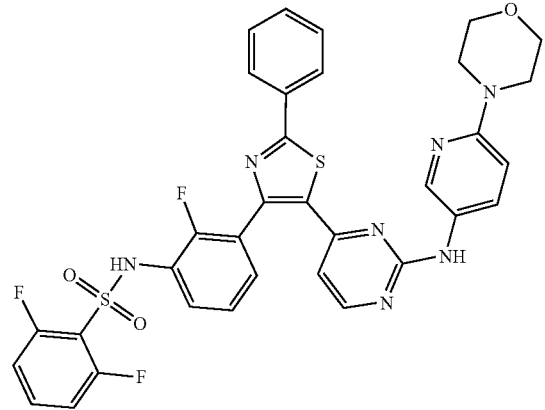
4
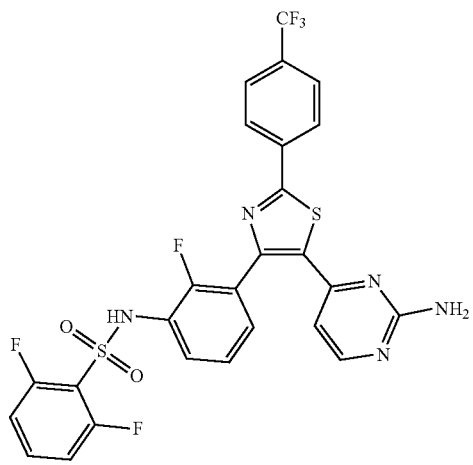
5
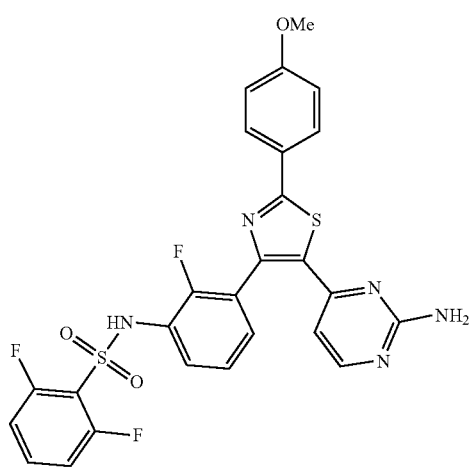
6
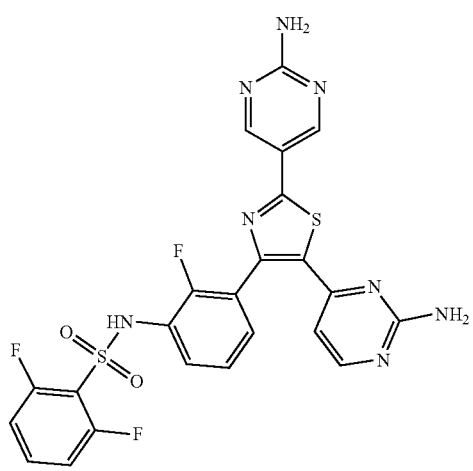

-continued
7
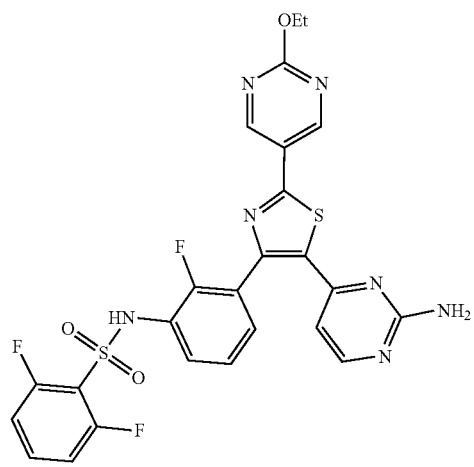
8
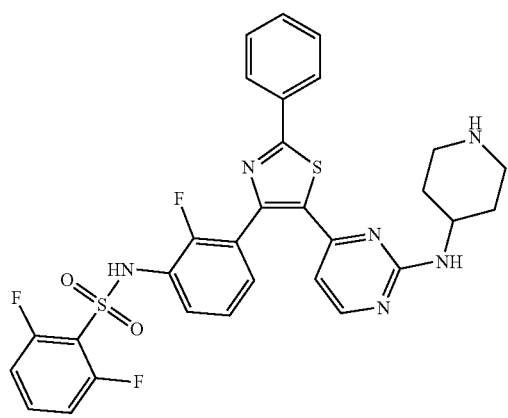
9
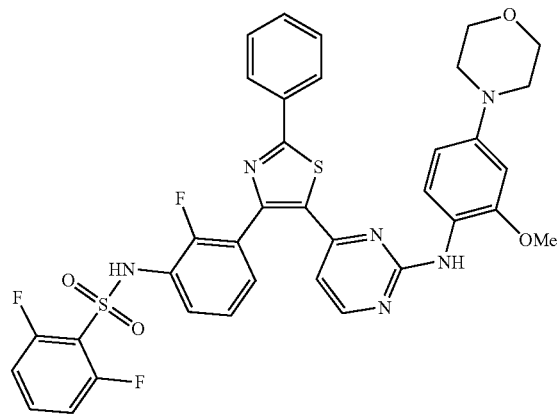
-continued
10
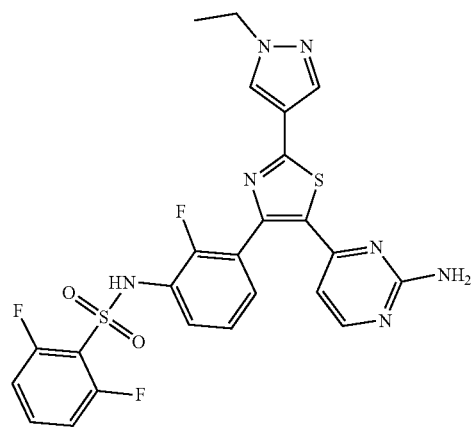
11
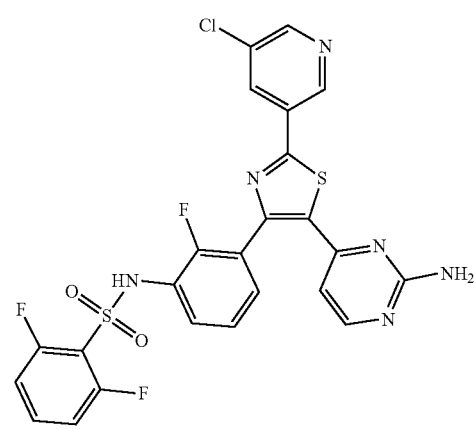
12
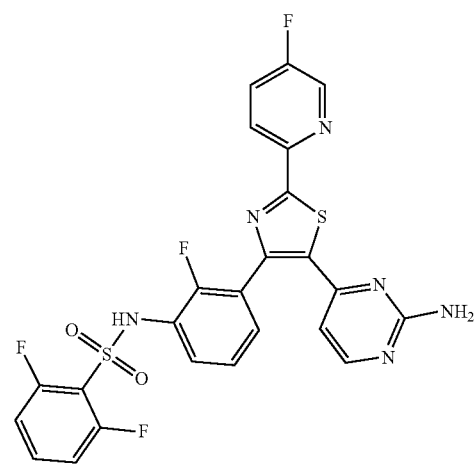

13
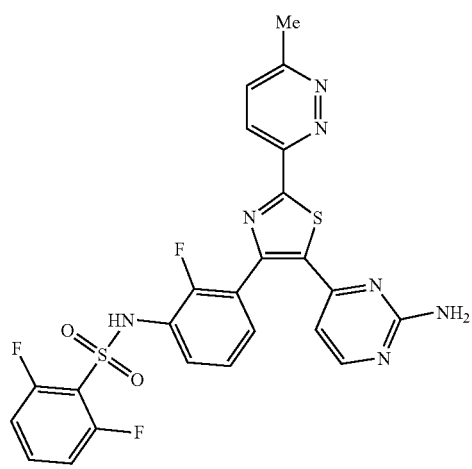
14
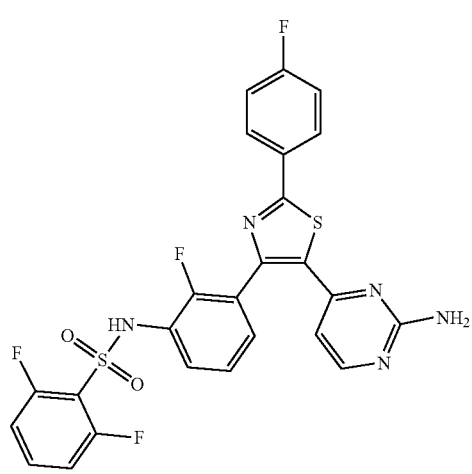
15
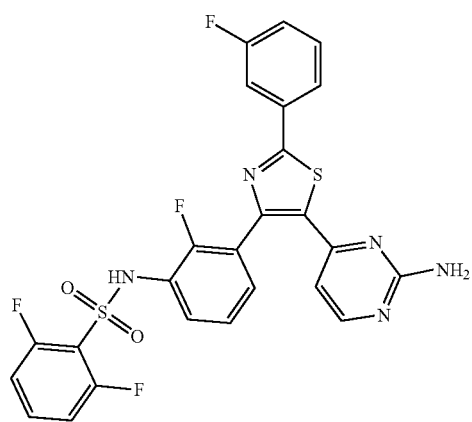
16
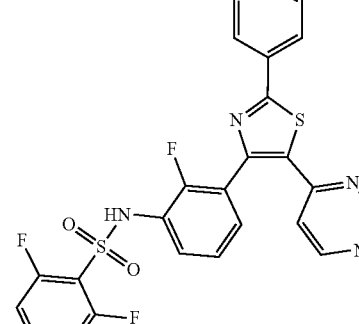
17
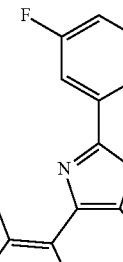
18
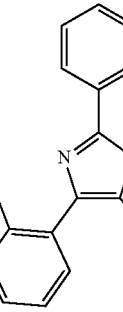
19
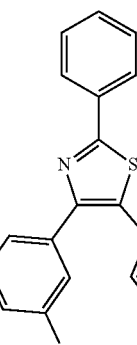

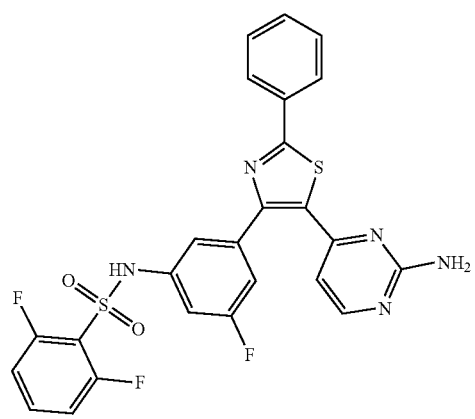
20
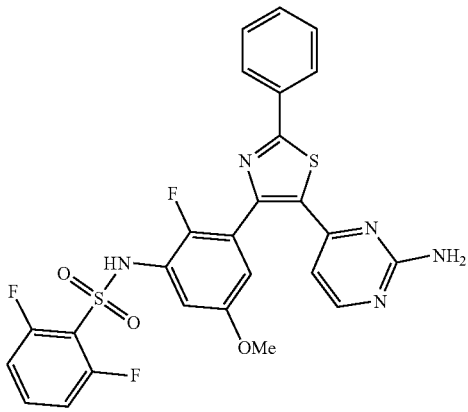
23
21
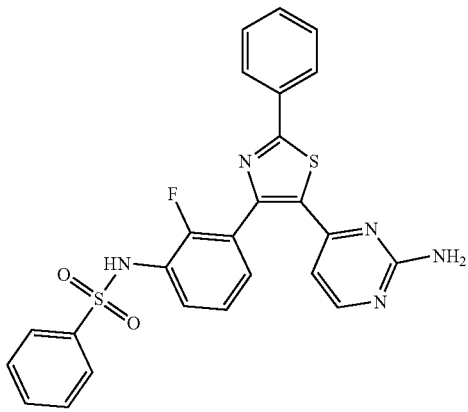
24
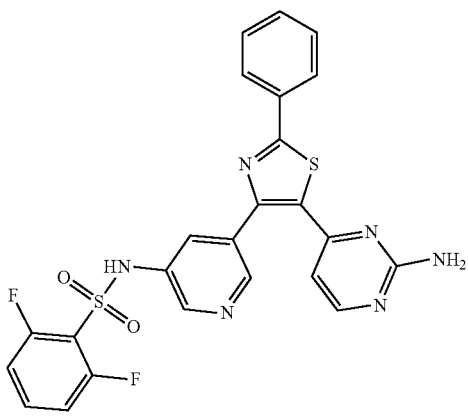
25
22
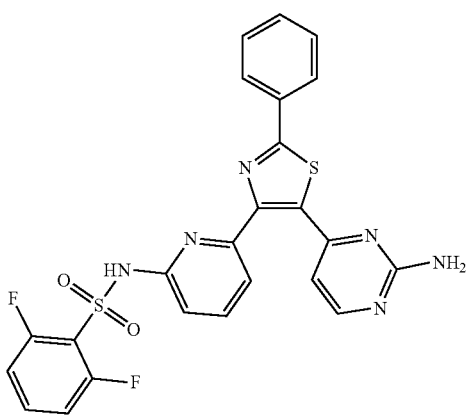
26

-continued
27
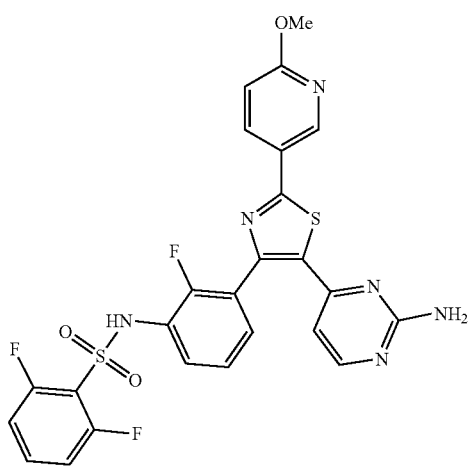
28
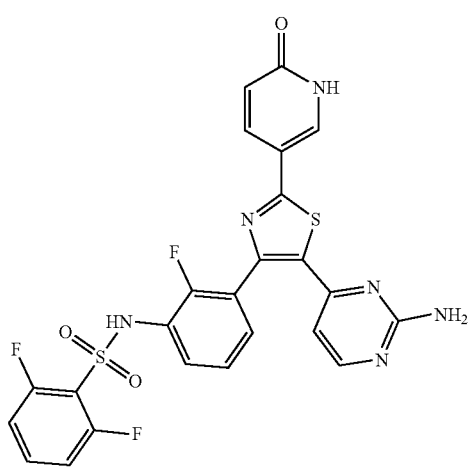
29
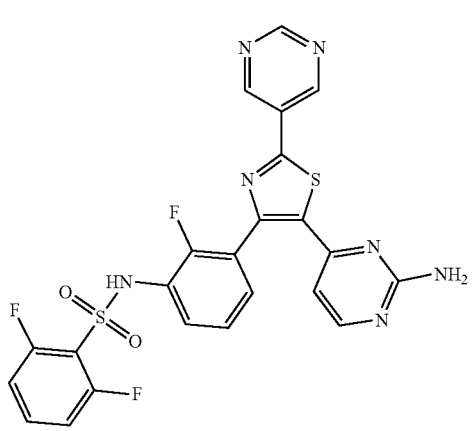
-continued
30
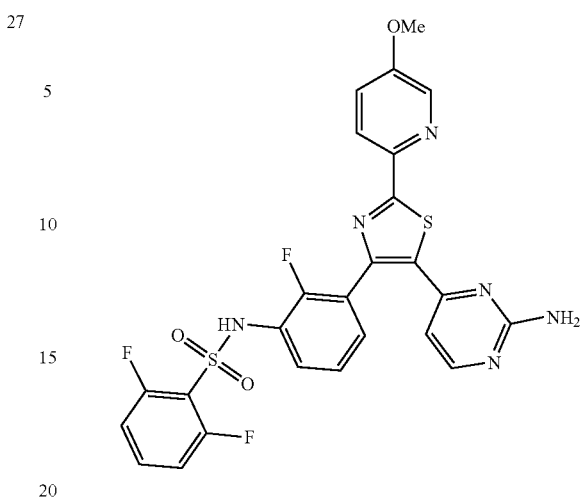
31
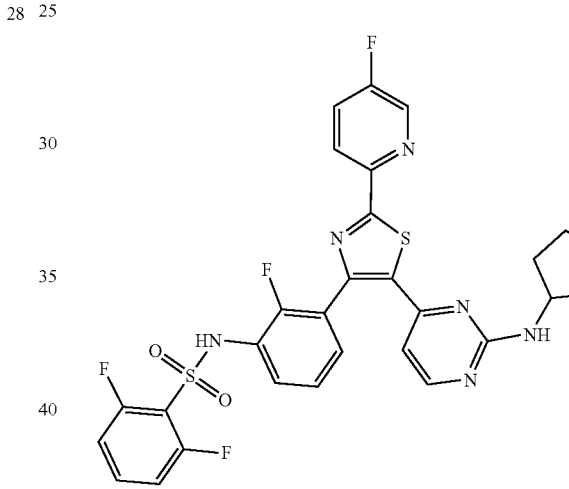
32
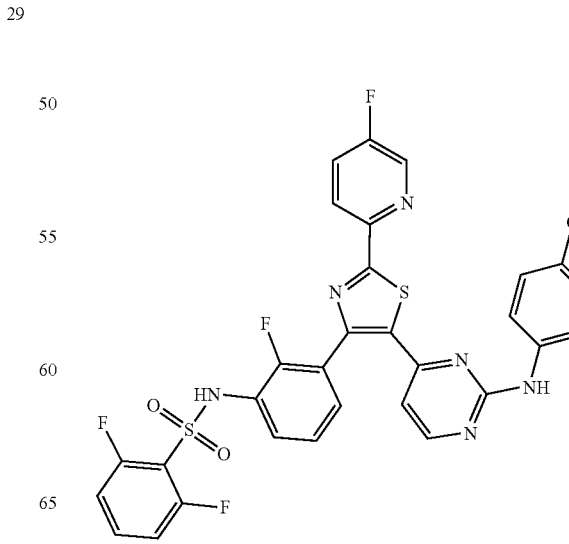

33
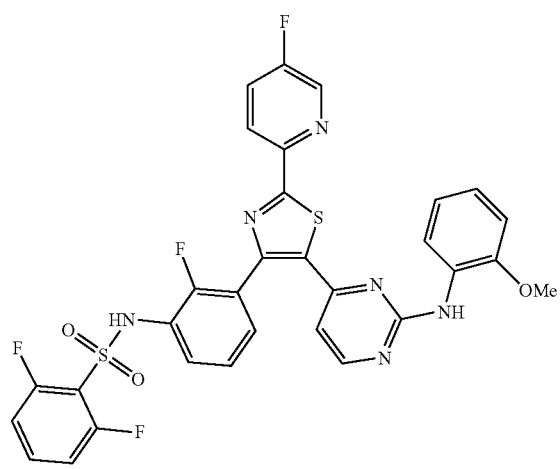
34
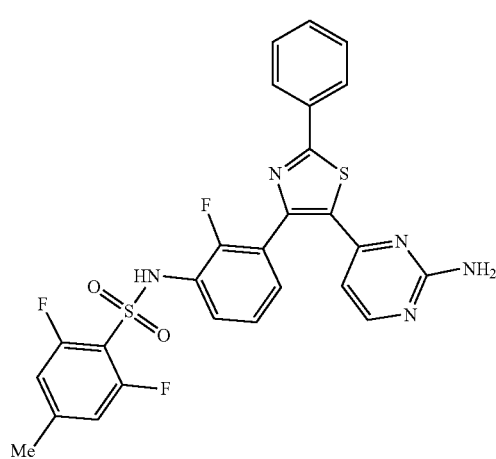
35
36
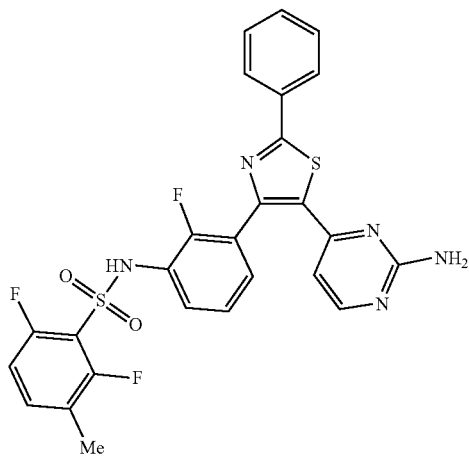
37
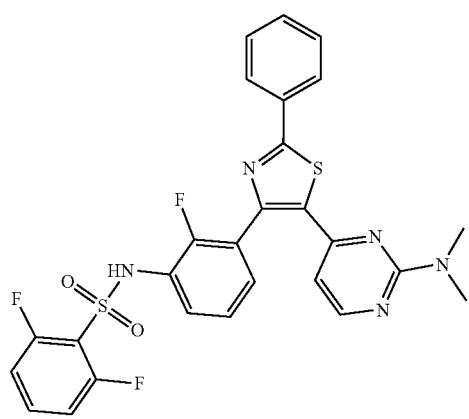
38

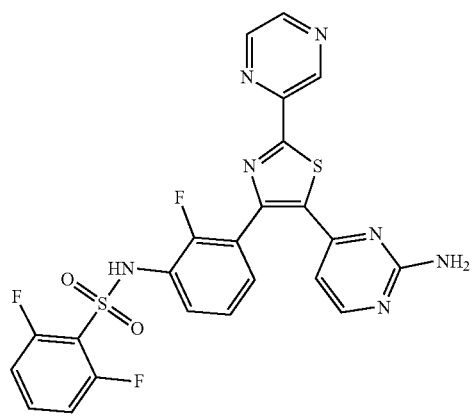
39
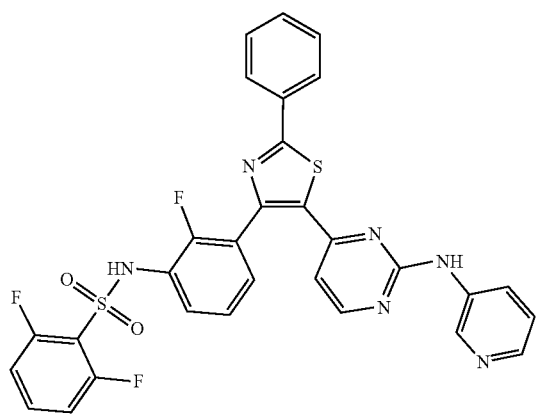
42
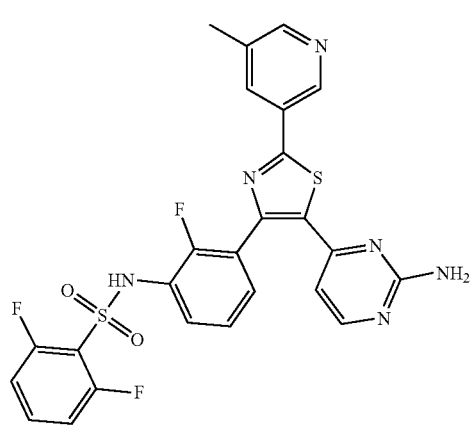
40
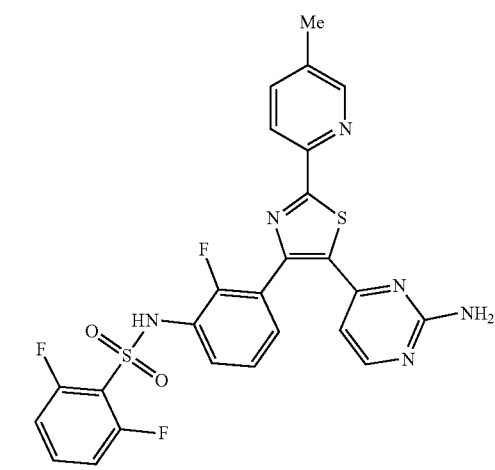
43
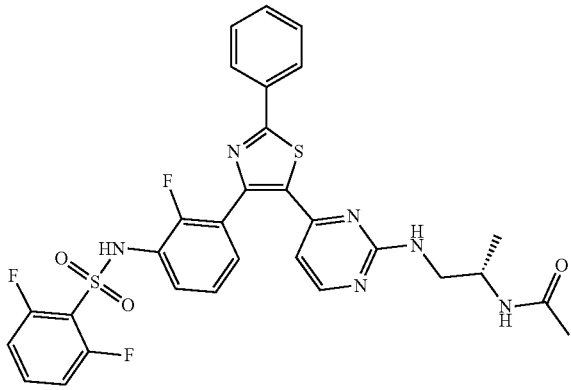
41
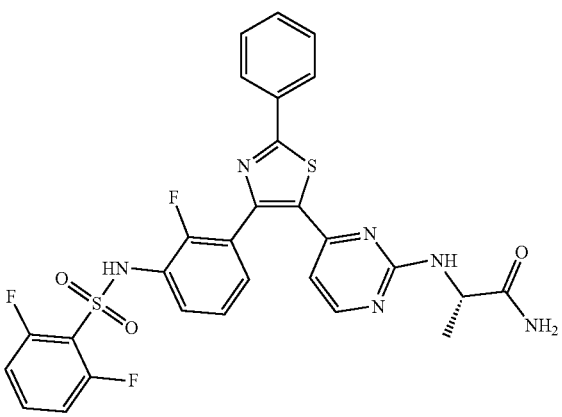
44

339
-continued
45
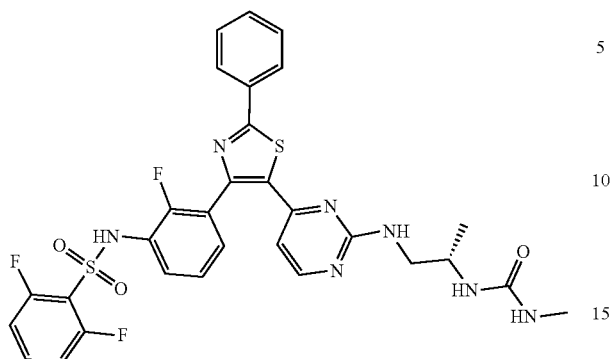
46
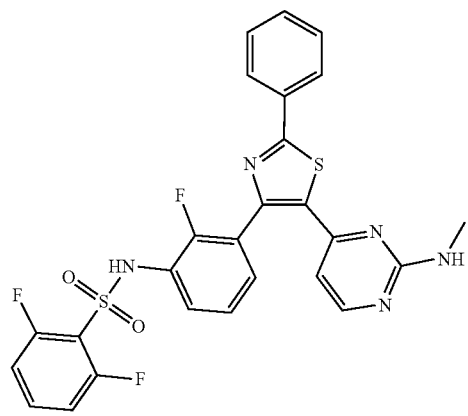
47
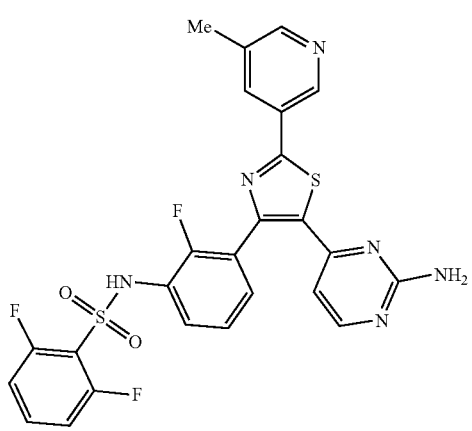
340
-continued
48
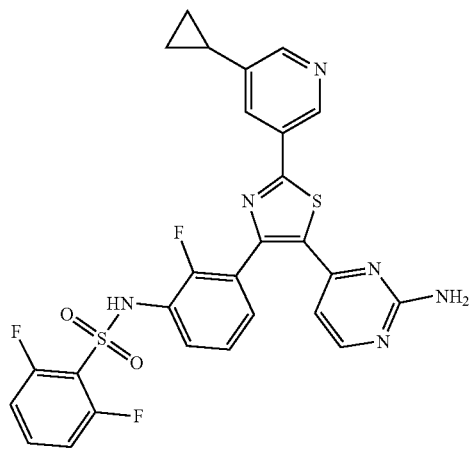
49
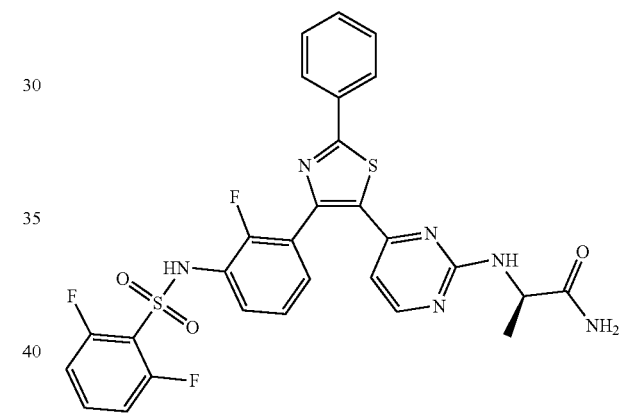
50
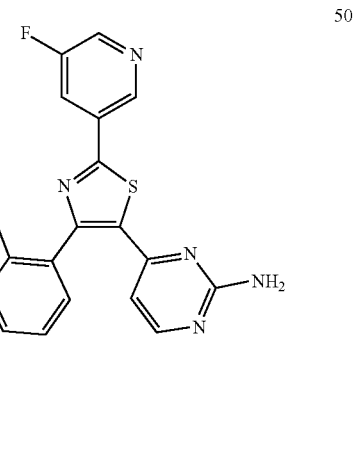

-continued
51
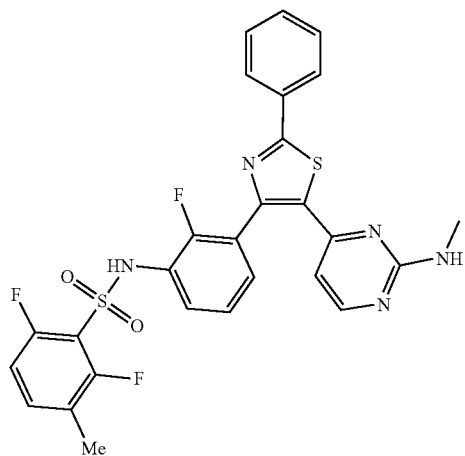
52
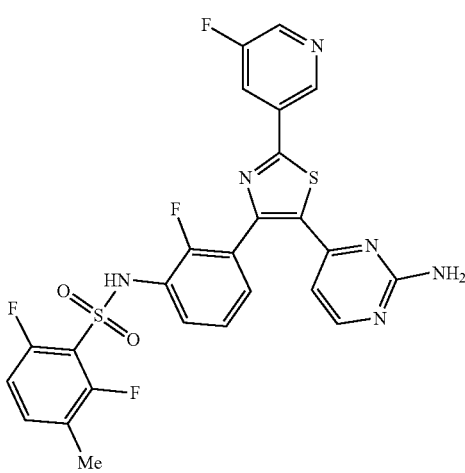
53
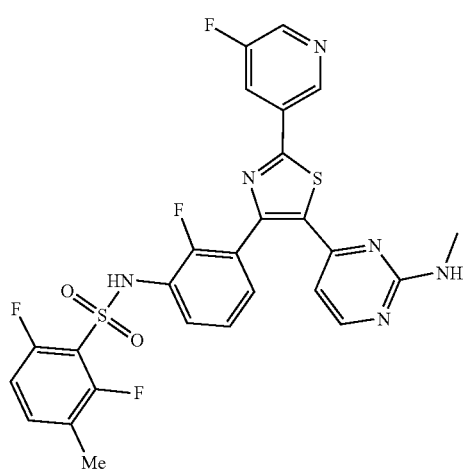
-continued
54
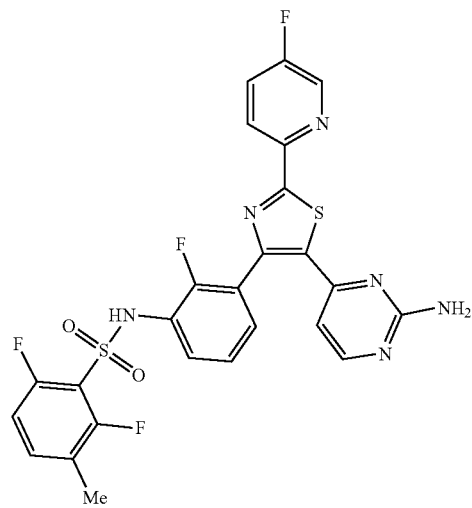
55
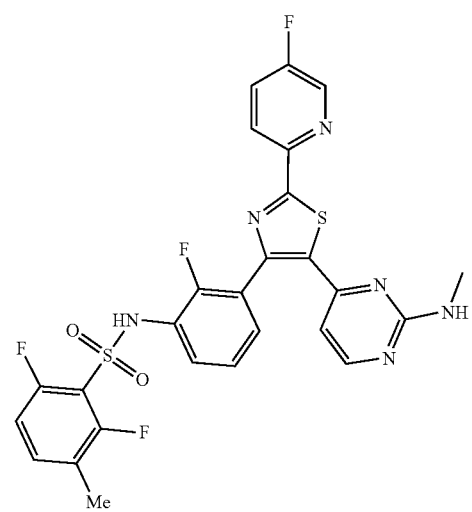
56
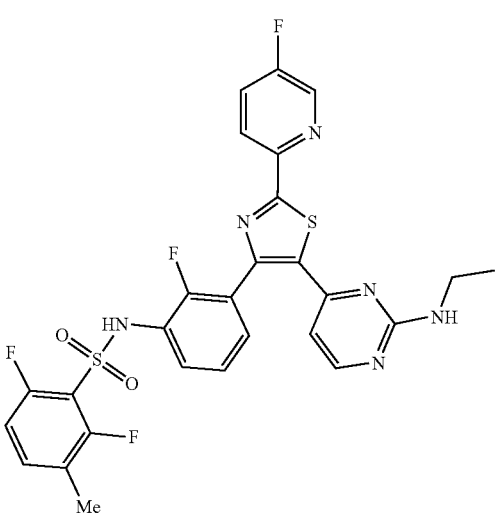

57
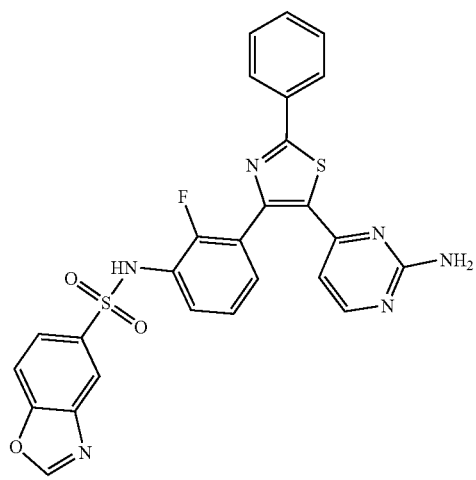
58
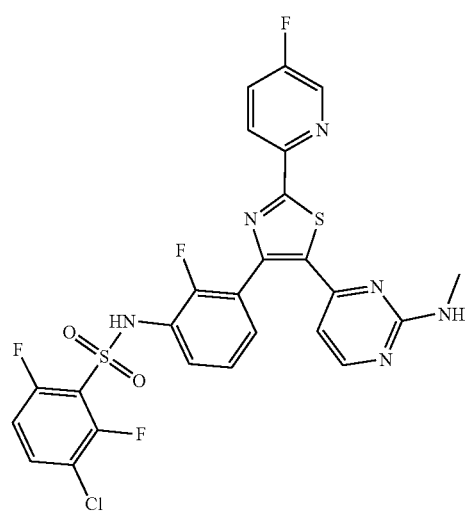
59
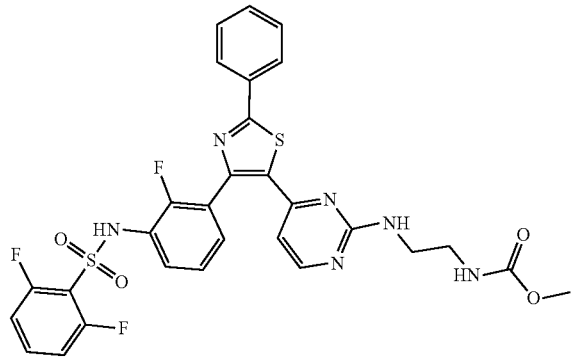
60
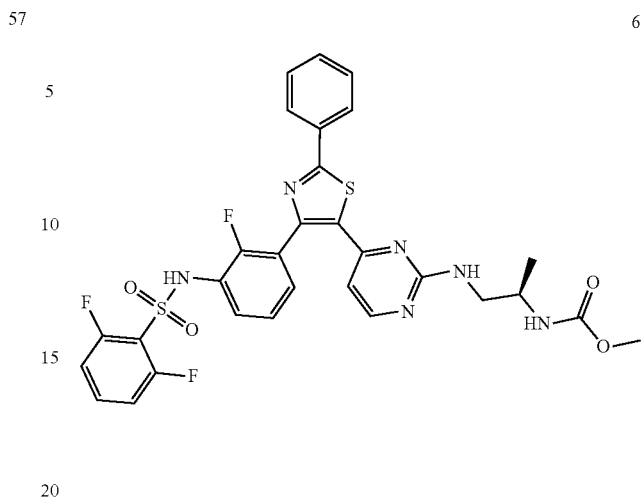
61
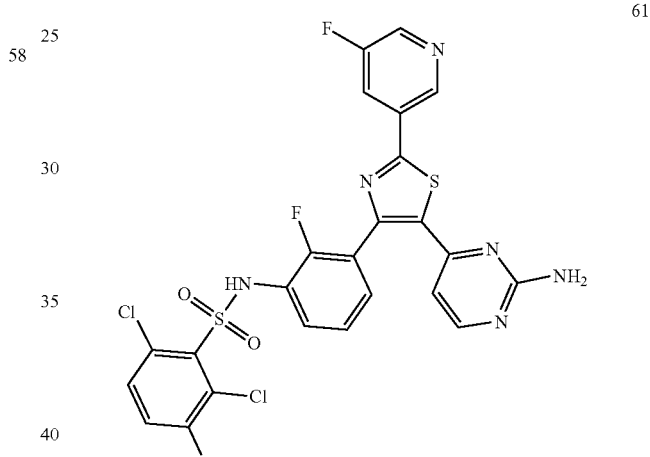
62
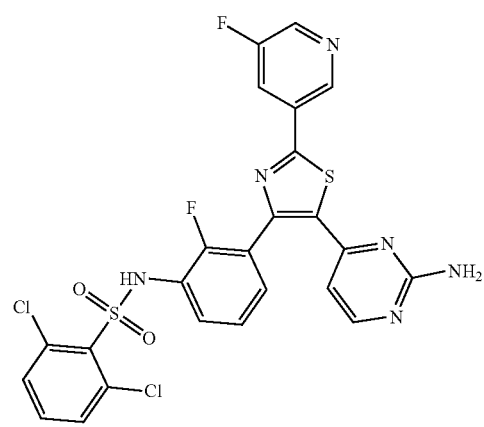

345
-continued
63
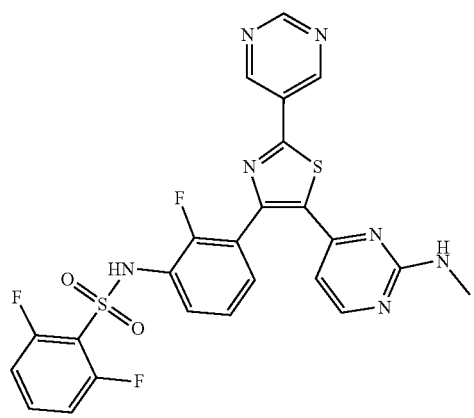
64
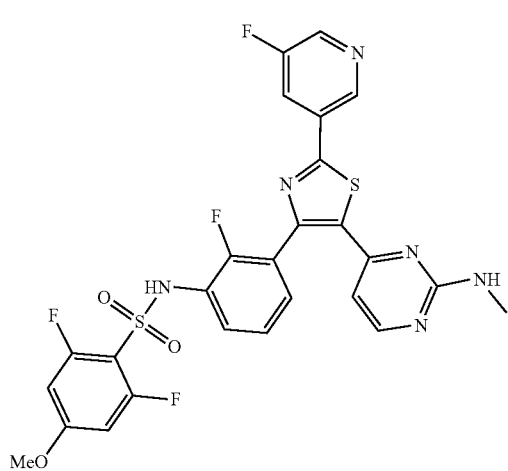
65
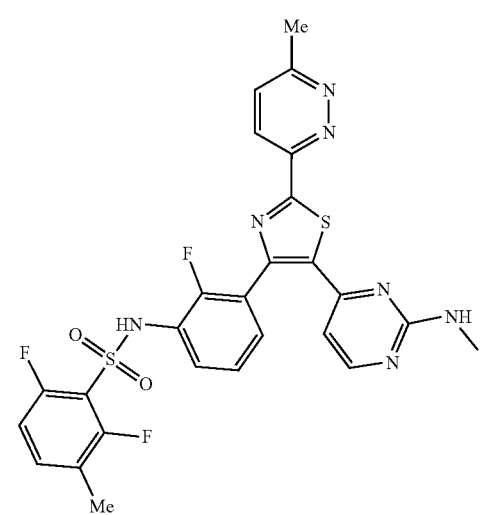
346
-continued
66
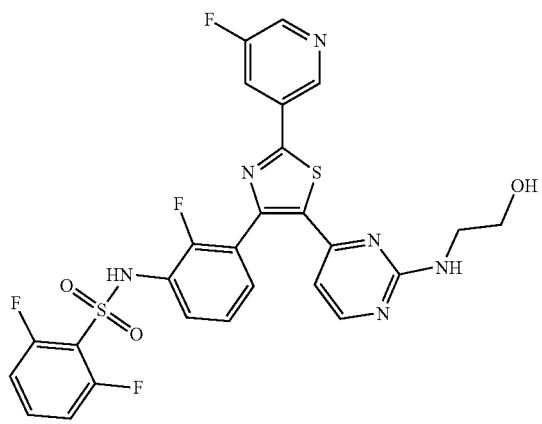
67
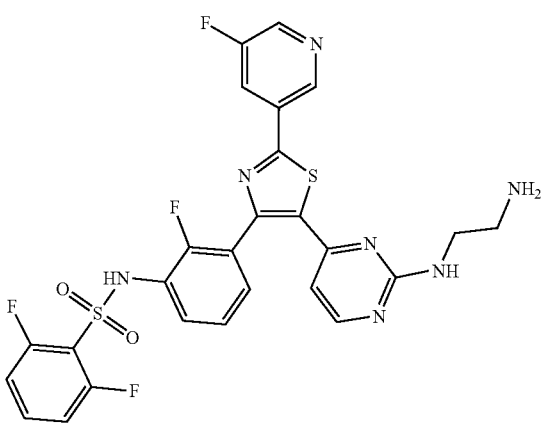
68
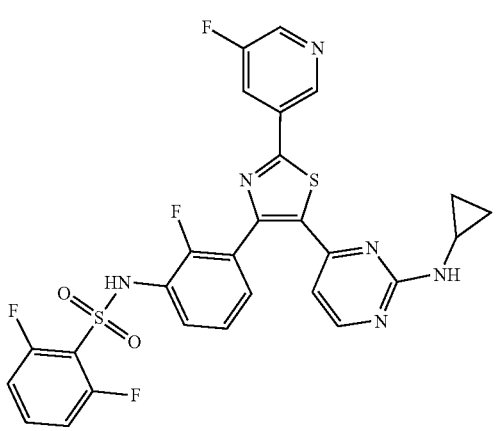

-continued
69
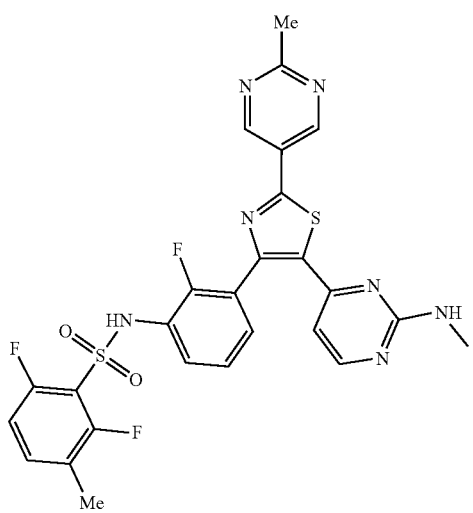
70
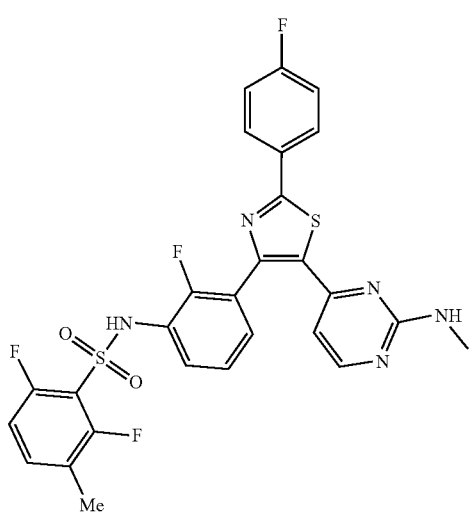
71
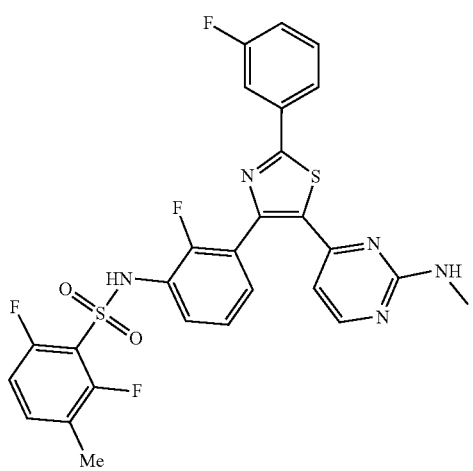
-continued
72
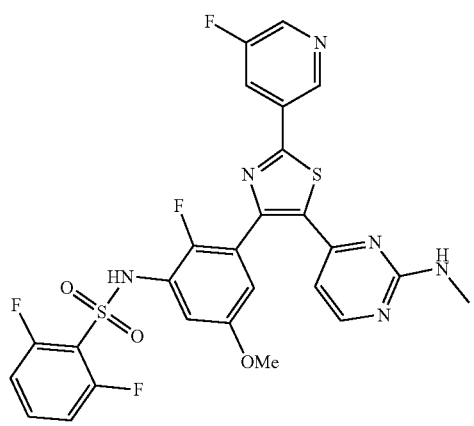
73
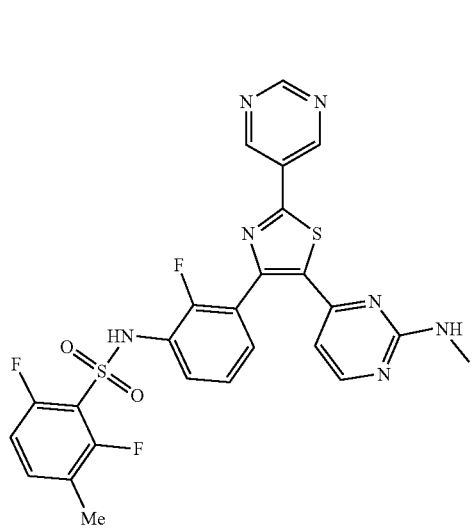
74
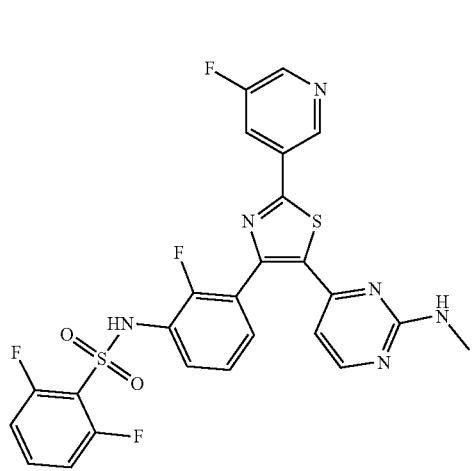

| 75 | 78 |
|---|---|
| 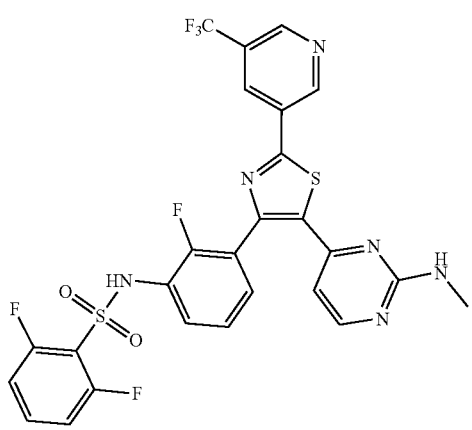 | 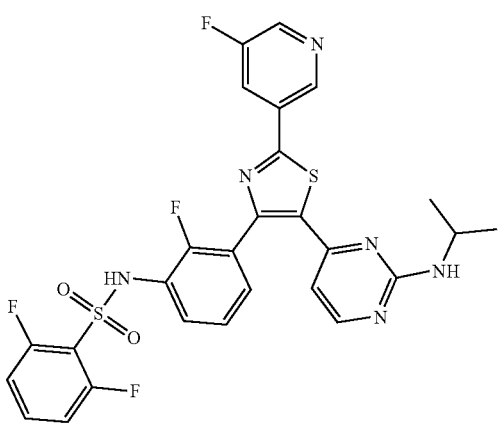 |
| 76 | 79 |
| 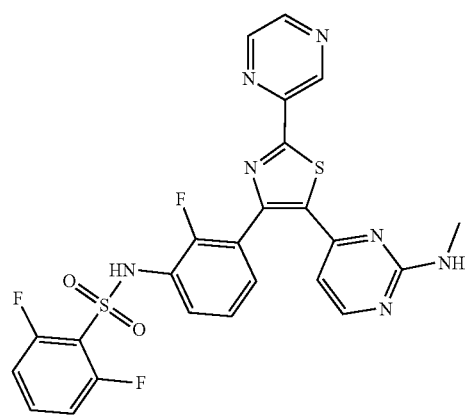 | 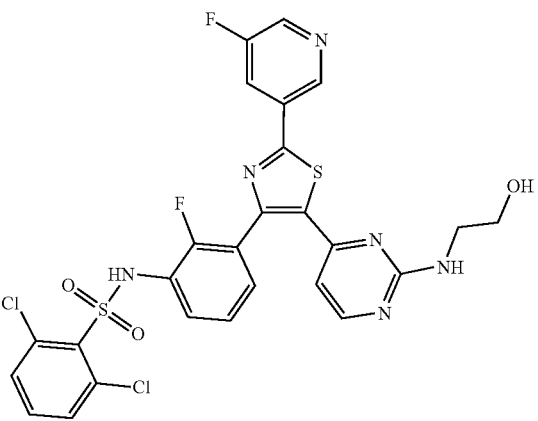 |
| 77 | 80 |
| 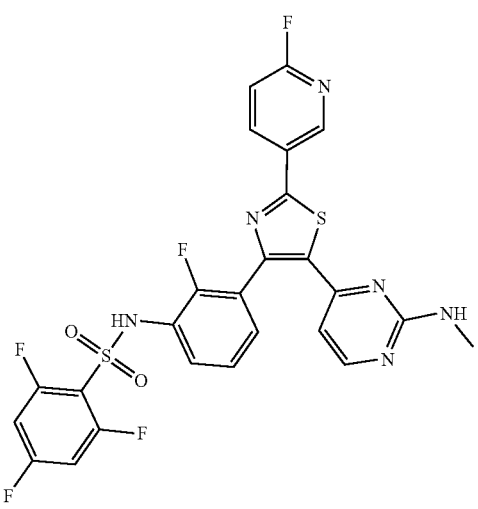 | 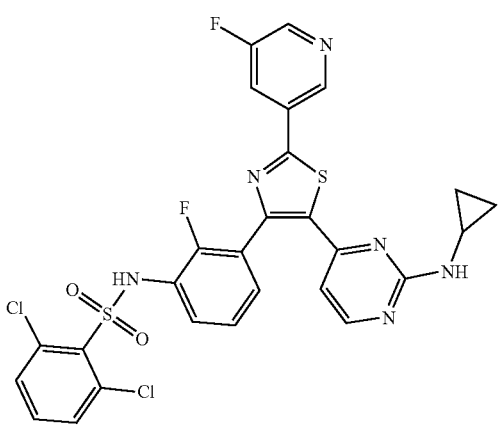 |

81 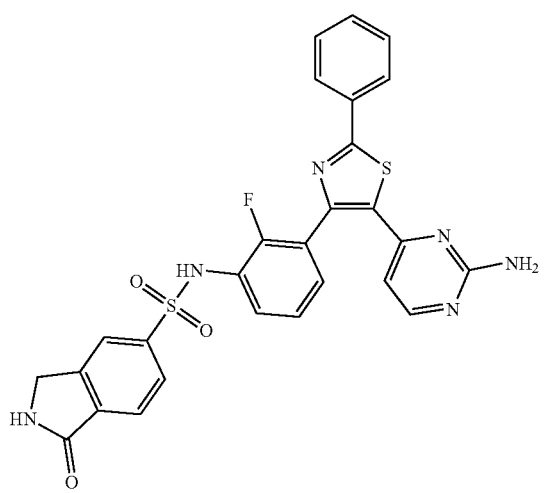
82 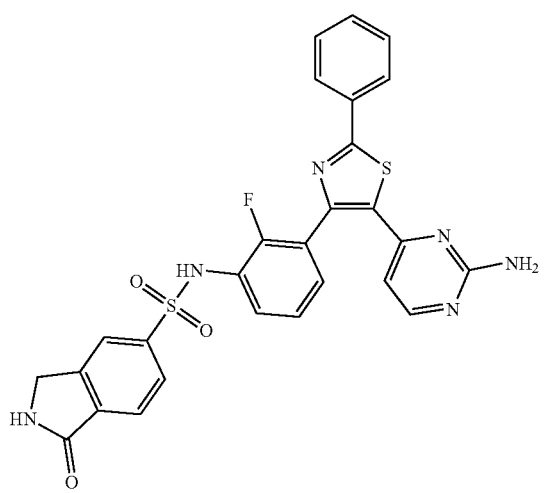
83 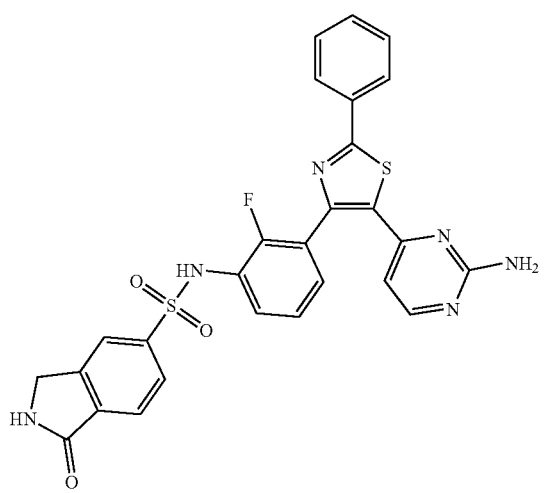
84 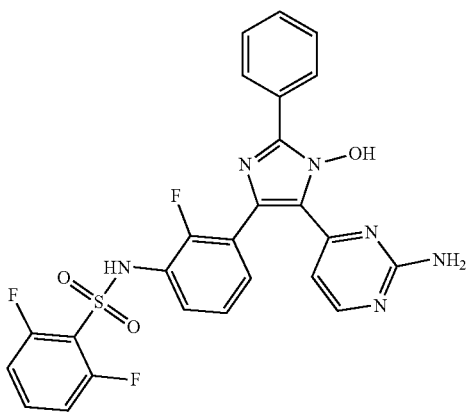
85 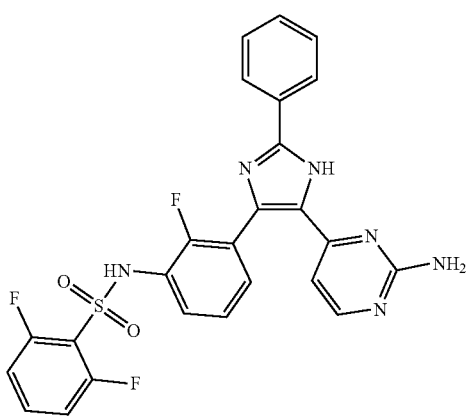
86 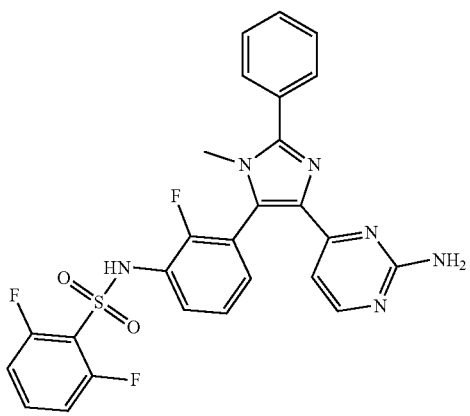
87 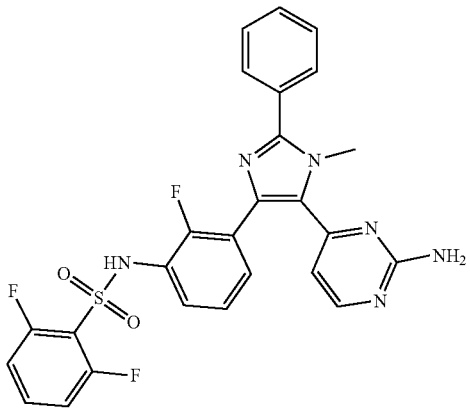

88 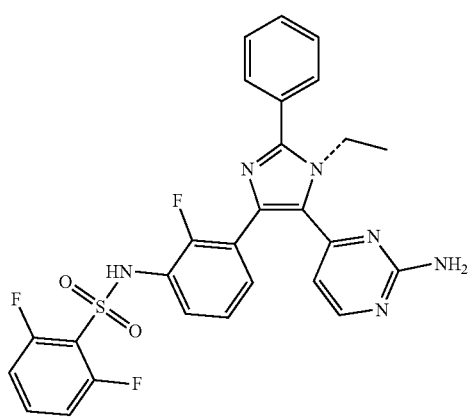
89 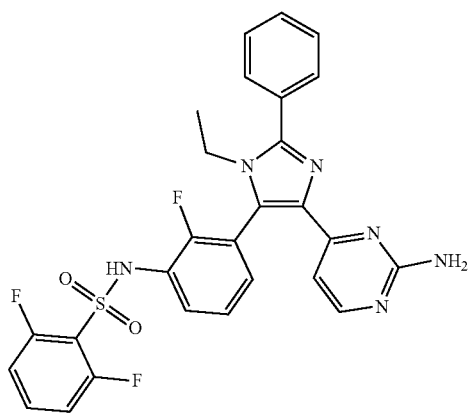
90 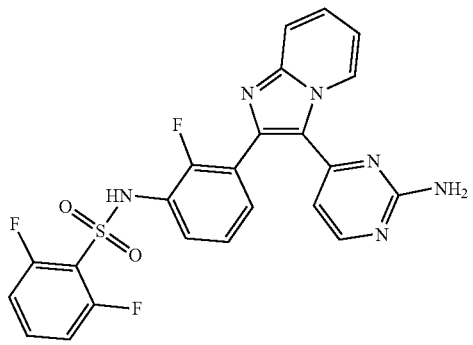
91 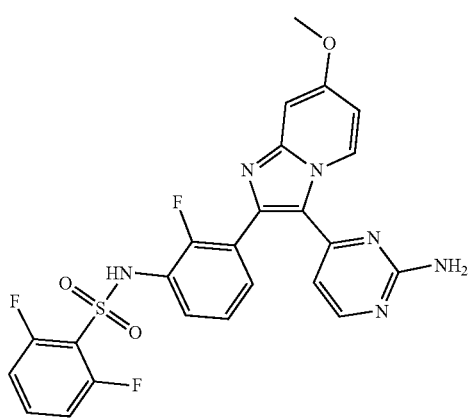
92 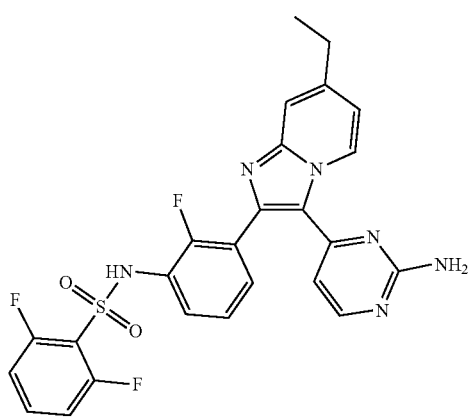
93 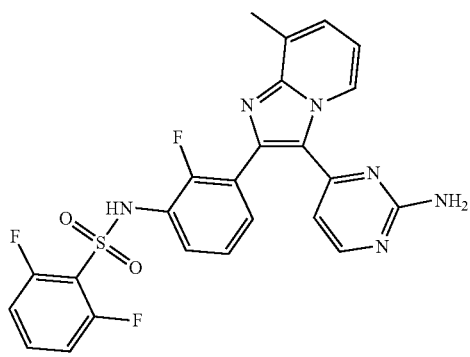
94 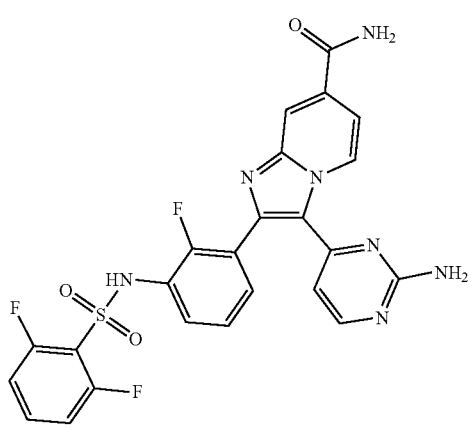
95 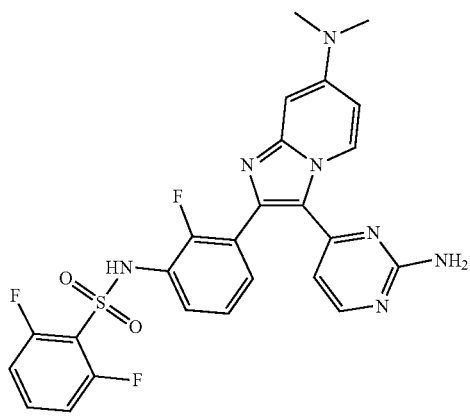

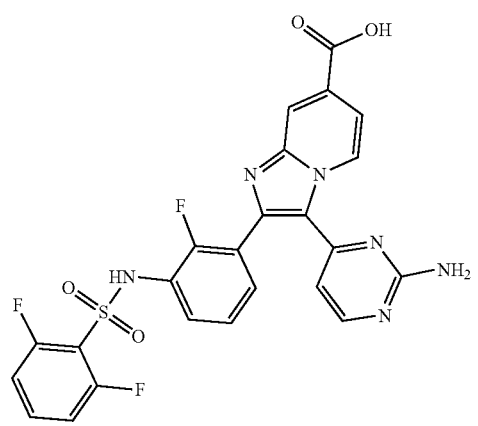
96
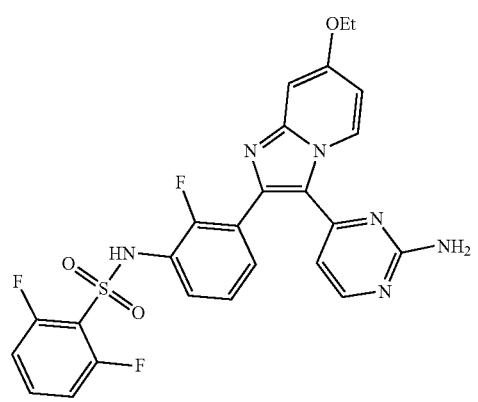
97
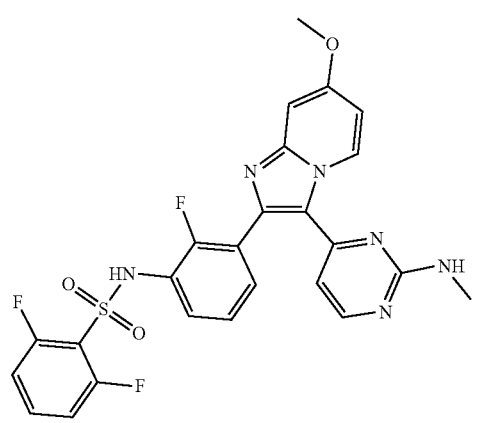
98
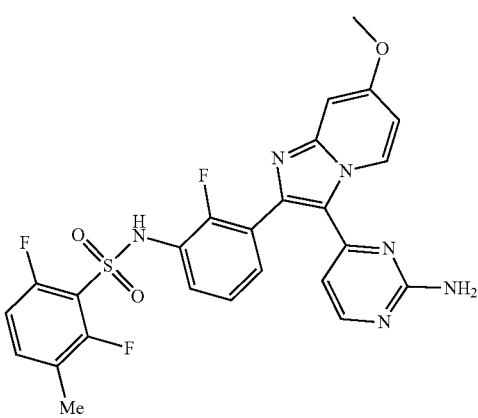
99
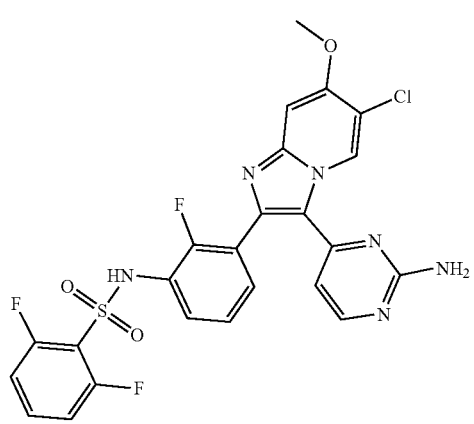
100
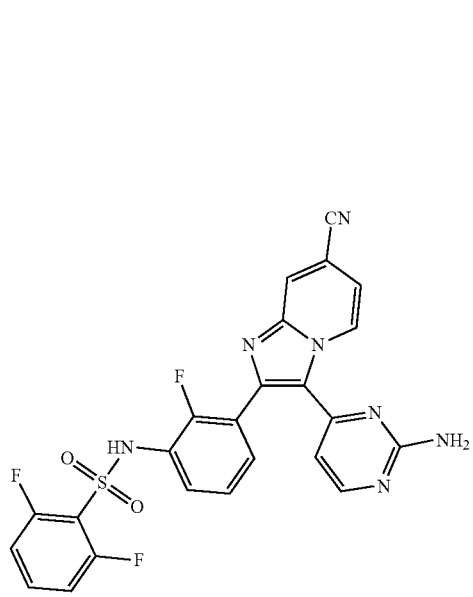
101
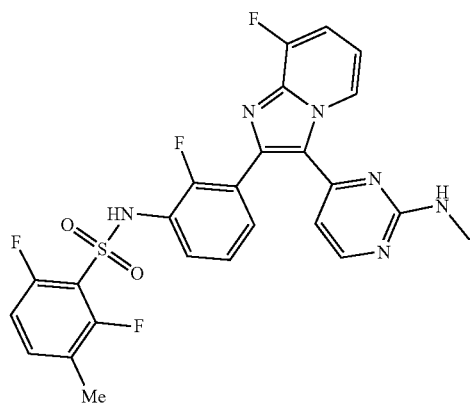
102

103
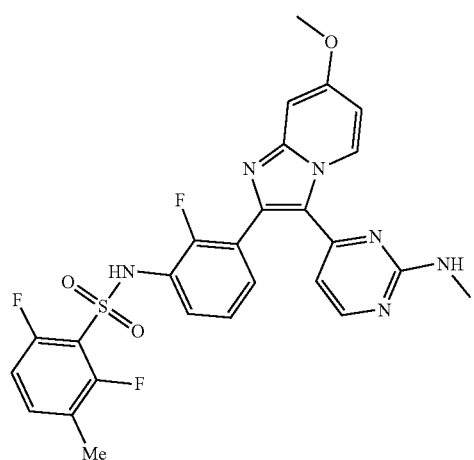
104
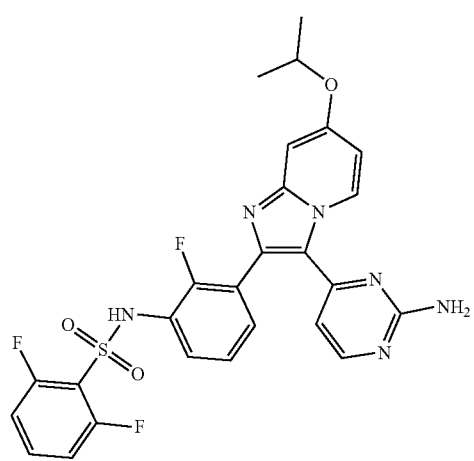
105
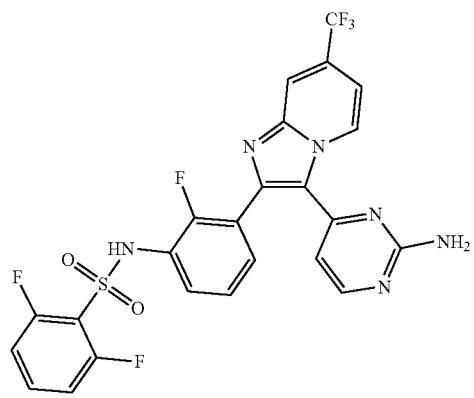
106
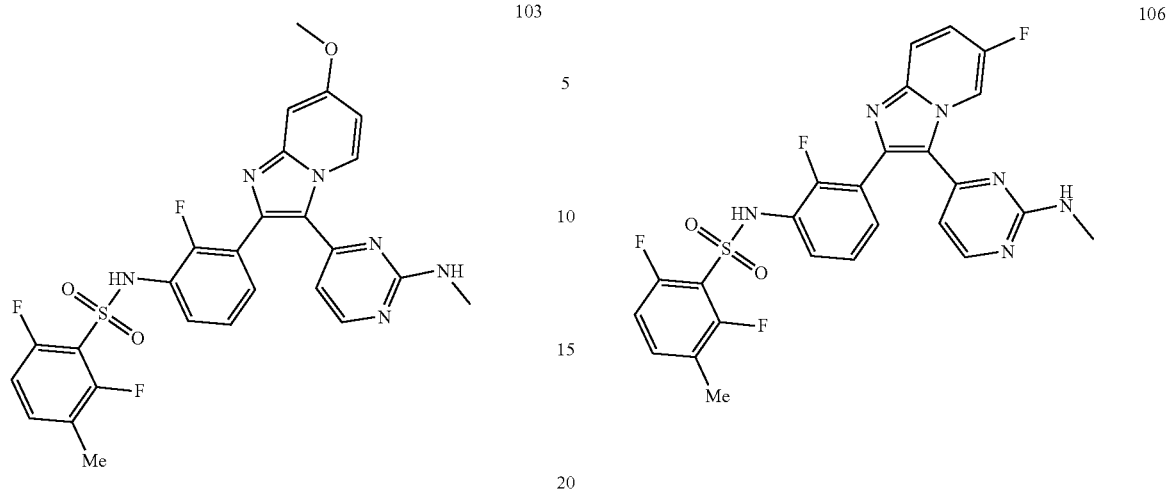
108
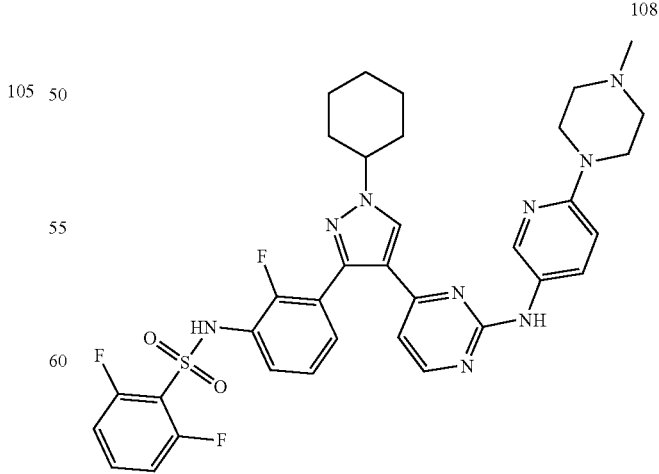

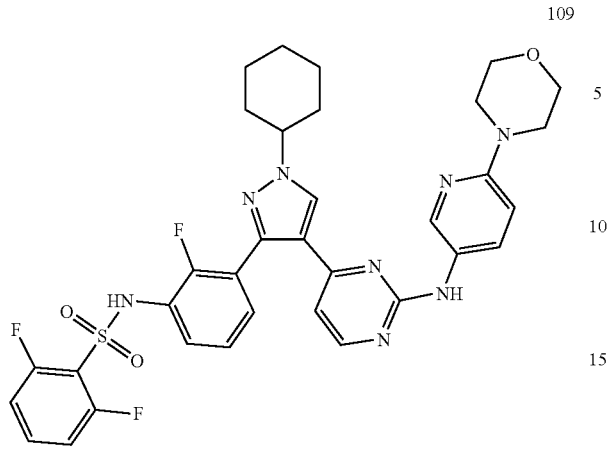
109
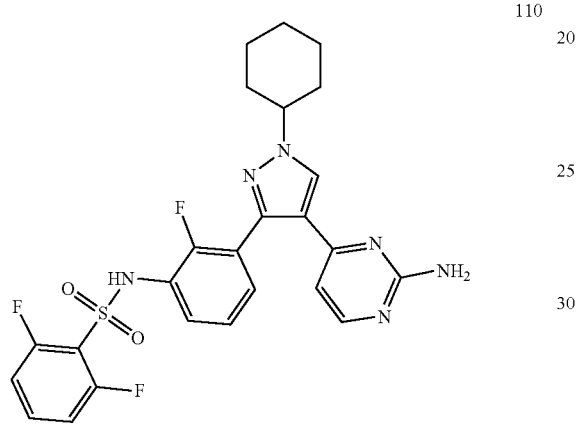
110
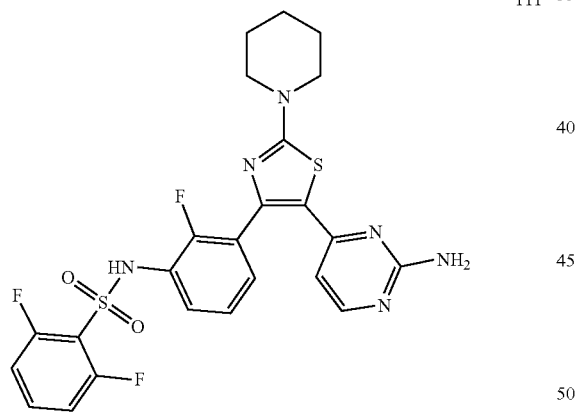
111
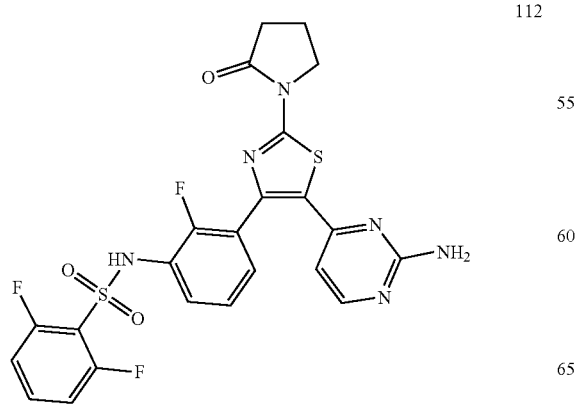
112
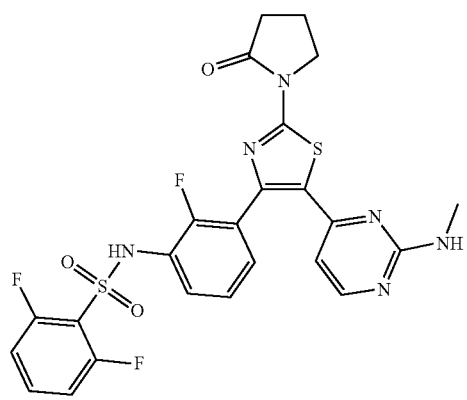
113
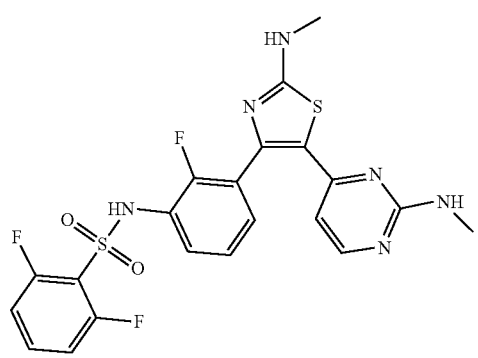
114
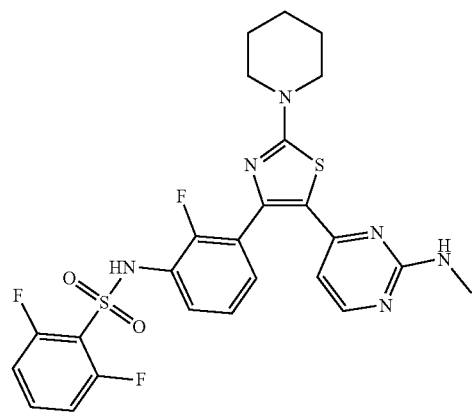
115
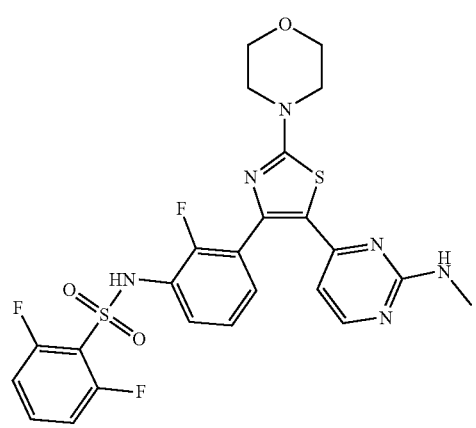
116

117
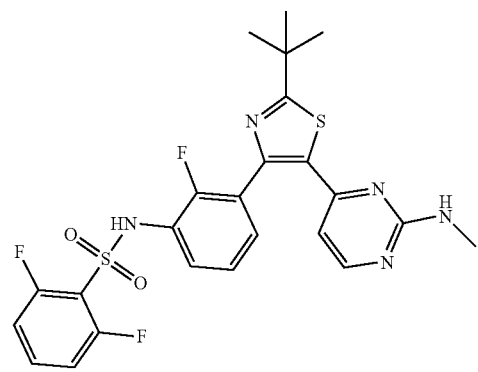
118
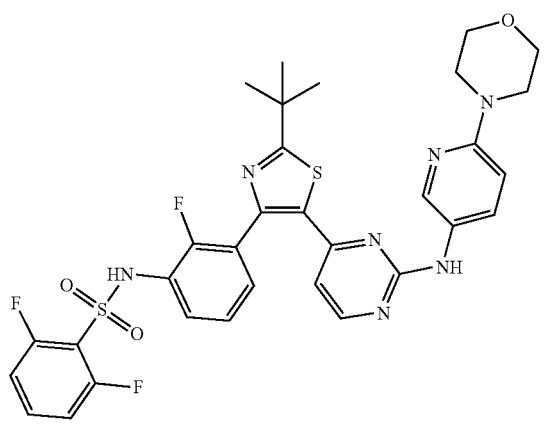
119
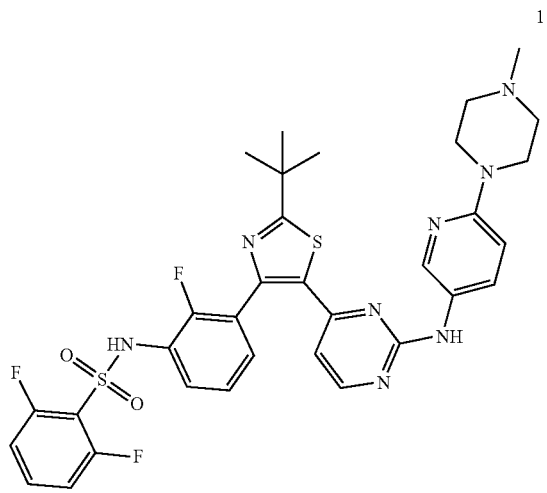
120
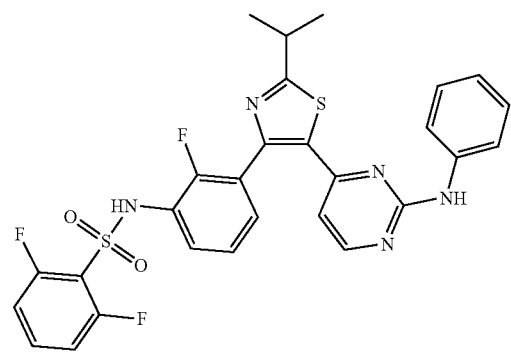
121
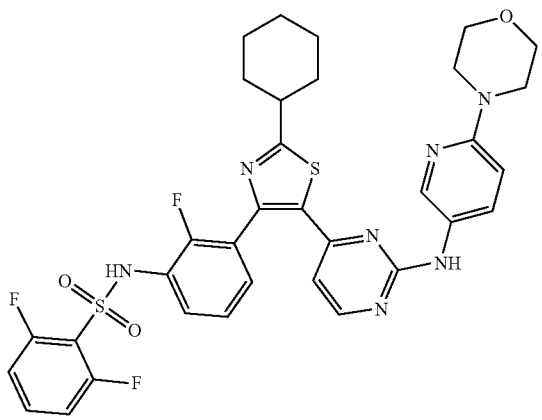
123
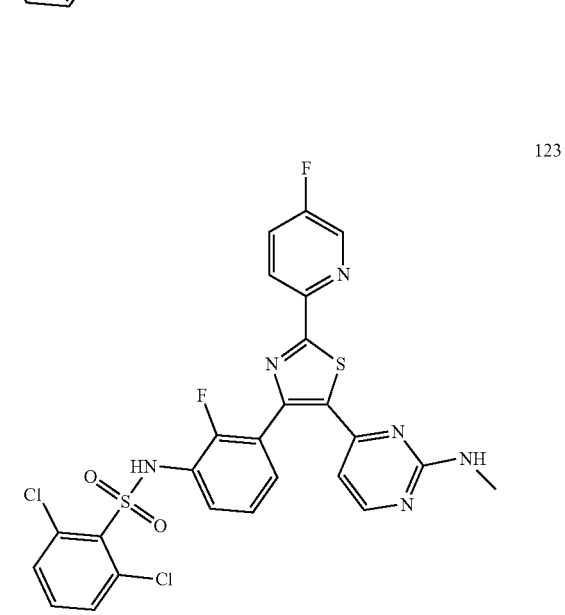
124
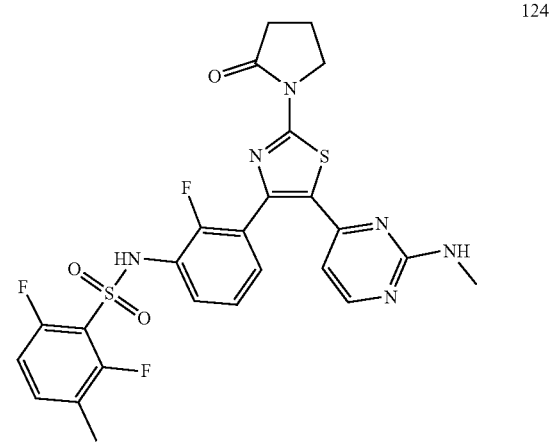

125 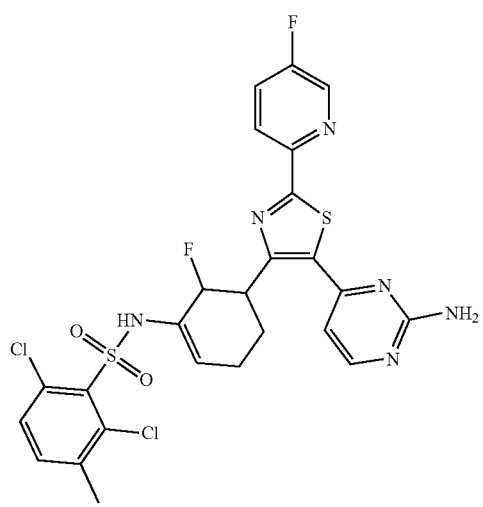
126 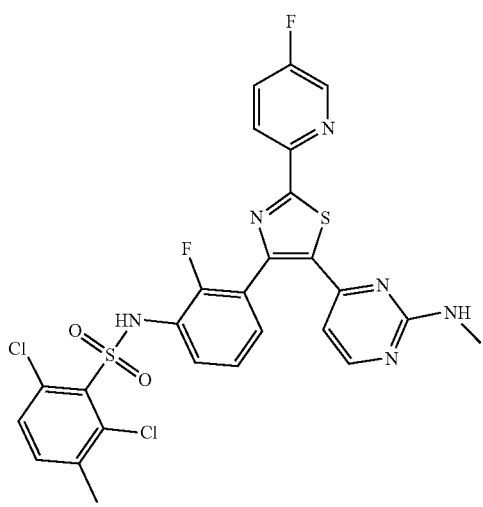
127 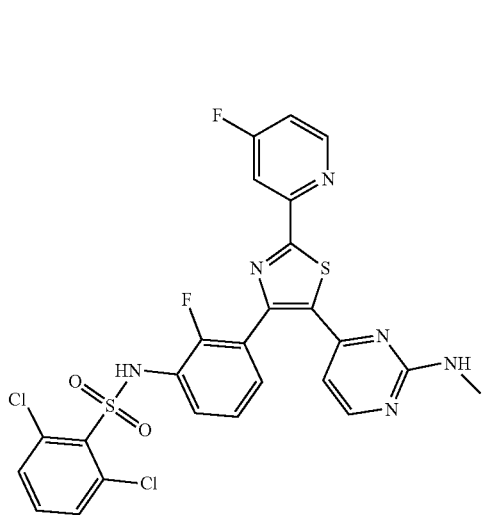
128 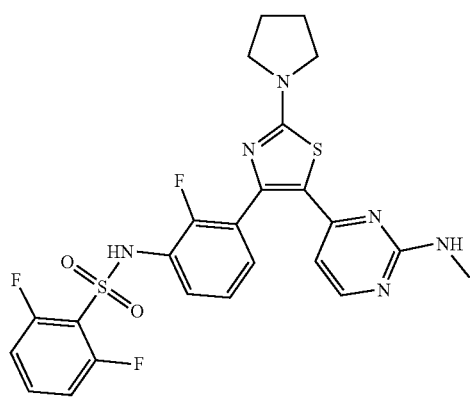
129 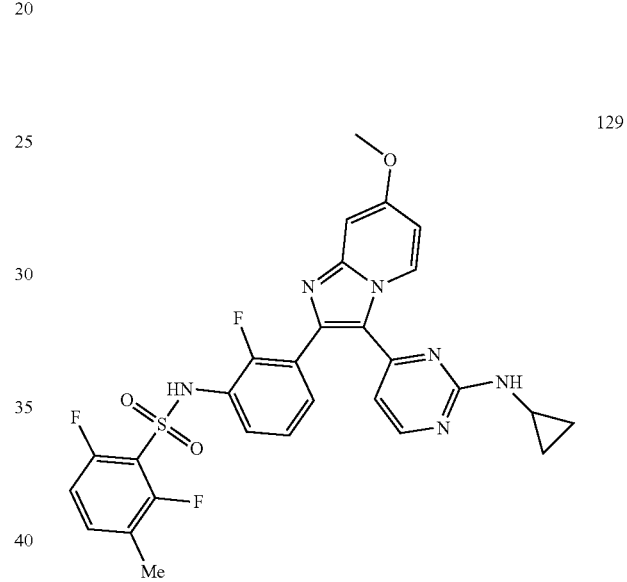
130 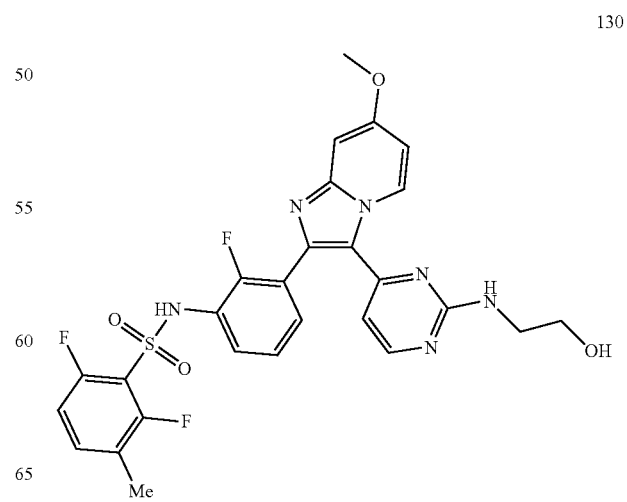

365
-continued
131
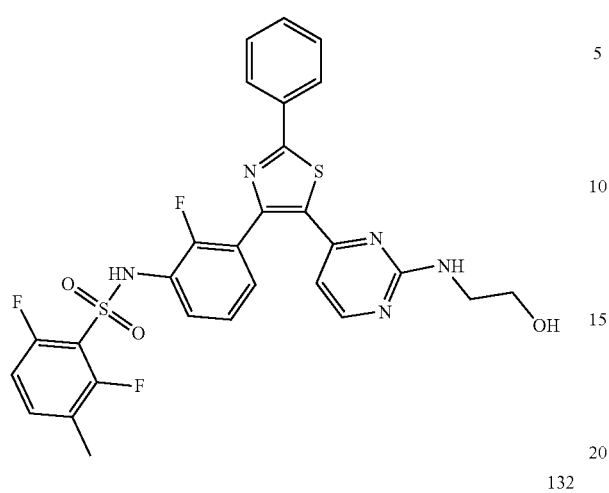
132
366
-continued
134
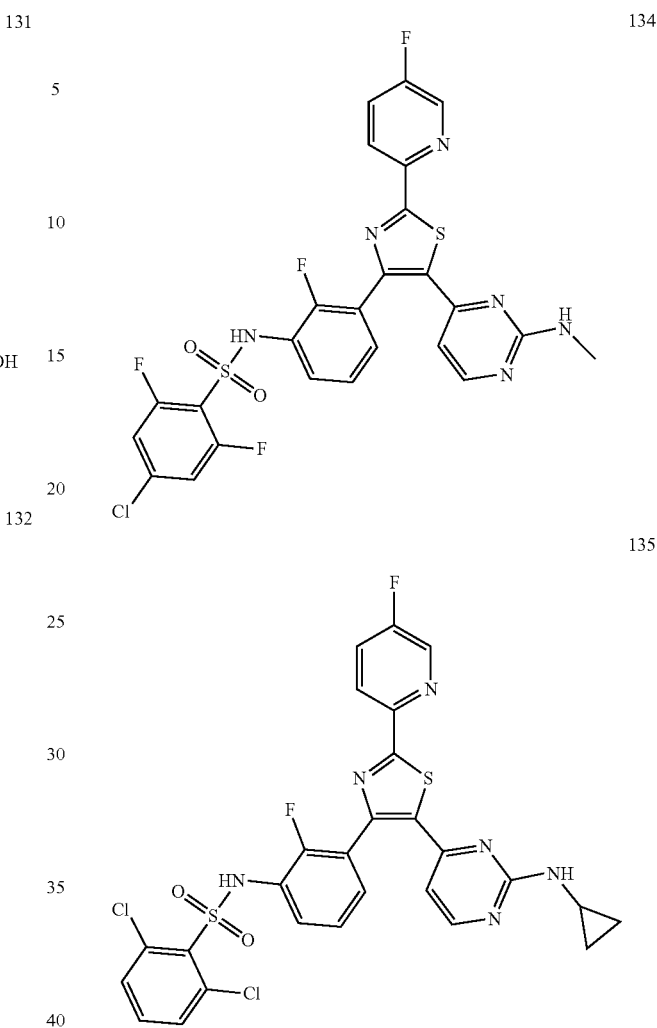
135
133
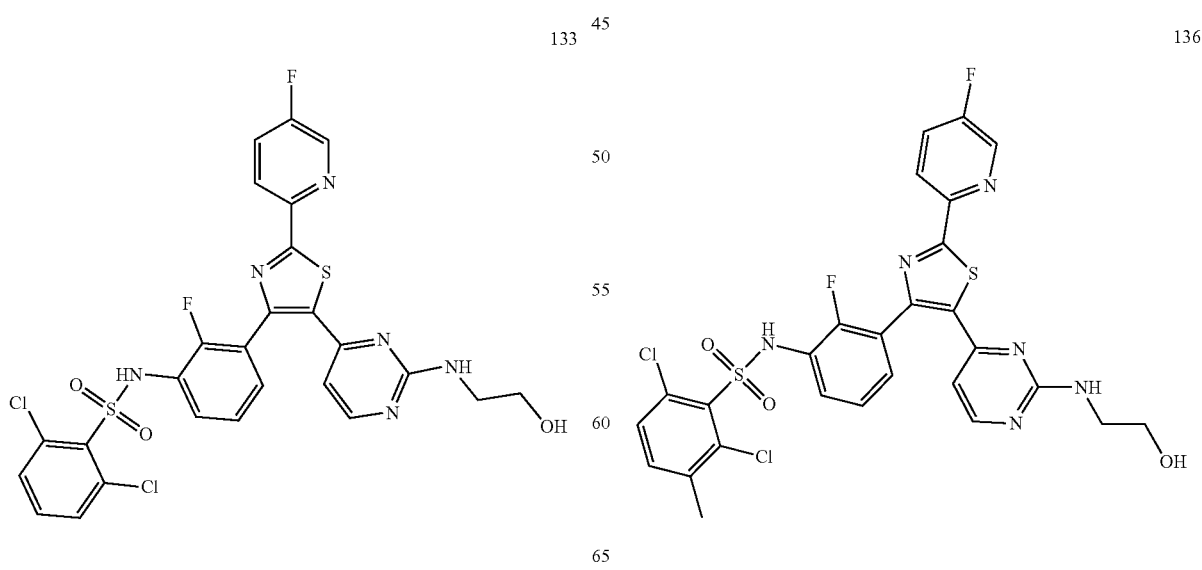
136

137
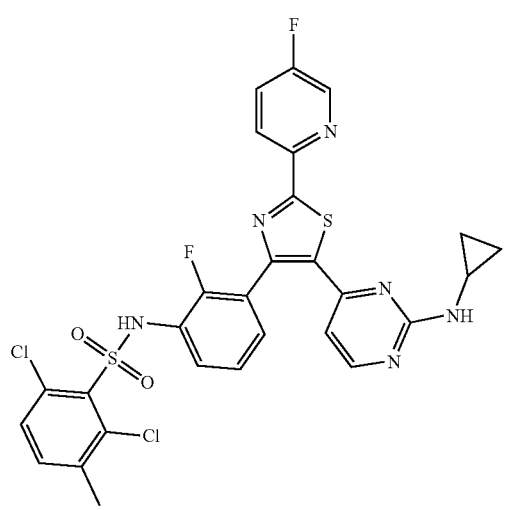
138
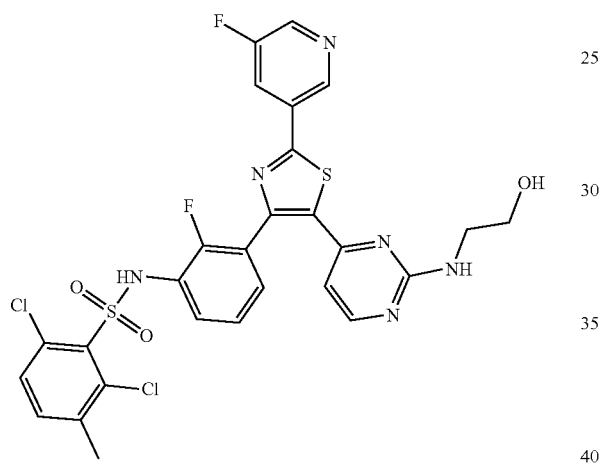
139
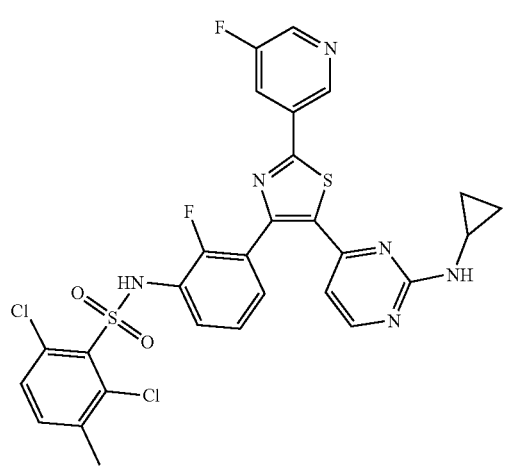
140
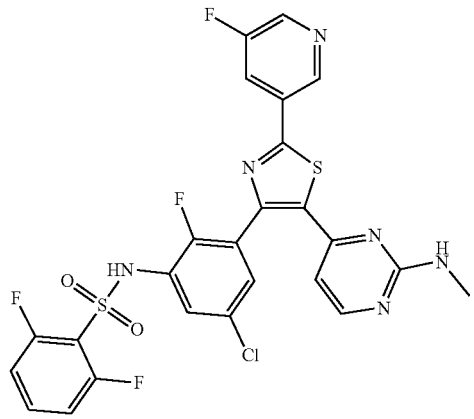
141
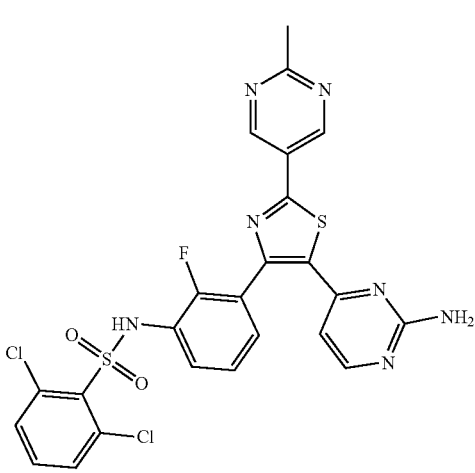
142
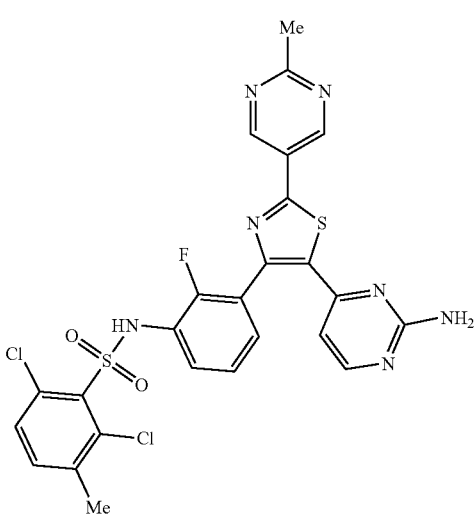

-continued
143
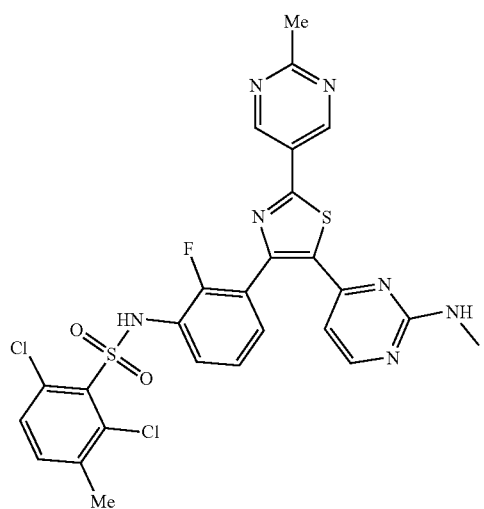
144
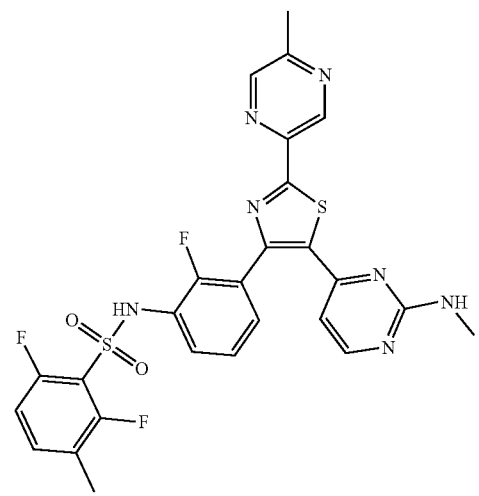
145
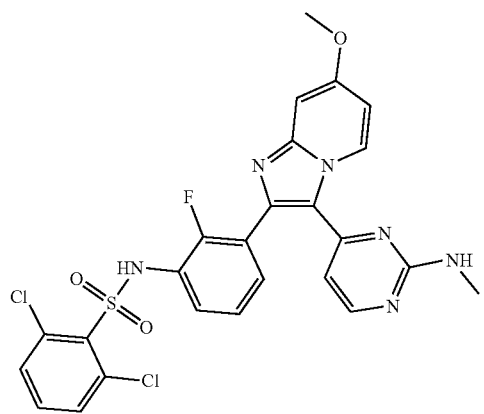
-continued
146
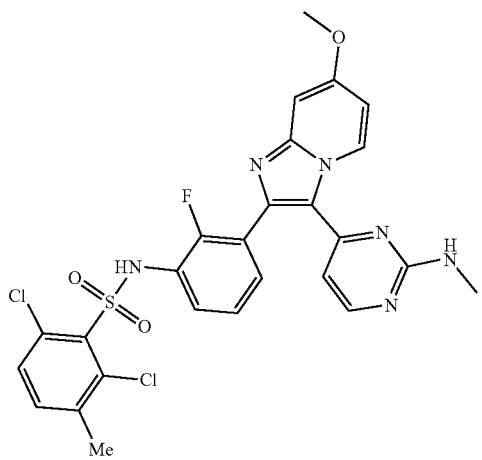
147
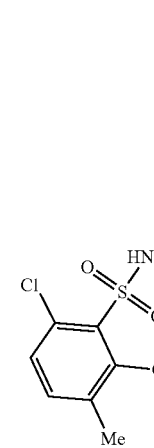
148
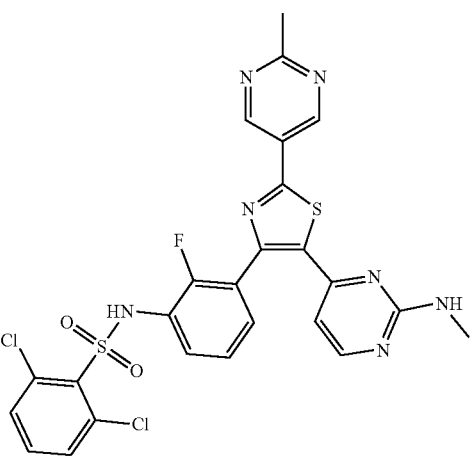

371
-continued
149
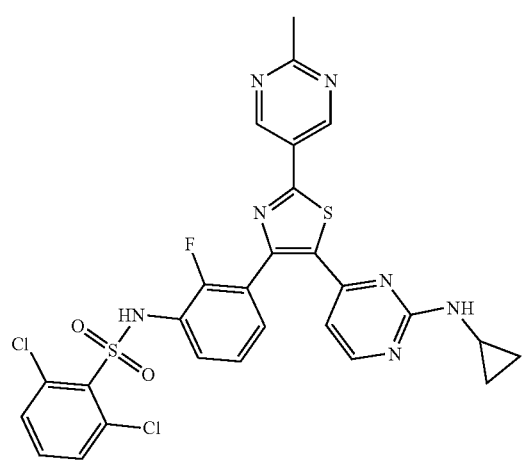
150
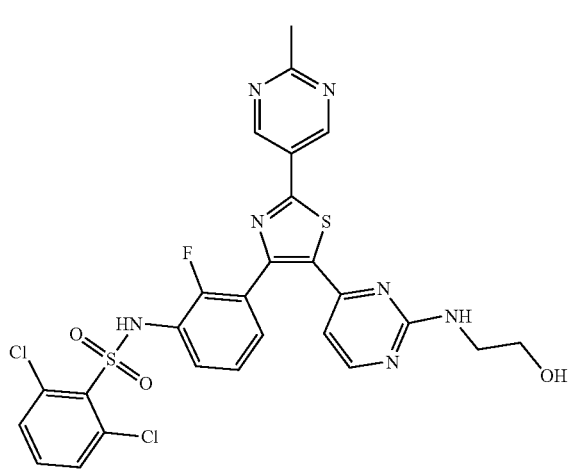
151
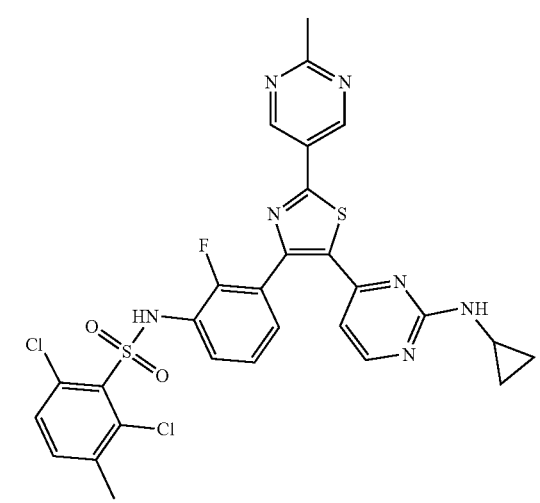
372
-continued
152
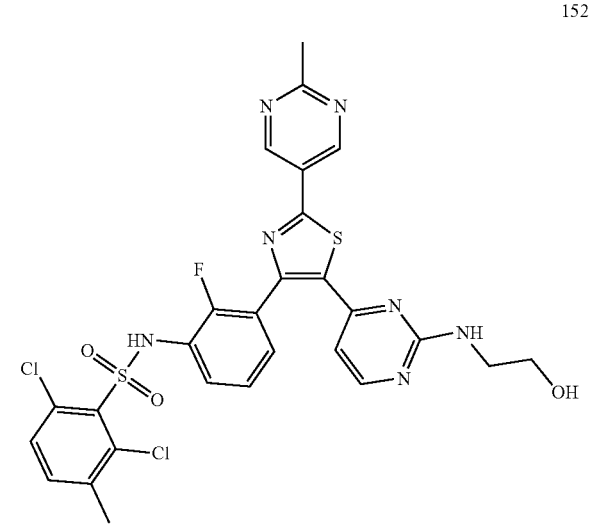
153
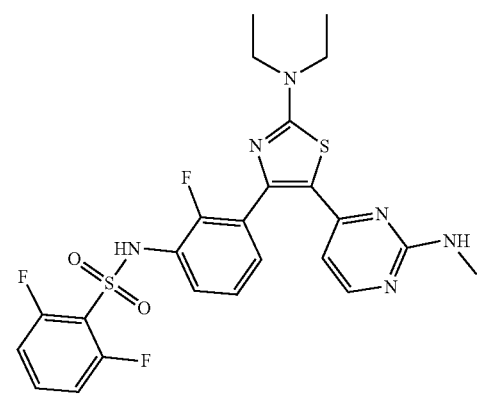
154
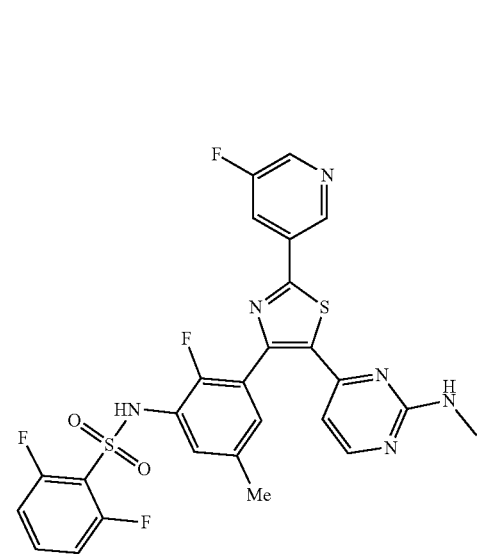

155
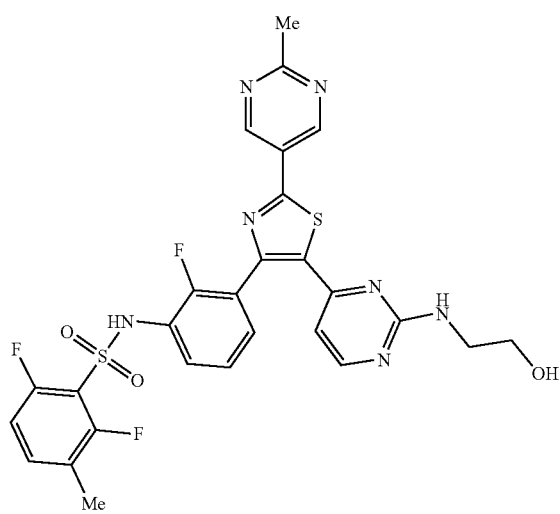
156
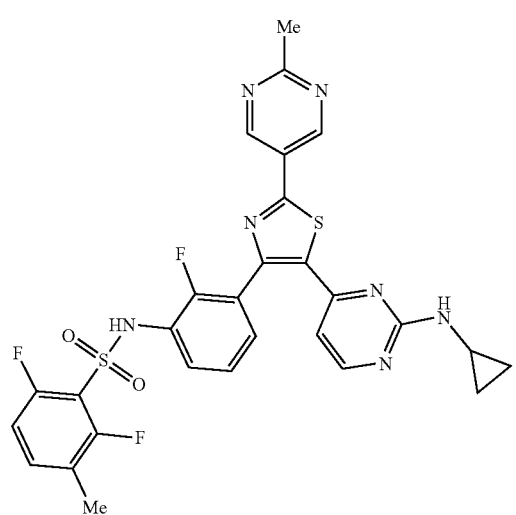
157
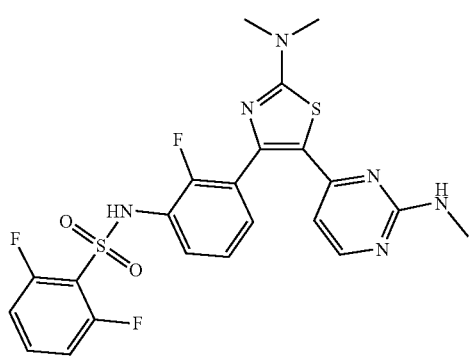
158
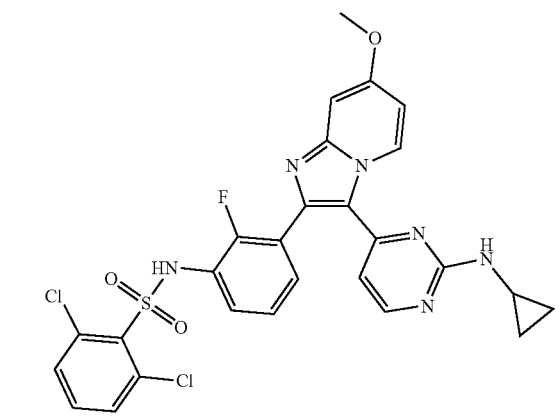
159
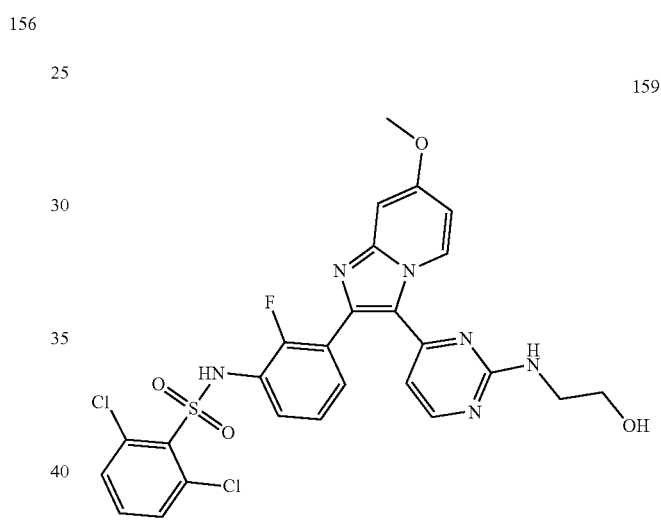
160
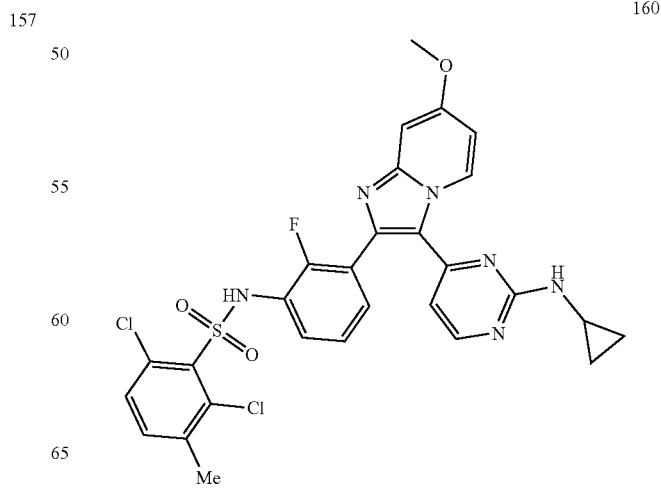

161 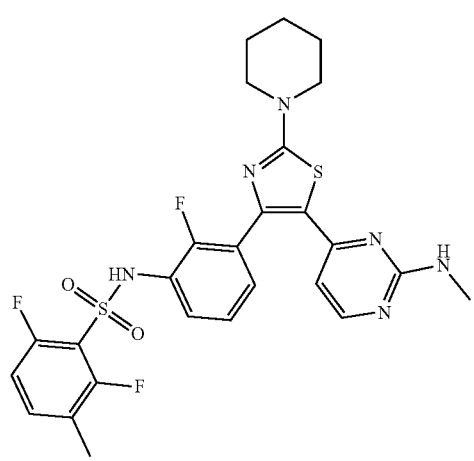
162 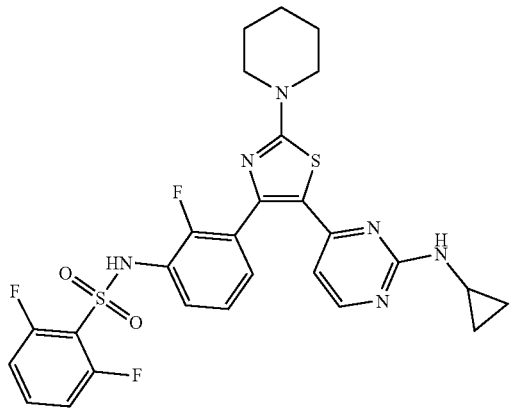
163
164 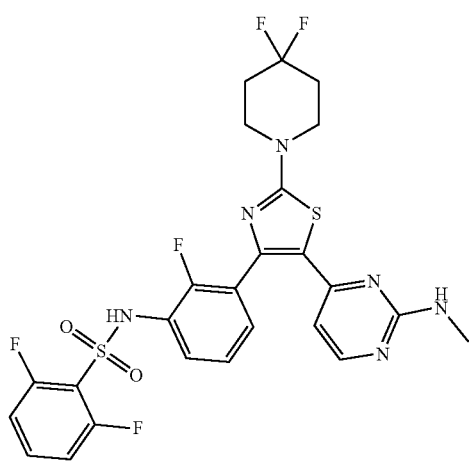
165
166 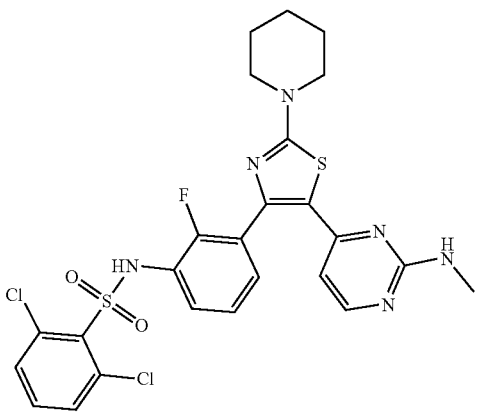

167
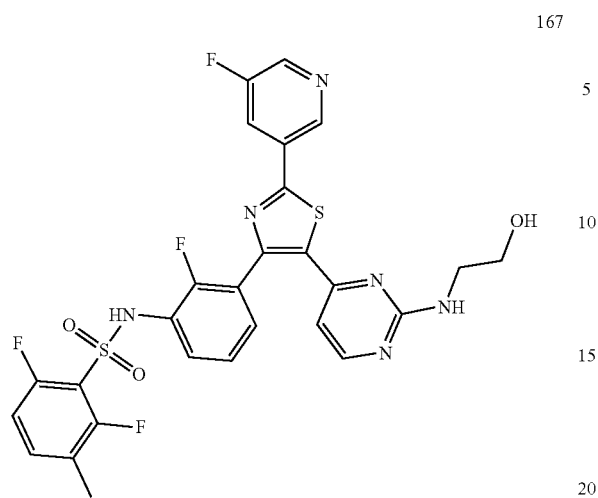
168
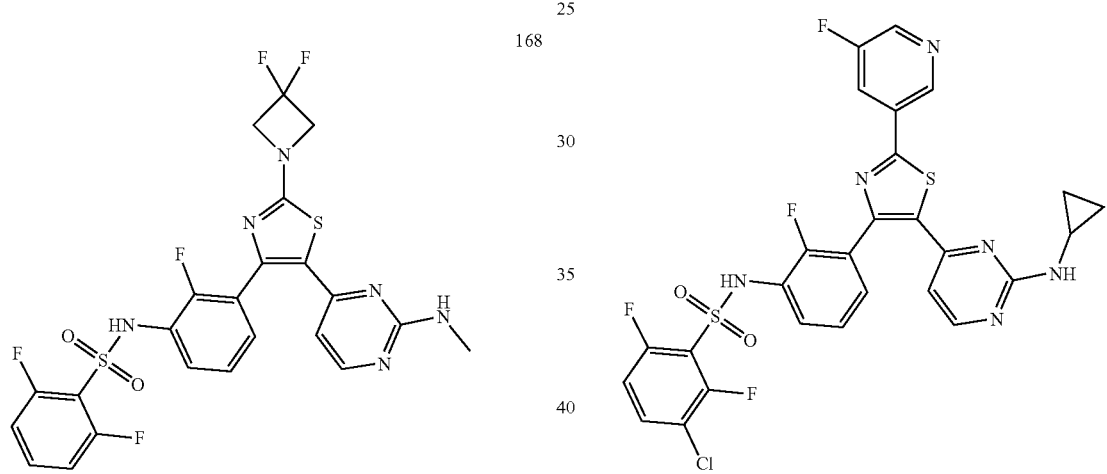
169
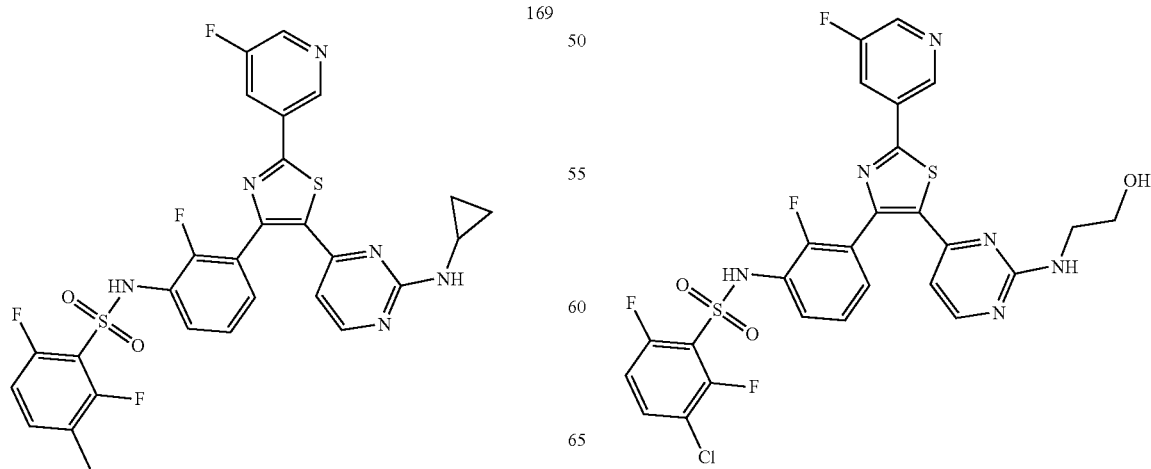
170
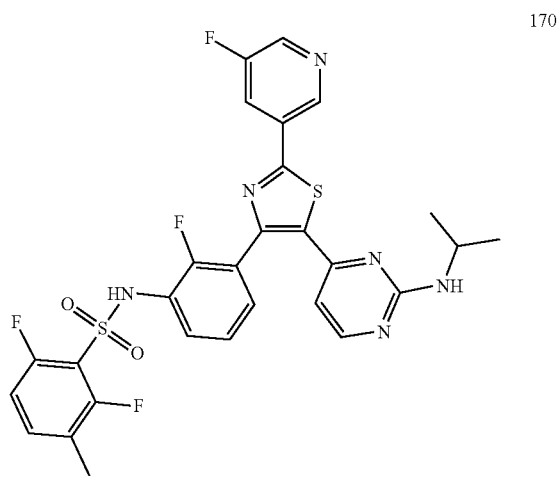
171
172

173
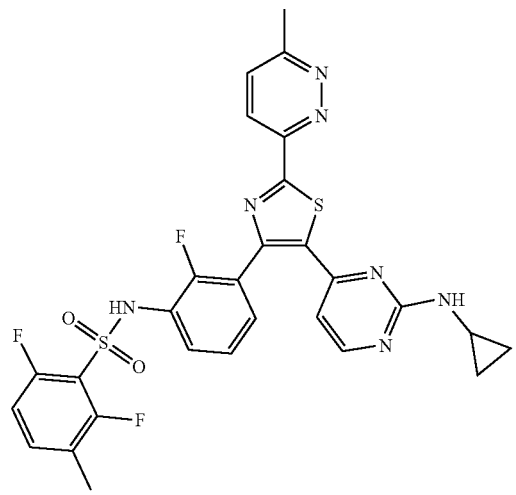
174
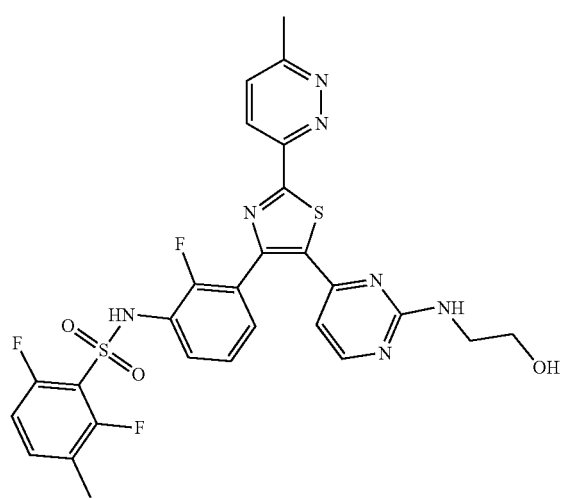
175
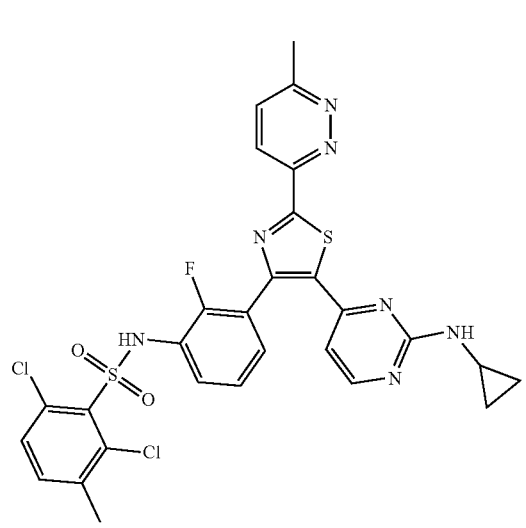
176
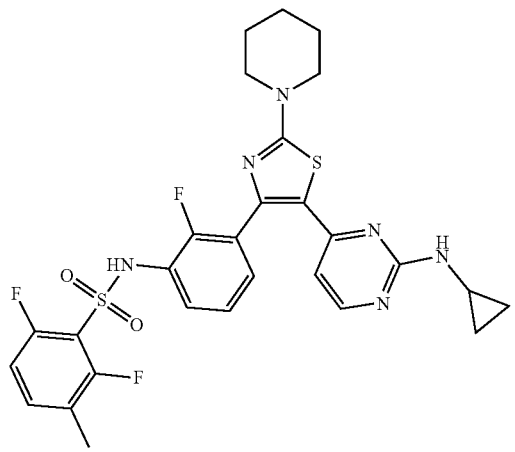
177
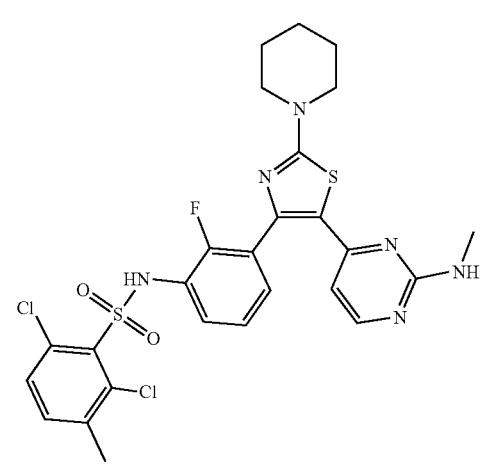
178
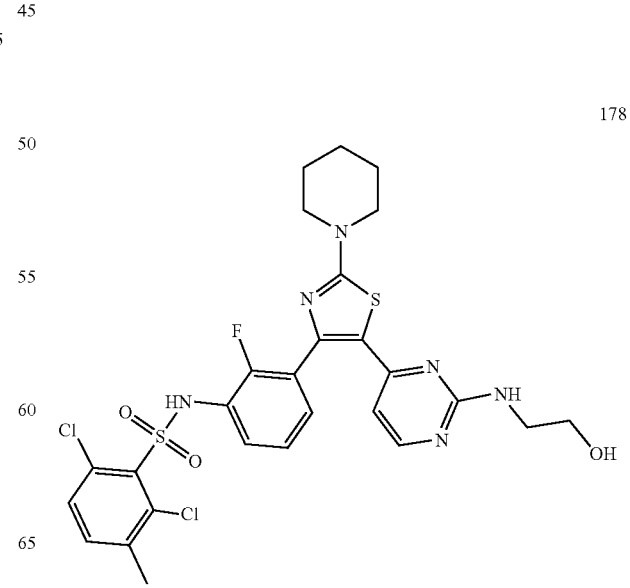

179
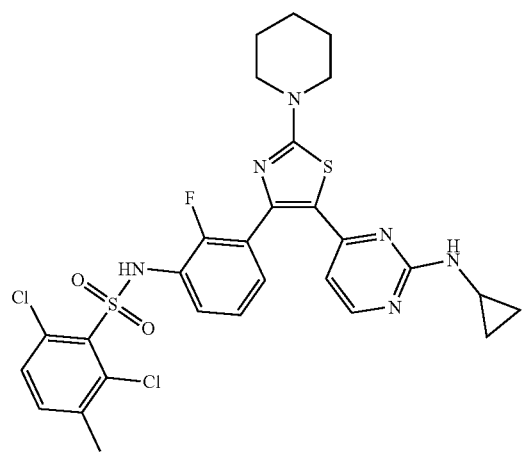
180
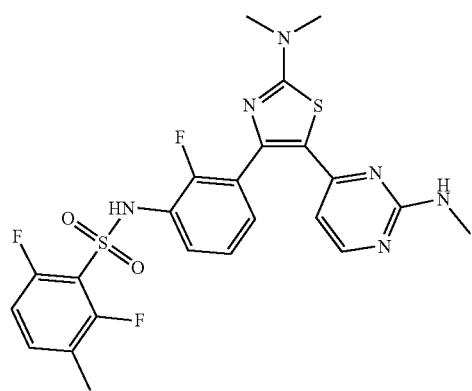
181
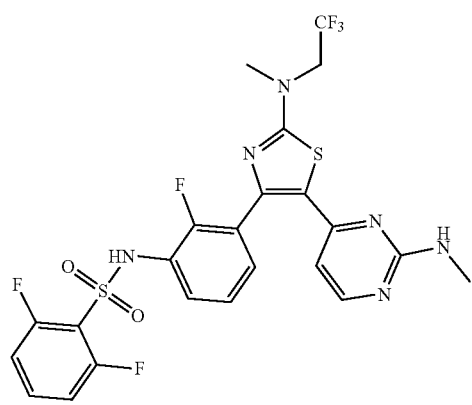
182
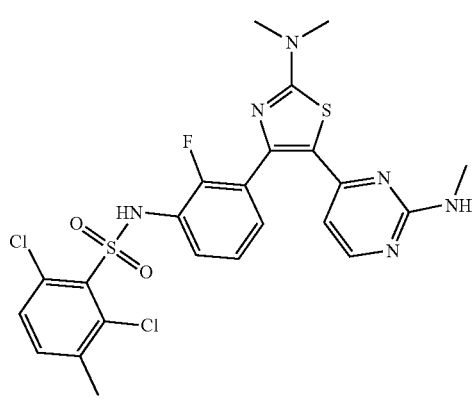
183
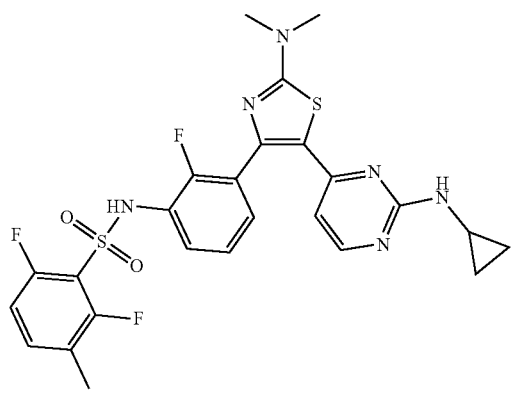
184
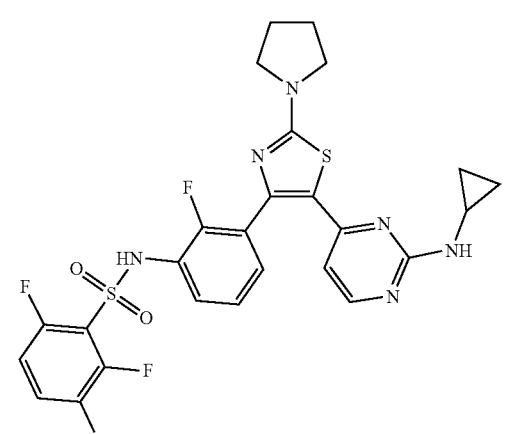
185
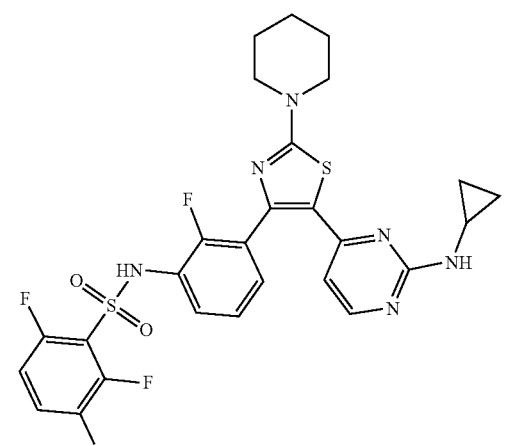

186

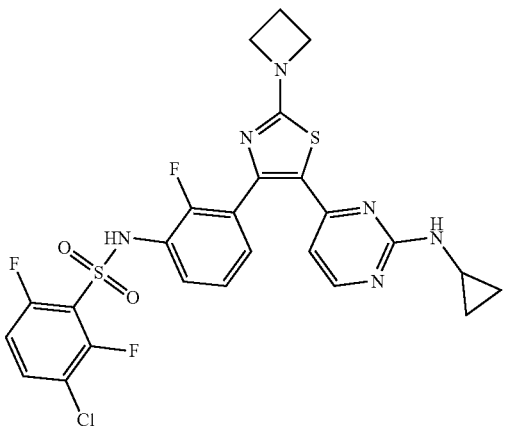

187

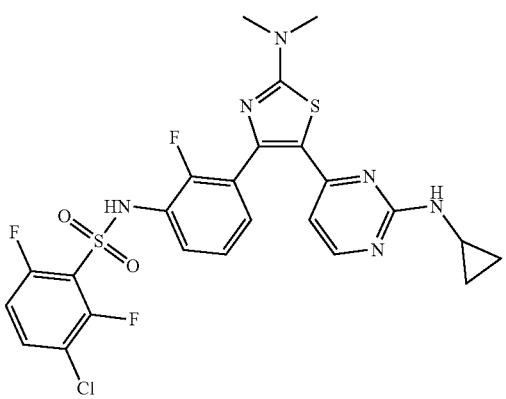

188

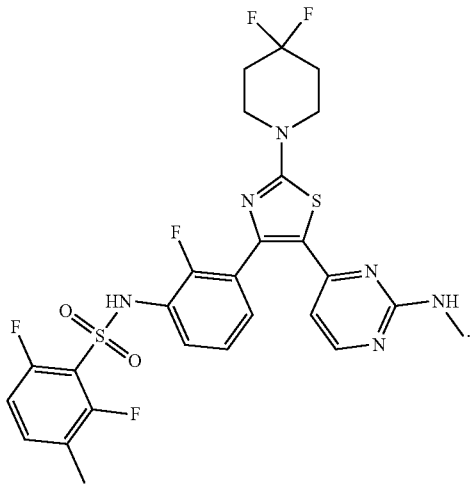

189

-continued

27. A pharmaceutical composition comprising the compound of claim 1, or a pharmaceutically acceptable salt thereof, and a pharmaceutically acceptable excipient.

28. A method of treating cancer comprising administering to a subject in need thereof a therapeutically effective amount of the compound of claim 1, or a pharmaceutically acceptable salt thereof, or a pharmaceutical composition comprising the compound or pharmaceutically acceptable salt thereof.

29. The method of claim 28, wherein the cancer is lung cancer, breast cancer, prostate cancer, ovarian cancer, endometrial cancer, cervical cancer, bladder cancer, head and neck cancer, renal cell carcinoma, esophageal cancer, pancreatic cancer, brain cancer, cancers of the gastrointestinal tract, liver cancer, leukemia, lymphoma, melanoma, multiple myeloma, Ewing's sarcoma, and/or osteosarcoma.

30. A method of (1) inhibiting C-terminal Src Kinase (CSK), (2) treating a disease or disorder, wherein inhibition of CSK activity is beneficial for the treatment of the disease or disorder, or (3) promoting immune response in a subject in need thereof, the method comprising administering to the subject an effective amount of the compound of claim 1, or a pharmaceutically acceptable salt thereof, or a pharmaceutical composition comprising the compound or pharmaceutically acceptable salt thereof.

31. A method of treating cancer comprising administering to a subject in need thereof a therapeutically effective amount of the compound of claim 17, or a pharmaceutically acceptable salt thereof, or a pharmaceutical composition comprising the compound or pharmaceutically acceptable salt thereof.

32. A method of treating cancer comprising administering to a subject in need thereof a therapeutically effective amount of the compound of claim 24, or a pharmaceutically acceptable salt thereof, or a pharmaceutical composition comprising the compound or pharmaceutically acceptable salt thereof.

33. A method of treating cancer comprising administering to a subject in need thereof a therapeutically effective amount of the compound of claim 26, or a pharmaceutically acceptable salt thereof, or a pharmaceutical composition comprising the compound or pharmaceutically acceptable salt thereof.

34. A method of inhibiting C-terminal Src Kinase (CSK), comprising administering to a subject in need thereof an effective amount of the compound of claim 17, or a pharmaceutically acceptable salt thereof, or a pharmaceutical composition comprising the compound or pharmaceutically acceptable salt thereof.

35. A method of inhibiting C-terminal Src Kinase (CSK), comprising administering to a subject in need thereof an effective amount of the compound of claim 24, or a pharmaceutically acceptable salt thereof, or a pharmaceutical composition comprising the compound or pharmaceutically acceptable salt thereof.

36. A method of inhibiting C-terminal Src Kinase (CSK), comprising administering to a subject in need thereof an effective amount of the compound of claim 26, or a pharmaceutically acceptable salt thereof, or a pharmaceutical composition comprising the compound or pharmaceutically acceptable salt thereof.

37. A compound according to Formula III-E, or a pharmaceutically acceptable salt thereof, Formula III-E

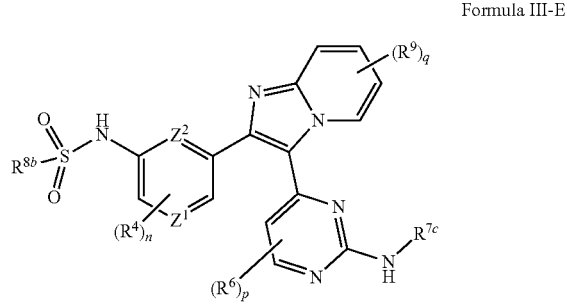

wherein:
- $R^4$ at each occurrence is independently a halogen, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- n is 0, 1, or 2,
- $Z^1$ and $Z^2$ are independently N or $CR^{100}$;
- wherein $R^{100}$ is hydrogen, halogen, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- $R^6$ at each occurrence is independently a halogen, cyano, —OH, an optionally substituted $C_{1-6}$ alkyl, an optionally substituted $C_{3-6}$ cycloalkyl, an optionally substituted $C_{1-6}$ alkoxy, or an optionally substituted $C_{3-6}$ cycloalkoxy;
- p is 0, 1, or 2;
- $R^{7c}$ is hydrogen, an optionally substituted $C_{1-6}$ alkyl, an optionally substituted $C_{3-6}$ cycloalkyl, an optionally substituted aryl, an optionally substituted heteroaryl, or an optionally substituted heterocyclyl;
- $R^{8b}$ is a substituted phenyl,
- q is 0, 1, or 2,
- $R^9$ at each occurrence is independently halogen, an optionally substituted $C_{1-6}$ alkyl, an optionally substituted $C_{3-6}$ cycloalkyl, an optionally substituted $C_{1-6}$ alkoxy, an optionally substituted $C_{3-6}$ cycloalkoxy, an optionally substituted phenyl, an optionally substituted heteroaryl, an optionally substituted heterocyclyl, —OH, cyano, —$COR^{110}$, —$COOR^{111}$, —$CONR^{112}R^{113}$, —$NR^{114}R^{115}$,
- wherein $R^{110}$ and $R^{111}$ are independently hydrogen, an optionally substituted $C_{1-6}$ alkyl, an optionally substituted $C_{3-6}$ cycloalkyl, an optionally substituted phenyl, an optionally substituted heteroaryl, or an optionally substituted heterocyclyl; and
- $R^{112}$, $R^{113}$, $R^{114}$, and $R^{115}$ are each independently hydrogen, nitrogen protecting group, an optionally substituted $C_{1-6}$ alkyl, an optionally substituted $C_{3-6}$ cycloalkyl, an optionally substituted phenyl, an optionally substituted 5 or 6 membered heteroaryl, or an optionally substituted 4-7 membered heterocyclyl.

38. A method of inhibiting C-terminal Src Kinase (CSK), comprising administering to a subject in need thereof an effective amount of the compound of claim 37, or a pharmaceutically acceptable salt thereof, or a pharmaceutical composition comprising the compound or pharmaceutically acceptable salt thereof.

\* \* \* \* \*